(12) United States Patent
Karpusas et al.

(10) Patent No.: US 7,723,073 B2
(45) Date of Patent: May 25, 2010

(54) ANTIBODIES TO VLA-1

(75) Inventors: Michael Karpusas, Upper Darby, PA (US); Paul D. Lyne, Arlington, MA (US); Jose William Saldanha, Enfield (GB); Ellen A. Garber, Cambridge, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

(21) Appl. No.: 12/015,213

(22) Filed: Jan. 16, 2008

(65) Prior Publication Data

US 2009/0010930 A1 Jan. 8, 2009

Related U.S. Application Data

(62) Division of application No. 10/474,832, filed as application No. PCT/US02/11521 on Apr. 12, 2002, now Pat. No. 7,358,054.

(60) Provisional application No. 60/283,794, filed on Apr. 13, 2001, provisional application No. 60/303,689, filed on Jul. 6, 2001.

(51) Int. Cl.
C12P 21/06 (2006.01)
C12N 15/87 (2006.01)
C12N 5/20 (2006.01)
C12N 1/20 (2006.01)
C12N 15/00 (2006.01)
C07H 21/04 (2006.01)

(52) U.S. Cl. ............ 435/69.1; 435/455; 435/326; 435/252.3; 435/320.1; 536/23.53

(58) Field of Classification Search .............. None
See application file for complete search history.

(56) References Cited

U.S. PATENT DOCUMENTS

| | | | |
|---|---|---|---|
| 5,391,481 A | 2/1995 | Chess et al. | 435/7.24 |
| 5,565,332 A | 10/1996 | Hoogenboom et al. | 435/69.1 |
| 5,648,260 A | 7/1997 | Winter et al. | 435/252.3 |
| 5,733,743 A | 3/1998 | Johnson et al. | 435/69.1 |
| 5,788,966 A | 8/1998 | Chess et al. | 424/144.1 |
| 5,789,650 A | 8/1998 | Lonberg et al. | 800/2 |
| 5,798,230 A | 8/1998 | Bornkamm et al. | 435/70.21 |
| 5,827,690 A | 10/1998 | Meade et al. | 435/69.6 |
| 5,855,888 A | 1/1999 | Nishida et al. | 424/156.1 |
| 5,859,205 A * | 1/1999 | Adair et al. | 530/387.3 |
| 6,001,961 A | 12/1999 | Jonczyk et al. | 530/317 |
| 6,016,159 A | 1/2000 | Faris | 348/57 |
| 6,075,181 A | 6/2000 | Kucherlapati et al. | 800/25 |
| 6,127,524 A | 10/2000 | Casipit et al. | 530/387.3 |
| 6,150,584 A | 11/2000 | Kucherlapati et al. | 800/18 |
| 6,162,963 A | 12/2000 | Kucherlapati et al. | 800/18 |
| 6,180,370 B1 | 1/2001 | Queen et al. | 435/69.6 |
| 6,291,650 B1 | 9/2001 | Winter et al. | 530/387.3 |
| 6,300,064 B1 | 10/2001 | Knappik et al. | 435/6 |
| 6,303,313 B1 | 10/2001 | Wigler et al. | 435/6 |
| 6,307,026 B1 | 10/2001 | King et al. | 530/387.3 |
| 6,326,403 B1 | 12/2001 | Hölzemann et al. | 514/563 |
| 6,632,927 B2 * | 10/2003 | Adair et al. | 530/387.3 |

FOREIGN PATENT DOCUMENTS

| | | |
|---|---|---|
| EP | 0 239 400 A2 | 9/1987 |
| EP | 0 843 961 A1 | 5/1998 |
| JP | 08-131185 | 5/1996 |
| JP | 08131185 | 5/1996 |
| WO | WO 90/07861 A1 | 7/1990 |
| WO | WO 99/61040 A2 | 12/1999 |
| WO | WO 99/61040 A3 | 12/1999 |
| WO | WO 00/20459 A1 | 4/2000 |
| WO | WO 00/72881 A1 | 12/2000 |
| WO | WO 01/73444 A2 | 10/2001 |
| WO | WO 01/96365 A1 | 12/2001 |

OTHER PUBLICATIONS

Portolano et al., Lack of promiscuity in autoantigen-specific H and L chain combinations as revealed by human H and L chain "roulette". J Immunol. Feb. 1, 1993;150(3):880-7.*

Padlan EA.. Anatomy of the antibody molecule. Mol Immunol. Feb. 1994;31(3):169-217.*

Panka et al. Variable region framework differences result in decreased or increased affinity of variant anti-digoxin antibodies. Proc Natl Acad Sci U S A. May 1988;85(9):3080-4.*

E.T. Baldwin et al.,"Cation Binding to the Integrin CD11b I Domain and Activation Model Assessment," *Structure*,6:923-935 (1998).

R. Briesewitz et al., "Expression of Native and Truncated Forms of the Human Integrin $\alpha_1$ Subunit," *J. Biol. Chem.*, 268:2989-2996 (1993).

P. Carter et al., "Humanization of an Anti-p185$^{HER2}$ Antibody for Human Cancer Therapy," *Proc. Natl. Acad. Sci. USA*, 89:4285-4289 (1992).

C. Chothia et al., "Conformations of Immunoglobulin Hypervariable Regions," *Nature*, 342:877-883 (1989).

M.S. Co et al., "Humanized Antibodies for Antiviral Therapy," *Proc. Nat. Acad. Sci. USA*, 88:2869-2873 (1991).

A.L. Corbi et al., "The Human Leukocyte Adhesion Glycoprotein Mac-1 (Complement Receptor Type 3, CD11b) $\alpha$ Subunit," *J. Biol. Chem.*, 263:12403-12411 (1988).

(Continued)

*Primary Examiner*—Maher M Haddad
(74) *Attorney, Agent, or Firm*—Lando & Anastasi, LLP

(57) ABSTRACT

Antibodies that specifically bind to VLA-1 integrin and methods of using these antibodies to treat immunological disorders in a subject. Also included are crystal structures of complexes formed by VLA-1 antibodies and their ligands, and VLA-1 antagonists and agonists identified by using the structure coordinates of these structures.

17 Claims, 131 Drawing Sheets

OTHER PUBLICATIONS

A.L. Corbi et al., "cDNA Cloning and Complete Primary Structure of the α Subunit of a Leukocyte Adhesion Glycoprotein, P150,95," *EMBO J.*, 6:4023-4028 (1987).

D. Cosgrove, et al., "Integrin α1β1 and Transforming Growth Factor-β1 Play Distinct Roles in Alport Glomerular Pathogenesis and Serve as Dual Targets for Metabolic Therapy," *Am. J. Path.*, 157:1649-1659 (2000).

D.R. Davies and G.H. Cohen, "Interactions of Protein Antigens with Antibodies," *Proc. Natl. Acad. Sci. USA*, 93:7-12 (1996).

A.R. de Fougerolles et al., "Global Expression Analysis of Extracellular Matrix-Integrin Interactions in Monocytes," *Immunity*, 13:749-758 (2000).

C.P. Edwards et al., "Identification of Amino Acids in the CD11a I-domain Important for Binding of the Leukocyte Function-associated Antigen-1 (LFA-1) to Intercellular Adhesion Molecule-1 (ICAM-1)", *J. Biol. Chem.*, 270, 12635-12640 (1995).

C. Eigenbrot et al., "X-ray Structures of the Antigen-binding Domains from Three Variants of Humanized anti-p185$^{HER2}$ Antibody 4D5 and Comparison with Molecular Modeling," *J. Mol. Biol.*, 229:969-995 (1993).

J. Emsley et al., "Structural Basis of Collagen Recognition by Integrin α2β1," *Cell*, 100:47-56 (2000).

J. Emsley et al., "Crystal Structure of the I Domain from Integrin α2β1," *J. Biol. Chem.*, 272:28512-28517 (1997).

J. Foote and G. Winter, "Antibody Framework Residues Affecting the Conformation of the Hypervariable Loops," *J. Mol. Biol.*, 224:487-499 (1992).

A.A. Gaspari and S.I. Katz, "Contact Hypersensitivity," *Current Protocols in Immunology*. J.E. Coligan, A.M. Kruisbeek, D.H. Margulies, E.M. Shevach, and W. Strober, editors. John Wiley & Sons, New York. Section 4.2.1-4.2.5 (1991).

P.J. Gotwals et al., "Divalent Cations Stabilize the α1β1 Integrin I Domain," *Biochemistry*, 38:8280-8288 (1999).

P.J. Gotwals et al., "The α1β1 Integrin Is Expressed during Neointima Formation in Rat Arteries and Mediates Collagen Matrix Reorganization," *J. Clin. Invest.*, 97:2469-2477 (1996).

M.H. Grayson et al., βdβ2 Integrin Is Expressed on Human Eosinophils and Functions as an Alternative Ligand for Vascular Cell Adhesion Molecule 1 (VCAM-1), *J. Exp. Med.*, 188:2187-2191 (1988).

L.L. Green et al., "Antigen-specific Human Monoclonal Antibodies From Mice Engineered With Human Ig Heavy and Light Chain YACs," *Nature Genetics*, 7:13-21 (1994).

M.E. Hemler et al., "Very Late Activation Antigens on Rheumatoid Synovial Fluid T Lymphocytes: Association with Stages of T Cell Activation," *J. Clin. Invest.*, 78:696-702 (1986).

M.E. Hemler at al., "VLA-1: A T Cell Surface Antigen which Defines a Novel Late Stage of Human T Cell Activation," *Eur. J. Immunol.*, 15:502-508 (1985).

C. Huang and B.D. Stollar, "A Majority of Ig H Chain cDNA of Normal Human Adult Blood Lymphocytes Resembles cDNA for Fetal Ig and Natural Autoantibodies," *J. Immunol.*, 151:5290-5300 (1993).

B. Hurtrel et al., "Different Time Course Patterns of Local Expression of Delayed-Type Hypersensitivity to Sheep Red Blood Cells in Mice," *Cell. Immunol.*, 142:252-263 (1992).

J.R. Huth et al., "NMR and Mutagenesis Evidence for an I Domain Allosteric Site that Regulates Lymphocyte Function-Associated Antigen 1 Ligand Binding," *Proc. Natl, Acad. Sci. U.S.A.*, 97:5231-5236 (2000).

M.J. Ignatius et al., "Molecular Cloning of the Rat Integrin $α_1$-Subunit: A Receptor for Laminin and Collagen," *J. Cell Biol.*, 111, 709-720 (1990).

S. Jones and J.M. Thornton, "Principles of Protein-Protein Interactions," *Proc. Natl. Acad. Sci. USA*, 93:13-20 (1996).

P.T. Jones et al., "Replacing the Complementarity-Determining Regions in a Human Antibody with Those from a Mouse," *Nature*, 321:522-525 (1986).

K. Kakimoto et al., "The Effect of Anti-adhesion Molecule Antibody on the Development of Collagen-Induced Arthritis," *Cell. Immunol.*, 142:326-337 (1992).

T. Kamata et al., "Critical Threonine and Aspartic Acid Residues within the I Domains of β2 Integrins for Interactions with Intercellular Adhesion Molecule 1 (ICAM-1) and C3bi," *J. Biol. Chem.*, 270:12531-12535 (1995).

P.J. Keely et al., "Alteration of Collagen-Dependent Adhesion, Motility, and Morphogenesis by the Expression of Antisense $α_2$ Integrin mRNA in Mammary Cells," *J. Cell Sci.*, 108:595-607 (1995).

A. Kern, et al., "The Role of the I Domain in Ligand Binding of the Human Integrin $α_1β_1$," *J. Biol. Chem.*, 269:22811-22816 (1994).

T. Kinashi and T.A. Springer, "Adhesion Molecules in Hematopoietic Cells," *Blood Cells*, 20:25-44 (1994).

S.L. King, et al., "Echovirus 1 Interaction with the Human Very Late Antigen-2 (Integrin α2β1) I Domain," *J. Biol. Chem.*, 272:28518-28522 (1997).

C.G. Knight et al., "The Collagen-binding A-domains of Integrins $α_1β_1$ and $β_2β_1$ Recognize the Same Specific Amino Acid Sequence, GFOGER, in Native (Triple-helical) Collagens," *J. Biol. Chem.*, 275:35-40 (2000).

F. Kolbinger et al., "Humanization of a Mouse Anti-human IgE Antibody: A Potential Therapeutic for IgE-mediated Allergies," *Protein Eng.*, 6:971-980 (1993).

O. Langholz et al., "Collagen and Collagenase Gene Expression in Three-dimensional Collagen Lattices Are Differentially Regulated by α1β1 and α2β1Integrins," *J. Cell Biol.*, 131:1903-1915 (1995).

R.S. Larson et al., "Primary Structure of the Leukocyte Function-associated Molecule-1 α Subunit: An Integrin with an Embedded Domain Defining a Protein Superfamily," *J. Cell Biol.*, 108:703-712 (1989).

J.-O. Lee et al., "Crystal Structure of the A Domain from the α Subunit of Integrin CR3 (CD11b/CD18)," *Cell*, 80:631-638 (1995).

J.-O. Lee et al., "Two Conformations of the Integrin A-domain (I-domain): A Pathway for Activation?" *Structure*, 3:1333-1340 (1995).

F. Mackay et al., "Lymphotoxin β Receptor Triggering Induces Activation of the Nuclear Factor κB Transcription Factor in Some Cell Types," *J. Biol. Chem.*, 271:24934-24938 (1996).

M.J. Mendez et al., "Functional Transplant of Megabase Human Immunoglobulin Loci Recapitulates Human Antibody Response in Mice," *Nature Genetics*, 15:146-156 (1997).

D.L. Mendrick et al., "Glomerular Epithelial and Mesangial Cells Differentially Modulate the Binding Specificities of VLA-1 and VLA-2," *Lab. Invest.*, 72:367-375 (1995).

D.L. Mendrick and D.M. Kelly, "Temporal Expression of VLA-2 and Modulation of its Ligand Specificity by Rat Glomerular Epithelial Cells In vitro," *Lab. Invest.*, 69:690-702 (1993).

M. Michishita et al., "A Novel Divalent Cation-Binding Site in the A Domain of the β2 Integrin CR3 (CD11b/CD18) is Essential for Ligand Binding," *Cell*, 72:857-867 (1993).

S. Miyake et al., "β1 Integrin-mediated Interaction with Extracellular Matrix Proteins Regulates Cytokine Gene Expression in Synovial Fluid Cells of Rheumatoid Arthritis Patients," *J. Exp. Med.*, 177:863-868 (1993).

K. Miyake et al., "Evidence for a Role of the Integrin VLA-4 in Lympho-hemopoiesis," *J. Exp. Med.*, 173:599-607 (1991).

P. Mombaerts et al., "RAG-1-Deficient Mice Have No Mature B and T Lymphocytes," *Cell*, 68:869-877 (1992).

L. Mori et al., "Attenuation of Collagen-Induced Arthritis in 55-kDa TNF Receptor Type 1 (TNFR1)-IgG1-Treated and TNFR1-Deficient Mice," *J. Immunol.*, 157:3178-3182 (1996).

Y.A. Muller et al., "VEGF and the Fab Fragment of a Humanized Neutralizing Antibody: Crystal Structure of the Complex at 2.4 Å Resolution and Mutational Analysis of the Interface," *Structure*, 6:1153-1167 (1998).

M. Nolte et al., "Crystal Structure of the α1β1 Integrin I-Domain: Insights into Integrin I-Domain Function," *FEBS Lett.*, 452:379-385 (1999).

K. Noto et al., "Identification and Functional Characterization of Mouse CD29 with a mAb," *Int. Immunol.*, 7:835-842 (1995).

R. Orlandi et al., "Cloning Immunoglobulin Variable Domains for Expression by the Polymerase Chain Reaction," *Proc. Natl. Acad. Sci. USA*, 86:3833-3837 (1989).

D. Plows et al., "Mice Lacking Mature T and B Lymphocytes Develop Arthritic Lesions After Immunization with Type II Collagen," *J. Immunol.*, 162:1018-1023 (1999).

A. Qu and D.J. Leahy, "The Role of the Divalent Cation in the Structure of the I Domain from the CD11a/CD18 Integrin," *Structure*, 4:931-942 (1996).

A. Qu and D.J. Leahy, "Crystal Structure of the I-Domain from the CD11a/CD18 (LFA-1, $\alpha_L\beta2$) Integrin," *Proc. Natl. Acad. Sci. USA*, 92:10277-10281 (1995).

R.L. Rich et al., "Trench-shaped Binding Sites Promote Multiple Classes of Interactions between Collagen and the Adherence Receptors, $\alpha_1\beta_1$ Integrin and *Staphylococcus aureus* Cna MSCRAMM," *J. Biol. Chem.*, 274:24906-24913 (1999).

L. Riechmann et al., "Reshaping Human Antibodies for Therapy," *Nature*, 332:323-327 (1988).

T. Riikonen et al., "Transforming Growth Factor-$\beta$ Regulates Collagen Gel Contraction by Increasing $\alpha2\beta1$ Integrin Expression in Osteogenic Cells," *J. Biol. Chem.*, 270:376-382 (1995).

A. Scheynius et al. "Reduced Contact Sensitivity Reactions in Mice Treated with Monoclonal Antibodies to Leukocyte Function-Associated Molecule-1 and Intercellular Adhesion Molecule-1," *J. Immunol.*, 150:655-663 (1993).

J.A. Schiro et al., "Integrin $\alpha^2\beta_1$ (VLA-2) Mediates Reorganization and Contraction of Collagen Matrices by Human Cells," *Cell*, 67:403-410 (1991).

D. Seiffge, "Protective Effects of Monoclonal Antibody to VLA-4 on Leukocyte Adhesion and Course of Disease in Adjuvant Arthritis in Rats," *J. Rheumatol.*, 23:2086-2091 (1996).

S.K. Shaw et al., "Molecular Cloning of the Human Mucosal Lymphocyte Integrin $\alpha^E$ Subunit," *J. Biol. Chem.*, 269:6016-6025 (1994).

A. Sonnenberg et al., "A Complex of Platelet Glycoproteins Ic and IIa Identified by a Rat Monoclonal Antibody," *J. Biol. Chem.*, 262:10376-10383 (1987).

T.A. Springer, "Adhesion Receptors of the Immune System," *Nature*, 346:425-434 (1990).

Y. Takada and M.E. Hemler, "The Primary Structure of the VLA-2/Collagen Receptor $\alpha^2$ Subunit (Platelet GPIa): Homology to Other Integrins and the Presence of a Possible Collagen-binding Domain," *J. Cell Biol.*, 109:397-407 (1989).

P.C. Taylor et al., "Transfer of Type II Collagen-Induced Arthritis From DBA/1 to Severe Combined Immunodeficiency Mice Can Be Prevented by Blockage of Mac-1," *Immunology*, 88:315-321 (1996).

T.F. Tedder et al., "L-Selectin-deficient Mice Have Impaired Leukocyte Recruitment Into Inflammatory Sites," *J. Exp. Med.*, 181:2259-2264 (1995).

P.R. Tempest et al., "Reshaping a Human Monoclonal Antibody to Inhibit Human Respiratory Syncytial Virus Infection In vivo," *Bio/Technology*, 9:266-271 (1991).

M. Terashita et al., "Enhancement of Delayed-Type Hypersensitivity to Sheep Red Blood Cells in Mice by Granulocyte Colony-Stimulating Factor Administration at the Elicitation Phase," *J. Immunol.*, 156:4638-4643 (1996).

K. Terato et al., "Collagen-Induced Arthritis in Mice: Synergistic Effect of *E. coli* Lipopolysaccharide Bypasses Epitope Specificity in the Induction of Arthritis with Monoclonal Antibodies to Type II Collagen," *Autoimmunity*, 22:137-147 (1995).

K. Terato et al., "Induction of Arthritis with Monoclonal Antibodies to Collagen," *J. Immunol.*, 148:2103-2108 (1992).

K. Tomizuka et al., "Functional Expression and Germline Transmission of a Human Chromosome Fragment in Chimaeric Mice," *Nature Genetics*, 16:133-143 (1997).

M. Verhoeyen et al., "Reshaping Human Antibodies: Grafting an Antilysozyme Activity," *Science*, 239:1534-1536 (1988).

E.S. Ward et al., "Binding Activities of a Repertoire of Single Immunoglobulin Variable Domains Secreted from *Escherichia coli*," *Nature*, 341:544-546 (1989).

M. Welschof et al., "Amino Acid Sequence based PCR Primers for Amplification of Rearranged Human Heavy and Light Chain Immunoglobulin Variable Region Genes," *J. Immunol. Meth.*, 179:203-214 (1995).

I. Bank et al., "Analysis of Recombinant Human $\alpha1$ Integrin I-Domain with a Function-Blocking Monoclonal Antibody 1B3.1," *Isr. Med. Assoc. J.*, 2:19-20 (2000).

S.C.G. Brezinsky et al., "A Simple Method for Enriching Populations of Transfected CHO Cells for Cells of Higher Specific Productivity," *J. Immunol. Methods*, 277:141-155 (2003).

H. T. Cook et al., "Treatment with an Antibody to VLA-1 Integrin Reduces Glomerular and Tubulointerstitial Scarring in a Rat Model of Crescentic Glomerulonephritis," *Am. J. Pathol.*, 161:1265-1272 (2002).

T. O. Fischmann et al., "Crystallographic Refinement of the Three-Dimensional Structure of the FabD1.3-Lysozyme Complex at 2.5-Å Resolution," *J. Biol. Chem.*, 266:12915-12920 (1991).

M. A. Holmes et al., "Conformational Correction Mechanisms Aiding Antigen Recognition by a Humanized Antibody," *J. Exp. Med.*, 187:479-485 (1998).

A. Ianaro et al., "Anti-Very Late Antigen-1 Monoclonal Antibody Modulates the Development of Secondary Lesion and T-Cell Response in Experimental Arthritis," *Lab. Invest.*, 80:73-80 (2000).

M. Karpusas et al., "Crystal Structure of the $\alpha1\beta1$ Integrin I Domain in Complex with an Antibody Fab Fragment," *J. Mol. Biol.*, 327:1031-1041 (2003).

Y. Li et al., "Three-Dimensional Structures of the Free and Antigen-Bound Fab from Monoclonal Antilysozyme Antibody HyHEL-63," *Biochemistry*, 39:6296-6309 (2000).

N. S. Sampson et al., "Global Gene Expression Analysis Reveals a Role for the $\alpha_1$ Integrin in Renal Pathogenesis," *J. Biol. Chem.*, 276:34182-34188 (2001).

R. Briesewitz et al., "Expression of Native and Truncated Forms of the Human Integrin $\alpha1$ Subunit," *J. Bio. Chem.*, 268:2989-2996 (1993).

A. R. de Fougerolles et al., "Regulation of Inflammation by Collagen-Binding Integrins $\alpha1\beta1$ and $\alpha2\beta1$* in Models of Hypersensitivity and Arthritis," *J. Clin. Invest.*, 105:721-729 (2000).

M. Fabbri et al., "A Functional Monoclonal Antibody Recognizing the Human alpha1-Integrin I-Domain," *Tissue Antigens*, 48:47-51 (1996).

Shimoka, "Computational Design of an Integrin I Domain, etc.", Nature Structural Biology, vol. 7, No. 8 (Aug. 2000), pp. 674-678.

Bella Jordi, "Integrin-collagen complex:a metal glutamate handshake", Structure (London), vol. 8, No. 6 Jun. 15, 2000), pp. R121-R126.

Leibiger et al., "Variable domain-linked oligosaccharides of a human monoclonal IgG: structure and influence on antigen binding," *Biochem. J.* 338:529-238, 1999.

Shakin-Eshleman et al., "The Amino Acid at the $X$ Position of an Asn-$X$-Ser Sequon is an Important Determinant of N-Linked Core-glycosylation Efficiency," *J. Biol. Chem.* 271:6363-6366, 1996.

Wright and Morrison, "Effect of Altered $C_H2$-associated Carbohydrate Structure on the Functional Properties and In Vivo Fate of Chimeric Mouse-Human Immunoglobulin G1," *J. Exp. Med.* 180:1087-1096, 1994.

* cited by examiner

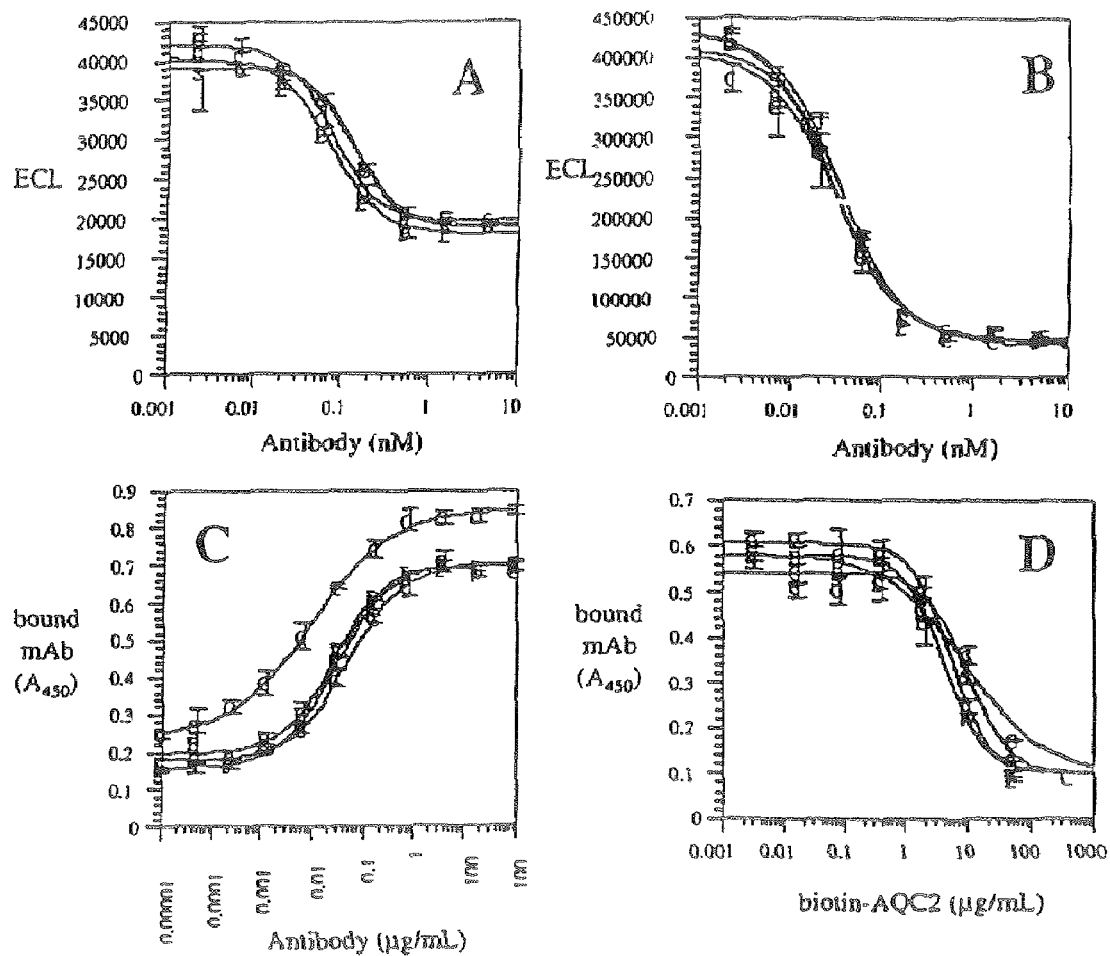
FIGS. 16 A, B, C, D

Fig. 19: A-1

| ATOM | 1 | CB | THR | 145 | 131.250 | 52.244 | -9.297 | 1.00 | 82.68 | A | C |
|---|---|---|---|---|---|---|---|---|---|---|---|
| ATOM | 2 | OG1 | THR | 145 | 131.373 | 51.127 | -10.191 | 1.00 | 82.68 | A | O |
| ATOM | 3 | CG2 | THR | 145 | 132.601 | 52.936 | -9.145 | 1.00 | 82.68 | A | C |
| ATOM | 4 | C | THR | 145 | 129.280 | 51.301 | -8.080 | 1.00 | 146.54 | A | C |
| ATOM | 5 | O | THR | 145 | 128.489 | 51.352 | -7.134 | 1.00 | 146.94 | A | O |
| ATOM | 6 | N | THR | 145 | 131.576 | 50.663 | -7.360 | 1.00 | 144.92 | A | N |
| ATOM | 7 | CA | THR | 145 | 130.726 | 51.757 | -7.915 | 1.00 | 144.52 | A | C |
| ATOM | 8 | N | GLN | 146 | 128.941 | 50.856 | -9.288 | 1.00 | 36.14 | A | N |
| ATOM | 9 | CA | GLN | 146 | 127.592 | 50.397 | -9.569 | 1.00 | 34.29 | A | C |
| ATOM | 10 | CB | GLN | 146 | 127.046 | 51.086 | -10.823 | 1.00 | 99.89 | A | C |
| ATOM | 11 | CG | GLN | 146 | 127.887 | 50.902 | -12.065 | 1.00 | 99.89 | A | C |
| ATOM | 12 | CD | GLN | 146 | 127.274 | 51.575 | -13.279 | 1.00 | 99.89 | A | C |
| ATOM | 13 | OE1 | GLN | 146 | 127.787 | 51.454 | -14.392 | 1.00 | 99.89 | A | O |
| ATOM | 14 | NE2 | GLN | 146 | 126.170 | 52.290 | -13.070 | 1.00 | 99.89 | A | N |
| ATOM | 15 | C | GLN | 146 | 127.535 | 48.883 | -9.721 | 1.00 | 34.71 | A | C |
| ATOM | 16 | O | GLN | 146 | 128.084 | 48.314 | -10.667 | 1.00 | 36.57 | A | O |
| ATOM | 17 | N | LEU | 147 | 126.876 | 48.240 | -8.762 | 1.00 | 33.54 | A | N |
| ATOM | 18 | CA | LEU | 147 | 126.718 | 46.794 | -8.767 | 1.00 | 32.67 | A | C |
| ATOM | 19 | CB | LEU | 147 | 127.491 | 46.143 | -7.609 | 1.00 | 35.25 | A | C |
| ATOM | 20 | CG | LEU | 147 | 128.963 | 46.398 | -7.301 | 1.00 | 35.44 | A | C |
| ATOM | 21 | CD1 | LEU | 147 | 129.205 | 47.877 | -7.087 | 1.00 | 30.65 | A | C |
| ATOM | 22 | CD2 | LEU | 147 | 129.325 | 45.637 | -6.037 | 1.00 | 35.29 | A | C |
| ATOM | 23 | C | LEU | 147 | 125.247 | 46.451 | -8.575 | 1.00 | 31.65 | A | C |
| ATOM | 24 | O | LEU | 147 | 124.506 | 47.194 | -7.939 | 1.00 | 32.95 | A | O |
| ATOM | 25 | N | ASP | 148 | 124.832 | 45.325 | -9.142 | 1.00 | 25.19 | A | N |
| ATOM | 26 | CA | ASP | 148 | 123.477 | 44.817 | -8.976 | 1.00 | 22.65 | A | C |
| ATOM | 27 | CB | ASP | 148 | 122.907 | 44.329 | -10.302 | 1.00 | 27.55 | A | C |
| ATOM | 28 | CG | ASP | 148 | 122.330 | 45.446 | -11.125 | 1.00 | 27.17 | A | C |
| ATOM | 29 | OD1 | ASP | 148 | 121.787 | 45.158 | -12.208 | 1.00 | 26.28 | A | O |
| ATOM | 30 | OD2 | ASP | 148 | 122.413 | 46.612 | -10.686 | 1.00 | 25.35 | A | O |
| ATOM | 31 | C | ASP | 148 | 123.664 | 43.638 | -8.025 | 1.00 | 19.03 | A | C |
| ATOM | 32 | O | ASP | 148 | 124.119 | 42.567 | -8.422 | 1.00 | 18.33 | A | O |
| ATOM | 33 | N | ILE | 149 | 123.341 | 43.848 | -6.760 | 1.00 | 16.75 | A | N |
| ATOM | 34 | CA | ILE | 149 | 123.502 | 42.809 | -5.761 | 1.00 | 15.69 | A | C |
| ATOM | 35 | CB | ILE | 149 | 124.041 | 43.391 | -4.442 | 1.00 | 18.53 | A | C |
| ATOM | 36 | CG2 | ILE | 149 | 124.401 | 42.269 | -3.485 | 1.00 | 13.54 | A | C |
| ATOM | 37 | CG1 | ILE | 149 | 125.271 | 44.251 | -4.718 | 1.00 | 14.25 | A | C |
| ATOM | 38 | CD1 | ILE | 149 | 125.819 | 44.932 | -3.497 | 1.00 | 17.00 | A | C |
| ATOM | 39 | C | ILE | 149 | 122.185 | 42.129 | -5.456 | 1.00 | 17.34 | A | C |
| ATOM | 40 | O | ILE | 149 | 121.191 | 42.794 | -5.181 | 1.00 | 17.74 | A | O |
| ATOM | 41 | N | VAL | 150 | 122.175 | 40.805 | -5.526 | 1.00 | 11.00 | A | N |
| ATOM | 42 | CA | VAL | 150 | 120.987 | 40.036 | -5.193 | 1.00 | 12.56 | A | C |
| ATOM | 43 | CB | VAL | 150 | 120.571 | 39.089 | -6.336 | 1.00 | 16.85 | A | C |
| ATOM | 44 | CG1 | VAL | 150 | 119.409 | 38.210 | -5.885 | 1.00 | 19.04 | A | C |
| ATOM | 45 | CG2 | VAL | 150 | 120.164 | 39.894 | -7.555 | 1.00 | 18.66 | A | C |
| ATOM | 46 | C | VAL | 150 | 121.367 | 39.212 | -3.970 | 1.00 | 10.12 | A | C |
| ATOM | 47 | O | VAL | 150 | 122.387 | 38.526 | -3.973 | 1.00 | 8.27 | A | O |
| ATOM | 48 | N | ILE | 151 | 120.573 | 39.303 | -2.912 | 1.00 | 20.50 | A | N |
| ATOM | 49 | CA | ILE | 151 | 120.856 | 38.537 | -1.699 | 1.00 | 19.30 | A | C |
| ATOM | 50 | CB | ILE | 151 | 120.653 | 39.392 | -0.439 | 1.00 | 14.22 | A | C |
| ATOM | 51 | CG2 | ILE | 151 | 121.039 | 38.601 | 0.785 | 1.00 | 10.58 | A | C |
| ATOM | 52 | CG1 | ILE | 151 | 121.515 | 40.659 | -0.532 | 1.00 | 12.64 | A | C |
| ATOM | 53 | CD1 | ILE | 151 | 121.283 | 41.660 | 0.593 | 1.00 | 14.62 | A | C |
| ATOM | 54 | C | ILE | 151 | 119.931 | 37.329 | -1.646 | 1.00 | 17.42 | A | C |
| ATOM | 55 | O | ILE | 151 | 118.715 | 37.459 | -1.777 | 1.00 | 17.66 | A | O |
| ATOM | 56 | N | VAL | 152 | 120.511 | 36.150 | -1.470 | 1.00 | 17.56 | A | N |
| ATOM | 57 | CA | VAL | 152 | 119.741 | 34.915 | -1.428 | 1.00 | 18.41 | A | C |
| ATOM | 58 | CB | VAL | 152 | 120.395 | 33.849 | -2.309 | 1.00 | 11.45 | A | C |
| ATOM | 59 | CG1 | VAL | 152 | 119.470 | 32.664 | -2.460 | 1.00 | 10.58 | A | C |
| ATOM | 60 | CG2 | VAL | 152 | 120.758 | 34.458 | -3.667 | 1.00 | 7.89 | A | C |
| ATOM | 61 | C | VAL | 152 | 119.675 | 34.404 | -0.003 | 1.00 | 16.31 | A | C |
| ATOM | 62 | O | VAL | 152 | 120.602 | 33.755 | 0.469 | 1.00 | 9.91 | A | O |
| ATOM | 63 | N | LEU | 153 | 118.568 | 34.692 | 0.672 | 1.00 | 19.79 | A | N |
| ATOM | 64 | CA | LEU | 153 | 118.367 | 34.297 | 2.061 | 1.00 | 19.90 | A | C |
| ATOM | 65 | CB | LEU | 153 | 117.530 | 35.361 | 2.766 | 1.00 | 21.44 | A | C |
| ATOM | 66 | CG | LEU | 153 | 118.250 | 36.403 | 3.623 | 1.00 | 23.22 | A | C |
| ATOM | 67 | CD1 | LEU | 153 | 119.699 | 36.561 | 3.185 | 1.00 | 23.73 | A | C |
| ATOM | 68 | CD2 | LEU | 153 | 117.494 | 37.721 | 3.530 | 1.00 | 25.76 | A | C |
| ATOM | 69 | C | LEU | 153 | 117.732 | 32.929 | 2.300 | 1.00 | 20.96 | A | C |
| ATOM | 70 | O | LEU | 153 | 116.724 | 32.574 | 1.690 | 1.00 | 19.96 | A | O |
| ATOM | 71 | N | ASP | 154 | 118.336 | 32.165 | 3.200 | 1.00 | 19.89 | A | N |
| ATOM | 72 | CA | ASP | 154 | 117.820 | 30.854 | 3.554 | 1.00 | 19.37 | A | C |
| ATOM | 73 | CB | ASP | 154 | 118.952 | 29.983 | 4.129 | 1.00 | 22.72 | A | C |

Fig. 19: A-2

| | | | | | | | | | | |
|---|---|---|---|---|---|---|---|---|---|---|
| ATOM | 74 | CG | ASP | 154 | 118.486 | 28.601 | 4.546 | 1.00 | 21.92 | A C |
| ATOM | 75 | OD1 | ASP | 154 | 117.266 | 28.363 | 4.537 | 1.00 | 25.43 | A O |
| ATOM | 76 | OD2 | ASP | 154 | 119.340 | 27.754 | 4.893 | 1.00 | 18.24 | A O |
| ATOM | 77 | C | ASP | 154 | 116.770 | 31.153 | 4.623 | 1.00 | 22.71 | A C |
| ATOM | 78 | O | ASP | 154 | 117.062 | 31.802 | 5.630 | 1.00 | 19.03 | A O |
| ATOM | 79 | N | GLY | 155 | 115.540 | 30.718 | 4.393 | 1.00 | 3.06 | A N |
| ATOM | 80 | CA | GLY | 155 | 114.491 | 30.948 | 5.370 | 1.00 | 5.13 | A C |
| ATOM | 81 | C | GLY | 155 | 113.840 | 29.638 | 5.788 | 1.00 | 6.39 | A C |
| ATOM | 82 | O | GLY | 155 | 112.751 | 29.633 | 6.368 | 1.00 | 8.88 | A O |
| ATOM | 83 | N | SER | 156 | 114.512 | 28.521 | 5.494 | 1.00 | 19.70 | A N |
| ATOM | 84 | CA | SER | 156 | 114.011 | 27.191 | 5.832 | 1.00 | 24.28 | A C |
| ATOM | 85 | CB | SER | 156 | 114.994 | 26.111 | 5.353 | 1.00 | 33.45 | A C |
| ATOM | 86 | OG | SER | 156 | 116.261 | 26.252 | 5.967 | 1.00 | 36.37 | A O |
| ATOM | 87 | C | SER | 156 | 113.773 | 27.054 | 7.330 | 1.00 | 21.27 | A C |
| ATOM | 88 | O | SER | 156 | 114.270 | 27.843 | 8.128 | 1.00 | 24.45 | A O |
| ATOM | 89 | N | ASN | 157 | 113.008 | 26.037 | 7.700 | 1.00 | 21.98 | A N |
| ATOM | 90 | CA | ASN | 157 | 112.686 | 25.802 | 9.091 | 1.00 | 19.06 | A C |
| ATOM | 91 | CB | ASN | 157 | 112.027 | 24.435 | 9.247 | 1.00 | 21.82 | A C |
| ATOM | 92 | CG | ASN | 157 | 110.586 | 24.434 | 8.785 | 1.00 | 23.31 | A C |
| ATOM | 93 | OD1 | ASN | 157 | 109.944 | 23.385 | 8.706 | 1.00 | 20.38 | A O |
| ATOM | 94 | ND2 | ASN | 157 | 110.066 | 25.612 | 8.479 | 1.00 | 20.59 | A N |
| ATOM | 95 | C | ASN | 157 | 113.859 | 25.913 | 10.048 | 1.00 | 17.03 | A C |
| ATOM | 96 | O | ASN | 157 | 113.720 | 26.498 | 11.132 | 1.00 | 15.01 | A O |
| ATOM | 97 | N | SER | 158 | 115.006 | 25.367 | 9.653 | 1.00 | 15.99 | A N |
| ATOM | 98 | CA | SER | 158 | 116.179 | 25.378 | 10.510 | 1.00 | 14.20 | A C |
| ATOM | 99 | CB | SER | 158 | 117.327 | 24.603 | 9.864 | 1.00 | 26.18 | A C |
| ATOM | 100 | OG | SER | 158 | 117.597 | 25.067 | 8.562 | 1.00 | 28.89 | A O |
| ATOM | 101 | C | SER | 158 | 116.656 | 26.753 | 10.941 | 1.00 | 14.97 | A C |
| ATOM | 102 | O | SER | 158 | 117.053 | 26.930 | 12.097 | 1.00 | 12.14 | A O |
| ATOM | 103 | N | ILE | 159 | 116.623 | 27.730 | 10.039 | 1.00 | 8.33 | A N |
| ATOM | 104 | CA | ILE | 159 | 117.050 | 29.083 | 10.379 | 1.00 | 12.93 | A C |
| ATOM | 105 | CB | ILE | 159 | 116.801 | 30.035 | 9.193 | 1.00 | 9.66 | A C |
| ATOM | 106 | CG2 | ILE | 159 | 117.138 | 31.479 | 9.592 | 1.00 | 9.57 | A C |
| ATOM | 107 | CG1 | ILE | 159 | 117.650 | 29.609 | 8.000 | 1.00 | 14.44 | A C |
| ATOM | 108 | CD1 | ILE | 159 | 119.134 | 29.804 | 8.204 | 1.00 | 19.60 | A C |
| ATOM | 109 | C | ILE | 159 | 116.292 | 29.604 | 11.616 | 1.00 | 17.24 | A C |
| ATOM | 110 | O | ILE | 159 | 115.059 | 29.575 | 11.659 | 1.00 | 16.65 | A O |
| ATOM | 111 | N | TYR | 160 | 117.032 | 30.084 | 12.611 | 1.00 | 29.54 | A N |
| ATOM | 112 | CA | TYR | 160 | 116.438 | 30.600 | 13.849 | 1.00 | 31.67 | A C |
| ATOM | 113 | CB | TYR | 160 | 115.775 | 29.455 | 14.639 | 1.00 | 16.89 | A C |
| ATOM | 114 | CG | TYR | 160 | 115.094 | 29.869 | 15.941 | 1.00 | 13.65 | A C |
| ATOM | 115 | CD1 | TYR | 160 | 113.717 | 30.089 | 15.993 | 1.00 | 16.07 | A C |
| ATOM | 116 | CE1 | TYR | 160 | 113.098 | 30.466 | 17.186 | 1.00 | 13.67 | A C |
| ATOM | 117 | CD2 | TYR | 160 | 115.828 | 30.038 | 17.116 | 1.00 | 11.30 | A C |
| ATOM | 118 | CE2 | TYR | 160 | 115.211 | 30.416 | 18.304 | 1.00 | 15.01 | A C |
| ATOM | 119 | CZ | TYR | 160 | 113.841 | 30.627 | 18.338 | 1.00 | 14.36 | A C |
| ATOM | 120 | OH | TYR | 160 | 113.227 | 30.987 | 19.522 | 1.00 | 19.36 | A O |
| ATOM | 121 | C | TYR | 160 | 117.498 | 31.264 | 14.734 | 1.00 | 33.39 | A C |
| ATOM | 122 | O | TYR | 160 | 118.567 | 30.703 | 14.970 | 1.00 | 39.31 | A O |
| ATOM | 123 | N | PRO | 161 | 117.206 | 32.467 | 15.248 | 1.00 | 31.87 | A N |
| ATOM | 124 | CD | PRO | 161 | 117.983 | 33.002 | 16.380 | 1.00 | 14.17 | A C |
| ATOM | 125 | CA | PRO | 161 | 115.969 | 33.234 | 15.055 | 1.00 | 30.15 | A C |
| ATOM | 126 | CB | PRO | 161 | 115.831 | 33.976 | 16.379 | 1.00 | 18.55 | A C |
| ATOM | 127 | CG | PRO | 161 | 117.278 | 34.291 | 16.703 | 1.00 | 21.71 | A C |
| ATOM | 128 | C | PRO | 161 | 116.038 | 34.183 | 13.852 | 1.00 | 28.81 | A C |
| ATOM | 129 | O | PRO | 161 | 117.074 | 34.792 | 13.580 | 1.00 | 28.13 | A O |
| ATOM | 130 | N | TRP | 162 | 114.919 | 34.320 | 13.149 | 1.00 | 29.23 | A N |
| ATOM | 131 | CA | TRP | 162 | 114.839 | 35.170 | 11.967 | 1.00 | 30.30 | A C |
| ATOM | 132 | CB | TRP | 162 | 113.368 | 35.250 | 11.493 | 1.00 | 29.17 | A C |
| ATOM | 133 | CG | TRP | 162 | 113.214 | 35.826 | 10.120 | 1.00 | 29.69 | A C |
| ATOM | 134 | CD2 | TRP | 162 | 113.838 | 35.375 | 8.912 | 1.00 | 24.53 | A C |
| ATOM | 135 | CE2 | TRP | 162 | 113.338 | 36.175 | 7.859 | 1.00 | 28.08 | A C |
| ATOM | 136 | CE3 | TRP | 162 | 114.768 | 34.373 | 8.615 | 1.00 | 23.94 | A C |
| ATOM | 137 | CD1 | TRP | 162 | 112.387 | 36.854 | 9.758 | 1.00 | 28.88 | A C |
| ATOM | 138 | NE1 | TRP | 162 | 112.455 | 37.071 | 8.403 | 1.00 | 30.75 | A N |
| ATOM | 139 | CZ2 | TRP | 162 | 113.741 | 36.000 | 6.532 | 1.00 | 26.62 | A C |
| ATOM | 140 | CZ3 | TRP | 162 | 115.167 | 34.202 | 7.288 | 1.00 | 22.27 | A C |
| ATOM | 141 | CH2 | TRP | 162 | 114.652 | 35.012 | 6.268 | 1.00 | 27.18 | A C |
| ATOM | 142 | C | TRP | 162 | 115.381 | 36.579 | 12.210 | 1.00 | 32.08 | A C |
| ATOM | 143 | O | TRP | 162 | 116.074 | 37.133 | 11.352 | 1.00 | 31.23 | A O |
| ATOM | 144 | N | GLU | 163 | 115.077 | 37.147 | 13.381 | 1.00 | 25.22 | A N |
| ATOM | 145 | CA | GLU | 163 | 115.510 | 38.504 | 13.734 | 1.00 | 27.00 | A C |
| ATOM | 146 | CB | GLU | 163 | 115.108 | 38.857 | 15.172 | 1.00 | 105.95 | A C |

Fig. 19: A-3

```
ATOM    147  CG   GLU  163    115.906  38.145  16.248  1.00  112.26  A  C
ATOM    148  CD   GLU  163    115.816  38.833  17.603  1.00  114.40  A  C
ATOM    149  OE1  GLU  163    116.310  39.975  17.732  1.00  116.11  A  O
ATOM    150  OE2  GLU  163    115.253  38.232  18.541  1.00  113.36  A  O
ATOM    151  C    GLU  163    117.008  38.723  13.557  1.00   26.66  A  C
ATOM    152  O    GLU  163    117.448  39.799  13.136  1.00   22.83  A  O
ATOM    153  N    SER  164    117.800  37.709  13.865  1.00   20.71  A  N
ATOM    154  CA   SER  164    119.241  37.850  13.715  1.00   17.90  A  C
ATOM    155  CB   SER  164    119.955  36.647  14.335  1.00   27.61  A  C
ATOM    156  OG   SER  164    119.716  36.582  15.731  1.00   33.50  A  O
ATOM    157  C    SER  164    119.601  37.988  12.235  1.00   18.66  A  C
ATOM    158  O    SER  164    120.436  38.813  11.863  1.00   21.86  A  O
ATOM    159  N    VAL  165    118.956  37.179  11.398  1.00    9.03  A  N
ATOM    160  CA   VAL  165    119.189  37.213   9.961  1.00    8.42  A  C
ATOM    161  CB   VAL  165    118.303  36.166   9.226  1.00   21.53  A  C
ATOM    162  CG1  VAL  165    118.296  36.430   7.721  1.00   22.92  A  C
ATOM    163  CG2  VAL  165    118.826  34.760   9.505  1.00   24.53  A  C
ATOM    164  C    VAL  165    118.873  38.595   9.411  1.00    9.58  A  C
ATOM    165  O    VAL  165    119.610  39.131   8.574  1.00   11.40  A  O
ATOM    166  N    ILE  166    117.772  39.169   9.887  1.00   17.73  A  N
ATOM    167  CA   ILE  166    117.351  40.482   9.427  1.00   17.05  A  C
ATOM    168  CB   ILE  166    115.903  40.763   9.840  1.00   21.02  A  C
ATOM    169  CG2  ILE  166    115.489  42.162   9.413  1.00   20.23  A  C
ATOM    170  CG1  ILE  166    114.997  39.737   9.164  1.00   20.88  A  C
ATOM    171  CD1  ILE  166    113.538  39.919   9.499  1.00   17.28  A  C
ATOM    172  C    ILE  166    118.281  41.564   9.929  1.00   16.50  A  C
ATOM    173  O    ILE  166    118.560  42.520   9.206  1.00   18.25  A  O
ATOM    174  N    ALA  167    118.774  41.413  11.157  1.00   25.46  A  N
ATOM    175  CA   ALA  167    119.711  42.391  11.710  1.00   26.06  A  C
ATOM    176  CB   ALA  167    120.095  42.021  13.100  1.00    7.73  A  C
ATOM    177  C    ALA  167    120.941  42.371  10.823  1.00   27.27  A  C
ATOM    178  O    ALA  167    121.546  43.414  10.544  1.00   23.87  A  O
ATOM    179  N    PHE  168    121.303  41.167  10.383  1.00   18.13  A  N
ATOM    180  CA   PHE  168    122.442  40.989   9.498  1.00   16.65  A  C
ATOM    181  CB   PHE  168    122.626  39.513   9.158  1.00   32.51  A  C
ATOM    182  CG   PHE  168    123.514  39.273   7.970  1.00   31.01  A  C
ATOM    183  CD1  PHE  168    122.968  39.066   6.701  1.00   32.61  A  C
ATOM    184  CD2  PHE  168    124.894  39.290   8.106  1.00   29.32  A  C
ATOM    185  CE1  PHE  168    123.792  38.882   5.585  1.00   31.09  A  C
ATOM    186  CE2  PHE  168    125.724  39.109   7.000  1.00   31.14  A  C
ATOM    187  CZ   PHE  168    125.173  38.906   5.738  1.00   33.63  A  C
ATOM    188  C    PHE  168    122.222  41.796   8.227  1.00   17.51  A  C
ATOM    189  O    PHE  168    123.139  42.475   7.750  1.00   13.95  A  O
ATOM    190  N    LEU  169    121.007  41.719   7.680  1.00   16.88  A  N
ATOM    191  CA   LEU  169    120.677  42.467   6.471  1.00   19.47  A  C
ATOM    192  CB   LEU  169    119.262  42.140   6.000  1.00   14.12  A  C
ATOM    193  CG   LEU  169    119.041  40.860   5.213  1.00   13.28  A  C
ATOM    194  CD1  LEU  169    117.662  40.952   4.603  1.00    9.74  A  C
ATOM    195  CD2  LEU  169    120.100  40.694   4.127  1.00   10.14  A  C
ATOM    196  C    LEU  169    120.777  43.966   6.731  1.00   21.77  A  C
ATOM    197  O    LEU  169    121.409  44.694   5.968  1.00   23.20  A  O
ATOM    198  N    ASN  170    120.150  44.419   7.815  1.00   20.45  A  N
ATOM    199  CA   ASN  170    120.159  45.832   8.175  1.00   17.58  A  C
ATOM    200  CB   ASN  170    119.534  46.018   9.562  1.00   31.53  A  C
ATOM    201  CG   ASN  170    119.017  47.426   9.791  1.00   34.95  A  C
ATOM    202  OD1  ASN  170    119.740  48.282  10.284  1.00   30.48  A  O
ATOM    203  ND2  ASN  170    117.762  47.671   9.421  1.00   32.86  A  N
ATOM    204  C    ASN  170    121.587  46.341   8.151  1.00   17.59  A  C
ATOM    205  O    ASN  170    121.941  47.174   7.321  1.00   17.80  A  O
ATOM    206  N    ASP  171    122.412  45.812   9.040  1.00   11.82  A  N
ATOM    207  CA   ASP  171    123.816  46.218   9.120  1.00   13.94  A  C
ATOM    208  CB   ASP  171    124.588  45.282  10.048  1.00   56.27  A  C
ATOM    209  CG   ASP  171    124.405  45.627  11.508  1.00   63.92  A  C
ATOM    210  OD1  ASP  171    123.248  45.689  11.971  1.00   66.14  A  O
ATOM    211  OD2  ASP  171    125.427  45.834  12.196  1.00   65.78  A  O
ATOM    212  C    ASP  171    124.509  46.244   7.760  1.00   15.43  A  C
ATOM    213  O    ASP  171    125.223  47.194   7.435  1.00   14.15  A  O
ATOM    214  N    LEU  172    124.289  45.200   6.966  1.00   15.45  A  N
ATOM    215  CA   LEU  172    124.910  45.099   5.650  1.00   16.13  A  C
ATOM    216  CB   LEU  172    124.633  43.717   5.047  1.00   10.67  A  C
ATOM    217  CG   LEU  172    125.667  43.058   4.123  1.00   10.16  A  C
ATOM    218  CD1  LEU  172    124.905  42.379   2.979  1.00    7.76  A  C
ATOM    219  CD2  LEU  172    126.672  44.070   3.594  1.00    8.33  A  C
```

Fig. 19: A-4

| | | | | | | | | | | |
|---|---|---|---|---|---|---|---|---|---|---|
| ATOM | 220 | C | LEU | 172 | 124.401 | 46.178 | 4.699 | 1.00 | 16.47 | A C |
| ATOM | 221 | O | LEU | 172 | 125.182 | 46.951 | 4.156 | 1.00 | 16.46 | A O |
| ATOM | 222 | N | LEU | 173 | 123.088 | 46.226 | 4.509 | 1.00 | 30.03 | A N |
| ATOM | 223 | CA | LEU | 173 | 122.475 | 47.193 | 3.609 | 1.00 | 32.78 | A C |
| ATOM | 224 | CB | LEU | 173 | 120.967 | 46.932 | 3.474 | 1.00 | 23.11 | A C |
| ATOM | 225 | CG | LEU | 173 | 120.357 | 45.803 | 2.627 | 1.00 | 24.46 | A C |
| ATOM | 226 | CD1 | LEU | 173 | 121.069 | 45.702 | 1.292 | 1.00 | 27.98 | A C |
| ATOM | 227 | CD2 | LEU | 173 | 120.456 | 44.501 | 3.353 | 1.00 | 25.01 | A C |
| ATOM | 228 | C | LEU | 173 | 122.675 | 48.663 | 3.984 | 1.00 | 34.21 | A C |
| ATOM | 229 | O | LEU | 173 | 122.937 | 49.495 | 3.105 | 1.00 | 30.93 | A C |
| ATOM | 230 | N | LYS | 174 | 122.558 | 48.989 | 5.271 | 1.00 | 33.34 | A N |
| ATOM | 231 | CA | LYS | 174 | 122.684 | 50.379 | 5.693 | 1.00 | 33.56 | A C |
| ATOM | 232 | CB | LYS | 174 | 122.428 | 50.508 | 7.193 | 1.00 | 32.34 | A C |
| ATOM | 233 | CG | LYS | 174 | 123.590 | 50.195 | 8.102 | 1.00 | 32.67 | A C |
| ATOM | 234 | CD | LYS | 174 | 123.170 | 50.471 | 9.551 | 1.00 | 31.92 | A C |
| ATOM | 235 | CE | LYS | 174 | 124.365 | 50.601 | 10.504 | 1.00 | 27.17 | A C |
| ATOM | 236 | NZ | LYS | 174 | 125.178 | 49.351 | 10.664 | 1.00 | 23.64 | A N |
| ATOM | 237 | C | LYS | 174 | 124.004 | 51.046 | 5.317 | 1.00 | 31.92 | A C |
| ATOM | 238 | O | LYS | 174 | 124.060 | 52.256 | 5.142 | 1.00 | 32.79 | A O |
| ATOM | 239 | N | ARG | 175 | 125.059 | 50.255 | 5.176 | 1.00 | 34.34 | A N |
| ATOM | 240 | CA | ARG | 175 | 126.385 | 50.759 | 4.797 | 1.00 | 36.57 | A C |
| ATOM | 241 | CB | ARG | 175 | 127.468 | 49.712 | 5.125 | 1.00 | 50.56 | A C |
| ATOM | 242 | CG | ARG | 175 | 127.708 | 49.400 | 6.606 | 1.00 | 57.49 | A C |
| ATOM | 243 | CD | ARG | 175 | 128.550 | 48.120 | 6.760 | 1.00 | 61.77 | A C |
| ATOM | 244 | NE | ARG | 175 | 129.398 | 48.107 | 7.957 | 1.00 | 66.67 | A N |
| ATOM | 245 | CZ | ARG | 175 | 128.954 | 48.049 | 9.211 | 1.00 | 70.25 | A C |
| ATOM | 246 | NH1 | ARG | 175 | 127.653 | 47.997 | 9.461 | 1.00 | 70.45 | A N |
| ATOM | 247 | NH2 | ARG | 175 | 129.819 | 48.039 | 10.219 | 1.00 | 71.15 | A N |
| ATOM | 248 | C | ARG | 175 | 126.461 | 51.051 | 3.288 | 1.00 | 34.10 | A C |
| ATOM | 249 | O | ARG | 175 | 127.487 | 51.522 | 2.796 | 1.00 | 33.94 | A O |
| ATOM | 250 | N | MET | 176 | 125.384 | 50.766 | 2.557 | 1.00 | 18.81 | A N |
| ATOM | 251 | CA | MET | 176 | 125.371 | 50.959 | 1.104 | 1.00 | 15.29 | A C |
| ATOM | 252 | CB | MET | 176 | 124.758 | 49.728 | 0.431 | 1.00 | 45.67 | A C |
| ATOM | 253 | CG | MET | 176 | 125.646 | 48.505 | 0.474 | 1.00 | 42.57 | A C |
| ATOM | 254 | SD | MET | 176 | 124.887 | 47.063 | -0.292 | 1.00 | 46.71 | A S |
| ATOM | 255 | CE | MET | 176 | 124.633 | 46.046 | 1.139 | 1.00 | 40.22 | A C |
| ATOM | 256 | C | MET | 176 | 124.679 | 52.199 | 0.546 | 1.00 | 18.80 | A C |
| ATOM | 257 | O | MET | 176 | 123.797 | 52.768 | 1.176 | 1.00 | 18.87 | A O |
| ATOM | 258 | N | ASP | 177 | 125.098 | 52.605 | -0.652 | 1.00 | 31.75 | A N |
| ATOM | 259 | CA | ASP | 177 | 124.504 | 53.744 | -1.344 | 1.00 | 34.24 | A C |
| ATOM | 260 | CB | ASP | 177 | 125.584 | 54.671 | -1.903 | 1.00 | 129.70 | A C |
| ATOM | 261 | CG | ASP | 177 | 126.196 | 55.556 | -0.838 | 1.00 | 132.65 | A C |
| ATOM | 262 | OD1 | ASP | 177 | 127.004 | 56.437 | -1.194 | 1.00 | 132.32 | A O |
| ATOM | 263 | OD2 | ASP | 177 | 125.869 | 55.372 | 0.354 | 1.00 | 134.30 | A O |
| ATOM | 264 | C | ASP | 177 | 123.638 | 53.207 | -2.480 | 1.00 | 34.16 | A C |
| ATOM | 265 | O | ASP | 177 | 124.085 | 53.107 | -3.617 | 1.00 | 33.88 | A O |
| ATOM | 266 | N | ILE | 178 | 122.402 | 52.848 | -2.153 | 1.00 | 22.62 | A N |
| ATOM | 267 | CA | ILE | 178 | 121.464 | 52.307 | -3.122 | 1.00 | 22.76 | A C |
| ATOM | 268 | CB | ILE | 178 | 120.326 | 51.524 | -2.407 | 1.00 | 26.30 | A C |
| ATOM | 269 | CG2 | ILE | 178 | 119.208 | 51.207 | -3.390 | 1.00 | 24.58 | A C |
| ATOM | 270 | CG1 | ILE | 178 | 120.866 | 50.222 | -1.803 | 1.00 | 27.36 | A C |
| ATOM | 271 | CD1 | ILE | 178 | 121.188 | 50.292 | -0.325 | 1.00 | 29.20 | A C |
| ATOM | 272 | C | ILE | 178 | 120.848 | 53.398 | -4.009 | 1.00 | 21.90 | A C |
| ATOM | 273 | O | ILE | 178 | 120.532 | 54.501 | -3.539 | 1.00 | 23.39 | A O |
| ATOM | 274 | N | GLY | 179 | 120.669 | 53.077 | -5.292 | 1.00 | 18.17 | A N |
| ATOM | 275 | CA | GLY | 179 | 120.091 | 54.029 | -6.226 | 1.00 | 17.89 | A C |
| ATOM | 276 | C | GLY | 179 | 120.123 | 53.536 | -7.658 | 1.00 | 18.65 | A C |
| ATOM | 277 | O | GLY | 179 | 121.019 | 52.786 | -8.023 | 1.00 | 16.80 | A O |
| ATOM | 278 | N | PRO | 180 | 119.150 | 53.937 | -8.498 | 1.00 | 18.34 | A N |
| ATOM | 279 | CD | PRO | 180 | 117.980 | 54.770 | -8.159 | 1.00 | 16.60 | A C |
| ATOM | 280 | CA | PRO | 180 | 119.094 | 53.512 | -9.901 | 1.00 | 19.40 | A C |
| ATOM | 281 | CB | PRO | 180 | 118.044 | 54.442 | -10.498 | 1.00 | 15.44 | A C |
| ATOM | 282 | CG | PRO | 180 | 117.074 | 54.573 | -9.365 | 1.00 | 17.83 | A C |
| ATOM | 283 | C | PRO | 180 | 120.432 | 53.622 | -10.597 | 1.00 | 21.18 | A C |
| ATOM | 284 | O | PRO | 180 | 120.706 | 52.877 | -11.529 | 1.00 | 21.82 | A O |
| ATOM | 285 | N | LYS | 181 | 121.262 | 54.553 | -10.139 | 1.00 | 25.85 | A N |
| ATOM | 286 | CA | LYS | 181 | 122.581 | 54.751 | -10.732 | 1.00 | 26.27 | A C |
| ATOM | 287 | CB | LYS | 181 | 122.737 | 56.167 | -11.253 | 1.00 | 26.21 | A C |
| ATOM | 288 | CG | LYS | 181 | 121.801 | 56.557 | -12.403 | 1.00 | 26.81 | A C |
| ATOM | 289 | CD | LYS | 181 | 122.014 | 55.683 | -13.627 | 1.00 | 25.67 | A C |
| ATOM | 290 | CE | LYS | 181 | 121.014 | 56.031 | -14.719 | 1.00 | 28.19 | A C |
| ATOM | 291 | NZ | LYS | 181 | 121.097 | 55.146 | -15.923 | 1.00 | 27.76 | A N |
| ATOM | 292 | C | LYS | 181 | 123.684 | 54.451 | -9.729 | 1.00 | 25.62 | A C |

Fig. 19: A-5

| ATOM | 293 | O | LYS | 181 | 124.854 | 54.742 | -9.975 | 1.00 | 23.94 | A | O |
|---|---|---|---|---|---|---|---|---|---|---|---|
| ATOM | 294 | N | GLN | 182 | 123.300 | 53.870 | -8.599 | 1.00 | 34.95 | A | N |
| ATOM | 295 | CA | GLN | 182 | 124.246 | 53.513 | -7.548 | 1.00 | 33.61 | A | C |
| ATOM | 296 | CB | GLN | 182 | 123.797 | 54.096 | -6.207 | 1.00 | 89.66 | A | C |
| ATOM | 297 | CG | GLN | 182 | 123.331 | 55.528 | -6.251 | 1.00 | 90.94 | A | C |
| ATOM | 298 | CD | GLN | 182 | 124.443 | 56.478 | -6.597 | 1.00 | 92.56 | A | C |
| ATOM | 299 | OE1 | GLN | 182 | 125.007 | 56.418 | -7.686 | 1.00 | 93.40 | A | O |
| ATOM | 300 | NE2 | GLN | 182 | 124.772 | 57.364 | -5.667 | 1.00 | 93.92 | A | N |
| ATOM | 301 | C | GLN | 182 | 124.258 | 51.991 | -7.439 | 1.00 | 32.52 | A | C |
| ATOM | 302 | O | GLN | 182 | 124.398 | 51.278 | -8.429 | 1.00 | 36.85 | A | O |
| ATOM | 303 | N | THR | 183 | 124.096 | 51.507 | -6.216 | 1.00 | 26.87 | A | N |
| ATOM | 304 | CA | THR | 183 | 124.052 | 50.083 | -5.953 | 1.00 | 23.79 | A | C |
| ATOM | 305 | CB | THR | 183 | 124.642 | 49.767 | -4.584 | 1.00 | 30.55 | A | C |
| ATOM | 306 | OG1 | THR | 183 | 125.983 | 50.262 | -4.526 | 1.00 | 27.00 | A | O |
| ATOM | 307 | CG2 | THR | 183 | 124.629 | 48.274 | -4.331 | 1.00 | 28.23 | A | C |
| ATOM | 308 | C | THR | 183 | 122.590 | 49.687 | -5.944 | 1.00 | 23.45 | A | C |
| ATOM | 309 | O | THR | 183 | 121.752 | 50.380 | -5.368 | 1.00 | 21.98 | A | O |
| ATOM | 310 | N | GLN | 184 | 122.269 | 48.592 | -6.608 | 1.00 | 25.73 | A | N |
| ATOM | 311 | CA | GLN | 184 | 120.897 | 48.127 | -6.612 | 1.00 | 21.38 | A | C |
| ATOM | 312 | CB | GLN | 184 | 120.399 | 47.898 | -8.042 | 1.00 | 35.06 | A | C |
| ATOM | 313 | CG | GLN | 184 | 120.016 | 49.181 | -8.770 | 1.00 | 34.81 | A | C |
| ATOM | 314 | CD | GLN | 184 | 118.982 | 48.942 | -9.856 | 1.00 | 34.28 | A | C |
| ATOM | 315 | OE1 | GLN | 184 | 119.215 | 48.164 | -10.781 | 1.00 | 29.98 | A | O |
| ATOM | 316 | NE2 | GLN | 184 | 117.834 | 49.604 | -9.748 | 1.00 | 32.58 | A | N |
| ATOM | 317 | C | GLN | 184 | 120.862 | 46.839 | -5.800 | 1.00 | 21.76 | A | C |
| ATOM | 318 | O | GLN | 184 | 121.832 | 46.067 | -5.780 | 1.00 | 19.15 | A | O |
| ATOM | 319 | N | VAL | 185 | 119.753 | 46.599 | -5.112 | 1.00 | 33.23 | A | N |
| ATOM | 320 | CA | VAL | 185 | 119.634 | 45.408 | -4.298 | 1.00 | 31.60 | A | C |
| ATOM | 321 | CB | VAL | 185 | 119.868 | 45.742 | -2.810 | 1.00 | 20.42 | A | C |
| ATOM | 322 | CG1 | VAL | 185 | 119.572 | 44.535 | -1.938 | 1.00 | 20.41 | A | C |
| ATOM | 323 | CG2 | VAL | 185 | 121.294 | 46.148 | -2.614 | 1.00 | 6.28 | A | C |
| ATOM | 324 | C | VAL | 185 | 118.297 | 44.701 | -4.445 | 1.00 | 32.19 | A | C |
| ATOM | 325 | O | VAL | 185 | 117.237 | 45.322 | -4.469 | 1.00 | 29.34 | A | O |
| ATOM | 326 | N | GLY | 186 | 118.369 | 43.382 | -4.554 | 1.00 | 17.76 | A | N |
| ATOM | 327 | CA | GLY | 186 | 117.177 | 42.573 | -4.672 | 1.00 | 19.39 | A | C |
| ATOM | 328 | C | GLY | 186 | 117.355 | 41.424 | -3.711 | 1.00 | 17.37 | A | C |
| ATOM | 329 | O | GLY | 186 | 118.470 | 40.929 | -3.543 | 1.00 | 22.73 | A | O |
| ATOM | 330 | N | ILE | 187 | 116.278 | 40.995 | -3.073 | 1.00 | 15.41 | A | N |
| ATOM | 331 | CA | ILE | 187 | 116.395 | 39.906 | -2.133 | 1.00 | 14.00 | A | C |
| ATOM | 332 | CB | ILE | 187 | 116.117 | 40.403 | -0.675 | 1.00 | 10.12 | A | C |
| ATOM | 333 | CG2 | ILE | 187 | 116.053 | 39.225 | 0.299 | 1.00 | 7.45 | A | C |
| ATOM | 334 | CG1 | ILE | 187 | 117.232 | 41.364 | -0.253 | 1.00 | 10.64 | A | C |
| ATOM | 335 | CD1 | ILE | 187 | 117.156 | 41.817 | 1.176 | 1.00 | 11.59 | A | C |
| ATOM | 336 | C | ILE | 187 | 115.496 | 38.731 | -2.485 | 1.00 | 13.29 | A | C |
| ATOM | 337 | O | ILE | 187 | 114.301 | 38.896 | -2.768 | 1.00 | 12.19 | A | O |
| ATOM | 338 | N | VAL | 188 | 116.097 | 37.546 | -2.473 | 1.00 | 16.67 | A | N |
| ATOM | 339 | CA | VAL | 188 | 115.403 | 36.303 | -2.769 | 1.00 | 16.34 | A | C |
| ATOM | 340 | CB | VAL | 188 | 116.082 | 35.567 | -3.951 | 1.00 | 11.96 | A | C |
| ATOM | 341 | CG1 | VAL | 188 | 115.642 | 34.122 | -3.993 | 1.00 | 7.23 | A | C |
| ATOM | 342 | CG2 | VAL | 188 | 115.742 | 36.251 | -5.248 | 1.00 | 12.38 | A | C |
| ATOM | 343 | C | VAL | 188 | 115.464 | 35.404 | -1.536 | 1.00 | 14.88 | A | C |
| ATOM | 344 | O | VAL | 188 | 116.509 | 35.286 | -0.895 | 1.00 | 14.29 | A | O |
| ATOM | 345 | N | GLN | 189 | 114.348 | 34.774 | -1.194 | 1.00 | 30.23 | A | N |
| ATOM | 346 | CA | GLN | 189 | 114.335 | 33.873 | -0.049 | 1.00 | 29.91 | A | C |
| ATOM | 347 | CB | GLN | 189 | 113.374 | 34.363 | 1.039 | 1.00 | 26.02 | A | C |
| ATOM | 348 | CG | GLN | 189 | 113.277 | 33.399 | 2.210 | 1.00 | 23.53 | A | C |
| ATOM | 349 | CD | GLN | 189 | 112.257 | 33.807 | 3.267 | 1.00 | 24.24 | A | C |
| ATOM | 350 | OE1 | GLN | 189 | 111.891 | 32.998 | 4.125 | 1.00 | 25.46 | A | O |
| ATOM | 351 | NE2 | GLN | 189 | 111.800 | 35.058 | 3.219 | 1.00 | 25.28 | A | N |
| ATOM | 352 | C | GLN | 189 | 113.911 | 32.490 | -0.520 | 1.00 | 25.90 | A | C |
| ATOM | 353 | O | GLN | 189 | 113.056 | 32.366 | -1.401 | 1.00 | 25.26 | A | O |
| ATOM | 354 | N | TYR | 190 | 114.516 | 31.455 | 0.063 | 1.00 | 12.87 | A | N |
| ATOM | 355 | CA | TYR | 190 | 114.196 | 30.084 | -0.310 | 1.00 | 16.39 | A | C |
| ATOM | 356 | CB | TYR | 190 | 115.267 | 29.539 | -1.257 | 1.00 | 17.86 | A | C |
| ATOM | 357 | CG | TYR | 190 | 116.599 | 29.241 | -0.590 | 1.00 | 13.63 | A | C |
| ATOM | 358 | CD1 | TYR | 190 | 116.887 | 27.963 | -0.092 | 1.00 | 13.63 | A | C |
| ATOM | 359 | CE1 | TYR | 190 | 118.104 | 27.687 | 0.517 | 1.00 | 13.63 | A | C |
| ATOM | 360 | CD2 | TYR | 190 | 117.569 | 30.233 | -0.453 | 1.00 | 13.63 | A | C |
| ATOM | 361 | CE2 | TYR | 190 | 118.787 | 29.968 | 0.159 | 1.00 | 13.63 | A | C |
| ATOM | 362 | CZ | TYR | 190 | 119.053 | 28.698 | 0.640 | 1.00 | 13.63 | A | C |
| ATOM | 363 | OH | TYR | 190 | 120.278 | 28.442 | 1.228 | 1.00 | 13.63 | A | O |
| ATOM | 364 | C | TYR | 190 | 114.035 | 29.135 | 0.878 | 1.00 | 18.24 | A | C |
| ATOM | 365 | O | TYR | 190 | 114.456 | 29.424 | 2.003 | 1.00 | 18.32 | A | O |

Fig. 19: A-6

| | | | | | | | | | | |
|---|---|---|---|---|---|---|---|---|---|---|
| ATOM | 366 | N | GLY | 191 | 113.417 | 27.994 | 0.588 | 1.00 | 15.40 | A N |
| ATOM | 367 | CA | GLY | 191 | 113.171 | 26.954 | 1.572 | 1.00 | 13.15 | A C |
| ATOM | 368 | C | GLY | 191 | 112.683 | 25.776 | 0.764 | 1.00 | 14.59 | A C |
| ATOM | 369 | O | GLY | 191 | 113.482 | 25.084 | 0.139 | 1.00 | 17.97 | A O |
| ATOM | 370 | N | GLU | 192 | 111.371 | 25.552 | 0.769 | 1.00 | 27.03 | A N |
| ATOM | 371 | CA | GLU | 192 | 110.764 | 24.475 | -0.020 | 1.00 | 29.04 | A C |
| ATOM | 372 | CB | GLU | 192 | 109.400 | 24.089 | 0.537 | 1.00 | 28.96 | A C |
| ATOM | 373 | CG | GLU | 192 | 109.412 | 23.507 | 1.929 | 1.00 | 29.34 | A C |
| ATOM | 374 | CD | GLU | 192 | 108.020 | 23.089 | 2.390 | 1.00 | 29.53 | A C |
| ATOM | 375 | OE1 | GLU | 192 | 107.890 | 22.532 | 3.505 | 1.00 | 32.42 | A O |
| ATOM | 376 | OE2 | GLU | 192 | 107.051 | 23.322 | 1.633 | 1.00 | 27.40 | A O |
| ATOM | 377 | C | GLU | 192 | 110.562 | 25.062 | -1.410 | 1.00 | 28.85 | A C |
| ATOM | 378 | O | GLU | 192 | 110.692 | 24.380 | -2.422 | 1.00 | 30.22 | A O |
| ATOM | 379 | N | ASN | 193 | 110.236 | 26.350 | -1.433 | 1.00 | 34.68 | A N |
| ATOM | 380 | CA | ASN | 193 | 110.019 | 27.088 | -2.668 | 1.00 | 35.89 | A C |
| ATOM | 381 | CB | ASN | 193 | 108.566 | 27.527 | -2.769 | 1.00 | 60.91 | A C |
| ATOM | 382 | CG | ASN | 193 | 107.606 | 26.388 | -2.564 | 1.00 | 64.08 | A C |
| ATOM | 383 | OD1 | ASN | 193 | 107.545 | 25.804 | -1.488 | 1.00 | 68.19 | A O |
| ATOM | 384 | ND2 | ASN | 193 | 106.849 | 26.058 | -3.601 | 1.00 | 66.19 | A N |
| ATOM | 385 | C | ASN | 193 | 110.910 | 28.315 | -2.640 | 1.00 | 34.07 | A C |
| ATOM | 386 | O | ASN | 193 | 111.759 | 28.459 | -1.760 | 1.00 | 35.07 | A O |
| ATOM | 387 | N | VAL | 194 | 110.712 | 29.206 | -3.598 | 1.00 | 31.94 | A N |
| ATOM | 388 | CA | VAL | 194 | 111.511 | 30.423 | -3.660 | 1.00 | 34.28 | A C |
| ATOM | 389 | CB | VAL | 194 | 112.524 | 30.365 | -4.803 | 1.00 | 32.89 | A C |
| ATOM | 390 | CG1 | VAL | 194 | 113.514 | 31.495 | -4.671 | 1.00 | 33.92 | A C |
| ATOM | 391 | CG2 | VAL | 194 | 113.227 | 29.036 | -4.799 | 1.00 | 30.16 | A C |
| ATOM | 392 | C | VAL | 194 | 110.601 | 31.608 | -3.914 | 1.00 | 32.05 | A C |
| ATOM | 393 | O | VAL | 194 | 109.651 | 31.507 | -4.688 | 1.00 | 30.17 | A O |
| ATOM | 394 | N | THR | 195 | 110.877 | 32.730 | -3.261 | 1.00 | 26.46 | A N |
| ATOM | 395 | CA | THR | 195 | 110.058 | 33.915 | -3.474 | 1.00 | 27.64 | A C |
| ATOM | 396 | CB | THR | 195 | 109.050 | 34.135 | -2.307 | 1.00 | 36.45 | A C |
| ATOM | 397 | OG1 | THR | 195 | 109.728 | 34.654 | -1.163 | 1.00 | 40.46 | A O |
| ATOM | 398 | CG2 | THR | 195 | 108.396 | 32.820 | -1.918 | 1.00 | 38.08 | A C |
| ATOM | 399 | C | THR | 195 | 110.927 | 35.161 | -3.656 | 1.00 | 28.48 | A C |
| ATOM | 400 | O | THR | 195 | 111.977 | 35.309 | -3.032 | 1.00 | 31.07 | A O |
| ATOM | 401 | N | HIS | 196 | 110.492 | 36.040 | -4.545 | 1.00 | 36.83 | A N |
| ATOM | 402 | CA | HIS | 196 | 111.196 | 37.261 | -4.819 | 1.00 | 36.93 | A C |
| ATOM | 403 | CB | HIS | 196 | 110.843 | 37.772 | -6.225 | 1.00 | 33.18 | A C |
| ATOM | 404 | CG | HIS | 196 | 111.434 | 36.951 | -7.326 | 1.00 | 29.68 | A C |
| ATOM | 405 | CD2 | HIS | 196 | 110.933 | 35.910 | -8.032 | 1.00 | 30.31 | A C |
| ATOM | 406 | ND1 | HIS | 196 | 112.707 | 37.169 | -7.813 | 1.00 | 28.33 | A N |
| ATOM | 407 | CE1 | HIS | 196 | 112.965 | 36.296 | -8.772 | 1.00 | 25.05 | A C |
| ATOM | 408 | NE2 | HIS | 196 | 111.905 | 35.521 | -8.924 | 1.00 | 23.26 | A N |
| ATOM | 409 | C | HIS | 196 | 110.730 | 38.315 | -3.802 | 1.00 | 36.79 | A C |
| ATOM | 410 | O | HIS | 196 | 109.687 | 38.933 | -3.997 | 1.00 | 35.45 | A O |
| ATOM | 411 | N | GLU | 197 | 111.480 | 38.508 | -2.721 | 1.00 | 21.51 | A N |
| ATOM | 412 | CA | GLU | 197 | 111.069 | 39.488 | -1.732 | 1.00 | 18.84 | A C |
| ATOM | 413 | CB | GLU | 197 | 112.091 | 39.588 | -0.604 | 1.00 | 43.52 | A C |
| ATOM | 414 | CG | GLU | 197 | 112.094 | 38.384 | 0.339 | 1.00 | 43.86 | A C |
| ATOM | 415 | CD | GLU | 197 | 110.717 | 38.043 | 0.882 | 1.00 | 42.93 | A C |
| ATOM | 416 | OE1 | GLU | 197 | 109.909 | 38.967 | 1.100 | 1.00 | 41.51 | A O |
| ATOM | 417 | OE2 | GLU | 197 | 110.444 | 36.847 | 1.111 | 1.00 | 44.59 | A O |
| ATOM | 418 | C | GLU | 197 | 110.882 | 40.832 | -2.442 | 1.00 | 16.31 | A C |
| ATOM | 419 | O | GLU | 197 | 109.802 | 41.419 | -2.403 | 1.00 | 21.51 | A O |
| ATOM | 420 | N | PHE | 198 | 111.921 | 41.325 | -3.098 | 1.00 | 11.53 | A N |
| ATOM | 421 | CA | PHE | 198 | 111.786 | 42.562 | -3.845 | 1.00 | 13.33 | A C |
| ATOM | 422 | CB | PHE | 198 | 111.803 | 43.785 | -2.901 | 1.00 | 15.90 | A C |
| ATOM | 423 | CG | PHE | 198 | 113.092 | 44.003 | -2.153 | 1.00 | 14.15 | A C |
| ATOM | 424 | CD1 | PHE | 198 | 114.262 | 44.390 | -2.823 | 1.00 | 20.29 | A C |
| ATOM | 425 | CD2 | PHE | 198 | 113.115 | 43.912 | -0.756 | 1.00 | 10.34 | A C |
| ATOM | 426 | CE1 | PHE | 198 | 115.427 | 44.685 | -2.113 | 1.00 | 16.32 | A C |
| ATOM | 427 | CE2 | PHE | 198 | 114.274 | 44.208 | -0.039 | 1.00 | 14.80 | A C |
| ATOM | 428 | CZ | PHE | 198 | 115.431 | 44.594 | -0.719 | 1.00 | 18.60 | A C |
| ATOM | 429 | C | PHE | 198 | 112.829 | 42.652 | -4.956 | 1.00 | 16.01 | A C |
| ATOM | 430 | O | PHE | 198 | 113.974 | 42.239 | -4.771 | 1.00 | 17.30 | A O |
| ATOM | 431 | N | ASN | 199 | 112.418 | 43.152 | -6.123 | 1.00 | 19.42 | A N |
| ATOM | 432 | CA | ASN | 199 | 113.321 | 43.265 | -7.276 | 1.00 | 19.71 | A C |
| ATOM | 433 | CB | ASN | 199 | 112.540 | 43.562 | -8.548 | 1.00 | 30.06 | A C |
| ATOM | 434 | CG | ASN | 199 | 111.465 | 42.548 | -8.824 | 1.00 | 31.32 | A C |
| ATOM | 435 | OD1 | ASN | 199 | 111.726 | 41.350 | -8.934 | 1.00 | 32.85 | A O |
| ATOM | 436 | ND2 | ASN | 199 | 110.236 | 43.029 | -8.948 | 1.00 | 30.20 | A N |
| ATOM | 437 | C | ASN | 199 | 114.458 | 44.288 | -7.173 | 1.00 | 22.17 | A C |
| ATOM | 438 | O | ASN | 199 | 114.430 | 45.215 | -6.351 | 1.00 | 19.98 | A O |

Fig. 19: A-7

| | | | | | | | | | | | |
|---|---|---|---|---|---|---|---|---|---|---|---|
| ATOM | 439 | N | LEU | 200 | 115.445 | 44.107 | -8.044 | 1.00 | 18.99 | A | N |
| ATOM | 440 | CA | LEU | 200 | 116.619 | 44.958 | -8.078 | 1.00 | 20.95 | A | C |
| ATOM | 441 | CB | LEU | 200 | 117.556 | 44.524 | -9.212 | 1.00 | 24.87 | A | C |
| ATOM | 442 | CG | LEU | 200 | 118.631 | 43.490 | -8.869 | 1.00 | 22.72 | A | C |
| ATOM | 443 | CD1 | LEU | 200 | 119.348 | 43.048 | -10.130 | 1.00 | 27.84 | A | C |
| ATOM | 444 | CD2 | LEU | 200 | 119.617 | 44.089 | -7.869 | 1.00 | 23.89 | A | C |
| ATOM | 445 | C | LEU | 200 | 116.282 | 46.415 | -8.246 | 1.00 | 21.35 | A | C |
| ATOM | 446 | O | LEU | 200 | 116.960 | 47.274 | -7.688 | 1.00 | 22.37 | A | O |
| ATOM | 447 | N | ASN | 201 | 115.231 | 46.691 | -9.011 | 1.00 | 18.94 | A | N |
| ATOM | 448 | CA | ASN | 201 | 114.816 | 48.061 | -9.284 | 1.00 | 20.79 | A | C |
| ATOM | 449 | CB | ASN | 201 | 114.546 | 48.208 | -10.773 | 1.00 | 21.69 | A | C |
| ATOM | 450 | CG | ASN | 201 | 113.401 | 47.336 | -11.236 | 1.00 | 23.97 | A | C |
| ATOM | 451 | OD1 | ASN | 201 | 113.119 | 47.246 | -12.424 | 1.00 | 24.11 | A | O |
| ATOM | 452 | ND2 | ASN | 201 | 112.727 | 46.684 | -10.292 | 1.00 | 21.81 | A | N |
| ATOM | 453 | C | ASN | 201 | 113.572 | 48.510 | -8.509 | 1.00 | 20.84 | A | C |
| ATOM | 454 | O | ASN | 201 | 112.969 | 49.522 | -8.851 | 1.00 | 16.74 | A | O |
| ATOM | 455 | N | LYS | 202 | 113.182 | 47.770 | -7.477 | 1.00 | 23.30 | A | N |
| ATOM | 456 | CA | LYS | 202 | 111.998 | 48.137 | -6.710 | 1.00 | 23.42 | A | C |
| ATOM | 457 | CB | LYS | 202 | 111.621 | 47.022 | -5.741 | 1.00 | 34.18 | A | C |
| ATOM | 458 | CG | LYS | 202 | 110.337 | 47.265 | -4.944 | 1.00 | 35.72 | A | C |
| ATOM | 459 | CD | LYS | 202 | 109.099 | 47.092 | -5.803 | 1.00 | 37.63 | A | C |
| ATOM | 460 | CE | LYS | 202 | 109.162 | 45.813 | -6.678 | 1.00 | 43.38 | A | C |
| ATOM | 461 | NZ | LYS | 202 | 109.316 | 44.491 | -5.962 | 1.00 | 42.40 | A | N |
| ATOM | 462 | C | LYS | 202 | 112.188 | 49.428 | -5.930 | 1.00 | 22.29 | A | C |
| ATOM | 463 | O | LYS | 202 | 111.338 | 50.313 | -5.984 | 1.00 | 19.57 | A | O |
| ATOM | 464 | N | TYR | 203 | 113.292 | 49.538 | -5.203 | 1.00 | 24.72 | A | N |
| ATOM | 465 | CA | TYR | 203 | 113.538 | 50.731 | -4.407 | 1.00 | 24.40 | A | C |
| ATOM | 466 | CB | TYR | 203 | 113.769 | 50.348 | -2.942 | 1.00 | 32.57 | A | C |
| ATOM | 467 | CG | TYR | 203 | 112.679 | 49.461 | -2.396 | 1.00 | 31.24 | A | C |
| ATOM | 468 | CD1 | TYR | 203 | 112.869 | 48.086 | -2.282 | 1.00 | 31.85 | A | C |
| ATOM | 469 | CE1 | TYR | 203 | 111.842 | 47.251 | -1.844 | 1.00 | 28.32 | A | C |
| ATOM | 470 | CD2 | TYR | 203 | 111.427 | 49.986 | -2.050 | 1.00 | 34.13 | A | C |
| ATOM | 471 | CE2 | TYR | 203 | 110.393 | 49.161 | -1.611 | 1.00 | 36.88 | A | C |
| ATOM | 472 | CZ | TYR | 203 | 110.607 | 47.794 | -1.512 | 1.00 | 36.50 | A | C |
| ATOM | 473 | OH | TYR | 203 | 109.590 | 46.962 | -1.095 | 1.00 | 41.50 | A | O |
| ATOM | 474 | C | TYR | 203 | 114.713 | 51.541 | -4.938 | 1.00 | 25.04 | A | C |
| ATOM | 475 | O | TYR | 203 | 115.755 | 50.986 | -5.280 | 1.00 | 23.21 | A | O |
| ATOM | 476 | N | SER | 204 | 114.536 | 52.861 | -4.998 | 1.00 | 28.94 | A | N |
| ATOM | 477 | CA | SER | 204 | 115.557 | 53.764 | -5.513 | 1.00 | 30.79 | A | C |
| ATOM | 478 | CB | SER | 204 | 114.892 | 54.863 | -6.338 | 1.00 | 29.83 | A | C |
| ATOM | 479 | OG | SER | 204 | 113.945 | 55.577 | -5.558 | 1.00 | 31.66 | A | O |
| ATOM | 480 | C | SER | 204 | 116.372 | 54.402 | -4.412 | 1.00 | 33.37 | A | C |
| ATOM | 481 | O | SER | 204 | 117.247 | 55.214 | -4.680 | 1.00 | 33.88 | A | O |
| ATOM | 482 | N | SER | 205 | 116.089 | 54.027 | -3.173 | 1.00 | 27.33 | A | N |
| ATOM | 483 | CA | SER | 205 | 116.787 | 54.615 | -2.048 | 1.00 | 26.99 | A | C |
| ATOM | 484 | CB | SER | 205 | 115.874 | 55.628 | -1.378 | 1.00 | 50.70 | A | C |
| ATOM | 485 | OG | SER | 205 | 116.409 | 56.032 | -0.137 | 1.00 | 56.19 | A | O |
| ATOM | 486 | C | SER | 205 | 117.251 | 53.608 | -1.016 | 1.00 | 25.12 | A | C |
| ATOM | 487 | O | SER | 205 | 116.650 | 52.551 | -0.857 | 1.00 | 21.38 | A | O |
| ATOM | 488 | N | THR | 206 | 118.318 | 53.949 | -0.301 | 1.00 | 23.44 | A | N |
| ATOM | 489 | CA | THR | 206 | 118.854 | 53.075 | 0.735 | 1.00 | 24.79 | A | C |
| ATOM | 490 | CB | THR | 206 | 120.176 | 53.614 | 1.286 | 1.00 | 12.85 | A | C |
| ATOM | 491 | OG1 | THR | 206 | 121.137 | 53.683 | 0.227 | 1.00 | 11.66 | A | O |
| ATOM | 492 | CG2 | THR | 206 | 120.696 | 52.712 | 2.392 | 1.00 | 11.22 | A | C |
| ATOM | 493 | C | THR | 206 | 117.889 | 52.879 | 1.900 | 1.00 | 25.38 | A | C |
| ATOM | 494 | O | THR | 206 | 117.798 | 51.785 | 2.447 | 1.00 | 28.17 | A | O |
| ATOM | 495 | N | GLU | 207 | 117.173 | 53.926 | 2.299 | 1.00 | 23.18 | A | N |
| ATOM | 496 | CA | GLU | 207 | 116.238 | 53.746 | 3.394 | 1.00 | 22.34 | A | C |
| ATOM | 497 | CB | GLU | 207 | 115.800 | 55.083 | 3.986 | 1.00 | 114.79 | A | C |
| ATOM | 498 | CG | GLU | 207 | 115.317 | 56.095 | 2.992 | 1.00 | 115.51 | A | C |
| ATOM | 499 | CD | GLU | 207 | 114.757 | 57.325 | 3.675 | 1.00 | 116.92 | A | C |
| ATOM | 500 | OE1 | GLU | 207 | 115.428 | 57.857 | 4.587 | 1.00 | 116.15 | A | O |
| ATOM | 501 | OE2 | GLU | 207 | 113.648 | 57.761 | 3.302 | 1.00 | 115.82 | A | O |
| ATOM | 502 | C | GLU | 207 | 115.038 | 52.937 | 2.908 | 1.00 | 22.84 | A | C |
| ATOM | 503 | O | GLU | 207 | 114.515 | 52.094 | 3.640 | 1.00 | 22.79 | A | O |
| ATOM | 504 | N | GLU | 208 | 114.614 | 53.163 | 1.668 | 1.00 | 31.71 | A | N |
| ATOM | 505 | CA | GLU | 208 | 113.485 | 52.412 | 1.126 | 1.00 | 33.44 | A | C |
| ATOM | 506 | CB | GLU | 208 | 113.168 | 52.841 | -0.308 | 1.00 | 38.62 | A | C |
| ATOM | 507 | CG | GLU | 208 | 112.661 | 54.265 | -0.441 | 1.00 | 36.09 | A | C |
| ATOM | 508 | CD | GLU | 208 | 112.288 | 54.633 | -1.875 | 1.00 | 35.61 | A | C |
| ATOM | 509 | OE1 | GLU | 208 | 111.943 | 55.811 | -2.111 | 1.00 | 41.38 | A | O |
| ATOM | 510 | OE2 | GLU | 208 | 112.338 | 53.757 | -2.767 | 1.00 | 34.33 | A | O |
| ATOM | 511 | C | GLU | 208 | 113.808 | 50.920 | 1.148 | 1.00 | 34.14 | A | C |

Fig. 19: A-8

| | | | | | | | | | | | |
|---|---|---|---|---|---|---|---|---|---|---|---|
| ATOM | 512 | O | GLU | 208 | 112.942 | 50.093 | 1.426 | 1.00 | 35.14 | A | O |
| ATOM | 513 | N | VAL | 209 | 115.057 | 50.575 | 0.855 | 1.00 | 17.60 | A | N |
| ATOM | 514 | CA | VAL | 209 | 115.472 | 49.180 | 0.853 | 1.00 | 16.52 | A | C |
| ATOM | 515 | CB | VAL | 209 | 116.790 | 48.982 | 0.077 | 1.00 | 10.63 | A | C |
| ATOM | 516 | CG1 | VAL | 209 | 117.501 | 47.719 | 0.538 | 1.00 | 10.96 | A | C |
| ATOM | 517 | CG2 | VAL | 209 | 116.491 | 48.889 | -1.398 | 1.00 | 11.65 | A | C |
| ATOM | 518 | C | VAL | 209 | 115.656 | 48.691 | 2.276 | 1.00 | 14.54 | A | C |
| ATOM | 519 | O | VAL | 209 | 115.278 | 47.558 | 2.596 | 1.00 | 13.50 | A | O |
| ATOM | 520 | N | LEU | 210 | 116.230 | 49.548 | 3.123 | 1.00 | 19.45 | A | N |
| ATOM | 521 | CA | LEU | 210 | 116.459 | 49.205 | 4.521 | 1.00 | 19.78 | A | C |
| ATOM | 522 | CB | LEU | 210 | 117.148 | 50.354 | 5.242 | 1.00 | 21.61 | A | C |
| ATOM | 523 | CG | LEU | 210 | 118.589 | 50.100 | 5.683 | 1.00 | 21.85 | A | C |
| ATOM | 524 | CD1 | LEU | 210 | 119.093 | 51.347 | 6.358 | 1.00 | 18.40 | A | C |
| ATOM | 525 | CD2 | LEU | 210 | 118.687 | 48.916 | 6.632 | 1.00 | 15.30 | A | C |
| ATOM | 526 | C | LEU | 210 | 115.148 | 48.894 | 5.223 | 1.00 | 18.04 | A | C |
| ATOM | 527 | O | LEU | 210 | 115.078 | 48.022 | 6.093 | 1.00 | 18.81 | A | O |
| ATOM | 528 | N | VAL | 211 | 114.107 | 49.618 | 4.839 | 1.00 | 25.49 | A | N |
| ATOM | 529 | CA | VAL | 211 | 112.798 | 49.443 | 5.432 | 1.00 | 25.25 | A | C |
| ATOM | 530 | CB | VAL | 211 | 111.916 | 50.685 | 5.175 | 1.00 | 19.83 | A | C |
| ATOM | 531 | CG1 | VAL | 211 | 110.457 | 50.391 | 5.537 | 1.00 | 22.01 | A | C |
| ATOM | 532 | CG2 | VAL | 211 | 112.446 | 51.859 | 5.989 | 1.00 | 20.44 | A | C |
| ATOM | 533 | C | VAL | 211 | 112.107 | 48.214 | 4.871 | 1.00 | 24.50 | A | C |
| ATOM | 534 | O | VAL | 211 | 111.437 | 47.483 | 5.593 | 1.00 | 25.18 | A | O |
| ATOM | 535 | N | ALA | 212 | 112.262 | 47.986 | 3.577 | 1.00 | 29.23 | A | N |
| ATOM | 536 | CA | ALA | 212 | 111.624 | 46.839 | 2.964 | 1.00 | 28.21 | A | C |
| ATOM | 537 | CB | ALA | 212 | 111.725 | 46.935 | 1.439 | 1.00 | 1.87 | A | C |
| ATOM | 538 | C | ALA | 212 | 112.275 | 45.559 | 3.465 | 1.00 | 26.02 | A | C |
| ATOM | 539 | O | ALA | 212 | 111.603 | 44.543 | 3.657 | 1.00 | 25.96 | A | O |
| ATOM | 540 | N | ALA | 213 | 113.587 | 45.618 | 3.680 | 1.00 | 33.07 | A | N |
| ATOM | 541 | CA | ALA | 213 | 114.339 | 44.464 | 4.147 | 1.00 | 34.24 | A | C |
| ATOM | 542 | CB | ALA | 213 | 115.803 | 44.787 | 4.176 | 1.00 | 20.72 | A | C |
| ATOM | 543 | C | ALA | 213 | 113.875 | 44.011 | 5.522 | 1.00 | 33.04 | A | C |
| ATOM | 544 | O | ALA | 213 | 113.659 | 42.824 | 5.746 | 1.00 | 30.67 | A | O |
| ATOM | 545 | N | ASN | 214 | 113.723 | 44.952 | 6.446 | 1.00 | 10.19 | A | N |
| ATOM | 546 | CA | ASN | 214 | 113.268 | 44.608 | 7.788 | 1.00 | 14.06 | A | C |
| ATOM | 547 | CB | ASN | 214 | 113.357 | 45.817 | 8.713 | 1.00 | 18.34 | A | C |
| ATOM | 548 | CG | ASN | 214 | 114.763 | 46.094 | 9.158 | 1.00 | 20.07 | A | C |
| ATOM | 549 | OD1 | ASN | 214 | 115.597 | 46.563 | 8.377 | 1.00 | 22.00 | A | O |
| ATOM | 550 | ND2 | ASN | 214 | 115.045 | 45.794 | 10.425 | 1.00 | 20.49 | A | N |
| ATOM | 551 | C | ASN | 214 | 111.847 | 44.081 | 7.828 | 1.00 | 16.45 | A | C |
| ATOM | 552 | O | ASN | 214 | 111.448 | 43.500 | 8.825 | 1.00 | 17.17 | A | O |
| ATOM | 553 | N | LYS | 215 | 111.080 | 44.289 | 6.764 | 1.00 | 16.88 | A | N |
| ATOM | 554 | CA | LYS | 215 | 109.705 | 43.817 | 6.744 | 1.00 | 17.32 | A | C |
| ATOM | 555 | CB | LYS | 215 | 108.804 | 44.772 | 5.926 | 1.00 | 20.45 | A | C |
| ATOM | 556 | CG | LYS | 215 | 108.670 | 46.176 | 6.531 | 1.00 | 28.03 | A | C |
| ATOM | 557 | CD | LYS | 215 | 107.387 | 46.902 | 6.115 | 1.00 | 31.57 | A | C |
| ATOM | 558 | CE | LYS | 215 | 107.304 | 47.155 | 4.607 | 1.00 | 35.03 | A | C |
| ATOM | 559 | NZ | LYS | 215 | 106.135 | 48.007 | 4.237 | 1.00 | 36.02 | A | N |
| ATOM | 560 | C | LYS | 215 | 109.617 | 42.399 | 6.193 | 1.00 | 15.45 | A | C |
| ATOM | 561 | O | LYS | 215 | 108.529 | 41.825 | 6.124 | 1.00 | 16.67 | A | O |
| ATOM | 562 | N | ILE | 216 | 110.757 | 41.824 | 5.812 | 1.00 | 28.84 | A | N |
| ATOM | 563 | CA | ILE | 216 | 110.754 | 40.475 | 5.262 | 1.00 | 25.66 | A | C |
| ATOM | 564 | CB | ILE | 216 | 112.088 | 40.123 | 4.594 | 1.00 | 13.08 | A | C |
| ATOM | 565 | CG2 | ILE | 216 | 112.088 | 38.681 | 4.163 | 1.00 | 9.86 | A | C |
| ATOM | 566 | CG1 | ILE | 216 | 112.298 | 41.002 | 3.362 | 1.00 | 9.76 | A | C |
| ATOM | 567 | CD1 | ILE | 216 | 113.597 | 40.713 | 2.626 | 1.00 | 6.72 | A | C |
| ATOM | 568 | C | ILE | 216 | 110.459 | 39.445 | 6.333 | 1.00 | 24.10 | A | C |
| ATOM | 569 | O | ILE | 216 | 111.076 | 39.441 | 7.404 | 1.00 | 24.80 | A | O |
| ATOM | 570 | N | VAL | 217 | 109.503 | 38.574 | 6.017 | 1.00 | 14.68 | A | N |
| ATOM | 571 | CA | VAL | 217 | 109.065 | 37.511 | 6.904 | 1.00 | 16.45 | A | C |
| ATOM | 572 | CB | VAL | 217 | 107.535 | 37.425 | 6.901 | 1.00 | 9.81 | A | C |
| ATOM | 573 | CG1 | VAL | 217 | 107.065 | 36.144 | 7.569 | 1.00 | 9.81 | A | C |
| ATOM | 574 | CG2 | VAL | 217 | 106.967 | 38.647 | 7.626 | 1.00 | 9.81 | A | C |
| ATOM | 575 | C | VAL | 217 | 109.641 | 36.173 | 6.483 | 1.00 | 17.61 | A | C |
| ATOM | 576 | O | VAL | 217 | 109.794 | 35.895 | 5.298 | 1.00 | 17.07 | A | O |
| ATOM | 577 | N | GLN | 218 | 109.959 | 35.348 | 7.474 | 1.00 | 15.74 | A | N |
| ATOM | 578 | CA | GLN | 218 | 110.512 | 34.024 | 7.234 | 1.00 | 16.40 | A | C |
| ATOM | 579 | CB | GLN | 218 | 111.064 | 33.446 | 8.531 | 1.00 | 14.26 | A | C |
| ATOM | 580 | CG | GLN | 218 | 111.752 | 32.109 | 8.372 | 1.00 | 14.26 | A | C |
| ATOM | 581 | CD | GLN | 218 | 112.331 | 31.589 | 9.675 | 1.00 | 14.26 | A | C |
| ATOM | 582 | OE1 | GLN | 218 | 113.166 | 30.685 | 9.668 | 1.00 | 14.26 | A | O |
| ATOM | 583 | NE2 | GLN | 218 | 111.887 | 32.156 | 10.802 | 1.00 | 14.26 | A | N |
| ATOM | 584 | C | GLN | 218 | 109.392 | 33.151 | 6.719 | 1.00 | 15.85 | A | C |

Fig. 19: A-9

| ATOM | 585 | O   | GLN | 218 | 108.335 | 33.103 | 7.328  | 1.00 | 19.60 | A | O |
|------|-----|-----|-----|-----|---------|--------|--------|------|-------|---|---|
| ATOM | 586 | N   | ARG | 219 | 109.622 | 32.464 | 5.604  | 1.00 | 16.04 | A | N |
| ATOM | 587 | CA  | ARG | 219 | 108.599 | 31.602 | 5.005  | 1.00 | 15.69 | A | C |
| ATOM | 588 | CB  | ARG | 219 | 108.595 | 31.786 | 3.489  | 1.00 | 43.49 | A | C |
| ATOM | 589 | CG  | ARG | 219 | 109.053 | 33.163 | 3.054  | 1.00 | 43.49 | A | C |
| ATOM | 590 | CD  | ARG | 219 | 108.719 | 33.421 | 1.606  | 1.00 | 43.49 | A | C |
| ATOM | 591 | NE  | ARG | 219 | 107.365 | 33.952 | 1.454  | 1.00 | 43.49 | A | N |
| ATOM | 592 | CZ  | ARG | 219 | 107.042 | 35.232 | 1.606  | 1.00 | 43.49 | A | C |
| ATOM | 593 | NH1 | ARG | 219 | 107.978 | 36.122 | 1.915  | 1.00 | 43.49 | A | N |
| ATOM | 594 | NH2 | ARG | 219 | 105.786 | 35.621 | 1.443  | 1.00 | 43.49 | A | N |
| ATOM | 595 | C   | ARG | 219 | 108.814 | 30.127 | 5.350  | 1.00 | 16.90 | A | C |
| ATOM | 596 | O   | ARG | 219 | 108.073 | 29.253 | 4.886  | 1.00 | 16.91 | A | O |
| ATOM | 597 | N   | GLY | 220 | 109.838 | 29.867 | 6.160  | 1.00 | 9.58  | A | N |
| ATOM | 598 | CA  | GLY | 220 | 110.148 | 28.513 | 6.567  | 1.00 | 9.19  | A | C |
| ATOM | 599 | C   | GLY | 220 | 110.442 | 27.562 | 5.422  | 1.00 | 8.86  | A | C |
| ATOM | 600 | O   | GLY | 220 | 110.682 | 27.993 | 4.288  | 1.00 | 7.20  | A | O |
| ATOM | 601 | N   | GLY | 221 | 110.435 | 26.266 | 5.730  | 1.00 | 16.50 | A | N |
| ATOM | 602 | CA  | GLY | 221 | 110.682 | 25.265 | 4.718  | 1.00 | 15.07 | A | C |
| ATOM | 603 | C   | GLY | 221 | 111.117 | 23.954 | 5.314  | 1.00 | 15.49 | A | C |
| ATOM | 604 | O   | GLY | 221 | 112.038 | 23.928 | 6.124  | 1.00 | 12.29 | A | O |
| ATOM | 605 | N   | ARG | 222 | 110.459 | 22.865 | 4.927  | 1.00 | 35.34 | A | N |
| ATOM | 606 | CA  | ARG | 222 | 110.815 | 21.543 | 5.433  | 1.00 | 36.05 | A | C |
| ATOM | 607 | CB  | ARG | 222 | 109.652 | 20.567 | 5.235  | 1.00 | 22.30 | A | C |
| ATOM | 608 | CG  | ARG | 222 | 108.505 | 20.791 | 6.201  | 1.00 | 22.30 | A | C |
| ATOM | 609 | CD  | ARG | 222 | 107.252 | 20.047 | 5.779  | 1.00 | 22.30 | A | C |
| ATOM | 610 | NE  | ARG | 222 | 106.621 | 20.647 | 4.614  | 1.00 | 22.30 | A | N |
| ATOM | 611 | CZ  | ARG | 222 | 105.459 | 20.247 | 4.103  | 1.00 | 22.30 | A | C |
| ATOM | 612 | NH1 | ARG | 222 | 104.795 | 19.241 | 4.654  | 1.00 | 22.30 | A | N |
| ATOM | 613 | NH2 | ARG | 222 | 104.951 | 20.857 | 3.042  | 1.00 | 22.30 | A | N |
| ATOM | 614 | C   | ARG | 222 | 112.062 | 21.036 | 4.723  | 1.00 | 36.10 | A | C |
| ATOM | 615 | O   | ARG | 222 | 112.626 | 20.017 | 5.107  | 1.00 | 36.87 | A | O |
| ATOM | 616 | N   | GLN | 223 | 112.473 | 21.750 | 3.678  | 1.00 | 27.48 | A | N |
| ATOM | 617 | CA  | GLN | 223 | 113.672 | 21.428 | 2.912  | 1.00 | 25.77 | A | C |
| ATOM | 618 | CB  | GLN | 223 | 113.328 | 20.858 | 1.535  | 1.00 | 13.17 | A | C |
| ATOM | 619 | CG  | GLN | 223 | 112.830 | 19.417 | 1.508  | 1.00 | 14.61 | A | C |
| ATOM | 620 | CD  | GLN | 223 | 111.346 | 19.312 | 1.790  | 1.00 | 15.02 | A | C |
| ATOM | 621 | OE1 | GLN | 223 | 110.533 | 20.016 | 1.190  | 1.00 | 15.42 | A | O |
| ATOM | 622 | NE2 | GLN | 223 | 110.981 | 18.417 | 2.698  | 1.00 | 15.46 | A | N |
| ATOM | 623 | C   | GLN | 223 | 114.498 | 22.706 | 2.724  | 1.00 | 26.51 | A | C |
| ATOM | 624 | O   | GLN | 223 | 114.057 | 23.799 | 3.069  | 1.00 | 25.99 | A | O |
| ATOM | 625 | N   | THR | 224 | 115.696 | 22.567 | 2.172  | 1.00 | 24.40 | A | N |
| ATOM | 626 | CA  | THR | 224 | 116.581 | 23.704 | 1.948  | 1.00 | 22.28 | A | C |
| ATOM | 627 | CB  | THR | 224 | 117.795 | 23.633 | 2.897  | 1.00 | 14.98 | A | C |
| ATOM | 628 | OG1 | THR | 224 | 117.328 | 23.565 | 4.246  | 1.00 | 14.97 | A | O |
| ATOM | 629 | CG2 | THR | 224 | 118.683 | 24.849 | 2.747  | 1.00 | 11.28 | A | C |
| ATOM | 630 | C   | THR | 224 | 117.061 | 23.662 | 0.500  | 1.00 | 19.29 | A | C |
| ATOM | 631 | O   | THR | 224 | 118.122 | 23.129 | 0.202  | 1.00 | 15.78 | A | O |
| ATOM | 632 | N   | MET | 225 | 116.272 | 24.234 | -0.395 | 1.00 | 14.15 | A | N |
| ATOM | 633 | CA  | MET | 225 | 116.607 | 24.236 | -1.810 | 1.00 | 15.04 | A | C |
| ATOM | 634 | CB  | MET | 225 | 115.346 | 24.481 | -2.636 | 1.00 | 22.98 | A | C |
| ATOM | 635 | CG  | MET | 225 | 114.183 | 23.602 | -2.267 | 1.00 | 20.41 | A | C |
| ATOM | 636 | SD  | MET | 225 | 114.421 | 21.883 | -2.704 | 1.00 | 28.15 | A | S |
| ATOM | 637 | CE  | MET | 225 | 112.675 | 21.302 | -2.554 | 1.00 | 24.73 | A | C |
| ATOM | 638 | C   | MET | 225 | 117.653 | 25.275 | -2.204 | 1.00 | 16.07 | A | C |
| ATOM | 639 | O   | MET | 225 | 117.426 | 26.054 | -3.136 | 1.00 | 17.53 | A | O |
| ATOM | 640 | N   | THR | 226 | 118.791 | 25.297 | -1.513 | 1.00 | 16.19 | A | N |
| ATOM | 641 | CA  | THR | 226 | 119.841 | 26.259 | -1.840 | 1.00 | 15.66 | A | C |
| ATOM | 642 | CB  | THR | 226 | 121.155 | 25.905 | -1.129 | 1.00 | 25.30 | A | C |
| ATOM | 643 | OG1 | THR | 226 | 120.925 | 25.825 | 0.284  | 1.00 | 27.32 | A | O |
| ATOM | 644 | CG2 | THR | 226 | 122.216 | 26.959 | -1.414 | 1.00 | 23.02 | A | C |
| ATOM | 645 | C   | THR | 226 | 120.100 | 26.337 | -3.356 | 1.00 | 14.26 | A | C |
| ATOM | 646 | O   | THR | 226 | 120.229 | 27.418 | -3.917 | 1.00 | 8.95  | A | O |
| ATOM | 647 | N   | ALA | 227 | 120.158 | 25.190 | -4.019 | 1.00 | 9.41  | A | N |
| ATOM | 648 | CA  | ALA | 227 | 120.408 | 25.162 | -5.448 | 1.00 | 8.35  | A | C |
| ATOM | 649 | CB  | ALA | 227 | 120.422 | 23.738 | -5.939 | 1.00 | 23.80 | A | C |
| ATOM | 650 | C   | ALA | 227 | 119.342 | 25.951 | -6.188 | 1.00 | 9.01  | A | C |
| ATOM | 651 | O   | ALA | 227 | 119.644 | 26.759 | -7.067 | 1.00 | 9.81  | A | O |
| ATOM | 652 | N   | LEU | 228 | 118.085 | 25.711 | -5.842 | 1.00 | 28.18 | A | N |
| ATOM | 653 | CA  | LEU | 228 | 116.985 | 26.410 | -6.489 | 1.00 | 26.62 | A | C |
| ATOM | 654 | CB  | LEU | 228 | 115.649 | 25.860 | -5.988 | 1.00 | 14.81 | A | C |
| ATOM | 655 | CG  | LEU | 228 | 114.372 | 26.485 | -6.557 | 1.00 | 22.70 | A | C |
| ATOM | 656 | CD1 | LEU | 228 | 114.356 | 26.363 | -8.080 | 1.00 | 20.29 | A | C |
| ATOM | 657 | CD2 | LEU | 228 | 113.163 | 25.801 | -5.947 | 1.00 | 19.75 | A | C |

Fig. 19: A-10

| ATOM | 658 | C | LEU | 228 | 117.067 | 27.909 | -6.221 | 1.00 | 25.80 | A | C |
|---|---|---|---|---|---|---|---|---|---|---|---|
| ATOM | 659 | O | LEU | 228 | 116.885 | 28.719 | -7.129 | 1.00 | 28.78 | A | O |
| ATOM | 660 | N | GLY | 229 | 117.341 | 28.274 | -4.971 | 1.00 | 23.50 | A | N |
| ATOM | 661 | CA | GLY | 229 | 117.449 | 29.679 | -4.624 | 1.00 | 25.86 | A | C |
| ATOM | 662 | C | GLY | 229 | 118.464 | 30.407 | -5.495 | 1.00 | 28.42 | A | C |
| ATOM | 663 | O | GLY | 229 | 118.149 | 31.428 | -6.108 | 1.00 | 29.01 | A | O |
| ATOM | 664 | N | ILE | 230 | 119.682 | 29.876 | -5.562 | 1.00 | 20.49 | A | N |
| ATOM | 665 | CA | ILE | 230 | 120.736 | 30.498 | -6.354 | 1.00 | 21.82 | A | C |
| ATOM | 666 | CB | ILE | 230 | 122.096 | 29.779 | -6.195 | 1.00 | 2.66 | A | C |
| ATOM | 667 | CG2 | ILE | 230 | 123.168 | 30.546 | -6.953 | 1.00 | 2.66 | A | C |
| ATOM | 668 | CG1 | ILE | 230 | 122.486 | 29.692 | -4.720 | 1.00 | 2.66 | A | C |
| ATOM | 669 | CD1 | ILE | 230 | 123.773 | 28.920 | -4.474 | 1.00 | 2.66 | A | C |
| ATOM | 670 | C | ILE | 230 | 120.386 | 30.508 | -7.830 | 1.00 | 22.08 | A | C |
| ATOM | 671 | O | ILE | 230 | 120.614 | 31.498 | -8.511 | 1.00 | 20.01 | A | O |
| ATOM | 672 | N | ASP | 231 | 119.841 | 29.409 | -8.333 | 1.00 | 32.19 | A | N |
| ATOM | 673 | CA | ASP | 231 | 119.473 | 29.352 | -9.743 | 1.00 | 30.59 | A | C |
| ATOM | 674 | CB | ASP | 231 | 118.959 | 27.958 | -10.103 | 1.00 | 35.41 | A | C |
| ATOM | 675 | CG | ASP | 231 | 118.860 | 27.739 | -11.604 | 1.00 | 42.41 | A | C |
| ATOM | 676 | OD1 | ASP | 231 | 119.910 | 27.778 | -12.281 | 1.00 | 41.17 | A | O |
| ATOM | 677 | OD2 | ASP | 231 | 117.735 | 27.525 | -12.103 | 1.00 | 45.95 | A | O |
| ATOM | 678 | C | ASP | 231 | 118.392 | 30.395 | -10.048 | 1.00 | 31.57 | A | C |
| ATOM | 679 | O | ASP | 231 | 118.429 | 31.048 | -11.090 | 1.00 | 28.79 | A | O |
| ATOM | 680 | N | THR | 232 | 117.443 | 30.554 | -9.126 | 1.00 | 18.29 | A | N |
| ATOM | 681 | CA | THR | 232 | 116.347 | 31.510 | -9.296 | 1.00 | 17.08 | A | C |
| ATOM | 682 | CB | THR | 232 | 115.287 | 31.347 | -8.194 | 1.00 | 20.70 | A | C |
| ATOM | 683 | OG1 | THR | 232 | 114.714 | 30.041 | -8.279 | 1.00 | 19.21 | A | O |
| ATOM | 684 | CG2 | THR | 232 | 114.191 | 32.370 | -8.358 | 1.00 | 14.24 | A | C |
| ATOM | 685 | C | THR | 232 | 116.859 | 32.937 | -9.264 | 1.00 | 17.71 | A | C |
| ATOM | 686 | O | THR | 232 | 116.390 | 33.801 | -10.010 | 1.00 | 17.88 | A | O |
| ATOM | 687 | N | ALA | 233 | 117.815 | 33.187 | -8.379 | 1.00 | 19.66 | A | N |
| ATOM | 688 | CA | ALA | 233 | 118.395 | 34.517 | -8.270 | 1.00 | 22.31 | A | C |
| ATOM | 689 | CB | ALA | 233 | 119.364 | 34.580 | -7.099 | 1.00 | 15.15 | A | C |
| ATOM | 690 | C | ALA | 233 | 119.125 | 34.796 | -9.575 | 1.00 | 24.62 | A | C |
| ATOM | 691 | O | ALA | 233 | 119.187 | 35.929 | -10.031 | 1.00 | 26.53 | A | O |
| ATOM | 692 | N | ARG | 234 | 119.666 | 33.746 | -10.180 | 1.00 | 30.19 | A | N |
| ATOM | 693 | CA | ARG | 234 | 120.390 | 33.879 | -11.434 | 1.00 | 33.29 | A | C |
| ATOM | 694 | CB | ARG | 234 | 121.241 | 32.637 | -11.693 | 1.00 | 15.32 | A | C |
| ATOM | 695 | CG | ARG | 234 | 122.345 | 32.875 | -12.693 | 1.00 | 15.32 | A | C |
| ATOM | 696 | CD | ARG | 234 | 122.760 | 31.617 | -13.460 | 1.00 | 15.32 | A | C |
| ATOM | 697 | NE | ARG | 234 | 121.839 | 31.311 | -14.554 | 1.00 | 15.32 | A | N |
| ATOM | 698 | CZ | ARG | 234 | 120.875 | 30.405 | -14.481 | 1.00 | 15.32 | A | C |
| ATOM | 699 | NH1 | ARG | 234 | 120.708 | 29.713 | -13.368 | 1.00 | 15.32 | A | N |
| ATOM | 700 | NH2 | ARG | 234 | 120.078 | 30.188 | -15.511 | 1.00 | 15.32 | A | N |
| ATOM | 701 | C | ARG | 234 | 119.446 | 34.083 | -12.619 | 1.00 | 35.42 | A | C |
| ATOM | 702 | O | ARG | 234 | 119.409 | 35.153 | -13.215 | 1.00 | 35.47 | A | O |
| ATOM | 703 | N | LYS | 235 | 118.666 | 33.057 | -12.941 | 1.00 | 67.48 | A | N |
| ATOM | 704 | CA | LYS | 235 | 117.767 | 33.124 | -14.085 | 1.00 | 67.43 | A | C |
| ATOM | 705 | CB | LYS | 235 | 117.204 | 31.730 | -14.397 | 1.00 | 53.18 | A | C |
| ATOM | 706 | CG | LYS | 235 | 115.965 | 31.308 | -13.615 | 1.00 | 54.33 | A | C |
| ATOM | 707 | CD | LYS | 235 | 115.583 | 29.867 | -13.970 | 1.00 | 54.15 | A | C |
| ATOM | 708 | CE | LYS | 235 | 114.146 | 29.517 | -13.590 | 1.00 | 54.95 | A | C |
| ATOM | 709 | NZ | LYS | 235 | 113.873 | 29.660 | -12.135 | 1.00 | 55.71 | A | N |
| ATOM | 710 | C | LYS | 235 | 116.628 | 34.134 | -14.017 | 1.00 | 67.57 | A | C |
| ATOM | 711 | O | LYS | 235 | 116.074 | 34.500 | -15.054 | 1.00 | 67.91 | A | O |
| ATOM | 712 | N | GLU | 236 | 116.277 | 34.596 | -12.822 | 1.00 | 98.68 | A | N |
| ATOM | 713 | CA | GLU | 236 | 115.186 | 35.558 | -12.693 | 1.00 | 100.30 | A | C |
| ATOM | 714 | CB | GLU | 236 | 114.087 | 34.999 | -11.781 | 1.00 | 50.64 | A | C |
| ATOM | 715 | CG | GLU | 236 | 113.008 | 34.192 | -12.510 | 1.00 | 53.41 | A | C |
| ATOM | 716 | CD | GLU | 236 | 112.199 | 33.276 | -11.582 | 1.00 | 55.89 | A | C |
| ATOM | 717 | OE1 | GLU | 236 | 111.660 | 33.760 | -10.565 | 1.00 | 55.98 | A | O |
| ATOM | 718 | OE2 | GLU | 236 | 112.098 | 32.065 | -11.875 | 1.00 | 55.73 | A | O |
| ATOM | 719 | C | GLU | 236 | 115.627 | 36.917 | -12.174 | 1.00 | 98.85 | A | C |
| ATOM | 720 | O | GLU | 236 | 115.638 | 37.900 | -12.912 | 1.00 | 100.28 | A | O |
| ATOM | 721 | N | ALA | 237 | 115.991 | 36.969 | -10.899 | 1.00 | 71.25 | A | N |
| ATOM | 722 | CA | ALA | 237 | 116.405 | 38.218 | -10.276 | 1.00 | 68.72 | A | C |
| ATOM | 723 | CB | ALA | 237 | 117.046 | 37.934 | -8.932 | 1.00 | 56.85 | A | C |
| ATOM | 724 | C | ALA | 237 | 117.349 | 39.046 | -11.139 | 1.00 | 67.56 | A | C |
| ATOM | 725 | O | ALA | 237 | 117.225 | 40.267 | -11.200 | 1.00 | 65.98 | A | O |
| ATOM | 726 | N | PHE | 238 | 118.283 | 38.385 | -11.812 | 1.00 | 41.81 | A | N |
| ATOM | 727 | CA | PHE | 238 | 119.256 | 39.080 | -12.651 | 1.00 | 41.24 | A | C |
| ATOM | 728 | CB | PHE | 238 | 120.606 | 38.369 | -12.591 | 1.00 | 47.57 | A | C |
| ATOM | 729 | CG | PHE | 238 | 121.413 | 38.696 | -11.378 | 1.00 | 46.60 | A | C |
| ATOM | 730 | CD1 | PHE | 238 | 121.686 | 37.725 | -10.419 | 1.00 | 47.83 | A | C |

Fig. 19: A-11

| | | | | | | | | | | |
|---|---|---|---|---|---|---|---|---|---|---|
| ATOM | 731 | CD2 | PHE | 238 | 121.931 | 39.970 | -11.208 | 1.00 | 44.20 | A | C |
| ATOM | 732 | CE1 | PHE | 238 | 122.476 | 38.023 | -9.298 | 1.00 | 45.63 | A | C |
| ATOM | 733 | CE2 | PHE | 238 | 122.719 | 40.282 | -10.094 | 1.00 | 50.51 | A | C |
| ATOM | 734 | CZ | PHE | 238 | 122.993 | 39.305 | -9.137 | 1.00 | 51.93 | A | C |
| ATOM | 735 | C | PHE | 238 | 118.861 | 39.252 | -14.116 | 1.00 | 43.09 | A | C |
| ATOM | 736 | O | PHE | 238 | 119.699 | 39.129 | -15.017 | 1.00 | 43.19 | A | O |
| ATOM | 737 | N | THR | 239 | 117.586 | 39.520 | -14.362 | 1.00 | 28.84 | A | N |
| ATOM | 738 | CA | THR | 239 | 117.117 | 39.744 | -15.724 | 1.00 | 32.78 | A | C |
| ATOM | 739 | CB | THR | 239 | 115.952 | 38.821 | -16.086 | 1.00 | 22.29 | A | C |
| ATOM | 740 | OG1 | THR | 239 | 114.866 | 39.059 | -15.191 | 1.00 | 20.25 | A | O |
| ATOM | 741 | CG2 | THR | 239 | 116.363 | 37.382 | -15.988 | 1.00 | 25.20 | A | C |
| ATOM | 742 | C | THR | 239 | 116.655 | 41.202 | -15.798 | 1.00 | 33.04 | A | C |
| ATOM | 743 | O | THR | 239 | 115.955 | 41.695 | -14.902 | 1.00 | 33.54 | A | O |
| ATOM | 744 | N | GLU | 240 | 117.067 | 41.881 | -16.868 | 1.00 | 73.11 | A | N |
| ATOM | 745 | CA | GLU | 240 | 116.755 | 43.291 | -17.085 | 1.00 | 73.36 | A | C |
| ATOM | 746 | CB | GLU | 240 | 116.995 | 43.654 | -18.549 | 1.00 | 97.49 | A | C |
| ATOM | 747 | CG | GLU | 240 | 117.147 | 45.141 | -18.793 | 1.00 | 102.13 | A | C |
| ATOM | 748 | CD | GLU | 240 | 117.738 | 45.441 | -20.152 | 1.00 | 105.04 | A | C |
| ATOM | 749 | OE1 | GLU | 240 | 118.794 | 44.858 | -20.483 | 1.00 | 105.14 | A | O |
| ATOM | 750 | OE2 | GLU | 240 | 117.151 | 46.263 | -20.885 | 1.00 | 105.11 | A | O |
| ATOM | 751 | C | GLU | 240 | 115.336 | 43.665 | -16.689 | 1.00 | 74.71 | A | C |
| ATOM | 752 | O | GLU | 240 | 115.083 | 44.772 | -16.210 | 1.00 | 75.92 | A | O |
| ATOM | 753 | N | ALA | 241 | 114.417 | 42.730 | -16.885 | 1.00 | 32.59 | A | N |
| ATOM | 754 | CA | ALA | 241 | 113.016 | 42.952 | -16.552 | 1.00 | 33.44 | A | C |
| ATOM | 755 | CB | ALA | 241 | 112.170 | 41.769 | -17.051 | 1.00 | 4.05 | A | C |
| ATOM | 756 | C | ALA | 241 | 112.802 | 43.165 | -15.044 | 1.00 | 32.91 | A | C |
| ATOM | 757 | O | ALA | 241 | 111.809 | 43.759 | -14.622 | 1.00 | 34.37 | A | O |
| ATOM | 758 | N | ARG | 242 | 113.725 | 42.678 | -14.223 | 1.00 | 31.60 | A | N |
| ATOM | 759 | CA | ARG | 242 | 113.585 | 42.851 | -12.786 | 1.00 | 31.34 | A | C |
| ATOM | 760 | CB | ARG | 242 | 113.757 | 41.500 | -12.079 | 1.00 | 27.81 | A | C |
| ATOM | 761 | CG | ARG | 242 | 112.489 | 40.658 | -12.052 | 1.00 | 28.01 | A | C |
| ATOM | 762 | CD | ARG | 242 | 112.669 | 39.440 | -11.160 | 1.00 | 28.87 | A | C |
| ATOM | 763 | NE | ARG | 242 | 111.425 | 39.010 | -10.515 | 1.00 | 30.07 | A | N |
| ATOM | 764 | CZ | ARG | 242 | 110.582 | 38.106 | -11.011 | 1.00 | 29.27 | A | C |
| ATOM | 765 | NH1 | ARG | 242 | 110.846 | 37.525 | -12.176 | 1.00 | 28.32 | A | N |
| ATOM | 766 | NH2 | ARG | 242 | 109.485 | 37.769 | -10.334 | 1.00 | 31.29 | A | N |
| ATOM | 767 | C | ARG | 242 | 114.557 | 43.898 | -12.231 | 1.00 | 32.54 | A | C |
| ATOM | 768 | O | ARG | 242 | 114.824 | 43.954 | -11.026 | 1.00 | 35.55 | A | O |
| ATOM | 769 | N | GLY | 243 | 115.080 | 44.733 | -13.122 | 1.00 | 38.70 | A | N |
| ATOM | 770 | CA | GLY | 243 | 115.996 | 45.775 | -12.706 | 1.00 | 36.85 | A | C |
| ATOM | 771 | C | GLY | 243 | 117.468 | 45.462 | -12.890 | 1.00 | 35.13 | A | C |
| ATOM | 772 | O | GLY | 243 | 118.318 | 46.139 | -12.308 | 1.00 | 34.75 | A | O |
| ATOM | 773 | N | ALA | 244 | 117.792 | 44.447 | -13.683 | 1.00 | 32.25 | A | N |
| ATOM | 774 | CA | ALA | 244 | 119.190 | 44.119 | -13.896 | 1.00 | 30.25 | A | C |
| ATOM | 775 | CB | ALA | 244 | 119.326 | 42.709 | -14.442 | 1.00 | 67.28 | A | C |
| ATOM | 776 | C | ALA | 244 | 119.750 | 45.130 | -14.886 | 1.00 | 32.13 | A | C |
| ATOM | 777 | O | ALA | 244 | 119.437 | 45.088 | -16.068 | 1.00 | 31.59 | A | O |
| ATOM | 778 | N | ARG | 245 | 120.566 | 46.054 | -14.401 | 1.00 | 18.96 | A | N |
| ATOM | 779 | CA | ARG | 245 | 121.154 | 47.074 | -15.258 | 1.00 | 19.79 | A | C |
| ATOM | 780 | CB | ARG | 245 | 121.853 | 48.130 | -14.399 | 1.00 | 36.60 | A | C |
| ATOM | 781 | CG | ARG | 245 | 120.888 | 49.043 | -13.655 | 1.00 | 39.07 | A | C |
| ATOM | 782 | CD | ARG | 245 | 121.614 | 49.991 | -12.741 | 1.00 | 39.28 | A | C |
| ATOM | 783 | NE | ARG | 245 | 122.309 | 49.254 | -11.701 | 1.00 | 33.70 | A | N |
| ATOM | 784 | CZ | ARG | 245 | 122.997 | 49.824 | -10.726 | 1.00 | 33.52 | A | C |
| ATOM | 785 | NH1 | ARG | 245 | 123.084 | 51.145 | -10.662 | 1.00 | 32.72 | A | N |
| ATOM | 786 | NH2 | ARG | 245 | 123.590 | 49.075 | -9.810 | 1.00 | 30.81 | A | N |
| ATOM | 787 | C | ARG | 245 | 122.131 | 46.493 | -16.266 | 1.00 | 18.16 | A | C |
| ATOM | 788 | O | ARG | 245 | 123.003 | 45.710 | -15.911 | 1.00 | 14.27 | A | O |
| ATOM | 789 | N | ARG | 246 | 121.985 | 46.896 | -17.525 | 1.00 | 55.16 | A | N |
| ATOM | 790 | CA | ARG | 246 | 122.848 | 46.429 | -18.607 | 1.00 | 57.95 | A | C |
| ATOM | 791 | CB | ARG | 246 | 122.447 | 47.078 | -19.928 | 1.00 | 115.62 | A | C |
| ATOM | 792 | CG | ARG | 246 | 123.405 | 46.764 | -21.067 | 1.00 | 120.98 | A | C |
| ATOM | 793 | CD | ARG | 246 | 123.057 | 47.546 | -22.318 | 1.00 | 126.90 | A | C |
| ATOM | 794 | NE | ARG | 246 | 121.637 | 47.444 | -22.641 | 1.00 | 129.81 | A | N |
| ATOM | 795 | CZ | ARG | 246 | 120.981 | 46.298 | -22.804 | 1.00 | 132.92 | A | C |
| ATOM | 796 | NH1 | ARG | 246 | 121.615 | 45.138 | -22.676 | 1.00 | 132.61 | A | N |
| ATOM | 797 | NH2 | ARG | 246 | 119.685 | 46.314 | -23.094 | 1.00 | 133.70 | A | N |
| ATOM | 798 | C | ARG | 246 | 124.313 | 46.736 | -18.354 | 1.00 | 55.77 | A | C |
| ATOM | 799 | O | ARG | 246 | 124.671 | 47.879 | -18.092 | 1.00 | 58.40 | A | O |
| ATOM | 800 | N | GLY | 247 | 125.151 | 45.711 | -18.475 | 1.00 | 47.75 | A | N |
| ATOM | 801 | CA | GLY | 247 | 126.587 | 45.878 | -18.302 | 1.00 | 50.33 | A | C |
| ATOM | 802 | C | GLY | 247 | 127.097 | 46.294 | -16.934 | 1.00 | 50.40 | A | C |
| ATOM | 803 | O | GLY | 247 | 128.129 | 46.958 | -16.824 | 1.00 | 53.36 | A | O |

Fig. 19: A-12

```
ATOM    804  N   VAL 248     126.382  45.911 -15.887  1.00  40.38      A  N
ATOM    805  CA  VAL 248     126.790  46.248 -14.535  1.00  38.39      A  C
ATOM    806  CB  VAL 248     125.653  46.928 -13.780  1.00  41.70      A  C
ATOM    807  CG1 VAL 248     126.049  47.136 -12.331  1.00  39.35      A  C
ATOM    808  CG2 VAL 248     125.331  48.250 -14.436  1.00  33.47      A  C
ATOM    809  C   VAL 248     127.173  44.970 -13.807  1.00  41.41      A  C
ATOM    810  O   VAL 248     126.530  43.936 -13.993  1.00  45.46      A  O
ATOM    811  N   LYS 249     128.208  45.036 -12.975  1.00  30.45      A  N
ATOM    812  CA  LYS 249     128.645  43.852 -12.250  1.00  31.36      A  C
ATOM    813  CB  LYS 249     129.799  44.186 -11.299  1.00  85.59      A  C
ATOM    814  CG  LYS 249     130.426  42.940 -10.690  1.00  91.11      A  C
ATOM    815  CD  LYS 249     130.844  41.943 -11.782  1.00  92.18      A  C
ATOM    816  CE  LYS 249     131.040  40.539 -11.224  1.00  94.54      A  C
ATOM    817  NZ  LYS 249     131.548  39.546 -12.218  1.00  97.36      A  N
ATOM    818  C   LYS 249     127.503  43.190 -11.473  1.00  30.02      A  C
ATOM    819  O   LYS 249     126.706  43.862 -10.815  1.00  29.84      A  O
ATOM    820  N   LYS 250     127.432  41.864 -11.559  1.00  29.51      A  N
ATOM    821  CA  LYS 250     126.396  41.110 -10.879  1.00  29.16      A  C
ATOM    822  CB  LYS 250     125.763  40.134 -11.871  1.00  45.59      A  C
ATOM    823  CG  LYS 250     125.050  40.864 -12.996  1.00  44.19      A  C
ATOM    824  CD  LYS 250     124.892  40.022 -14.263  1.00  45.74      A  C
ATOM    825  CE  LYS 250     123.827  38.928 -14.135  1.00  44.90      A  C
ATOM    826  NZ  LYS 250     123.513  38.274 -15.453  1.00  46.72      A  N
ATOM    827  C   LYS 250     126.979  40.391  -9.663  1.00  28.51      A  C
ATOM    828  O   LYS 250     127.849  39.541  -9.804  1.00  28.19      A  O
ATOM    829  N   VAL 251     126.493  40.754  -8.474  1.00  23.05      A  N
ATOM    830  CA  VAL 251     126.954  40.173  -7.219  1.00  22.96      A  C
ATOM    831  CB  VAL 251     127.504  41.263  -6.307  1.00  28.85      A  C
ATOM    832  CG1 VAL 251     127.901  40.676  -4.959  1.00  27.00      A  C
ATOM    833  CG2 VAL 251     128.678  41.928  -6.974  1.00  30.06      A  C
ATOM    834  C   VAL 251     125.863  39.421  -6.451  1.00  21.44      A  C
ATOM    835  O   VAL 251     124.778  39.945  -6.232  1.00  17.44      A  O
ATOM    836  N   MET 252     126.168  38.199  -6.023  1.00  19.32      A  N
ATOM    837  CA  MET 252     125.212  37.383  -5.278  1.00  20.30      A  C
ATOM    838  CB  MET 252     124.949  36.073  -6.024  1.00  19.49      A  C
ATOM    839  CG  MET 252     123.850  35.212  -5.425  1.00  18.18      A  C
ATOM    840  SD  MET 252     123.556  33.701  -6.379  1.00  22.23      A  S
ATOM    841  CE  MET 252     123.009  34.366  -7.960  1.00  13.54      A  C
ATOM    842  C   MET 252     125.730  37.072  -3.875  1.00  19.32      A  C
ATOM    843  O   MET 252     126.880  36.675  -3.704  1.00  21.69      A  O
ATOM    844  N   VAL 253     124.886  37.261  -2.869  1.00  11.70      A  N
ATOM    845  CA  VAL 253     125.286  36.971  -1.505  1.00  12.85      A  C
ATOM    846  CB  VAL 253     125.173  38.221  -0.593  1.00   5.67      A  C
ATOM    847  CG1 VAL 253     125.508  37.856   0.842  1.00   7.09      A  C
ATOM    848  CG2 VAL 253     126.118  39.310  -1.079  1.00   5.31      A  C
ATOM    849  C   VAL 253     124.370  35.881  -0.974  1.00  12.42      A  C
ATOM    850  O   VAL 253     123.166  36.093  -0.870  1.00  10.86      A  O
ATOM    851  N   ILE 254     124.936  34.716  -0.649  1.00  26.88      A  N
ATOM    852  CA  ILE 254     124.142  33.597  -0.126  1.00  23.78      A  C
ATOM    853  CB  ILE 254     124.457  32.266  -0.847  1.00  10.72      A  C
ATOM    854  CG2 ILE 254     123.584  31.171  -0.294  1.00   7.19      A  C
ATOM    855  CG1 ILE 254     124.220  32.397  -2.352  1.00   9.30      A  C
ATOM    856  CD1 ILE 254     125.307  33.140  -3.078  1.00   8.93      A  C
ATOM    857  C   ILE 254     124.379  33.370   1.359  1.00  21.87      A  C
ATOM    858  O   ILE 254     125.508  33.431   1.833  1.00  23.74      A  O
ATOM    859  N   VAL 255     123.300  33.105   2.084  1.00  38.19      A  N
ATOM    860  CA  VAL 255     123.379  32.858   3.516  1.00  36.93      A  C
ATOM    861  CB  VAL 255     122.733  33.994   4.328  1.00  13.80      A  C
ATOM    862  CG1 VAL 255     123.224  33.949   5.753  1.00  12.25      A  C
ATOM    863  CG2 VAL 255     123.056  35.325   3.713  1.00  14.44      A  C
ATOM    864  C   VAL 255     122.592  31.594   3.798  1.00  34.68      A  C
ATOM    865  O   VAL 255     121.431  31.491   3.403  1.00  36.68      A  O
ATOM    866  N   THR 256     123.210  30.632   4.474  1.00  19.22      A  N
ATOM    867  CA  THR 256     122.514  29.387   4.798  1.00  20.04      A  C
ATOM    868  CB  THR 256     122.477  28.457   3.566  1.00  10.08      A  C
ATOM    869  OG1 THR 256     122.032  27.147   3.952  1.00   6.12      A  O
ATOM    870  CG2 THR 256     123.851  28.387   2.926  1.00   8.93      A  C
ATOM    871  C   THR 256     123.128  28.650   5.995  1.00  23.52      A  C
ATOM    872  O   THR 256     124.303  28.831   6.310  1.00  19.68      A  O
ATOM    873  N   ASP 257     122.323  27.829   6.663  1.00  46.58      A  N
ATOM    874  CA  ASP 257     122.794  27.097   7.830  1.00  46.96      A  C
ATOM    875  CB  ASP 257     122.069  27.585   9.091  1.00  21.89      A  C
ATOM    876  CG  ASP 257     120.655  27.009   9.225  1.00  27.25      A  C
```

Fig. 19: A-13

| | | | | | | | | | | | |
|---|---|---|---|---|---|---|---|---|---|---|---|
| ATOM | 877 | OD1 | ASP | 257 | 120.089 | 26.573 | 8.191 | 1.00 | 27.72 | A | O |
| ATOM | 878 | OD2 | ASP | 257 | 120.110 | 27.006 | 10.362 | 1.00 | 32.52 | A | O |
| ATOM | 879 | C | ASP | 257 | 122.599 | 25.596 | 7.693 | 1.00 | 43.55 | A | C |
| ATOM | 880 | O | ASP | 257 | 122.525 | 24.883 | 8.695 | 1.00 | 42.79 | A | O |
| ATOM | 881 | N | GLY | 258 | 122.510 | 25.106 | 6.461 | 1.00 | 42.38 | A | N |
| ATOM | 882 | CA | GLY | 258 | 122.330 | 23.678 | 6.283 | 1.00 | 44.80 | A | C |
| ATOM | 883 | C | GLY | 258 | 122.618 | 23.150 | 4.896 | 1.00 | 48.62 | A | C |
| ATOM | 884 | O | GLY | 258 | 122.523 | 23.871 | 3.903 | 1.00 | 44.34 | A | O |
| ATOM | 885 | N | GLU | 259 | 122.984 | 21.876 | 4.832 | 1.00 | 88.78 | A | N |
| ATOM | 886 | CA | GLU | 259 | 123.265 | 21.230 | 3.562 | 1.00 | 90.66 | A | C |
| ATOM | 887 | CB | GLU | 259 | 123.650 | 19.770 | 3.782 | 1.00 | 87.02 | A | C |
| ATOM | 888 | CG | GLU | 259 | 124.983 | 19.588 | 4.461 | 1.00 | 94.80 | A | C |
| ATOM | 889 | CD | GLU | 259 | 125.130 | 18.214 | 5.070 | 1.00 | 98.61 | A | C |
| ATOM | 890 | OE1 | GLU | 259 | 126.256 | 17.861 | 5.481 | 1.00 | 105.36 | A | O |
| ATOM | 891 | OE2 | GLU | 259 | 124.115 | 17.490 | 5.147 | 1.00 | 98.63 | A | O |
| ATOM | 892 | C | GLU | 259 | 122.004 | 21.298 | 2.727 | 1.00 | 89.52 | A | C |
| ATOM | 893 | O | GLU | 259 | 120.927 | 20.906 | 3.174 | 1.00 | 86.69 | A | O |
| ATOM | 894 | N | SER | 260 | 122.140 | 21.815 | 1.517 | 1.00 | 31.72 | A | N |
| ATOM | 895 | CA | SER | 260 | 121.007 | 21.922 | 0.615 | 1.00 | 34.88 | A | C |
| ATOM | 896 | CB | SER | 260 | 121.435 | 22.606 | -0.685 | 1.00 | 104.64 | A | C |
| ATOM | 897 | OG | SER | 260 | 122.467 | 21.872 | -1.325 | 1.00 | 105.15 | A | O |
| ATOM | 898 | C | SER | 260 | 120.489 | 20.526 | 0.304 | 1.00 | 34.78 | A | C |
| ATOM | 899 | O | SER | 260 | 121.257 | 19.571 | 0.315 | 1.00 | 30.81 | A | O |
| ATOM | 900 | N | HIS | 261 | 119.192 | 20.409 | 0.039 | 1.00 | 119.42 | A | N |
| ATOM | 901 | CA | HIS | 261 | 118.609 | 19.114 | -0.284 | 1.00 | 123.77 | A | C |
| ATOM | 902 | CB | HIS | 261 | 117.107 | 19.116 | 0.020 | 1.00 | 89.56 | A | C |
| ATOM | 903 | CG | HIS | 261 | 116.789 | 19.030 | 1.482 | 1.00 | 92.76 | A | C |
| ATOM | 904 | CD2 | HIS | 261 | 116.610 | 19.997 | 2.413 | 1.00 | 91.87 | A | C |
| ATOM | 905 | ND1 | HIS | 261 | 116.648 | 17.830 | 2.147 | 1.00 | 94.24 | A | N |
| ATOM | 906 | CE1 | HIS | 261 | 116.393 | 18.065 | 3.422 | 1.00 | 94.31 | A | C |
| ATOM | 907 | NE2 | HIS | 261 | 116.365 | 19.372 | 3.610 | 1.00 | 91.58 | A | N |
| ATOM | 908 | C | HIS | 261 | 118.866 | 18.815 | -1.754 | 1.00 | 124.83 | A | C |
| ATOM | 909 | O | HIS | 261 | 118.732 | 17.676 | -2.203 | 1.00 | 122.05 | A | O |
| ATOM | 910 | N | ASP | 262 | 119.251 | 19.850 | -2.495 | 1.00 | 94.20 | A | N |
| ATOM | 911 | CA | ASP | 262 | 119.556 | 19.709 | -3.913 | 1.00 | 99.17 | A | C |
| ATOM | 912 | CB | ASP | 262 | 118.838 | 20.798 | -4.732 | 1.00 | 77.35 | A | C |
| ATOM | 913 | CG | ASP | 262 | 118.558 | 22.065 | -3.929 | 1.00 | 77.35 | A | C |
| ATOM | 914 | OD1 | ASP | 262 | 119.382 | 22.429 | -3.067 | 1.00 | 77.35 | A | O |
| ATOM | 915 | OD2 | ASP | 262 | 117.515 | 22.708 | -4.179 | 1.00 | 77.35 | A | O |
| ATOM | 916 | C | ASP | 262 | 121.065 | 19.758 | -4.191 | 1.00 | 99.22 | A | C |
| ATOM | 917 | O | ASP | 262 | 121.510 | 20.456 | -5.104 | 1.00 | 99.08 | A | O |
| ATOM | 918 | N | ASN | 263 | 121.842 | 19.009 | -3.406 | 1.00 | 48.33 | A | N |
| ATOM | 919 | CA | ASN | 263 | 123.300 | 18.956 | -3.558 | 1.00 | 49.50 | A | C |
| ATOM | 920 | CB | ASN | 263 | 123.896 | 17.820 | -2.719 | 1.00 | 78.20 | A | C |
| ATOM | 921 | CG | ASN | 263 | 123.359 | 17.781 | -1.303 | 1.00 | 82.57 | A | C |
| ATOM | 922 | OD1 | ASN | 263 | 123.578 | 18.703 | -0.511 | 1.00 | 84.07 | A | O |
| ATOM | 923 | ND2 | ASN | 263 | 122.651 | 16.702 | -0.974 | 1.00 | 77.07 | A | N |
| ATOM | 924 | C | ASN | 263 | 123.657 | 18.684 | -5.012 | 1.00 | 50.14 | A | C |
| ATOM | 925 | O | ASN | 263 | 124.574 | 19.286 | -5.572 | 1.00 | 49.04 | A | O |
| ATOM | 926 | N | TYR | 264 | 122.915 | 17.754 | -5.601 | 1.00 | 83.05 | A | N |
| ATOM | 927 | CA | TYR | 264 | 123.112 | 17.330 | -6.976 | 1.00 | 80.90 | A | C |
| ATOM | 928 | CB | TYR | 264 | 121.905 | 16.512 | -7.431 | 1.00 | 165.37 | A | C |
| ATOM | 929 | CG | TYR | 264 | 121.684 | 15.297 | -6.568 | 1.00 | 165.37 | A | C |
| ATOM | 930 | CD1 | TYR | 264 | 121.294 | 15.427 | -5.234 | 1.00 | 165.37 | A | C |
| ATOM | 931 | CE1 | TYR | 264 | 121.137 | 14.312 | -4.419 | 1.00 | 165.37 | A | C |
| ATOM | 932 | CD2 | TYR | 264 | 121.909 | 14.016 | -7.067 | 1.00 | 165.37 | A | C |
| ATOM | 933 | CE2 | TYR | 264 | 121.753 | 12.892 | -6.262 | 1.00 | 165.37 | A | C |
| ATOM | 934 | CZ | TYR | 264 | 121.369 | 13.048 | -4.939 | 1.00 | 165.37 | A | C |
| ATOM | 935 | OH | TYR | 264 | 121.224 | 11.940 | -4.139 | 1.00 | 165.37 | A | O |
| ATOM | 936 | C | TYR | 264 | 123.396 | 18.439 | -7.977 | 1.00 | 79.55 | A | C |
| ATOM | 937 | O | TYR | 264 | 124.509 | 18.536 | -8.498 | 1.00 | 76.68 | A | O |
| ATOM | 938 | N | ARG | 265 | 122.406 | 19.283 | -8.245 | 1.00 | 83.26 | A | N |
| ATOM | 939 | CA | ARG | 265 | 122.605 | 20.340 | -9.224 | 1.00 | 82.16 | A | C |
| ATOM | 940 | CB | ARG | 265 | 121.297 | 20.636 | -9.957 | 1.00 | 36.62 | A | C |
| ATOM | 941 | CG | ARG | 265 | 120.182 | 21.225 | -9.142 | 1.00 | 37.07 | A | C |
| ATOM | 942 | CD | ARG | 265 | 119.267 | 21.953 | -10.110 | 1.00 | 38.90 | A | C |
| ATOM | 943 | NE | ARG | 265 | 118.140 | 22.620 | -9.464 | 1.00 | 44.29 | A | N |
| ATOM | 944 | CZ | ARG | 265 | 117.562 | 23.714 | -9.947 | 1.00 | 44.46 | A | C |
| ATOM | 945 | NH1 | ARG | 265 | 118.016 | 24.257 | -11.071 | 1.00 | 49.09 | A | N |
| ATOM | 946 | NH2 | ARG | 265 | 116.528 | 24.258 | -9.321 | 1.00 | 48.43 | A | N |
| ATOM | 947 | C | ARG | 265 | 123.211 | 21.644 | -8.720 | 1.00 | 81.41 | A | C |
| ATOM | 948 | O | ARG | 265 | 123.137 | 22.668 | -9.396 | 1.00 | 82.72 | A | O |
| ATOM | 949 | N | LEU | 266 | 123.819 | 21.614 | -7.543 | 1.00 | 27.19 | A | N |

Fig. 19: A-14

| | | | | | | | | | | |
|---|---|---|---|---|---|---|---|---|---|---|
| ATOM | 950 | CA | LEU | 266 | 124.435 | 22.815 | -7.003 | 1.00 | 28.76 | A C |
| ATOM | 951 | CB | LEU | 266 | 124.798 | 22.601 | -5.539 | 1.00 | 4.24 | A C |
| ATOM | 952 | CG | LEU | 266 | 125.336 | 23.820 | -4.797 | 1.00 | 3.45 | A C |
| ATOM | 953 | CD1 | LEU | 266 | 124.393 | 24.999 | -4.976 | 1.00 | 5.79 | A C |
| ATOM | 954 | CD2 | LEU | 266 | 125.502 | 23.466 | -3.320 | 1.00 | 1.87 | A C |
| ATOM | 955 | C | LEU | 266 | 125.684 | 23.084 | -7.828 | 1.00 | 31.58 | A C |
| ATOM | 956 | O | LEU | 266 | 126.086 | 24.226 | -8.022 | 1.00 | 31.46 | A O |
| ATOM | 957 | N | LYS | 267 | 126.286 | 22.007 | -8.317 | 1.00 | 45.65 | A N |
| ATOM | 958 | CA | LYS | 267 | 127.479 | 22.088 | -9.149 | 1.00 | 47.96 | A C |
| ATOM | 959 | CB | LYS | 267 | 127.949 | 20.673 | -9.497 | 1.00 | 72.30 | A C |
| ATOM | 960 | CG | LYS | 267 | 129.239 | 20.583 | -10.298 | 1.00 | 72.30 | A C |
| ATOM | 961 | CD | LYS | 267 | 130.428 | 20.277 | -9.403 | 1.00 | 72.30 | A C |
| ATOM | 962 | CE | LYS | 267 | 131.649 | 19.894 | -10.230 | 1.00 | 72.30 | A C |
| ATOM | 963 | NZ | LYS | 267 | 132.793 | 19.452 | -9.381 | 1.00 | 72.30 | A N |
| ATOM | 964 | C | LYS | 267 | 127.103 | 22.842 | -10.427 | 1.00 | 47.45 | A C |
| ATOM | 965 | O | LYS | 267 | 127.763 | 23.810 | -10.809 | 1.00 | 46.97 | A O |
| ATOM | 966 | N | GLN | 268 | 126.032 | 22.389 | -11.074 | 1.00 | 32.65 | A N |
| ATOM | 967 | CA | GLN | 268 | 125.553 | 22.999 | -12.303 | 1.00 | 31.62 | A C |
| ATOM | 968 | CB | GLN | 268 | 124.292 | 22.295 | -12.798 | 1.00 | 88.56 | A C |
| ATOM | 969 | CG | GLN | 268 | 124.449 | 20.845 | -13.182 | 1.00 | 88.56 | A C |
| ATOM | 970 | CD | GLN | 268 | 123.119 | 20.227 | -13.576 | 1.00 | 88.56 | A C |
| ATOM | 971 | OE1 | GLN | 268 | 123.059 | 19.078 | -14.010 | 1.00 | 88.56 | A O |
| ATOM | 972 | NE2 | GLN | 268 | 122.041 | 20.992 | -13.423 | 1.00 | 88.56 | A N |
| ATOM | 973 | C | GLN | 268 | 125.221 | 24.474 | -12.100 | 1.00 | 27.37 | A C |
| ATOM | 974 | O | GLN | 268 | 125.678 | 25.332 | -12.851 | 1.00 | 28.55 | A O |
| ATOM | 975 | N | VAL | 269 | 124.410 | 24.767 | -11.089 | 1.00 | 11.19 | A N |
| ATOM | 976 | CA | VAL | 269 | 124.007 | 26.140 | -10.830 | 1.00 | 8.94 | A C |
| ATOM | 977 | CB | VAL | 269 | 123.088 | 26.223 | -9.598 | 1.00 | 22.95 | A C |
| ATOM | 978 | CG1 | VAL | 269 | 122.650 | 27.667 | -9.374 | 1.00 | 18.60 | A C |
| ATOM | 979 | CG2 | VAL | 269 | 121.872 | 25.334 | -9.801 | 1.00 | 20.81 | A C |
| ATOM | 980 | C | VAL | 269 | 125.198 | 27.076 | -10.649 | 1.00 | 8.53 | A C |
| ATOM | 981 | O | VAL | 269 | 125.286 | 28.093 | -11.318 | 1.00 | 11.37 | A O |
| ATOM | 982 | N | ILE | 270 | 126.114 | 26.744 | -9.746 | 1.00 | 5.57 | A N |
| ATOM | 983 | CA | ILE | 270 | 127.291 | 27.585 | -9.535 | 1.00 | 6.19 | A C |
| ATOM | 984 | CB | ILE | 270 | 128.281 | 26.944 | -8.533 | 1.00 | 12.81 | A C |
| ATOM | 985 | CG2 | ILE | 270 | 129.592 | 27.731 | -8.504 | 1.00 | 7.43 | A C |
| ATOM | 986 | CG1 | ILE | 270 | 127.671 | 26.926 | -7.135 | 1.00 | 10.37 | A C |
| ATOM | 987 | CD1 | ILE | 270 | 127.367 | 28.317 | -6.591 | 1.00 | 11.49 | A C |
| ATOM | 988 | C | ILE | 270 | 128.001 | 27.775 | -10.870 | 1.00 | 10.06 | A C |
| ATOM | 989 | O | ILE | 270 | 128.549 | 28.838 | -11.140 | 1.00 | 8.84 | A O |
| ATOM | 990 | N | GLN | 271 | 127.981 | 26.729 | -11.696 | 1.00 | 7.96 | A N |
| ATOM | 991 | CA | GLN | 271 | 128.605 | 26.751 | -13.011 | 1.00 | 10.02 | A C |
| ATOM | 992 | CB | GLN | 271 | 128.434 | 25.394 | -13.698 | 1.00 | 84.89 | A C |
| ATOM | 993 | CG | GLN | 271 | 129.267 | 25.214 | -14.947 | 1.00 | 86.79 | A C |
| ATOM | 994 | CD | GLN | 271 | 130.744 | 25.366 | -14.665 | 1.00 | 89.29 | A C |
| ATOM | 995 | OE1 | GLN | 271 | 131.244 | 26.477 | -14.506 | 1.00 | 89.62 | A O |
| ATOM | 996 | NE2 | GLN | 271 | 131.451 | 24.243 | -14.583 | 1.00 | 90.86 | A N |
| ATOM | 997 | C | GLN | 271 | 127.962 | 27.842 | -13.860 | 1.00 | 12.48 | A C |
| ATOM | 998 | O | GLN | 271 | 128.644 | 28.733 | -14.348 | 1.00 | 15.17 | A O |
| ATOM | 999 | N | ASP | 272 | 126.648 | 27.770 | -14.031 | 1.00 | 33.57 | A N |
| ATOM | 1000 | CA | ASP | 272 | 125.929 | 28.758 | -14.818 | 1.00 | 34.85 | A C |
| ATOM | 1001 | CB | ASP | 272 | 124.430 | 28.459 | -14.786 | 1.00 | 74.39 | A C |
| ATOM | 1002 | CG | ASP | 272 | 124.084 | 27.142 | -15.454 | 1.00 | 76.01 | A C |
| ATOM | 1003 | OD1 | ASP | 272 | 123.000 | 26.589 | -15.163 | 1.00 | 78.08 | A O |
| ATOM | 1004 | OD2 | ASP | 272 | 124.893 | 26.665 | -16.278 | 1.00 | 82.27 | A O |
| ATOM | 1005 | C | ASP | 272 | 126.194 | 30.163 | -14.283 | 1.00 | 35.65 | A C |
| ATOM | 1006 | O | ASP | 272 | 126.190 | 31.131 | -15.042 | 1.00 | 33.10 | A O |
| ATOM | 1007 | N | CYS | 273 | 126.426 | 30.280 | -12.978 | 1.00 | 42.88 | A N |
| ATOM | 1008 | CA | CYS | 273 | 126.698 | 31.582 | -12.387 | 1.00 | 41.31 | A C |
| ATOM | 1009 | CB | CYS | 273 | 126.630 | 31.516 | -10.862 | 1.00 | 24.14 | A C |
| ATOM | 1010 | SG | CYS | 273 | 124.940 | 31.489 | -10.191 | 1.00 | 22.24 | A S |
| ATOM | 1011 | C | CYS | 273 | 128.059 | 32.090 | -12.826 | 1.00 | 41.68 | A C |
| ATOM | 1012 | O | CYS | 273 | 128.244 | 33.288 | -13.008 | 1.00 | 35.99 | A O |
| ATOM | 1013 | N | GLU | 274 | 129.010 | 31.178 | -12.994 | 1.00 | 20.07 | A N |
| ATOM | 1014 | CA | GLU | 274 | 130.364 | 31.531 | -13.440 | 1.00 | 22.87 | A C |
| ATOM | 1015 | CB | GLU | 274 | 131.317 | 30.338 | -13.298 | 1.00 | 39.18 | A C |
| ATOM | 1016 | CG | GLU | 274 | 132.090 | 30.309 | -11.989 | 1.00 | 44.30 | A C |
| ATOM | 1017 | CD | GLU | 274 | 133.041 | 31.490 | -11.836 | 1.00 | 49.41 | A C |
| ATOM | 1018 | OE1 | GLU | 274 | 133.622 | 31.659 | -10.740 | 1.00 | 51.28 | A O |
| ATOM | 1019 | OE2 | GLU | 274 | 133.212 | 32.251 | -12.812 | 1.00 | 53.97 | A O |
| ATOM | 1020 | C | GLU | 274 | 130.345 | 31.984 | -14.893 | 1.00 | 25.29 | A C |
| ATOM | 1021 | O | GLU | 274 | 131.031 | 32.931 | -15.266 | 1.00 | 27.49 | A O |
| ATOM | 1022 | N | ASP | 275 | 129.550 | 31.298 | -15.707 | 1.00 | 41.03 | A N |

Fig. 19: A-15

```
ATOM   1023  CA   ASP  275    129.421  31.625 -17.119  1.00   39.77   A    C
ATOM   1024  CB   ASP  275    128.538  30.594 -17.822  1.00   63.42   A    C
ATOM   1025  CG   ASP  275    129.106  29.203 -17.757  1.00   64.69   A    C
ATOM   1026  OD1  ASP  275    129.987  28.959 -16.906  1.00   68.39   A    O
ATOM   1027  OD2  ASP  275    128.657  28.352 -18.551  1.00   66.35   A    O
ATOM   1028  C    ASP  275    128.789  32.996 -17.295  1.00   38.76   A    C
ATOM   1029  O    ASP  275    128.883  33.595 -18.367  1.00   34.31   A    O
ATOM   1030  N    GLU  276    128.137  33.485 -16.247  1.00   28.36   A    N
ATOM   1031  CA   GLU  276    127.479  34.771 -16.328  1.00   28.01   A    C
ATOM   1032  CB   GLU  276    126.019  34.617 -15.913  1.00   53.33   A    C
ATOM   1033  CG   GLU  276    125.310  33.520 -16.700  1.00   53.20   A    C
ATOM   1034  CD   GLU  276    123.807  33.493 -16.487  1.00   54.30   A    C
ATOM   1035  OE1  GLU  276    123.150  32.629 -17.102  1.00   55.01   A    O
ATOM   1036  OE2  GLU  276    123.280  34.330 -15.717  1.00   51.24   A    O
ATOM   1037  C    GLU  276    128.172  35.841 -15.504  1.00   26.84   A    C
ATOM   1038  O    GLU  276    127.621  36.919 -15.288  1.00   27.95   A    O
ATOM   1039  N    ASN  277    129.382  35.535 -15.050  1.00   28.50   A    N
ATOM   1040  CA   ASN  277    130.185  36.472 -14.268  1.00   28.47   A    C
ATOM   1041  CB   ASN  277    130.607  37.655 -15.140  1.00   86.35   A    C
ATOM   1042  CG   ASN  277    131.230  37.218 -16.439  1.00   91.27   A    C
ATOM   1043  OD1  ASN  277    132.263  36.548 -16.451  1.00   91.09   A    O
ATOM   1044  ND2  ASN  277    130.601  37.589 -17.550  1.00   90.23   A    N
ATOM   1045  C    ASN  277    129.493  37.014 -13.018  1.00   24.82   A    C
ATOM   1046  O    ASN  277    129.476  38.226 -12.790  1.00   25.80   A    O
ATOM   1047  N    ILE  278    128.925  36.127 -12.207  1.00   15.37   A    N
ATOM   1048  CA   ILE  278    128.261  36.560 -10.989  1.00   15.82   A    C
ATOM   1049  CB   ILE  278    126.963  35.773 -10.747  1.00   17.43   A    C
ATOM   1050  CG2  ILE  278    126.304  36.243  -9.454  1.00   18.82   A    C
ATOM   1051  CG1  ILE  278    126.016  35.949 -11.932  1.00   14.88   A    C
ATOM   1052  CD1  ILE  278    124.742  35.153 -11.796  1.00   17.16   A    C
ATOM   1053  C    ILE  278    129.168  36.345  -9.780  1.00   16.42   A    C
ATOM   1054  O    ILE  278    129.363  35.212  -9.354  1.00   16.76   A    O
ATOM   1055  N    GLN  279    129.737  37.426  -9.244  1.00   26.25   A    N
ATOM   1056  CA   GLN  279    130.578  37.335  -8.053  1.00   25.85   A    C
ATOM   1057  CB   GLN  279    131.035  38.716  -7.605  1.00   41.76   A    C
ATOM   1058  CG   GLN  279    131.959  39.382  -8.574  1.00   47.54   A    C
ATOM   1059  CD   GLN  279    133.158  38.524  -8.894  1.00   51.46   A    C
ATOM   1060  OE1  GLN  279    133.992  38.255  -8.023  1.00   45.70   A    O
ATOM   1061  NE2  GLN  279    133.252  38.078 -10.146  1.00   51.05   A    N
ATOM   1062  C    GLN  279    129.716  36.736  -6.958  1.00   23.72   A    C
ATOM   1063  O    GLN  279    128.609  37.216  -6.692  1.00   20.64   A    O
ATOM   1064  N    ARG  280    130.214  35.697  -6.310  1.00   16.06   A    N
ATOM   1065  CA   ARG  280    129.440  35.054  -5.258  1.00   17.58   A    C
ATOM   1066  CB   ARG  280    129.107  33.620  -5.661  1.00   19.51   A    C
ATOM   1067  CG   ARG  280    128.413  33.488  -6.997  1.00   18.14   A    C
ATOM   1068  CD   ARG  280    128.274  32.021  -7.371  1.00   17.81   A    C
ATOM   1069  NE   ARG  280    129.576  31.365  -7.441  1.00   14.86   A    N
ATOM   1070  CZ   ARG  280    130.427  31.489  -8.452  1.00   18.77   A    C
ATOM   1071  NH1  ARG  280    130.131  32.241  -9.493  1.00   21.69   A    N
ATOM   1072  NH2  ARG  280    131.579  30.846  -8.422  1.00   23.71   A    N
ATOM   1073  C    ARG  280    130.123  35.037  -3.892  1.00   17.24   A    C
ATOM   1074  O    ARG  280    131.269  34.592  -3.750  1.00   16.97   A    O
ATOM   1075  N    PHE  281    129.406  35.539  -2.894  1.00   21.33   A    N
ATOM   1076  CA   PHE  281    129.889  35.538  -1.527  1.00   23.32   A    C
ATOM   1077  CB   PHE  281    129.848  36.933  -0.924  1.00   12.57   A    C
ATOM   1078  CG   PHE  281    130.754  37.900  -1.603  1.00   15.70   A    C
ATOM   1079  CD1  PHE  281    130.419  38.434  -2.837  1.00   19.55   A    C
ATOM   1080  CD2  PHE  281    131.968  38.250  -1.024  1.00   17.43   A    C
ATOM   1081  CE1  PHE  281    131.281  39.305  -3.487  1.00   19.61   A    C
ATOM   1082  CE2  PHE  281    132.842  39.120  -1.665  1.00   15.16   A    C
ATOM   1083  CZ   PHE  281    132.498  39.650  -2.900  1.00   16.59   A    C
ATOM   1084  C    PHE  281    128.925  34.646  -0.785  1.00   24.03   A    C
ATOM   1085  O    PHE  281    127.710  34.867  -0.821  1.00   26.40   A    O
ATOM   1086  N    SER  282    129.449  33.613  -0.141  1.00   13.47   A    N
ATOM   1087  CA   SER  282    128.594  32.705   0.602  1.00   15.32   A    C
ATOM   1088  CB   SER  282    128.746  31.272   0.084  1.00   11.38   A    C
ATOM   1089  OG   SER  282    130.081  30.816   0.216  1.00    7.93   A    O
ATOM   1090  C    SER  282    128.947  32.782   2.069  1.00   17.20   A    C
ATOM   1091  O    SER  282    130.066  33.135   2.435  1.00   21.06   A    O
ATOM   1092  N    ILE  283    127.969  32.477   2.908  1.00   24.08   A    N
ATOM   1093  CA   ILE  283    128.164  32.504   4.343  1.00   22.00   A    C
ATOM   1094  CB   ILE  283    127.517  33.733   4.968  1.00   17.91   A    C
ATOM   1095  CG2  ILE  283    127.843  33.791   6.442  1.00   18.72   A    C
```

Fig. 19: A-16

| ATOM | 1096 | CG1 | ILE | 283 | 128.045 | 34.986 | 4.281 | 1.00 | 14.38 | A | C |
|---|---|---|---|---|---|---|---|---|---|---|---|
| ATOM | 1097 | CD1 | ILE | 283 | 127.103 | 36.171 | 4.383 | 1.00 | 17.94 | A | C |
| ATOM | 1098 | C | ILE | 283 | 127.510 | 31.273 | 4.912 | 1.00 | 21.07 | A | C |
| ATOM | 1099 | O | ILE | 283 | 126.394 | 30.917 | 4.536 | 1.00 | 20.93 | A | O |
| ATOM | 1100 | N | ALA | 284 | 128.204 | 30.618 | 5.823 | 1.00 | 29.93 | A | N |
| ATOM | 1101 | CA | ALA | 284 | 127.663 | 29.421 | 6.412 | 1.00 | 29.95 | A | C |
| ATOM | 1102 | CB | ALA | 284 | 128.548 | 28.253 | 6.070 | 1.00 | 1.87 | A | C |
| ATOM | 1103 | C | ALA | 284 | 127.507 | 29.536 | 7.920 | 1.00 | 28.08 | A | C |
| ATOM | 1104 | O | ALA | 284 | 128.482 | 29.740 | 8.641 | 1.00 | 26.74 | A | O |
| ATOM | 1105 | N | ILE | 285 | 126.270 | 29.422 | 8.389 | 1.00 | 31.23 | A | N |
| ATOM | 1106 | CA | ILE | 285 | 125.997 | 29.457 | 9.817 | 1.00 | 25.43 | A | C |
| ATOM | 1107 | CB | ILE | 285 | 124.529 | 29.859 | 10.107 | 1.00 | 43.54 | A | C |
| ATOM | 1108 | CG2 | ILE | 285 | 124.187 | 29.569 | 11.555 | 1.00 | 38.36 | A | C |
| ATOM | 1109 | CG1 | ILE | 285 | 124.306 | 31.344 | 9.791 | 1.00 | 38.87 | A | C |
| ATOM | 1110 | CD1 | ILE | 285 | 124.206 | 31.670 | 8.315 | 1.00 | 40.01 | A | C |
| ATOM | 1111 | C | ILE | 285 | 126.227 | 28.022 | 10.296 | 1.00 | 28.75 | A | C |
| ATOM | 1112 | O | ILE | 285 | 125.523 | 27.106 | 9.872 | 1.00 | 30.49 | A | O |
| ATOM | 1113 | N | LEU | 286 | 127.205 | 27.818 | 11.169 | 1.00 | 38.23 | A | N |
| ATOM | 1114 | CA | LEU | 286 | 127.497 | 26.471 | 11.649 | 1.00 | 38.71 | A | C |
| ATOM | 1115 | CB | LEU | 286 | 128.999 | 26.313 | 11.876 | 1.00 | 50.51 | A | C |
| ATOM | 1116 | CG | LEU | 286 | 129.917 | 26.722 | 10.727 | 1.00 | 53.33 | A | C |
| ATOM | 1117 | CD1 | LEU | 286 | 131.340 | 26.363 | 11.105 | 1.00 | 55.89 | A | C |
| ATOM | 1118 | CD2 | LEU | 286 | 129.513 | 26.019 | 9.441 | 1.00 | 55.00 | A | C |
| ATOM | 1119 | C | LEU | 286 | 126.760 | 26.069 | 12.923 | 1.00 | 39.16 | A | C |
| ATOM | 1120 | O | LEU | 286 | 127.068 | 25.036 | 13.517 | 1.00 | 40.00 | A | O |
| ATOM | 1121 | N | GLY | 287 | 125.789 | 26.875 | 13.339 | 1.00 | 72.80 | A | N |
| ATOM | 1122 | CA | GLY | 287 | 125.042 | 26.579 | 14.551 | 1.00 | 71.58 | A | C |
| ATOM | 1123 | C | GLY | 287 | 124.586 | 25.139 | 14.700 | 1.00 | 69.16 | A | C |
| ATOM | 1124 | O | GLY | 287 | 125.056 | 24.419 | 15.583 | 1.00 | 73.26 | A | O |
| ATOM | 1125 | N | THR | 296 | 131.112 | 19.210 | 10.542 | 1.00 | 87.02 | A | N |
| ATOM | 1126 | CA | THR | 296 | 130.609 | 20.333 | 9.766 | 1.00 | 87.06 | A | C |
| ATOM | 1127 | CB | THR | 296 | 130.702 | 21.652 | 10.554 | 1.00 | 100.17 | A | C |
| ATOM | 1128 | OG1 | THR | 296 | 132.071 | 21.903 | 10.895 | 1.00 | 105.23 | A | O |
| ATOM | 1129 | CG2 | THR | 296 | 129.861 | 21.592 | 11.817 | 1.00 | 100.04 | A | C |
| ATOM | 1130 | C | THR | 296 | 131.387 | 20.535 | 8.479 | 1.00 | 88.04 | A | C |
| ATOM | 1131 | O | THR | 296 | 130.985 | 21.331 | 7.631 | 1.00 | 86.85 | A | O |
| ATOM | 1132 | N | GLU | 297 | 132.497 | 19.825 | 8.322 | 1.00 | 78.34 | A | N |
| ATOM | 1133 | CA | GLU | 297 | 133.304 | 20.020 | 7.128 | 1.00 | 81.80 | A | C |
| ATOM | 1134 | CB | GLU | 297 | 134.577 | 19.171 | 7.169 | 1.00 | 125.47 | A | C |
| ATOM | 1135 | CG | GLU | 297 | 134.403 | 17.709 | 6.851 | 1.00 | 132.50 | A | C |
| ATOM | 1136 | CD | GLU | 297 | 135.690 | 17.103 | 6.342 | 1.00 | 133.75 | A | C |
| ATOM | 1137 | OE1 | GLU | 297 | 135.709 | 15.886 | 6.067 | 1.00 | 135.24 | A | O |
| ATOM | 1138 | OE2 | GLU | 297 | 136.682 | 17.853 | 6.212 | 1.00 | 137.19 | A | O |
| ATOM | 1139 | C | GLU | 297 | 132.550 | 19.770 | 5.832 | 1.00 | 79.84 | A | C |
| ATOM | 1140 | O | GLU | 297 | 132.581 | 20.609 | 4.931 | 1.00 | 79.34 | A | O |
| ATOM | 1141 | N | LYS | 298 | 131.865 | 18.638 | 5.728 | 1.00 | 42.69 | A | N |
| ATOM | 1142 | CA | LYS | 298 | 131.125 | 18.352 | 4.505 | 1.00 | 42.69 | A | C |
| ATOM | 1143 | CB | LYS | 298 | 130.281 | 17.087 | 4.678 | 1.00 | 102.63 | A | C |
| ATOM | 1144 | CG | LYS | 298 | 129.695 | 16.562 | 3.376 | 1.00 | 111.34 | A | C |
| ATOM | 1145 | CD | LYS | 298 | 129.117 | 15.166 | 3.545 | 1.00 | 113.06 | A | C |
| ATOM | 1146 | CE | LYS | 298 | 130.167 | 14.187 | 4.057 | 1.00 | 116.88 | A | C |
| ATOM | 1147 | NZ | LYS | 298 | 131.378 | 14.159 | 3.195 | 1.00 | 121.20 | A | N |
| ATOM | 1148 | C | LYS | 298 | 130.228 | 19.547 | 4.143 | 1.00 | 40.29 | A | C |
| ATOM | 1149 | O | LYS | 298 | 130.032 | 19.853 | 2.964 | 1.00 | 41.17 | A | O |
| ATOM | 1150 | N | PHE | 299 | 129.700 | 20.218 | 5.167 | 1.00 | 38.43 | A | N |
| ATOM | 1151 | CA | PHE | 299 | 128.839 | 21.380 | 4.978 | 1.00 | 36.67 | A | C |
| ATOM | 1152 | CB | PHE | 299 | 128.100 | 21.712 | 6.283 | 1.00 | 55.97 | A | C |
| ATOM | 1153 | CG | PHE | 299 | 127.256 | 22.967 | 6.209 | 1.00 | 48.41 | A | C |
| ATOM | 1154 | CD1 | PHE | 299 | 126.319 | 23.146 | 5.186 | 1.00 | 44.86 | A | C |
| ATOM | 1155 | CD2 | PHE | 299 | 127.400 | 23.970 | 7.160 | 1.00 | 46.14 | A | C |
| ATOM | 1156 | CE1 | PHE | 299 | 125.545 | 24.307 | 5.117 | 1.00 | 44.27 | A | C |
| ATOM | 1157 | CE2 | PHE | 299 | 126.627 | 25.132 | 7.095 | 1.00 | 40.55 | A | C |
| ATOM | 1158 | CZ | PHE | 299 | 125.701 | 25.299 | 6.073 | 1.00 | 39.06 | A | C |
| ATOM | 1159 | C | PHE | 299 | 129.684 | 22.573 | 4.544 | 1.00 | 37.02 | A | C |
| ATOM | 1160 | O | PHE | 299 | 129.439 | 23.190 | 3.504 | 1.00 | 32.83 | A | O |
| ATOM | 1161 | N | VAL | 300 | 130.682 | 22.896 | 5.352 | 1.00 | 13.94 | A | N |
| ATOM | 1162 | CA | VAL | 300 | 131.551 | 24.010 | 5.034 | 1.00 | 18.89 | A | C |
| ATOM | 1163 | CB | VAL | 300 | 132.752 | 24.068 | 5.993 | 1.00 | 40.51 | A | C |
| ATOM | 1164 | CG1 | VAL | 300 | 133.769 | 25.076 | 5.493 | 1.00 | 44.08 | A | C |
| ATOM | 1165 | CG2 | VAL | 300 | 132.282 | 24.451 | 7.382 | 1.00 | 44.52 | A | C |
| ATOM | 1166 | C | VAL | 300 | 132.061 | 23.893 | 3.607 | 1.00 | 17.53 | A | C |
| ATOM | 1167 | O | VAL | 300 | 132.177 | 24.889 | 2.906 | 1.00 | 18.03 | A | O |
| ATOM | 1168 | N | GLU | 301 | 132.365 | 22.679 | 3.164 | 1.00 | 18.30 | A | N |

Fig. 19: A-17

| ATOM | 1169 | CA  | GLU | 301 | 132.866 | 22.513 | 1.808  | 1.00 | 18.96 | A | C |
|------|------|-----|-----|-----|---------|--------|--------|------|-------|---|---|
| ATOM | 1170 | CB  | GLU | 301 | 133.407 | 21.094 | 1.605  | 1.00 | 40.16 | A | C |
| ATOM | 1171 | CG  | GLU | 301 | 134.058 | 20.854 | 0.243  | 1.00 | 42.43 | A | C |
| ATOM | 1172 | CD  | GLU | 301 | 135.049 | 21.943 | -0.155 | 1.00 | 48.24 | A | C |
| ATOM | 1173 | OE1 | GLU | 301 | 135.956 | 22.267 | 0.645  | 1.00 | 47.79 | A | O |
| ATOM | 1174 | OE2 | GLU | 301 | 134.918 | 22.469 | -1.282 | 1.00 | 50.51 | A | O |
| ATOM | 1175 | C   | GLU | 301 | 131.770 | 22.832 | 0.791  | 1.00 | 17.53 | A | C |
| ATOM | 1176 | O   | GLU | 301 | 132.034 | 23.458 | -0.242 | 1.00 | 15.61 | A | O |
| ATOM | 1177 | N   | GLU | 302 | 130.541 | 22.420 | 1.097  | 1.00 | 32.12 | A | N |
| ATOM | 1178 | CA  | GLU | 302 | 129.412 | 22.667 | 0.210  | 1.00 | 31.93 | A | C |
| ATOM | 1179 | CB  | GLU | 302 | 128.127 | 22.084 | 0.801  | 1.00 | 76.04 | A | C |
| ATOM | 1180 | CG  | GLU | 302 | 126.894 | 22.274 | -0.071 | 1.00 | 75.79 | A | C |
| ATOM | 1181 | CD  | GLU | 302 | 125.659 | 21.594 | 0.501  | 1.00 | 72.72 | A | C |
| ATOM | 1182 | OE1 | GLU | 302 | 125.651 | 20.349 | 0.584  | 1.00 | 72.70 | A | O |
| ATOM | 1183 | OE2 | GLU | 302 | 124.698 | 22.302 | 0.872  | 1.00 | 77.14 | A | O |
| ATOM | 1184 | C   | GLU | 302 | 129.237 | 24.158 | -0.033 | 1.00 | 35.00 | A | C |
| ATOM | 1185 | O   | GLU | 302 | 129.040 | 24.580 | -1.170 | 1.00 | 34.26 | A | O |
| ATOM | 1186 | N   | ILE | 303 | 129.334 | 24.953 | 1.031  | 1.00 | 23.69 | A | N |
| ATOM | 1187 | CA  | ILE | 303 | 129.171 | 26.405 | 0.936  | 1.00 | 23.74 | A | C |
| ATOM | 1188 | CB  | ILE | 303 | 128.933 | 27.019 | 2.326  | 1.00 | 28.42 | A | C |
| ATOM | 1189 | CG2 | ILE | 303 | 128.555 | 28.480 | 2.199  | 1.00 | 23.60 | A | C |
| ATOM | 1190 | CG1 | ILE | 303 | 127.823 | 26.245 | 3.046  | 1.00 | 26.02 | A | C |
| ATOM | 1191 | CD1 | ILE | 303 | 126.599 | 25.926 | 2.183  | 1.00 | 22.48 | A | C |
| ATOM | 1192 | C   | ILE | 303 | 130.340 | 27.129 | 0.267  | 1.00 | 25.77 | A | C |
| ATOM | 1193 | O   | ILE | 303 | 130.133 | 28.036 | -0.553 | 1.00 | 28.26 | A | O |
| ATOM | 1194 | N   | LYS | 304 | 131.564 | 26.740 | 0.612  | 1.00 | 28.18 | A | N |
| ATOM | 1195 | CA  | LYS | 304 | 132.733 | 27.363 | 0.003  | 1.00 | 28.98 | A | C |
| ATOM | 1196 | CB  | LYS | 304 | 134.018 | 26.713 | 0.501  | 1.00 | 31.11 | A | C |
| ATOM | 1197 | CG  | LYS | 304 | 134.415 | 27.051 | 1.915  | 1.00 | 37.78 | A | C |
| ATOM | 1198 | CD  | LYS | 304 | 135.810 | 26.502 | 2.199  | 1.00 | 39.31 | A | C |
| ATOM | 1199 | CE  | LYS | 304 | 136.298 | 26.803 | 3.599  | 1.00 | 42.04 | A | C |
| ATOM | 1200 | NZ  | LYS | 304 | 137.673 | 26.262 | 3.857  | 1.00 | 44.22 | A | N |
| ATOM | 1201 | C   | LYS | 304 | 132.665 | 27.210 | -1.512 | 1.00 | 25.07 | A | C |
| ATOM | 1202 | O   | LYS | 304 | 133.033 | 28.118 | -2.252 | 1.00 | 29.15 | A | O |
| ATOM | 1203 | N   | SER | 305 | 132.195 | 26.054 | -1.965 | 1.00 | 30.32 | A | N |
| ATOM | 1204 | CA  | SER | 305 | 132.100 | 25.785 | -3.386 | 1.00 | 27.48 | A | C |
| ATOM | 1205 | CB  | SER | 305 | 131.702 | 24.329 | -3.635 | 1.00 | 18.09 | A | C |
| ATOM | 1206 | OG  | SER | 305 | 130.352 | 24.088 | -3.293 | 1.00 | 14.77 | A | O |
| ATOM | 1207 | C   | SER | 305 | 131.094 | 26.709 | -4.044 | 1.00 | 28.00 | A | C |
| ATOM | 1208 | O   | SER | 305 | 131.137 | 26.917 | -5.263 | 1.00 | 30.57 | A | O |
| ATOM | 1209 | N   | ILE | 306 | 130.181 | 27.258 | -3.247 | 1.00 | 37.08 | A | N |
| ATOM | 1210 | CA  | ILE | 306 | 129.180 | 28.176 | -3.783 | 1.00 | 33.83 | A | C |
| ATOM | 1211 | CB  | ILE | 306 | 127.990 | 28.319 | -2.831 | 1.00 | 15.00 | A | C |
| ATOM | 1212 | CG2 | ILE | 306 | 127.190 | 29.565 | -3.167 | 1.00 | 15.73 | A | C |
| ATOM | 1213 | CG1 | ILE | 306 | 127.118 | 27.069 | -2.929 | 1.00 | 17.63 | A | C |
| ATOM | 1214 | CD1 | ILE | 306 | 125.993 | 27.029 | -1.916 | 1.00 | 15.34 | A | C |
| ATOM | 1215 | C   | ILE | 306 | 129.812 | 29.544 | -4.008 | 1.00 | 31.59 | A | C |
| ATOM | 1216 | O   | ILE | 306 | 129.361 | 30.333 | -4.851 | 1.00 | 32.12 | A | O |
| ATOM | 1217 | N   | ALA | 307 | 130.874 | 29.805 | -3.251 | 1.00 | 20.26 | A | N |
| ATOM | 1218 | CA  | ALA | 307 | 131.584 | 31.062 | -3.349 | 1.00 | 22.45 | A | C |
| ATOM | 1219 | CB  | ALA | 307 | 132.444 | 31.260 | -2.118 | 1.00 | 5.65  | A | C |
| ATOM | 1220 | C   | ALA | 307 | 132.441 | 31.113 | -4.611 | 1.00 | 22.11 | A | C |
| ATOM | 1221 | O   | ALA | 307 | 132.622 | 30.103 | -5.302 | 1.00 | 21.10 | A | O |
| ATOM | 1222 | N   | SER | 308 | 132.953 | 32.307 | -4.906 | 1.00 | 24.29 | A | N |
| ATOM | 1223 | CA  | SER | 308 | 133.796 | 32.533 | -6.072 | 1.00 | 27.22 | A | C |
| ATOM | 1224 | CB  | SER | 308 | 133.489 | 33.899 | -6.700 | 1.00 | 15.61 | A | C |
| ATOM | 1225 | OG  | SER | 308 | 132.299 | 33.860 | -7.460 | 1.00 | 19.00 | A | O |
| ATOM | 1226 | C   | SER | 308 | 135.264 | 32.482 | -5.690 | 1.00 | 30.87 | A | C |
| ATOM | 1227 | O   | SER | 308 | 135.625 | 32.797 | -4.555 | 1.00 | 28.21 | A | O |
| ATOM | 1228 | N   | GLU | 309 | 136.103 | 32.069 | -6.640 | 1.00 | 26.43 | A | N |
| ATOM | 1229 | CA  | GLU | 309 | 137.542 | 32.008 | -6.418 | 1.00 | 29.92 | A | C |
| ATOM | 1230 | CB  | GLU | 309 | 138.224 | 31.266 | -7.569 | 1.00 | 73.14 | A | C |
| ATOM | 1231 | CG  | GLU | 309 | 137.811 | 29.809 | -7.737 | 1.00 | 78.51 | A | C |
| ATOM | 1232 | CD  | GLU | 309 | 138.181 | 28.950 | -6.541 | 1.00 | 81.27 | A | C |
| ATOM | 1233 | OE1 | GLU | 309 | 138.103 | 27.708 | -6.651 | 1.00 | 83.60 | A | O |
| ATOM | 1234 | OE2 | GLU | 309 | 138.544 | 29.514 | -5.487 | 1.00 | 85.42 | A | O |
| ATOM | 1235 | C   | GLU | 309 | 138.009 | 33.461 | -6.396 | 1.00 | 30.67 | A | C |
| ATOM | 1236 | O   | GLU | 309 | 137.580 | 34.257 | -7.230 | 1.00 | 32.32 | A | O |
| ATOM | 1237 | N   | PRO | 310 | 138.882 | 33.834 | -5.442 | 1.00 | 19.51 | A | N |
| ATOM | 1238 | CD  | PRO | 310 | 139.395 | 35.217 | -5.381 | 1.00 | 49.07 | A | C |
| ATOM | 1239 | CA  | PRO | 310 | 139.483 | 33.029 | -4.377 | 1.00 | 19.70 | A | C |
| ATOM | 1240 | CB  | PRO | 310 | 140.703 | 33.851 | -3.982 | 1.00 | 50.90 | A | C |
| ATOM | 1241 | CG  | PRO | 310 | 140.182 | 35.231 | -4.065 | 1.00 | 50.46 | A | C |

Fig. 19: A-18

| ATOM | 1242 | C | PRO | 310 | 138.569 | 32.751 | -3.178 | 1.00 | 20.19 | A | C |
|---|---|---|---|---|---|---|---|---|---|---|---|
| ATOM | 1243 | O | PRO | 310 | 138.229 | 33.654 | -2.394 | 1.00 | 16.98 | A | O |
| ATOM | 1244 | N | THR | 311 | 138.197 | 31.483 | -3.043 | 1.00 | 25.93 | A | N |
| ATOM | 1245 | CA | THR | 311 | 137.352 | 31.013 | -1.957 | 1.00 | 26.80 | A | C |
| ATOM | 1246 | CB | THR | 311 | 137.618 | 29.521 | -1.695 | 1.00 | 73.61 | A | C |
| ATOM | 1247 | OG1 | THR | 311 | 137.053 | 29.145 | -0.434 | 1.00 | 77.77 | A | O |
| ATOM | 1248 | CG2 | THR | 311 | 139.118 | 29.244 | -1.696 | 1.00 | 76.69 | A | C |
| ATOM | 1249 | C | THR | 311 | 137.521 | 31.781 | -0.643 | 1.00 | 28.67 | A | C |
| ATOM | 1250 | O | THR | 311 | 136.535 | 32.173 | -0.025 | 1.00 | 29.84 | A | O |
| ATOM | 1251 | N | GLU | 312 | 138.759 | 32.009 | -0.223 | 1.00 | 47.89 | A | N |
| ATOM | 1252 | CA | GLU | 312 | 139.007 | 32.713 | 1.029 | 1.00 | 46.51 | A | C |
| ATOM | 1253 | CB | GLU | 312 | 140.506 | 32.751 | 1.340 | 1.00 | 98.24 | A | C |
| ATOM | 1254 | CG | GLU | 312 | 141.354 | 33.411 | 0.268 | 1.00 | 100.00 | A | C |
| ATOM | 1255 | CD | GLU | 312 | 142.621 | 34.031 | 0.825 | 1.00 | 99.11 | A | C |
| ATOM | 1256 | OE1 | GLU | 312 | 143.491 | 34.431 | 0.024 | 1.00 | 102.46 | A | O |
| ATOM | 1257 | OE2 | GLU | 312 | 142.742 | 34.130 | 2.065 | 1.00 | 99.98 | A | O |
| ATOM | 1258 | C | GLU | 312 | 138.453 | 34.134 | 1.092 | 1.00 | 45.13 | A | C |
| ATOM | 1259 | O | GLU | 312 | 137.997 | 34.576 | 2.147 | 1.00 | 45.09 | A | O |
| ATOM | 1260 | N | LYS | 313 | 138.490 | 34.856 | -0.021 | 1.00 | 49.11 | A | N |
| ATOM | 1261 | CA | LYS | 313 | 137.990 | 36.226 | -0.024 | 1.00 | 48.31 | A | C |
| ATOM | 1262 | CB | LYS | 313 | 138.797 | 37.091 | -1.000 | 1.00 | 91.02 | A | C |
| ATOM | 1263 | CG | LYS | 313 | 140.171 | 37.508 | -0.486 | 1.00 | 90.90 | A | C |
| ATOM | 1264 | CD | LYS | 313 | 140.081 | 38.565 | 0.620 | 1.00 | 87.20 | A | C |
| ATOM | 1265 | CE | LYS | 313 | 139.966 | 39.982 | 0.066 | 1.00 | 89.24 | A | C |
| ATOM | 1266 | NZ | LYS | 313 | 138.804 | 40.159 | -0.842 | 1.00 | 93.72 | A | N |
| ATOM | 1267 | C | LYS | 313 | 136.511 | 36.307 | -0.374 | 1.00 | 49.46 | A | C |
| ATOM | 1268 | O | LYS | 313 | 135.973 | 37.397 | -0.580 | 1.00 | 51.78 | A | O |
| ATOM | 1269 | N | HIS | 314 | 135.849 | 35.159 | -0.427 | 1.00 | 27.67 | A | N |
| ATOM | 1270 | CA | HIS | 314 | 134.437 | 35.137 | -0.775 | 1.00 | 28.52 | A | C |
| ATOM | 1271 | CB | HIS | 314 | 134.274 | 34.652 | -2.212 | 1.00 | 32.51 | A | C |
| ATOM | 1272 | CG | HIS | 314 | 134.872 | 35.574 | -3.224 | 1.00 | 29.37 | A | C |
| ATOM | 1273 | CD2 | HIS | 314 | 136.073 | 35.552 | -3.849 | 1.00 | 28.84 | A | C |
| ATOM | 1274 | ND1 | HIS | 314 | 134.220 | 36.697 | -3.683 | 1.00 | 28.95 | A | N |
| ATOM | 1275 | CE1 | HIS | 314 | 134.992 | 37.326 | -4.551 | 1.00 | 28.24 | A | C |
| ATOM | 1276 | NE2 | HIS | 314 | 136.122 | 36.652 | -4.669 | 1.00 | 28.63 | A | N |
| ATOM | 1277 | C | HIS | 314 | 133.587 | 34.277 | 0.141 | 1.00 | 28.65 | A | C |
| ATOM | 1278 | O | HIS | 314 | 132.366 | 34.238 | -0.008 | 1.00 | 32.05 | A | O |
| ATOM | 1279 | N | PHE | 315 | 134.230 | 33.591 | 1.081 | 1.00 | 32.99 | A | N |
| ATOM | 1280 | CA | PHE | 315 | 133.519 | 32.723 | 2.013 | 1.00 | 32.79 | A | C |
| ATOM | 1281 | CB | PHE | 315 | 134.045 | 31.294 | 1.878 | 1.00 | 35.38 | A | C |
| ATOM | 1282 | CG | PHE | 315 | 133.476 | 30.339 | 2.884 | 1.00 | 30.36 | A | C |
| ATOM | 1283 | CD1 | PHE | 315 | 132.123 | 30.026 | 2.877 | 1.00 | 32.20 | A | C |
| ATOM | 1284 | CD2 | PHE | 315 | 134.298 | 29.749 | 3.839 | 1.00 | 28.44 | A | C |
| ATOM | 1285 | CE1 | PHE | 315 | 131.592 | 29.144 | 3.800 | 1.00 | 27.15 | A | C |
| ATOM | 1286 | CE2 | PHE | 315 | 133.783 | 28.866 | 4.769 | 1.00 | 29.14 | A | C |
| ATOM | 1287 | CZ | PHE | 315 | 132.421 | 28.560 | 4.749 | 1.00 | 30.81 | A | C |
| ATOM | 1288 | C | PHE | 315 | 133.640 | 33.198 | 3.466 | 1.00 | 33.51 | A | C |
| ATOM | 1289 | O | PHE | 315 | 134.706 | 33.643 | 3.896 | 1.00 | 34.91 | A | O |
| ATOM | 1290 | N | PHE | 316 | 132.539 | 33.104 | 4.210 | 1.00 | 26.09 | A | N |
| ATOM | 1291 | CA | PHE | 316 | 132.513 | 33.516 | 5.610 | 1.00 | 23.14 | A | C |
| ATOM | 1292 | CB | PHE | 316 | 131.707 | 34.803 | 5.780 | 1.00 | 27.51 | A | C |
| ATOM | 1293 | CG | PHE | 316 | 132.343 | 36.008 | 5.155 | 1.00 | 31.13 | A | C |
| ATOM | 1294 | CD1 | PHE | 316 | 132.125 | 36.312 | 3.822 | 1.00 | 26.72 | A | C |
| ATOM | 1295 | CD2 | PHE | 316 | 133.182 | 36.827 | 5.903 | 1.00 | 27.98 | A | C |
| ATOM | 1296 | CE1 | PHE | 316 | 132.737 | 37.420 | 3.237 | 1.00 | 29.29 | A | C |
| ATOM | 1297 | CE2 | PHE | 316 | 133.799 | 37.931 | 5.334 | 1.00 | 31.09 | A | C |
| ATOM | 1298 | CZ | PHE | 316 | 133.577 | 38.230 | 3.998 | 1.00 | 31.32 | A | C |
| ATOM | 1299 | C | PHE | 316 | 131.909 | 32.438 | 6.497 | 1.00 | 21.07 | A | C |
| ATOM | 1300 | O | PHE | 316 | 130.901 | 31.831 | 6.153 | 1.00 | 20.31 | A | O |
| ATOM | 1301 | N | ASN | 317 | 132.533 | 32.220 | 7.647 | 1.00 | 37.16 | A | N |
| ATOM | 1302 | CA | ASN | 317 | 132.093 | 31.214 | 8.599 | 1.00 | 38.38 | A | C |
| ATOM | 1303 | CB | ASN | 317 | 133.288 | 30.385 | 9.047 | 1.00 | 74.28 | A | C |
| ATOM | 1304 | CG | ASN | 317 | 133.055 | 28.919 | 8.888 | 1.00 | 77.27 | A | C |
| ATOM | 1305 | OD1 | ASN | 317 | 131.954 | 28.433 | 9.138 | 1.00 | 79.20 | A | O |
| ATOM | 1306 | ND2 | ASN | 317 | 134.088 | 28.190 | 8.478 | 1.00 | 75.53 | A | N |
| ATOM | 1307 | C | ASN | 317 | 131.487 | 31.893 | 9.817 | 1.00 | 39.34 | A | C |
| ATOM | 1308 | O | ASN | 317 | 132.001 | 32.902 | 10.285 | 1.00 | 40.20 | A | O |
| ATOM | 1309 | N | VAL | 318 | 130.398 | 31.348 | 10.336 | 1.00 | 30.64 | A | N |
| ATOM | 1310 | CA | VAL | 318 | 129.763 | 31.924 | 11.521 | 1.00 | 29.27 | A | C |
| ATOM | 1311 | CB | VAL | 318 | 128.531 | 32.778 | 11.144 | 1.00 | 70.89 | A | C |
| ATOM | 1312 | CG1 | VAL | 318 | 127.896 | 33.349 | 12.386 | 1.00 | 71.02 | A | C |
| ATOM | 1313 | CG2 | VAL | 318 | 128.942 | 33.899 | 10.223 | 1.00 | 70.87 | A | C |
| ATOM | 1314 | C | VAL | 318 | 129.331 | 30.808 | 12.482 | 1.00 | 24.42 | A | C |

Fig. 19: A-19

| ATOM | 1315 | O   | VAL | 318 | 128.872 | 29.744 | 12.053 | 1.00 | 25.09 | A | O |
|------|------|-----|-----|-----|---------|--------|--------|------|-------|---|---|
| ATOM | 1316 | N   | SER | 319 | 129.482 | 31.045 | 13.779 | 1.00 | 32.47 | A | N |
| ATOM | 1317 | CA  | SER | 319 | 129.108 | 30.035 | 14.752 | 1.00 | 31.73 | A | C |
| ATOM | 1318 | CB  | SER | 319 | 129.669 | 30.384 | 16.134 | 1.00 | 29.19 | A | C |
| ATOM | 1319 | OG  | SER | 319 | 129.289 | 31.687 | 16.538 | 1.00 | 41.14 | A | O |
| ATOM | 1320 | C   | SER | 319 | 127.600 | 29.840 | 14.831 | 1.00 | 30.33 | A | C |
| ATOM | 1321 | O   | SER | 319 | 127.132 | 28.716 | 14.963 | 1.00 | 28.40 | A | O |
| ATOM | 1322 | N   | ASP | 320 | 126.839 | 30.926 | 14.741 | 1.00 | 32.33 | A | N |
| ATOM | 1323 | CA  | ASP | 320 | 125.382 | 30.846 | 14.816 | 1.00 | 32.31 | A | C |
| ATOM | 1324 | CB  | ASP | 320 | 124.934 | 30.632 | 16.275 | 1.00 | 63.91 | A | C |
| ATOM | 1325 | CG  | ASP | 320 | 125.369 | 31.760 | 17.209 | 1.00 | 62.36 | A | C |
| ATOM | 1326 | OD1 | ASP | 320 | 126.586 | 31.992 | 17.364 | 1.00 | 61.04 | A | O |
| ATOM | 1327 | OD2 | ASP | 320 | 124.486 | 32.412 | 17.801 | 1.00 | 62.91 | A | O |
| ATOM | 1328 | C   | ASP | 320 | 124.698 | 32.088 | 14.237 | 1.00 | 30.68 | A | C |
| ATOM | 1329 | O   | ASP | 320 | 125.367 | 33.072 | 13.905 | 1.00 | 30.46 | A | O |
| ATOM | 1330 | N   | GLU | 321 | 123.371 | 32.042 | 14.110 | 1.00 | 35.58 | A | N |
| ATOM | 1331 | CA  | GLU | 321 | 122.614 | 33.173 | 13.569 | 1.00 | 36.56 | A | C |
| ATOM | 1332 | CB  | GLU | 321 | 121.126 | 33.029 | 13.889 | 1.00 | 84.00 | A | C |
| ATOM | 1333 | CG  | GLU | 321 | 120.285 | 32.398 | 12.796 | 1.00 | 77.84 | A | C |
| ATOM | 1334 | CD  | GLU | 321 | 120.602 | 30.938 | 12.569 | 1.00 | 77.59 | A | C |
| ATOM | 1335 | OE1 | GLU | 321 | 120.595 | 30.164 | 13.549 | 1.00 | 79.02 | A | O |
| ATOM | 1336 | OE2 | GLU | 321 | 120.849 | 30.565 | 11.404 | 1.00 | 81.63 | A | O |
| ATOM | 1337 | C   | GLU | 321 | 123.101 | 34.500 | 14.134 | 1.00 | 40.55 | A | C |
| ATOM | 1338 | O   | GLU | 321 | 123.278 | 35.475 | 13.397 | 1.00 | 37.31 | A | O |
| ATOM | 1339 | N   | LEU | 322 | 123.323 | 34.519 | 15.447 | 1.00 | 25.97 | A | N |
| ATOM | 1340 | CA  | LEU | 322 | 123.769 | 35.717 | 16.155 | 1.00 | 28.66 | A | C |
| ATOM | 1341 | CB  | LEU | 322 | 123.925 | 35.407 | 17.648 | 1.00 | 49.06 | A | C |
| ATOM | 1342 | CG  | LEU | 322 | 122.646 | 35.281 | 18.477 | 1.00 | 47.69 | A | C |
| ATOM | 1343 | CD1 | LEU | 322 | 121.935 | 36.625 | 18.486 | 1.00 | 49.43 | A | C |
| ATOM | 1344 | CD2 | LEU | 322 | 121.745 | 34.194 | 17.917 | 1.00 | 52.74 | A | C |
| ATOM | 1345 | C   | LEU | 322 | 125.052 | 36.368 | 15.644 | 1.00 | 30.25 | A | C |
| ATOM | 1346 | O   | LEU | 322 | 125.106 | 37.580 | 15.459 | 1.00 | 33.60 | A | O |
| ATOM | 1347 | N   | ALA | 323 | 126.080 | 35.558 | 15.424 | 1.00 | 27.12 | A | N |
| ATOM | 1348 | CA  | ALA | 323 | 127.358 | 36.071 | 14.965 | 1.00 | 27.55 | A | C |
| ATOM | 1349 | CB  | ALA | 323 | 128.420 | 34.994 | 15.112 | 1.00 | 20.92 | A | C |
| ATOM | 1350 | C   | ALA | 323 | 127.368 | 36.631 | 13.539 | 1.00 | 27.96 | A | C |
| ATOM | 1351 | O   | ALA | 323 | 128.363 | 37.227 | 13.120 | 1.00 | 27.98 | A | O |
| ATOM | 1352 | N   | LEU | 324 | 126.280 | 36.451 | 12.794 | 1.00 | 44.60 | A | N |
| ATOM | 1353 | CA  | LEU | 324 | 126.231 | 36.961 | 11.427 | 1.00 | 43.08 | A | C |
| ATOM | 1354 | CB  | LEU | 324 | 124.807 | 36.875 | 10.867 | 1.00 | 12.96 | A | C |
| ATOM | 1355 | CG  | LEU | 324 | 124.398 | 35.546 | 10.215 | 1.00 | 11.69 | A | C |
| ATOM | 1356 | CD1 | LEU | 324 | 122.900 | 35.547 |  9.935 | 1.00 | 10.83 | A | C |
| ATOM | 1357 | CD2 | LEU | 324 | 125.197 | 35.331 |  8.938 | 1.00 |  9.62 | A | C |
| ATOM | 1358 | C   | LEU | 324 | 126.734 | 38.400 | 11.346 | 1.00 | 46.61 | A | C |
| ATOM | 1359 | O   | LEU | 324 | 127.545 | 38.735 | 10.484 | 1.00 | 43.15 | A | O |
| ATOM | 1360 | N   | VAL | 325 | 126.257 | 39.244 | 12.252 | 1.00 | 37.14 | A | N |
| ATOM | 1361 | CA  | VAL | 325 | 126.657 | 40.645 | 12.297 | 1.00 | 40.67 | A | C |
| ATOM | 1362 | CB  | VAL | 325 | 126.111 | 41.328 | 13.549 | 1.00 | 15.02 | A | C |
| ATOM | 1363 | CG1 | VAL | 325 | 124.613 | 41.517 | 13.425 | 1.00 | 15.13 | A | C |
| ATOM | 1364 | CG2 | VAL | 325 | 126.453 | 40.503 | 14.773 | 1.00 | 18.41 | A | C |
| ATOM | 1365 | C   | VAL | 325 | 128.168 | 40.840 | 12.304 | 1.00 | 43.49 | A | C |
| ATOM | 1366 | O   | VAL | 325 | 128.706 | 41.663 | 11.560 | 1.00 | 45.55 | A | O |
| ATOM | 1367 | N   | THR | 326 | 128.844 | 40.088 | 13.161 | 1.00 | 37.74 | A | N |
| ATOM | 1368 | CA  | THR | 326 | 130.289 | 40.164 | 13.286 | 1.00 | 39.15 | A | C |
| ATOM | 1369 | CB  | THR | 326 | 130.768 | 39.218 | 14.391 | 1.00 | 28.63 | A | C |
| ATOM | 1370 | OG1 | THR | 326 | 130.648 | 37.863 | 13.944 | 1.00 | 30.54 | A | O |
| ATOM | 1371 | CG2 | THR | 326 | 129.911 | 39.398 | 15.643 | 1.00 | 31.00 | A | C |
| ATOM | 1372 | C   | THR | 326 | 130.996 | 39.790 | 11.985 | 1.00 | 39.16 | A | C |
| ATOM | 1373 | O   | THR | 326 | 132.105 | 39.268 | 12.005 | 1.00 | 37.98 | A | O |
| ATOM | 1374 | N   | ILE | 327 | 130.358 | 40.065 | 10.854 | 1.00 | 29.50 | A | N |
| ATOM | 1375 | CA  | ILE | 327 | 130.922 | 39.739 |  9.552 | 1.00 | 29.69 | A | C |
| ATOM | 1376 | CB  | ILE | 327 | 130.407 | 38.343 |  9.098 | 1.00 | 36.77 | A | C |
| ATOM | 1377 | CG2 | ILE | 327 | 129.867 | 38.372 |  7.679 | 1.00 | 37.54 | A | C |
| ATOM | 1378 | CG1 | ILE | 327 | 131.539 | 37.335 |  9.199 | 1.00 | 37.13 | A | C |
| ATOM | 1379 | CD1 | ILE | 327 | 131.100 | 35.928 |  8.903 | 1.00 | 36.80 | A | C |
| ATOM | 1380 | C   | ILE | 327 | 130.572 | 40.816 |  8.520 | 1.00 | 30.20 | A | C |
| ATOM | 1381 | O   | ILE | 327 | 131.284 | 41.008 |  7.530 | 1.00 | 30.45 | A | O |
| ATOM | 1382 | N   | VAL | 328 | 129.478 | 41.527 |  8.766 | 1.00 | 25.26 | A | N |
| ATOM | 1383 | CA  | VAL | 328 | 129.040 | 42.565 |  7.851 | 1.00 | 27.40 | A | C |
| ATOM | 1384 | CB  | VAL | 328 | 127.851 | 43.363 |  8.436 | 1.00 | 56.37 | A | C |
| ATOM | 1385 | CG1 | VAL | 328 | 126.752 | 42.408 |  8.838 | 1.00 | 58.32 | A | C |
| ATOM | 1386 | CG2 | VAL | 328 | 128.301 | 44.197 |  9.626 | 1.00 | 57.64 | A | C |
| ATOM | 1387 | C   | VAL | 328 | 130.159 | 43.539 |  7.485 | 1.00 | 27.32 | A | C |

Fig. 19: A-20

```
ATOM   1388  O    VAL   328     130.220  44.017   6.355  1.00   26.60      A  O
ATOM   1389  N    LYS   329     131.047  43.837   8.426  1.00   32.39      A  N
ATOM   1390  CA   LYS   329     132.121  44.773   8.124  1.00   31.60      A  C
ATOM   1391  CB   LYS   329     132.949  45.076   9.378  1.00   57.11      A  C
ATOM   1392  CG   LYS   329     133.861  46.291   9.242  1.00   68.66      A  C
ATOM   1393  CD   LYS   329     134.737  46.454  10.474  1.00   70.98      A  C
ATOM   1394  CE   LYS   329     135.540  47.746  10.437  1.00   74.02      A  C
ATOM   1395  NZ   LYS   329     134.660  48.952  10.496  1.00   77.70      A  N
ATOM   1396  C    LYS   329     133.014  44.194   7.036  1.00   29.77      A  C
ATOM   1397  O    LYS   329     133.205  44.802   5.978  1.00   30.98      A  O
ATOM   1398  N    ALA   330     133.551  43.008   7.293  1.00   29.12      A  N
ATOM   1399  CA   ALA   330     134.425  42.365   6.331  1.00   29.15      A  C
ATOM   1400  CB   ALA   330     134.997  41.091   6.922  1.00   30.19      A  C
ATOM   1401  C    ALA   330     133.681  42.056   5.043  1.00   30.30      A  C
ATOM   1402  O    ALA   330     134.207  42.269   3.955  1.00   30.20      A  O
ATOM   1403  N    LEU   331     132.457  41.551   5.168  1.00   22.22      A  N
ATOM   1404  CA   LEU   331     131.661  41.206   3.994  1.00   19.86      A  C
ATOM   1405  CB   LEU   331     130.284  40.667   4.403  1.00   36.97      A  C
ATOM   1406  CG   LEU   331     129.567  39.761   3.389  1.00   33.39      A  C
ATOM   1407  CD1  LEU   331     128.110  39.600   3.787  1.00   35.02      A  C
ATOM   1408  CD2  LEU   331     129.658  40.343   1.996  1.00   29.08      A  C
ATOM   1409  C    LEU   331     131.483  42.467   3.162  1.00   19.89      A  C
ATOM   1410  O    LEU   331     131.741  42.468   1.961  1.00   19.24      A  O
ATOM   1411  N    GLY   332     131.045  43.535   3.830  1.00   15.82      A  N
ATOM   1412  CA   GLY   332     130.824  44.811   3.179  1.00   16.92      A  C
ATOM   1413  C    GLY   332     132.024  45.309   2.402  1.00   17.18      A  C
ATOM   1414  O    GLY   332     131.911  45.651   1.224  1.00   21.05      A  O
ATOM   1415  N    GLU   333     133.185  45.347   3.045  1.00   34.74      A  N
ATOM   1416  CA   GLU   333     134.369  45.831   2.362  1.00   32.80      A  C
ATOM   1417  CB   GLU   333     135.472  46.165   3.371  1.00   75.29      A  C
ATOM   1418  CG   GLU   333     136.139  44.968   4.005  1.00   73.66      A  C
ATOM   1419  CD   GLU   333     137.251  45.363   4.959  1.00   73.68      A  C
ATOM   1420  OE1  GLU   333     137.953  44.459   5.456  1.00   75.73      A  O
ATOM   1421  OE2  GLU   333     137.421  46.575   5.215  1.00   67.80      A  O
ATOM   1422  C    GLU   333     134.888  44.841   1.322  1.00   31.78      A  C
ATOM   1423  O    GLU   333     135.370  45.236   0.261  1.00   31.40      A  O
ATOM   1424  N    ARG   334     134.781  43.552   1.610  1.00   50.02      A  N
ATOM   1425  CA   ARG   334     135.275  42.563   0.669  1.00   53.40      A  C
ATOM   1426  CB   ARG   334     135.064  41.152   1.215  1.00   83.27      A  C
ATOM   1427  CG   ARG   334     136.000  40.123   0.607  1.00   82.56      A  C
ATOM   1428  CD   ARG   334     136.564  39.198   1.677  1.00   81.32      A  C
ATOM   1429  NE   ARG   334     137.441  39.901   2.612  1.00   76.87      A  N
ATOM   1430  CZ   ARG   334     137.888  39.383   3.753  1.00   80.96      A  C
ATOM   1431  NH1  ARG   334     137.537  38.148   4.108  1.00   77.70      A  N
ATOM   1432  NH2  ARG   334     138.686  40.097   4.539  1.00   87.10      A  N
ATOM   1433  C    ARG   334     134.556  42.757  -0.654  1.00   54.70      A  C
ATOM   1434  O    ARG   334     135.170  42.716  -1.716  1.00   51.62      A  O
ATOM   1435  N    ILE   335     133.253  42.988  -0.591  1.00   36.48      A  N
ATOM   1436  CA   ILE   335     132.473  43.214  -1.803  1.00   36.41      A  C
ATOM   1437  CB   ILE   335     130.940  42.967  -1.539  1.00   33.09      A  C
ATOM   1438  CG2  ILE   335     130.524  43.522  -0.203  1.00   35.87      A  C
ATOM   1439  CG1  ILE   335     130.094  43.611  -2.630  1.00   34.31      A  C
ATOM   1440  CD1  ILE   335     128.612  43.520  -2.368  1.00   37.10      A  C
ATOM   1441  C    ILE   335     132.742  44.663  -2.215  1.00   34.70      A  C
ATOM   1442  O    ILE   335     132.421  45.092  -3.326  1.00   37.30      A  O
ATOM   1443  N    PHE   336     133.392  45.377  -1.299  1.00  108.43      A  N
ATOM   1444  CA   PHE   336     133.744  46.789  -1.419  1.00  108.06      A  C
ATOM   1445  CB   PHE   336     135.092  46.989  -2.157  1.00   57.00      A  C
ATOM   1446  CG   PHE   336     135.114  46.540  -3.601  1.00   53.32      A  C
ATOM   1447  CD1  PHE   336     134.135  46.941  -4.508  1.00   52.74      A  C
ATOM   1448  CD2  PHE   336     136.178  45.779  -4.073  1.00   51.27      A  C
ATOM   1449  CE1  PHE   336     134.219  46.589  -5.868  1.00   43.07      A  C
ATOM   1450  CE2  PHE   336     136.271  45.426  -5.422  1.00   45.63      A  C
ATOM   1451  CZ   PHE   336     135.292  45.832  -6.319  1.00   46.09      A  C
ATOM   1452  C    PHE   336     132.662  47.670  -2.020  1.00  108.09      A  C
ATOM   1453  O    PHE   336     131.623  47.131  -2.453  1.00   87.71      A  O
ATOM   1454  OXT  PHE   336     132.864  48.902  -2.024  1.00   40.49      A  O
ATOM   1455  CB   GLU     1     119.537  12.185  27.786  1.00   88.08      H  C
ATOM   1456  CG   GLU     1     118.650  11.120  28.419  1.00   88.08      H  C
ATOM   1457  CD   GLU     1     119.399  10.237  29.409  1.00   88.08      H  C
ATOM   1458  OE1  GLU     1     120.127  10.777  30.271  1.00   88.08      H  O
ATOM   1459  OE2  GLU     1     119.251   8.998  29.324  1.00   88.08      H  O
ATOM   1460  C    GLU     1     118.366  14.360  28.176  1.00   62.78      H  C
```

Fig. 19: A-21

| ATOM | 1461 | O | GLU | 1 | 117.763 | 15.033 | 29.012 | 1.00 | 62.78 | H | O |
|------|------|------|-----|----|---------|--------|--------|------|--------|---|---|
| ATOM | 1462 | N | GLU | 1 | 119.687 | 13.262 | 30.016 | 1.00 | 62.78 | H | N |
| ATOM | 1463 | CA | GLU | 1 | 119.580 | 13.515 | 28.553 | 1.00 | 62.78 | H | C |
| ATOM | 1464 | N | VAL | 2 | 118.019 | 14.312 | 26.896 | 1.00 | 44.26 | H | N |
| ATOM | 1465 | CA | VAL | 2 | 116.896 | 15.064 | 26.359 | 1.00 | 44.26 | H | C |
| ATOM | 1466 | CB | VAL | 2 | 117.154 | 15.460 | 24.909 | 1.00 | 15.14 | H | C |
| ATOM | 1467 | CG1 | VAL | 2 | 118.610 | 15.840 | 24.732 | 1.00 | 15.14 | H | C |
| ATOM | 1468 | CG2 | VAL | 2 | 116.807 | 14.309 | 23.997 | 1.00 | 15.14 | H | C |
| ATOM | 1469 | C | VAL | 2 | 115.677 | 14.174 | 26.353 | 1.00 | 44.26 | H | C |
| ATOM | 1470 | O | VAL | 2 | 115.803 | 12.951 | 26.347 | 1.00 | 44.26 | H | O |
| ATOM | 1471 | N | GLN | 3 | 114.497 | 14.780 | 26.340 | 1.00 | 25.45 | H | N |
| ATOM | 1472 | CA | GLN | 3 | 113.280 | 13.984 | 26.288 | 1.00 | 25.45 | H | C |
| ATOM | 1473 | CB | GLN | 3 | 113.191 | 13.046 | 27.494 | 1.00 | 105.15 | H | C |
| ATOM | 1474 | CG | GLN | 3 | 113.307 | 13.707 | 28.841 | 1.00 | 105.15 | H | C |
| ATOM | 1475 | CD | GLN | 3 | 113.015 | 12.733 | 29.961 | 1.00 | 105.15 | H | C |
| ATOM | 1476 | OE1 | GLN | 3 | 113.554 | 11.623 | 29.990 | 1.00 | 105.15 | H | O |
| ATOM | 1477 | NE2 | GLN | 3 | 112.157 | 13.139 | 30.892 | 1.00 | 105.15 | H | N |
| ATOM | 1478 | C | GLN | 3 | 111.961 | 14.708 | 26.119 | 1.00 | 25.45 | H | C |
| ATOM | 1479 | O | GLN | 3 | 111.809 | 15.887 | 26.438 | 1.00 | 25.45 | H | O |
| ATOM | 1480 | N | LEU | 4 | 111.009 | 13.959 | 25.588 | 1.00 | 27.88 | H | N |
| ATOM | 1481 | CA | LEU | 4 | 109.668 | 14.446 | 25.339 | 1.00 | 27.88 | H | C |
| ATOM | 1482 | CB | LEU | 4 | 109.347 | 14.369 | 23.842 | 1.00 | 33.14 | H | C |
| ATOM | 1483 | CG | LEU | 4 | 110.367 | 14.924 | 22.847 | 1.00 | 33.14 | H | C |
| ATOM | 1484 | CD1 | LEU | 4 | 109.821 | 14.772 | 21.438 | 1.00 | 33.14 | H | C |
| ATOM | 1485 | CD2 | LEU | 4 | 110.646 | 16.385 | 23.155 | 1.00 | 33.14 | H | C |
| ATOM | 1486 | C | LEU | 4 | 108.755 | 13.507 | 26.095 | 1.00 | 27.88 | H | C |
| ATOM | 1487 | O | LEU | 4 | 108.871 | 12.282 | 25.960 | 1.00 | 27.88 | H | O |
| ATOM | 1488 | N | VAL | 5 | 107.858 | 14.061 | 26.901 | 1.00 | 26.47 | H | N |
| ATOM | 1489 | CA | VAL | 5 | 106.942 | 13.215 | 27.656 | 1.00 | 26.47 | H | C |
| ATOM | 1490 | CB | VAL | 5 | 107.176 | 13.329 | 29.197 | 1.00 | 25.39 | H | C |
| ATOM | 1491 | CG1 | VAL | 5 | 107.281 | 14.772 | 29.606 | 1.00 | 25.39 | H | C |
| ATOM | 1492 | CG2 | VAL | 5 | 106.046 | 12.654 | 29.947 | 1.00 | 25.39 | H | C |
| ATOM | 1493 | C | VAL | 5 | 105.520 | 13.578 | 27.297 | 1.00 | 26.47 | H | C |
| ATOM | 1494 | O | VAL | 5 | 105.031 | 14.664 | 27.635 | 1.00 | 26.47 | H | O |
| ATOM | 1495 | N | GLU | 6 | 104.868 | 12.650 | 26.601 | 1.00 | 23.78 | H | N |
| ATOM | 1496 | CA | GLU | 6 | 103.495 | 12.835 | 26.133 | 1.00 | 23.78 | H | C |
| ATOM | 1497 | CB | GLU | 6 | 103.258 | 11.995 | 24.885 | 1.00 | 29.58 | H | C |
| ATOM | 1498 | CG | GLU | 6 | 104.409 | 12.017 | 23.933 | 1.00 | 29.58 | H | C |
| ATOM | 1499 | CD | GLU | 6 | 104.188 | 11.109 | 22.756 | 1.00 | 29.58 | H | C |
| ATOM | 1500 | OE1 | GLU | 6 | 105.194 | 10.664 | 22.168 | 1.00 | 29.58 | H | O |
| ATOM | 1501 | OE2 | GLU | 6 | 103.013 | 10.846 | 22.413 | 1.00 | 29.58 | H | O |
| ATOM | 1502 | C | GLU | 6 | 102.429 | 12.485 | 27.155 | 1.00 | 23.78 | H | C |
| ATOM | 1503 | O | GLU | 6 | 102.680 | 11.740 | 28.101 | 1.00 | 23.78 | H | O |
| ATOM | 1504 | N | SER | 7 | 101.242 | 13.047 | 26.937 | 1.00 | 26.30 | H | N |
| ATOM | 1505 | CA | SER | 7 | 100.061 | 12.823 | 27.766 | 1.00 | 26.30 | H | C |
| ATOM | 1506 | CB | SER | 7 | 100.177 | 13.535 | 29.102 | 1.00 | 32.56 | H | C |
| ATOM | 1507 | OG | SER | 7 | 100.574 | 14.871 | 28.906 | 1.00 | 32.56 | H | O |
| ATOM | 1508 | C | SER | 7 | 98.886 | 13.381 | 26.998 | 1.00 | 26.30 | H | C |
| ATOM | 1509 | O | SER | 7 | 99.060 | 14.248 | 26.136 | 1.00 | 26.30 | H | O |
| ATOM | 1510 | N | GLY | 8 | 97.693 | 12.872 | 27.287 | 1.00 | 41.74 | H | N |
| ATOM | 1511 | CA | GLY | 8 | 96.514 | 13.360 | 26.598 | 1.00 | 41.74 | H | C |
| ATOM | 1512 | C | GLY | 8 | 95.807 | 12.321 | 25.752 | 1.00 | 41.74 | H | C |
| ATOM | 1513 | O | GLY | 8 | 94.745 | 12.603 | 25.201 | 1.00 | 41.74 | H | O |
| ATOM | 1514 | N | GLY | 9 | 96.383 | 11.127 | 25.637 | 1.00 | 47.50 | H | N |
| ATOM | 1515 | CA | GLY | 9 | 95.751 | 10.079 | 24.851 | 1.00 | 47.50 | H | C |
| ATOM | 1516 | C | GLY | 9 | 94.431 | 9.601 | 25.446 | 1.00 | 47.50 | H | C |
| ATOM | 1517 | O | GLY | 9 | 94.038 | 10.020 | 26.536 | 1.00 | 47.50 | H | O |
| ATOM | 1518 | N | GLY | 10 | 93.732 | 8.723 | 24.735 | 1.00 | 16.50 | H | N |
| ATOM | 1519 | CA | GLY | 10 | 92.469 | 8.225 | 25.244 | 1.00 | 16.50 | H | C |
| ATOM | 1520 | C | GLY | 10 | 91.485 | 7.806 | 24.169 | 1.00 | 16.50 | H | C |
| ATOM | 1521 | O | GLY | 10 | 91.830 | 7.701 | 22.990 | 1.00 | 16.50 | H | O |
| ATOM | 1522 | N | LEU | 11 | 90.251 | 7.559 | 24.595 | 1.00 | 37.61 | H | N |
| ATOM | 1523 | CA | LEU | 11 | 89.175 | 7.137 | 23.710 | 1.00 | 37.61 | H | C |
| ATOM | 1524 | CB | LEU | 11 | 88.388 | 6.003 | 24.365 | 1.00 | 18.32 | H | C |
| ATOM | 1525 | CG | LEU | 11 | 86.959 | 5.715 | 23.885 | 1.00 | 18.32 | H | C |
| ATOM | 1526 | CD1 | LEU | 11 | 86.962 | 5.148 | 22.463 | 1.00 | 18.32 | H | C |
| ATOM | 1527 | CD2 | LEU | 11 | 86.313 | 4.729 | 24.856 | 1.00 | 18.32 | H | C |
| ATOM | 1528 | C | LEU | 11 | 88.235 | 8.292 | 23.436 | 1.00 | 37.61 | H | C |
| ATOM | 1529 | O | LEU | 11 | 87.769 | 8.943 | 24.365 | 1.00 | 37.61 | H | O |
| ATOM | 1530 | N | VAL | 12 | 87.961 | 8.550 | 22.165 | 1.00 | 31.23 | H | N |
| ATOM | 1531 | CA | VAL | 12 | 87.048 | 9.624 | 21.792 | 1.00 | 31.23 | H | C |
| ATOM | 1532 | CB | VAL | 12 | 87.794 | 10.800 | 21.144 | 1.00 | 52.64 | H | C |
| ATOM | 1533 | CG1 | VAL | 12 | 88.609 | 11.532 | 22.192 | 1.00 | 52.64 | H | C |

Fig. 19: A-22

| | | | | | | | | | | | |
|---|---|---|---|---|---|---|---|---|---|---|---|
| ATOM | 1534 | CG2 | VAL | 12 | 88.699 | 10.290 | 20.039 | 1.00 | 52.64 | H | C |
| ATOM | 1535 | C | VAL | 12 | 86.062 | 9.045 | 20.794 | 1.00 | 31.23 | H | C |
| ATOM | 1536 | O | VAL | 12 | 86.365 | 8.057 | 20.138 | 1.00 | 31.23 | H | O |
| ATOM | 1537 | N | GLN | 13 | 84.882 | 9.640 | 20.681 | 1.00 | 27.32 | H | N |
| ATOM | 1538 | CA | GLN | 13 | 83.894 | 9.126 | 19.741 | 1.00 | 27.32 | H | C |
| ATOM | 1539 | CB | GLN | 13 | 82.493 | 9.391 | 20.270 | 1.00 | 92.40 | H | C |
| ATOM | 1540 | CG | GLN | 13 | 82.206 | 8.652 | 21.553 | 1.00 | 92.40 | H | C |
| ATOM | 1541 | CD | GLN | 13 | 80.808 | 8.906 | 22.056 | 1.00 | 92.40 | H | C |
| ATOM | 1542 | OE1 | GLN | 13 | 79.836 | 8.766 | 21.310 | 1.00 | 92.40 | H | O |
| ATOM | 1543 | NE2 | GLN | 13 | 80.693 | 9.276 | 23.329 | 1.00 | 92.40 | H | N |
| ATOM | 1544 | C | GLN | 13 | 84.063 | 9.747 | 18.356 | 1.00 | 27.32 | H | C |
| ATOM | 1545 | O | GLN | 13 | 84.400 | 10.924 | 18.227 | 1.00 | 27.32 | H | O |
| ATOM | 1546 | N | PRO | 14 | 83.834 | 8.955 | 17.298 | 1.00 | 39.48 | H | N |
| ATOM | 1547 | CD | PRO | 14 | 83.418 | 7.539 | 17.302 | 1.00 | 31.44 | H | C |
| ATOM | 1548 | CA | PRO | 14 | 83.971 | 9.452 | 15.929 | 1.00 | 39.48 | H | C |
| ATOM | 1549 | CB | PRO | 14 | 83.219 | 8.406 | 15.118 | 1.00 | 31.44 | H | C |
| ATOM | 1550 | CG | PRO | 14 | 83.584 | 7.145 | 15.837 | 1.00 | 31.44 | H | C |
| ATOM | 1551 | C | PRO | 14 | 83.401 | 10.849 | 15.766 | 1.00 | 39.48 | H | C |
| ATOM | 1552 | O | PRO | 14 | 82.235 | 11.076 | 16.053 | 1.00 | 39.48 | H | O |
| ATOM | 1553 | N | GLY | 15 | 84.233 | 11.784 | 15.319 | 1.00 | 28.44 | H | N |
| ATOM | 1554 | CA | GLY | 15 | 83.788 | 13.154 | 15.130 | 1.00 | 28.44 | H | C |
| ATOM | 1555 | C | GLY | 15 | 84.048 | 14.065 | 16.323 | 1.00 | 28.44 | H | C |
| ATOM | 1556 | O | GLY | 15 | 83.759 | 15.265 | 16.269 | 1.00 | 28.44 | H | O |
| ATOM | 1557 | N | GLY | 16 | 84.588 | 13.496 | 17.401 | 1.00 | 22.09 | H | N |
| ATOM | 1558 | CA | GLY | 16 | 84.880 | 14.266 | 18.601 | 1.00 | 22.09 | H | C |
| ATOM | 1559 | C | GLY | 16 | 86.286 | 14.826 | 18.571 | 1.00 | 22.09 | H | C |
| ATOM | 1560 | O | GLY | 16 | 86.900 | 14.912 | 17.507 | 1.00 | 22.09 | H | O |
| ATOM | 1561 | N | SER | 17 | 86.819 | 15.202 | 19.726 | 1.00 | 31.69 | H | N |
| ATOM | 1562 | CA | SER | 17 | 88.161 | 15.762 | 19.749 | 1.00 | 31.69 | H | C |
| ATOM | 1563 | CB | SER | 17 | 88.085 | 17.272 | 19.592 | 1.00 | 54.23 | H | C |
| ATOM | 1564 | OG | SER | 17 | 87.308 | 17.829 | 20.625 | 1.00 | 54.23 | H | O |
| ATOM | 1565 | C | SER | 17 | 88.953 | 15.416 | 21.000 | 1.00 | 31.69 | H | C |
| ATOM | 1566 | O | SER | 17 | 88.427 | 14.824 | 21.944 | 1.00 | 31.69 | H | O |
| ATOM | 1567 | N | LEU | 18 | 90.227 | 15.794 | 20.995 | 1.00 | 31.76 | H | N |
| ATOM | 1568 | CA | LEU | 18 | 91.132 | 15.515 | 22.105 | 1.00 | 31.76 | H | C |
| ATOM | 1569 | CB | LEU | 18 | 91.452 | 14.019 | 22.124 | 1.00 | 63.56 | H | C |
| ATOM | 1570 | CG | LEU | 18 | 92.462 | 13.465 | 23.124 | 1.00 | 63.56 | H | C |
| ATOM | 1571 | CD1 | LEU | 18 | 92.121 | 13.932 | 24.536 | 1.00 | 63.56 | H | C |
| ATOM | 1572 | CD2 | LEU | 18 | 92.462 | 11.942 | 23.017 | 1.00 | 63.56 | H | C |
| ATOM | 1573 | C | LEU | 18 | 92.407 | 16.334 | 21.899 | 1.00 | 31.76 | H | C |
| ATOM | 1574 | O | LEU | 18 | 92.622 | 16.884 | 20.815 | 1.00 | 31.76 | H | O |
| ATOM | 1575 | N | ARG | 19 | 93.243 | 16.443 | 22.928 | 1.00 | 39.26 | H | N |
| ATOM | 1576 | CA | ARG | 19 | 94.475 | 17.207 | 22.781 | 1.00 | 39.26 | H | C |
| ATOM | 1577 | CB | ARG | 19 | 94.303 | 18.650 | 23.258 | 1.00 | 32.50 | H | C |
| ATOM | 1578 | CG | ARG | 19 | 95.571 | 19.474 | 23.063 | 1.00 | 32.50 | H | C |
| ATOM | 1579 | CD | ARG | 19 | 95.481 | 20.862 | 23.667 | 1.00 | 32.50 | H | C |
| ATOM | 1580 | NE | ARG | 19 | 95.387 | 20.846 | 25.125 | 1.00 | 32.50 | H | N |
| ATOM | 1581 | CZ | ARG | 19 | 95.262 | 21.936 | 25.879 | 1.00 | 32.50 | H | C |
| ATOM | 1582 | NH1 | ARG | 19 | 95.220 | 23.138 | 25.322 | 1.00 | 32.50 | H | N |
| ATOM | 1583 | NH2 | ARG | 19 | 95.162 | 21.824 | 27.193 | 1.00 | 32.50 | H | N |
| ATOM | 1584 | C | ARG | 19 | 95.668 | 16.606 | 23.500 | 1.00 | 39.26 | H | C |
| ATOM | 1585 | O | ARG | 19 | 95.687 | 16.469 | 24.732 | 1.00 | 39.26 | H | O |
| ATOM | 1586 | N | LEU | 20 | 96.677 | 16.266 | 22.709 | 1.00 | 36.74 | H | N |
| ATOM | 1587 | CA | LEU | 20 | 97.896 | 15.695 | 23.241 | 1.00 | 36.74 | H | C |
| ATOM | 1588 | CB | LEU | 20 | 98.534 | 14.737 | 22.222 | 1.00 | 31.69 | H | C |
| ATOM | 1589 | CG | LEU | 20 | 97.601 | 13.846 | 21.390 | 1.00 | 31.69 | H | C |
| ATOM | 1590 | CD1 | LEU | 20 | 98.426 | 12.870 | 20.555 | 1.00 | 31.69 | H | C |
| ATOM | 1591 | CD2 | LEU | 20 | 96.659 | 13.093 | 22.292 | 1.00 | 31.69 | H | C |
| ATOM | 1592 | C | LEU | 20 | 98.854 | 16.838 | 23.533 | 1.00 | 36.74 | H | C |
| ATOM | 1593 | O | LEU | 20 | 98.866 | 17.856 | 22.840 | 1.00 | 36.74 | H | O |
| ATOM | 1594 | N | SER | 21 | 99.638 | 16.664 | 24.584 | 1.00 | 25.68 | H | N |
| ATOM | 1595 | CA | SER | 21 | 100.635 | 17.640 | 24.974 | 1.00 | 25.68 | H | C |
| ATOM | 1596 | CB | SER | 21 | 100.273 | 18.278 | 26.307 | 1.00 | 13.03 | H | C |
| ATOM | 1597 | OG | SER | 21 | 99.718 | 17.320 | 27.175 | 1.00 | 13.03 | H | O |
| ATOM | 1598 | C | SER | 21 | 101.901 | 16.838 | 25.099 | 1.00 | 25.68 | H | C |
| ATOM | 1599 | O | SER | 21 | 101.851 | 15.635 | 25.336 | 1.00 | 25.68 | H | O |
| ATOM | 1600 | N | CYS | 22 | 103.036 | 17.498 | 24.931 | 1.00 | 22.18 | H | N |
| ATOM | 1601 | CA | CYS | 22 | 104.321 | 16.822 | 25.008 | 1.00 | 22.18 | H | C |
| ATOM | 1602 | C | CYS | 22 | 105.255 | 17.765 | 25.713 | 1.00 | 22.18 | H | C |
| ATOM | 1603 | O | CYS | 22 | 105.491 | 18.863 | 25.229 | 1.00 | 22.18 | H | O |
| ATOM | 1604 | CB | CYS | 22 | 104.804 | 16.543 | 23.603 | 1.00 | 57.35 | H | C |
| ATOM | 1605 | SG | CYS | 22 | 106.473 | 15.867 | 23.383 | 1.00 | 57.35 | H | S |
| ATOM | 1606 | N | ALA | 23 | 105.769 | 17.349 | 26.867 | 1.00 | 26.87 | H | N |

Fig. 19: A-23

```
ATOM   1607  CA   ALA   23    106.669  18.191  27.654  1.00   26.87   H  C
ATOM   1608  CB   ALA   23    106.470  17.937  29.141  1.00    9.84   H  C
ATOM   1609  C    ALA   23    108.125  17.989  27.284  1.00   26.87   H  C
ATOM   1610  O    ALA   23    108.683  16.899  27.437  1.00   26.87   H  O
ATOM   1611  N    ALA   24    108.738  19.058  26.800  1.00   13.29   H  N
ATOM   1612  CA   ALA   24    110.124  18.988  26.409  1.00   13.29   H  C
ATOM   1613  CB   ALA   24    110.357  19.851  25.183  1.00   45.62   H  C
ATOM   1614  C    ALA   24    111.023  19.432  27.552  1.00   13.29   H  C
ATOM   1615  O    ALA   24    110.664  20.304  28.356  1.00   13.29   H  O
ATOM   1616  N    SER   25    112.194  18.819  27.617  1.00   22.11   H  N
ATOM   1617  CA   SER   25    113.168  19.152  28.634  1.00   22.11   H  C
ATOM   1618  CB   SER   25    112.731  18.582  29.982  1.00   51.20   H  C
ATOM   1619  OG   SER   25    112.401  17.214  29.862  1.00   51.20   H  O
ATOM   1620  C    SER   25    114.526  18.591  28.232  1.00   22.11   H  C
ATOM   1621  O    SER   25    114.614  17.539  27.590  1.00   22.11   H  O
ATOM   1622  N    GLY   26    115.582  19.306  28.591  1.00   10.76   H  N
ATOM   1623  CA   GLY   26    116.914  18.844  28.263  1.00   10.76   H  C
ATOM   1624  C    GLY   26    117.553  19.585  27.107  1.00   10.76   H  C
ATOM   1625  O    GLY   26    118.728  19.367  26.809  1.00   10.76   H  O
ATOM   1626  N    PHE   27    116.794  20.458  26.448  1.00   18.08   H  N
ATOM   1627  CA   PHE   27    117.325  21.207  25.318  1.00   18.08   H  C
ATOM   1628  CB   PHE   27    117.241  20.373  24.031  1.00   16.53   H  C
ATOM   1629  CG   PHE   27    115.842  19.974  23.651  1.00   16.53   H  C
ATOM   1630  CD1  PHE   27    115.089  19.140  24.476  1.00   16.53   H  C
ATOM   1631  CD2  PHE   27    115.269  20.448  22.476  1.00   16.53   H  C
ATOM   1632  CE1  PHE   27    113.770  18.782  24.137  1.00   16.53   H  C
ATOM   1633  CE2  PHE   27    113.958  20.101  22.125  1.00   16.53   H  C
ATOM   1634  CZ   PHE   27    113.203  19.268  22.954  1.00   16.53   H  C
ATOM   1635  C    PHE   27    116.592  22.528  25.135  1.00   18.08   H  C
ATOM   1636  O    PHE   27    115.566  22.780  25.763  1.00   18.08   H  O
ATOM   1637  N    THR   28    117.139  23.377  24.276  1.00   42.88   H  N
ATOM   1638  CA   THR   28    116.544  24.672  24.017  1.00   42.88   H  C
ATOM   1639  CB   THR   28    117.575  25.604  23.381  1.00   53.65   H  C
ATOM   1640  OG1  THR   28    118.841  25.399  24.018  1.00   53.65   H  O
ATOM   1641  CG2  THR   28    117.168  27.056  23.561  1.00   53.65   H  C
ATOM   1642  C    THR   28    115.369  24.463  23.074  1.00   42.88   H  C
ATOM   1643  O    THR   28    115.484  24.666  21.868  1.00   42.88   H  O
ATOM   1644  N    PHE   29    114.239  24.051  23.644  1.00   29.92   H  N
ATOM   1645  CA   PHE   29    113.004  23.772  22.901  1.00   29.92   H  C
ATOM   1646  CB   PHE   29    111.855  23.614  23.906  1.00    3.95   H  C
ATOM   1647  CG   PHE   29    110.503  23.347  23.276  1.00    3.95   H  C
ATOM   1648  CD1  PHE   29    110.208  22.102  22.696  1.00    3.95   H  C
ATOM   1649  CD2  PHE   29    109.504  24.336  23.283  1.00    3.95   H  C
ATOM   1650  CE1  PHE   29    108.939  21.852  22.139  1.00    3.95   H  C
ATOM   1651  CE2  PHE   29    108.234  24.092  22.727  1.00    3.95   H  C
ATOM   1652  CZ   PHE   29    107.953  22.860  22.160  1.00    3.95   H  C
ATOM   1653  C    PHE   29    112.611  24.777  21.797  1.00   29.92   H  C
ATOM   1654  O    PHE   29    112.390  24.389  20.647  1.00   29.92   H  O
ATOM   1655  N    SER   30    112.539  26.058  22.144  1.00   32.50   H  N
ATOM   1656  CA   SER   30    112.139  27.105  21.199  1.00   32.50   H  C
ATOM   1657  CB   SER   30    112.335  28.473  21.852  1.00   67.50   H  C
ATOM   1658  OG   SER   30    113.644  28.591  22.372  1.00   67.50   H  O
ATOM   1659  C    SER   30    112.799  27.107  19.812  1.00   32.50   H  C
ATOM   1660  O    SER   30    112.191  27.504  18.816  1.00   32.50   H  O
ATOM   1661  N    ARG   31    114.037  26.649  19.751  1.00   18.89   H  N
ATOM   1662  CA   ARG   31    114.801  26.636  18.515  1.00   18.89   H  C
ATOM   1663  CB   ARG   31    116.292  26.604  18.886  1.00   48.17   H  C
ATOM   1664  CG   ARG   31    117.217  25.955  17.887  1.00   48.17   H  C
ATOM   1665  CD   ARG   31    118.650  26.425  18.112  1.00   48.17   H  C
ATOM   1666  NE   ARG   31    119.135  26.203  19.476  1.00   48.17   H  N
ATOM   1667  CZ   ARG   31    120.228  26.777  19.980  1.00   48.17   H  C
ATOM   1668  NH1  ARG   31    120.950  27.608  19.238  1.00   48.17   H  N
ATOM   1669  NH2  ARG   31    120.604  26.524  21.226  1.00   48.17   H  N
ATOM   1670  C    ARG   31    114.463  25.523  17.521  1.00   18.89   H  C
ATOM   1671  O    ARG   31    114.520  25.723  16.313  1.00   18.89   H  O
ATOM   1672  N    TYR   32    114.095  24.353  18.027  1.00   15.47   H  N
ATOM   1673  CA   TYR   32    113.791  23.200  17.179  1.00   15.47   H  C
ATOM   1674  CB   TYR   32    113.949  21.922  17.996  1.00    6.03   H  C
ATOM   1675  CG   TYR   32    115.367  21.653  18.426  1.00    6.03   H  C
ATOM   1676  CD1  TYR   32    115.934  22.336  19.500  1.00    6.03   H  C
ATOM   1677  CE1  TYR   32    117.249  22.097  19.889  1.00    6.03   H  C
ATOM   1678  CD2  TYR   32    116.153  20.722  17.747  1.00    6.03   H  C
ATOM   1679  CE2  TYR   32    117.467  20.477  18.122  1.00    6.03   H  C
```

Fig. 19: A-24

```
ATOM   1680  CZ   TYR   32     118.013   21.165   19.198  1.00     6.03      H  C
ATOM   1681  OH   TYR   32     119.317   20.907   19.597  1.00     6.03      H  O
ATOM   1682  C    TYR   32     112.426   23.184   16.534  1.00    15.47      H  C
ATOM   1683  O    TYR   32     111.480   23.748   17.058  1.00    15.47      H  O
ATOM   1684  N    THR   33     112.309   22.545   15.382  1.00    10.91      H  N
ATOM   1685  CA   THR   33     110.988   22.451   14.792  1.00    10.91      H  C
ATOM   1686  CB   THR   33     111.032   22.556   13.230  1.00    11.96      H  C
ATOM   1687  OG1  THR   33     111.079   21.259   12.639  1.00    11.96      H  O
ATOM   1688  CG2  THR   33     112.251   23.338   12.786  1.00    11.96      H  C
ATOM   1689  C    THR   33     110.501   21.082   15.303  1.00    10.91      H  C
ATOM   1690  O    THR   33     111.188   20.061   15.157  1.00    10.91      H  O
ATOM   1691  N    MET   34     109.348   21.070   15.960  1.00    21.14      H  N
ATOM   1692  CA   MET   34     108.815   19.835   16.518  1.00    21.14      H  C
ATOM   1693  CB   MET   34     108.188   20.094   17.888  1.00    16.88      H  C
ATOM   1694  CG   MET   34     109.035   20.899   18.847  1.00    16.88      H  C
ATOM   1695  SD   MET   34     110.603   20.131   19.122  1.00    16.88      H  S
ATOM   1696  CE   MET   34     110.155   18.770   20.240  1.00    16.88      H  C
ATOM   1697  C    MET   34     107.760   19.218   15.614  1.00    21.14      H  C
ATOM   1698  O    MET   34     107.160   19.905   14.781  1.00    21.14      H  O
ATOM   1699  N    SER   35     107.519   17.925   15.802  1.00    15.88      H  N
ATOM   1700  CA   SER   35     106.533   17.232   14.997  1.00    15.88      H  C
ATOM   1701  CB   SER   35     107.205   16.581   13.794  1.00    13.53      H  C
ATOM   1702  OG   SER   35     107.895   17.550   13.034  1.00    13.53      H  O
ATOM   1703  C    SER   35     105.767   16.168   15.763  1.00    15.88      H  C
ATOM   1704  O    SER   35     106.058   15.867   16.926  1.00    15.88      H  O
ATOM   1705  N    TRP   36     104.765   15.617   15.087  1.00    13.73      H  N
ATOM   1706  CA   TRP   36     103.948   14.556   15.626  1.00    13.73      H  C
ATOM   1707  CB   TRP   36     102.510   15.023   15.849  1.00    20.04      H  C
ATOM   1708  CG   TRP   36     102.337   15.903   17.039  1.00    20.04      H  C
ATOM   1709  CD2  TRP   36     102.259   15.489   18.406  1.00    20.04      H  C
ATOM   1710  CE2  TRP   36     102.112   16.654   19.186  1.00    20.04      H  C
ATOM   1711  CE3  TRP   36     102.301   14.248   19.046  1.00    20.04      H  C
ATOM   1712  CD1  TRP   36     102.236   17.255   17.045  1.00    20.04      H  C
ATOM   1713  NE1  TRP   36     102.100   17.716   18.329  1.00    20.04      H  N
ATOM   1714  CZ2  TRP   36     102.004   16.622   20.576  1.00    20.04      H  C
ATOM   1715  CZ3  TRP   36     102.192   14.211   20.442  1.00    20.04      H  C
ATOM   1716  CH2  TRP   36     102.044   15.396   21.190  1.00    20.04      H  C
ATOM   1717  C    TRP   36     103.978   13.470   14.565  1.00    13.73      H  C
ATOM   1718  O    TRP   36     103.879   13.769   13.373  1.00    13.73      H  O
ATOM   1719  N    VAL   37     104.138   12.221   15.006  1.00    21.09      H  N
ATOM   1720  CA   VAL   37     104.179   11.054   14.125  1.00    21.09      H  C
ATOM   1721  CB   VAL   37     105.622   10.464   14.053  1.00     6.36      H  C
ATOM   1722  CG1  VAL   37     105.591    9.017   13.642  1.00     6.36      H  C
ATOM   1723  CG2  VAL   37     106.461   11.253   13.057  1.00     6.36      H  C
ATOM   1724  C    VAL   37     103.229   10.041   14.748  1.00    21.09      H  C
ATOM   1725  O    VAL   37     103.144    9.940   15.963  1.00    21.09      H  O
ATOM   1726  N    ARG   38     102.508    9.294   13.929  1.00    17.98      H  N
ATOM   1727  CA   ARG   38     101.562    8.309   14.454  1.00    17.98      H  C
ATOM   1728  CB   ARG   38     100.133    8.697   14.058  1.00    13.99      H  C
ATOM   1729  CG   ARG   38     100.106    9.210   12.633  1.00    13.99      H  C
ATOM   1730  CD   ARG   38      98.899    8.817   11.839  1.00    13.99      H  C
ATOM   1731  NE   ARG   38      97.664    9.434   12.289  1.00    13.99      H  N
ATOM   1732  CZ   ARG   38      96.652    9.707   11.470  1.00    13.99      H  C
ATOM   1733  NH1  ARG   38      96.744    9.432   10.171  1.00    13.99      H  N
ATOM   1734  NH2  ARG   38      95.533   10.224   11.960  1.00    13.99      H  N
ATOM   1735  C    ARG   38     101.856    6.925   13.895  1.00    17.98      H  C
ATOM   1736  O    ARG   38     102.468    6.785   12.840  1.00    17.98      H  O
ATOM   1737  N    GLN   39     101.386    5.909   14.604  1.00    17.63      H  N
ATOM   1738  CA   GLN   39     101.560    4.521   14.200  1.00    17.63      H  C
ATOM   1739  CB   GLN   39     102.659    3.866   15.051  1.00    12.11      H  C
ATOM   1740  CG   GLN   39     102.976    2.424   14.712  1.00    12.11      H  C
ATOM   1741  CD   GLN   39     104.396    2.025   15.134  1.00    12.11      H  C
ATOM   1742  OE1  GLN   39     104.811    2.262   16.272  1.00    12.11      H  O
ATOM   1743  NE2  GLN   39     105.143    1.414   14.212  1.00    12.11      H  N
ATOM   1744  C    GLN   39     100.206    3.847   14.429  1.00    17.63      H  C
ATOM   1745  O    GLN   39      99.712    3.770   15.562  1.00    17.63      H  O
ATOM   1746  N    ALA   40      99.590    3.399   13.344  1.00    55.11      H  N
ATOM   1747  CA   ALA   40      98.300    2.737   13.436  1.00    55.11      H  C
ATOM   1748  CB   ALA   40      97.605    2.754   12.088  1.00    43.12      H  C
ATOM   1749  C    ALA   40      98.536    1.302   13.881  1.00    55.11      H  C
ATOM   1750  O    ALA   40      99.626    0.762   13.687  1.00    55.11      H  O
ATOM   1751  N    PRO   41      97.517    0.670   14.491  1.00    55.83      H  N
ATOM   1752  CD   PRO   41      96.189    1.237   14.782  1.00    86.02      H  C
```

Fig. 19: A-25

| | | | | | | | | | | |
|---|---|---|---|---|---|---|---|---|---|---|
| ATOM | 1753 | CA | PRO | 41 | 97.600 | -0.712 | 14.969 | 1.00 | 55.83 | H C |
| ATOM | 1754 | CB | PRO | 41 | 96.169 | -1.009 | 15.400 | 1.00 | 86.02 | H C |
| ATOM | 1755 | CG | PRO | 41 | 95.681 | 0.315 | 15.859 | 1.00 | 86.02 | H C |
| ATOM | 1756 | C | PRO | 41 | 98.057 | -1.624 | 13.838 | 1.00 | 55.83 | H C |
| ATOM | 1757 | O | PRO | 41 | 97.423 | -1.670 | 12.781 | 1.00 | 55.83 | H O |
| ATOM | 1758 | N | GLY | 42 | 99.160 | -2.335 | 14.061 | 1.00 | 43.01 | H N |
| ATOM | 1759 | CA | GLY | 42 | 99.684 | -3.227 | 13.042 | 1.00 | 43.01 | H C |
| ATOM | 1760 | C | GLY | 42 | 100.227 | -2.529 | 11.800 | 1.00 | 43.01 | H C |
| ATOM | 1761 | O | GLY | 42 | 100.480 | -3.175 | 10.775 | 1.00 | 43.01 | H O |
| ATOM | 1762 | N | LYS | 43 | 100.415 | -1.212 | 11.882 | 1.00 | 46.16 | H N |
| ATOM | 1763 | CA | LYS | 43 | 100.922 | -0.446 | 10.750 | 1.00 | 46.16 | H C |
| ATOM | 1764 | CB | LYS | 43 | 99.896 | 0.612 | 10.334 | 1.00 | 59.60 | H C |
| ATOM | 1765 | CG | LYS | 43 | 98.800 | 0.081 | 9.421 | 1.00 | 59.60 | H C |
| ATOM | 1766 | CD | LYS | 43 | 98.003 | -1.023 | 10.079 | 1.00 | 59.60 | H C |
| ATOM | 1767 | CE | LYS | 43 | 97.230 | -1.831 | 9.047 | 1.00 | 59.60 | H C |
| ATOM | 1768 | NZ | LYS | 43 | 98.125 | -2.590 | 8.124 | 1.00 | 59.60 | H N |
| ATOM | 1769 | C | LYS | 43 | 102.278 | 0.215 | 10.994 | 1.00 | 46.16 | H C |
| ATOM | 1770 | O | LYS | 43 | 102.889 | 0.060 | 12.063 | 1.00 | 46.16 | H O |
| ATOM | 1771 | N | GLY | 44 | 102.742 | 0.942 | 9.976 | 1.00 | 50.42 | H N |
| ATOM | 1772 | CA | GLY | 44 | 104.016 | 1.631 | 10.054 | 1.00 | 50.42 | H C |
| ATOM | 1773 | C | GLY | 44 | 103.916 | 3.004 | 10.691 | 1.00 | 50.42 | H C |
| ATOM | 1774 | O | GLY | 44 | 103.001 | 3.281 | 11.462 | 1.00 | 50.42 | H O |
| ATOM | 1775 | N | LEU | 45 | 104.862 | 3.870 | 10.347 | 1.00 | 25.59 | H N |
| ATOM | 1776 | CA | LEU | 45 | 104.933 | 5.229 | 10.883 | 1.00 | 25.59 | H C |
| ATOM | 1777 | CB | LEU | 45 | 106.387 | 5.544 | 11.224 | 1.00 | 8.94 | H C |
| ATOM | 1778 | CG | LEU | 45 | 107.011 | 4.480 | 12.118 | 1.00 | 8.94 | H C |
| ATOM | 1779 | CD1 | LEU | 45 | 108.520 | 4.578 | 12.054 | 1.00 | 8.94 | H C |
| ATOM | 1780 | CD2 | LEU | 45 | 106.481 | 4.638 | 13.541 | 1.00 | 8.94 | H C |
| ATOM | 1781 | C | LEU | 45 | 104.394 | 6.259 | 9.893 | 1.00 | 25.59 | H C |
| ATOM | 1782 | O | LEU | 45 | 104.613 | 6.142 | 8.684 | 1.00 | 25.59 | H O |
| ATOM | 1783 | N | GLU | 46 | 103.698 | 7.268 | 10.411 | 1.00 | 28.67 | H N |
| ATOM | 1784 | CA | GLU | 46 | 103.111 | 8.308 | 9.569 | 1.00 | 28.67 | H C |
| ATOM | 1785 | CB | GLU | 46 | 101.617 | 8.045 | 9.370 | 1.00 | 21.38 | H C |
| ATOM | 1786 | CG | GLU | 46 | 100.977 | 8.902 | 8.304 | 1.00 | 21.38 | H C |
| ATOM | 1787 | CD | GLU | 46 | 99.555 | 8.471 | 7.972 | 1.00 | 21.38 | H C |
| ATOM | 1788 | OE1 | GLU | 46 | 98.711 | 8.399 | 8.903 | 1.00 | 21.38 | H O |
| ATOM | 1789 | OE2 | GLU | 46 | 99.283 | 8.214 | 6.776 | 1.00 | 21.38 | H O |
| ATOM | 1790 | C | GLU | 46 | 103.304 | 9.698 | 10.152 | 1.00 | 28.67 | H C |
| ATOM | 1791 | O | GLU | 46 | 102.942 | 9.962 | 11.301 | 1.00 | 28.67 | H O |
| ATOM | 1792 | N | TRP | 47 | 103.887 | 10.579 | 9.347 | 1.00 | 2.61 | H N |
| ATOM | 1793 | CA | TRP | 47 | 104.132 | 11.944 | 9.758 | 1.00 | 2.61 | H C |
| ATOM | 1794 | CB | TRP | 47 | 105.055 | 12.618 | 8.757 | 1.00 | 14.19 | H C |
| ATOM | 1795 | CG | TRP | 47 | 105.068 | 14.095 | 8.904 | 1.00 | 14.19 | H C |
| ATOM | 1796 | CD2 | TRP | 47 | 104.446 | 15.035 | 8.036 | 1.00 | 14.19 | H C |
| ATOM | 1797 | CE2 | TRP | 47 | 104.681 | 16.323 | 8.578 | 1.00 | 14.19 | H C |
| ATOM | 1798 | CE3 | TRP | 47 | 103.709 | 14.919 | 6.852 | 1.00 | 14.19 | H C |
| ATOM | 1799 | CD1 | TRP | 47 | 105.644 | 14.824 | 9.914 | 1.00 | 14.19 | H C |
| ATOM | 1800 | NE1 | TRP | 47 | 105.418 | 16.161 | 9.723 | 1.00 | 14.19 | H N |
| ATOM | 1801 | CZ2 | TRP | 47 | 104.201 | 17.490 | 7.969 | 1.00 | 14.19 | H C |
| ATOM | 1802 | CZ3 | TRP | 47 | 103.233 | 16.074 | 6.248 | 1.00 | 14.19 | H C |
| ATOM | 1803 | CH2 | TRP | 47 | 103.480 | 17.344 | 6.808 | 1.00 | 14.19 | H C |
| ATOM | 1804 | C | TRP | 47 | 102.791 | 12.673 | 9.802 | 1.00 | 2.61 | H C |
| ATOM | 1805 | O | TRP | 47 | 102.083 | 12.752 | 8.796 | 1.00 | 2.61 | H O |
| ATOM | 1806 | N | VAL | 48 | 102.443 | 13.215 | 10.962 | 1.00 | 34.26 | H N |
| ATOM | 1807 | CA | VAL | 48 | 101.165 | 13.895 | 11.114 | 1.00 | 34.26 | H C |
| ATOM | 1808 | CB | VAL | 48 | 100.576 | 13.639 | 12.523 | 1.00 | 16.29 | H C |
| ATOM | 1809 | CG1 | VAL | 48 | 99.137 | 14.148 | 12.623 | 1.00 | 16.29 | H C |
| ATOM | 1810 | CG2 | VAL | 48 | 100.624 | 12.187 | 12.812 | 1.00 | 16.29 | H C |
| ATOM | 1811 | C | VAL | 48 | 101.246 | 15.393 | 10.884 | 1.00 | 34.26 | H C |
| ATOM | 1812 | O | VAL | 48 | 100.563 | 15.932 | 10.015 | 1.00 | 34.26 | H O |
| ATOM | 1813 | N | ALA | 49 | 102.078 | 16.068 | 11.665 | 1.00 | 19.79 | H N |
| ATOM | 1814 | CA | ALA | 49 | 102.198 | 17.505 | 11.533 | 1.00 | 19.79 | H C |
| ATOM | 1815 | CB | ALA | 49 | 101.052 | 18.193 | 12.288 | 1.00 | 1.87 | H C |
| ATOM | 1816 | C | ALA | 49 | 103.542 | 17.994 | 12.041 | 1.00 | 19.79 | H C |
| ATOM | 1817 | O | ALA | 49 | 104.295 | 17.244 | 12.645 | 1.00 | 19.79 | H O |
| ATOM | 1818 | N | THR | 50 | 103.816 | 19.271 | 11.795 | 1.00 | 29.76 | H N |
| ATOM | 1819 | CA | THR | 50 | 105.067 | 19.906 | 12.184 | 1.00 | 29.76 | H C |
| ATOM | 1820 | CB | THR | 50 | 106.142 | 19.637 | 11.127 | 1.00 | 20.69 | H C |
| ATOM | 1821 | OG1 | THR | 50 | 106.390 | 18.232 | 11.065 | 1.00 | 20.69 | H O |
| ATOM | 1822 | CG2 | THR | 50 | 107.422 | 20.357 | 11.460 | 1.00 | 20.69 | H C |
| ATOM | 1823 | C | THR | 50 | 104.897 | 21.416 | 12.327 | 1.00 | 29.76 | H C |
| ATOM | 1824 | O | THR | 50 | 104.113 | 22.035 | 11.616 | 1.00 | 29.76 | H O |
| ATOM | 1825 | N | ILE | 51 | 105.649 | 21.994 | 13.258 | 1.00 | 20.54 | H N |

Fig. 19: A-26

| | | | | | | | | | | |
|---|---|---|---|---|---|---|---|---|---|---|
| ATOM | 1826 | CA | ILE | 51 | 105.626 | 23.424 | 13.530 | 1.00 | 20.54 | H C |
| ATOM | 1827 | CB | ILE | 51 | 104.824 | 23.714 | 14.816 | 1.00 | 27.11 | H C |
| ATOM | 1828 | CG2 | ILE | 51 | 105.430 | 22.955 | 15.975 | 1.00 | 27.11 | H C |
| ATOM | 1829 | CG1 | ILE | 51 | 104.805 | 25.217 | 15.108 | 1.00 | 27.11 | H C |
| ATOM | 1830 | CD1 | ILE | 51 | 104.073 | 25.593 | 16.389 | 1.00 | 27.11 | H C |
| ATOM | 1831 | C | ILE | 51 | 107.090 | 23.813 | 13.723 | 1.00 | 20.54 | H C |
| ATOM | 1832 | O | ILE | 51 | 107.781 | 23.208 | 14.533 | 1.00 | 20.54 | H O |
| ATOM | 1833 | N | SER | 52 | 107.565 | 24.803 | 12.970 | 1.00 | 28.49 | H N |
| ATOM | 1834 | CA | SER | 52 | 108.962 | 25.234 | 13.047 | 1.00 | 28.49 | H C |
| ATOM | 1835 | CB | SER | 52 | 109.356 | 26.018 | 11.797 | 1.00 | 35.37 | H C |
| ATOM | 1836 | OG | SER | 52 | 108.819 | 27.332 | 11.832 | 1.00 | 35.37 | H O |
| ATOM | 1837 | C | SER | 52 | 109.236 | 26.105 | 14.256 | 1.00 | 28.49 | H C |
| ATOM | 1838 | O | SER | 52 | 108.316 | 26.461 | 14.994 | 1.00 | 28.49 | H O |
| ATOM | 1839 | N | GLY | 53 | 110.509 | 26.452 | 14.451 | 1.00 | 16.74 | H N |
| ATOM | 1840 | CA | GLY | 53 | 110.864 | 27.295 | 15.568 | 1.00 | 16.74 | H C |
| ATOM | 1841 | C | GLY | 53 | 110.203 | 28.651 | 15.410 | 1.00 | 16.74 | H C |
| ATOM | 1842 | O | GLY | 53 | 110.093 | 29.412 | 16.369 | 1.00 | 16.74 | H O |
| ATOM | 1843 | N | GLY | 54 | 109.746 | 28.939 | 14.192 | 1.00 | 26.55 | H N |
| ATOM | 1844 | CA | GLY | 54 | 109.120 | 30.218 | 13.907 | 1.00 | 26.55 | H C |
| ATOM | 1845 | C | GLY | 54 | 107.605 | 30.253 | 13.815 | 1.00 | 26.55 | H C |
| ATOM | 1846 | O | GLY | 54 | 107.020 | 31.317 | 13.607 | 1.00 | 26.55 | H O |
| ATOM | 1847 | N | GLY | 55 | 106.953 | 29.105 | 13.948 | 1.00 | 34.83 | H N |
| ATOM | 1848 | CA | GLY | 55 | 105.505 | 29.105 | 13.889 | 1.00 | 34.83 | H C |
| ATOM | 1849 | C | GLY | 55 | 104.878 | 28.610 | 12.604 | 1.00 | 34.83 | H C |
| ATOM | 1850 | O | GLY | 55 | 103.657 | 28.663 | 12.458 | 1.00 | 34.83 | H O |
| ATOM | 1851 | N | HIS | 56 | 105.683 | 28.149 | 11.655 | 1.00 | 20.17 | H N |
| ATOM | 1852 | CA | HIS | 56 | 105.091 | 27.643 | 10.426 | 1.00 | 20.17 | H C |
| ATOM | 1853 | CB | HIS | 56 | 106.117 | 27.522 | 9.302 | 1.00 | 75.35 | H C |
| ATOM | 1854 | CG | HIS | 56 | 106.829 | 28.797 | 8.996 | 1.00 | 75.35 | H C |
| ATOM | 1855 | CD2 | HIS | 56 | 106.561 | 29.773 | 8.096 | 1.00 | 75.35 | H C |
| ATOM | 1856 | ND1 | HIS | 56 | 107.959 | 29.201 | 9.677 | 1.00 | 75.35 | H N |
| ATOM | 1857 | CE1 | HIS | 56 | 108.356 | 30.370 | 9.209 | 1.00 | 75.35 | H C |
| ATOM | 1858 | NE2 | HIS | 56 | 107.525 | 30.739 | 8.250 | 1.00 | 75.35 | H N |
| ATOM | 1859 | C | HIS | 56 | 104.585 | 26.266 | 10.774 | 1.00 | 20.17 | H C |
| ATOM | 1860 | O | HIS | 56 | 105.309 | 25.465 | 11.350 | 1.00 | 20.17 | H O |
| ATOM | 1861 | N | THR | 57 | 103.331 | 25.994 | 10.458 | 1.00 | 9.30 | H N |
| ATOM | 1862 | CA | THR | 57 | 102.793 | 24.676 | 10.728 | 1.00 | 9.30 | H C |
| ATOM | 1863 | CB | THR | 57 | 101.437 | 24.766 | 11.475 | 1.00 | 25.93 | H C |
| ATOM | 1864 | OG1 | THR | 57 | 100.483 | 25.493 | 10.691 | 1.00 | 25.93 | H O |
| ATOM | 1865 | CG2 | THR | 57 | 101.624 | 25.460 | 12.821 | 1.00 | 25.93 | H C |
| ATOM | 1866 | C | THR | 57 | 102.657 | 23.911 | 9.403 | 1.00 | 9.30 | H C |
| ATOM | 1867 | O | THR | 57 | 102.437 | 24.503 | 8.348 | 1.00 | 9.30 | H O |
| ATOM | 1868 | N | TYR | 58 | 102.849 | 22.598 | 9.463 | 1.00 | 10.35 | H N |
| ATOM | 1869 | CA | TYR | 58 | 102.739 | 21.729 | 8.293 | 1.00 | 10.35 | H C |
| ATOM | 1870 | CB | TYR | 58 | 104.115 | 21.217 | 7.912 | 1.00 | 22.31 | H C |
| ATOM | 1871 | CG | TYR | 58 | 105.023 | 22.324 | 7.485 | 1.00 | 22.31 | H C |
| ATOM | 1872 | CD1 | TYR | 58 | 105.051 | 22.744 | 6.167 | 1.00 | 22.31 | H C |
| ATOM | 1873 | CE1 | TYR | 58 | 105.871 | 23.765 | 5.768 | 1.00 | 22.31 | H C |
| ATOM | 1874 | CD2 | TYR | 58 | 105.843 | 22.967 | 8.399 | 1.00 | 22.31 | H C |
| ATOM | 1875 | CE2 | TYR | 58 | 106.667 | 23.997 | 8.007 | 1.00 | 22.31 | H C |
| ATOM | 1876 | CZ | TYR | 58 | 106.674 | 24.388 | 6.689 | 1.00 | 22.31 | H C |
| ATOM | 1877 | OH | TYR | 58 | 107.478 | 25.419 | 6.279 | 1.00 | 22.31 | H O |
| ATOM | 1878 | C | TYR | 58 | 101.812 | 20.565 | 8.535 | 1.00 | 10.35 | H C |
| ATOM | 1879 | O | TYR | 58 | 101.699 | 20.164 | 9.801 | 1.00 | 10.35 | H O |
| ATOM | 1880 | N | TYR | 59 | 101.147 | 20.007 | 7.634 | 1.00 | 15.64 | H N |
| ATOM | 1881 | CA | TYR | 59 | 100.219 | 18.936 | 7.931 | 1.00 | 15.64 | H C |
| ATOM | 1882 | CB | TYR | 59 | 98.843 | 19.542 | 8.203 | 1.00 | 11.32 | H C |
| ATOM | 1883 | CG | TYR | 59 | 98.803 | 20.511 | 9.360 | 1.00 | 11.32 | H C |
| ATOM | 1884 | CD1 | TYR | 59 | 98.625 | 20.058 | 10.661 | 1.00 | 11.32 | H C |
| ATOM | 1885 | CE1 | TYR | 59 | 98.540 | 20.942 | 11.731 | 1.00 | 11.32 | H C |
| ATOM | 1886 | CD2 | TYR | 59 | 98.912 | 21.886 | 9.148 | 1.00 | 11.32 | H C |
| ATOM | 1887 | CE2 | TYR | 59 | 98.835 | 22.783 | 10.208 | 1.00 | 11.32 | H C |
| ATOM | 1888 | CZ | TYR | 59 | 98.640 | 22.302 | 11.502 | 1.00 | 11.32 | H C |
| ATOM | 1889 | OH | TYR | 59 | 98.498 | 23.177 | 12.557 | 1.00 | 11.32 | H O |
| ATOM | 1890 | C | TYR | 59 | 100.071 | 17.883 | 6.856 | 1.00 | 15.64 | H C |
| ATOM | 1891 | O | TYR | 59 | 100.150 | 18.182 | 5.666 | 1.00 | 15.64 | H O |
| ATOM | 1892 | N | LEU | 60 | 99.854 | 16.644 | 7.286 | 1.00 | 33.81 | H N |
| ATOM | 1893 | CA | LEU | 60 | 99.616 | 15.539 | 6.366 | 1.00 | 33.81 | H C |
| ATOM | 1894 | CB | LEU | 60 | 99.625 | 14.217 | 7.135 | 1.00 | 13.27 | H C |
| ATOM | 1895 | CG | LEU | 60 | 99.371 | 12.896 | 6.406 | 1.00 | 13.27 | H C |
| ATOM | 1896 | CD1 | LEU | 60 | 100.681 | 12.371 | 5.800 | 1.00 | 13.27 | H C |
| ATOM | 1897 | CD2 | LEU | 60 | 98.804 | 11.882 | 7.397 | 1.00 | 13.27 | H C |
| ATOM | 1898 | C | LEU | 60 | 98.198 | 15.861 | 5.869 | 1.00 | 33.81 | H C |

Fig. 19: A-27

| | | | | | | | | | | | |
|---|---|---|---|---|---|---|---|---|---|---|---|
| ATOM | 1899 | O | LEU | 60 | 97.329 | 16.255 | 6.659 | 1.00 | 33.81 | H | O |
| ATOM | 1900 | N | ASP | 61 | 97.962 | 15.710 | 4.573 | 1.00 | 24.56 | H | N |
| ATOM | 1901 | CA | ASP | 61 | 96.659 | 16.028 | 3.991 | 1.00 | 24.56 | H | C |
| ATOM | 1902 | CB | ASP | 61 | 96.639 | 15.579 | 2.530 | 1.00 | 55.35 | H | C |
| ATOM | 1903 | CG | ASP | 61 | 97.719 | 16.260 | 1.708 | 1.00 | 55.35 | H | C |
| ATOM | 1904 | OD1 | ASP | 61 | 98.919 | 16.083 | 2.023 | 1.00 | 55.35 | H | O |
| ATOM | 1905 | OD2 | ASP | 61 | 97.374 | 16.981 | 0.754 | 1.00 | 55.35 | H | O |
| ATOM | 1906 | C | ASP | 61 | 95.436 | 15.495 | 4.731 | 1.00 | 24.56 | H | C |
| ATOM | 1907 | O | ASP | 61 | 94.515 | 16.254 | 5.043 | 1.00 | 24.56 | H | O |
| ATOM | 1908 | N | SER | 62 | 95.432 | 14.198 | 5.024 | 1.00 | 20.78 | H | N |
| ATOM | 1909 | CA | SER | 62 | 94.317 | 13.567 | 5.717 | 1.00 | 20.78 | H | C |
| ATOM | 1910 | CB | SER | 62 | 94.630 | 12.085 | 5.955 | 1.00 | 31.68 | H | C |
| ATOM | 1911 | OG | SER | 62 | 95.820 | 11.902 | 6.708 | 1.00 | 31.68 | H | O |
| ATOM | 1912 | C | SER | 62 | 93.882 | 14.216 | 7.044 | 1.00 | 20.78 | H | C |
| ATOM | 1913 | O | SER | 62 | 92.732 | 14.053 | 7.475 | 1.00 | 20.78 | H | O |
| ATOM | 1914 | N | VAL | 63 | 94.779 | 14.949 | 7.695 | 1.00 | 24.27 | H | N |
| ATOM | 1915 | CA | VAL | 63 | 94.439 | 15.567 | 8.968 | 1.00 | 24.27 | H | C |
| ATOM | 1916 | CB | VAL | 63 | 95.478 | 15.202 | 10.049 | 1.00 | 45.54 | H | C |
| ATOM | 1917 | CG1 | VAL | 63 | 95.642 | 13.698 | 10.110 | 1.00 | 45.54 | H | C |
| ATOM | 1918 | CG2 | VAL | 63 | 96.812 | 15.873 | 9.752 | 1.00 | 45.54 | H | C |
| ATOM | 1919 | C | VAL | 63 | 94.374 | 17.083 | 8.839 | 1.00 | 24.27 | H | C |
| ATOM | 1920 | O | VAL | 63 | 94.112 | 17.812 | 9.823 | 1.00 | 24.27 | H | O |
| ATOM | 1921 | N | LYS | 64 | 94.611 | 17.556 | 7.618 | 1.00 | 38.99 | H | N |
| ATOM | 1922 | CA | LYS | 64 | 94.611 | 18.985 | 7.348 | 1.00 | 38.99 | H | C |
| ATOM | 1923 | CB | LYS | 64 | 94.983 | 19.235 | 5.889 | 1.00 | 39.16 | H | C |
| ATOM | 1924 | CG | LYS | 64 | 95.736 | 20.528 | 5.671 | 1.00 | 39.16 | H | C |
| ATOM | 1925 | CD | LYS | 64 | 96.417 | 20.521 | 4.309 | 1.00 | 39.16 | H | C |
| ATOM | 1926 | CE | LYS | 64 | 97.432 | 19.380 | 4.176 | 1.00 | 39.16 | H | C |
| ATOM | 1927 | NZ | LYS | 64 | 98.011 | 19.296 | 2.803 | 1.00 | 39.16 | H | N |
| ATOM | 1928 | C | LYS | 64 | 93.262 | 19.607 | 7.667 | 1.00 | 38.99 | H | C |
| ATOM | 1929 | O | LYS | 64 | 92.240 | 19.212 | 7.121 | 1.00 | 38.99 | H | O |
| ATOM | 1930 | N | GLY | 65 | 93.263 | 20.577 | 8.567 | 1.00 | 28.42 | H | N |
| ATOM | 1931 | CA | GLY | 65 | 92.019 | 21.219 | 8.918 | 1.00 | 28.42 | H | C |
| ATOM | 1932 | C | GLY | 65 | 91.277 | 20.501 | 10.021 | 1.00 | 28.42 | H | C |
| ATOM | 1933 | O | GLY | 65 | 90.271 | 21.005 | 10.509 | 1.00 | 28.42 | H | O |
| ATOM | 1934 | N | ARG | 66 | 91.751 | 19.324 | 10.414 | 1.00 | 48.07 | H | N |
| ATOM | 1935 | CA | ARG | 66 | 91.098 | 18.588 | 11.488 | 1.00 | 48.07 | H | C |
| ATOM | 1936 | CB | ARG | 66 | 90.783 | 17.154 | 11.064 | 1.00 | 36.61 | H | C |
| ATOM | 1937 | CG | ARG | 66 | 89.845 | 17.052 | 9.887 | 1.00 | 36.61 | H | C |
| ATOM | 1938 | CD | ARG | 66 | 89.484 | 15.608 | 9.571 | 1.00 | 36.61 | H | C |
| ATOM | 1939 | NE | ARG | 66 | 90.654 | 14.750 | 9.346 | 1.00 | 36.61 | H | N |
| ATOM | 1940 | CZ | ARG | 66 | 91.133 | 13.877 | 10.236 | 1.00 | 36.61 | H | C |
| ATOM | 1941 | NH1 | ARG | 66 | 90.545 | 13.739 | 11.421 | 1.00 | 36.61 | H | N |
| ATOM | 1942 | NH2 | ARG | 66 | 92.203 | 13.144 | 9.944 | 1.00 | 36.61 | H | N |
| ATOM | 1943 | C | ARG | 66 | 92.018 | 18.568 | 12.687 | 1.00 | 48.07 | H | C |
| ATOM | 1944 | O | ARG | 66 | 91.584 | 18.312 | 13.808 | 1.00 | 48.07 | H | O |
| ATOM | 1945 | N | PHE | 67 | 93.296 | 18.839 | 12.438 | 1.00 | 31.81 | H | N |
| ATOM | 1946 | CA | PHE | 67 | 94.304 | 18.854 | 13.490 | 1.00 | 31.81 | H | C |
| ATOM | 1947 | CB | PHE | 67 | 95.372 | 17.802 | 13.211 | 1.00 | 34.94 | H | C |
| ATOM | 1948 | CG | PHE | 67 | 94.937 | 16.394 | 13.444 | 1.00 | 34.94 | H | C |
| ATOM | 1949 | CD1 | PHE | 67 | 93.763 | 15.907 | 12.902 | 1.00 | 34.94 | H | C |
| ATOM | 1950 | CD2 | PHE | 67 | 95.748 | 15.530 | 14.158 | 1.00 | 34.94 | H | C |
| ATOM | 1951 | CE1 | PHE | 67 | 93.400 | 14.564 | 13.063 | 1.00 | 34.94 | H | C |
| ATOM | 1952 | CE2 | PHE | 67 | 95.400 | 14.192 | 14.326 | 1.00 | 34.94 | H | C |
| ATOM | 1953 | CZ | PHE | 67 | 94.222 | 13.706 | 13.777 | 1.00 | 34.94 | H | C |
| ATOM | 1954 | C | PHE | 67 | 94.989 | 20.209 | 13.520 | 1.00 | 31.81 | H | C |
| ATOM | 1955 | O | PHE | 67 | 95.054 | 20.899 | 12.501 | 1.00 | 31.81 | H | O |
| ATOM | 1956 | N | THR | 68 | 95.511 | 20.587 | 14.683 | 1.00 | 27.20 | H | N |
| ATOM | 1957 | CA | THR | 68 | 96.233 | 21.851 | 14.804 | 1.00 | 27.20 | H | C |
| ATOM | 1958 | CB | THR | 68 | 95.344 | 22.998 | 15.384 | 1.00 | 14.56 | H | C |
| ATOM | 1959 | OG1 | THR | 68 | 94.400 | 23.434 | 14.399 | 1.00 | 14.56 | H | O |
| ATOM | 1960 | CG2 | THR | 68 | 96.196 | 24.192 | 15.758 | 1.00 | 14.56 | H | C |
| ATOM | 1961 | C | THR | 68 | 97.466 | 21.680 | 15.689 | 1.00 | 27.20 | H | C |
| ATOM | 1962 | O | THR | 68 | 97.355 | 21.393 | 16.882 | 1.00 | 27.20 | H | O |
| ATOM | 1963 | N | ILE | 69 | 98.643 | 21.847 | 15.099 | 1.00 | 22.74 | H | N |
| ATOM | 1964 | CA | ILE | 69 | 99.869 | 21.718 | 15.861 | 1.00 | 22.74 | H | C |
| ATOM | 1965 | CB | ILE | 69 | 100.991 | 21.084 | 15.020 | 1.00 | 13.28 | H | C |
| ATOM | 1966 | CG2 | ILE | 69 | 101.417 | 22.022 | 13.933 | 1.00 | 13.28 | H | C |
| ATOM | 1967 | CG1 | ILE | 69 | 102.188 | 20.736 | 15.908 | 1.00 | 13.28 | H | C |
| ATOM | 1968 | CD1 | ILE | 69 | 103.226 | 19.848 | 15.206 | 1.00 | 13.28 | H | C |
| ATOM | 1969 | C | ILE | 69 | 100.287 | 23.096 | 16.336 | 1.00 | 22.74 | H | C |
| ATOM | 1970 | O | ILE | 69 | 100.282 | 24.065 | 15.578 | 1.00 | 22.74 | H | O |
| ATOM | 1971 | N | SER | 70 | 100.632 | 23.188 | 17.608 | 1.00 | 15.22 | H | N |

Fig. 19: A-28

```
ATOM   1972  CA   SER  70     101.032  24.460  18.183  1.00   15.22   H   C
ATOM   1973  CB   SER  70      99.834  25.147  18.851  1.00    3.12   H   C
ATOM   1974  OG   SER  70      99.588  24.606  20.144  1.00    3.12   H   O
ATOM   1975  C    SER  70     102.088  24.203  19.235  1.00   15.22   H   C
ATOM   1976  O    SER  70     102.392  23.053  19.557  1.00   15.22   H   O
ATOM   1977  N    ARG  71     102.636  25.281  19.780  1.00   42.13   H   N
ATOM   1978  CA   ARG  71     103.640  25.158  20.813  1.00   42.13   H   C
ATOM   1979  CB   ARG  71     105.039  25.089  20.210  1.00   12.52   H   C
ATOM   1980  CG   ARG  71     105.417  26.296  19.388  1.00   12.52   H   C
ATOM   1981  CD   ARG  71     106.906  26.507  19.436  1.00   12.52   H   C
ATOM   1982  NE   ARG  71     107.644  25.627  18.540  1.00   12.52   H   N
ATOM   1983  CZ   ARG  71     108.844  25.114  18.816  1.00   12.52   H   C
ATOM   1984  NH1  ARG  71     109.444  25.380  19.970  1.00   12.52   H   N
ATOM   1985  NH2  ARG  71     109.456  24.354  17.924  1.00   12.52   H   N
ATOM   1986  C    ARG  71     103.568  26.341  21.739  1.00   42.13   H   C
ATOM   1987  O    ARG  71     103.115  27.416  21.352  1.00   42.13   H   O
ATOM   1988- N    ASP  72     104.003  26.131  22.973  1.00   26.38   H   N
ATOM   1989  CA   ASP  72     104.034  27.197  23.954  1.00   26.38   H   C
ATOM   1990  CB   ASP  72     102.949  27.026  25.007  1.00   47.03   H   C
ATOM   1991  CG   ASP  72     103.003  28.108  26.050  1.00   47.03   H   C
ATOM   1992  OD1  ASP  72     102.157  28.112  26.964  1.00   47.03   H   O
ATOM   1993  OD2  ASP  72     103.907  28.959  25.953  1.00   47.03   H   O
ATOM   1994  C    ASP  72     105.402  27.159  24.607  1.00   26.38   H   C
ATOM   1995  O    ASP  72     105.618  26.508  25.633  1.00   26.38   H   O
ATOM   1996  N    ASN  73     106.325  27.868  23.979  1.00   50.64   H   N
ATOM   1997  CA   ASN  73     107.692  27.939  24.441  1.00   50.64   H   C
ATOM   1998  CB   ASN  73     108.522  28.747  23.446  1.00   30.24   H   C
ATOM   1999  CG   ASN  73     108.584  28.091  22.086  1.00   30.24   H   C
ATOM   2000  OD1  ASN  73     109.170  28.625  21.149  1.00   30.24   H   O
ATOM   2001  ND2  ASN  73     107.984  26.917  21.974  1.00   30.24   H   N
ATOM   2002  C    ASN  73     107.827  28.516  25.841  1.00   50.64   H   C
ATOM   2003  O    ASN  73     108.898  28.436  26.438  1.00   50.64   H   O
ATOM   2004  N    SER  74     106.758  29.097  26.376  1.00   33.75   H   N
ATOM   2005  CA   SER  74     106.848  29.644  27.723  1.00   33.75   H   C
ATOM   2006  CB   SER  74     105.593  30.429  28.093  1.00   48.57   H   C
ATOM   2007  OG   SER  74     104.534  29.556  28.444  1.00   48.57   H   O
ATOM   2008  C    SER  74     106.979  28.456  28.653  1.00   33.75   H   C
ATOM   2009  O    SER  74     107.681  28.530  29.660  1.00   33.75   H   O
ATOM   2010  N    LYS  75     106.312  27.354  28.302  1.00   39.57   H   N
ATOM   2011  CA   LYS  75     106.352  26.142  29.119  1.00   39.57   H   C
ATOM   2012  CB   LYS  75     104.973  25.889  29.732  1.00   42.48   H   C
ATOM   2013  CG   LYS  75     103.842  25.924  28.731  1.00   42.48   H   C
ATOM   2014  CD   LYS  75     102.482  25.985  29.418  1.00   42.48   H   C
ATOM   2015  CE   LYS  75     102.156  27.393  29.918  1.00   42.48   H   C
ATOM   2016  NZ   LYS  75     103.090  27.928  30.963  1.00   42.48   H   N
ATOM   2017  C    LYS  75     106.843  24.894  28.380  1.00   39.57   H   C
ATOM   2018  O    LYS  75     106.497  23.767  28.744  1.00   39.57   H   O
ATOM   2019  N    ASN  76     107.660  25.110  27.353  1.00   44.84   H   N
ATOM   2020  CA   ASN  76     108.245  24.043  26.539  1.00   44.84   H   C
ATOM   2021  CB   ASN  76     109.572  23.608  27.139  1.00   31.30   H   C
ATOM   2022  CG   ASN  76     110.528  24.766  27.312  1.00   31.30   H   C
ATOM   2023  OD1  ASN  76     111.666  24.593  27.739  1.00   31.30   H   O
ATOM   2024  ND2  ASN  76     110.067  25.965  26.979  1.00   31.30   H   N
ATOM   2025  C    ASN  76     107.362  22.827  26.322  1.00   44.84   H   C
ATOM   2026  O    ASN  76     107.793  21.681  26.479  1.00   44.84   H   O
ATOM   2027  N    THR  77     106.121  23.090  25.941  1.00   30.42   H   N
ATOM   2028  CA   THR  77     105.181  22.032  25.686  1.00   30.42   H   C
ATOM   2029  CB   THR  77     103.989  22.131  26.628  1.00   46.49   H   C
ATOM   2030  OG1  THR  77     104.446  21.977  27.974  1.00   46.49   H   O
ATOM   2031  CG2  THR  77     102.975  21.045  26.319  1.00   46.49   H   C
ATOM   2032  C    THR  77     104.708  22.182  24.254  1.00   30.42   H   C
ATOM   2033  O    THR  77     104.488  23.291  23.786  1.00   30.42   H   O
ATOM   2034  N    LEU  78     104.583  21.056  23.563  1.00   20.66   H   N
ATOM   2035  CA   LEU  78     104.135  21.017  22.185  1.00   20.66   H   C
ATOM   2036  CB   LEU  78     104.978  20.024  21.394  1.00   19.59   H   C
ATOM   2037  CG   LEU  78     104.550  19.758  19.953  1.00   19.59   H   C
ATOM   2038  CD1  LEU  78     104.575  21.055  19.166  1.00   19.59   H   C
ATOM   2039  CD2  LEU  78     105.470  18.731  19.320  1.00   19.59   H   C
ATOM   2040  C    LEU  78     102.716  20.520  22.298  1.00   20.66   H   C
ATOM   2041  O    LEU  78     102.368  19.921  23.312  1.00   20.66   H   O
ATOM   2042  N    TYR  79     101.902  20.753  21.271  1.00   30.75   H   N
ATOM   2043  CA   TYR  79     100.498  20.333  21.294  1.00   30.75   H   C
ATOM   2044  CB   TYR  79      99.591  21.494  21.728  1.00   47.95   H   C
```

Fig. 19: A-29

```
ATOM   2045  CG   TYR    79      99.809  22.008  23.119  1.00   47.95      H  C
ATOM   2046  CD1  TYR    79      99.166  21.430  24.205  1.00   47.95      H  C
ATOM   2047  CE1  TYR    79      99.357  21.916  25.491  1.00   47.95      H  C
ATOM   2048  CD2  TYR    79     100.655  23.085  23.349  1.00   47.95      H  C
ATOM   2049  CE2  TYR    79     100.857  23.579  24.628  1.00   47.95      H  C
ATOM   2050  CZ   TYR    79     100.204  22.991  25.695  1.00   47.95      H  C
ATOM   2051  OH   TYR    79     100.404  23.493  26.958  1.00   47.95      H  C
ATOM   2052  C    TYR    79      99.966  19.863  19.950  1.00   30.75      H  C
ATOM   2053  O    TYR    79     100.418  20.316  18.898  1.00   30.75      H  C
ATOM   2054  N    LEU    80      98.981  18.969  20.003  1.00   19.83      H  N
ATOM   2055  CA   LEU    80      98.308  18.472  18.811  1.00   19.83      H  C
ATOM   2056  CB   LEU    80      98.776  17.070  18.397  1.00    5.08      H  C
ATOM   2057  CG   LEU    80      98.132  16.598  17.076  1.00    5.08      H  C
ATOM   2058  CD1  LEU    80      98.706  17.386  15.914  1.00    5.08      H  C
ATOM   2059  CD2  LEU    80      98.352  15.111  16.874  1.00    5.08      H  C
ATOM   2060  C    LEU    80      96.836  18.411  19.182  1.00   19.83      H  C
ATOM   2061  O    LEU    80      96.398  17.503  19.879  1.00   19.83      H  O
ATOM   2062  N    GLN    81      96.091  19.412  18.742  1.00   24.43      H  N
ATOM   2063  CA   GLN    81      94.671  19.463  19.004  1.00   24.43      H  C
ATOM   2064  CB   GLN    81      94.169  20.911  18.966  1.00   60.73      H  C
ATOM   2065  CG   GLN    81      92.710  21.093  19.399  1.00   60.73      H  C
ATOM   2066  CD   GLN    81      92.505  20.974  20.911  1.00   60.73      H  C
ATOM   2067  OE1  GLN    81      92.981  21.810  21.691  1.00   60.73      H  O
ATOM   2068  NE2  GLN    81      91.787  19.935  21.328  1.00   60.73      H  N
ATOM   2069  C    GLN    81      94.064  18.672  17.867  1.00   24.43      H  C
ATOM   2070  O    GLN    81      94.376  18.921  16.698  1.00   24.43      H  O
ATOM   2071  N    MET    82      93.205  17.718  18.210  1.00   35.69      H  N
ATOM   2072  CA   MET    82      92.559  16.878  17.211  1.00   35.69      H  C
ATOM   2073  CB   MET    82      92.989  15.424  17.383  1.00   24.95      H  C
ATOM   2074  CG   MET    82      94.481  15.209  17.363  1.00   24.95      H  C
ATOM   2075  SD   MET    82      94.896  13.491  17.609  1.00   24.95      H  S
ATOM   2076  CE   MET    82      94.985  13.427  19.373  1.00   24.95      H  C
ATOM   2077  C    MET    82      91.051  16.957  17.316  1.00   35.69      H  C
ATOM   2078  O    MET    82      90.479  16.599  18.338  1.00   35.69      H  O
ATOM   2079  N    ASN    83      90.414  17.416  16.247  1.00   28.29      H  N
ATOM   2080  CA   ASN    83      88.968  17.536  16.204  1.00   28.29      H  C
ATOM   2081  CB   ASN    83      88.550  18.989  15.985  1.00   66.28      H  C
ATOM   2082  CG   ASN    83      89.274  19.943  16.899  1.00   66.28      H  C
ATOM   2083  OD1  ASN    83      89.213  19.819  18.121  1.00   66.28      H  O
ATOM   2084  ND2  ASN    83      89.970  20.910  16.309  1.00   66.28      H  N
ATOM   2085  C    ASN    83      88.502  16.728  15.025  1.00   28.29      H  C
ATOM   2086  O    ASN    83      89.306  16.348  14.185  1.00   28.29      H  O
ATOM   2087  N    SER    84      87.199  16.486  14.954  1.00   57.41      H  N
ATOM   2088  CA   SER    84      86.618  15.739  13.847  1.00   57.41      H  C
ATOM   2089  CB   SER    84      86.648  16.584  12.574  1.00   29.12      H  C
ATOM   2090  OG   SER    84      86.027  17.836  12.786  1.00   29.12      H  O
ATOM   2091  C    SER    84      87.374  14.450  13.603  1.00   57.41      H  C
ATOM   2092  O    SER    84      87.642  14.085  12.456  1.00   57.41      H  O
ATOM   2093  N    LEU    85      87.725  13.769  14.687  1.00   32.34      H  N
ATOM   2094  CA   LEU    85      88.452  12.513  14.595  1.00   32.34      H  C
ATOM   2095  CB   LEU    85      88.818  12.009  15.990  1.00   15.22      H  C
ATOM   2096  CG   LEU    85      89.913  12.880  16.600  1.00   15.22      H  C
ATOM   2097  CD1  LEU    85      90.082  12.594  18.078  1.00   15.22      H  C
ATOM   2098  CD2  LEU    85      91.204  12.636  15.828  1.00   15.22      H  C
ATOM   2099  C    LEU    85      87.641  11.460  13.877  1.00   32.34      H  C
ATOM   2100  O    LEU    85      86.434  11.369  14.050  1.00   32.34      H  O
ATOM   2101  N    ARG    86      88.319  10.680  13.049  1.00   24.27      H  N
ATOM   2102  CA   ARG    86      87.686   9.604  12.316  1.00   24.27      H  C
ATOM   2103  CB   ARG    86      87.858   9.801  10.815  1.00   51.87      H  C
ATOM   2104  CG   ARG    86      87.146  11.026  10.286  1.00   51.87      H  C
ATOM   2105  CD   ARG    86      86.864  10.887   8.808  1.00   51.87      H  C
ATOM   2106  NE   ARG    86      87.237  12.088   8.076  1.00   51.87      H  N
ATOM   2107  CZ   ARG    86      86.470  12.581   8.043  1.00   51.87      H  C
ATOM   2108  NH1  ARG    86      89.444  11.967   8.707  1.00   51.87      H  N
ATOM   2109  NH2  ARG    86      88.733  13.676   7.334  1.00   51.87      H  N
ATOM   2110  C    ARG    86      88.387   8.343  12.769  1.00   24.27      H  C
ATOM   2111  O    ARG    86      89.367   8.416  13.514  1.00   24.27      H  O
ATOM   2112  N    ALA    87      87.894   7.191  12.335  1.00   40.98      H  N
ATOM   2113  CA   ALA    87      88.499   5.928  12.733  1.00   40.98      H  C
ATOM   2114  CB   ALA    87      87.678   4.763  12.196  1.00   28.01      H  C
ATOM   2115  C    ALA    87      89.937   5.833  12.242  1.00   40.98      H  C
ATOM   2116  O    ALA    87      90.824   5.425  12.989  1.00   40.98      H  O
ATOM   2117  N    GLU    88      90.169   6.222  10.993  1.00   32.24      H  N
```

Fig. 19: A-30

| | | | | | | | | | | |
|---|---|---|---|---|---|---|---|---|---|---|
| ATOM | 2118 | CA | GLU | 88 | 91.511 | 6.157 | 10.433 | 1.00 | 32.24 | H C |
| ATOM | 2119 | CB | GLU | 88 | 91.583 | 6.890 | 9.094 | 1.00 | 72.38 | H C |
| ATOM | 2120 | CG | GLU | 88 | 90.432 | 6.614 | 8.169 | 1.00 | 72.38 | H C |
| ATOM | 2121 | CD | GLU | 88 | 89.327 | 7.623 | 8.336 | 1.00 | 72.38 | H C |
| ATOM | 2122 | OE1 | GLU | 88 | 89.529 | 8.792 | 7.937 | 1.00 | 72.38 | H O |
| ATOM | 2123 | OE2 | GLU | 88 | 88.265 | 7.246 | 8.874 | 1.00 | 72.38 | H O |
| ATOM | 2124 | C | GLU | 88 | 92.529 | 6.780 | 11.372 | 1.00 | 32.24 | H C |
| ATOM | 2125 | O | GLU | 88 | 93.691 | 6.370 | 11.417 | 1.00 | 32.24 | H O |
| ATOM | 2126 | N | ASP | 89 | 92.080 | 7.772 | 12.128 | 1.00 | 18.63 | H N |
| ATOM | 2127 | CA | ASP | 89 | 92.935 | 8.497 | 13.054 | 1.00 | 18.63 | H C |
| ATOM | 2128 | CB | ASP | 89 | 92.212 | 9.764 | 13.507 | 1.00 | 29.25 | H C |
| ATOM | 2129 | CG | ASP | 89 | 92.073 | 10.775 | 12.392 | 1.00 | 29.25 | H C |
| ATOM | 2130 | OD1 | ASP | 89 | 91.297 | 11.732 | 12.553 | 1.00 | 29.25 | H O |
| ATOM | 2131 | OD2 | ASP | 89 | 92.748 | 10.622 | 11.355 | 1.00 | 29.25 | H O |
| ATOM | 2132 | C | ASP | 89 | 93.434 | 7.724 | 14.268 | 1.00 | 18.63 | H C |
| ATOM | 2133 | O | ASP | 89 | 94.391 | 8.149 | 14.922 | 1.00 | 18.63 | H O |
| ATOM | 2134 | N | THR | 90 | 92.817 | 6.588 | 14.575 | 1.00 | 29.66 | H N |
| ATOM | 2135 | CA | THR | 90 | 93.261 | 5.845 | 15.749 | 1.00 | 29.66 | H C |
| ATOM | 2136 | CB | THR | 90 | 92.303 | 4.668 | 16.113 | 1.00 | 30.61 | H C |
| ATOM | 2137 | OG1 | THR | 90 | 92.601 | 3.537 | 15.293 | 1.00 | 30.61 | H O |
| ATOM | 2138 | CG2 | THR | 90 | 90.828 | 5.072 | 15.903 | 1.00 | 30.61 | H C |
| ATOM | 2139 | C | THR | 90 | 94.664 | 5.311 | 15.527 | 1.00 | 29.66 | H C |
| ATOM | 2140 | O | THR | 90 | 94.961 | 4.727 | 14.492 | 1.00 | 29.66 | H O |
| ATOM | 2141 | N | ALA | 91 | 95.532 | 5.553 | 16.499 | 1.00 | 11.25 | H N |
| ATOM | 2142 | CA | ALA | 91 | 96.918 | 5.094 | 16.451 | 1.00 | 11.25 | H C |
| ATOM | 2143 | CB | ALA | 91 | 97.629 | 5.690 | 15.259 | 1.00 | 1.87 | H C |
| ATOM | 2144 | C | ALA | 91 | 97.611 | 5.536 | 17.729 | 1.00 | 11.25 | H C |
| ATOM | 2145 | O | ALA | 91 | 96.972 | 6.044 | 18.646 | 1.00 | 11.25 | H O |
| ATOM | 2146 | N | VAL | 92 | 98.915 | 5.312 | 17.797 | 1.00 | 22.44 | H N |
| ATOM | 2147 | CA | VAL | 92 | 99.694 | 5.755 | 18.947 | 1.00 | 22.44 | H C |
| ATOM | 2148 | CB | VAL | 92 | 100.654 | 4.665 | 19.465 | 1.00 | 21.44 | H C |
| ATOM | 2149 | CG1 | VAL | 92 | 101.306 | 3.966 | 18.298 | 1.00 | 21.44 | H C |
| ATOM | 2150 | CG2 | VAL | 92 | 101.716 | 5.284 | 20.346 | 1.00 | 21.44 | H C |
| ATOM | 2151 | C | VAL | 92 | 100.482 | 6.913 | 18.363 | 1.00 | 22.44 | H C |
| ATOM | 2152 | O | VAL | 92 | 101.107 | 6.771 | 17.310 | 1.00 | 22.44 | H O |
| ATOM | 2153 | N | TYR | 93 | 100.413 | 8.066 | 19.019 | 1.00 | 21.58 | H N |
| ATOM | 2154 | CA | TYR | 93 | 101.105 | 9.261 | 18.538 | 1.00 | 21.58 | H C |
| ATOM | 2155 | CB | TYR | 93 | 103.161 | 10.470 | 18.585 | 1.00 | 12.38 | H C |
| ATOM | 2156 | CG | TYR | 93 | 99.000 | 10.385 | 17.624 | 1.00 | 12.38 | H C |
| ATOM | 2157 | CD1 | TYR | 93 | 98.023 | 9.399 | 17.759 | 1.00 | 12.38 | H C |
| ATOM | 2158 | CE1 | TYR | 93 | 96.975 | 9.287 | 16.836 | 1.00 | 12.38 | H C |
| ATOM | 2159 | CD2 | TYR | 93 | 98.899 | 11.264 | 16.553 | 1.00 | 12.38 | H C |
| ATOM | 2160 | CE2 | TYR | 93 | 97.863 | 11.165 | 15.634 | 1.00 | 12.38 | H C |
| ATOM | 2161 | CZ | TYR | 93 | 96.908 | 10.173 | 15.773 | 1.00 | 12.38 | H C |
| ATOM | 2162 | OH | TYR | 93 | 95.915 | 10.043 | 14.827 | 1.00 | 12.38 | H O |
| ATOM | 2163 | C | TYR | 93 | 102.384 | 9.577 | 19.312 | 1.00 | 21.58 | H C |
| ATOM | 2164 | O | TYR | 93 | 102.466 | 9.401 | 20.531 | 1.00 | 21.58 | H O |
| ATOM | 2165 | N | TYR | 94 | 103.381 | 10.049 | 18.579 | 1.00 | 19.04 | H N |
| ATOM | 2166 | CA | TYR | 94 | 104.668 | 10.409 | 19.151 | 1.00 | 19.04 | H C |
| ATOM | 2167 | CB | TYR | 94 | 105.789 | 9.576 | 18.533 | 1.00 | 29.80 | H C |
| ATOM | 2168 | CG | TYR | 94 | 105.548 | 8.101 | 18.431 | 1.00 | 29.80 | H C |
| ATOM | 2169 | CD1 | TYR | 94 | 105.948 | 7.237 | 19.454 | 1.00 | 29.80 | H C |
| ATOM | 2170 | CE1 | TYR | 94 | 105.768 | 5.876 | 19.345 | 1.00 | 29.80 | H C |
| ATOM | 2171 | CD2 | TYR | 94 | 104.958 | 7.563 | 17.298 | 1.00 | 29.80 | H C |
| ATOM | 2172 | CE2 | TYR | 94 | 104.773 | 6.204 | 17.177 | 1.00 | 29.80 | H C |
| ATOM | 2173 | CZ | TYR | 94 | 105.179 | 5.363 | 18.202 | 1.00 | 29.80 | H C |
| ATOM | 2174 | OH | TYR | 94 | 104.996 | 4.007 | 18.071 | 1.00 | 29.80 | H O |
| ATOM | 2175 | C | TYR | 94 | 104.991 | 11.853 | 18.805 | 1.00 | 19.04 | H C |
| ATOM | 2176 | O | TYR | 94 | 104.867 | 12.244 | 17.642 | 1.00 | 19.04 | H O |
| ATOM | 2177 | N | CYS | 95 | 105.383 | 12.654 | 19.791 | 1.00 | 25.07 | H N |
| ATOM | 2178 | CA | CYS | 95 | 105.806 | 14.000 | 19.466 | 1.00 | 25.07 | H C |
| ATOM | 2179 | C | CYS | 95 | 107.228 | 13.689 | 19.096 | 1.00 | 25.07 | H C |
| ATOM | 2180 | O | CYS | 95 | 107.716 | 12.584 | 19.342 | 1.00 | 25.07 | H O |
| ATOM | 2181 | CB | CYS | 95 | 105.784 | 14.942 | 20.647 | 1.00 | 46.53 | H C |
| ATOM | 2182 | SG | CYS | 95 | 106.112 | 14.206 | 22.267 | 1.00 | 46.53 | H S |
| ATOM | 2183 | N | THR | 96 | 107.931 | 14.657 | 18.549 | 1.00 | 31.61 | H N |
| ATOM | 2184 | CA | THR | 96 | 109.253 | 14.331 | 18.115 | 1.00 | 31.61 | H C |
| ATOM | 2185 | CB | THR | 96 | 109.088 | 13.445 | 16.861 | 1.00 | 32.15 | H C |
| ATOM | 2186 | OG1 | THR | 96 | 110.331 | 12.862 | 16.494 | 1.00 | 32.15 | H O |
| ATOM | 2187 | CG2 | THR | 96 | 108.554 | 14.260 | 15.708 | 1.00 | 32.15 | H C |
| ATOM | 2188 | C | THR | 96 | 110.045 | 15.591 | 17.830 | 1.00 | 31.61 | H C |
| ATOM | 2189 | O | THR | 96 | 109.530 | 16.548 | 17.260 | 1.00 | 31.61 | H O |
| ATOM | 2190 | N | ARG | 97 | 111.292 | 15.610 | 18.270 | 1.00 | 26.02 | H N |

Fig. 19: A-31

| | | | | | | | | | | | |
|---|---|---|---|---|---|---|---|---|---|---|---|
| ATOM | 2191 | CA | ARG | 97 | 112.135 | 16.759 | 17.996 | 1.00 | 26.02 | H | C |
| ATOM | 2192 | CB | ARG | 97 | 113.220 | 16.959 | 19.053 | 1.00 | 22.53 | H | C |
| ATOM | 2193 | CG | ARG | 97 | 114.076 | 18.184 | 18.766 | 1.00 | 22.53 | H | C |
| ATOM | 2194 | CD | ARG | 97 | 115.204 | 18.345 | 19.764 | 1.00 | 22.53 | H | C |
| ATOM | 2195 | NE | ARG | 97 | 116.357 | 17.532 | 19.411 | 1.00 | 22.53 | H | N |
| ATOM | 2196 | CZ | ARG | 97 | 117.494 | 17.509 | 20.099 | 1.00 | 22.53 | H | C |
| ATOM | 2197 | NH1 | ARG | 97 | 117.635 | 18.257 | 21.183 | 1.00 | 22.53 | H | N |
| ATOM | 2198 | NH2 | ARG | 97 | 118.494 | 16.739 | 19.704 | 1.00 | 22.53 | H | N |
| ATOM | 2199 | C | ARG | 97 | 112.799 | 16.473 | 16.665 | 1.00 | 26.02 | H | C |
| ATOM | 2200 | O | ARG | 97 | 113.145 | 15.322 | 16.357 | 1.00 | 26.02 | H | O |
| ATOM | 2201 | N | GLY | 98 | 112.980 | 17.528 | 15.882 | 1.00 | 13.43 | H | N |
| ATOM | 2202 | CA | GLY | 98 | 113.586 | 17.367 | 14.582 | 1.00 | 13.43 | H | C |
| ATOM | 2203 | C | GLY | 98 | 114.947 | 17.995 | 14.496 | 1.00 | 13.43 | H | C |
| ATOM | 2204 | O | GLY | 98 | 115.308 | 18.850 | 15.281 | 1.00 | 13.43 | H | O |
| ATOM | 2205 | N | PHE | 99 | 115.719 | 17.537 | 13.534 | 1.00 | 20.13 | H | N |
| ATOM | 2206 | CA | PHE | 99 | 117.038 | 18.065 | 13.315 | 1.00 | 20.13 | H | C |
| ATOM | 2207 | CB | PHE | 99 | 118.018 | 16.902 | 13.211 | 1.00 | 25.23 | H | C |
| ATOM | 2208 | CG | PHE | 99 | 119.338 | 17.271 | 12.628 | 1.00 | 25.23 | H | C |
| ATOM | 2209 | CD1 | PHE | 99 | 119.587 | 17.079 | 11.279 | 1.00 | 25.23 | H | C |
| ATOM | 2210 | CD2 | PHE | 99 | 120.326 | 17.828 | 13.420 | 1.00 | 25.23 | H | C |
| ATOM | 2211 | CE1 | PHE | 99 | 120.804 | 17.437 | 10.721 | 1.00 | 25.23 | H | C |
| ATOM | 2212 | CE2 | PHE | 99 | 121.543 | 18.191 | 12.875 | 1.00 | 25.23 | H | C |
| ATOM | 2213 | CZ | PHE | 99 | 121.784 | 17.994 | 11.517 | 1.00 | 25.23 | H | C |
| ATOM | 2214 | C | PHE | 99 | 116.887 | 18.819 | 11.996 | 1.00 | 20.13 | H | C |
| ATOM | 2215 | O | PHE | 99 | 115.950 | 18.551 | 11.241 | 1.00 | 20.13 | H | O |
| ATOM | 2216 | N | GLY | 100 | 117.768 | 19.774 | 11.719 | 1.00 | 15.08 | H | N |
| ATOM | 2217 | CA | GLY | 100 | 117.655 | 20.513 | 10.469 | 1.00 | 15.08 | H | C |
| ATOM | 2218 | C | GLY | 100 | 116.285 | 21.139 | 10.274 | 1.00 | 15.08 | H | C |
| ATOM | 2219 | O | GLY | 100 | 115.682 | 21.636 | 11.216 | 1.00 | 15.08 | H | O |
| ATOM | 2220 | N | ASP | 101 | 115.779 | 21.128 | 9.050 | 1.00 | 7.89 | H | N |
| ATOM | 2221 | CA | ASP | 101 | 114.462 | 21.692 | 8.812 | 1.00 | 7.89 | H | C |
| ATOM | 2222 | CB | ASP | 101 | 114.195 | 21.848 | 7.302 | 1.00 | 13.13 | H | C |
| ATOM | 2223 | CG | ASP | 101 | 115.328 | 22.587 | 6.564 | 1.00 | 13.13 | H | C |
| ATOM | 2224 | OD1 | ASP | 101 | 115.921 | 23.558 | 7.105 | 1.00 | 13.13 | H | O |
| ATOM | 2225 | OD2 | ASP | 101 | 115.616 | 22.190 | 5.417 | 1.00 | 13.13 | H | O |
| ATOM | 2226 | C | ASP | 101 | 113.406 | 20.785 | 9.460 | 1.00 | 7.89 | H | C |
| ATOM | 2227 | O | ASP | 101 | 112.222 | 20.844 | 9.124 | 1.00 | 7.89 | H | O |
| ATOM | 2228 | N | GLY | 102 | 113.854 | 19.924 | 10.374 | 1.00 | 22.31 | H | N |
| ATOM | 2229 | CA | GLY | 102 | 112.952 | 19.043 | 11.100 | 1.00 | 22.31 | H | C |
| ATOM | 2230 | C | GLY | 102 | 112.588 | 17.674 | 10.562 | 1.00 | 22.31 | H | C |
| ATOM | 2231 | O | GLY | 102 | 111.927 | 16.915 | 11.263 | 1.00 | 22.31 | H | O |
| ATOM | 2232 | N | GLY | 103 | 113.001 | 17.347 | 9.343 | 1.00 | 25.09 | H | N |
| ATOM | 2233 | CA | GLY | 103 | 112.662 | 16.054 | 8.772 | 1.00 | 25.09 | H | C |
| ATOM | 2234 | C | GLY | 103 | 113.342 | 14.844 | 9.403 | 1.00 | 25.09 | H | C |
| ATOM | 2235 | O | GLY | 103 | 112.948 | 13.703 | 9.156 | 1.00 | 25.09 | H | O |
| ATOM | 2236 | N | TYR | 104 | 114.376 | 15.071 | 10.202 | 1.00 | 22.52 | H | N |
| ATOM | 2237 | CA | TYR | 104 | 115.070 | 13.961 | 10.844 | 1.00 | 22.52 | H | C |
| ATOM | 2238 | CB | TYR | 104 | 116.578 | 14.114 | 10.715 | 1.00 | 15.87 | H | C |
| ATOM | 2239 | CG | TYR | 104 | 117.342 | 13.175 | 11.599 | 1.00 | 15.87 | H | C |
| ATOM | 2240 | CD1 | TYR | 104 | 118.507 | 13.600 | 12.233 | 1.00 | 15.87 | H | C |
| ATOM | 2241 | CE1 | TYR | 104 | 119.198 | 12.776 | 13.100 | 1.00 | 15.87 | H | C |
| ATOM | 2242 | CD2 | TYR | 104 | 116.884 | 11.880 | 11.844 | 1.00 | 15.87 | H | C |
| ATOM | 2243 | CE2 | TYR | 104 | 117.575 | 11.034 | 12.713 | 1.00 | 15.87 | H | C |
| ATOM | 2244 | CZ | TYR | 104 | 118.734 | 11.498 | 13.343 | 1.00 | 15.87 | H | C |
| ATOM | 2245 | OH | TYR | 104 | 119.417 | 10.713 | 14.239 | 1.00 | 15.87 | H | O |
| ATOM | 2246 | C | TYR | 104 | 114.665 | 13.991 | 12.296 | 1.00 | 22.52 | H | C |
| ATOM | 2247 | O | TYR | 104 | 114.933 | 14.956 | 13.001 | 1.00 | 22.52 | H | O |
| ATOM | 2248 | N | PHE | 105 | 114.036 | 12.909 | 12.733 | 1.00 | 16.00 | H | N |
| ATOM | 2249 | CA | PHE | 105 | 113.501 | 12.806 | 14.073 | 1.00 | 16.00 | H | C |
| ATOM | 2250 | CB | PHE | 105 | 112.292 | 11.890 | 14.031 | 1.00 | 16.01 | H | C |
| ATOM | 2251 | CG | PHE | 105 | 111.269 | 12.327 | 13.020 | 1.00 | 16.01 | H | C |
| ATOM | 2252 | CD1 | PHE | 105 | 110.782 | 13.627 | 13.038 | 1.00 | 16.01 | H | C |
| ATOM | 2253 | CD2 | PHE | 105 | 110.827 | 11.459 | 12.023 | 1.00 | 16.01 | H | C |
| ATOM | 2254 | CE1 | PHE | 105 | 109.880 | 14.059 | 12.091 | 1.00 | 16.01 | H | C |
| ATOM | 2255 | CE2 | PHE | 105 | 109.918 | 11.885 | 11.067 | 1.00 | 16.01 | H | C |
| ATOM | 2256 | CZ | PHE | 105 | 109.443 | 13.190 | 11.101 | 1.00 | 16.01 | H | C |
| ATOM | 2257 | C | PHE | 105 | 114.442 | 12.433 | 15.179 | 1.00 | 16.00 | H | C |
| ATOM | 2258 | O | PHE | 105 | 114.543 | 11.283 | 15.595 | 1.00 | 16.00 | H | O |
| ATOM | 2259 | N | ASP | 106 | 115.105 | 13.481 | 15.642 | 1.00 | 29.40 | H | N |
| ATOM | 2260 | CA | ASP | 106 | 116.089 | 13.519 | 16.714 | 1.00 | 29.40 | H | C |
| ATOM | 2261 | CB | ASP | 106 | 116.251 | 14.976 | 17.117 | 1.00 | 39.43 | H | C |
| ATOM | 2262 | CG | ASP | 106 | 117.656 | 15.400 | 17.133 | 1.00 | 39.43 | H | C |
| ATOM | 2263 | OD1 | ASP | 106 | 118.492 | 14.528 | 17.433 | 1.00 | 39.43 | H | O |

Fig. 19: A-32

```
ATOM   2264  OD2 ASP   106     117.922   16.591   16.859  1.00   39.43      H    O
ATOM   2265  C   ASP   106     115.797   12.728   17.993  1.00   29.40      H    C
ATOM   2266  O   ASP   106     116.567   11.861   18.396  1.00   29.40      H    O
ATOM   2267  N   VAL   107     114.687   13.094   18.635  1.00    7.69      H    N
ATOM   2268  CA  VAL   107     114.248   12.533   19.906  1.00    7.69      H    C
ATOM   2269  CB  VAL   107     114.402   13.600   21.026  1.00   10.61      H    C
ATOM   2270  CG1 VAL   107     113.985   13.045   22.374  1.00   10.61      H    C
ATOM   2271  CG2 VAL   107     115.838   14.116   21.048  1.00   10.61      H    C
ATOM   2272  C   VAL   107     112.778   12.199   19.765  1.00    7.69      H    C
ATOM   2273  O   VAL   107     112.107   12.835   18.970  1.00    7.69      H    O
ATOM   2274  N   TRP   108     112.285   11.224   20.540  1.00   26.84      H    N
ATOM   2275  CA  TRP   108     110.871   10.795   20.510  1.00   26.84      H    C
ATOM   2276  CB  TRP   108     110.729    9.405   19.868  1.00    1.87      H    C
ATOM   2277  CG  TRP   108     111.201    9.329   18.468  1.00    1.87      H    C
ATOM   2278  CD2 TRP   108     110.431    8.950   17.328  1.00    1.87      H    C
ATOM   2279  CE2 TRP   108     111.287    9.020   16.201  1.00    1.87      H    C
ATOM   2280  CE3 TRP   108     109.102    8.557   17.142  1.00    1.87      H    C
ATOM   2281  CD1 TRP   108     112.460    9.606   18.008  1.00    1.87      H    C
ATOM   2282  NE1 TRP   108     112.520    9.422   16.648  1.00    1.87      H    N
ATOM   2283  CZ2 TRP   108     110.854    8.710   14.904  1.00    1.87      H    C
ATOM   2284  CZ3 TRP   108     108.667    8.244   15.836  1.00    1.87      H    C
ATOM   2285  CH2 TRP   108     109.547    8.325   14.742  1.00    1.87      H    C
ATOM   2286  C   TRP   108     110.204   10.724   21.881  1.00   26.84      H    C
ATOM   2287  O   TRP   108     110.859   10.503   22.899  1.00   26.84      H    O
ATOM   2288  N   GLY   109     108.889   10.907   21.889  1.00   15.55      H    N
ATOM   2289  CA  GLY   109     108.134   10.811   23.125  1.00   15.55      H    C
ATOM   2290  C   GLY   109     107.896    9.331   23.386  1.00   15.55      H    C
ATOM   2291  O   GLY   109     108.170    8.502   22.511  1.00   15.55      H    O
ATOM   2292  N   GLN   110     107.393    8.971   24.563  1.00   21.92      H    N
ATOM   2293  CA  GLN   110     107.161    7.554   24.852  1.00   21.92      H    C
ATOM   2294  CB  GLN   110     106.800    7.338   26.325  1.00   44.26      H    C
ATOM   2295  CG  GLN   110     105.404    7.798   26.703  1.00   44.26      H    C
ATOM   2296  CD  GLN   110     105.321    9.283   26.957  1.00   44.26      H    C
ATOM   2297  OE1 GLN   110     105.573   10.102   26.071  1.00   44.26      H    O
ATOM   2298  NE2 GLN   110     104.967    9.642   28.181  1.00   44.26      H    N
ATOM   2299  C   GLN   110     106.051    6.979   23.973  1.00   21.92      H    C
ATOM   2300  O   GLN   110     106.054    5.798   23.651  1.00   21.92      H    O
ATOM   2301  N   GLY   111     105.114    7.824   23.574  1.00   22.63      H    N
ATOM   2302  CA  GLY   111     104.014    7.361   22.761  1.00   22.63      H    C
ATOM   2303  C   GLY   111     102.758    7.463   23.597  1.00   22.63      H    C
ATOM   2304  O   GLY   111     102.834    7.414   24.827  1.00   22.63      H    O
ATOM   2305  N   THR   112     101.611    7.619   22.938  1.00   17.52      H    N
ATOM   2306  CA  THR   112     100.333    7.740   23.630  1.00   17.52      H    C
ATOM   2307  CB  THR   112     100.058    9.211   24.030  1.00   34.98      H    C
ATOM   2308  OG1 THR   112      98.958    9.261   24.939  1.00   34.98      H    O
ATOM   2309  CG2 THR   112      99.734   10.055   22.809  1.00   34.98      H    C
ATOM   2310  C   THR   112      99.228    7.203   22.717  1.00   17.52      H    C
ATOM   2311  O   THR   112      99.133    7.559   21.533  1.00   17.52      H    O
ATOM   2312  N   LEU   113      98.396    6.340   23.292  1.00   32.82      H    N
ATOM   2313  CA  LEU   113      97.318    5.668   22.576  1.00   32.82      H    C
ATOM   2314  CB  LEU   113      96.953    4.374   23.328  1.00   26.98      H    C
ATOM   2315  CG  LEU   113      95.842    3.431   22.856  1.00   26.98      H    C
ATOM   2316  CD1 LEU   113      94.455    4.057   23.105  1.00   26.98      H    C
ATOM   2317  CD2 LEU   113      96.055    3.115   21.392  1.00   26.98      H    C
ATOM   2318  C   LEU   113      96.073    6.498   22.354  1.00   32.82      H    C
ATOM   2319  O   LEU   113      95.448    6.964   23.299  1.00   32.82      H    O
ATOM   2320  N   VAL   114      95.708    6.671   21.094  1.00   38.48      H    N
ATOM   2321  CA  VAL   114      94.506    7.419   20.767  1.00   38.48      H    C
ATOM   2322  CB  VAL   114      94.809    8.658   19.870  1.00   53.69      H    C
ATOM   2323  CG1 VAL   114      93.518    9.420   19.571  1.00   53.69      H    C
ATOM   2324  CG2 VAL   114      95.798    9.575   20.562  1.00   53.69      H    C
ATOM   2325  C   VAL   114      93.557    6.484   20.022  1.00   38.48      H    C
ATOM   2326  O   VAL   114      93.859    6.003   18.928  1.00   38.48      H    O
ATOM   2327  N   THR   115      92.411    6.216   20.629  1.00   29.76      H    N
ATOM   2328  CA  THR   115      91.414    5.356   20.012  1.00   29.76      H    C
ATOM   2329  CB  THR   115      91.081    4.125   20.916  1.00   30.84      H    C
ATOM   2330  OG1 THR   115      92.292    3.453   21.300  1.00   30.84      H    O
ATOM   2331  CG2 THR   115      90.180    3.151   20.170  1.00   30.84      H    C
ATOM   2332  C   THR   115      90.133    6.164   19.803  1.00   29.76      H    C
ATOM   2333  O   THR   115      89.700    6.905   20.694  1.00   29.76      H    O
ATOM   2334  N   VAL   116      89.543    6.056   18.619  1.00   38.29      H    N
ATOM   2335  CA  VAL   116      88.289    6.747   18.371  1.00   38.29      H    C
ATOM   2336  CB  VAL   116      88.395    7.822   17.240  1.00   10.28      H    C
```

Fig. 19: A-33

| ATOM | 2337 | CG1 | VAL | 116 | 89.861 | 8.088 | 16.922 | 1.00 | 10.28 | H | C |
|---|---|---|---|---|---|---|---|---|---|---|---|
| ATOM | 2338 | CG2 | VAL | 116 | 87.575 | 7.415 | 15.994 | 1.00 | 10.28 | H | C |
| ATOM | 2339 | C | VAL | 116 | 87.303 | 5.656 | 17.996 | 1.00 | 38.29 | H | C |
| ATOM | 2340 | O | VAL | 116 | 87.545 | 4.888 | 17.063 | 1.00 | 38.29 | H | O |
| ATOM | 2341 | N | SER | 117 | 86.207 | 5.579 | 18.746 | 1.00 | 41.53 | H | N |
| ATOM | 2342 | CA | SER | 117 | 85.193 | 4.565 | 18.517 | 1.00 | 41.53 | H | C |
| ATOM | 2343 | CB | SER | 117 | 85.768 | 3.182 | 18.851 | 1.00 | 61.62 | H | C |
| ATOM | 2344 | OG | SER | 117 | 84.788 | 2.165 | 18.751 | 1.00 | 61.62 | H | O |
| ATOM | 2345 | C | SER | 117 | 83.959 | 4.815 | 19.366 | 1.00 | 41.53 | H | C |
| ATOM | 2346 | O | SER | 117 | 84.049 | 5.336 | 20.482 | 1.00 | 41.53 | H | O |
| ATOM | 2347 | N | SER | 118 | 82.808 | 4.431 | 18.828 | 1.00 | 36.79 | H | N |
| ATOM | 2348 | CA | SER | 118 | 81.538 | 4.581 | 19.525 | 1.00 | 36.79 | H | C |
| ATOM | 2349 | CB | SER | 118 | 80.401 | 4.226 | 18.579 | 1.00 | 49.30 | H | C |
| ATOM | 2350 | OG | SER | 118 | 80.598 | 2.919 | 18.069 | 1.00 | 49.30 | H | O |
| ATOM | 2351 | C | SER | 118 | 81.510 | 3.649 | 20.740 | 1.00 | 36.79 | H | C |
| ATOM | 2352 | O | SER | 118 | 80.753 | 3.853 | 21.685 | 1.00 | 35.84 | H | O |
| ATOM | 2353 | N | ALA | 119 | 82.339 | 2.616 | 20.707 | 1.00 | 26.31 | H | N |
| ATOM | 2354 | CA | ALA | 119 | 82.412 | 1.679 | 21.815 | 1.00 | 26.31 | H | C |
| ATOM | 2355 | CB | ALA | 119 | 83.569 | 0.707 | 21.617 | 1.00 | 20.55 | H | C |
| ATOM | 2356 | C | ALA | 119 | 82.611 | 2.461 | 23.100 | 1.00 | 26.31 | H | C |
| ATOM | 2357 | O | ALA | 119 | 83.319 | 3.477 | 23.124 | 1.00 | 26.31 | H | O |
| ATOM | 2358 | N | SER | 120 | 81.988 | 1.975 | 24.166 | 1.00 | 39.08 | H | N |
| ATOM | 2359 | CA | SER | 120 | 82.074 | 2.621 | 25.462 | 1.00 | 39.08 | H | C |
| ATOM | 2360 | CB | SER | 120 | 80.711 | 2.597 | 26.151 | 1.00 | 57.76 | H | C |
| ATOM | 2361 | OG | SER | 120 | 79.720 | 3.179 | 25.329 | 1.00 | 57.76 | H | O |
| ATOM | 2362 | C | SER | 120 | 83.086 | 1.938 | 26.353 | 1.00 | 39.08 | H | C |
| ATOM | 2363 | O | SER | 120 | 83.194 | 0.715 | 26.362 | 1.00 | 39.08 | H | O |
| ATOM | 2364 | N | THR | 121 | 83.837 | 2.734 | 27.100 | 1.00 | 26.62 | H | N |
| ATOM | 2365 | CA | THR | 121 | 84.813 | 2.188 | 28.023 | 1.00 | 25.63 | H | C |
| ATOM | 2366 | CB | THR | 121 | 85.274 | 3.267 | 29.002 | 1.00 | 27.79 | H | C |
| ATOM | 2367 | OG1 | THR | 121 | 85.860 | 4.353 | 28.268 | 1.00 | 32.58 | H | O |
| ATOM | 2368 | CG2 | THR | 121 | 86.273 | 2.691 | 30.007 | 1.00 | 25.52 | H | C |
| ATOM | 2369 | C | THR | 121 | 84.108 | 1.078 | 28.801 | 1.00 | 26.35 | H | C |
| ATOM | 2370 | O | THR | 121 | 82.919 | 1.189 | 29.098 | 1.00 | 29.95 | H | O |
| ATOM | 2371 | N | LYS | 122 | 84.828 | 0.007 | 29.116 | 1.00 | 53.26 | H | N |
| ATOM | 2372 | CA | LYS | 122 | 84.243 | -1.102 | 29.864 | 1.00 | 50.64 | H | C |
| ATOM | 2373 | CB | LYS | 122 | 83.333 | -1.930 | 28.947 | 1.00 | 42.70 | H | C |
| ATOM | 2374 | CG | LYS | 122 | 83.009 | -3.347 | 29.437 | 1.00 | 44.07 | H | C |
| ATOM | 2375 | CD | LYS | 122 | 82.469 | -3.373 | 30.864 | 1.00 | 47.16 | H | C |
| ATOM | 2376 | CE | LYS | 122 | 82.216 | -4.805 | 31.337 | 1.00 | 51.36 | H | C |
| ATOM | 2377 | NZ | LYS | 122 | 81.986 | -4.880 | 32.809 | 1.00 | 50.23 | H | N |
| ATOM | 2378 | C | LYS | 122 | 85.301 | -1.991 | 30.496 | 1.00 | 52.40 | H | C |
| ATOM | 2379 | O | LYS | 122 | 86.154 | -2.548 | 29.809 | 1.00 | 54.02 | H | O |
| ATOM | 2380 | N | GLY | 123 | 85.240 | -2.114 | 31.817 | 1.00 | 42.56 | H | N |
| ATOM | 2381 | CA | GLY | 123 | 86.188 | -2.952 | 32.530 | 1.00 | 42.89 | H | C |
| ATOM | 2382 | C | GLY | 123 | 86.213 | -4.396 | 32.035 | 1.00 | 44.35 | H | C |
| ATOM | 2383 | O | GLY | 123 | 85.222 | -4.907 | 31.503 | 1.00 | 40.33 | H | O |
| ATOM | 2384 | N | PRO | 124 | 87.346 | -5.090 | 32.198 | 1.00 | 44.81 | H | N |
| ATOM | 2385 | CD | PRO | 124 | 88.680 | -4.632 | 32.633 | 1.00 | 21.78 | H | C |
| ATOM | 2386 | CA | PRO | 124 | 87.397 | -6.472 | 31.731 | 1.00 | 46.19 | H | C |
| ATOM | 2387 | CB | PRO | 124 | 88.868 | -6.668 | 31.439 | 1.00 | 22.93 | H | C |
| ATOM | 2388 | CG | PRO | 124 | 89.504 | -5.905 | 32.561 | 1.00 | 22.69 | H | C |
| ATOM | 2389 | C | PRO | 124 | 86.899 | -7.461 | 32.764 | 1.00 | 45.69 | H | C |
| ATOM | 2390 | O | PRO | 124 | 86.854 | -7.170 | 33.961 | 1.00 | 46.94 | H | O |
| ATOM | 2391 | N | SER | 125 | 86.507 | -8.631 | 32.287 | 1.00 | 43.49 | H | N |
| ATOM | 2392 | CA | SER | 125 | 86.053 | -9.678 | 33.176 | 1.00 | 38.23 | H | C |
| ATOM | 2393 | CB | SER | 125 | 84.858 | -10.416 | 32.579 | 1.00 | 23.34 | H | C |
| ATOM | 2394 | OG | SER | 125 | 83.756 | -9.544 | 32.402 | 1.00 | 25.34 | H | O |
| ATOM | 2395 | C | SER | 125 | 87.262 | -10.576 | 33.200 | 1.00 | 33.52 | H | C |
| ATOM | 2396 | O | SER | 125 | 87.738 | -10.972 | 32.139 | 1.00 | 32.91 | H | O |
| ATOM | 2397 | N | VAL | 126 | 87.787 | -10.873 | 34.386 | 1.00 | 23.96 | H | N |
| ATOM | 2398 | CA | VAL | 126 | 88.962 | -11.727 | 34.452 | 1.00 | 20.86 | H | C |
| ATOM | 2399 | CB | VAL | 126 | 90.135 | -11.003 | 35.174 | 1.00 | 22.19 | H | C |
| ATOM | 2400 | CG1 | VAL | 126 | 89.894 | -9.504 | 35.113 | 1.00 | 17.46 | H | C |
| ATOM | 2401 | CG2 | VAL | 126 | 90.331 | -11.507 | 36.597 | 1.00 | 22.90 | H | C |
| ATOM | 2402 | C | VAL | 126 | 88.666 | -13.091 | 35.065 | 1.00 | 20.51 | H | C |
| ATOM | 2403 | O | VAL | 126 | 88.382 | -13.227 | 36.256 | 1.00 | 24.79 | H | O |
| ATOM | 2404 | N | PHE | 127 | 88.713 | -14.105 | 34.213 | 1.00 | 27.15 | H | N |
| ATOM | 2405 | CA | PHE | 127 | 88.443 | -15.464 | 34.625 | 1.00 | 29.56 | H | C |
| ATOM | 2406 | CB | PHE | 127 | 87.628 | -16.167 | 33.544 | 1.00 | 16.06 | H | C |
| ATOM | 2407 | CG | PHE | 127 | 86.392 | -15.419 | 33.141 | 1.00 | 12.41 | H | C |
| ATOM | 2408 | CD1 | PHE | 127 | 85.380 | -15.167 | 34.071 | 1.00 | 11.21 | H | C |
| ATOM | 2409 | CD2 | PHE | 127 | 86.255 | -14.922 | 31.840 | 1.00 | 10.06 | H | C |

Fig. 19: A-34

```
ATOM   2410  CE1 PHE  127      84.254 -14.428  33.721  1.00  12.93           H   C
ATOM   2411  CE2 PHE  127      85.126 -14.174  31.470  1.00   6.89           H   C
ATOM   2412  CZ  PHE  127      84.125 -13.925  32.413  1.00   6.94           H   C
ATOM   2413  C   PHE  127      89.763 -16.183  34.825  1.00  31.37           H   C
ATOM   2414  O   PHE  127      90.806 -15.733  34.351  1.00  34.05           H   O
ATOM   2415  N   PRO  128      89.743 -17.310  35.540  1.00  21.35           H   N
ATOM   2416  CD  PRO  128      88.681 -17.812  36.434  1.00  32.37           H   C
ATOM   2417  CA  PRO  128      90.996 -18.039  35.752  1.00  22.25           H   C
ATOM   2418  CB  PRO  128      90.823 -18.577  37.161  1.00  34.03           H   C
ATOM   2419  CG  PRO  128      89.358 -18.983  37.130  1.00  33.18           H   C
ATOM   2420  C   PRO  128      91.198 -19.176  34.739  1.00  21.65           H   C
ATOM   2421  O   PRO  128      90.235 -19.770  34.244  1.00  21.29           H   O
ATOM   2422  N   LEU  129      92.457 -19.457  34.432  1.00  17.17           H   N
ATOM   2423  CA  LEU  129      92.811 -20.557  33.545  1.00  19.61           H   C
ATOM   2424  CB  LEU  129      93.683 -20.061  32.396  1.00  18.81           H   C
ATOM   2425  CG  LEU  129      93.086 -18.872  31.635  1.00  18.17           H   C
ATOM   2426  CD1 LEU  129      94.115 -18.254  30.696  1.00  16.12           H   C
ATOM   2427  CD2 LEU  129      91.886 -19.341  30.870  1.00  11.94           H   C
ATOM   2428  C   LEU  129      93.601 -21.457  34.497  1.00  23.45           H   C
ATOM   2429  O   LEU  129      94.824 -21.481  34.499  1.00  25.82           H   O
ATOM   2430  N   ALA  130      92.870 -22.179  35.332  1.00  16.93           H   N
ATOM   2431  CA  ALA  130      93.455 -23.046  36.341  1.00  18.97           H   C
ATOM   2432  CB  ALA  130      92.363 -23.561  37.256  1.00  49.82           H   C
ATOM   2433  C   ALA  130      94.280 -24.219  35.846  1.00  18.88           H   C
ATOM   2434  O   ALA  130      93.928 -24.876  34.869  1.00  20.61           H   O
ATOM   2435  N   PRO  131      95.401 -24.490  36.534  1.00  29.98           H   N
ATOM   2436  CD  PRO  131      95.929 -23.703  37.665  1.00  16.68           H   C
ATOM   2437  CA  PRO  131      96.301 -25.595  36.198  1.00  27.20           H   C
ATOM   2438  CB  PRO  131      97.453 -25.424  37.196  1.00  12.88           H   C
ATOM   2439  CG  PRO  131      96.815 -24.691  38.354  1.00  15.86           H   C
ATOM   2440  C   PRO  131      95.534 -26.897  36.405  1.00  26.68           H   C
ATOM   2441  O   PRO  131      94.666 -26.978  37.274  1.00  27.16           H   O
ATOM   2442  N   SER  132      95.838 -27.912  35.607  1.00  64.88           H   N
ATOM   2443  CA  SER  132      95.138 -29.187  35.720  1.00  67.56           H   C
ATOM   2444  CB  SER  132      93.745 -29.075  35.086  1.00  44.77           H   C
ATOM   2445  OG  SER  132      93.824 -28.747  33.704  1.00  46.53           H   O
ATOM   2446  C   SER  132      95.918 -30.284  35.020  1.00  69.15           H   C
ATOM   2447  O   SER  132      97.107 -30.139  34.757  1.00  69.80           H   O
ATOM   2448  N   SER  133      95.247 -31.391  34.732  1.00  58.75           H   N
ATOM   2449  CA  SER  133      95.894 -32.483  34.024  1.00  61.13           H   C
ATOM   2450  CB  SER  133      95.007 -33.738  34.068  1.00  91.14           H   C
ATOM   2451  OG  SER  133      93.668 -33.456  33.684  1.00 100.88           H   O
ATOM   2452  C   SER  133      96.121 -32.017  32.576  1.00  60.76           H   C
ATOM   2453  O   SER  133      97.091 -32.413  31.927  1.00  61.01           H   O
ATOM   2454  N   LYS  134      95.220 -31.156  32.095  1.00 101.65           H   N
ATOM   2455  CA  LYS  134      95.285 -30.605  30.739  1.00 102.79           H   C
ATOM   2456  CB  LYS  134      93.951 -29.962  30.341  1.00  44.82           H   C
ATOM   2457  CG  LYS  134      92.703 -30.784  30.609  1.00  52.94           H   C
ATOM   2458  CD  LYS  134      92.058 -30.452  31.959  1.00  55.86           H   C
ATOM   2459  CE  LYS  134      90.686 -31.127  32.091  1.00  53.71           H   C
ATOM   2460  NZ  LYS  134      89.988 -30.792  33.367  1.00  52.28           H   N
ATOM   2461  C   LYS  134      96.364 -29.531  30.655  1.00 102.96           H   C
ATOM   2462  O   LYS  134      96.932 -29.284  29.589  1.00 104.03           H   O
ATOM   2463  N   SER  135      96.619 -28.885  31.791  1.00  77.03           H   N
ATOM   2464  CA  SER  135      97.611 -27.818  31.896  1.00  76.76           H   C
ATOM   2465  CB  SER  135      97.069 -26.698  32.784  1.00  81.66           H   C
ATOM   2466  OG  SER  135      95.726 -26.390  32.443  1.00  81.07           H   O
ATOM   2467  C   SER  135      98.911 -28.358  32.488  1.00  71.98           H   C
ATOM   2468  O   SER  135      99.733 -27.601  33.006  1.00  72.29           H   O
ATOM   2469  N   THR  136      99.075 -29.676  32.418  1.00  86.02           H   N
ATOM   2470  CA  THR  136     100.262 -30.351  32.932  1.00  86.44           H   C
ATOM   2471  CB  THR  136      99.897 -31.391  34.036  1.00  47.16           H   C
ATOM   2472  OG1 THR  136      99.491 -30.715  35.237  1.00  47.25           H   O
ATOM   2473  CG2 THR  136     101.096 -32.281  34.354  1.00  50.70           H   C
ATOM   2474  C   THR  136     100.977 -31.072  31.788  1.00  86.90           H   C
ATOM   2475  O   THR  136     100.334 -31.615  30.885  1.00  85.81           H   O
ATOM   2476  N   SER  137     102.309 -31.059  31.836  1.00  82.54           H   N
ATOM   2477  CA  SER  137     103.164 -31.700  30.834  1.00  82.34           H   C
ATOM   2478  CB  SER  137     103.113 -30.942  29.495  1.00  65.40           H   C
ATOM   2479  OG  SER  137     101.863 -31.097  28.841  1.00  66.87           H   O
ATOM   2480  C   SER  137     104.600 -31.715  31.352  1.00  82.68           H   C
ATOM   2481  O   SER  137     105.321 -30.722  31.244  1.00  84.11           H   O
ATOM   2482  N   GLY  138     105.016 -32.845  31.911  1.00  62.73           H   N
```

Fig. 19: A-35

| | | | | | | | | | | |
|---|---|---|---|---|---|---|---|---|---|---|
| ATOM | 2483 | CA | GLY | 138 | 106.361 | -32.941 | 32.438 | 1.00 | 62.79 | H | C |
| ATOM | 2484 | C | GLY | 138 | 106.394 | -32.371 | 33.840 | 1.00 | 65.01 | H | C |
| ATOM | 2485 | O | GLY | 138 | 105.392 | -32.410 | 34.555 | 1.00 | 65.52 | H | O |
| ATOM | 2486 | N | GLY | 139 | 107.537 | -31.827 | 34.237 | 1.00 | 45.62 | H | N |
| ATOM | 2487 | CA | GLY | 139 | 107.645 | -31.267 | 35.570 | 1.00 | 45.97 | H | C |
| ATOM | 2488 | C | GLY | 139 | 107.037 | -29.884 | 35.680 | 1.00 | 46.52 | H | C |
| ATOM | 2489 | O | GLY | 139 | 107.020 | -29.297 | 36.762 | 1.00 | 50.66 | H | O |
| ATOM | 2490 | N | THR | 140 | 106.527 | -29.365 | 34.568 | 1.00 | 41.37 | H | N |
| ATOM | 2491 | CA | THR | 140 | 105.941 | -28.030 | 34.571 | 1.00 | 35.80 | H | C |
| ATOM | 2492 | CB | THR | 140 | 106.626 | -27.108 | 33.533 | 1.00 | 32.97 | H | C |
| ATOM | 2493 | OG1 | THR | 140 | 105.886 | -27.138 | 32.311 | 1.00 | 30.01 | H | O |
| ATOM | 2494 | CG2 | THR | 140 | 108.052 | -27.574 | 33.250 | 1.00 | 33.92 | H | C |
| ATOM | 2495 | C | THR | 140 | 104.434 | -27.993 | 34.299 | 1.00 | 32.68 | H | C |
| ATOM | 2496 | O | THR | 140 | 103.884 | -28.820 | 33.560 | 1.00 | 31.27 | H | O |
| ATOM | 2497 | N | ALA | 141 | 103.777 | -27.013 | 34.914 | 1.00 | 23.19 | H | N |
| ATOM | 2498 | CA | ALA | 141 | 102.350 | -26.817 | 34.752 | 1.00 | 23.90 | H | C |
| ATOM | 2499 | CB | ALA | 141 | 101.647 | -26.986 | 36.087 | 1.00 | 31.87 | H | C |
| ATOM | 2500 | C | ALA | 141 | 102.121 | -25.408 | 34.206 | 1.00 | 24.06 | H | C |
| ATOM | 2501 | O | ALA | 141 | 102.930 | -24.498 | 34.415 | 1.00 | 28.34 | H | O |
| ATOM | 2502 | N | ALA | 142 | 101.022 | -25.239 | 33.487 | 1.00 | 36.28 | H | N |
| ATOM | 2503 | CA | ALA | 142 | 100.685 | -23.948 | 32.924 | 1.00 | 31.12 | H | C |
| ATOM | 2504 | CB | ALA | 142 | 100.507 | -24.062 | 31.419 | 1.00 | 1.87 | H | C |
| ATOM | 2505 | C | ALA | 142 | 99.389 | -23.519 | 33.588 | 1.00 | 29.11 | H | C |
| ATOM | 2506 | O | ALA | 142 | 98.565 | -24.359 | 33.961 | 1.00 | 33.50 | H | O |
| ATOM | 2507 | N | LEU | 143 | 99.233 | -22.211 | 33.751 | 1.00 | 27.06 | H | N |
| ATOM | 2508 | CA | LEU | 143 | 98.054 | -21.611 | 34.372 | 1.00 | 31.22 | H | C |
| ATOM | 2509 | CB | LEU | 143 | 98.154 | -21.670 | 35.900 | 1.00 | 28.24 | H | C |
| ATOM | 2510 | CG | LEU | 143 | 99.269 | -20.865 | 36.582 | 1.00 | 30.55 | H | C |
| ATOM | 2511 | CD1 | LEU | 143 | 98.702 | -19.526 | 36.991 | 1.00 | 23.14 | H | C |
| ATOM | 2512 | CD2 | LEU | 143 | 99.817 | -21.596 | 37.809 | 1.00 | 37.29 | H | C |
| ATOM | 2513 | C | LEU | 143 | 98.068 | -20.169 | 33.913 | 1.00 | 34.46 | H | C |
| ATOM | 2514 | O | LEU | 143 | 99.069 | -19.700 | 33.364 | 1.00 | 32.14 | H | O |
| ATOM | 2515 | N | GLY | 144 | 96.970 | -19.458 | 34.128 | 1.00 | 25.78 | H | N |
| ATOM | 2516 | CA | GLY | 144 | 96.922 | -18.074 | 33.694 | 1.00 | 28.57 | H | C |
| ATOM | 2517 | C | GLY | 144 | 95.578 | -17.425 | 33.896 | 1.00 | 31.81 | H | C |
| ATOM | 2518 | O | GLY | 144 | 94.693 | -17.985 | 34.543 | 1.00 | 35.57 | H | O |
| ATOM | 2519 | N | CYS | 145 | 95.420 | -16.235 | 33.335 | 1.00 | 24.76 | H | N |
| ATOM | 2520 | CA | CYS | 145 | 94.177 | -15.501 | 33.471 | 1.00 | 23.67 | H | C |
| ATOM | 2521 | C | CYS | 145 | 93.665 | -15.071 | 32.122 | 1.00 | 21.65 | H | C |
| ATOM | 2522 | O | CYS | 145 | 94.437 | -14.868 | 31.188 | 1.00 | 22.23 | H | O |
| ATOM | 2523 | CB | CYS | 145 | 94.385 | -14.273 | 34.363 | 1.00 | 28.67 | H | C |
| ATOM | 2524 | SG | CYS | 145 | 94.354 | -14.658 | 36.141 | 1.00 | 36.96 | H | S |
| ATOM | 2525 | N | LEU | 146 | 92.351 | -14.940 | 32.024 | 1.00 | 43.52 | H | N |
| ATOM | 2526 | CA | LEU | 146 | 91.712 | -14.512 | 30.792 | 1.00 | 43.76 | H | C |
| ATOM | 2527 | CB | LEU | 146 | 90.715 | -15.580 | 30.314 | 1.00 | 38.89 | H | C |
| ATOM | 2528 | CG | LEU | 146 | 89.754 | -15.245 | 29.164 | 1.00 | 28.77 | H | C |
| ATOM | 2529 | CD1 | LEU | 146 | 90.519 | -14.669 | 27.982 | 1.00 | 25.69 | H | C |
| ATOM | 2530 | CD2 | LEU | 146 | 88.989 | -16.489 | 28.755 | 1.00 | 35.84 | H | C |
| ATOM | 2531 | C | LEU | 146 | 90.997 | -13.188 | 31.055 | 1.00 | 45.61 | H | C |
| ATOM | 2532 | O | LEU | 146 | 89.943 | -13.160 | 31.690 | 1.00 | 45.79 | H | O |
| ATOM | 2533 | N | VAL | 147 | 91.609 | -12.098 | 30.593 | 1.00 | 12.91 | H | N |
| ATOM | 2534 | CA | VAL | 147 | 91.069 | -10.732 | 30.716 | 1.00 | 12.94 | H | C |
| ATOM | 2535 | CB | VAL | 147 | 92.231 | -9.696 | 30.638 | 1.00 | 24.21 | H | C |
| ATOM | 2536 | CG1 | VAL | 147 | 91.703 | -8.291 | 30.722 | 1.00 | 25.32 | H | C |
| ATOM | 2537 | CG2 | VAL | 147 | 93.212 | -9.947 | 31.778 | 1.00 | 13.52 | H | C |
| ATOM | 2538 | C | VAL | 147 | 90.101 | -10.563 | 29.532 | 1.00 | 18.31 | H | C |
| ATOM | 2539 | O | VAL | 147 | 90.532 | -10.460 | 28.381 | 1.00 | 18.59 | H | O |
| ATOM | 2540 | N | LYS | 148 | 88.798 | -10.519 | 29.806 | 1.00 | 25.16 | H | N |
| ATOM | 2541 | CA | LYS | 148 | 87.835 | -10.467 | 28.709 | 1.00 | 29.22 | H | C |
| ATOM | 2542 | CB | LYS | 148 | 87.140 | -11.827 | 28.609 | 1.00 | 15.56 | H | C |
| ATOM | 2543 | CG | LYS | 148 | 86.353 | -12.032 | 27.348 | 1.00 | 22.92 | H | C |
| ATOM | 2544 | CD | LYS | 148 | 85.731 | -13.405 | 27.355 | 1.00 | 22.16 | H | C |
| ATOM | 2545 | CE | LYS | 148 | 84.795 | -13.570 | 26.190 | 1.00 | 24.54 | H | C |
| ATOM | 2546 | NZ | LYS | 148 | 85.514 | -13.308 | 24.928 | 1.00 | 22.92 | H | N |
| ATOM | 2547 | C | LYS | 148 | 86.777 | -9.372 | 28.646 | 1.00 | 32.79 | H | C |
| ATOM | 2548 | O | LYS | 148 | 86.332 | -8.844 | 29.664 | 1.00 | 33.18 | H | O |
| ATOM | 2549 | N | ASP | 149 | 86.387 | -9.069 | 27.409 | 1.00 | 55.13 | H | N |
| ATOM | 2550 | CA | ASP | 149 | 85.381 | -8.070 | 27.078 | 1.00 | 53.92 | H | C |
| ATOM | 2551 | CB | ASP | 149 | 83.993 | -8.595 | 27.429 | 1.00 | 38.49 | H | C |
| ATOM | 2552 | CG | ASP | 149 | 83.635 | -9.853 | 26.661 | 1.00 | 42.52 | H | C |
| ATOM | 2553 | OD1 | ASP | 149 | 83.797 | -9.882 | 25.421 | 1.00 | 46.52 | H | O |
| ATOM | 2554 | OD2 | ASP | 149 | 83.181 | -10.817 | 27.305 | 1.00 | 41.08 | H | O |
| ATOM | 2555 | C | ASP | 149 | 85.585 | -6.690 | 27.698 | 1.00 | 56.06 | H | C |

Fig. 19: A-36

```
ATOM   2556  O    ASP  149      84.720   -6.175   28.415  1.00  57.30      H  O
ATOM   2557  N    TYR  150      86.734   -6.091   27.399  1.00  33.00      H  N
ATOM   2558  CA   TYR  150      87.072   -4.770   27.897  1.00  33.34      H  C
ATOM   2559  CB   TYR  150      88.306   -4.844   28.797  1.00  39.19      H  C
ATOM   2560  CG   TYR  150      89.622   -5.155   28.097  1.00  44.75      H  C
ATOM   2561  CD1  TYR  150      90.405   -4.137   27.556  1.00  44.06      H  C
ATOM   2562  CE1  TYR  150      91.653   -4.401   26.994  1.00  46.40      H  C
ATOM   2563  CD2  TYR  150      90.121   -6.457   28.046  1.00  44.23      H  C
ATOM   2564  CE2  TYR  150      91.369   -6.730   27.483  1.00  43.19      H  C
ATOM   2565  CZ   TYR  150      92.130   -5.694   26.963  1.00  45.07      H  C
ATOM   2566  OH   TYR  150      93.376   -5.942   26.431  1.00  42.66      H  O
ATOM   2567  C    TYR  150      87.331   -3.838   26.723  1.00  34.19      H  C
ATOM   2568  O    TYR  150      87.420   -4.275   25.569  1.00  36.79      H  O
ATOM   2569  N    PHE  151      87.450   -2.549   27.034  1.00  53.36      H  N
ATOM   2570  CA   PHE  151      87.686   -1.522   26.034  1.00  51.06      H  C
ATOM   2571  CB   PHE  151      86.520   -1.506   25.038  1.00  22.52      H  C
ATOM   2572  CG   PHE  151      86.663   -0.500   23.923  1.00  22.34      H  C
ATOM   2573  CD1  PHE  151      86.509    0.865   24.164  1.00  21.58      H  C
ATOM   2574  CD2  PHE  151      86.896   -0.923   22.616  1.00  24.08      H  C
ATOM   2575  CE1  PHE  151      86.576    1.789   23.117  1.00  22.62      H  C
ATOM   2576  CE2  PHE  151      86.968   -0.003   21.558  1.00  25.39      H  C
ATOM   2577  CZ   PHE  151      86.805    1.351   21.809  1.00  25.56      H  C
ATOM   2578  C    PHE  151      87.819   -0.175   26.734  1.00  48.17      H  C
ATOM   2579  O    PHE  151      87.161    0.084   27.737  1.00  47.45      H  O
ATOM   2580  N    PRO  152      88.712    0.685   26.232  1.00  46.09      H  N
ATOM   2581  CD   PRO  152      88.959    2.055   26.730  1.00   7.14      H  C
ATOM   2582  CA   PRO  152      89.554    0.388   25.065  1.00  47.66      H  C
ATOM   2583  CB   PRO  152      89.773    1.765   24.464  1.00  12.39      H  C
ATOM   2584  CG   PRO  152      90.017    2.594   25.730  1.00   9.55      H  C
ATOM   2585  C    PRO  152      90.835   -0.199   25.636  1.00  47.42      H  C
ATOM   2586  O    PRO  152      90.826   -0.716   26.748  1.00  49.63      H  O
ATOM   2587  N    GLU  153      91.933   -0.128   24.894  1.00  48.37      H  N
ATOM   2588  CA   GLU  153      93.200   -0.620   25.422  1.00  45.01      H  C
ATOM   2589  CB   GLU  153      94.232   -0.788   24.308  1.00  35.76      H  C
ATOM   2590  CG   GLU  153      93.983   -1.951   23.370  1.00  41.71      H  C
ATOM   2591  CD   GLU  153      94.465   -3.279   23.920  1.00  49.73      H  C
ATOM   2592  OE1  GLU  153      94.329   -4.276   23.191  1.00  53.96      H  O
ATOM   2593  OE2  GLU  153      94.979   -3.337   25.062  1.00  49.06      H  O
ATOM   2594  C    GLU  153      93.667    0.487   26.355  1.00  40.62      H  C
ATOM   2595  O    GLU  153      93.160    1.611   26.288  1.00  43.09      H  O
ATOM   2596  N    PRO  154      94.626    0.193   27.242  1.00  31.67      H  N
ATOM   2597  CD   PRO  154      95.605    1.250   27.562  1.00  24.24      H  C
ATOM   2598  CA   PRO  154      95.266   -1.107   27.404  1.00  32.01      H  C
ATOM   2599  CB   PRO  154      96.707   -0.803   27.072  1.00  23.56      H  C
ATOM   2600  CG   PRO  154      96.899    0.447   27.855  1.00  23.31      H  C
ATOM   2601  C    PRO  154      95.127   -1.577   28.846  1.00  37.33      H  C
ATOM   2602  O    PRO  154      94.929   -0.788   29.770  1.00  40.93      H  O
ATOM   2603  N    VAL  155      95.270   -2.874   29.029  1.00  27.89      H  N
ATOM   2604  CA   VAL  155      95.171   -3.468   30.339  1.00  28.93      H  C
ATOM   2605  CB   VAL  155      94.167   -4.647   30.309  1.00  32.63      H  C
ATOM   2606  CG1  VAL  155      94.624   -5.699   29.306  1.00  39.44      H  C
ATOM   2607  CG2  VAL  155      94.030   -5.243   31.690  1.00  38.09      H  C
ATOM   2608  C    VAL  155      96.561   -3.969   30.715  1.00  29.75      H  C
ATOM   2609  O    VAL  155      97.319   -4.427   29.856  1.00  34.58      H  O
ATOM   2610  N    THR  156      96.898   -3.864   31.995  1.00  30.47      H  N
ATOM   2611  CA   THR  156      98.195   -4.322   32.482  1.00  30.67      H  C
ATOM   2612  CB   THR  156      98.855   -3.316   33.458  1.00  37.06      H  C
ATOM   2613  OG1  THR  156      98.554   -3.699   34.810  1.00  41.96      H  O
ATOM   2614  CG2  THR  156      98.346   -1.895   33.213  1.00  35.30      H  C
ATOM   2615  C    THR  156      97.956   -5.589   33.276  1.00  28.26      H  C
ATOM   2616  O    THR  156      96.915   -5.736   33.906  1.00  24.33      H  O
ATOM   2617  N    VAL  157      98.914   -6.501   33.250  1.00  20.40      H  N
ATOM   2618  CA   VAL  157      98.784   -7.731   34.014  1.00  23.86      H  C
ATOM   2619  CB   VAL  157      98.263   -8.918   33.149  1.00   6.55      H  C
ATOM   2620  CG1  VAL  157      98.307  -10.191   33.970  1.00   2.70      H  C
ATOM   2621  CG2  VAL  157      96.817   -8.649   32.662  1.00   8.40      H  C
ATOM   2622  C    VAL  157     100.122   -8.142   34.618  1.00  25.91      H  C
ATOM   2623  O    VAL  157     101.130   -8.220   33.918  1.00  28.24      H  O
ATOM   2624  N    SER  158     100.127   -8.401   35.918  1.00  37.92      H  N
ATOM   2625  CA   SER  158     101.333   -8.840   36.606  1.00  38.42      H  C
ATOM   2626  CB   SER  158     101.852   -7.738   37.521  1.00  26.79      H  C
ATOM   2627  OG   SER  158     101.008   -7.591   38.648  1.00  29.78      H  O
ATOM   2628  C    SER  158     100.947  -10.064   37.439  1.00  37.35      H  C
```

Fig. 19: A-37

| ATOM | 2629 | O | SER | 158 | 99.765 | -10.366 | 37.583 | 1.00 | 35.45 | H | O |
|---|---|---|---|---|---|---|---|---|---|---|---|
| ATOM | 2630 | N | TRP | 159 | 101.926 | -10.772 | 37.989 | 1.00 | 38.23 | H | N |
| ATOM | 2631 | CA | TRP | 159 | 101.604 | -11.945 | 38.790 | 1.00 | 38.96 | H | C |
| ATOM | 2632 | CB | TRP | 159 | 102.060 | -13.224 | 38.074 | 1.00 | 33.06 | H | C |
| ATOM | 2633 | CG | TRP | 159 | 101.197 | -13.555 | 36.899 | 1.00 | 30.80 | H | C |
| ATOM | 2634 | CD2 | TRP | 159 | 100.089 | -14.463 | 36.879 | 1.00 | 31.04 | H | C |
| ATOM | 2635 | CE2 | TRP | 159 | 99.540 | -14.423 | 35.577 | 1.00 | 29.21 | H | C |
| ATOM | 2636 | CE3 | TRP | 159 | 99.507 | -15.307 | 37.836 | 1.00 | 31.84 | H | C |
| ATOM | 2637 | CD1 | TRP | 159 | 101.271 | -13.015 | 35.649 | 1.00 | 26.46 | H | C |
| ATOM | 2638 | NE1 | TRP | 159 | 100.280 | -13.531 | 34.848 | 1.00 | 30.17 | H | N |
| ATOM | 2639 | CZ2 | TRP | 159 | 98.439 | -15.196 | 35.204 | 1.00 | 33.73 | H | C |
| ATOM | 2640 | CZ3 | TRP | 159 | 98.407 | -16.079 | 37.465 | 1.00 | 33.56 | H | C |
| ATOM | 2641 | CH2 | TRP | 159 | 97.887 | -16.018 | 36.158 | 1.00 | 34.95 | H | C |
| ATOM | 2642 | C | TRP | 159 | 102.166 | -11.908 | 40.203 | 1.00 | 41.53 | H | C |
| ATOM | 2643 | O | TRP | 159 | 103.355 | -11.670 | 40.412 | 1.00 | 40.45 | H | O |
| ATOM | 2644 | N | ASN | 160 | 101.295 | -12.163 | 41.170 | 1.00 | 50.63 | H | N |
| ATOM | 2645 | CA | ASN | 160 | 101.699 | -12.153 | 42.557 | 1.00 | 51.18 | H | C |
| ATOM | 2646 | CB | ASN | 160 | 102.753 | -13.230 | 42.814 | 1.00 | 31.23 | H | C |
| ATOM | 2647 | CG | ASN | 160 | 102.145 | -14.619 | 42.946 | 1.00 | 28.65 | H | C |
| ATOM | 2648 | OD1 | ASN | 160 | 100.924 | -14.784 | 42.911 | 1.00 | 22.55 | H | O |
| ATOM | 2649 | ND2 | ASN | 160 | 103.000 | -15.630 | 43.107 | 1.00 | 28.71 | H | N |
| ATOM | 2650 | C | ASN | 160 | 102.245 | -10.777 | 42.891 | 1.00 | 53.56 | H | C |
| ATOM | 2651 | O | ASN | 160 | 103.277 | -10.637 | 43.554 | 1.00 | 51.84 | H | O |
| ATOM | 2652 | N | SER | 161 | 101.548 | -9.758 | 42.397 | 1.00 | 57.36 | H | N |
| ATOM | 2653 | CA | SER | 161 | 101.915 | -8.372 | 42.651 | 1.00 | 58.07 | H | C |
| ATOM | 2654 | CB | SER | 161 | 101.833 | -8.106 | 44.161 | 1.00 | 44.49 | H | C |
| ATOM | 2655 | OG | SER | 161 | 100.611 | -8.586 | 44.713 | 1.00 | 48.26 | H | O |
| ATOM | 2656 | C | SER | 161 | 103.305 | -7.997 | 42.118 | 1.00 | 57.98 | H | C |
| ATOM | 2657 | O | SER | 161 | 103.779 | -6.883 | 42.329 | 1.00 | 58.91 | H | O |
| ATOM | 2658 | N | GLY | 162 | 103.957 | -8.927 | 41.431 | 1.00 | 43.40 | H | N |
| ATOM | 2659 | CA | GLY | 162 | 105.271 | -8.641 | 40.886 | 1.00 | 41.61 | H | C |
| ATOM | 2660 | C | GLY | 162 | 106.343 | -9.670 | 41.195 | 1.00 | 41.13 | H | C |
| ATOM | 2661 | O | GLY | 162 | 107.340 | -9.756 | 40.475 | 1.00 | 41.89 | H | O |
| ATOM | 2662 | N | ALA | 163 | 106.144 | -10.460 | 42.248 | 1.00 | 32.79 | H | N |
| ATOM | 2663 | CA | ALA | 163 | 107.135 | -11.462 | 42.644 | 1.00 | 33.15 | H | C |
| ATOM | 2664 | CB | ALA | 163 | 106.845 | -11.956 | 44.065 | 1.00 | 7.75 | H | C |
| ATOM | 2665 | C | ALA | 163 | 107.265 | -12.651 | 41.702 | 1.00 | 33.69 | H | C |
| ATOM | 2666 | O | ALA | 163 | 108.154 | -13.473 | 41.868 | 1.00 | 36.52 | H | O |
| ATOM | 2667 | N | LEU | 164 | 106.378 | -12.750 | 40.722 | 1.00 | 33.04 | H | N |
| ATOM | 2668 | CA | LEU | 164 | 106.412 | -13.847 | 39.755 | 1.00 | 28.09 | H | C |
| ATOM | 2669 | CB | LEU | 164 | 105.146 | -14.701 | 39.869 | 1.00 | 29.67 | H | C |
| ATOM | 2670 | CG | LEU | 164 | 105.008 | -15.851 | 38.870 | 1.00 | 27.43 | H | C |
| ATOM | 2671 | CD1 | LEU | 164 | 105.976 | -16.963 | 39.215 | 1.00 | 24.01 | H | C |
| ATOM | 2672 | CD2 | LEU | 164 | 103.605 | -16.370 | 38.903 | 1.00 | 22.28 | H | C |
| ATOM | 2673 | C | LEU | 164 | 106.483 | -13.227 | 38.370 | 1.00 | 26.00 | H | C |
| ATOM | 2674 | O | LEU | 164 | 105.492 | -12.663 | 37.893 | 1.00 | 20.06 | H | O |
| ATOM | 2675 | N | THR | 165 | 107.656 | -13.326 | 37.740 | 1.00 | 28.49 | H | N |
| ATOM | 2676 | CA | THR | 165 | 107.893 | -12.758 | 36.410 | 1.00 | 32.54 | H | C |
| ATOM | 2677 | CB | THR | 165 | 108.927 | -11.613 | 36.462 | 1.00 | 18.33 | H | C |
| ATOM | 2678 | OG1 | THR | 165 | 110.114 | -12.057 | 37.139 | 1.00 | 21.15 | H | O |
| ATOM | 2679 | CG2 | THR | 165 | 108.348 | -10.419 | 37.184 | 1.00 | 20.86 | H | C |
| ATOM | 2680 | C | THR | 165 | 108.394 | -13.770 | 35.397 | 1.00 | 33.42 | H | C |
| ATOM | 2681 | O | THR | 165 | 108.028 | -13.717 | 34.227 | 1.00 | 34.44 | H | O |
| ATOM | 2682 | N | SER | 166 | 109.244 | -14.683 | 35.849 | 1.00 | 63.46 | H | N |
| ATOM | 2683 | CA | SER | 166 | 109.804 | -15.702 | 34.973 | 1.00 | 62.93 | H | C |
| ATOM | 2684 | CB | SER | 166 | 110.901 | -16.472 | 35.710 | 1.00 | 37.10 | H | C |
| ATOM | 2685 | OG | SER | 166 | 111.503 | -17.442 | 34.870 | 1.00 | 42.11 | H | O |
| ATOM | 2686 | C | SER | 166 | 108.748 | -16.678 | 34.458 | 1.00 | 60.85 | H | C |
| ATOM | 2687 | O | SER | 166 | 107.955 | -17.226 | 35.227 | 1.00 | 60.31 | H | O |
| ATOM | 2688 | N | GLY | 167 | 108.744 | -16.895 | 33.148 | 1.00 | 58.61 | H | N |
| ATOM | 2689 | CA | GLY | 167 | 107.784 | -17.812 | 32.566 | 1.00 | 55.44 | H | C |
| ATOM | 2690 | C | GLY | 167 | 106.425 | -17.181 | 32.332 | 1.00 | 49.55 | H | C |
| ATOM | 2691 | O | GLY | 167 | 105.462 | -17.878 | 32.010 | 1.00 | 51.52 | H | O |
| ATOM | 2692 | N | VAL | 168 | 106.340 | -15.864 | 32.491 | 1.00 | 12.32 | H | N |
| ATOM | 2693 | CA | VAL | 168 | 105.081 | -15.183 | 32.280 | 1.00 | 12.04 | H | C |
| ATOM | 2694 | CB | VAL | 168 | 104.933 | -13.970 | 33.190 | 1.00 | 2.74 | H | C |
| ATOM | 2695 | CG1 | VAL | 168 | 103.590 | -13.273 | 32.906 | 1.00 | 2.74 | H | C |
| ATOM | 2696 | CG2 | VAL | 168 | 105.070 | -14.398 | 34.630 | 1.00 | 2.83 | H | C |
| ATOM | 2697 | C | VAL | 168 | 104.965 | -14.687 | 30.852 | 1.00 | 11.82 | H | C |
| ATOM | 2698 | O | VAL | 168 | 105.894 | -14.087 | 30.319 | 1.00 | 11.28 | H | O |
| ATOM | 2699 | N | HIS | 169 | 103.807 | -14.931 | 30.253 | 1.00 | 28.24 | H | N |
| ATOM | 2700 | CA | HIS | 169 | 103.518 | -14.512 | 28.891 | 1.00 | 24.96 | H | C |
| ATOM | 2701 | CB | HIS | 169 | 103.566 | -15.695 | 27.924 | 1.00 | 1.87 | H | C |

Fig. 19: A-38

| | | | | | | | | | | | |
|---|---|---|---|---|---|---|---|---|---|---|---|
| ATOM | 2702 | CG | HIS | 169 | 104.935 | -16.209 | 27.634 | 1.00 | 1.87 | H | C |
| ATOM | 2703 | CD2 | HIS | 169 | 105.456 | -17.452 | 27.739 | 1.00 | 10.72 | H | C |
| ATOM | 2704 | ND1 | HIS | 169 | 105.935 | -15.415 | 27.114 | 1.00 | 4.04 | H | N |
| ATOM | 2705 | CE1 | HIS | 169 | 107.015 | -16.147 | 26.912 | 1.00 | 11.56 | H | C |
| ATOM | 2706 | NE2 | HIS | 169 | 106.750 | -17.387 | 27.282 | 1.00 | 3.03 | H | N |
| ATOM | 2707 | C | HIS | 169 | 102.106 | -13.934 | 28.818 | 1.00 | 26.88 | H | C |
| ATOM | 2708 | O | HIS | 169 | 101.143 | -14.679 | 28.610 | 1.00 | 27.44 | H | O |
| ATOM | 2709 | N | THR | 170 | 101.960 | -12.628 | 28.995 | 1.00 | 15.52 | H | N |
| ATOM | 2710 | CA | THR | 170 | 100.637 | -12.030 | 28.885 | 1.00 | 14.61 | H | C |
| ATOM | 2711 | CB | THR | 170 | 100.472 | -10.872 | 29.894 | 1.00 | 20.19 | H | C |
| ATOM | 2712 | OG1 | THR | 170 | 99.403 | -10.021 | 29.470 | 1.00 | 14.32 | H | O |
| ATOM | 2713 | CG2 | THR | 170 | 101.760 | -10.096 | 30.042 | 1.00 | 25.14 | H | C |
| ATOM | 2714 | C | THR | 170 | 100.487 | -11.553 | 27.433 | 1.00 | 15.32 | H | C |
| ATOM | 2715 | O | THR | 170 | 101.023 | -10.532 | 27.053 | 1.00 | 11.65 | H | O |
| ATOM | 2716 | N | PHE | 171 | 99.762 | -12.324 | 26.630 | 1.00 | 23.28 | H | N |
| ATOM | 2717 | CA | PHE | 171 | 99.587 | -12.046 | 25.206 | 1.00 | 17.85 | H | C |
| ATOM | 2718 | CB | PHE | 171 | 98.695 | -13.110 | 24.554 | 1.00 | 15.23 | H | C |
| ATOM | 2719 | CG | PHE | 171 | 99.138 | -14.521 | 24.806 | 1.00 | 7.97 | H | C |
| ATOM | 2720 | CD1 | PHE | 171 | 98.731 | -15.195 | 25.955 | 1.00 | 8.65 | H | C |
| ATOM | 2721 | CD2 | PHE | 171 | 99.978 | -15.174 | 23.903 | 1.00 | 7.84 | H | C |
| ATOM | 2722 | CE1 | PHE | 171 | 99.153 | -16.492 | 26.202 | 1.00 | 17.36 | H | C |
| ATOM | 2723 | CE2 | PHE | 171 | 100.407 | -16.473 | 24.144 | 1.00 | 15.22 | H | C |
| ATOM | 2724 | CZ | PHE | 171 | 99.993 | -17.133 | 25.295 | 1.00 | 16.34 | H | C |
| ATOM | 2725 | C | PHE | 171 | 99.032 | -10.692 | 24.793 | 1.00 | 18.20 | H | C |
| ATOM | 2726 | O | PHE | 171 | 98.344 | -10.015 | 25.552 | 1.00 | 23.73 | H | O |
| ATOM | 2727 | N | PRO | 172 | 99.341 | -10.278 | 23.557 | 1.00 | 21.77 | H | N |
| ATOM | 2728 | CD | PRO | 172 | 100.227 | -10.890 | 22.550 | 1.00 | 20.32 | H | C |
| ATOM | 2729 | CA | PRO | 172 | 98.827 | -8.999 | 23.088 | 1.00 | 23.20 | H | C |
| ATOM | 2730 | CB | PRO | 172 | 99.595 | -8.775 | 21.782 | 1.00 | 20.71 | H | C |
| ATOM | 2731 | CG | PRO | 172 | 99.834 | -10.148 | 21.287 | 1.00 | 18.82 | H | C |
| ATOM | 2732 | C | PRO | 172 | 97.339 | -9.235 | 22.876 | 1.00 | 25.11 | H | C |
| ATOM | 2733 | O | PRO | 172 | 96.916 | -10.364 | 22.645 | 1.00 | 23.46 | H | O |
| ATOM | 2734 | N | ALA | 173 | 96.551 | -8.172 | 22.960 | 1.00 | 24.67 | H | N |
| ATOM | 2735 | CA | ALA | 173 | 95.104 | -8.267 | 22.815 | 1.00 | 27.18 | H | C |
| ATOM | 2736 | CB | ALA | 173 | 94.439 | -7.079 | 23.498 | 1.00 | 1.87 | H | C |
| ATOM | 2737 | C | ALA | 173 | 94.604 | -8.379 | 21.391 | 1.00 | 30.18 | H | C |
| ATOM | 2738 | O | ALA | 173 | 95.304 | -8.080 | 20.426 | 1.00 | 32.13 | H | O |
| ATOM | 2739 | N | VAL | 174 | 93.365 | -8.820 | 21.277 | 1.00 | 21.72 | H | N |
| ATOM | 2740 | CA | VAL | 174 | 92.753 | -8.964 | 19.984 | 1.00 | 23.16 | H | C |
| ATOM | 2741 | CB | VAL | 174 | 92.841 | -10.406 | 19.511 | 1.00 | 28.95 | H | C |
| ATOM | 2742 | CG1 | VAL | 174 | 92.103 | -10.566 | 18.201 | 1.00 | 32.21 | H | C |
| ATOM | 2743 | CG2 | VAL | 174 | 94.305 | -10.797 | 19.356 | 1.00 | 26.32 | H | C |
| ATOM | 2744 | C | VAL | 174 | 91.302 | -8.508 | 20.058 | 1.00 | 25.36 | H | C |
| ATOM | 2745 | O | VAL | 174 | 90.611 | -8.718 | 21.069 | 1.00 | 25.35 | H | O |
| ATOM | 2746 | N | LEU | 175 | 90.860 | -7.856 | 18.987 | 1.00 | 41.55 | H | N |
| ATOM | 2747 | CA | LEU | 175 | 89.504 | -7.338 | 18.890 | 1.00 | 40.23 | H | C |
| ATOM | 2748 | CB | LEU | 175 | 89.443 | -6.276 | 17.787 | 1.00 | 23.29 | H | C |
| ATOM | 2749 | CG | LEU | 175 | 88.728 | -4.928 | 17.990 | 1.00 | 20.94 | H | C |
| ATOM | 2750 | CD1 | LEU | 175 | 88.634 | -4.511 | 19.463 | 1.00 | 21.45 | H | C |
| ATOM | 2751 | CD2 | LEU | 175 | 89.518 | -3.900 | 17.186 | 1.00 | 22.78 | H | C |
| ATOM | 2752 | C | LEU | 175 | 88.539 | -8.474 | 18.588 | 1.00 | 42.85 | H | C |
| ATOM | 2753 | O | LEU | 175 | 88.738 | -9.233 | 17.638 | 1.00 | 45.50 | H | O |
| ATOM | 2754 | N | GLN | 176 | 87.500 | -8.592 | 19.407 | 1.00 | 41.11 | H | N |
| ATOM | 2755 | CA | GLN | 176 | 86.514 | -9.645 | 19.228 | 1.00 | 42.33 | H | C |
| ATOM | 2756 | CB | GLN | 176 | 85.852 | -9.990 | 20.564 | 1.00 | 38.15 | H | C |
| ATOM | 2757 | CG | GLN | 176 | 86.817 | -10.276 | 21.703 | 1.00 | 37.93 | H | C |
| ATOM | 2758 | CD | GLN | 176 | 86.109 | -10.801 | 22.939 | 1.00 | 36.82 | H | C |
| ATOM | 2759 | OE1 | GLN | 176 | 85.562 | -11.899 | 22.923 | 1.00 | 36.67 | H | O |
| ATOM | 2760 | NE2 | GLN | 176 | 86.108 | -10.014 | 24.011 | 1.00 | 33.13 | H | N |
| ATOM | 2761 | C | GLN | 176 | 85.439 | -9.207 | 18.245 | 1.00 | 44.39 | H | C |
| ATOM | 2762 | O | GLN | 176 | 85.274 | -8.018 | 17.969 | 1.00 | 34.09 | H | O |
| ATOM | 2763 | N | SER | 177 | 84.708 | -10.182 | 17.718 | 1.00 | 59.83 | H | N |
| ATOM | 2764 | CA | SER | 177 | 83.624 | -9.902 | 16.790 | 1.00 | 58.61 | H | C |
| ATOM | 2765 | CB | SER | 177 | 82.804 | -11.177 | 16.558 | 1.00 | 104.21 | H | C |
| ATOM | 2766 | OG | SER | 177 | 81.708 | -10.945 | 15.689 | 1.00 | 104.01 | H | O |
| ATOM | 2767 | C | SER | 177 | 82.759 | -8.832 | 17.448 | 1.00 | 60.09 | H | C |
| ATOM | 2768 | O | SER | 177 | 82.169 | -7.985 | 16.778 | 1.00 | 62.26 | H | O |
| ATOM | 2769 | N | SER | 178 | 82.722 | -8.877 | 18.778 | 1.00 | 34.26 | H | N |
| ATOM | 2770 | CA | SER | 178 | 81.942 | -7.952 | 19.596 | 1.00 | 32.97 | H | C |
| ATOM | 2771 | CB | SER | 178 | 81.798 | -8.510 | 21.016 | 1.00 | 67.89 | H | C |
| ATOM | 2772 | OG | SER | 178 | 83.057 | -8.636 | 21.663 | 1.00 | 66.22 | H | O |
| ATOM | 2773 | C | SER | 178 | 82.538 | -6.554 | 19.671 | 1.00 | 32.95 | H | C |
| ATOM | 2774 | O | SER | 178 | 81.921 | -5.640 | 20.210 | 1.00 | 35.05 | H | O |

Fig. 19: A-39

```
ATOM   2775  N   GLY 179      83.738  -6.382  19.135  1.00  43.45    H  N
ATOM   2776  CA  GLY 179      84.357  -5.072  19.191  1.00  46.81    H  C
ATOM   2777  C   GLY 179      84.972  -4.821  20.552  1.00  50.21    H  C
ATOM   2778  O   GLY 179      85.380  -3.707  20.869  1.00  50.30    H  O
ATOM   2779  N   LEU 180      85.020  -5.862  21.369  1.00  30.24    H  N
ATOM   2780  CA  LEU 180      85.620  -5.749  22.686  1.00  32.27    H  C
ATOM   2781  CB  LEU 180      84.706  -6.380  23.730  1.00  33.41    H  C
ATOM   2782  CG  LEU 180      83.485  -5.524  24.054  1.00  32.78    H  C
ATOM   2783  CD1 LEU 180      82.513  -6.292  24.902  1.00  27.00    H  C
ATOM   2784  CD2 LEU 180      83.943  -4.278  24.781  1.00  32.58    H  C
ATOM   2785  C   LEU 180      86.974  -6.442  22.672  1.00  32.86    H  C
ATOM   2786  O   LEU 180      87.135  -7.488  22.054  1.00  36.18    H  O
ATOM   2787  N   TYR 181      87.952  -5.843  23.336  1.00  31.41    H  N
ATOM   2788  CA  TYR 181      89.293  -6.409  23.387  1.00  32.68    H  C
ATOM   2789  CB  TYR 181      90.297  -5.323  23.792  1.00  57.58    H  C
ATOM   2790  CG  TYR 181      90.773  -4.445  22.651  1.00  56.39    H  C
ATOM   2791  CD1 TYR 181      91.591  -4.961  21.647  1.00  57.58    H  C
ATOM   2792  CE1 TYR 181      92.063  -4.155  20.605  1.00  57.08    H  C
ATOM   2793  CD2 TYR 181      90.430  -3.092  22.585  1.00  56.67    H  C
ATOM   2794  CE2 TYR 181      90.899  -2.273  21.543  1.00  57.48    H  C
ATOM   2795  CZ  TYR 181      91.717  -2.816  20.559  1.00  58.33    H  C
ATOM   2796  OH  TYR 181      92.202  -2.033  19.533  1.00  62.35    H  O
ATOM   2797  C   TYR 181      89.361  -7.573  24.375  1.00  31.73    H  C
ATOM   2798  O   TYR 181      88.581  -7.638  25.324  1.00  32.08    H  O
ATOM   2799  N   SER 182      90.287  -8.499  24.149  1.00  35.13    H  N
ATOM   2800  CA  SER 182      90.446  -9.642  25.045  1.00  32.04    H  C
ATOM   2801  CB  SER 182      89.439 -10.741  24.700  1.00  65.40    H  C
ATOM   2802  OG  SER 182      89.612 -11.868  25.543  1.00  59.63    H  O
ATOM   2803  C   SER 182      91.860 -10.209  24.970  1.00  33.65    H  C
ATOM   2804  O   SER 182      92.494 -10.187  23.906  1.00  37.13    H  O
ATOM   2805  N   LEU 183      92.351 -10.713  26.101  1.00  28.98    H  N
ATOM   2806  CA  LEU 183      93.689 -11.290  26.152  1.00  24.91    H  C
ATOM   2807  CB  LEU 183      94.753 -10.179  26.189  1.00  31.36    H  C
ATOM   2808  CG  LEU 183      94.913  -9.263  27.414  1.00  23.12    H  C
ATOM   2809  CD1 LEU 183      95.475 -10.014  28.625  1.00  27.02    H  C
ATOM   2810  CD2 LEU 183      95.849  -8.148  27.036  1.00  19.84    H  C
ATOM   2811  C   LEU 183      93.898 -12.209  27.342  1.00  24.58    H  C
ATOM   2812  O   LEU 183      93.179 -12.135  28.326  1.00  18.76    H  O
ATOM   2813  N   SER 184      94.894 -13.077  27.250  1.00  26.13    H  N
ATOM   2814  CA  SER 184      95.205 -13.967  28.357  1.00  26.65    H  C
ATOM   2815  CB  SER 184      95.000 -15.445  27.968  1.00  16.60    H  C
ATOM   2816  OG  SER 184      93.638 -15.750  27.710  1.00  22.49    H  O
ATOM   2817  C   SER 184      96.660 -13.752  28.784  1.00  22.47    H  C
ATOM   2818  O   SER 184      97.546 -13.511  27.953  1.00  21.27    H  O
ATOM   2819  N   SER 185      96.896 -13.786  30.087  1.00  27.49    H  N
ATOM   2820  CA  SER 185      98.251 -13.670  30.575  1.00  25.55    H  C
ATOM   2821  CB  SER 185      98.389 -12.634  31.678  1.00  27.24    H  C
ATOM   2822  OG  SER 185      99.760 -12.516  32.031  1.00  25.68    H  O
ATOM   2823  C   SER 185      98.460 -15.060  31.123  1.00  23.97    H  C
ATOM   2824  O   SER 185      97.652 -15.551  31.912  1.00  25.28    H  O
ATOM   2825  N   VAL 186      99.533 -15.699  30.679  1.00  29.81    H  N
ATOM   2826  CA  VAL 186      99.830 -17.060  31.064  1.00  29.28    H  C
ATOM   2827  CB  VAL 186      99.717 -17.966  29.831  1.00  20.56    H  C
ATOM   2828  CG1 VAL 186     100.305 -19.306  30.112  1.00  20.80    H  C
ATOM   2829  CG2 VAL 186      98.253 -18.121  29.446  1.00  19.74    H  C
ATOM   2830  C   VAL 186     101.204 -17.193  31.664  1.00  30.42    H  C
ATOM   2831  O   VAL 186     102.097 -16.416  31.357  1.00  31.20    H  O
ATOM   2832  N   VAL 187     101.359 -18.179  32.540  1.00  29.47    H  N
ATOM   2833  CA  VAL 187     102.645 -18.457  33.173  1.00  26.42    H  C
ATOM   2834  CB  VAL 187     102.739 -17.797  34.586  1.00  27.93    H  C
ATOM   2835  CG1 VAL 187     101.681 -18.385  35.507  1.00  26.86    H  C
ATOM   2836  CG2 VAL 187     104.134 -17.994  35.180  1.00  26.29    H  C
ATOM   2837  C   VAL 187     102.842 -19.975  33.309  1.00  20.75    H  C
ATOM   2838  O   VAL 187     101.882 -20.743  33.316  1.00  22.47    H  O
ATOM   2839  N   THR 188     104.098 -20.397  33.377  1.00   5.29    H  N
ATOM   2840  CA  THR 188     104.441 -21.807  33.539  1.00   7.86    H  C
ATOM   2841  CB  THR 188     105.280 -22.327  32.366  1.00  35.20    H  C
ATOM   2842  OG1 THR 188     106.425 -21.487  32.194  1.00  33.25    H  O
ATOM   2843  CG2 THR 188     104.453 -22.337  31.078  1.00  39.96    H  C
ATOM   2844  C   THR 188     105.270 -21.870  34.802  1.00  13.86    H  C
ATOM   2845  O   THR 188     106.194 -21.077  34.975  1.00  18.45    H  O
ATOM   2846  N   VAL 189     104.921 -22.799  35.688  1.00  28.00    H  N
ATOM   2847  CA  VAL 189     105.613 -22.963  36.965  1.00  25.42    H  C
```

Fig. 19: A-40

| ATOM | 2848 | CB | VAL | 189 | 104.755 | -22.412 | 38.137 | 1.00 | 24.28 | H | C |
|---|---|---|---|---|---|---|---|---|---|---|---|
| ATOM | 2849 | CG1 | VAL | 189 | 104.399 | -20.951 | 37.904 | 1.00 | 17.23 | H | C |
| ATOM | 2850 | CG2 | VAL | 189 | 103.478 | -23.234 | 38.270 | 1.00 | 17.84 | H | C |
| ATOM | 2851 | C | VAL | 189 | 105.875 | -24.439 | 37.242 | 1.00 | 32.15 | H | C |
| ATOM | 2852 | O | VAL | 189 | 105.386 | -25.309 | 36.523 | 1.00 | 35.18 | H | O |
| ATOM | 2853 | N | PRO | 190 | 106.671 | -24.738 | 38.280 | 1.00 | 50.39 | H | N |
| ATOM | 2854 | CD | PRO | 190 | 107.545 | -23.823 | 39.036 | 1.00 | 32.03 | H | C |
| ATOM | 2855 | CA | PRO | 190 | 106.962 | -26.133 | 38.624 | 1.00 | 50.40 | H | C |
| ATOM | 2856 | CB | PRO | 190 | 107.911 | -26.001 | 39.814 | 1.00 | 29.50 | H | C |
| ATOM | 2857 | CG | PRO | 190 | 108.651 | -24.746 | 39.514 | 1.00 | 29.72 | H | C |
| ATOM | 2858 | C | PRO | 190 | 105.650 | -26.801 | 39.018 | 1.00 | 50.46 | H | C |
| ATOM | 2859 | O | PRO | 190 | 104.899 | -26.267 | 39.834 | 1.00 | 48.43 | H | O |
| ATOM | 2860 | N | SER | 191 | 105.357 | -27.953 | 38.436 | 1.00 | 54.29 | H | N |
| ATOM | 2861 | CA | SER | 191 | 104.122 | -28.638 | 38.774 | 1.00 | 60.79 | H | C |
| ATOM | 2862 | CB | SER | 191 | 104.111 | -30.036 | 38.157 | 1.00 | 30.49 | H | C |
| ATOM | 2863 | OG | SER | 191 | 104.076 | -29.980 | 36.740 | 1.00 | 31.07 | H | O |
| ATOM | 2864 | C | SER | 191 | 104.009 | -28.730 | 40.297 | 1.00 | 63.91 | H | C |
| ATOM | 2865 | O | SER | 191 | 102.986 | -28.361 | 40.882 | 1.00 | 66.82 | H | O |
| ATOM | 2866 | N | SER | 192 | 105.084 | -29.201 | 40.924 | 1.00 | 39.50 | H | N |
| ATOM | 2867 | CA | SER | 192 | 105.177 | -29.374 | 42.376 | 1.00 | 40.99 | H | C |
| ATOM | 2868 | CB | SER | 192 | 106.602 | -29.776 | 42.739 | 1.00 | 41.75 | H | C |
| ATOM | 2869 | OG | SER | 192 | 107.475 | -28.675 | 42.565 | 1.00 | 41.65 | H | O |
| ATOM | 2870 | C | SER | 192 | 104.795 | -28.150 | 43.220 | 1.00 | 42.26 | H | C |
| ATOM | 2871 | O | SER | 192 | 104.403 | -28.286 | 44.381 | 1.00 | 48.17 | H | O |
| ATOM | 2872 | N | SER | 193 | 104.923 | -26.960 | 42.645 | 1.00 | 20.64 | H | N |
| ATOM | 2873 | CA | SER | 193 | 104.601 | -25.733 | 43.365 | 1.00 | 22.36 | H | C |
| ATOM | 2874 | CB | SER | 193 | 105.396 | -24.567 | 42.771 | 1.00 | 39.90 | H | C |
| ATOM | 2875 | OG | SER | 193 | 104.973 | -24.284 | 41.447 | 1.00 | 36.65 | H | O |
| ATOM | 2876 | C | SER | 193 | 103.097 | -25.380 | 43.392 | 1.00 | 22.92 | H | C |
| ATOM | 2877 | O | SER | 193 | 102.697 | -24.363 | 43.563 | 1.00 | 25.84 | H | O |
| ATOM | 2878 | N | LEU | 194 | 102.268 | -26.218 | 42.776 | 1.00 | 41.78 | H | N |
| ATOM | 2879 | CA | LEU | 194 | 100.827 | -25.974 | 42.741 | 1.00 | 45.87 | H | C |
| ATOM | 2880 | CB | LEU | 194 | 100.172 | -26.850 | 41.677 | 1.00 | 23.80 | H | C |
| ATOM | 2881 | CG | LEU | 194 | 100.533 | -26.605 | 40.216 | 1.00 | 21.31 | H | C |
| ATOM | 2882 | CD1 | LEU | 194 | 99.975 | -27.739 | 39.377 | 1.00 | 19.27 | H | C |
| ATOM | 2883 | CD2 | LEU | 194 | 99.973 | -25.246 | 39.757 | 1.00 | 15.31 | H | C |
| ATOM | 2884 | C | LEU | 194 | 100.177 | -26.276 | 44.080 | 1.00 | 49.01 | H | C |
| ATOM | 2885 | O | LEU | 194 | 99.209 | -25.623 | 44.478 | 1.00 | 48.38 | H | O |
| ATOM | 2886 | N | GLY | 195 | 100.718 | -27.272 | 44.770 | 1.00 | 65.65 | H | N |
| ATOM | 2887 | CA | GLY | 195 | 100.160 | -27.676 | 46.043 | 1.00 | 68.76 | H | C |
| ATOM | 2888 | C | GLY | 195 | 100.625 | -26.877 | 47.235 | 1.00 | 66.22 | H | C |
| ATOM | 2889 | O | GLY | 195 | 100.051 | -26.992 | 48.314 | 1.00 | 68.30 | H | O |
| ATOM | 2890 | N | THR | 196 | 101.659 | -26.067 | 47.053 | 1.00 | 33.26 | H | N |
| ATOM | 2891 | CA | THR | 196 | 102.175 | -25.265 | 48.155 | 1.00 | 32.73 | H | C |
| ATOM | 2892 | CB | THR | 196 | 103.575 | -25.763 | 48.585 | 1.00 | 30.77 | H | C |
| ATOM | 2893 | OG1 | THR | 196 | 104.489 | -25.676 | 47.478 | 1.00 | 28.63 | H | O |
| ATOM | 2894 | CG2 | THR | 196 | 103.488 | -27.213 | 49.071 | 1.00 | 27.23 | H | C |
| ATOM | 2895 | C | THR | 196 | 102.251 | -23.786 | 47.813 | 1.00 | 35.97 | H | C |
| ATOM | 2896 | O | THR | 196 | 102.179 | -22.933 | 48.695 | 1.00 | 36.72 | H | O |
| ATOM | 2897 | N | GLN | 197 | 102.389 | -23.488 | 46.527 | 1.00 | 53.90 | H | N |
| ATOM | 2898 | CA | GLN | 197 | 102.478 | -22.110 | 46.060 | 1.00 | 54.25 | H | C |
| ATOM | 2899 | CB | GLN | 197 | 103.480 | -22.031 | 44.906 | 1.00 | 42.12 | H | C |
| ATOM | 2900 | CG | GLN | 197 | 104.561 | -20.975 | 45.045 | 1.00 | 45.66 | H | C |
| ATOM | 2901 | CD | GLN | 197 | 104.051 | -19.587 | 44.765 | 1.00 | 49.49 | H | C |
| ATOM | 2902 | OE1 | GLN | 197 | 103.257 | -19.032 | 45.528 | 1.00 | 50.05 | H | O |
| ATOM | 2903 | NE2 | GLN | 197 | 104.500 | -19.013 | 43.656 | 1.00 | 49.01 | H | N |
| ATOM | 2904 | C | GLN | 197 | 101.105 | -21.617 | 45.604 | 1.00 | 52.98 | H | C |
| ATOM | 2905 | O | GLN | 197 | 100.314 | -22.382 | 45.050 | 1.00 | 55.53 | H | O |
| ATOM | 2906 | N | THR | 198 | 100.829 | -20.338 | 45.847 | 1.00 | 30.38 | H | N |
| ATOM | 2907 | CA | THR | 198 | 99.559 | -19.719 | 45.470 | 1.00 | 29.29 | H | C |
| ATOM | 2908 | CB | THR | 198 | 98.922 | -18.970 | 46.677 | 1.00 | 45.77 | H | C |
| ATOM | 2909 | OG1 | THR | 198 | 97.546 | -18.682 | 46.404 | 1.00 | 43.55 | H | O |
| ATOM | 2910 | CG2 | THR | 198 | 99.643 | -17.644 | 46.929 | 1.00 | 47.95 | H | C |
| ATOM | 2911 | C | THR | 198 | 99.811 | -18.719 | 44.338 | 1.00 | 27.94 | H | C |
| ATOM | 2912 | O | THR | 198 | 100.722 | -17.891 | 44.413 | 1.00 | 31.22 | H | O |
| ATOM | 2913 | N | TYR | 199 | 99.008 | -18.789 | 43.285 | 1.00 | 40.84 | H | N |
| ATOM | 2914 | CA | TYR | 199 | 99.191 | -17.874 | 42.168 | 1.00 | 31.26 | H | C |
| ATOM | 2915 | CB | TYR | 199 | 99.402 | -18.681 | 40.880 | 1.00 | 39.46 | H | C |
| ATOM | 2916 | CG | TYR | 199 | 100.677 | -19.496 | 40.904 | 1.00 | 33.83 | H | C |
| ATOM | 2917 | CD1 | TYR | 199 | 101.911 | -18.901 | 40.630 | 1.00 | 31.63 | H | C |
| ATOM | 2918 | CE1 | TYR | 199 | 103.107 | -19.626 | 40.735 | 1.00 | 31.28 | H | C |
| ATOM | 2919 | CD2 | TYR | 199 | 100.662 | -20.847 | 41.282 | 1.00 | 32.94 | H | C |
| ATOM | 2920 | CE2 | TYR | 199 | 101.850 | -21.590 | 41.392 | 1.00 | 33.91 | H | C |

Fig. 19: A-41

| | | | | | | | | | | |
|---|---|---|---|---|---|---|---|---|---|---|
| ATOM | 2921 | CZ | TYR | 199 | 103.069 | -20.972 | 41.118 | 1.00 | 33.40 | H C |
| ATOM | 2922 | OH | TYR | 199 | 104.244 | -21.685 | 41.223 | 1.00 | 37.29 | H O |
| ATOM | 2923 | C | TYR | 199 | 98.029 | -16.897 | 42.014 | 1.00 | 31.50 | H C |
| ATOM | 2924 | O | TYR | 199 | 96.876 | -17.302 | 41.913 | 1.00 | 32.18 | H O |
| ATOM | 2925 | N | ILE | 200 | 98.342 | -15.605 | 42.026 | 1.00 | 38.61 | H N |
| ATOM | 2926 | CA | ILE | 200 | 97.329 | -14.566 | 41.858 | 1.00 | 39.11 | H C |
| ATOM | 2927 | CB | ILE | 200 | 97.265 | -13.574 | 43.051 | 1.00 | 27.10 | H C |
| ATOM | 2928 | CG2 | ILE | 200 | 96.185 | -12.540 | 42.793 | 1.00 | 26.36 | H C |
| ATOM | 2929 | CG1 | ILE | 200 | 96.978 | -14.301 | 44.363 | 1.00 | 30.59 | H C |
| ATOM | 2930 | CD1 | ILE | 200 | 98.119 | -15.184 | 44.842 | 1.00 | 36.15 | H C |
| ATOM | 2931 | C | ILE | 200 | 97.730 | -13.736 | 40.649 | 1.00 | 41.59 | H C |
| ATOM | 2932 | O | ILE | 200 | 98.916 | -13.517 | 40.415 | 1.00 | 45.01 | H O |
| ATOM | 2933 | N | CYS | 201 | 96.758 | -13.283 | 39.867 | 1.00 | 30.01 | H N |
| ATOM | 2934 | CA | CYS | 201 | 97.092 | -12.434 | 38.735 | 1.00 | 27.23 | H C |
| ATOM | 2935 | C | CYS | 201 | 96.476 | -11.075 | 39.011 | 1.00 | 24.60 | H C |
| ATOM | 2936 | O | CYS | 201 | 95.307 | -10.967 | 39.386 | 1.00 | 22.36 | H O |
| ATOM | 2937 | CB | CYS | 201 | 96.577 | -12.997 | 37.394 | 1.00 | 42.80 | H C |
| ATOM | 2938 | SG | CYS | 201 | 94.784 | -12.909 | 37.090 | 1.00 | 39.16 | H S |
| ATOM | 2939 | N | ASN | 202 | 97.282 | -10.035 | 38.849 | 1.00 | 26.40 | H N |
| ATOM | 2940 | CA | ASN | 202 | 96.819 | -8.683 | 39.080 | 1.00 | 32.39 | H C |
| ATOM | 2941 | CB | ASN | 202 | 97.884 | -7.902 | 39.846 | 1.00 | 36.85 | H C |
| ATOM | 2942 | CG | ASN | 202 | 98.507 | -8.720 | 40.954 | 1.00 | 39.80 | H C |
| ATOM | 2943 | OD1 | ASN | 202 | 99.570 | -9.314 | 40.779 | 1.00 | 38.11 | H O |
| ATOM | 2944 | ND2 | ASN | 202 | 97.837 | -8.776 | 42.097 | 1.00 | 41.02 | H N |
| ATOM | 2945 | C | ASN | 202 | 96.530 | -8.025 | 37.743 | 1.00 | 36.08 | H C |
| ATOM | 2946 | O | ASN | 202 | 97.419 | -7.867 | 36.911 | 1.00 | 40.34 | H O |
| ATOM | 2947 | N | VAL | 203 | 95.273 | -7.668 | 37.533 | 1.00 | 28.99 | H N |
| ATOM | 2948 | CA | VAL | 203 | 94.868 | -7.017 | 36.295 | 1.00 | 29.18 | H C |
| ATOM | 2949 | CB | VAL | 203 | 93.691 | -7.781 | 35.624 | 1.00 | 21.70 | H C |
| ATOM | 2950 | CG1 | VAL | 203 | 93.321 | -7.134 | 34.274 | 1.00 | 17.35 | H C |
| ATOM | 2951 | CG2 | VAL | 203 | 94.067 | -9.236 | 35.450 | 1.00 | 25.16 | H C |
| ATOM | 2952 | C | VAL | 203 | 94.443 | -5.580 | 36.615 | 1.00 | 32.31 | H C |
| ATOM | 2953 | O | VAL | 203 | 93.808 | -5.320 | 37.643 | 1.00 | 27.84 | H O |
| ATOM | 2954 | N | ASN | 204 | 94.799 | -4.648 | 35.741 | 1.00 | 45.86 | H N |
| ATOM | 2955 | CA | ASN | 204 | 94.442 | -3.266 | 35.979 | 1.00 | 50.50 | H C |
| ATOM | 2956 | CB | ASN | 204 | 95.565 | -2.570 | 36.739 | 1.00 | 59.79 | H C |
| ATOM | 2957 | CG | ASN | 204 | 95.186 | -1.176 | 37.164 | 1.00 | 65.34 | H C |
| ATOM | 2958 | OD1 | ASN | 204 | 94.801 | -0.347 | 36.338 | 1.00 | 69.10 | H O |
| ATOM | 2959 | ND2 | ASN | 204 | 95.287 | -0.906 | 38.459 | 1.00 | 65.59 | H N |
| ATOM | 2960 | C | ASN | 204 | 94.109 | -2.486 | 34.709 | 1.00 | 51.54 | H C |
| ATOM | 2961 | O | ASN | 204 | 94.985 | -2.164 | 33.905 | 1.00 | 51.77 | H O |
| ATOM | 2962 | N | HIS | 205 | 92.828 | -2.176 | 34.550 | 1.00 | 30.40 | H N |
| ATOM | 2963 | CA | HIS | 205 | 92.338 | -1.431 | 33.396 | 1.00 | 29.10 | H C |
| ATOM | 2964 | CB | HIS | 205 | 90.994 | -1.998 | 32.957 | 1.00 | 20.87 | H C |
| ATOM | 2965 | CG | HIS | 205 | 90.444 | -1.371 | 31.718 | 1.00 | 25.68 | H C |
| ATOM | 2966 | CD2 | HIS | 205 | 89.209 | -0.889 | 31.437 | 1.00 | 28.69 | H C |
| ATOM | 2967 | ND1 | HIS | 205 | 91.165 | -1.282 | 30.548 | 1.00 | 23.44 | H N |
| ATOM | 2968 | CE1 | HIS | 205 | 90.396 | -0.780 | 29.597 | 1.00 | 25.19 | H C |
| ATOM | 2969 | NE2 | HIS | 205 | 89.203 | -0.534 | 30.110 | 1.00 | 28.16 | H N |
| ATOM | 2970 | C | HIS | 205 | 92.157 | 0.022 | 33.793 | 1.00 | 30.12 | H C |
| ATOM | 2971 | O | HIS | 205 | 91.057 | 0.429 | 34.173 | 1.00 | 28.02 | H O |
| ATOM | 2972 | N | LYS | 206 | 93.228 | 0.805 | 33.714 | 1.00 | 50.94 | H N |
| ATOM | 2973 | CA | LYS | 206 | 93.138 | 2.209 | 34.084 | 1.00 | 49.11 | H C |
| ATOM | 2974 | CB | LYS | 206 | 94.486 | 2.906 | 33.867 | 1.00 | 50.82 | H C |
| ATOM | 2975 | CG | LYS | 206 | 95.536 | 2.476 | 34.895 | 1.00 | 57.82 | H C |
| ATOM | 2976 | CD | LYS | 206 | 96.809 | 3.325 | 34.857 | 1.00 | 61.64 | H C |
| ATOM | 2977 | CE | LYS | 206 | 97.793 | 2.906 | 35.959 | 1.00 | 63.00 | H C |
| ATOM | 2978 | NZ | LYS | 206 | 99.049 | 3.715 | 35.960 | 1.00 | 66.30 | H N |
| ATOM | 2979 | C | LYS | 206 | 92.017 | 2.949 | 33.353 | 1.00 | 47.68 | H C |
| ATOM | 2980 | O | LYS | 206 | 91.318 | 3.765 | 33.955 | 1.00 | 46.73 | H O |
| ATOM | 2981 | N | PRO | 207 | 91.810 | 2.650 | 32.057 | 1.00 | 33.42 | H N |
| ATOM | 2982 | CD | PRO | 207 | 92.613 | 1.722 | 31.239 | 1.00 | 21.52 | H C |
| ATOM | 2983 | CA | PRO | 207 | 90.770 | 3.285 | 31.241 | 1.00 | 34.06 | H C |
| ATOM | 2984 | CB | PRO | 207 | 90.831 | 2.501 | 29.936 | 1.00 | 21.18 | H C |
| ATOM | 2985 | CG | PRO | 207 | 92.286 | 2.156 | 29.831 | 1.00 | 24.69 | H C |
| ATOM | 2986 | C | PRO | 207 | 89.366 | 3.280 | 31.846 | 1.00 | 34.36 | H C |
| ATOM | 2987 | O | PRO | 207 | 88.452 | 3.927 | 31.311 | 1.00 | 32.31 | H O |
| ATOM | 2988 | N | SER | 208 | 89.190 | 2.545 | 32.944 | 1.00 | 25.18 | H N |
| ATOM | 2989 | CA | SER | 208 | 87.893 | 2.481 | 33.628 | 1.00 | 28.11 | H C |
| ATOM | 2990 | CB | SER | 208 | 87.055 | 1.320 | 33.094 | 1.00 | 29.27 | H C |
| ATOM | 2991 | OG | SER | 208 | 87.724 | 0.096 | 33.315 | 1.00 | 27.44 | H O |
| ATOM | 2992 | C | SER | 208 | 88.120 | 2.314 | 35.126 | 1.00 | 31.08 | H C |
| ATOM | 2993 | O | SER | 208 | 87.266 | 1.789 | 35.846 | 1.00 | 34.78 | H O |

Fig. 19: A-42

| | | | | | | | | | | |
|---|---|---|---|---|---|---|---|---|---|---|
| ATOM | 2994 | N | ASN | 209 | 89.284 | 2.777 | 35.573 | 1.00 | 68.02 | H N |
| ATOM | 2995 | CA | ASN | 209 | 89.678 | 2.701 | 36.970 | 1.00 | 70.18 | H C |
| ATOM | 2996 | CB | ASN | 209 | 89.073 | 3.879 | 37.741 | 1.00 | 49.77 | H C |
| ATOM | 2997 | CG | ASN | 209 | 89.673 | 4.044 | 39.125 | 1.00 | 56.50 | H C |
| ATOM | 2998 | OD1 | ASN | 209 | 90.885 | 3.963 | 39.301 | 1.00 | 62.08 | H O |
| ATOM | 2999 | ND2 | ASN | 209 | 88.824 | 4.290 | 40.114 | 1.00 | 57.03 | H N |
| ATOM | 3000 | C | ASN | 209 | 89.267 | 1.360 | 37.593 | 1.00 | 68.80 | H C |
| ATOM | 3001 | O | ASN | 209 | 88.708 | 1.304 | 38.690 | 1.00 | 68.05 | H O |
| ATOM | 3002 | N | THR | 210 | 89.555 | 0.282 | 36.871 | 1.00 | 35.45 | H N |
| ATOM | 3003 | CA | THR | 210 | 89.246 | -1.061 | 37.322 | 1.00 | 37.08 | H C |
| ATOM | 3004 | CB | THR | 210 | 88.640 | -1.883 | 36.201 | 1.00 | 55.80 | H C |
| ATOM | 3005 | OG1 | THR | 210 | 87.416 | -1.273 | 35.787 | 1.00 | 56.14 | H O |
| ATOM | 3006 | CG2 | THR | 210 | 88.367 | -3.303 | 36.668 | 1.00 | 57.05 | H C |
| ATOM | 3007 | C | THR | 210 | 90.538 | -1.719 | 37.762 | 1.00 | 36.35 | H C |
| ATOM | 3008 | O | THR | 210 | 91.613 | -1.388 | 37.266 | 1.00 | 34.79 | H O |
| ATOM | 3009 | N | LYS | 211 | 90.426 | -2.655 | 38.692 | 1.00 | 33.96 | H N |
| ATOM | 3010 | CA | LYS | 211 | 91.588 | -3.352 | 39.207 | 1.00 | 34.09 | H C |
| ATOM | 3011 | CB | LYS | 211 | 92.366 | -2.422 | 40.154 | 1.00 | 52.60 | H C |
| ATOM | 3012 | CG | LYS | 211 | 93.360 | -3.095 | 41.117 | 1.00 | 57.40 | H C |
| ATOM | 3013 | CD | LYS | 211 | 94.338 | -4.040 | 40.416 | 1.00 | 62.07 | H C |
| ATOM | 3014 | CE | LYS | 211 | 95.636 | -4.228 | 41.216 | 1.00 | 64.56 | H C |
| ATOM | 3015 | NZ | LYS | 211 | 95.432 | -4.548 | 42.660 | 1.00 | 65.70 | H N |
| ATOM | 3016 | C | LYS | 211 | 91.147 | -4.609 | 39.935 | 1.00 | 32.12 | H C |
| ATOM | 3017 | O | LYS | 211 | 90.611 | -4.525 | 41.036 | 1.00 | 32.03 | H O |
| ATOM | 3018 | N | VAL | 212 | 91.357 | -5.772 | 39.322 | 1.00 | 43.02 | H N |
| ATOM | 3019 | CA | VAL | 212 | 90.971 | -7.017 | 39.973 | 1.00 | 37.80 | H C |
| ATOM | 3020 | CB | VAL | 212 | 89.728 | -7.685 | 39.308 | 1.00 | 28.95 | H C |
| ATOM | 3021 | CG1 | VAL | 212 | 88.671 | -6.639 | 39.021 | 1.00 | 26.33 | H C |
| ATOM | 3022 | CG2 | VAL | 212 | 90.125 | -8.431 | 38.059 | 1.00 | 26.83 | H C |
| ATOM | 3023 | C | VAL | 212 | 92.086 | -8.042 | 40.020 | 1.00 | 39.84 | H C |
| ATOM | 3024 | O | VAL | 212 | 92.832 | -8.224 | 39.057 | 1.00 | 39.92 | H O |
| ATOM | 3025 | N | ASP | 213 | 92.184 | -8.709 | 41.162 | 1.00 | 52.39 | H N |
| ATOM | 3026 | CA | ASP | 213 | 93.177 | -9.743 | 41.376 | 1.00 | 49.02 | H C |
| ATOM | 3027 | CB | ASP | 213 | 93.900 | -9.493 | 42.692 | 1.00 | 46.86 | H C |
| ATOM | 3028 | CG | ASP | 213 | 94.548 | -8.128 | 42.740 | 1.00 | 52.80 | H C |
| ATOM | 3029 | OD1 | ASP | 213 | 95.420 | -7.852 | 41.887 | 1.00 | 56.11 | H O |
| ATOM | 3030 | OD2 | ASP | 213 | 94.182 | -7.329 | 43.626 | 1.00 | 57.38 | H O |
| ATOM | 3031 | C | ASP | 213 | 92.433 | -11.067 | 41.423 | 1.00 | 46.03 | H C |
| ATOM | 3032 | O | ASP | 213 | 91.537 | -11.248 | 42.236 | 1.00 | 45.16 | H O |
| ATOM | 3033 | N | LYS | 214 | 92.796 | -11.993 | 40.548 | 1.00 | 33.42 | H N |
| ATOM | 3034 | CA | LYS | 214 | 92.124 | -13.282 | 40.502 | 1.00 | 29.46 | H C |
| ATOM | 3035 | CB | LYS | 214 | 91.732 | -13.602 | 39.055 | 0.00 | 52.86 | H C |
| ATOM | 3036 | CG | LYS | 214 | 90.422 | -14.370 | 38.875 | 0.00 | 47.62 | H C |
| ATOM | 3037 | CD | LYS | 214 | 90.398 | -15.699 | 39.614 | 0.00 | 43.68 | H C |
| ATOM | 3038 | CE | LYS | 214 | 89.852 | -15.541 | 41.024 | 0.00 | 41.24 | H C |
| ATOM | 3039 | NZ | LYS | 214 | 88.452 | -15.037 | 41.021 | 0.00 | 39.27 | H N |
| ATOM | 3040 | C | LYS | 214 | 93.027 | -14.377 | 41.047 | 1.00 | 29.68 | H C |
| ATOM | 3041 | O | LYS | 214 | 94.160 | -14.549 | 40.585 | 1.00 | 27.06 | H O |
| ATOM | 3042 | N | LYS | 215 | 92.533 | -15.103 | 42.045 | 1.00 | 38.49 | H N |
| ATOM | 3043 | CA | LYS | 215 | 93.289 | -16.207 | 42.617 | 1.00 | 34.59 | H C |
| ATOM | 3044 | CB | LYS | 215 | 92.788 | -16.531 | 44.032 | 0.00 | 48.10 | H C |
| ATOM | 3045 | CG | LYS | 215 | 92.812 | -15.343 | 44.987 | 0.00 | 42.43 | H C |
| ATOM | 3046 | CD | LYS | 215 | 92.403 | -15.737 | 46.401 | 0.00 | 38.17 | H C |
| ATOM | 3047 | CE | LYS | 215 | 93.458 | -16.597 | 47.089 | 0.00 | 35.48 | H C |
| ATOM | 3048 | NZ | LYS | 215 | 93.695 | -17.895 | 46.397 | 0.00 | 33.32 | H N |
| ATOM | 3049 | C | LYS | 215 | 93.042 | -17.391 | 41.675 | 1.00 | 36.50 | H C |
| ATOM | 3050 | O | LYS | 215 | 91.901 | -17.770 | 41.413 | 1.00 | 38.63 | H O |
| ATOM | 3051 | N | VAL | 216 | 94.113 | -17.939 | 41.122 | 1.00 | 32.15 | H N |
| ATOM | 3052 | CA | VAL | 216 | 93.996 | -19.081 | 40.224 | 1.00 | 32.08 | H C |
| ATOM | 3053 | CB | VAL | 216 | 94.801 | -18.850 | 38.923 | 1.00 | 21.03 | H C |
| ATOM | 3054 | CG1 | VAL | 216 | 94.435 | -19.912 | 37.880 | 1.00 | 20.14 | H C |
| ATOM | 3055 | CG2 | VAL | 216 | 94.482 | -17.480 | 38.375 | 1.00 | 18.92 | H C |
| ATOM | 3056 | C | VAL | 216 | 94.504 | -20.334 | 40.948 | 1.00 | 33.21 | H C |
| ATOM | 3057 | O | VAL | 216 | 95.696 | -20.441 | 41.248 | 1.00 | 33.32 | H O |
| ATOM | 3058 | N | GLU | 217 | 93.586 | -21.269 | 41.219 | 1.00 | 45.06 | H N |
| ATOM | 3059 | CA | GLU | 217 | 93.871 | -22.508 | 41.949 | 1.00 | 48.19 | H C |
| ATOM | 3060 | CB | GLU | 217 | 93.065 | -22.532 | 43.250 | 1.00 | 91.11 | H C |
| ATOM | 3061 | CG | GLU | 217 | 93.114 | -21.248 | 44.065 | 1.00 | 95.99 | H C |
| ATOM | 3062 | CD | GLU | 217 | 91.872 | -21.005 | 44.901 | 1.00 | 101.94 | H C |
| ATOM | 3063 | OE1 | GLU | 217 | 90.757 | -21.353 | 44.453 | 1.00 | 105.02 | H O |
| ATOM | 3064 | OE2 | GLU | 217 | 92.013 | -20.475 | 46.029 | 1.00 | 105.37 | H O |
| ATOM | 3065 | C | GLU | 217 | 93.426 | -23.720 | 41.109 | 1.00 | 48.96 | H C |
| ATOM | 3066 | O | GLU | 217 | 92.500 | -23.643 | 40.332 | 1.00 | 51.24 | H O |

Fig. 19: A-43

| ATOM | 3067 | N | PRO | 218 | 94.078 | -24.870 | 41.265 | 1.00 | 42.53 | H | N |
|---|---|---|---|---|---|---|---|---|---|---|---|
| ATOM | 3068 | CD | PRO | 218 | 95.339 | -25.074 | 41.993 | 1.00 | 48.02 | H | C |
| ATOM | 3069 | CA | PRO | 218 | 93.711 | -26.079 | 40.509 | 1.00 | 40.69 | H | C |
| ATOM | 3070 | CB | PRO | 218 | 94.962 | -26.924 | 40.609 | 1.00 | 42.70 | H | C |
| ATOM | 3071 | CG | PRO | 218 | 95.482 | -26.557 | 41.957 | 1.00 | 44.19 | H | C |
| ATOM | 3072 | C | PRO | 218 | 92.544 | -26.782 | 41.183 | 1.00 | 41.85 | H | C |
| ATOM | 3073 | O | PRO | 218 | 92.513 | -26.844 | 42.403 | 1.00 | 45.36 | H | O |
| ATOM | 3074 | N | LYS | 219 | 91.638 | -27.354 | 40.396 | 1.00 | 112.06 | H | N |
| ATOM | 3075 | CA | LYS | 219 | 90.475 | -28.045 | 40.934 | 1.00 | 111.92 | H | C |
| ATOM | 3076 | CB | LYS | 219 | 89.635 | -28.618 | 39.794 | 0.00 | 52.93 | H | C |
| ATOM | 3077 | CG | LYS | 219 | 89.522 | -27.658 | 38.654 | 0.00 | 47.21 | H | C |
| ATOM | 3078 | CD | LYS | 219 | 88.205 | -27.801 | 37.948 | 0.00 | 42.71 | H | C |
| ATOM | 3079 | CE | LYS | 219 | 88.174 | -26.793 | 36.845 | 0.00 | 39.84 | H | C |
| ATOM | 3080 | NZ | LYS | 219 | 86.847 | -26.599 | 36.249 | 0.00 | 37.57 | H | N |
| ATOM | 3081 | C | LYS | 219 | 90.867 | -29.169 | 41.892 | 1.00 | 116.73 | H | C |
| ATOM | 3082 | O | LYS | 219 | 90.330 | -29.223 | 43.021 | 1.00 | 116.18 | H | O |
| ATOM | 3083 | OXT | LYS | 219 | 91.705 | -30.007 | 41.503 | 1.00 | 36.39 | H | O |
| ATOM | 3084 | CB | ILE | 2 | 109.298 | 10.543 | -2.157 | 1.00 | 31.85 | L | C |
| ATOM | 3085 | CG2 | ILE | 2 | 110.285 | 9.382 | -2.130 | 1.00 | 31.85 | L | C |
| ATOM | 3086 | CG1 | ILE | 2 | 109.803 | 11.664 | -3.069 | 1.00 | 31.85 | L | C |
| ATOM | 3087 | CD1 | ILE | 2 | 111.143 | 12.240 | -2.656 | 1.00 | 31.85 | L | C |
| ATOM | 3088 | C | ILE | 2 | 107.518 | 8.858 | -1.778 | 1.00 | 41.66 | L | C |
| ATOM | 3089 | O | ILE | 2 | 107.155 | 9.019 | -0.613 | 1.00 | 41.66 | L | O |
| ATOM | 3090 | N | ILE | 2 | 106.898 | 11.133 | -2.646 | 1.00 | 41.66 | L | N |
| ATOM | 3091 | CA | ILE | 2 | 107.922 | 10.043 | -2.648 | 1.00 | 41.66 | L | C |
| ATOM | 3092 | N | GLN | 3 | 107.597 | 7.665 | -2.361 | 1.00 | 28.81 | L | N |
| ATOM | 3093 | CA | GLN | 3 | 107.244 | 6.433 | -1.669 | 1.00 | 28.81 | L | C |
| ATOM | 3094 | CB | GLN | 3 | 106.206 | 5.677 | -2.484 | 1.00 | 56.92 | L | C |
| ATOM | 3095 | CG | GLN | 3 | 105.708 | 4.412 | -1.837 | 1.00 | 56.92 | L | C |
| ATOM | 3096 | CD | GLN | 3 | 104.579 | 3.778 | -2.622 | 1.00 | 56.92 | L | C |
| ATOM | 3097 | OE1 | GLN | 3 | 104.124 | 2.681 | -2.298 | 1.00 | 56.92 | L | O |
| ATOM | 3098 | NE2 | GLN | 3 | 104.116 | 4.469 | -3.661 | 1.00 | 56.92 | L | N |
| ATOM | 3099 | C | GLN | 3 | 108.482 | 5.557 | -1.428 | 1.00 | 28.81 | L | C |
| ATOM | 3100 | O | GLN | 3 | 109.297 | 5.322 | -2.327 | 1.00 | 28.81 | L | O |
| ATOM | 3101 | N | LEU | 4 | 108.615 | 5.088 | -0.195 | 1.00 | 39.62 | L | N |
| ATOM | 3102 | CA | LEU | 4 | 109.744 | 4.260 | 0.198 | 1.00 | 39.62 | L | C |
| ATOM | 3103 | CB | LEU | 4 | 110.377 | 4.820 | 1.469 | 1.00 | 19.64 | L | C |
| ATOM | 3104 | CG | LEU | 4 | 111.546 | 5.792 | 1.348 | 1.00 | 19.64 | L | C |
| ATOM | 3105 | CD1 | LEU | 4 | 111.407 | 6.643 | 0.092 | 1.00 | 19.64 | L | C |
| ATOM | 3106 | CD2 | LEU | 4 | 111.614 | 6.640 | 2.617 | 1.00 | 19.64 | L | C |
| ATOM | 3107 | C | LEU | 4 | 109.323 | 2.823 | 0.445 | 1.00 | 39.62 | L | C |
| ATOM | 3108 | O | LEU | 4 | 108.470 | 2.548 | 1.289 | 1.00 | 39.62 | L | O |
| ATOM | 3109 | N | THR | 5 | 109.935 | 1.903 | -0.289 | 1.00 | 16.92 | L | N |
| ATOM | 3110 | CA | THR | 5 | 109.634 | 0.485 | -0.152 | 1.00 | 16.92 | L | C |
| ATOM | 3111 | CB | THR | 5 | 108.945 | -0.038 | -1.437 | 1.00 | 21.45 | L | C |
| ATOM | 3112 | OG1 | THR | 5 | 109.307 | -1.402 | -1.651 | 1.00 | 21.45 | L | O |
| ATOM | 3113 | CG2 | THR | 5 | 109.324 | 0.802 | -2.641 | 1.00 | 21.45 | L | C |
| ATOM | 3114 | C | THR | 5 | 110.908 | -0.312 | 0.186 | 1.00 | 16.92 | L | C |
| ATOM | 3115 | O | THR | 5 | 111.849 | -0.382 | -0.601 | 1.00 | 16.92 | L | O |
| ATOM | 3116 | N | GLN | 6 | 110.919 | -0.880 | 1.391 | 1.00 | 17.69 | L | N |
| ATOM | 3117 | CA | GLN | 6 | 112.040 | -1.661 | 1.933 | 1.00 | 17.69 | L | C |
| ATOM | 3118 | CB | GLN | 6 | 112.078 | -1.544 | 3.468 | 1.00 | 15.96 | L | C |
| ATOM | 3119 | CG | GLN | 6 | 111.898 | -0.138 | 4.014 | 1.00 | 15.96 | L | C |
| ATOM | 3120 | CD | GLN | 6 | 112.007 | -0.060 | 5.535 | 1.00 | 15.96 | L | C |
| ATOM | 3121 | OE1 | GLN | 6 | 111.626 | 0.944 | 6.139 | 1.00 | 15.96 | L | O |
| ATOM | 3122 | NE2 | GLN | 6 | 112.541 | -1.115 | 6.158 | 1.00 | 15.96 | L | N |
| ATOM | 3123 | C | GLN | 6 | 111.962 | -3.143 | 1.588 | 1.00 | 17.69 | L | C |
| ATOM | 3124 | O | GLN | 6 | 110.882 | -3.675 | 1.352 | 1.00 | 17.69 | L | O |
| ATOM | 3125 | N | SER | 7 | 113.107 | -3.814 | 1.595 | 1.00 | 44.56 | L | N |
| ATOM | 3126 | CA | SER | 7 | 113.148 | -5.238 | 1.293 | 1.00 | 44.56 | L | C |
| ATOM | 3127 | CB | SER | 7 | 113.109 | -5.470 | -0.214 | 1.00 | 33.18 | L | C |
| ATOM | 3128 | OG | SER | 7 | 114.194 | -4.813 | -0.837 | 1.00 | 33.18 | L | O |
| ATOM | 3129 | C | SER | 7 | 114.394 | -5.898 | 1.855 | 1.00 | 44.56 | L | C |
| ATOM | 3130 | O | SER | 7 | 115.480 | -5.328 | 1.811 | 1.00 | 44.56 | L | O |
| ATOM | 3131 | N | PRO | 8 | 114.246 | -7.107 | 2.415 | 1.00 | 19.10 | L | N |
| ATOM | 3132 | CD | PRO | 8 | 115.292 | -7.921 | 3.063 | 1.00 | 16.76 | L | C |
| ATOM | 3133 | CA | PRO | 8 | 112.945 | -7.771 | 2.494 | 1.00 | 19.10 | L | C |
| ATOM | 3134 | CB | PRO | 8 | 113.303 | -9.161 | 3.004 | 1.00 | 16.76 | L | C |
| ATOM | 3135 | CG | PRO | 8 | 114.481 | -8.882 | 3.905 | 1.00 | 16.76 | L | C |
| ATOM | 3136 | C | PRO | 8 | 112.068 | -7.023 | 3.479 | 1.00 | 19.10 | L | C |
| ATOM | 3137 | O | PRO | 8 | 112.517 | -6.069 | 4.125 | 1.00 | 19.10 | L | O |
| ATOM | 3138 | N | SER | 9 | 110.822 | -7.460 | 3.589 | 1.00 | 12.41 | L | N |
| ATOM | 3139 | CA | SER | 9 | 109.885 | -6.851 | 4.516 | 1.00 | 12.41 | L | C |

Fig. 19: A-44

| | | | | | | | | | | | |
|---|---|---|---|---|---|---|---|---|---|---|---|
| ATOM | 3140 | CB | SER | 9 | 108.466 | -7.059 | 4.023 | 1.00 | 25.43 | L | C |
| ATOM | 3141 | OG | SER | 9 | 108.345 | -6.555 | 2.707 | 1.00 | 25.43 | L | O |
| ATOM | 3142 | C | SER | 9 | 110.083 | -7.558 | 5.837 | 1.00 | 12.41 | L | C |
| ATOM | 3143 | O | SER | 9 | 109.904 | -6.983 | 6.904 | 1.00 | 12.41 | L | O |
| ATOM | 3144 | N | SER | 10 | 110.492 | -8.817 | 5.745 | 1.00 | 33.63 | L | N |
| ATOM | 3145 | CA | SER | 10 | 110.720 | -9.645 | 6.910 | 1.00 | 33.63 | L | C |
| ATOM | 3146 | CB | SER | 10 | 109.490 | -10.517 | 7.144 | 1.00 | 43.13 | L | C |
| ATOM | 3147 | OG | SER | 10 | 109.614 | -11.248 | 8.338 | 1.00 | 43.13 | L | O |
| ATOM | 3148 | C | SER | 10 | 111.942 | -10.504 | 6.624 | 1.00 | 33.63 | L | C |
| ATOM | 3149 | O | SER | 10 | 112.226 | -10.814 | 5.470 | 1.00 | 33.63 | L | O |
| ATOM | 3150 | N | LEU | 11 | 112.677 | -10.880 | 7.666 | 1.00 | 38.19 | L | N |
| ATOM | 3151 | CA | LEU | 11 | 113.867 | -11.709 | 7.484 | 1.00 | 38.19 | L | C |
| ATOM | 3152 | CB | LEU | 11 | 115.020 | -10.880 | 6.894 | 1.00 | 33.64 | L | C |
| ATOM | 3153 | CG | LEU | 11 | 115.721 | -9.849 | 7.793 | 1.00 | 33.64 | L | C |
| ATOM | 3154 | CD1 | LEU | 11 | 116.757 | -10.532 | 8.667 | 1.00 | 33.64 | L | C |
| ATOM | 3155 | CD2 | LEU | 11 | 116.401 | -8.807 | 6.927 | 1.00 | 33.64 | L | C |
| ATOM | 3156 | C | LEU | 11 | 114.319 | -12.335 | 8.792 | 1.00 | 38.19 | L | C |
| ATOM | 3157 | O | LEU | 11 | 114.365 | -11.672 | 9.829 | 1.00 | 38.19 | L | O |
| ATOM | 3158 | N | SER | 12 | 114.661 | -13.616 | 8.736 | 1.00 | 42.98 | L | N |
| ATOM | 3159 | CA | SER | 12 | 115.128 | -14.320 | 9.916 | 1.00 | 42.98 | L | C |
| ATOM | 3160 | CB | SER | 12 | 114.334 | -15.612 | 10.103 | 1.00 | 67.78 | L | C |
| ATOM | 3161 | OG | SER | 12 | 114.474 | -16.092 | 11.426 | 1.00 | 67.78 | L | O |
| ATOM | 3162 | C | SER | 12 | 116.611 | -14.628 | 9.738 | 1.00 | 42.98 | L | C |
| ATOM | 3163 | O | SER | 12 | 117.031 | -15.118 | 8.697 | 1.00 | 42.98 | L | O |
| ATOM | 3164 | N | ALA | 13 | 117.407 | -14.320 | 10.749 | 1.00 | 25.03 | L | N |
| ATOM | 3165 | CA | ALA | 13 | 118.836 | -14.575 | 10.667 | 1.00 | 25.03 | L | C |
| ATOM | 3166 | CB | ALA | 13 | 119.556 | -13.340 | 10.124 | 1.00 | 41.64 | L | C |
| ATOM | 3167 | C | ALA | 13 | 119.390 | -14.952 | 12.037 | 1.00 | 25.03 | L | C |
| ATOM | 3168 | O | ALA | 13 | 118.829 | -14.571 | 13.067 | 1.00 | 25.03 | L | O |
| ATOM | 3169 | N | SER | 14 | 120.493 | -15.701 | 12.045 | 1.00 | 32.48 | L | N |
| ATOM | 3170 | CA | SER | 14 | 121.111 | -16.132 | 13.294 | 1.00 | 32.48 | L | C |
| ATOM | 3171 | CB | SER | 14 | 121.594 | -17.569 | 13.160 | 1.00 | 77.12 | L | C |
| ATOM | 3172 | OG | SER | 14 | 122.348 | -17.721 | 11.975 | 1.00 | 77.12 | L | O |
| ATOM | 3173 | C | SER | 14 | 122.269 | -15.231 | 13.691 | 1.00 | 32.48 | L | C |
| ATOM | 3174 | O | SER | 14 | 122.893 | -14.595 | 12.841 | 1.00 | 32.48 | L | O |
| ATOM | 3175 | N | VAL | 15 | 122.545 | -15.166 | 14.988 | 1.00 | 47.29 | L | N |
| ATOM | 3176 | CA | VAL | 15 | 123.637 | -14.336 | 15.470 | 1.00 | 47.29 | L | C |
| ATOM | 3177 | CB | VAL | 15 | 123.996 | -14.657 | 16.937 | 1.00 | 53.16 | L | C |
| ATOM | 3178 | CG1 | VAL | 15 | 123.121 | -13.847 | 17.881 | 1.00 | 53.16 | L | C |
| ATOM | 3179 | CG2 | VAL | 15 | 123.808 | -16.148 | 17.198 | 1.00 | 53.16 | L | C |
| ATOM | 3180 | C | VAL | 15 | 124.858 | -14.575 | 14.606 | 1.00 | 47.29 | L | C |
| ATOM | 3181 | O | VAL | 15 | 125.164 | -15.712 | 14.250 | 1.00 | 47.29 | L | O |
| ATOM | 3182 | N | GLY | 16 | 125.537 | -13.495 | 14.247 | 1.00 | 32.44 | L | N |
| ATOM | 3183 | CA | GLY | 16 | 126.728 | -13.615 | 13.431 | 1.00 | 32.44 | L | C |
| ATOM | 3184 | C | GLY | 16 | 126.506 | -13.463 | 11.945 | 1.00 | 32.44 | L | C |
| ATOM | 3185 | O | GLY | 16 | 127.467 | -13.306 | 11.191 | 1.00 | 32.44 | L | O |
| ATOM | 3186 | N | ASP | 17 | 125.255 | -13.524 | 11.510 | 1.00 | 32.03 | L | N |
| ATOM | 3187 | CA | ASP | 17 | 124.959 | -13.367 | 10.092 | 1.00 | 32.03 | L | C |
| ATOM | 3188 | CB | ASP | 17 | 123.533 | -13.814 | 9.788 | 1.00 | 55.01 | L | C |
| ATOM | 3189 | CG | ASP | 17 | 123.344 | -15.291 | 9.961 | 1.00 | 55.01 | L | C |
| ATOM | 3190 | OD1 | ASP | 17 | 122.211 | -15.771 | 9.739 | 1.00 | 55.01 | L | O |
| ATOM | 3191 | OD2 | ASP | 17 | 124.331 | -15.965 | 10.320 | 1.00 | 55.01 | L | O |
| ATOM | 3192 | C | ASP | 17 | 125.109 | -11.905 | 9.677 | 1.00 | 32.03 | L | C |
| ATOM | 3193 | O | ASP | 17 | 125.041 | -10.997 | 10.517 | 1.00 | 32.03 | L | O |
| ATOM | 3194 | N | ARG | 18 | 125.324 | -11.680 | 8.385 | 1.00 | 40.86 | L | N |
| ATOM | 3195 | CA | ARG | 18 | 125.447 | -10.325 | 7.875 | 1.00 | 40.86 | L | C |
| ATOM | 3196 | CB | ARG | 18 | 126.587 | -10.231 | 6.865 | 1.00 | 78.37 | L | C |
| ATOM | 3197 | CG | ARG | 18 | 126.790 | -8.842 | 6.293 | 1.00 | 78.37 | L | C |
| ATOM | 3198 | CD | ARG | 18 | 128.223 | -8.662 | 5.812 | 1.00 | 78.37 | L | C |
| ATOM | 3199 | NE | ARG | 18 | 128.413 | -7.408 | 5.087 | 1.00 | 78.37 | L | N |
| ATOM | 3200 | CZ | ARG | 18 | 127.841 | -7.131 | 3.918 | 1.00 | 78.37 | L | C |
| ATOM | 3201 | NH1 | ARG | 18 | 127.042 | -8.021 | 3.336 | 1.00 | 78.37 | L | N |
| ATOM | 3202 | NH2 | ARG | 18 | 128.064 | -5.960 | 3.334 | 1.00 | 78.37 | L | N |
| ATOM | 3203 | C | ARG | 18 | 124.116 | -9.986 | 7.220 | 1.00 | 40.86 | L | C |
| ATOM | 3204 | O | ARG | 18 | 123.690 | -10.656 | 6.284 | 1.00 | 40.86 | L | O |
| ATOM | 3205 | N | VAL | 19 | 123.455 | -8.948 | 7.721 | 1.00 | 26.42 | L | N |
| ATOM | 3206 | CA | VAL | 19 | 122.157 | -8.549 | 7.193 | 1.00 | 26.42 | L | C |
| ATOM | 3207 | CB | VAL | 19 | 121.154 | -8.426 | 8.335 | 1.00 | 32.94 | L | C |
| ATOM | 3208 | CG1 | VAL | 19 | 119.768 | -8.214 | 7.783 | 1.00 | 32.94 | L | C |
| ATOM | 3209 | CG2 | VAL | 19 | 121.204 | -9.678 | 9.194 | 1.00 | 32.94 | L | C |
| ATOM | 3210 | C | VAL | 19 | 122.200 | -7.235 | 6.420 | 1.00 | 26.42 | L | C |
| ATOM | 3211 | O | VAL | 19 | 122.902 | -6.306 | 6.798 | 1.00 | 26.42 | L | O |
| ATOM | 3212 | N | THR | 20 | 121.443 | -7.160 | 5.333 | 1.00 | 42.24 | L | N |

Fig. 19: A-45

```
ATOM   3213  CA  THR 20    121.408  -5.950   4.519  1.00  42.24  L  C
ATOM   3214  CB  THR 20    122.310  -6.097   3.289  1.00  29.90  L  C
ATOM   3215  OG1 THR 20    123.660  -6.127   3.714  1.00  29.90  L  O
ATOM   3216  CG2 THR 20    122.099  -4.944   2.326  1.00  29.90  L  C
ATOM   3217  C   THR 20    120.008  -5.582   4.050  1.00  42.24  L  C
ATOM   3218  O   THR 20    119.477  -6.202   3.127  1.00  42.24  L  O
ATOM   3219  N   ILE 21    119.418  -4.568   4.683  1.00  13.95  L  N
ATOM   3220  CA  ILE 21    118.077  -4.114   4.326  1.00  13.95  L  C
ATOM   3221  CB  ILE 21    117.349  -3.486   5.541  1.00  24.11  L  C
ATOM   3222  CG2 ILE 21    115.892  -3.176   5.186  1.00  24.11  L  C
ATOM   3223  CG1 ILE 21    117.390  -4.457   6.720  1.00  24.11  L  C
ATOM   3224  CD1 ILE 21    116.709  -3.936   7.960  1.00  24.11  L  C
ATOM   3225  C   ILE 21    118.180  -3.081   3.217  1.00  13.95  L  C
ATOM   3226  O   ILE 21    119.036  -2.208   3.251  1.00  13.95  L  O
ATOM   3227  N   THR 22    117.305  -3.190   2.230  1.00  27.07  L  N
ATOM   3228  CA  THR 22    117.304  -2.266   1.107  1.00  27.07  L  C
ATOM   3229  CB  THR 22    117.335  -3.022  -0.239  1.00  29.03  L  C
ATOM   3230  OG1 THR 22    118.613  -3.642  -0.404  1.00  29.03  L  O
ATOM   3231  CG2 THR 22    117.084  -2.084  -1.391  1.00  29.03  L  C
ATOM   3232  C   THR 22    116.067  -1.385   1.123  1.00  27.07  L  C
ATOM   3233  O   THR 22    114.951  -1.871   1.313  1.00  27.07  L  O
ATOM   3234  N   CYS 23    116.281  -0.089   0.916  1.00  32.83  L  N
ATOM   3235  CA  CYS 23    115.203   0.896   0.882  1.00  32.83  L  C
ATOM   3236  C   CYS 23    115.259   1.546  -0.489  1.00  32.83  L  C
ATOM   3237  O   CYS 23    116.250   2.187  -0.837  1.00  32.83  L  O
ATOM   3238  CB  CYS 23    115.424   1.947   1.973  1.00  18.66  L  C
ATOM   3239  SG  CYS 23    114.216   3.310   2.141  1.00  18.66  L  S
ATOM   3240  N   SER 24    114.199   1.355  -1.268  1.00  11.34  L  N
ATOM   3241  CA  SER 24    114.110   1.924  -2.612  1.00  11.34  L  C
ATOM   3242  CB  SER 24    113.696   0.853  -3.614  1.00  28.67  L  C
ATOM   3243  OG  SER 24    114.642  -0.190  -3.632  1.00  28.67  L  O
ATOM   3244  C   SER 24    113.096   3.058  -2.641  1.00  11.34  L  C
ATOM   3245  O   SER 24    111.971   2.910  -2.154  1.00  11.34  L  O
ATOM   3246  N   ALA 25    113.496   4.186  -3.217  1.00  32.05  L  N
ATOM   3247  CA  ALA 25    112.617   5.343  -3.286  1.00  32.05  L  C
ATOM   3248  CB  ALA 25    113.312   6.567  -2.707  1.00  44.86  L  C
ATOM   3249  C   ALA 25    112.139   5.633  -4.699  1.00  32.05  L  C
ATOM   3250  O   ALA 25    112.918   5.619  -5.658  1.00  32.05  L  O
ATOM   3251  N   SER 26    110.839   5.901  -4.803  1.00  26.80  L  N
ATOM   3252  CA  SER 26    110.179   6.204  -6.070  1.00  26.80  L  C
ATOM   3253  CB  SER 26    108.717   6.572  -5.814  1.00  23.33  L  C
ATOM   3254  OG  SER 26    108.617   7.713  -4.984  1.00  23.33  L  O
ATOM   3255  C   SER 26    110.866   7.338  -6.813  1.00  26.80  L  C
ATOM   3256  O   SER 26    110.814   7.404  -8.032  1.00  26.80  L  O
ATOM   3257  N   SER 27    111.496   8.234  -6.066  1.00  22.71  L  N
ATOM   3258  CA  SER 27    112.210   9.363  -6.644  1.00  22.71  L  C
ATOM   3259  CB  SER 27    111.439  10.661  -6.406  1.00  47.74  L  C
ATOM   3260  OG  SER 27    110.105  10.552  -6.862  1.00  47.74  L  O
ATOM   3261  C   SER 27    113.547   9.438  -5.934  1.00  22.71  L  C
ATOM   3262  O   SER 27    113.666   8.982  -4.805  1.00  22.71  L  O
ATOM   3263  N   SER 28    114.555  10.004  -6.586  1.00  37.73  L  N
ATOM   3264  CA  SER 28    115.874  10.121  -5.972  1.00  37.73  L  C
ATOM   3265  CB  SER 28    116.890  10.583  -7.010  1.00  36.75  L  C
ATOM   3266  OG  SER 28    116.486  11.818  -7.573  1.00  36.75  L  O
ATOM   3267  C   SER 28    115.846  11.106  -4.804  1.00  37.73  L  C
ATOM   3268  O   SER 28    115.043  12.038  -4.775  1.00  37.73  L  O
ATOM   3269  N   VAL 29    116.726  10.890  -3.838  1.00  35.34  L  N
ATOM   3270  CA  VAL 29    116.807  11.753  -2.669  1.00  35.34  L  C
ATOM   3271  CB  VAL 29    116.002  11.154  -1.484  1.00  39.96  L  C
ATOM   3272  CG1 VAL 29    114.521  11.097  -1.842  1.00  39.96  L  C
ATOM   3273  CG2 VAL 29    116.506   9.755  -1.147  1.00  39.96  L  C
ATOM   3274  C   VAL 29    118.277  11.895  -2.289  1.00  35.34  L  C
ATOM   3275  O   VAL 29    119.076  11.001  -2.571  1.00  35.34  L  O
ATOM   3276  N   ASN 30    118.641  13.007  -1.658  1.00  55.44  L  N
ATOM   3277  CA  ASN 30    120.033  13.236  -1.278  1.00  55.44  L  C
ATOM   3278  CB  ASN 30    120.252  14.722  -0.974  1.00  66.75  L  C
ATOM   3279  CG  ASN 30    119.176  15.292  -0.071  1.00  66.75  L  C
ATOM   3280  OD1 ASN 30    118.006  15.359  -0.453  1.00  66.75  L  O
ATOM   3281  ND2 ASN 30    119.561  15.694   1.138  1.00  66.75  L  N
ATOM   3282  C   ASN 30    120.510  12.386  -0.095  1.00  55.44  L  C
ATOM   3283  O   ASN 30    121.705  12.099   0.033  1.00  55.44  L  O
ATOM   3284  N   HIS 31    119.586  11.985   0.770  1.00  34.66  L  N
ATOM   3285  CA  HIS 31    119.947  11.172   1.923  1.00  34.66  L  C
```

Fig. 19: A-46

```
ATOM   3286  CB  HIS  31    120.290  12.049   3.132  1.00  51.96  L  C
ATOM   3287  CG  HIS  31    121.623  12.725   3.042  1.00  51.96  L  C
ATOM   3288  CD2 HIS  31    122.763  12.534   3.744  1.00  51.96  L  C
ATOM   3289  ND1 HIS  31    121.879  13.763   2.172  1.00  51.96  L  N
ATOM   3290  CE1 HIS  31    123.118  14.186   2.345  1.00  51.96  L  C
ATOM   3291  NE2 HIS  31    123.676  13.457   3.294  1.00  51.96  L  N
ATOM   3292  C   HIS  31    118.811  10.241   2.316  1.00  34.66  L  C
ATOM   3293  O   HIS  31    117.736  10.267   1.707  1.00  34.66  L  O
ATOM   3294  N   MET  32    119.070   9.415   3.332  1.00  24.85  L  N
ATOM   3295  CA  MET  32    118.081   8.489   3.864  1.00  24.85  L  C
ATOM   3296  CB  MET  32    118.189   7.126   3.187  1.00  22.87  L  C
ATOM   3297  CG  MET  32    116.961   6.226   3.394  1.00  22.87  L  C
ATOM   3298  SD  MET  32    115.381   6.922   2.757  1.00  22.87  L  S
ATOM   3299  CE  MET  32    115.727   7.028   1.012  1.00  22.87  L  C
ATOM   3300  C   MET  32    118.316   8.340   5.360  1.00  24.85  L  C
ATOM   3301  O   MET  32    119.454   8.377   5.831  1.00  24.85  L  O
ATOM   3302  N   PHE  33    117.244   8.180   6.118  1.00   7.47  L  N
ATOM   3303  CA  PHE  33    117.391   8.029   7.554  1.00   7.47  L  C
ATOM   3304  CB  PHE  33    116.693   9.171   8.285  1.00  11.22  L  C
ATOM   3305  CG  PHE  33    117.205  10.533   7.901  1.00  11.22  L  C
ATOM   3306  CD1 PHE  33    116.901  11.078   6.652  1.00  11.22  L  C
ATOM   3307  CD2 PHE  33    118.017  11.259   8.776  1.00  11.22  L  C
ATOM   3308  CE1 PHE  33    117.399  12.325   6.275  1.00  11.22  L  C
ATOM   3309  CE2 PHE  33    118.519  12.501   8.407  1.00  11.22  L  C
ATOM   3310  CZ  PHE  33    118.207  13.035   7.149  1.00  11.22  L  C
ATOM   3311  C   PHE  33    116.817   6.702   7.994  1.00   7.47  L  C
ATOM   3312  O   PHE  33    115.959   6.150   7.320  1.00   7.47  L  O
ATOM   3313  N   TRP  34    117.301   6.186   9.118  1.00  15.67  L  N
ATOM   3314  CA  TRP  34    116.815   4.912   9.618  1.00  15.67  L  C
ATOM   3315  CB  TRP  34    117.859   3.818   9.414  1.00  16.49  L  C
ATOM   3316  CG  TRP  34    118.217   3.590   7.992  1.00  16.49  L  C
ATOM   3317  CD2 TRP  34    117.671   2.592   7.123  1.00  16.49  L  C
ATOM   3318  CE2 TRP  34    118.315   2.732   5.872  1.00  16.49  L  C
ATOM   3319  CE3 TRP  34    116.702   1.596   7.279  1.00  16.49  L  C
ATOM   3320  CD1 TRP  34    119.137   4.278   7.259  1.00  16.49  L  C
ATOM   3321  NE1 TRP  34    119.205   3.767   5.984  1.00  16.49  L  N
ATOM   3322  CZ2 TRP  34    118.024   1.914   4.782  1.00  16.49  L  C
ATOM   3323  CZ3 TRP  34    116.409   0.780   6.194  1.00  16.49  L  C
ATOM   3324  CH2 TRP  34    117.069   0.945   4.960  1.00  16.49  L  C
ATOM   3325  C   TRP  34    116.459   4.960  11.086  1.00  15.67  L  C
ATOM   3326  O   TRP  34    117.149   5.593  11.882  1.00  15.67  L  O
ATOM   3327  N   TYR  35    115.370   4.288  11.437  1.00  19.71  L  N
ATOM   3328  CA  TYR  35    114.939   4.229  12.820  1.00  19.71  L  C
ATOM   3329  CB  TYR  35    113.591   4.922  13.007  1.00  25.75  L  C
ATOM   3330  CG  TYR  35    113.623   6.381  12.621  1.00  25.75  L  C
ATOM   3331  CD1 TYR  35    113.255   6.790  11.344  1.00  25.75  L  C
ATOM   3332  CE1 TYR  35    113.310   8.124  10.980  1.00  25.75  L  C
ATOM   3333  CD2 TYR  35    114.052   7.353  13.527  1.00  25.75  L  C
ATOM   3334  CE2 TYR  35    114.110   8.685  13.173  1.00  25.75  L  C
ATOM   3335  CZ  TYR  35    113.737   9.064  11.899  1.00  25.75  L  C
ATOM   3336  OH  TYR  35    113.776  10.384  11.540  1.00  25.75  L  O
ATOM   3337  C   TYR  35    114.821   2.781  13.207  1.00  19.71  L  C
ATOM   3338  O   TYR  35    114.508   1.937  12.373  1.00  19.71  L  O
ATOM   3339  N   GLN  36    115.100   2.491  14.468  1.00  30.18  L  N
ATOM   3340  CA  GLN  36    114.987   1.136  14.964  1.00  30.18  L  C
ATOM   3341  CB  GLN  36    116.292   0.659  15.597  1.00  33.56  L  C
ATOM   3342  CG  GLN  36    116.109  -0.625  16.387  1.00  33.56  L  C
ATOM   3343  CD  GLN  36    117.154  -0.806  17.464  1.00  33.56  L  C
ATOM   3344  OE1 GLN  36    118.296  -1.161  17.179  1.00  33.56  L  O
ATOM   3345  NE2 GLN  36    116.770  -0.550  18.716  1.00  33.56  L  N
ATOM   3346  C   GLN  36    113.902   1.124  16.017  1.00  30.18  L  C
ATOM   3347  O   GLN  36    113.986   1.852  17.008  1.00  30.18  L  O
ATOM   3348  N   GLN  37    112.877   0.311  15.803  1.00  31.84  L  N
ATOM   3349  CA  GLN  37    111.811   0.209  16.778  1.00  31.84  L  C
ATOM   3350  CB  GLN  37    110.467   0.599  16.162  1.00  26.28  L  C
ATOM   3351  CG  GLN  37    109.335   0.494  17.165  1.00  26.28  L  C
ATOM   3352  CD  GLN  37    108.003   0.979  16.632  1.00  26.28  L  C
ATOM   3353  OE1 GLN  37    107.573   0.597  15.537  1.00  26.28  L  O
ATOM   3354  NE2 GLN  37    107.328   1.819  17.417  1.00  26.28  L  N
ATOM   3355  C   GLN  37    111.729  -1.201  17.360  1.00  31.84  L  C
ATOM   3356  O   GLN  37    111.571  -2.189  16.637  1.00  31.84  L  O
ATOM   3357  N   LYS  38    111.861  -1.285  18.676  1.00  33.78  L  N
ATOM   3358  CA  LYS  38    111.776  -2.561  19.366  1.00  33.78  L  C
```

Fig. 19: A-47

```
ATOM   3359  CB  LYS  38    112.784   -2.618  20.519  1.00  38.31  L  C
ATOM   3360  CG  LYS  38    114.209   -2.306  20.094  1.00  38.31  L  C
ATOM   3361  CD  LYS  38    115.224   -2.552  21.207  1.00  38.31  L  C
ATOM   3362  CE  LYS  38    115.494   -4.034  21.402  1.00  38.31  L  C
ATOM   3363  NZ  LYS  38    115.954   -4.720  20.154  1.00  38.31  L  N
ATOM   3364  C   LYS  38    110.346   -2.671  19.889  1.00  33.78  L  C
ATOM   3365  O   LYS  38    109.770   -1.690  20.354  1.00  33.78  L  O
ATOM   3366  N   PRO  39    109.757   -3.873  19.818  1.00  36.51  L  N
ATOM   3367  CD  PRO  39    110.419   -5.128  19.422  1.00  56.09  L  C
ATOM   3368  CA  PRO  39    108.389   -4.139  20.271  1.00  36.51  L  C
ATOM   3369  CB  PRO  39    108.376   -5.652  20.409  1.00  56.09  L  C
ATOM   3370  CG  PRO  39    109.254   -6.072  19.283  1.00  56.09  L  C
ATOM   3371  C   PRO  39    107.976   -3.434  21.559  1.00  36.51  L  C
ATOM   3372  O   PRO  39    108.664   -3.523  22.573  1.00  36.51  L  O
ATOM   3373  N   GLY  40    106.846   -2.735  21.503  1.00  29.94  L  N
ATOM   3374  CA  GLY  40    106.330   -2.036  22.667  1.00  29.94  L  C
ATOM   3375  C   GLY  40    107.025   -0.738  23.034  1.00  29.94  L  C
ATOM   3376  O   GLY  40    106.669   -0.119  24.037  1.00  29.94  L  O
ATOM   3377  N   LYS  41    108.019   -0.332  22.243  1.00  32.57  L  N
ATOM   3378  CA  LYS  41    108.754    0.903  22.503  1.00  32.57  L  C
ATOM   3379  CB  LYS  41    110.231    0.611  22.804  1.00  82.45  L  C
ATOM   3380  CG  LYS  41    110.466   -0.251  24.040  1.00  82.45  L  C
ATOM   3381  CD  LYS  41    111.905   -0.157  24.579  1.00  82.45  L  C
ATOM   3382  CE  LYS  41    112.977   -0.603  23.575  1.00  82.45  L  C
ATOM   3383  NZ  LYS  41    113.257    0.396  22.496  1.00  82.45  L  N
ATOM   3384  C   LYS  41    108.656    1.860  21.319  1.00  32.57  L  C
ATOM   3385  O   LYS  41    108.243    1.480  20.227  1.00  32.57  L  O
ATOM   3386  N   ALA  42    109.029    3.112  21.547  1.00  30.66  L  N
ATOM   3387  CA  ALA  42    108.990    4.126  20.502  1.00  30.66  L  C
ATOM   3388  CB  ALA  42    108.980    5.513  21.129  1.00  32.87  L  C
ATOM   3389  C   ALA  42    110.209    3.973  19.606  1.00  30.66  L  C
ATOM   3390  O   ALA  42    111.235    3.436  20.028  1.00  30.66  L  O
ATOM   3391  N   PRO  43    110.112    4.435  18.351  1.00  23.79  L  N
ATOM   3392  CD  PRO  43    108.939    4.976  17.647  1.00   7.10  L  C
ATOM   3393  CA  PRO  43    111.248    4.323  17.440  1.00  23.79  L  C
ATOM   3394  CB  PRO  43    110.727    4.980  16.170  1.00   7.10  L  C
ATOM   3395  CG  PRO  43    109.275    4.677  16.212  1.00   7.10  L  C
ATOM   3396  C   PRO  43    112.476    5.042  18.007  1.00  23.79  L  C
ATOM   3397  O   PRO  43    112.359    5.903  18.877  1.00  23.79  L  O
ATOM   3398  N   LYS  44    113.652    4.678  17.514  1.00  26.42  L  N
ATOM   3399  CA  LYS  44    114.888    5.283  17.972  1.00  26.42  L  C
ATOM   3400  CB  LYS  44    115.656    4.289  18.843  1.00  45.11  L  C
ATOM   3401  CG  LYS  44    115.840    4.724  20.288  1.00  45.11  L  C
ATOM   3402  CD  LYS  44    116.535    3.651  21.131  1.00  45.11  L  C
ATOM   3403  CE  LYS  44    115.656    2.400  21.338  1.00  45.11  L  C
ATOM   3404  NZ  LYS  44    115.359    1.613  20.087  1.00  45.11  L  N
ATOM   3405  C   LYS  44    115.741    5.673  16.767  1.00  26.42  L  C
ATOM   3406  O   LYS  44    115.898    4.888  15.829  1.00  26.42  L  O
ATOM   3407  N   PRO  45    116.287    6.902  16.764  1.00  19.50  L  N
ATOM   3408  CD  PRO  45    116.146    7.943  17.794  1.00   7.61  L  C
ATOM   3409  CA  PRO  45    117.132    7.362  15.649  1.00  19.50  L  C
ATOM   3410  CB  PRO  45    117.638    8.720  16.120  1.00   7.61  L  C
ATOM   3411  CG  PRO  45    116.547    9.180  17.041  1.00   7.61  L  C
ATOM   3412  C   PRO  45    118.273    6.367  15.542  1.00  19.50  L  C
ATOM   3413  O   PRO  45    118.925    6.082  16.549  1.00  19.50  L  O
ATOM   3414  N   TRP  46    118.521    5.848  14.342  1.00  23.41  L  N
ATOM   3415  CA  TRP  46    119.581    4.861  14.158  1.00  23.41  L  C
ATOM   3416  CB  TRP  46    118.980    3.559  13.643  1.00  20.77  L  C
ATOM   3417  CG  TRP  46    119.662    2.382  14.178  1.00  20.77  L  C
ATOM   3418  CD2 TRP  46    119.738    2.007  15.554  1.00  20.77  L  C
ATOM   3419  CE2 TRP  46    120.509    0.829  15.624  1.00  20.77  L  C
ATOM   3420  CE3 TRP  46    119.229    2.554  16.737  1.00  20.77  L  C
ATOM   3421  CD1 TRP  46    120.365    1.446  13.481  1.00  20.77  L  C
ATOM   3422  NE1 TRP  46    120.879    0.504  14.345  1.00  20.77  L  N
ATOM   3423  CZ2 TRP  46    120.786    0.191  16.834  1.00  20.77  L  C
ATOM   3424  CZ3 TRP  46    119.505    1.918  17.938  1.00  20.77  L  C
ATOM   3425  CH2 TRP  46    120.276    0.750  17.977  1.00  20.77  L  C
ATOM   3426  C   TRP  46    120.691    5.302  13.209  1.00  23.41  L  C
ATOM   3427  O   TRP  46    121.871    5.174  13.507  1.00  23.41  L  O
ATOM   3428  N   ILE  47    120.306    5.806  12.048  1.00  21.62  L  N
ATOM   3429  CA  ILE  47    121.275    6.248  11.073  1.00  21.62  L  C
ATOM   3430  CB  ILE  47    121.515    5.160  10.008  1.00  12.16  L  C
ATOM   3431  CG2 ILE  47    122.473    5.668   8.929  1.00  12.16  L  C
```

Fig. 19: A-48

| | | | | | | | | | | |
|---|---|---|---|---|---|---|---|---|---|---|
| ATOM | 3432 | CG1 | ILE | 47 | 122.067 | 3.902 | 10.670 | 1.00 | 12.16 | L C |
| ATOM | 3433 | CD1 | ILE | 47 | 122.301 | 2.746 | 9.686 | 1.00 | 12.16 | L C |
| ATOM | 3434 | C | ILE | 47 | 120.694 | 7.482 | 10.408 | 1.00 | 21.62 | L C |
| ATOM | 3435 | O | ILE | 47 | 119.600 | 7.424 | 9.840 | 1.00 | 21.62 | L O |
| ATOM | 3436 | N | TYR | 48 | 121.408 | 8.603 | 10.510 | 1.00 | 27.63 | L N |
| ATOM | 3437 | CA | TYR | 48 | 120.961 | 9.842 | 9.887 | 1.00 | 27.63 | L C |
| ATOM | 3438 | CB | TYR | 48 | 120.899 | 10.992 | 10.892 | 1.00 | 47.89 | L C |
| ATOM | 3439 | CG | TYR | 48 | 122.206 | 11.318 | 11.564 | 1.00 | 47.89 | L C |
| ATOM | 3440 | CD1 | TYR | 48 | 122.762 | 10.454 | 12.502 | 1.00 | 47.89 | L C |
| ATOM | 3441 | CE1 | TYR | 48 | 123.961 | 10.766 | 13.143 | 1.00 | 47.89 | L C |
| ATOM | 3442 | CD2 | TYR | 48 | 122.881 | 12.503 | 11.277 | 1.00 | 47.89 | L C |
| ATOM | 3443 | CE2 | TYR | 48 | 124.078 | 12.827 | 11.907 | 1.00 | 47.89 | L C |
| ATOM | 3444 | CZ | TYR | 48 | 124.617 | 11.957 | 12.843 | 1.00 | 47.89 | L C |
| ATOM | 3445 | OH | TYR | 48 | 125.803 | 12.269 | 13.483 | 1.00 | 47.89 | L O |
| ATOM | 3446 | C | TYR | 48 | 121.922 | 10.181 | 8.766 | 1.00 | 27.63 | L C |
| ATOM | 3447 | O | TYR | 48 | 122.992 | 9.575 | 8.646 | 1.00 | 27.63 | L O |
| ATOM | 3448 | N | LEU | 49 | 121.535 | 11.150 | 7.948 | 1.00 | 28.95 | L N |
| ATOM | 3449 | CA | LEU | 49 | 122.344 | 11.550 | 6.811 | 1.00 | 28.95 | L C |
| ATOM | 3450 | CB | LEU | 49 | 123.421 | 12.568 | 7.232 | 1.00 | 11.18 | L C |
| ATOM | 3451 | CG | LEU | 49 | 123.051 | 14.040 | 7.473 | 1.00 | 11.18 | L C |
| ATOM | 3452 | CD1 | LEU | 49 | 122.174 | 14.552 | 6.344 | 1.00 | 11.18 | L C |
| ATOM | 3453 | CD2 | LEU | 49 | 122.333 | 14.178 | 8.780 | 1.00 | 11.18 | L C |
| ATOM | 3454 | C | LEU | 49 | 122.997 | 10.350 | 6.117 | 1.00 | 28.95 | L C |
| ATOM | 3455 | O | LEU | 49 | 124.204 | 10.323 | 5.920 | 1.00 | 28.95 | L O |
| ATOM | 3456 | N | THR | 50 | 122.192 | 9.351 | 5.777 | 1.00 | 29.56 | L N |
| ATOM | 3457 | CA | THR | 50 | 122.666 | 8.165 | 5.072 | 1.00 | 29.56 | L C |
| ATOM | 3458 | CB | THR | 50 | 123.352 | 8.566 | 3.770 | 1.00 | 23.05 | L C |
| ATOM | 3459 | OG1 | THR | 50 | 122.490 | 9.434 | 3.040 | 1.00 | 23.05 | L O |
| ATOM | 3460 | CG2 | THR | 50 | 123.647 | 7.335 | 2.923 | 1.00 | 23.05 | L C |
| ATOM | 3461 | C | THR | 50 | 123.582 | 7.152 | 5.767 | 1.00 | 29.56 | L C |
| ATOM | 3462 | O | THR | 50 | 123.229 | 5.976 | 5.888 | 1.00 | 29.56 | L O |
| ATOM | 3463 | N | SER | 51 | 124.757 | 7.586 | 6.203 | 1.00 | 25.90 | L N |
| ATOM | 3464 | CA | SER | 51 | 125.697 | 6.670 | 6.839 | 1.00 | 25.90 | L C |
| ATOM | 3465 | CB | SER | 51 | 126.976 | 6.594 | 6.003 | 1.00 | 41.07 | L C |
| ATOM | 3466 | OG | SER | 51 | 127.467 | 7.893 | 5.715 | 1.00 | 41.07 | L O |
| ATOM | 3467 | C | SER | 51 | 126.049 | 6.998 | 8.287 | 1.00 | 25.90 | L C |
| ATOM | 3468 | O | SER | 51 | 126.578 | 6.160 | 9.015 | 1.00 | 25.90 | L O |
| ATOM | 3469 | N | ASN | 52 | 125.749 | 8.211 | 8.712 | 1.00 | 36.32 | L N |
| ATOM | 3470 | CA | ASN | 52 | 126.050 | 8.615 | 10.075 | 1.00 | 36.32 | L C |
| ATOM | 3471 | CB | ASN | 52 | 125.741 | 10.092 | 10.247 | 1.00 | 35.00 | L C |
| ATOM | 3472 | CG | ASN | 52 | 126.708 | 10.954 | 9.499 | 1.00 | 35.00 | L C |
| ATOM | 3473 | OD1 | ASN | 52 | 127.881 | 11.022 | 9.857 | 1.00 | 35.00 | L O |
| ATOM | 3474 | ND2 | ASN | 52 | 126.236 | 11.608 | 8.439 | 1.00 | 35.00 | L N |
| ATOM | 3475 | C | ASN | 52 | 125.288 | 7.815 | 11.109 | 1.00 | 36.32 | L C |
| ATOM | 3476 | O | ASN | 52 | 124.059 | 7.766 | 11.078 | 1.00 | 36.32 | L O |
| ATOM | 3477 | N | LEU | 53 | 126.018 | 7.190 | 12.027 | 1.00 | 27.25 | L N |
| ATOM | 3478 | CA | LEU | 53 | 125.387 | 6.408 | 13.080 | 1.00 | 27.25 | L C |
| ATOM | 3479 | CB | LEU | 53 | 126.355 | 5.366 | 13.631 | 1.00 | 36.82 | L C |
| ATOM | 3480 | CG | LEU | 53 | 126.949 | 4.324 | 12.682 | 1.00 | 36.82 | L C |
| ATOM | 3481 | CD1 | LEU | 53 | 127.640 | 3.266 | 13.531 | 1.00 | 36.82 | L C |
| ATOM | 3482 | CD2 | LEU | 53 | 125.876 | 3.674 | 11.822 | 1.00 | 36.82 | L C |
| ATOM | 3483 | C | LEU | 53 | 124.938 | 7.312 | 14.219 | 1.00 | 27.25 | L C |
| ATOM | 3484 | O | LEU | 53 | 125.643 | 8.341 | 14.581 | 1.00 | 27.25 | L O |
| ATOM | 3485 | N | ALA | 54 | 123.763 | 7.043 | 14.779 | 1.00 | 46.43 | L N |
| ATOM | 3486 | CA | ALA | 54 | 123.251 | 7.827 | 15.897 | 1.00 | 46.43 | L C |
| ATOM | 3487 | CB | ALA | 54 | 121.938 | 7.272 | 16.373 | 1.00 | 9.56 | L C |
| ATOM | 3488 | C | ALA | 54 | 124.267 | 7.728 | 17.008 | 1.00 | 46.43 | L C |
| ATOM | 3489 | O | ALA | 54 | 125.380 | 7.254 | 16.794 | 1.00 | 46.43 | L O |
| ATOM | 3490 | N | SER | 55 | 123.891 | 8.140 | 18.208 | 1.00 | 82.41 | L N |
| ATOM | 3491 | CA | SER | 55 | 124.847 | 8.081 | 19.290 | 1.00 | 82.41 | L C |
| ATOM | 3492 | CB | SER | 55 | 124.439 | 9.036 | 20.406 | 1.00 | 85.12 | L C |
| ATOM | 3493 | OG | SER | 55 | 125.561 | 9.342 | 21.215 | 1.00 | 85.12 | L O |
| ATOM | 3494 | C | SER | 55 | 125.049 | 6.675 | 19.850 | 1.00 | 82.41 | L C |
| ATOM | 3495 | O | SER | 55 | 126.187 | 6.226 | 20.004 | 1.00 | 82.41 | L O |
| ATOM | 3496 | N | GLY | 56 | 123.957 | 5.970 | 20.137 | 1.00 | 57.94 | L N |
| ATOM | 3497 | CA | GLY | 56 | 124.074 | 4.632 | 20.701 | 1.00 | 57.94 | L C |
| ATOM | 3498 | C | GLY | 56 | 124.408 | 3.486 | 19.758 | 1.00 | 57.94 | L C |
| ATOM | 3499 | O | GLY | 56 | 125.101 | 2.545 | 20.136 | 1.00 | 57.94 | L O |
| ATOM | 3500 | N | VAL | 57 | 123.914 | 3.562 | 18.530 | 1.00 | 69.56 | L N |
| ATOM | 3501 | CA | VAL | 57 | 124.131 | 2.519 | 17.530 | 1.00 | 69.56 | L C |
| ATOM | 3502 | CB | VAL | 57 | 123.809 | 3.053 | 16.108 | 1.00 | 49.85 | L C |
| ATOM | 3503 | CG1 | VAL | 57 | 123.682 | 1.898 | 15.128 | 1.00 | 49.85 | L C |
| ATOM | 3504 | CG2 | VAL | 57 | 122.529 | 3.875 | 16.139 | 1.00 | 49.85 | L C |

Fig. 19: A-49

| | | | | | | | | | | |
|---|---|---|---|---|---|---|---|---|---|---|
| ATOM | 3505 | C | VAL | 57 | 125.544 | 1.929 | 17.513 | 1.00 | 69.56 | L C |
| ATOM | 3506 | O | VAL | 57 | 126.515 | 2.637 | 17.244 | 1.00 | 69.56 | L O |
| ATOM | 3507 | N | PRO | 58 | 125.674 | 0.618 | 17.799 | 1.00 | 24.22 | L N |
| ATOM | 3508 | CD | PRO | 58 | 124.609 | -0.342 | 18.141 | 1.00 | 44.23 | L C |
| ATOM | 3509 | CA | PRO | 58 | 126.978 | -0.046 | 17.802 | 1.00 | 24.22 | L C |
| ATOM | 3510 | CB | PRO | 58 | 126.638 | -1.472 | 18.237 | 1.00 | 44.23 | L C |
| ATOM | 3511 | CG | PRO | 58 | 125.244 | -1.653 | 17.772 | 1.00 | 44.23 | L C |
| ATOM | 3512 | C | PRO | 58 | 127.609 | 0.017 | 16.415 | 1.00 | 24.22 | L C |
| ATOM | 3513 | O | PRO | 58 | 126.903 | -0.083 | 15.400 | 1.00 | 24.22 | L O |
| ATOM | 3514 | N | SER | 59 | 128.935 | 0.174 | 16.381 | 1.00 | 54.17 | L N |
| ATOM | 3515 | CA | SER | 59 | 129.691 | 0.295 | 15.134 | 1.00 | 54.17 | L C |
| ATOM | 3516 | CB | SER | 59 | 131.184 | 0.489 | 15.438 | 1.00 | 118.98 | L C |
| ATOM | 3517 | OG | SER | 59 | 131.729 | -0.615 | 16.139 | 1.00 | 118.98 | L O |
| ATOM | 3518 | C | SER | 59 | 129.528 | -0.815 | 14.096 | 1.00 | 54.17 | L C |
| ATOM | 3519 | O | SER | 59 | 130.015 | -0.672 | 12.970 | 1.00 | 54.17 | L O |
| ATOM | 3520 | N | ARG | 60 | 128.861 | -1.914 | 14.449 | 1.00 | 62.94 | L N |
| ATOM | 3521 | CA | ARG | 60 | 128.659 | -2.983 | 13.473 | 1.00 | 62.94 | L C |
| ATOM | 3522 | CB | ARG | 60 | 128.247 | -4.291 | 14.159 | 1.00 | 67.90 | L C |
| ATOM | 3523 | CG | ARG | 60 | 127.110 | -4.165 | 15.136 | 1.00 | 67.90 | L C |
| ATOM | 3524 | CD | ARG | 60 | 126.572 | -5.533 | 15.506 | 1.00 | 67.90 | L C |
| ATOM | 3525 | NE | ARG | 60 | 125.638 | -5.453 | 16.621 | 1.00 | 67.90 | L N |
| ATOM | 3526 | CZ | ARG | 60 | 125.978 | -5.050 | 17.840 | 1.00 | 67.90 | L C |
| ATOM | 3527 | NH1 | ARG | 60 | 127.230 | -4.696 | 18.093 | 1.00 | 67.90 | L N |
| ATOM | 3528 | NH2 | ARG | 60 | 125.070 | -5.002 | 18.807 | 1.00 | 67.90 | L N |
| ATOM | 3529 | C | ARG | 60 | 127.596 | -2.555 | 12.459 | 1.00 | 62.94 | L C |
| ATOM | 3530 | O | ARG | 60 | 127.471 | -3.146 | 11.382 | 1.00 | 62.94 | L O |
| ATOM | 3531 | N | PHE | 61 | 126.839 | -1.517 | 12.814 | 1.00 | 65.80 | L N |
| ATOM | 3532 | CA | PHE | 61 | 125.799 | -0.979 | 11.943 | 1.00 | 65.80 | L C |
| ATOM | 3533 | CB | PHE | 61 | 124.718 | -0.270 | 12.752 | 1.00 | 20.54 | L C |
| ATOM | 3534 | CG | PHE | 61 | 123.650 | -1.177 | 13.278 | 1.00 | 20.54 | L C |
| ATOM | 3535 | CD1 | PHE | 61 | 123.613 | -1.519 | 14.628 | 1.00 | 20.54 | L C |
| ATOM | 3536 | CD2 | PHE | 61 | 122.656 | -1.662 | 12.428 | 1.00 | 20.54 | L C |
| ATOM | 3537 | CE1 | PHE | 61 | 122.593 | -2.330 | 15.133 | 1.00 | 20.54 | L C |
| ATOM | 3538 | CE2 | PHE | 61 | 121.627 | -2.476 | 12.914 | 1.00 | 20.54 | L C |
| ATOM | 3539 | CZ | PHE | 61 | 121.594 | -2.809 | 14.270 | 1.00 | 20.54 | L C |
| ATOM | 3540 | C | PHE | 61 | 126.389 | 0.019 | 10.964 | 1.00 | 65.80 | L C |
| ATOM | 3541 | O | PHE | 61 | 127.300 | 0.773 | 11.300 | 1.00 | 65.80 | L O |
| ATOM | 3542 | N | SER | 62 | 125.851 | 0.030 | 9.754 | 1.00 | 31.43 | L N |
| ATOM | 3543 | CA | SER | 62 | 126.317 | 0.941 | 8.722 | 1.00 | 31.43 | L C |
| ATOM | 3544 | CB | SER | 62 | 127.530 | 0.355 | 8.001 | 1.00 | 48.53 | L C |
| ATOM | 3545 | OG | SER | 62 | 127.212 | -0.890 | 7.412 | 1.00 | 48.53 | L O |
| ATOM | 3546 | C | SER | 62 | 125.211 | 1.216 | 7.714 | 1.00 | 31.43 | L C |
| ATOM | 3547 | O | SER | 62 | 124.402 | 0.340 | 7.395 | 1.00 | 31.43 | L O |
| ATOM | 3548 | N | GLY | 63 | 125.177 | 2.443 | 7.216 | 1.00 | 26.27 | L N |
| ATOM | 3549 | CA | GLY | 63 | 124.168 | 2.802 | 6.244 | 1.00 | 26.27 | L C |
| ATOM | 3550 | C | GLY | 63 | 124.870 | 3.245 | 4.988 | 1.00 | 26.27 | L C |
| ATOM | 3551 | O | GLY | 63 | 126.032 | 3.634 | 5.044 | 1.00 | 26.27 | L O |
| ATOM | 3552 | N | SER | 64 | 124.177 | 3.201 | 3.860 | 1.00 | 35.51 | L N |
| ATOM | 3553 | CA | SER | 64 | 124.789 | 3.605 | 2.610 | 1.00 | 35.51 | L C |
| ATOM | 3554 | CB | SER | 64 | 125.824 | 2.565 | 2.193 | 1.00 | 33.46 | L C |
| ATOM | 3555 | OG | SER | 64 | 126.422 | 2.920 | 0.964 | 1.00 | 33.46 | L O |
| ATOM | 3556 | C | SER | 64 | 123.772 | 3.783 | 1.495 | 1.00 | 35.51 | L C |
| ATOM | 3557 | O | SER | 64 | 122.614 | 3.371 | 1.622 | 1.00 | 35.51 | L O |
| ATOM | 3558 | N | GLY | 65 | 124.209 | 4.401 | 0.401 | 1.00 | 29.14 | L N |
| ATOM | 3559 | CA | GLY | 65 | 123.318 | 4.594 | -0.727 | 1.00 | 29.14 | L C |
| ATOM | 3560 | C | GLY | 65 | 123.334 | 5.963 | -1.370 | 1.00 | 29.14 | L C |
| ATOM | 3561 | O | GLY | 65 | 124.127 | 6.837 | -1.024 | 1.00 | 29.14 | L O |
| ATOM | 3562 | N | SER | 66 | 122.439 | 6.137 | -2.329 | 1.00 | 15.93 | L N |
| ATOM | 3563 | CA | SER | 66 | 122.305 | 7.389 | -3.052 | 1.00 | 15.93 | L C |
| ATOM | 3564 | CB | SER | 66 | 123.623 | 7.750 | -3.741 | 1.00 | 32.28 | L C |
| ATOM | 3565 | OG | SER | 66 | 124.127 | 6.657 | -4.482 | 1.00 | 32.28 | L O |
| ATOM | 3566 | C | SER | 66 | 121.171 | 7.264 | -4.076 | 1.00 | 15.93 | L C |
| ATOM | 3567 | O | SER | 66 | 120.609 | 6.184 | -4.284 | 1.00 | 15.93 | L O |
| ATOM | 3568 | N | GLY | 67 | 120.812 | 8.378 | -4.690 | 1.00 | 33.97 | L N |
| ATOM | 3569 | CA | GLY | 67 | 119.751 | 8.349 | -5.673 | 1.00 | 33.97 | L C |
| ATOM | 3570 | C | GLY | 67 | 118.469 | 7.706 | -5.194 | 1.00 | 33.97 | L C |
| ATOM | 3571 | O | GLY | 67 | 117.757 | 8.262 | -4.361 | 1.00 | 33.97 | L O |
| ATOM | 3572 | N | THR | 68 | 118.182 | 6.521 | -5.715 | 1.00 | 25.46 | L N |
| ATOM | 3573 | CA | THR | 68 | 116.954 | 5.828 | -5.366 | 1.00 | 25.46 | L C |
| ATOM | 3574 | CB | THR | 68 | 116.176 | 5.455 | -6.633 | 1.00 | 47.05 | L C |
| ATOM | 3575 | OG1 | THR | 68 | 117.003 | 4.636 | -7.471 | 1.00 | 47.05 | L O |
| ATOM | 3576 | CG2 | THR | 68 | 115.772 | 6.704 | -7.395 | 1.00 | 47.05 | L C |
| ATOM | 3577 | C | THR | 68 | 117.132 | 4.559 | -4.539 | 1.00 | 25.46 | L C |

Fig. 19: A-50

| ATOM | 3578 | O | THR | 68 | 116.144 | 3.963 | -4.103 | 1.00 | 25.46 | L | O |
|---|---|---|---|---|---|---|---|---|---|---|---|
| ATOM | 3579 | N | ASP | 69 | 118.374 | 4.134 | -4.327 | 1.00 | 17.04 | L | N |
| ATOM | 3580 | CA | ASP | 69 | 118.614 | 2.921 | -3.554 | 1.00 | 17.04 | L | C |
| ATOM | 3581 | CB | ASP | 69 | 119.156 | 1.812 | -4.463 | 1.00 | 63.22 | L | C |
| ATOM | 3582 | CG | ASP | 69 | 118.129 | 1.354 | -5.490 | 1.00 | 63.22 | L | C |
| ATOM | 3583 | OD1 | ASP | 69 | 117.087 | 0.791 | -5.083 | 1.00 | 63.22 | L | O |
| ATOM | 3584 | OD2 | ASP | 69 | 118.356 | 1.565 | -6.703 | 1.00 | 63.22 | L | O |
| ATOM | 3585 | C | ASP | 69 | 119.544 | 3.146 | -2.372 | 1.00 | 17.04 | L | C |
| ATOM | 3586 | O | ASP | 69 | 120.684 | 3.567 | -2.535 | 1.00 | 17.04 | L | O |
| ATOM | 3587 | N | TYR | 70 | 119.030 | 2.866 | -1.177 | 1.00 | 19.76 | L | N |
| ATOM | 3588 | CA | TYR | 70 | 119.778 | 3.037 | 0.061 | 1.00 | 19.76 | L | C |
| ATOM | 3589 | CB | TYR | 70 | 119.130 | 4.151 | 0.895 | 1.00 | 24.73 | L | C |
| ATOM | 3590 | CG | TYR | 70 | 119.424 | 5.544 | 0.369 | 1.00 | 24.73 | L | C |
| ATOM | 3591 | CD1 | TYR | 70 | 120.547 | 6.255 | 0.809 | 1.00 | 24.73 | L | C |
| ATOM | 3592 | CE1 | TYR | 70 | 120.865 | 7.511 | 0.281 | 1.00 | 24.73 | L | C |
| ATOM | 3593 | CD2 | TYR | 70 | 118.620 | 6.129 | -0.616 | 1.00 | 24.73 | L | C |
| ATOM | 3594 | CE2 | TYR | 70 | 118.931 | 7.384 | -1.153 | 1.00 | 24.73 | L | C |
| ATOM | 3595 | CZ | TYR | 70 | 120.053 | 8.062 | -0.700 | 1.00 | 24.73 | L | C |
| ATOM | 3596 | OH | TYR | 70 | 120.371 | 9.275 | -1.247 | 1.00 | 24.73 | L | O |
| ATOM | 3597 | C | TYR | 70 | 119.812 | 1.727 | 0.840 | 1.00 | 19.76 | L | C |
| ATOM | 3598 | O | TYR | 70 | 118.997 | 0.828 | 0.599 | 1.00 | 19.76 | L | O |
| ATOM | 3599 | N | THR | 71 | 120.751 | 1.603 | 1.772 | 1.00 | 26.87 | L | N |
| ATOM | 3600 | CA | THR | 71 | 120.837 | 0.366 | 2.535 | 1.00 | 26.87 | L | C |
| ATOM | 3601 | CB | THR | 71 | 121.754 | -0.661 | 1.828 | 1.00 | 34.85 | L | C |
| ATOM | 3602 | OG1 | THR | 71 | 123.107 | -0.192 | 1.860 | 1.00 | 34.85 | L | O |
| ATOM | 3603 | CG2 | THR | 71 | 121.329 | -0.863 | 0.376 | 1.00 | 34.85 | L | C |
| ATOM | 3604 | C | THR | 71 | 121.333 | 0.483 | 3.977 | 1.00 | 26.87 | L | C |
| ATOM | 3605 | O | THR | 71 | 122.160 | 1.335 | 4.306 | 1.00 | 26.87 | L | O |
| ATOM | 3606 | N | LEU | 72 | 120.800 | -0.385 | 4.829 | 1.00 | 24.40 | L | N |
| ATOM | 3607 | CA | LEU | 72 | 121.204 | -0.467 | 6.222 | 1.00 | 24.40 | L | C |
| ATOM | 3608 | CB | LEU | 72 | 119.987 | -0.412 | 7.150 | 1.00 | 25.91 | L | C |
| ATOM | 3609 | CG | LEU | 72 | 120.183 | -0.827 | 8.614 | 1.00 | 25.91 | L | C |
| ATOM | 3610 | CD1 | LEU | 72 | 121.539 | -0.387 | 9.105 | 1.00 | 25.91 | L | C |
| ATOM | 3611 | CD2 | LEU | 72 | 119.097 | -0.207 | 9.470 | 1.00 | 25.91 | L | C |
| ATOM | 3612 | C | LEU | 72 | 121.875 | -1.837 | 6.296 | 1.00 | 24.40 | L | C |
| ATOM | 3613 | O | LEU | 72 | 121.386 | -2.803 | 5.707 | 1.00 | 24.40 | L | O |
| ATOM | 3614 | N | THR | 73 | 123.000 | -1.930 | 6.990 | 1.00 | 38.15 | L | N |
| ATOM | 3615 | CA | THR | 73 | 123.695 | -3.204 | 7.066 | 1.00 | 38.15 | L | C |
| ATOM | 3616 | CB | THR | 73 | 124.907 | -3.217 | 6.110 | 1.00 | 35.63 | L | C |
| ATOM | 3617 | OG1 | THR | 73 | 124.556 | -2.566 | 4.885 | 1.00 | 35.63 | L | O |
| ATOM | 3618 | CG2 | THR | 73 | 125.328 | -4.649 | 5.797 | 1.00 | 35.63 | L | C |
| ATOM | 3619 | C | THR | 73 | 124.189 | -3.542 | 8.467 | 1.00 | 38.15 | L | C |
| ATOM | 3620 | O | THR | 73 | 124.719 | -2.690 | 9.177 | 1.00 | 38.15 | L | O |
| ATOM | 3621 | N | ILE | 74 | 123.997 | -4.791 | 8.866 | 1.00 | 31.55 | L | N |
| ATOM | 3622 | CA | ILE | 74 | 124.467 | -5.246 | 10.158 | 1.00 | 31.55 | L | C |
| ATOM | 3623 | CB | ILE | 74 | 123.342 | -5.884 | 10.988 | 1.00 | 39.02 | L | C |
| ATOM | 3624 | CG2 | ILE | 74 | 123.734 | -5.878 | 12.461 | 1.00 | 39.02 | L | C |
| ATOM | 3625 | CG1 | ILE | 74 | 122.041 | -5.099 | 10.821 | 1.00 | 39.02 | L | C |
| ATOM | 3626 | CD1 | ILE | 74 | 120.870 | -5.663 | 11.635 | 1.00 | 39.02 | L | C |
| ATOM | 3627 | C | ILE | 74 | 125.504 | -6.313 | 9.814 | 1.00 | 31.55 | L | C |
| ATOM | 3628 | O | ILE | 74 | 125.146 | -7.434 | 9.440 | 1.00 | 31.55 | L | O |
| ATOM | 3629 | N | SER | 75 | 126.782 | -5.951 | 9.921 | 1.00 | 48.74 | L | N |
| ATOM | 3630 | CA | SER | 75 | 127.888 | -6.857 | 9.605 | 1.00 | 48.74 | L | C |
| ATOM | 3631 | CB | SER | 75 | 129.209 | -6.106 | 9.727 | 1.00 | 44.70 | L | C |
| ATOM | 3632 | OG | SER | 75 | 129.306 | -5.485 | 10.994 | 1.00 | 44.70 | L | O |
| ATOM | 3633 | C | SER | 75 | 127.940 | -8.129 | 10.456 | 1.00 | 48.74 | L | C |
| ATOM | 3634 | O | SER | 75 | 128.346 | -9.184 | 9.970 | 1.00 | 48.74 | L | O |
| ATOM | 3635 | N | SER | 76 | 127.544 | -8.021 | 11.722 | 1.00 | 53.77 | L | N |
| ATOM | 3636 | CA | SER | 76 | 127.530 | -9.165 | 12.635 | 1.00 | 53.77 | L | C |
| ATOM | 3637 | CB | SER | 76 | 128.773 | -9.166 | 13.521 | 1.00 | 79.21 | L | C |
| ATOM | 3638 | OG | SER | 76 | 128.707 | -10.224 | 14.463 | 1.00 | 79.21 | L | O |
| ATOM | 3639 | C | SER | 76 | 126.288 | -9.102 | 13.515 | 1.00 | 53.77 | L | C |
| ATOM | 3640 | O | SER | 76 | 126.306 | -8.533 | 14.604 | 1.00 | 53.77 | L | O |
| ATOM | 3641 | N | LEU | 77 | 125.211 | -9.704 | 13.036 | 1.00 | 35.38 | L | N |
| ATOM | 3642 | CA | LEU | 77 | 123.946 | -9.691 | 13.756 | 1.00 | 35.38 | L | C |
| ATOM | 3643 | CB | LEU | 77 | 122.955 | -10.639 | 13.085 | 1.00 | 37.68 | L | C |
| ATOM | 3644 | CG | LEU | 77 | 121.514 | -10.154 | 12.995 | 1.00 | 37.68 | L | C |
| ATOM | 3645 | CD1 | LEU | 77 | 120.623 | -11.329 | 12.638 | 1.00 | 37.68 | L | C |
| ATOM | 3646 | CD2 | LEU | 77 | 121.080 | -9.548 | 14.317 | 1.00 | 37.68 | L | C |
| ATOM | 3647 | C | LEU | 77 | 124.096 | -10.080 | 15.215 | 1.00 | 35.38 | L | C |
| ATOM | 3648 | O | LEU | 77 | 124.714 | -11.086 | 15.531 | 1.00 | 35.38 | L | O |
| ATOM | 3649 | N | GLN | 78 | 123.527 | -9.279 | 16.105 | 1.00 | 50.91 | L | N |
| ATOM | 3650 | CA | GLN | 78 | 123.589 | -9.577 | 17.527 | 1.00 | 50.91 | L | C |

Fig. 19: A-51

| | | | | | | | | | | |
|---|---|---|---|---|---|---|---|---|---|---|
| ATOM | 3651 | CB  | GLN | 78 | 124.201 | -8.408  | 18.290 | 1.00 | 82.93  | L | C |
| ATOM | 3652 | CG  | GLN | 78 | 125.653 | -8.159  | 17.938 | 1.00 | 82.93  | L | C |
| ATOM | 3653 | CD  | GLN | 78 | 126.525 | -9.385  | 18.135 | 1.00 | 82.93  | L | C |
| ATOM | 3654 | OE1 | GLN | 78 | 126.509 | -10.007 | 19.200 | 1.00 | 82.93  | L | O |
| ATOM | 3655 | NE2 | GLN | 78 | 127.299 | -9.736  | 17.109 | 1.00 | 82.93  | L | N |
| ATOM | 3656 | C   | GLN | 78 | 122.192 | -9.880  | 18.062 | 1.00 | 50.91  | L | C |
| ATOM | 3657 | O   | GLN | 78 | 121.197 | -9.411  | 17.519 | 1.00 | 50.91  | L | O |
| ATOM | 3658 | N   | PRO | 79 | 122.104 | -10.680 | 19.135 | 1.00 | 74.65  | L | N |
| ATOM | 3659 | CD  | PRO | 79 | 123.228 | -11.171 | 19.952 | 1.00 | 43.98  | L | C |
| ATOM | 3660 | CA  | PRO | 79 | 120.821 | -11.049 | 19.743 | 1.00 | 74.65  | L | C |
| ATOM | 3661 | CB  | PRO | 79 | 121.243 | -11.963 | 20.887 | 1.00 | 43.98  | L | C |
| ATOM | 3662 | CG  | PRO | 79 | 122.577 | -11.373 | 21.284 | 1.00 | 43.98  | L | C |
| ATOM | 3663 | C   | PRO | 79 | 120.033 | -9.830  | 20.224 | 1.00 | 74.65  | L | C |
| ATOM | 3664 | O   | PRO | 79 | 118.855 | -9.922  | 20.577 | 1.00 | 74.65  | L | O |
| ATOM | 3665 | N   | GLU | 80 | 120.697 | -8.685  | 20.221 | 1.00 | 42.25  | L | N |
| ATOM | 3666 | CA  | GLU | 80 | 120.080 | -7.451  | 20.659 | 1.00 | 42.25  | L | C |
| ATOM | 3667 | CB  | GLU | 80 | 121.085 | -6.697  | 21.527 | 1.00 | 40.93  | L | C |
| ATOM | 3668 | CG  | GLU | 80 | 122.485 | -6.700  | 20.958 | 1.00 | 40.93  | L | C |
| ATOM | 3669 | CD  | GLU | 80 | 123.424 | -5.786  | 21.726 | 1.00 | 40.93  | L | C |
| ATOM | 3670 | OE1 | GLU | 80 | 123.013 | -4.648  | 22.033 | 1.00 | 40.93  | L | O |
| ATOM | 3671 | OE2 | GLU | 80 | 124.572 | -6.197  | 22.009 | 1.00 | 40.93  | L | O |
| ATOM | 3672 | C   | GLU | 80 | 119.602 | -6.575  | 19.489 | 1.00 | 42.25  | L | C |
| ATOM | 3673 | O   | GLU | 80 | 118.723 | -5.726  | 19.656 | 1.00 | 42.25  | L | O |
| ATOM | 3674 | N   | ASP | 81 | 120.189 | -6.787  | 18.312 | 1.00 | 42.48  | L | N |
| ATOM | 3675 | CA  | ASP | 81 | 119.835 | -6.037  | 17.108 | 1.00 | 42.48  | L | C |
| ATOM | 3676 | CB  | ASP | 81 | 120.867 | -6.254  | 16.005 | 1.00 | 43.12  | L | C |
| ATOM | 3677 | CG  | ASP | 81 | 122.262 | -5.914  | 16.441 | 1.00 | 43.12  | L | C |
| ATOM | 3678 | OD1 | ASP | 81 | 122.422 | -5.003  | 17.281 | 1.00 | 43.12  | L | O |
| ATOM | 3679 | OD2 | ASP | 81 | 123.205 | -6.549  | 15.924 | 1.00 | 43.12  | L | O |
| ATOM | 3680 | C   | ASP | 81 | 118.495 | -6.488  | 16.564 | 1.00 | 42.48  | L | C |
| ATOM | 3681 | O   | ASP | 81 | 118.086 | -6.063  | 15.488 | 1.00 | 42.48  | L | O |
| ATOM | 3682 | N   | PHE | 82 | 117.810 | -7.351  | 17.299 | 1.00 | 48.53  | L | N |
| ATOM | 3683 | CA  | PHE | 82 | 116.544 | -7.856  | 16.822 | 1.00 | 48.53  | L | C |
| ATOM | 3684 | CB  | PHE | 82 | 116.337 | -9.265  | 17.368 | 1.00 | 189.91 | L | C |
| ATOM | 3685 | CG  | PHE | 82 | 117.320 | -10.260 | 16.810 | 1.00 | 189.91 | L | C |
| ATOM | 3686 | CD1 | PHE | 82 | 117.227 | -10.676 | 15.485 | 1.00 | 189.91 | L | C |
| ATOM | 3687 | CD2 | PHE | 82 | 118.369 | -10.741 | 17.587 | 1.00 | 189.91 | L | C |
| ATOM | 3688 | CE1 | PHE | 82 | 118.164 | -11.554 | 14.940 | 1.00 | 189.91 | L | C |
| ATOM | 3689 | CE2 | PHE | 82 | 119.311 | -11.622 | 17.048 | 1.00 | 189.91 | L | C |
| ATOM | 3690 | CZ  | PHE | 82 | 119.207 | -12.027 | 15.725 | 1.00 | 189.91 | L | C |
| ATOM | 3691 | C   | PHE | 82 | 115.359 | -6.953  | 17.094 | 1.00 | 48.53  | L | C |
| ATOM | 3692 | O   | PHE | 82 | 114.857 | -6.863  | 18.216 | 1.00 | 48.53  | L | O |
| ATOM | 3693 | N   | ALA | 83 | 114.939 | -6.271  | 16.032 | 1.00 | 31.52  | L | N |
| ATOM | 3694 | CA  | ALA | 83 | 113.813 | -5.350  | 16.052 | 1.00 | 31.52  | L | C |
| ATOM | 3695 | CB  | ALA | 83 | 114.217 | -4.051  | 16.723 | 1.00 | 63.37  | L | C |
| ATOM | 3696 | C   | ALA | 83 | 113.398 | -5.090  | 14.605 | 1.00 | 31.52  | L | C |
| ATOM | 3697 | O   | ALA | 83 | 113.816 | -5.808  | 13.693 | 1.00 | 31.52  | L | O |
| ATOM | 3698 | N   | THR | 84 | 112.565 | -4.075  | 14.395 | 1.00 | 28.09  | L | N |
| ATOM | 3699 | CA  | THR | 84 | 112.124 | -3.733  | 13.045 | 1.00 | 28.09  | L | C |
| ATOM | 3700 | CB  | THR | 84 | 110.572 | -3.799  | 12.928 | 1.00 | 15.50  | L | C |
| ATOM | 3701 | OG1 | THR | 84 | 110.127 | -3.002  | 11.822 | 1.00 | 15.50  | L | O |
| ATOM | 3702 | CG2 | THR | 84 | 109.922 | -3.332  | 14.207 | 1.00 | 15.50  | L | C |
| ATOM | 3703 | C   | THR | 84 | 112.664 | -2.346  | 12.659 | 1.00 | 28.09  | L | C |
| ATOM | 3704 | O   | THR | 84 | 112.505 | -1.373  | 13.400 | 1.00 | 28.09  | L | O |
| ATOM | 3705 | N   | TYR | 85 | 113.316 | -2.282  | 11.496 | 1.00 | 21.31  | L | N |
| ATOM | 3706 | CA  | TYR | 85 | 113.935 | -1.055  | 11.000 | 1.00 | 21.31  | L | C |
| ATOM | 3707 | CB  | TYR | 85 | 115.367 | -1.338  | 10.517 | 1.00 | 19.63  | L | C |
| ATOM | 3708 | CG  | TYR | 85 | 116.240 | -1.976  | 11.566 | 1.00 | 19.63  | L | C |
| ATOM | 3709 | CD1 | TYR | 85 | 115.988 | -3.279  | 12.021 | 1.00 | 19.63  | L | C |
| ATOM | 3710 | CE1 | TYR | 85 | 116.718 | -3.834  | 13.061 | 1.00 | 19.63  | L | C |
| ATOM | 3711 | CD2 | TYR | 85 | 117.255 | -1.259  | 12.174 | 1.00 | 19.63  | L | C |
| ATOM | 3712 | CE2 | TYR | 85 | 117.990 | -1.807  | 13.217 | 1.00 | 19.63  | L | C |
| ATOM | 3713 | CZ  | TYR | 85 | 117.711 | -3.087  | 13.655 | 1.00 | 19.63  | L | C |
| ATOM | 3714 | OH  | TYR | 85 | 118.405 | -3.592  | 14.722 | 1.00 | 19.63  | L | O |
| ATOM | 3715 | C   | TYR | 85 | 113.173 | -0.365  | 9.882  | 1.00 | 21.31  | L | C |
| ATOM | 3716 | O   | TYR | 85 | 112.768 | -0.996  | 8.900  | 1.00 | 21.31  | L | O |
| ATOM | 3717 | N   | TYR | 86 | 113.015 | 0.948   | 10.046 | 1.00 | 18.01  | L | N |
| ATOM | 3718 | CA  | TYR | 86 | 112.321 | 1.806   | 9.090  | 1.00 | 18.01  | L | C |
| ATOM | 3719 | CB  | TYR | 86 | 111.242 | 2.632   | 9.790  | 1.00 | 24.73  | L | C |
| ATOM | 3720 | CG  | TYR | 86 | 110.130 | 1.846   | 10.421 | 1.00 | 24.73  | L | C |
| ATOM | 3721 | CD1 | TYR | 86 | 109.020 | 1.459   | 9.679  | 1.00 | 24.73  | L | C |
| ATOM | 3722 | CE1 | TYR | 86 | 107.971 | 0.756   | 10.278 | 1.00 | 24.73  | L | C |
| ATOM | 3723 | CD2 | TYR | 86 | 110.177 | 1.508   | 11.773 | 1.00 | 24.73  | L | C |

Fig. 19: A-52

```
ATOM   3724  CE2  TYR  86    109.140    0.804   12.378  1.00  24.73   L  C
ATOM   3725  CZ   TYR  86    108.042    0.438   11.628  1.00  24.73   L  C
ATOM   3726  OH   TYR  86    107.002   -0.204   12.238  1.00  24.73   L  O
ATOM   3727  C    TYR  86    113.280    2.798    8.465  1.00  18.01   L  C
ATOM   3728  O    TYR  86    114.110    3.378    9.158  1.00  18.01   L  O
ATOM   3729  N    CYS  87    113.170    2.996    7.158  1.00  20.53   L  N
ATOM   3730  CA   CYS  87    113.989    3.999    6.494  1.00  20.53   L  C
ATOM   3731  C    CYS  87    113.021    5.156    6.335  1.00  20.53   L  C
ATOM   3732  O    CYS  87    111.806    4.954    6.351  1.00  20.53   L  O
ATOM   3733  CB   CYS  87    114.509    3.527    5.133  1.00  17.33   L  C
ATOM   3734  SG   CYS  87    113.306    2.900    3.921  1.00  17.33   L  S
ATOM   3735  N    GLN  88    113.545    6.363    6.212  1.00  10.63   L  N
ATOM   3736  CA   GLN  88    112.696    7.534    6.083  1.00  10.63   L  C
ATOM   3737  CB   GLN  88    112.393    8.083    7.482  1.00  18.09   L  C
ATOM   3738  CG   GLN  88    111.509    9.303    7.525  1.00  18.09   L  C
ATOM   3739  CD   GLN  88    112.256   10.547    7.971  1.00  18.09   L  C
ATOM   3740  OE1  GLN  88    112.946   10.539    8.987  1.00  18.09   L  O
ATOM   3741  NE2  GLN  88    112.106   11.627    7.219  1.00  18.09   L  N
ATOM   3742  C    GLN  88    113.390    8.583    5.219  1.00  10.63   L  C
ATOM   3743  O    GLN  88    114.626    8.680    5.198  1.00  10.63   L  O
ATOM   3744  N    GLN  89    112.600    9.357    4.483  1.00  11.94   L  N
ATOM   3745  CA   GLN  89    113.171   10.386    3.625  1.00  11.94   L  C
ATOM   3746  CB   GLN  89    112.877   10.073    2.152  1.00  25.01   L  C
ATOM   3747  CG   GLN  89    111.407   10.008    1.776  1.00  25.01   L  C
ATOM   3748  CD   GLN  89    110.786   11.377    1.579  1.00  25.01   L  C
ATOM   3749  OE1  GLN  89    111.373   12.247    0.935  1.00  25.01   L  O
ATOM   3750  NE2  GLN  89    109.591   11.571    2.119  1.00  25.01   L  N
ATOM   3751  C    GLN  89    112.606   11.732    4.023  1.00  11.94   L  C
ATOM   3752  O    GLN  89    111.498   11.802    4.552  1.00  11.94   L  O
ATOM   3753  N    TRP  90    113.375   12.794    3.792  1.00  19.62   L  N
ATOM   3754  CA   TRP  90    112.948   14.144    4.145  1.00  19.62   L  C
ATOM   3755  CB   TRP  90    113.773   14.667    5.336  1.00  17.27   L  C
ATOM   3756  CG   TRP  90    115.220   15.018    5.023  1.00  17.27   L  C
ATOM   3757  CD2  TRP  90    116.174   15.611    5.918  1.00  17.27   L  C
ATOM   3758  CE2  TRP  90    117.373   15.797    5.189  1.00  17.27   L  C
ATOM   3759  CE3  TRP  90    116.132   16.005    7.267  1.00  17.27   L  C
ATOM   3760  CD1  TRP  90    115.869   14.867    3.823  1.00  17.27   L  C
ATOM   3761  NE1  TRP  90    117.156   15.334    3.918  1.00  17.27   L  N
ATOM   3762  CZ2  TRP  90    118.522   16.363    5.759  1.00  17.27   L  C
ATOM   3763  CZ3  TRP  90    117.284   16.570    7.839  1.00  17.27   L  C
ATOM   3764  CH2  TRP  90    118.462   16.741    7.080  1.00  17.27   L  C
ATOM   3765  C    TRP  90    113.074   15.093    2.947  1.00  19.62   L  C
ATOM   3766  O    TRP  90    112.783   16.289    3.048  1.00  19.62   L  O
ATOM   3767  N    SER  91    113.494   14.552    1.807  1.00  12.71   L  N
ATOM   3768  CA   SER  91    113.662   15.359    0.600  1.00  12.71   L  C
ATOM   3769  CB   SER  91    114.504   14.587   -0.414  1.00  23.55   L  C
ATOM   3770  OG   SER  91    115.762   14.248    0.137  1.00  23.55   L  O
ATOM   3771  C    SER  91    112.344   15.800   -0.054  1.00  12.71   L  C
ATOM   3772  O    SER  91    112.284   16.860   -0.680  1.00  12.71   L  O
ATOM   3773  N    GLY  92    111.297   14.986    0.096  1.00  23.24   L  N
ATOM   3774  CA   GLY  92    110.008   15.310   -0.493  1.00  23.24   L  C
ATOM   3775  C    GLY  92    108.867   15.347    0.509  1.00  23.24   L  C
ATOM   3776  O    GLY  92    108.931   14.718    1.567  1.00  23.24   L  O
ATOM   3777  N    ASN  93    107.811   16.078    0.169  1.00  31.94   L  N
ATOM   3778  CA   ASN  93    106.663   16.206    1.048  1.00  31.94   L  C
ATOM   3779  CB   ASN  93    106.307   17.670    1.203  1.00  23.71   L  C
ATOM   3780  CG   ASN  93    107.400   18.448    1.896  1.00  23.71   L  C
ATOM   3781  OD1  ASN  93    107.790   19.525    1.445  1.00  23.71   L  O
ATOM   3782  ND2  ASN  93    107.905   17.905    3.006  1.00  23.71   L  N
ATOM   3783  C    ASN  93    105.478   15.454    0.507  1.00  31.94   L  C
ATOM   3784  O    ASN  93    105.227   15.478   -0.692  1.00  31.94   L  O
ATOM   3785  N    PRO  94    104.724   14.779    1.386  1.00  29.10   L  N
ATOM   3786  CD   PRO  94    103.575   13.939    1.009  1.00   1.87   L  C
ATOM   3787  CA   PRO  94    104.950   14.713    2.830  1.00  29.10   L  C
ATOM   3788  CB   PRO  94    103.651   14.113    3.340  1.00   1.87   L  C
ATOM   3789  CG   PRO  94    103.336   13.137    2.269  1.00   1.87   L  C
ATOM   3790  C    PRO  94    106.131   13.823    3.167  1.00  29.10   L  C
ATOM   3791  O    PRO  94    106.516   12.987    2.361  1.00  29.10   L  O
ATOM   3792  N    TRP  95    106.711   14.011    4.349  1.00  16.41   L  N
ATOM   3793  CA   TRP  95    107.810   13.155    4.772  1.00  16.41   L  C
ATOM   3794  CB   TRP  95    108.425   13.629    6.094  1.00  13.37   L  C
ATOM   3795  CG   TRP  95    109.201   14.906    5.979  1.00  13.37   L  C
ATOM   3796  CD2  TRP  95    109.284   15.950    6.954  1.00  13.37   L  C
```

Fig. 19: A-53

| | | | | | | | | | | |
|---|---|---|---|---|---|---|---|---|---|---|
| ATOM | 3797 | CE2 | TRP | 95 | 110.104 | 16.960 | 6.412 | 1.00 | 13.37 | L | C |
| ATOM | 3798 | CE3 | TRP | 95 | 108.743 | 16.132 | 8.229 | 1.00 | 13.37 | L | C |
| ATOM | 3799 | CD1 | TRP | 95 | 109.963 | 15.312 | 4.917 | 1.00 | 13.37 | L | C |
| ATOM | 3800 | NE1 | TRP | 95 | 110.504 | 16.543 | 5.168 | 1.00 | 13.37 | L | N |
| ATOM | 3801 | CZ2 | TRP | 95 | 110.394 | 18.144 | 7.107 | 1.00 | 13.37 | L | C |
| ATOM | 3802 | CZ3 | TRP | 95 | 109.030 | 17.305 | 8.919 | 1.00 | 13.37 | L | C |
| ATOM | 3803 | CH2 | TRP | 95 | 109.845 | 18.297 | 8.358 | 1.00 | 13.37 | L | C |
| ATOM | 3804 | C | TRP | 95 | 107.226 | 11.751 | 4.942 | 1.00 | 16.41 | L | C |
| ATOM | 3805 | O | TRP | 95 | 106.136 | 11.575 | 5.484 | 1.00 | 16.41 | L | O |
| ATOM | 3806 | N | THR | 96 | 107.956 | 10.748 | 4.481 | 1.00 | 6.71 | L | N |
| ATOM | 3807 | CA | THR | 96 | 107.465 | 9.388 | 4.563 | 1.00 | 6.71 | L | C |
| ATOM | 3808 | CB | THR | 96 | 106.963 | 8.932 | 3.172 | 1.00 | 11.59 | L | C |
| ATOM | 3809 | OG1 | THR | 96 | 108.045 | 8.991 | 2.235 | 1.00 | 11.59 | L | O |
| ATOM | 3810 | CG2 | THR | 96 | 105.859 | 9.852 | 2.674 | 1.00 | 11.59 | L | C |
| ATOM | 3811 | C | THR | 96 | 108.489 | 8.369 | 5.087 | 1.00 | 6.71 | L | C |
| ATOM | 3812 | O | THR | 96 | 109.703 | 8.621 | 5.121 | 1.00 | 6.71 | L | O |
| ATOM | 3813 | N | PHE | 97 | 107.966 | 7.222 | 5.513 | 1.00 | 24.36 | L | N |
| ATOM | 3814 | CA | PHE | 97 | 108.777 | 6.119 | 6.013 | 1.00 | 24.36 | L | C |
| ATOM | 3815 | CB | PHE | 97 | 108.327 | 5.689 | 7.418 | 1.00 | 11.10 | L | C |
| ATOM | 3816 | CG | PHE | 97 | 108.422 | 6.762 | 8.461 | 1.00 | 11.10 | L | C |
| ATOM | 3817 | CD1 | PHE | 97 | 107.541 | 7.831 | 8.460 | 1.00 | 11.10 | L | C |
| ATOM | 3818 | CD2 | PHE | 97 | 109.391 | 6.685 | 9.470 | 1.00 | 11.10 | L | C |
| ATOM | 3819 | CE1 | PHE | 97 | 107.612 | 8.821 | 9.453 | 1.00 | 11.10 | L | C |
| ATOM | 3820 | CE2 | PHE | 97 | 109.475 | 7.665 | 10.468 | 1.00 | 11.10 | L | C |
| ATOM | 3821 | CZ | PHE | 97 | 108.577 | 8.738 | 13.456 | 1.00 | 11.10 | L | C |
| ATOM | 3822 | C | PHE | 97 | 108.532 | 4.950 | 5.062 | 1.00 | 24.36 | L | C |
| ATOM | 3823 | O | PHE | 97 | 107.613 | 4.990 | 4.241 | 1.00 | 24.36 | L | O |
| ATOM | 3824 | N | GLY | 98 | 109.362 | 3.919 | 5.168 | 1.00 | 21.54 | L | N |
| ATOM | 3825 | CA | GLY | 98 | 109.183 | 2.727 | 4.350 | 1.00 | 21.54 | L | C |
| ATOM | 3826 | C | GLY | 98 | 108.266 | 1.849 | 5.184 | 1.00 | 21.54 | L | C |
| ATOM | 3827 | O | GLY | 98 | 107.977 | 2.196 | 6.339 | 1.00 | 21.54 | L | O |
| ATOM | 3828 | N | GLN | 99 | 107.796 | 0.728 | 4.645 | 1.00 | 11.59 | L | N |
| ATOM | 3829 | CA | GLN | 99 | 106.894 | -0.114 | 5.442 | 1.00 | 11.59 | L | C |
| ATOM | 3830 | CB | GLN | 99 | 106.211 | -1.197 | 4.593 | 1.00 | 37.88 | L | C |
| ATOM | 3831 | CG | GLN | 99 | 106.810 | -1.403 | 3.238 | 1.00 | 37.88 | L | C |
| ATOM | 3832 | CD | GLN | 99 | 108.266 | -1.748 | 3.319 | 1.00 | 37.88 | L | C |
| ATOM | 3833 | OE1 | GLN | 99 | 108.638 | -2.821 | 3.796 | 1.00 | 37.88 | L | O |
| ATOM | 3834 | NE2 | GLN | 99 | 109.110 | -0.832 | 2.866 | 1.00 | 37.88 | L | N |
| ATOM | 3835 | C | GLN | 99 | 107.586 | -0.758 | 6.634 | 1.00 | 11.59 | L | C |
| ATOM | 3836 | O | GLN | 99 | 106.943 | -1.317 | 7.508 | 1.00 | 11.59 | L | O |
| ATOM | 3837 | N | GLY | 100 | 108.902 | -0.640 | 6.684 | 1.00 | 24.72 | L | N |
| ATOM | 3838 | CA | GLY | 100 | 109.633 | -1.225 | 7.785 | 1.00 | 24.72 | L | C |
| ATOM | 3839 | C | GLY | 100 | 110.055 | -2.630 | 7.425 | 1.00 | 24.72 | L | C |
| ATOM | 3840 | O | GLY | 100 | 109.402 | -3.279 | 6.606 | 1.00 | 24.72 | L | O |
| ATOM | 3841 | N | THR | 101 | 111.157 | -3.084 | 8.017 | 1.00 | 23.77 | L | N |
| ATOM | 3842 | CA | THR | 101 | 111.685 | -4.424 | 7.780 | 1.00 | 23.77 | L | C |
| ATOM | 3843 | CB | THR | 101 | 113.019 | -4.382 | 7.040 | 1.00 | 10.18 | L | C |
| ATOM | 3844 | OG1 | THR | 101 | 112.790 | -4.076 | 5.659 | 1.00 | 10.18 | L | O |
| ATOM | 3845 | CG2 | THR | 101 | 113.735 | -5.716 | 7.173 | 1.00 | 10.18 | L | C |
| ATOM | 3846 | C | THR | 101 | 111.908 | -5.076 | 9.129 | 1.00 | 23.77 | L | C |
| ATOM | 3847 | O | THR | 101 | 112.689 | -4.582 | 9.942 | 1.00 | 23.77 | L | O |
| ATOM | 3848 | N | LYS | 102 | 111.223 | -6.188 | 9.365 | 1.00 | 19.34 | L | N |
| ATOM | 3849 | CA | LYS | 102 | 111.347 | -6.858 | 10.641 | 1.00 | 19.34 | L | C |
| ATOM | 3850 | CB | LYS | 102 | 110.009 | -7.496 | 11.027 | 1.00 | 36.70 | L | C |
| ATOM | 3851 | CG | LYS | 102 | 109.872 | -7.774 | 12.521 | 1.00 | 36.70 | L | C |
| ATOM | 3852 | CD | LYS | 102 | 108.464 | -8.244 | 12.876 | 1.00 | 36.70 | L | C |
| ATOM | 3853 | CE | LYS | 102 | 108.313 | -8.467 | 14.372 | 1.00 | 36.70 | L | C |
| ATOM | 3854 | NZ | LYS | 102 | 108.632 | -7.218 | 15.120 | 1.00 | 36.70 | L | N |
| ATOM | 3855 | C | LYS | 102 | 112.449 | -7.907 | 10.608 | 1.00 | 19.34 | L | C |
| ATOM | 3856 | O | LYS | 102 | 112.530 | -8.703 | 9.661 | 1.00 | 19.34 | L | O |
| ATOM | 3857 | N | VAL | 103 | 113.304 | -7.894 | 11.634 | 1.00 | 20.01 | L | N |
| ATOM | 3858 | CA | VAL | 103 | 114.378 | -8.868 | 11.714 | 1.00 | 20.01 | L | C |
| ATOM | 3859 | CB | VAL | 103 | 115.793 | -8.188 | 11.567 | 1.00 | 24.69 | L | C |
| ATOM | 3860 | CG1 | VAL | 103 | 115.696 | -6.991 | 10.636 | 1.00 | 24.69 | L | C |
| ATOM | 3861 | CG2 | VAL | 103 | 116.361 | -7.780 | 12.908 | 1.00 | 24.69 | L | C |
| ATOM | 3862 | C | VAL | 103 | 114.280 | -9.654 | 13.031 | 1.00 | 20.01 | L | C |
| ATOM | 3863 | O | VAL | 103 | 114.380 | -9.075 | 14.117 | 1.00 | 20.01 | L | O |
| ATOM | 3864 | N | GLU | 104 | 114.047 | -10.969 | 12.927 | 1.00 | 25.78 | L | N |
| ATOM | 3865 | CA | GLU | 104 | 113.948 | -11.831 | 14.106 | 1.00 | 25.78 | L | C |
| ATOM | 3866 | CB | GLU | 104 | 112.662 | -12.666 | 14.098 | 1.00 | 117.28 | L | C |
| ATOM | 3867 | CG | GLU | 104 | 112.589 | -13.728 | 13.022 | 1.00 | 117.28 | L | C |
| ATOM | 3868 | CD | GLU | 104 | 112.095 | -13.176 | 11.705 | 1.00 | 117.28 | L | C |
| ATOM | 3869 | OE1 | GLU | 104 | 112.047 | -13.942 | 10.717 | 1.00 | 117.28 | L | O |

Fig. 19: A-54

| | | | | | | | | | | |
|---|---|---|---|---|---|---|---|---|---|---|
| ATOM | 3870 | OE2 | GLU | 104 | 111.747 | -11.975 | 11.660 | 1.00 | 117.28 | L | O |
| ATOM | 3871 | C | GLU | 104 | 115.148 | -12.759 | 14.179 | 1.00 | 25.78 | L | C |
| ATOM | 3872 | O | GLU | 104 | 115.852 | -12.955 | 13.185 | 1.00 | 25.78 | L | O |
| ATOM | 3873 | N | ILE | 105 | 115.368 | -13.324 | 15.365 | 1.00 | 16.82 | L | N |
| ATOM | 3874 | CA | ILE | 105 | 116.489 | -14.228 | 15.621 | 1.00 | 16.82 | L | C |
| ATOM | 3875 | CB | ILE | 105 | 116.771 | -14.386 | 17.124 | 1.00 | 41.57 | L | C |
| ATOM | 3876 | CG2 | ILE | 105 | 118.226 | -14.701 | 17.335 | 1.00 | 41.57 | L | C |
| ATOM | 3877 | CG1 | ILE | 105 | 116.372 | -13.111 | 17.873 | 1.00 | 41.57 | L | C |
| ATOM | 3878 | CD1 | ILE | 105 | 116.594 | -13.151 | 19.385 | 1.00 | 41.57 | L | C |
| ATOM | 3879 | C | ILE | 105 | 116.204 | -15.611 | 15.102 | 1.00 | 16.82 | L | C |
| ATOM | 3880 | O | ILE | 105 | 115.251 | -16.250 | 15.543 | 1.00 | 16.82 | L | O |
| ATOM | 3881 | N | LYS | 106 | 117.008 | -16.076 | 14.153 | 1.00 | 39.65 | L | N |
| ATOM | 3882 | CA | LYS | 106 | 116.807 | -17.422 | 13.653 | 1.00 | 39.65 | L | C |
| ATOM | 3883 | CB | LYS | 106 | 117.310 | -17.587 | 12.217 | 1.00 | 48.57 | L | C |
| ATOM | 3884 | CG | LYS | 106 | 116.947 | -18.952 | 11.631 | 1.00 | 48.57 | L | C |
| ATOM | 3885 | CD | LYS | 106 | 117.401 | -19.148 | 10.179 | 1.00 | 48.57 | L | C |
| ATOM | 3886 | CE | LYS | 106 | 117.087 | -20.579 | 9.702 | 1.00 | 48.57 | L | C |
| ATOM | 3887 | NZ | LYS | 106 | 117.672 | -20.948 | 8.369 | 1.00 | 48.57 | L | N |
| ATOM | 3888 | C | LYS | 106 | 117.598 | -18.310 | 14.600 | 1.00 | 39.65 | L | C |
| ATOM | 3889 | O | LYS | 106 | 118.804 | -18.122 | 14.782 | 1.00 | 38.70 | L | O |
| ATOM | 3890 | N | ARG | 107 | 116.894 | -19.242 | 15.235 | 1.00 | 14.86 | L | N |
| ATOM | 3891 | CA | ARG | 107 | 117.492 | -20.178 | 16.174 | 1.00 | 14.86 | L | C |
| ATOM | 3892 | CB | ARG | 107 | 117.158 | -19.771 | 17.605 | 1.00 | 20.96 | L | C |
| ATOM | 3893 | CG | ARG | 107 | 115.687 | -19.532 | 17.832 | 1.00 | 20.96 | L | C |
| ATOM | 3894 | CD | ARG | 107 | 115.296 | -19.930 | 19.239 | 1.00 | 20.96 | L | C |
| ATOM | 3895 | NE | ARG | 107 | 115.615 | -21.335 | 19.502 | 1.00 | 20.96 | L | N |
| ATOM | 3896 | CZ | ARG | 107 | 115.513 | -21.910 | 20.692 | 1.00 | 20.96 | L | C |
| ATOM | 3897 | NH1 | ARG | 107 | 115.096 | -21.206 | 21.732 | 1.00 | 20.96 | L | N |
| ATOM | 3898 | NH2 | ARG | 107 | 115.843 | -23.182 | 20.840 | 1.00 | 20.96 | L | N |
| ATOM | 3899 | C | ARG | 107 | 116.986 | -21.595 | 15.899 | 1.00 | 14.86 | L | C |
| ATOM | 3900 | O | ARG | 107 | 116.062 | -21.796 | 15.107 | 1.00 | 14.86 | L | O |
| ATOM | 3901 | N | THR | 108 | 117.606 | -22.575 | 16.545 | 1.00 | 15.74 | L | N |
| ATOM | 3902 | CA | THR | 108 | 117.220 | -23.963 | 16.354 | 1.00 | 15.74 | L | C |
| ATOM | 3903 | CB | THR | 108 | 118.025 | -24.921 | 17.260 | 1.00 | 26.88 | L | C |
| ATOM | 3904 | OG1 | THR | 108 | 118.232 | -24.320 | 18.548 | 1.00 | 26.88 | L | O |
| ATOM | 3905 | CG2 | THR | 108 | 119.347 | -25.257 | 16.618 | 1.00 | 26.88 | L | C |
| ATOM | 3906 | C | THR | 108 | 115.756 | -24.161 | 16.653 | 1.00 | 15.74 | L | C |
| ATOM | 3907 | O | THR | 108 | 115.179 | -23.450 | 17.481 | 1.00 | 15.74 | L | O |
| ATOM | 3908 | N | VAL | 109 | 115.170 | -25.134 | 15.963 | 1.00 | 14.98 | L | N |
| ATOM | 3909 | CA | VAL | 109 | 113.775 | -25.469 | 16.136 | 1.00 | 12.60 | L | C |
| ATOM | 3910 | CB | VAL | 109 | 113.368 | -26.593 | 15.189 | 1.00 | 15.46 | L | C |
| ATOM | 3911 | CG1 | VAL | 109 | 111.987 | -27.105 | 15.527 | 1.00 | 14.41 | L | C |
| ATOM | 3912 | CG2 | VAL | 109 | 113.383 | -26.074 | 13.789 | 1.00 | 13.59 | L | C |
| ATOM | 3913 | C | VAL | 109 | 113.517 | -25.909 | 17.565 | 1.00 | 13.54 | L | C |
| ATOM | 3914 | O | VAL | 109 | 114.393 | -26.477 | 18.236 | 1.00 | 21.28 | L | O |
| ATOM | 3915 | N | ALA | 110 | 112.313 | -25.637 | 18.036 | 1.00 | 11.81 | L | N |
| ATOM | 3916 | CA | ALA | 110 | 111.953 | -26.001 | 19.383 | 1.00 | 12.99 | L | C |
| ATOM | 3917 | CB | ALA | 110 | 112.312 | -24.878 | 20.330 | 1.00 | 8.30 | L | C |
| ATOM | 3918 | C | ALA | 110 | 110.463 | -26.281 | 19.426 | 1.00 | 13.63 | L | C |
| ATOM | 3919 | O | ALA | 110 | 109.654 | -25.390 | 19.158 | 1.00 | 15.92 | L | O |
| ATOM | 3920 | N | ALA | 111 | 110.112 | -27.525 | 19.758 | 1.00 | 25.70 | L | N |
| ATOM | 3921 | CA | ALA | 111 | 108.715 | -27.951 | 19.838 | 1.00 | 26.75 | L | C |
| ATOM | 3922 | CB | ALA | 111 | 108.641 | -29.446 | 20.087 | 1.00 | 23.32 | L | C |
| ATOM | 3923 | C | ALA | 111 | 107.981 | -27.198 | 20.936 | 1.00 | 25.59 | L | C |
| ATOM | 3924 | O | ALA | 111 | 108.525 | -26.926 | 22.008 | 1.00 | 29.44 | L | O |
| ATOM | 3925 | N | PRO | 112 | 106.720 | -26.857 | 20.686 | 1.00 | 20.76 | L | N |
| ATOM | 3926 | CD | PRO | 112 | 105.901 | -27.063 | 19.477 | 1.00 | 26.01 | L | C |
| ATOM | 3927 | CA | PRO | 112 | 105.975 | -26.125 | 21.707 | 1.00 | 26.81 | L | C |
| ATOM | 3928 | CB | PRO | 112 | 104.938 | -25.381 | 20.882 | 1.00 | 26.37 | L | C |
| ATOM | 3929 | CG | PRO | 112 | 104.550 | -26.457 | 19.876 | 1.00 | 24.71 | L | C |
| ATOM | 3930 | C | PRO | 112 | 105.322 | -27.058 | 22.703 | 1.00 | 30.67 | L | C |
| ATOM | 3931 | O | PRO | 112 | 104.936 | -28.166 | 22.353 | 1.00 | 31.28 | L | O |
| ATOM | 3932 | N | SER | 113 | 105.220 | -26.618 | 23.947 | 1.00 | 12.97 | L | N |
| ATOM | 3933 | CA | SER | 113 | 104.530 | -27.410 | 24.944 | 1.00 | 16.57 | L | C |
| ATOM | 3934 | CB | SER | 113 | 105.027 | -27.079 | 26.334 | 1.00 | 14.96 | L | C |
| ATOM | 3935 | OG | SER | 113 | 106.427 | -27.168 | 26.370 | 1.00 | 27.37 | L | O |
| ATOM | 3936 | C | SER | 113 | 103.099 | -26.913 | 24.815 | 1.00 | 15.10 | L | C |
| ATOM | 3937 | O | SER | 113 | 102.884 | -25.708 | 24.770 | 1.00 | 12.98 | L | O |
| ATOM | 3938 | N | VAL | 114 | 102.111 | -27.792 | 24.731 | 1.00 | 10.23 | L | N |
| ATOM | 3939 | CA | VAL | 114 | 100.766 | -27.258 | 24.630 | 1.00 | 9.98 | L | C |
| ATOM | 3940 | CB | VAL | 114 | 99.989 | -27.808 | 23.413 | 1.00 | 7.82 | L | C |
| ATOM | 3941 | CG1 | VAL | 114 | 100.921 | -27.972 | 22.212 | 1.00 | 4.17 | L | C |
| ATOM | 3942 | CG2 | VAL | 114 | 99.331 | -29.100 | 23.777 | 1.00 | 9.35 | L | C |

Fig. 19: A-55

```
ATOM   3943  C    VAL  114   99.992  -27.558  25.899  1.00   9.84  L  C
ATOM   3944  O    VAL  114  100.318  -28.494  26.628  1.00  12.49  L  O
ATOM   3945  N    PHE  115   98.981  -26.728  26.153  1.00  26.11  L  N
ATOM   3946  CA   PHE  115   98.109  -26.840  27.318  1.00  30.12  L  C
ATOM   3947  CB   PHE  115   98.581  -25.896  28.416  1.00  36.06  L  C
ATOM   3948  CG   PHE  115  100.030  -26.015  28.706  1.00  35.84  L  C
ATOM   3949  CD1  PHE  115  100.505  -27.040  29.513  1.00  38.16  L  C
ATOM   3950  CD2  PHE  115  100.935  -25.146  28.115  1.00  34.45  L  C
ATOM   3951  CE1  PHE  115  101.854  -27.203  29.723  1.00  41.30  L  C
ATOM   3952  CE2  PHE  115  102.287  -25.302  28.319  1.00  38.56  L  C
ATOM   3953  CZ   PHE  115  102.749  -26.335  29.126  1.00  39.82  L  C
ATOM   3954  C    PHE  115   96.727  -26.410  26.873  1.00  32.06  L  C
ATOM   3955  O    PHE  115   96.590  -25.543  26.017  1.00  32.56  L  O
ATOM   3956  N    ILE  116   95.694  -27.018  27.432  1.00  24.34  L  N
ATOM   3957  CA   ILE  116   94.354  -26.608  27.069  1.00  18.54  L  C
ATOM   3958  CB   ILE  116   93.606  -27.735  26.309  1.00  15.62  L  C
ATOM   3959  CG2  ILE  116   93.239  -28.855  27.249  1.00   4.34  L  C
ATOM   3960  CG1  ILE  116   92.377  -27.145  25.615  1.00  12.45  L  C
ATOM   3961  CD1  ILE  116   91.695  -28.089  24.646  1.00   4.28  L  C
ATOM   3962  C    ILE  116   93.661  -26.233  28.371  1.00  19.64  L  C
ATOM   3963  O    ILE  116   93.931  -26.834  29.412  1.00  19.05  L  O
ATOM   3964  N    PHE  117   92.802  -25.217  28.308  1.00  17.52  L  N
ATOM   3965  CA   PHE  117   92.066  -24.715  29.475  1.00  21.17  L  C
ATOM   3966  CB   PHE  117   92.501  -23.295  29.828  1.00  22.98  L  C
ATOM   3967  CG   PHE  117   93.922  -23.177  30.280  1.00  26.62  L  C
ATOM   3968  CD1  PHE  117   94.293  -23.562  31.559  1.00  29.31  L  C
ATOM   3969  CD2  PHE  117   94.882  -22.653  29.433  1.00  28.01  L  C
ATOM   3970  CE1  PHE  117   95.599  -23.421  31.988  1.00  28.27  L  C
ATOM   3971  CE2  PHE  117   96.186  -22.511  29.854  1.00  26.58  L  C
ATOM   3972  CZ   PHE  117   96.550  -22.895  31.134  1.00  28.58  L  C
ATOM   3973  C    PHE  117   90.585  -24.642  29.194  1.00  24.71  L  C
ATOM   3974  O    PHE  117   90.167  -23.964  28.261  1.00  29.18  L  O
ATOM   3975  N    PRO  118   89.768  -25.323  30.007  1.00  23.78  L  N
ATOM   3976  CD   PRO  118   90.235  -26.376  30.926  1.00   9.40  L  C
ATOM   3977  CA   PRO  118   88.300  -25.354  29.883  1.00  26.26  L  C
ATOM   3978  CB   PRO  118   87.907  -26.568  30.718  1.00   9.92  L  C
ATOM   3979  CG   PRO  118   89.159  -27.404  30.763  1.00  12.26  L  C
ATOM   3980  C    PRO  118   87.660  -24.081  30.455  1.00  29.72  L  C
ATOM   3981  O    PRO  118   88.231  -23.440  31.338  1.00  31.19  L  O
ATOM   3982  N    PRO  119   86.464  -23.699  29.966  1.00   9.50  L  N
ATOM   3983  CD   PRO  119   85.678  -24.330  28.892  1.00  26.21  L  C
ATOM   3984  CA   PRO  119   85.787  -22.493  30.479  1.00   9.82  L  C
ATOM   3985  CB   PRO  119   84.413  -22.555  29.826  1.00  24.20  L  C
ATOM   3986  CG   PRO  119   84.703  -23.219  28.519  1.00  27.52  L  C
ATOM   3987  C    PRO  119   85.682  -22.566  32.001  1.00  15.21  L  C
ATOM   3988  O    PRO  119   85.463  -23.630  32.561  1.00  17.89  L  O
ATOM   3989  N    SER  120   85.843  -21.435  32.665  1.00  31.09  L  N
ATOM   3990  CA   SER  120   85.765  -21.378  34.118  1.00  35.08  L  C
ATOM   3991  CB   SER  120   86.299  -20.027  34.586  1.00  17.54  L  C
ATOM   3992  OG   SER  120   85.709  -18.983  33.832  1.00  27.86  L  O
ATOM   3993  C    SER  120   84.334  -21.550  34.623  1.00  35.73  L  C
ATOM   3994  O    SER  120   83.370  -21.381  33.869  1.00  35.32  L  O
ATOM   3995  N    ASP  121   84.185  -21.896  35.897  1.00  24.20  L  N
ATOM   3996  CA   ASP  121   82.842  -22.015  36.465  1.00  27.07  L  C
ATOM   3997  CB   ASP  121   82.897  -22.458  37.937  1.00  55.35  L  C
ATOM   3998  CG   ASP  121   83.160  -23.950  38.101  1.00  60.98  L  C
ATOM   3999  OD1  ASP  121   82.573  -24.736  37.331  1.00  62.35  L  O
ATOM   4000  OD2  ASP  121   83.934  -24.337  39.008  1.00  63.66  L  O
ATOM   4001  C    ASP  121   82.194  -20.627  36.384  1.00  26.11  L  C
ATOM   4002  O    ASP  121   81.053  -20.474  35.941  1.00  23.12  L  O
ATOM   4003  N    GLU  122   82.954  -19.617  36.794  1.00  48.87  L  N
ATOM   4004  CA   GLU  122   82.490  -18.234  36.797  1.00  47.43  L  C
ATOM   4005  CB   GLU  122   83.596  -17.328  37.348  1.00  56.26  L  C
ATOM   4006  CG   GLU  122   83.180  -15.870  37.529  1.00  59.80  L  C
ATOM   4007  CD   GLU  122   84.328  -14.966  37.984  1.00  63.49  L  C
ATOM   4008  OE1  GLU  122   84.099  -13.741  38.109  1.00  64.12  L  O
ATOM   4009  OE2  GLU  122   85.453  -15.472  38.213  1.00  63.98  L  O
ATOM   4010  C    GLU  122   82.018  -17.703  35.434  1.00  47.22  L  C
ATOM   4011  O    GLU  122   80.884  -17.232  35.303  1.00  45.96  L  O
ATOM   4012  N    GLN  123   82.881  -17.774  34.424  1.00  34.52  L  N
ATOM   4013  CA   GLN  123   82.523  -17.273  33.102  1.00  32.32  L  C
ATOM   4014  CB   GLN  123   83.643  -17.511  32.097  1.00  23.68  L  C
ATOM   4015  CG   GLN  123   83.286  -17.000  30.723  1.00  24.85  L  C
```

Fig. 19: A-56

| ATOM | 4016 | CD | GLN | 123 | 84.089 | -17.644 | 29.635 | 1.00 | 26.94 | L | C |
| --- | --- | --- | --- | --- | --- | --- | --- | --- | --- | --- | --- |
| ATOM | 4017 | OE1 | GLN | 123 | 83.877 | -17.369 | 28.463 | 1.00 | 23.36 | L | O |
| ATOM | 4018 | NE2 | GLN | 123 | 85.017 | -18.511 | 30.010 | 1.00 | 24.66 | L | N |
| ATOM | 4019 | C | GLN | 123 | 81.256 | -17.909 | 32.565 | 1.00 | 32.32 | L | C |
| ATOM | 4020 | O | GLN | 123 | 80.424 | -17.233 | 31.969 | 1.00 | 29.27 | L | O |
| ATOM | 4021 | N | LEU | 124 | 81.128 | -19.218 | 32.745 | 1.00 | 36.22 | L | N |
| ATOM | 4022 | CA | LEU | 124 | 79.938 | -19.926 | 32.288 | 1.00 | 37.57 | L | C |
| ATOM | 4023 | CB | LEU | 124 | 80.075 | -21.425 | 32.570 | 1.00 | 20.16 | L | C |
| ATOM | 4024 | CG | LEU | 124 | 80.878 | -22.173 | 31.498 | 1.00 | 19.96 | L | C |
| ATOM | 4025 | CD1 | LEU | 124 | 81.099 | -23.623 | 31.892 | 1.00 | 15.21 | L | C |
| ATOM | 4026 | CD2 | LEU | 124 | 80.123 | -22.085 | 30.176 | 1.00 | 18.53 | L | C |
| ATOM | 4027 | C | LEU | 124 | 78.722 | -19.355 | 33.003 | 1.00 | 41.33 | L | C |
| ATOM | 4028 | O | LEU | 124 | 77.648 | -19.204 | 32.417 | 1.00 | 43.14 | L | O |
| ATOM | 4029 | N | LYS | 125 | 78.912 | -19.022 | 34.274 | 1.00 | 101.23 | L | N |
| ATOM | 4030 | CA | LYS | 125 | 77.856 | -18.441 | 35.090 | 1.00 | 102.45 | L | C |
| ATOM | 4031 | CB | LYS | 125 | 78.355 | -18.285 | 36.534 | 1.00 | 60.11 | L | C |
| ATOM | 4032 | CG | LYS | 125 | 77.286 | -18.376 | 37.612 | 1.00 | 62.95 | L | C |
| ATOM | 4033 | CD | LYS | 125 | 76.737 | -19.797 | 37.713 | 1.00 | 68.67 | L | C |
| ATOM | 4034 | CE | LYS | 125 | 75.726 | -19.942 | 38.847 | 1.00 | 73.14 | L | C |
| ATOM | 4035 | NZ | LYS | 125 | 75.101 | -21.299 | 38.895 | 1.00 | 74.11 | L | N |
| ATOM | 4036 | C | LYS | 125 | 77.545 | -17.065 | 34.494 | 1.00 | 104.22 | L | C |
| ATOM | 4037 | O | LYS | 125 | 77.004 | -16.195 | 35.168 | 1.00 | 105.97 | L | O |
| ATOM | 4038 | N | SER | 126 | 77.892 | -16.880 | 33.222 | 1.00 | 44.02 | L | N |
| ATOM | 4039 | CA | SER | 126 | 77.693 | -15.614 | 32.522 | 1.00 | 43.14 | L | C |
| ATOM | 4040 | CB | SER | 126 | 79.045 | -14.925 | 32.308 | 1.00 | 48.89 | L | C |
| ATOM | 4041 | OG | SER | 126 | 78.953 | -13.915 | 31.324 | 1.00 | 52.18 | L | O |
| ATOM | 4042 | C | SER | 126 | 76.995 | -15.769 | 31.176 | 1.00 | 41.22 | L | C |
| ATOM | 4043 | O | SER | 126 | 76.469 | -14.802 | 30.631 | 1.00 | 40.32 | L | O |
| ATOM | 4044 | N | GLY | 127 | 77.007 | -16.978 | 30.626 | 1.00 | 29.57 | L | N |
| ATOM | 4045 | CA | GLY | 127 | 76.340 | -17.190 | 29.355 | 1.00 | 30.30 | L | C |
| ATOM | 4046 | C | GLY | 127 | 77.266 | -17.332 | 28.168 | 1.00 | 29.68 | L | C |
| ATOM | 4047 | O | GLY | 127 | 76.818 | -17.391 | 27.022 | 1.00 | 30.41 | L | O |
| ATOM | 4048 | N | THR | 128 | 78.564 | -17.375 | 28.432 | 1.00 | 60.53 | L | N |
| ATOM | 4049 | CA | THR | 128 | 79.530 | -17.531 | 27.360 | 1.00 | 57.77 | L | C |
| ATOM | 4050 | CB | THR | 128 | 80.105 | -16.180 | 26.921 | 1.00 | 55.78 | L | C |
| ATOM | 4051 | OG1 | THR | 128 | 79.080 | -15.424 | 26.264 | 1.00 | 56.94 | L | O |
| ATOM | 4052 | CG2 | THR | 128 | 81.259 | -16.381 | 25.960 | 1.00 | 54.81 | L | C |
| ATOM | 4053 | C | THR | 128 | 80.643 | -18.434 | 27.830 | 1.00 | 56.24 | L | C |
| ATOM | 4054 | O | THR | 128 | 80.979 | -18.446 | 29.015 | 1.00 | 51.99 | L | O |
| ATOM | 4055 | N | ALA | 129 | 81.201 | -19.203 | 26.901 | 1.00 | 18.93 | L | N |
| ATOM | 4056 | CA | ALA | 129 | 82.275 | -20.125 | 27.232 | 1.00 | 17.83 | L | C |
| ATOM | 4057 | CB | ALA | 129 | 81.779 | -21.558 | 27.108 | 1.00 | 65.23 | L | C |
| ATOM | 4058 | C | ALA | 129 | 83.512 | -19.937 | 26.374 | 1.00 | 17.59 | L | C |
| ATOM | 4059 | O | ALA | 129 | 83.443 | -19.993 | 25.148 | 1.00 | 23.96 | L | O |
| ATOM | 4060 | N | SER | 130 | 84.652 | -19.729 | 27.020 | 1.00 | 24.31 | L | N |
| ATOM | 4061 | CA | SER | 130 | 85.905 | -19.560 | 26.298 | 1.00 | 19.76 | L | C |
| ATOM | 4062 | CB | SER | 130 | 86.565 | -18.256 | 26.741 | 1.00 | 18.21 | L | C |
| ATOM | 4063 | OG | SER | 130 | 85.724 | -17.142 | 26.477 | 1.00 | 20.32 | L | O |
| ATOM | 4064 | C | SER | 130 | 86.835 | -20.755 | 26.573 | 1.00 | 16.63 | L | C |
| ATOM | 4065 | O | SER | 130 | 87.037 | -21.141 | 27.732 | 1.00 | 19.43 | L | O |
| ATOM | 4066 | N | VAL | 131 | 87.370 | -21.371 | 25.521 | 1.00 | 11.62 | L | N |
| ATOM | 4067 | CA | VAL | 131 | 88.294 | -22.502 | 25.686 | 1.00 | 9.15 | L | C |
| ATOM | 4068 | CB | VAL | 131 | 87.848 | -23.743 | 24.872 | 1.00 | 17.04 | L | C |
| ATOM | 4069 | CG1 | VAL | 131 | 88.738 | -24.927 | 25.196 | 1.00 | 21.32 | L | C |
| ATOM | 4070 | CG2 | VAL | 131 | 86.413 | -24.081 | 25.180 | 1.00 | 16.62 | L | C |
| ATOM | 4071 | C | VAL | 131 | 89.647 | -22.030 | 25.156 | 1.00 | 9.42 | L | C |
| ATOM | 4072 | O | VAL | 131 | 89.731 | -21.557 | 24.025 | 1.00 | 13.02 | L | O |
| ATOM | 4073 | N | VAL | 132 | 90.704 | -22.146 | 25.956 | 1.00 | 21.24 | L | N |
| ATOM | 4074 | CA | VAL | 132 | 92.011 | -21.677 | 25.501 | 1.00 | 16.30 | L | C |
| ATOM | 4075 | CB | VAL | 132 | 92.573 | -20.538 | 26.414 | 1.00 | 43.77 | L | C |
| ATOM | 4076 | CG1 | VAL | 132 | 93.958 | -20.122 | 25.934 | 1.00 | 47.77 | L | C |
| ATOM | 4077 | CG2 | VAL | 132 | 91.645 | -19.324 | 26.393 | 1.00 | 44.24 | L | C |
| ATOM | 4078 | C | VAL | 132 | 93.081 | -22.743 | 25.374 | 1.00 | 17.14 | L | C |
| ATOM | 4079 | O | VAL | 132 | 93.372 | -23.482 | 26.320 | 1.00 | 14.49 | L | O |
| ATOM | 4080 | N | CYS | 133 | 93.662 | -22.793 | 24.178 | 1.00 | 23.86 | L | N |
| ATOM | 4081 | CA | CYS | 133 | 94.737 | -23.713 | 23.822 | 1.00 | 24.13 | L | C |
| ATOM | 4082 | C | CYS | 133 | 96.034 | -22.880 | 23.891 | 1.00 | 24.10 | L | C |
| ATOM | 4083 | O | CYS | 133 | 96.072 | -21.744 | 23.425 | 1.00 | 27.83 | L | O |
| ATOM | 4084 | CB | CYS | 133 | 94.486 | -24.219 | 22.399 | 1.00 | 19.56 | L | C |
| ATOM | 4085 | SG | CYS | 133 | 95.558 | -25.537 | 21.738 | 1.00 | 32.96 | L | S |
| ATOM | 4086 | N | LEU | 134 | 97.085 | -23.432 | 24.482 | 1.00 | 36.02 | L | N |
| ATOM | 4087 | CA | LEU | 134 | 98.343 | -22.709 | 24.591 | 1.00 | 34.35 | L | C |
| ATOM | 4088 | CB | LEU | 134 | 98.658 | -22.383 | 26.058 | 1.00 | 16.71 | L | C |

Fig. 19: A-57

```
ATOM   4089  CG   LEU  134    100.079  -21.843  26.376  1.00  12.52  L  C
ATOM   4090  CD1  LEU  134    100.297  -20.468  25.729  1.00   9.26  L  C
ATOM   4091  CD2  LEU  134    100.275  -21.746  27.892  1.00   9.75  L  C
ATOM   4092  C    LEU  134     99.532  -23.457  24.001  1.00  33.88  L  C
ATOM   4093  O    LEU  134     99.820  -24.595  24.378  1.00  33.96  L  O
ATOM   4094  N    LEU  135    100.206  -22.802  23.060  1.00  23.69  L  N
ATOM   4095  CA   LEU  135    101.406  -23.336  22.441  1.00  29.22  L  C
ATOM   4096  CB   LEU  135    101.353  -23.150  20.926  1.00   1.87  L  C
ATOM   4097  CG   LEU  135    100.337  -24.016  20.168  1.00   4.32  L  C
ATOM   4098  CD1  LEU  135     98.962  -23.751  20.672  1.00   5.12  L  C
ATOM   4099  CD2  LEU  135    100.392  -23.713  18.681  1.00   3.70  L  C
ATOM   4100  C    LEU  135    102.454  -22.437  23.097  1.00  29.43  L  C
ATOM   4101  O    LEU  135    102.401  -21.216  22.977  1.00  30.81  L  O
ATOM   4102  N    ASN  136    103.394  -23.047  23.810  1.00  17.75  L  N
ATOM   4103  CA   ASN  136    104.393  -22.299  24.550  1.00  20.05  L  C
ATOM   4104  CB   ASN  136    104.179  -22.576  26.016  1.00  15.03  L  C
ATOM   4105  CG   ASN  136    104.905  -21.615  26.885  1.00  19.57  L  C
ATOM   4106  OD1  ASN  136    105.767  -22.017  27.666  1.00  25.01  L  O
ATOM   4107  ND2  ASN  136    104.569  -20.327  26.769  1.00  19.54  L  N
ATOM   4108  C    ASN  136    105.856  -22.526  24.212  1.00  18.78  L  C
ATOM   4109  O    ASN  136    106.283  -23.651  23.963  1.00  17.25  L  O
ATOM   4110  N    ASN  137    106.619  -21.436  24.240  1.00  28.11  L  N
ATOM   4111  CA   ASN  137    108.053  -21.425  23.950  1.00  27.19  L  C
ATOM   4112  CB   ASN  137    108.869  -21.844  25.173  1.00  13.82  L  C
ATOM   4113  CG   ASN  137    108.594  -20.986  26.387  1.00  24.17  L  C
ATOM   4114  OD1  ASN  137    108.027  -19.901  26.281  1.00  19.30  L  O
ATOM   4115  ND2  ASN  137    109.009  -21.468  27.558  1.00  29.25  L  N
ATOM   4116  C    ASN  137    108.486  -22.292  22.783  1.00  25.42  L  C
ATOM   4117  O    ASN  137    109.125  -23.324  22.977  1.00  28.31  L  O
ATOM   4118  N    PHE  138    108.152  -21.880  21.571  1.00  45.01  L  N
ATOM   4119  CA   PHE  138    108.557  -22.652  20.412  1.00  41.21  L  C
ATOM   4120  CB   PHE  138    107.362  -23.361  19.777  1.00  23.11  L  C
ATOM   4121  CG   PHE  138    106.230  -22.452  19.442  1.00  20.89  L  C
ATOM   4122  CD1  PHE  138    105.342  -22.043  20.433  1.00  18.63  L  C
ATOM   4123  CD2  PHE  138    106.055  -21.993  18.137  1.00  19.93  L  C
ATOM   4124  CE1  PHE  138    104.289  -21.189  20.134  1.00  11.59  L  C
ATOM   4125  CE2  PHE  138    105.010  -21.138  17.818  1.00  16.52  L  C
ATOM   4126  CZ   PHE  138    104.118  -20.730  18.818  1.00  14.07  L  C
ATOM   4127  C    PHE  138    109.248  -21.794  19.369  1.00  36.81  L  C
ATOM   4128  O    PHE  138    109.456  -20.594  19.559  1.00  35.37  L  O
ATOM   4129  N    TYR  139    109.606  -22.437  18.267  1.00  17.70  L  N
ATOM   4130  CA   TYR  139    110.283  -21.797  17.159  1.00  20.93  L  C
ATOM   4131  CB   TYR  139    111.660  -21.300  17.579  1.00  31.56  L  C
ATOM   4132  CG   TYR  139    112.317  -20.472  16.502  1.00  31.46  L  C
ATOM   4133  CD1  TYR  139    112.207  -19.083  16.502  1.00  26.49  L  C
ATOM   4134  CE1  TYR  139    112.725  -18.327  15.462  1.00  25.20  L  C
ATOM   4135  CD2  TYR  139    112.974  -21.083  15.428  1.00  25.20  L  C
ATOM   4136  CE2  TYR  139    113.490  -20.336  14.386  1.00  25.20  L  C
ATOM   4137  CZ   TYR  139    113.358  -18.960  14.407  1.00  25.20  L  C
ATOM   4138  OH   TYR  139    113.820  -18.216  13.353  1.00  28.00  L  O
ATOM   4139  C    TYR  139    110.447  -22.917  16.166  1.00  20.32  L  C
ATOM   4140  O    TYR  139    110.798  -24.022  16.550  1.00  25.25  L  O
ATOM   4141  N    PRO  140    110.223  -22.662  14.876  1.00  34.32  L  N
ATOM   4142  CD   PRO  140    110.342  -23.783  13.937  1.00   6.42  L  C
ATOM   4143  CA   PRO  140    109.824  -21.443  14.171  1.00  30.02  L  C
ATOM   4144  CB   PRO  140    109.691  -21.901  12.723  1.00   2.76  L  C
ATOM   4145  CG   PRO  140    110.570  -23.070  12.643  1.00   4.42  L  C
ATOM   4146  C    PRO  140    108.502  -20.939  14.685  1.00  31.53  L  C
ATOM   4147  O    PRO  140    107.830  -21.612  15.466  1.00  29.36  L  O
ATOM   4148  N    ARG  141    108.119  -19.764  14.203  1.00  22.83  L  N
ATOM   4149  CA   ARG  141    106.871  -19.115  14.588  1.00  27.99  L  C
ATOM   4150  CB   ARG  141    106.931  -17.657  14.148  1.00  21.70  L  C
ATOM   4151  CG   ARG  141    105.753  -16.783  14.473  1.00  25.87  L  C
ATOM   4152  CD   ARG  141    106.157  -15.358  14.129  1.00  37.20  L  C
ATOM   4153  NE   ARG  141    105.187  -14.366  14.564  1.00  43.19  L  N
ATOM   4154  CZ   ARG  141    104.001  -14.188  13.995  1.00  43.90  L  C
ATOM   4155  NH1  ARG  141    103.642  -14.941  12.960  1.00  39.57  L  N
ATOM   4156  NH2  ARG  141    103.173  -13.262  14.464  1.00  42.44  L  N
ATOM   4157  C    ARG  141    105.668  -19.798  13.960  1.00  30.81  L  C
ATOM   4158  O    ARG  141    104.585  -19.815  14.537  1.00  34.71  L  O
ATOM   4159  N    GLU  142    105.860  -20.365  12.776  1.00  28.20  L  N
ATOM   4160  CA   GLU  142    104.756  -21.013  12.091  1.00  24.33  L  C
ATOM   4161  CB   GLU  142    105.171  -21.552  10.725  1.00   7.98  L  C
```

Fig. 19: A-58

| ATOM | 4162 | CG | GLU | 142 | 105.741 | -20.523 | 9.781 | 1.00 | 19.00 | L | C |
|---|---|---|---|---|---|---|---|---|---|---|---|
| ATOM | 4163 | CD | GLU | 142 | 107.096 | -20.051 | 10.217 | 1.00 | 27.12 | L | C |
| ATOM | 4164 | OE1 | GLU | 142 | 107.152 | -18.970 | 10.837 | 1.00 | 31.02 | L | O |
| ATOM | 4165 | OE2 | GLU | 142 | 108.095 | -20.772 | 9.952 | 1.00 | 33.88 | L | O |
| ATOM | 4166 | C | GLU | 142 | 104.154 | -22.151 | 12.878 | 1.00 | 22.94 | L | C |
| ATOM | 4167 | O | GLU | 142 | 104.753 | -23.220 | 13.021 | 1.00 | 26.95 | L | O |
| ATOM | 4168 | N | ALA | 143 | 102.958 | -21.909 | 13.386 | 1.00 | 30.55 | L | N |
| ATOM | 4169 | CA | ALA | 143 | 102.238 | -22.914 | 14.130 | 1.00 | 32.81 | L | C |
| ATOM | 4170 | CB | ALA | 143 | 102.260 | -22.593 | 15.640 | 1.00 | 21.32 | L | C |
| ATOM | 4171 | C | ALA | 143 | 100.819 | -22.862 | 13.579 | 1.00 | 34.94 | L | C |
| ATOM | 4172 | O | ALA | 143 | 100.373 | -21.832 | 13.058 | 1.00 | 38.69 | L | O |
| ATOM | 4173 | N | LYS | 144 | 100.120 | -23.981 | 13.677 | 1.00 | 46.96 | L | N |
| ATOM | 4174 | CA | LYS | 144 | 98.761 | -24.047 | 13.197 | 1.00 | 49.64 | L | C |
| ATOM | 4175 | CB | LYS | 144 | 98.734 | -24.807 | 11.870 | 1.00 | 34.36 | L | C |
| ATOM | 4176 | CG | LYS | 144 | 97.631 | -24.370 | 10.922 | 1.00 | 44.31 | L | C |
| ATOM | 4177 | CD | LYS | 144 | 97.441 | -25.358 | 9.772 | 1.00 | 55.06 | L | C |
| ATOM | 4178 | CE | LYS | 144 | 96.888 | -26.699 | 10.279 | 1.00 | 57.35 | L | C |
| ATOM | 4179 | NZ | LYS | 144 | 96.807 | -27.761 | 9.225 | 1.00 | 58.76 | L | N |
| ATOM | 4180 | C | LYS | 144 | 97.934 | -24.771 | 14.266 | 1.00 | 52.97 | L | C |
| ATOM | 4181 | O | LYS | 144 | 98.340 | -25.822 | 14.775 | 1.00 | 51.55 | L | O |
| ATOM | 4182 | N | VAL | 145 | 96.791 | -24.194 | 14.630 | 1.00 | 15.87 | L | N |
| ATOM | 4183 | CA | VAL | 145 | 95.927 | -24.813 | 15.629 | 1.00 | 21.71 | L | C |
| ATOM | 4184 | CB | VAL | 145 | 95.790 | -23.937 | 16.905 | 1.00 | 8.53 | L | C |
| ATOM | 4185 | CG1 | VAL | 145 | 94.817 | -24.597 | 17.889 | 1.00 | 7.53 | L | C |
| ATOM | 4186 | CG2 | VAL | 145 | 97.151 | -23.769 | 17.570 | 1.00 | 8.28 | L | C |
| ATOM | 4187 | C | VAL | 145 | 94.536 | -25.074 | 15.073 | 1.00 | 25.32 | L | C |
| ATOM | 4188 | O | VAL | 145 | 93.909 | -24.193 | 14.497 | 1.00 | 27.49 | L | O |
| ATOM | 4189 | N | GLN | 146 | 94.055 | -26.296 | 15.231 | 1.00 | 39.17 | L | N |
| ATOM | 4190 | CA | GLN | 146 | 92.729 | -26.611 | 14.743 | 1.00 | 38.70 | L | C |
| ATOM | 4191 | CB | GLN | 146 | 92.798 | -27.079 | 13.653 | 1.00 | 72.09 | L | C |
| ATOM | 4192 | CG | GLN | 146 | 93.678 | -27.281 | 12.482 | 1.00 | 76.00 | L | C |
| ATOM | 4193 | CD | GLN | 146 | 93.630 | -28.276 | 11.339 | 1.00 | 75.94 | L | C |
| ATOM | 4194 | OE1 | GLN | 146 | 92.616 | -28.399 | 10.654 | 1.00 | 76.92 | L | O |
| ATOM | 4195 | NE2 | GLN | 146 | 94.730 | -28.997 | 11.130 | 1.00 | 77.33 | L | N |
| ATOM | 4196 | C | GLN | 146 | 91.880 | -27.094 | 15.904 | 1.00 | 37.70 | L | C |
| ATOM | 4197 | O | GLN | 146 | 92.302 | -27.965 | 16.667 | 1.00 | 34.46 | L | O |
| ATOM | 4198 | N | TRP | 147 | 90.699 | -26.498 | 16.048 | 1.00 | 30.85 | L | N |
| ATOM | 4199 | CA | TRP | 147 | 89.777 | -26.878 | 17.102 | 1.00 | 30.91 | L | C |
| ATOM | 4200 | CB | TRP | 147 | 88.947 | -25.687 | 17.556 | 1.00 | 36.68 | L | C |
| ATOM | 4201 | CG | TRP | 147 | 89.689 | -24.788 | 18.432 | 1.00 | 34.29 | L | C |
| ATOM | 4202 | CD2 | TRP | 147 | 89.927 | -24.969 | 19.825 | 1.00 | 32.37 | L | C |
| ATOM | 4203 | CE2 | TRP | 147 | 90.723 | -23.885 | 20.258 | 1.00 | 33.31 | L | C |
| ATOM | 4204 | CE3 | TRP | 147 | 89.552 | -25.943 | 20.752 | 1.00 | 31.13 | L | C |
| ATOM | 4205 | CD1 | TRP | 147 | 90.326 | -23.641 | 18.077 | 1.00 | 36.68 | L | C |
| ATOM | 4206 | NE1 | TRP | 147 | 90.951 | -23.086 | 19.168 | 1.00 | 33.41 | L | N |
| ATOM | 4207 | CZ2 | TRP | 147 | 91.150 | -23.747 | 21.587 | 1.00 | 31.66 | L | C |
| ATOM | 4208 | CZ3 | TRP | 147 | 89.977 | -25.808 | 22.073 | 1.00 | 33.39 | L | C |
| ATOM | 4209 | CH2 | TRP | 147 | 90.767 | -24.716 | 22.476 | 1.00 | 33.58 | L | C |
| ATOM | 4210 | C | TRP | 147 | 88.844 | -27.963 | 16.611 | 1.00 | 33.36 | L | C |
| ATOM | 4211 | O | TRP | 147 | 88.440 | -27.968 | 15.453 | 1.00 | 34.42 | L | O |
| ATOM | 4212 | N | LYS | 148 | 88.495 | -28.877 | 17.501 | 1.00 | 28.86 | L | N |
| ATOM | 4213 | CA | LYS | 148 | 87.609 | -29.958 | 17.147 | 1.00 | 29.96 | L | C |
| ATOM | 4214 | CB | LYS | 148 | 88.431 | -31.196 | 16.787 | 1.00 | 35.94 | L | C |
| ATOM | 4215 | CG | LYS | 148 | 88.353 | -31.585 | 15.320 | 1.00 | 39.31 | L | C |
| ATOM | 4216 | CD | LYS | 148 | 89.726 | -31.865 | 14.715 | 1.00 | 45.24 | L | C |
| ATOM | 4217 | CE | LYS | 148 | 90.421 | -33.078 | 15.337 | 1.00 | 45.54 | L | C |
| ATOM | 4218 | NZ | LYS | 148 | 91.826 | -33.267 | 14.818 | 1.00 | 44.96 | L | N |
| ATOM | 4219 | C | LYS | 148 | 86.712 | -30.227 | 18.340 | 1.00 | 32.40 | L | C |
| ATOM | 4220 | O | LYS | 148 | 87.297 | -30.505 | 19.438 | 1.00 | 31.51 | L | O |
| ATOM | 4221 | N | VAL | 149 | 85.404 | -30.124 | 18.118 | 1.00 | 22.85 | L | N |
| ATOM | 4222 | CA | VAL | 149 | 84.406 | -30.352 | 19.161 | 1.00 | 20.04 | L | C |
| ATOM | 4223 | CB | VAL | 149 | 83.453 | -29.167 | 19.269 | 1.00 | 1.90 | L | C |
| ATOM | 4224 | CG1 | VAL | 149 | 82.408 | -29.440 | 20.364 | 1.00 | 1.90 | L | C |
| ATOM | 4225 | CG2 | VAL | 149 | 84.242 | -27.899 | 19.563 | 1.00 | 1.90 | L | C |
| ATOM | 4226 | C | VAL | 149 | 83.580 | -31.605 | 18.862 | 1.00 | 23.24 | L | C |
| ATOM | 4227 | O | VAL | 149 | 82.835 | -31.642 | 17.883 | 1.00 | 24.43 | L | O |
| ATOM | 4228 | N | ASP | 150 | 83.679 | -32.611 | 19.731 | 1.00 | 18.00 | L | N |
| ATOM | 4229 | CA | ASP | 150 | 82.974 | -33.863 | 19.502 | 1.00 | 21.30 | L | C |
| ATOM | 4230 | CB | ASP | 150 | 81.464 | -33.661 | 19.459 | 1.00 | 45.33 | L | C |
| ATOM | 4231 | CG | ASP | 150 | 80.862 | -33.543 | 20.840 | 1.00 | 50.39 | L | C |
| ATOM | 4232 | OD1 | ASP | 150 | 81.334 | -34.248 | 21.760 | 1.00 | 51.76 | L | O |
| ATOM | 4233 | OD2 | ASP | 150 | 79.910 | -32.756 | 21.007 | 1.00 | 53.67 | L | O |
| ATOM | 4234 | C | ASP | 150 | 83.487 | -34.293 | 18.152 | 1.00 | 22.51 | L | C |

Fig. 19: A-59

| | | | | | | | | | | |
|---|---|---|---|---|---|---|---|---|---|---|
| ATOM | 4235 | O   | ASP | 150 | 82.737 | -34.683 | 17.268 | 1.00 | 23.76 | L | O |
| ATOM | 4236 | N   | ASN | 151 | 84.800 | -34.161 | 18.007 | 1.00 | 36.79 | L | N |
| ATOM | 4237 | CA  | ASN | 151 | 85.493 | -34.524 | 16.789 | 1.00 | 39.62 | L | C |
| ATOM | 4238 | CB  | ASN | 151 | 85.425 | -36.041 | 16.614 | 1.00 | 29.22 | L | C |
| ATOM | 4239 | CG  | ASN | 151 | 86.220 | -36.776 | 17.683 | 1.00 | 38.58 | L | C |
| ATOM | 4240 | OD1 | ASN | 151 | 87.450 | -36.736 | 17.686 | 1.00 | 42.16 | L | O |
| ATOM | 4241 | ND2 | ASN | 151 | 85.522 | -37.430 | 18.608 | 1.00 | 39.63 | L | N |
| ATOM | 4242 | C   | ASN | 151 | 84.985 | -33.778 | 15.557 | 1.00 | 37.90 | L | C |
| ATOM | 4243 | O   | ASN | 151 | 85.224 | -34.183 | 14.425 | 1.00 | 41.98 | L | O |
| ATOM | 4244 | N   | ALA | 152 | 84.293 | -32.672 | 15.793 | 1.00 | 26.76 | L | N |
| ATOM | 4245 | CA  | ALA | 152 | 83.802 | -31.838 | 14.703 | 1.00 | 29.16 | L | C |
| ATOM | 4246 | CB  | ALA | 152 | 82.421 | -31.261 | 15.034 | 1.00 | 1.87  | L | C |
| ATOM | 4247 | C   | ALA | 152 | 84.801 | -30.698 | 14.501 | 1.00 | 30.47 | L | C |
| ATOM | 4248 | O   | ALA | 152 | 84.940 | -29.813 | 15.355 | 1.00 | 32.16 | L | O |
| ATOM | 4249 | N   | LEU | 153 | 85.502 | -30.724 | 13.375 | 1.00 | 37.66 | L | N |
| ATOM | 4250 | CA  | LEU | 153 | 86.470 | -29.684 | 13.073 | 1.00 | 38.47 | L | C |
| ATOM | 4251 | CB  | LEU | 153 | 87.021 | -29.896 | 11.656 | 1.00 | 33.69 | L | C |
| ATOM | 4252 | CG  | LEU | 153 | 87.944 | -28.864 | 11.005 | 1.00 | 36.76 | L | C |
| ATOM | 4253 | CD1 | LEU | 153 | 87.112 | -27.705 | 10.466 | 1.00 | 35.54 | L | C |
| ATOM | 4254 | CD2 | LEU | 153 | 88.999 | -28.394 | 12.004 | 1.00 | 35.80 | L | C |
| ATOM | 4255 | C   | LEU | 153 | 85.796 | -28.315 | 13.206 | 1.00 | 37.05 | L | C |
| ATOM | 4256 | O   | LEU | 153 | 84.632 | -28.150 | 12.870 | 1.00 | 37.53 | L | O |
| ATOM | 4257 | N   | GLN | 154 | 86.524 | -27.342 | 13.732 | 1.00 | 42.87 | L | N |
| ATOM | 4258 | CA  | GLN | 154 | 85.984 | -26.006 | 13.885 | 1.00 | 41.76 | L | C |
| ATOM | 4259 | CB  | GLN | 154 | 86.346 | -25.438 | 15.255 | 1.00 | 24.84 | L | C |
| ATOM | 4260 | CG  | GLN | 154 | 85.653 | -26.133 | 16.403 | 1.00 | 25.94 | L | C |
| ATOM | 4261 | CD  | GLN | 154 | 84.146 | -26.162 | 16.225 | 1.00 | 28.42 | L | C |
| ATOM | 4262 | OE1 | GLN | 154 | 83.495 | -25.115 | 16.127 | 1.00 | 30.98 | L | O |
| ATOM | 4263 | NE2 | GLN | 154 | 83.584 | -27.365 | 16.176 | 1.00 | 27.76 | L | N |
| ATOM | 4264 | C   | GLN | 154 | 86.574 | -25.139 | 12.793 | 1.00 | 40.20 | L | C |
| ATOM | 4265 | O   | GLN | 154 | 87.702 | -25.363 | 12.350 | 1.00 | 39.24 | L | O |
| ATOM | 4266 | N   | SER | 155 | 85.813 | -24.146 | 12.359 | 1.00 | 42.27 | L | N |
| ATOM | 4267 | CA  | SER | 155 | 86.269 | -23.257 | 11.306 | 1.00 | 44.34 | L | C |
| ATOM | 4268 | CB  | SER | 155 | 85.770 | -23.768 | 9.952  | 1.00 | 47.84 | L | C |
| ATOM | 4269 | OG  | SER | 155 | 86.319 | -23.035 | 8.872  | 1.00 | 49.98 | L | O |
| ATOM | 4270 | C   | SER | 155 | 85.693 | -21.888 | 11.600 | 1.00 | 40.94 | L | C |
| ATOM | 4271 | O   | SER | 155 | 86.208 | -20.864 | 11.160 | 1.00 | 39.18 | L | O |
| ATOM | 4272 | N   | GLY | 156 | 84.621 | -21.877 | 12.374 | 1.00 | 21.85 | L | N |
| ATOM | 4273 | CA  | GLY | 156 | 83.986 | -20.619 | 12.702 | 1.00 | 22.33 | L | C |
| ATOM | 4274 | C   | GLY | 156 | 84.732 | -19.585 | 13.544 | 1.00 | 22.19 | L | C |
| ATOM | 4275 | O   | GLY | 156 | 85.518 | -18.793 | 13.032 | 1.00 | 19.16 | L | O |
| ATOM | 4276 | N   | ASN | 157 | 84.484 | -19.595 | 14.850 | 1.00 | 39.06 | L | N |
| ATOM | 4277 | CA  | ASN | 157 | 85.088 | -18.595 | 15.697 | 1.00 | 40.50 | L | C |
| ATOM | 4278 | CB  | ASN | 157 | 83.992 | -17.700 | 16.281 | 1.00 | 106.22 | L | C |
| ATOM | 4279 | CG  | ASN | 157 | 83.201 | -16.977 | 15.200 | 1.00 | 109.22 | L | C |
| ATOM | 4280 | OD1 | ASN | 157 | 83.779 | -16.402 | 14.277 | 1.00 | 109.54 | L | O |
| ATOM | 4281 | ND2 | ASN | 157 | 81.874 | -16.999 | 15.313 | 1.00 | 114.95 | L | N |
| ATOM | 4282 | C   | ASN | 157 | 86.059 | -18.997 | 16.790 | 1.00 | 41.01 | L | C |
| ATOM | 4283 | O   | ASN | 157 | 85.713 | -19.566 | 17.827 | 1.00 | 40.41 | L | O |
| ATOM | 4284 | N   | SER | 158 | 87.299 | -18.635 | 16.520 | 1.00 | 42.44 | L | N |
| ATOM | 4285 | CA  | SER | 158 | 88.409 | -18.862 | 17.405 | 1.00 | 35.84 | L | C |
| ATOM | 4286 | CB  | SER | 158 | 89.078 | -20.173 | 17.047 | 1.00 | 10.55 | L | C |
| ATOM | 4287 | OG  | SER | 158 | 89.643 | -20.069 | 15.757 | 1.00 | 10.12 | L | O |
| ATOM | 4288 | C   | SER | 158 | 89.326 | -17.691 | 17.059 | 1.00 | 34.29 | L | C |
| ATOM | 4289 | O   | SER | 158 | 89.197 | -17.092 | 15.992 | 1.00 | 32.27 | L | O |
| ATOM | 4290 | N   | GLN | 159 | 90.238 | -17.345 | 17.952 | 1.00 | 34.35 | L | N |
| ATOM | 4291 | CA  | GLN | 159 | 91.133 | -16.250 | 17.652 | 1.00 | 31.73 | L | C |
| ATOM | 4292 | CB  | GLN | 159 | 90.538 | -14.932 | 18.130 | 1.00 | 20.18 | L | C |
| ATOM | 4293 | CG  | GLN | 159 | 89.399 | -14.413 | 17.266 | 1.00 | 21.46 | L | C |
| ATOM | 4294 | CD  | GLN | 159 | 89.053 | -12.981 | 17.608 | 1.00 | 25.67 | L | C |
| ATOM | 4295 | OE1 | GLN | 159 | 88.796 | -12.658 | 18.762 | 1.00 | 28.88 | L | O |
| ATOM | 4296 | NE2 | GLN | 159 | 89.051 | -12.114 | 16.606 | 1.00 | 25.13 | L | N |
| ATOM | 4297 | C   | GLN | 159 | 92.502 | -16.452 | 18.255 | 1.00 | 29.74 | L | C |
| ATOM | 4298 | O   | GLN | 159 | 92.647 | -16.711 | 19.449 | 1.00 | 28.24 | L | O |
| ATOM | 4299 | N   | GLU | 160 | 93.514 | -16.327 | 17.414 | 1.00 | 31.36 | L | N |
| ATOM | 4300 | CA  | GLU | 160 | 94.872 | -16.510 | 17.865 | 1.00 | 24.49 | L | C |
| ATOM | 4301 | CB  | GLU | 160 | 95.646 | -17.316 | 16.834 | 1.00 | 58.94 | L | C |
| ATOM | 4302 | CG  | GLU | 160 | 94.977 | -18.617 | 16.476 | 1.00 | 59.06 | L | C |
| ATOM | 4303 | CD  | GLU | 160 | 95.890 | -19.506 | 15.678 | 1.00 | 67.10 | L | C |
| ATOM | 4304 | OE1 | GLU | 160 | 95.463 | -20.619 | 15.285 | 1.00 | 71.37 | L | O |
| ATOM | 4305 | OE2 | GLU | 160 | 97.043 | -19.078 | 15.452 | 1.00 | 65.02 | L | O |
| ATOM | 4306 | C   | GLU | 160 | 95.591 | -15.199 | 18.140 | 1.00 | 20.89 | L | C |
| ATOM | 4307 | O   | GLU | 160 | 95.211 | -14.141 | 17.654 | 1.00 | 14.39 | L | O |

Fig. 19: A-60

| | | | | | | | | | | | |
|---|---|---|---|---|---|---|---|---|---|---|---|
| ATOM | 4308 | N | SER | 161 | 96.639 | -15.293 | 18.941 | 1.00 | 19.35 | L | N |
| ATOM | 4309 | CA | SER | 161 | 97.456 | -14.151 | 19.310 | 1.00 | 16.36 | L | C |
| ATOM | 4310 | CB | SER | 161 | 96.953 | -13.486 | 20.597 | 1.00 | 26.12 | L | C |
| ATOM | 4311 | OG | SER | 161 | 97.935 | -12.623 | 21.157 | 1.00 | 26.54 | L | O |
| ATOM | 4312 | C | SER | 161 | 98.811 | -14.751 | 19.556 | 1.00 | 11.36 | L | C |
| ATOM | 4313 | O | SER | 161 | 98.934 | -15.799 | 20.191 | 1.00 | 11.86 | L | O |
| ATOM | 4314 | N | VAL | 162 | 99.833 | -14.086 | 19.053 | 1.00 | 21.19 | L | N |
| ATOM | 4315 | CA | VAL | 162 | 101.170 | -14.592 | 19.215 | 1.00 | 22.81 | L | C |
| ATOM | 4316 | CB | VAL | 162 | 101.764 | -14.965 | 17.832 | 1.00 | 29.37 | L | C |
| ATOM | 4317 | CG1 | VAL | 162 | 101.449 | -13.865 | 16.834 | 1.00 | 33.68 | L | C |
| ATOM | 4318 | CG2 | VAL | 162 | 103.270 | -15.178 | 17.933 | 1.00 | 33.85 | L | C |
| ATOM | 4319 | C | VAL | 162 | 101.997 | -13.524 | 19.877 | 1.00 | 25.31 | L | C |
| ATOM | 4320 | O | VAL | 162 | 101.835 | -12.349 | 19.566 | 1.00 | 32.55 | L | O |
| ATOM | 4321 | N | THR | 163 | 102.861 | -13.928 | 20.805 | 1.00 | 22.97 | L | N |
| ATOM | 4322 | CA | THR | 163 | 103.735 | -12.975 | 21.475 | 1.00 | 21.36 | L | C |
| ATOM | 4323 | CB | THR | 163 | 104.424 | -13.567 | 22.719 | 1.00 | 4.31 | L | C |
| ATOM | 4324 | OG1 | THR | 163 | 105.214 | -14.705 | 22.342 | 1.00 | 10.67 | L | O |
| ATOM | 4325 | CG2 | THR | 163 | 103.411 | -13.966 | 23.748 | 1.00 | 4.70 | L | C |
| ATOM | 4326 | C | THR | 163 | 104.842 | -12.550 | 20.520 | 1.00 | 20.43 | L | C |
| ATOM | 4327 | O | THR | 163 | 104.880 | -12.951 | 19.350 | 1.00 | 20.01 | L | O |
| ATOM | 4328 | N | GLU | 164 | 105.741 | -11.722 | 21.022 | 1.00 | 16.64 | L | N |
| ATOM | 4329 | CA | GLU | 164 | 106.844 | -11.283 | 20.211 | 1.00 | 24.33 | L | C |
| ATOM | 4330 | CB | GLU | 164 | 107.182 | -9.828 | 20.515 | 1.00 | 53.60 | L | C |
| ATOM | 4331 | CG | GLU | 164 | 107.982 | -9.187 | 19.415 | 1.00 | 64.34 | L | C |
| ATOM | 4332 | CD | GLU | 164 | 107.202 | -9.144 | 18.126 | 1.00 | 70.19 | L | C |
| ATOM | 4333 | OE1 | GLU | 164 | 106.337 | -8.252 | 17.994 | 1.00 | 69.97 | L | O |
| ATOM | 4334 | OE2 | GLU | 164 | 107.442 | -10.011 | 17.257 | 1.00 | 73.61 | L | O |
| ATOM | 4335 | C | GLU | 164 | 107.989 | -12.190 | 20.635 | 1.00 | 22.81 | L | C |
| ATOM | 4336 | O | GLU | 164 | 107.990 | -12.697 | 21.765 | 1.00 | 25.48 | L | O |
| ATOM | 4337 | N | GLN | 165 | 108.948 | -12.407 | 19.734 | 1.00 | 26.35 | L | N |
| ATOM | 4338 | CA | GLN | 165 | 110.100 | -13.261 | 20.018 | 1.00 | 31.24 | L | C |
| ATOM | 4339 | CB | GLN | 165 | 111.181 | -13.024 | 18.967 | 1.00 | 24.53 | L | C |
| ATOM | 4340 | CG | GLN | 165 | 111.927 | -14.274 | 18.584 | 1.00 | 20.02 | L | C |
| ATOM | 4341 | CD | GLN | 165 | 112.911 | -14.054 | 17.454 | 1.00 | 22.62 | L | C |
| ATOM | 4342 | OE1 | GLN | 165 | 113.487 | -15.005 | 16.930 | 1.00 | 23.83 | L | O |
| ATOM | 4343 | NE2 | GLN | 165 | 113.118 | -12.794 | 17.080 | 1.00 | 19.11 | L | N |
| ATOM | 4344 | C | GLN | 165 | 110.633 | -12.941 | 21.412 | 1.00 | 35.11 | L | C |
| ATOM | 4345 | O | GLN | 165 | 110.857 | -11.783 | 21.739 | 1.00 | 31.98 | L | O |
| ATOM | 4346 | N | ASP | 166 | 110.826 | -13.963 | 22.236 | 1.00 | 20.85 | L | N |
| ATOM | 4347 | CA | ASP | 166 | 111.311 | -13.741 | 23.592 | 1.00 | 27.22 | L | C |
| ATOM | 4348 | CB | ASP | 166 | 111.206 | -15.030 | 24.402 | 1.00 | 40.40 | L | C |
| ATOM | 4349 | CG | ASP | 166 | 111.513 | -14.813 | 25.872 | 1.00 | 48.39 | L | C |
| ATOM | 4350 | OD1 | ASP | 166 | 112.706 | -14.808 | 26.246 | 1.00 | 51.89 | L | O |
| ATOM | 4351 | OD2 | ASP | 166 | 110.555 | -14.631 | 26.655 | 1.00 | 52.06 | L | O |
| ATOM | 4352 | C | ASP | 166 | 112.741 | -13.205 | 23.656 | 1.00 | 29.80 | L | C |
| ATOM | 4353 | O | ASP | 166 | 113.659 | -13.787 | 23.079 | 1.00 | 33.62 | L | O |
| ATOM | 4354 | N | SER | 167 | 112.923 | -12.098 | 24.371 | 1.00 | 40.62 | L | N |
| ATOM | 4355 | CA | SER | 167 | 114.238 | -11.463 | 24.521 | 1.00 | 38.35 | L | C |
| ATOM | 4356 | CB | SER | 167 | 114.089 | -10.092 | 25.191 | 1.00 | 42.38 | L | C |
| ATOM | 4357 | OG | SER | 167 | 113.564 | -10.221 | 26.499 | 1.00 | 53.10 | L | O |
| ATOM | 4358 | C | SER | 167 | 115.229 | -12.312 | 25.325 | 1.00 | 40.21 | L | C |
| ATOM | 4359 | O | SER | 167 | 116.373 | -11.913 | 25.544 | 1.00 | 45.86 | L | O |
| ATOM | 4360 | N | LYS | 168 | 114.777 | -13.475 | 25.782 | 1.00 | 39.00 | L | N |
| ATOM | 4361 | CA | LYS | 168 | 115.637 | -14.383 | 26.527 | 1.00 | 40.59 | L | C |
| ATOM | 4362 | CB | LYS | 168 | 114.966 | -14.809 | 27.837 | 1.00 | 73.78 | L | C |
| ATOM | 4363 | CG | LYS | 168 | 115.002 | -13.726 | 28.916 | 1.00 | 80.02 | L | C |
| ATOM | 4364 | CD | LYS | 168 | 114.141 | -12.523 | 28.554 | 1.00 | 89.23 | L | C |
| ATOM | 4365 | CE | LYS | 168 | 112.663 | -12.805 | 28.778 | 1.00 | 96.32 | L | C |
| ATOM | 4366 | NZ | LYS | 168 | 112.355 | -13.017 | 30.222 | 1.00 | 95.77 | L | N |
| ATOM | 4367 | C | LYS | 168 | 115.959 | -15.597 | 25.650 | 1.00 | 39.39 | L | C |
| ATOM | 4368 | O | LYS | 168 | 117.046 | -15.671 | 25.077 | 1.00 | 43.53 | L | O |
| ATOM | 4369 | N | ASP | 169 | 115.011 | -16.522 | 25.506 | 1.00 | 18.93 | L | N |
| ATOM | 4370 | CA | ASP | 169 | 115.240 | -17.716 | 24.686 | 1.00 | 15.08 | L | C |
| ATOM | 4371 | CB | ASP | 169 | 114.476 | -18.913 | 25.262 | 1.00 | 29.81 | L | C |
| ATOM | 4372 | CG | ASP | 169 | 112.992 | -18.648 | 25.407 | 1.00 | 32.60 | L | C |
| ATOM | 4373 | OD1 | ASP | 169 | 112.397 | -18.049 | 24.488 | 1.00 | 27.93 | L | O |
| ATOM | 4374 | OD2 | ASP | 169 | 112.415 | -19.054 | 26.441 | 1.00 | 29.85 | L | O |
| ATOM | 4375 | C | ASP | 169 | 114.914 | -17.596 | 23.193 | 1.00 | 15.61 | L | C |
| ATOM | 4376 | O | ASP | 169 | 115.038 | -18.571 | 22.459 | 1.00 | 9.73 | L | O |
| ATOM | 4377 | N | SER | 170 | 114.490 | -16.418 | 22.747 | 1.00 | 28.98 | L | N |
| ATOM | 4378 | CA | SER | 170 | 114.170 | -16.202 | 21.331 | 1.00 | 26.94 | L | C |
| ATOM | 4379 | CB | SER | 170 | 115.401 | -16.487 | 20.433 | 1.00 | 15.64 | L | C |
| ATOM | 4380 | OG | SER | 170 | 116.466 | -15.560 | 20.636 | 1.00 | 17.90 | L | O |

Fig. 19: A-61

| | | | | | | | | | | |
|---|---|---|---|---|---|---|---|---|---|---|
| ATOM | 4381 | C | SER | 170 | 112.995 | -17.042 | 20.825 | 1.00 | 25.42 | L | C |
| ATOM | 4382 | O | SER | 170 | 112.916 | -17.345 | 19.636 | 1.00 | 25.18 | L | O |
| ATOM | 4383 | N | THR | 171 | 112.071 | -17.411 | 21.702 | 1.00 | 22.07 | L | N |
| ATOM | 4384 | CA | THR | 171 | 110.946 | -18.222 | 21.247 | 1.00 | 22.16 | L | C |
| ATOM | 4385 | CB | THR | 171 | 110.658 | -19.406 | 22.212 | 1.00 | 16.53 | L | C |
| ATOM | 4386 | OG1 | THR | 171 | 110.127 | -18.911 | 23.452 | 1.00 | 18.93 | L | O |
| ATOM | 4387 | CG2 | THR | 171 | 111.939 | -20.191 | 22.471 | 1.00 | 18.13 | L | C |
| ATOM | 4388 | C | THR | 171 | 109.657 | -17.437 | 21.064 | 1.00 | 26.03 | L | C |
| ATOM | 4389 | O | THR | 171 | 109.601 | -16.235 | 21.327 | 1.00 | 31.48 | L | O |
| ATOM | 4390 | N | TYR | 172 | 108.633 | -18.147 | 20.596 | 1.00 | 7.82 | L | N |
| ATOM | 4391 | CA | TYR | 172 | 107.297 | -17.600 | 20.373 | 1.00 | 6.45 | L | C |
| ATOM | 4392 | CB | TYR | 172 | 106.934 | -17.706 | 18.894 | 1.00 | 43.65 | L | C |
| ATOM | 4393 | CG | TYR | 172 | 107.809 | -16.890 | 17.974 | 1.00 | 37.38 | L | C |
| ATOM | 4394 | CD1 | TYR | 172 | 107.652 | -15.507 | 17.865 | 1.00 | 32.97 | L | C |
| ATOM | 4395 | CE1 | TYR | 172 | 108.438 | -14.759 | 16.977 | 1.00 | 32.97 | L | C |
| ATOM | 4396 | CD2 | TYR | 172 | 108.776 | -17.508 | 17.181 | 1.00 | 37.97 | L | C |
| ATOM | 4397 | CE2 | TYR | 172 | 109.565 | -16.774 | 16.296 | 1.00 | 34.76 | L | C |
| ATOM | 4398 | CZ | TYR | 172 | 109.391 | -15.405 | 16.194 | 1.00 | 32.97 | L | C |
| ATOM | 4399 | OH | TYR | 172 | 110.163 | -14.703 | 15.294 | 1.00 | 32.97 | L | O |
| ATOM | 4400 | C | TYR | 172 | 106.255 | -18.364 | 21.212 | 1.00 | 6.45 | L | C |
| ATOM | 4401 | O | TYR | 172 | 106.431 | -19.539 | 21.528 | 1.00 | 9.78 | L | O |
| ATOM | 4402 | N | SER | 173 | 105.183 | -17.687 | 21.600 | 1.00 | 23.67 | L | N |
| ATOM | 4403 | CA | SER | 173 | 104.123 | -18.323 | 22.370 | 1.00 | 25.48 | L | C |
| ATOM | 4404 | CB | SER | 173 | 104.165 | -17.902 | 23.834 | 1.00 | 31.18 | L | C |
| ATOM | 4405 | OG | SER | 173 | 105.281 | -18.492 | 24.468 | 1.00 | 25.15 | L | O |
| ATOM | 4406 | C | SER | 173 | 102.836 | -17.886 | 21.728 | 1.00 | 26.94 | L | C |
| ATOM | 4407 | O | SER | 173 | 102.611 | -16.699 | 21.473 | 1.00 | 27.36 | L | O |
| ATOM | 4408 | N | LEU | 174 | 101.980 | -18.857 | 21.474 | 1.00 | 22.39 | L | N |
| ATOM | 4409 | CA | LEU | 174 | 100.734 | -18.593 | 20.791 | 1.00 | 25.49 | L | C |
| ATOM | 4410 | CB | LEU | 174 | 100.836 | -19.238 | 19.399 | 1.00 | 22.33 | L | C |
| ATOM | 4411 | CG | LEU | 174 | 99.682 | -19.165 | 18.422 | 1.00 | 13.39 | L | C |
| ATOM | 4412 | CD1 | LEU | 174 | 100.207 | -19.296 | 17.013 | 1.00 | 17.21 | L | C |
| ATOM | 4413 | CD2 | LEU | 174 | 98.663 | -20.257 | 18.769 | 1.00 | 10.23 | L | C |
| ATOM | 4414 | C | LEU | 174 | 99.510 | -19.075 | 21.562 | 1.00 | 27.64 | L | C |
| ATOM | 4415 | O | LEU | 174 | 99.542 | -20.111 | 22.229 | 1.00 | 30.82 | L | O |
| ATOM | 4416 | N | SER | 175 | 98.433 | -18.306 | 21.470 | 1.00 | 22.56 | L | N |
| ATOM | 4417 | CA | SER | 175 | 97.200 | -18.651 | 22.162 | 1.00 | 25.61 | L | C |
| ATOM | 4418 | CB | SER | 175 | 96.913 | -17.644 | 23.292 | 1.00 | 28.99 | L | C |
| ATOM | 4419 | OG | SER | 175 | 96.487 | -16.378 | 22.794 | 1.00 | 32.45 | L | O |
| ATOM | 4420 | C | SER | 175 | 96.009 | -18.693 | 21.214 | 1.00 | 29.48 | L | C |
| ATOM | 4421 | O | SER | 175 | 95.733 | -17.718 | 20.511 | 1.00 | 30.81 | L | O |
| ATOM | 4422 | N | SER | 176 | 95.316 | -19.829 | 21.181 | 1.00 | 31.99 | L | N |
| ATOM | 4423 | CA | SER | 176 | 94.125 | -19.957 | 20.346 | 1.00 | 32.77 | L | C |
| ATOM | 4424 | CB | SER | 176 | 94.154 | -21.247 | 19.514 | 1.00 | 10.71 | L | C |
| ATOM | 4425 | OG | SER | 176 | 93.247 | -21.176 | 18.421 | 1.00 | 10.34 | L | O |
| ATOM | 4426 | C | SER | 176 | 92.985 | -19.991 | 21.352 | 1.00 | 29.41 | L | C |
| ATOM | 4427 | O | SER | 176 | 93.042 | -20.712 | 22.350 | 1.00 | 29.56 | L | O |
| ATOM | 4428 | N | THR | 177 | 91.963 | -19.183 | 21.118 | 1.00 | 38.41 | L | N |
| ATOM | 4429 | CA | THR | 177 | 90.846 | -19.136 | 22.042 | 1.00 | 37.60 | L | C |
| ATOM | 4430 | CB | THR | 177 | 90.742 | -17.741 | 22.706 | 1.00 | 7.23 | L | C |
| ATOM | 4431 | OG1 | THR | 177 | 92.000 | -17.399 | 23.318 | 1.00 | 10.12 | L | O |
| ATOM | 4432 | CG2 | THR | 177 | 89.631 | -17.728 | 23.773 | 1.00 | 2.94 | L | C |
| ATOM | 4433 | C | THR | 177 | 89.551 | -19.455 | 21.311 | 1.00 | 35.94 | L | C |
| ATOM | 4434 | O | THR | 177 | 89.133 | -18.709 | 20.425 | 1.00 | 37.02 | L | O |
| ATOM | 4435 | N | LEU | 178 | 88.941 | -20.584 | 21.669 | 1.00 | 33.89 | L | N |
| ATOM | 4436 | CA | LEU | 178 | 87.682 | -21.015 | 21.072 | 1.00 | 32.44 | L | C |
| ATOM | 4437 | CB | LEU | 178 | 87.587 | -22.542 | 21.069 | 1.00 | 26.21 | L | C |
| ATOM | 4438 | CG | LEU | 178 | 86.291 | -23.170 | 20.539 | 1.00 | 27.24 | L | C |
| ATOM | 4439 | CD1 | LEU | 178 | 86.077 | -22.824 | 19.070 | 1.00 | 27.77 | L | C |
| ATOM | 4440 | CD2 | LEU | 178 | 86.367 | -24.683 | 20.730 | 1.00 | 15.35 | L | C |
| ATOM | 4441 | C | LEU | 178 | 86.552 | -20.412 | 21.901 | 1.00 | 32.70 | L | C |
| ATOM | 4442 | O | LEU | 178 | 86.476 | -20.589 | 23.120 | 1.00 | 29.14 | L | O |
| ATOM | 4443 | N | THR | 179 | 85.669 | -19.683 | 21.244 | 1.00 | 21.74 | L | N |
| ATOM | 4444 | CA | THR | 179 | 84.598 | -19.059 | 21.983 | 1.00 | 27.65 | L | C |
| ATOM | 4445 | CB | THR | 179 | 84.804 | -17.547 | 22.031 | 1.00 | 33.66 | L | C |
| ATOM | 4446 | OG1 | THR | 179 | 83.651 | -16.929 | 22.608 | 1.00 | 34.46 | L | O |
| ATOM | 4447 | CG2 | THR | 179 | 85.056 | -17.005 | 20.633 | 1.00 | 33.07 | L | C |
| ATOM | 4448 | C | THR | 179 | 83.223 | -19.377 | 21.430 | 1.00 | 32.00 | L | C |
| ATOM | 4449 | O | THR | 179 | 82.928 | -19.104 | 20.271 | 1.00 | 32.92 | L | O |
| ATOM | 4450 | N | LEU | 180 | 82.398 | -19.981 | 22.278 | 1.00 | 32.07 | L | N |
| ATOM | 4451 | CA | LEU | 180 | 81.035 | -20.349 | 21.922 | 1.00 | 33.73 | L | C |
| ATOM | 4452 | CB | LEU | 180 | 80.936 | -21.831 | 21.528 | 1.00 | 30.85 | L | C |
| ATOM | 4453 | CG | LEU | 180 | 82.059 | -22.804 | 21.881 | 1.00 | 33.56 | L | C |

Fig. 19: A-62

```
ATOM   4454  CD1 LEU 180      82.518 -22.589  23.309  1.00  36.03      L   C
ATOM   4455  CD2 LEU 180      81.552 -24.220  21.697  1.00  34.15      L   C
ATOM   4456  C   LEU 180      80.093 -20.062  23.084  1.00  37.58      L   C
ATOM   4457  O   LEU 180      80.526 -19.899  24.229  1.00  37.41      L   O
ATOM   4458  N   SER 181      78.801 -20.000  22.772  1.00  28.10      L   N
ATOM   4459  CA  SER 181      77.778 -19.711  23.770  1.00  31.26      L   C
ATOM   4460  CB  SER 181      76.433 -19.537  23.087  1.00  22.13      L   C
ATOM   4461  OG  SER 181      76.019 -20.764  22.513  1.00  25.39      L   O
ATOM   4462  C   SER 181      77.655 -20.802  24.815  1.00  33.74      L   C
ATOM   4463  O   SER 181      77.917 -21.978  24.533  1.00  33.98      L   O
ATOM   4464  N   LYS 182      77.247 -20.402  26.019  1.00  29.35      L   N
ATOM   4465  CA  LYS 182      77.060 -21.339  27.120  1.00  30.58      L   C
ATOM   4466  CB  LYS 182      76.375 -20.647  28.307  1.00  27.86      L   C
ATOM   4467  CG  LYS 182      76.341 -21.446  29.627  1.00  29.57      L   C
ATOM   4468  CD  LYS 182      74.912 -21.752  30.107  1.00  31.50      L   C
ATOM   4469  CE  LYS 182      74.863 -22.027  31.619  1.00  34.15      L   C
ATOM   4470  NZ  LYS 182      73.622 -22.756  32.099  1.00  38.40      L   N
ATOM   4471  C   LYS 182      76.167 -22.438  26.573  1.00  28.49      L   C
ATOM   4472  O   LYS 182      76.358 -23.618  26.878  1.00  20.36      L   O
ATOM   4473  N   ALA 183      75.206 -22.030  25.743  1.00  42.67      L   N
ATOM   4474  CA  ALA 183      74.252 -22.937  25.108  1.00  43.14      L   C
ATOM   4475  CB  ALA 183      73.319 -22.150  24.203  1.00  20.20      L   C
ATOM   4476  C   ALA 183      74.929 -24.053  24.313  1.00  42.26      L   C
ATOM   4477  O   ALA 183      74.645 -25.229  24.531  1.00  43.50      L   O
ATOM   4478  N   ASP 184      75.820 -23.691  23.395  1.00  37.65      L   N
ATOM   4479  CA  ASP 184      76.523 -24.692  22.587  1.00  39.98      L   C
ATOM   4480  CB  ASP 184      77.271 -24.023  21.434  1.00  60.24      L   C
ATOM   4481  CG  ASP 184      76.362 -23.219  20.545  1.00  66.97      L   C
ATOM   4482  OD1 ASP 184      75.360 -23.784  20.055  1.00  70.29      L   O
ATOM   4483  OD2 ASP 184      76.653 -22.023  20.335  1.00  70.50      L   O
ATOM   4484  C   ASP 184      77.519 -25.525  23.395  1.00  38.91      L   C
ATOM   4485  O   ASP 184      77.531 -26.753  23.308  1.00  36.50      L   O
ATOM   4486  N   TYR 185      78.362 -24.849  24.167  1.00  50.74      L   N
ATOM   4487  CA  TYR 185      79.352 -25.544  24.972  1.00  51.74      L   C
ATOM   4488  CB  TYR 185      80.011 -24.589  25.965  1.00  23.76      L   C
ATOM   4489  CG  TYR 185      81.104 -25.256  26.771  1.00  21.08      L   C
ATOM   4490  CD1 TYR 185      82.328 -25.552  26.192  1.00  16.43      L   C
ATOM   4491  CE1 TYR 185      83.332 -26.186  26.915  1.00  15.99      L   C
ATOM   4492  CD2 TYR 185      80.905 -25.613  28.104  1.00  17.64      L   C
ATOM   4493  CE2 TYR 185      81.902 -26.244  28.839  1.00  14.97      L   C
ATOM   4494  CZ  TYR 185      83.118 -26.526  28.235  1.00  14.93      L   C
ATOM   4495  OH  TYR 185      84.141 -27.119  28.944  1.00  16.56      L   O
ATOM   4496  C   TYR 185      78.729 -26.695  25.756  1.00  52.88      L   C
ATOM   4497  O   TYR 185      79.364 -27.728  25.978  1.00  52.42      L   O
ATOM   4498  N   GLU 186      77.484 -26.505  26.177  1.00  52.93      L   N
ATOM   4499  CA  GLU 186      76.787 -27.509  26.965  1.00  54.71      L   C
ATOM   4500  CB  GLU 186      75.643 -26.870  27.748  1.00  28.62      L   C
ATOM   4501  CG  GLU 186      76.067 -26.060  28.955  1.00  35.11      L   C
ATOM   4502  CD  GLU 186      74.876 -25.493  29.702  1.00  38.66      L   C
ATOM   4503  OE1 GLU 186      75.089 -24.850  30.746  1.00  41.21      L   O
ATOM   4504  OE2 GLU 186      73.725 -25.689  29.245  1.00  36.89      L   O
ATOM   4505  C   GLU 186      76.242 -28.694  26.190  1.00  52.40      L   C
ATOM   4506  O   GLU 186      76.029 -29.755  26.769  1.00  48.88      L   O
ATOM   4507  N   LYS 187      76.004 -28.538  24.895  1.00  35.74      L   N
ATOM   4508  CA  LYS 187      75.472 -29.662  24.147  1.00  37.64      L   C
ATOM   4509  CB  LYS 187      74.507 -29.173  23.057  1.00  53.22      L   C
ATOM   4510  CG  LYS 187      75.138 -28.512  21.849  1.00  54.27      L   C
ATOM   4511  CD  LYS 187      74.055 -27.941  20.930  1.00  53.80      L   C
ATOM   4512  CE  LYS 187      74.665 -27.203  19.740  1.00  49.76      L   C
ATOM   4513  NZ  LYS 187      73.707 -26.272  19.069  1.00  48.24      L   N
ATOM   4514  C   LYS 187      76.568 -30.553  23.549  1.00  36.73      L   C
ATOM   4515  O   LYS 187      76.297 -31.436  22.732  1.00  37.96      L   O
ATOM   4516  N   HIS 188      77.813 -30.333  23.972  1.00  23.77      L   N
ATOM   4517  CA  HIS 188      78.934 -31.124  23.468  1.00  21.36      L   C
ATOM   4518  CB  HIS 188      79.811 -30.257  22.562  1.00  41.13      L   C
ATOM   4519  CG  HIS 188      79.099 -29.774  21.338  1.00  42.53      L   C
ATOM   4520  CD2 HIS 188      78.800 -28.524  20.913  1.00  44.25      L   C
ATOM   4521  ND1 HIS 188      78.562 -30.633  20.405  1.00  41.45      L   N
ATOM   4522  CE1 HIS 188      77.961 -29.935  19.458  1.00  45.45      L   C
ATOM   4523  NE2 HIS 188      78.090 -28.652  19.743  1.00  43.75      L   N
ATOM   4524  C   HIS 188      79.743 -31.715  24.610  1.00  19.53      L   C
ATOM   4525  O   HIS 188      79.648 -31.253  25.751  1.00  19.70      L   O
ATOM   4526  N   LYS 189      80.521 -32.747  24.294  1.00  33.83      L   N
```

Fig. 19: A-63

| | | | | | | | | | | |
|---|---|---|---|---|---|---|---|---|---|---|
| ATOM | 4527 | CA | LYS | 189 | 81.334 | -33.445 | 25.281 | 1.00 | 33.86 | L | C |
| ATOM | 4528 | CB | LYS | 189 | 81.136 | -34.957 | 25.152 | 1.00 | 43.10 | L | C |
| ATOM | 4529 | CG | LYS | 189 | 79.898 | -35.516 | 25.815 | 1.00 | 47.03 | L | C |
| ATOM | 4530 | CD | LYS | 189 | 79.974 | -37.041 | 25.887 | 1.00 | 53.76 | L | C |
| ATOM | 4531 | CE | LYS | 189 | 79.997 | -37.680 | 24.505 | 1.00 | 59.30 | L | C |
| ATOM | 4532 | NZ | LYS | 189 | 78.694 | -37.545 | 23.794 | 1.00 | 59.64 | L | N |
| ATOM | 4533 | C | LYS | 189 | 82.831 | -33.155 | 25.201 | 1.00 | 33.18 | L | C |
| ATOM | 4534 | O | LYS | 189 | 83.435 | -32.657 | 26.155 | 1.00 | 36.85 | L | O |
| ATOM | 4535 | N | VAL | 190 | 83.435 | -33.482 | 24.069 | 1.00 | 39.67 | L | N |
| ATOM | 4536 | CA | VAL | 190 | 84.860 | -33.260 | 23.916 | 1.00 | 35.33 | L | C |
| ATOM | 4537 | CB | VAL | 190 | 85.516 | -34.439 | 23.214 | 1.00 | 33.71 | L | C |
| ATOM | 4538 | CG1 | VAL | 190 | 85.356 | -35.648 | 24.059 | 1.00 | 26.85 | L | C |
| ATOM | 4539 | CG2 | VAL | 190 | 84.880 | -34.657 | 21.855 | 1.00 | 36.79 | L | C |
| ATOM | 4540 | C | VAL | 190 | 85.249 | -31.992 | 23.170 | 1.00 | 35.17 | L | C |
| ATOM | 4541 | O | VAL | 190 | 84.656 | -31.641 | 22.141 | 1.00 | 36.62 | L | O |
| ATOM | 4542 | N | TYR | 191 | 86.256 | -31.319 | 23.718 | 1.00 | 27.65 | L | N |
| ATOM | 4543 | CA | TYR | 191 | 86.811 | -30.105 | 23.152 | 1.00 | 26.85 | L | C |
| ATOM | 4544 | CB | TYR | 191 | 86.554 | -28.934 | 24.095 | 1.00 | 16.61 | L | C |
| ATOM | 4545 | CG | TYR | 191 | 85.109 | -28.475 | 24.056 | 1.00 | 23.44 | L | C |
| ATOM | 4546 | CD1 | TYR | 191 | 84.654 | -27.650 | 23.030 | 1.00 | 27.57 | L | C |
| ATOM | 4547 | CE1 | TYR | 191 | 83.322 | -27.300 | 22.929 | 1.00 | 29.06 | L | C |
| ATOM | 4548 | CD2 | TYR | 191 | 84.178 | -28.937 | 24.991 | 1.00 | 24.37 | L | C |
| ATOM | 4549 | CE2 | TYR | 191 | 82.838 | -28.592 | 24.894 | 1.00 | 25.88 | L | C |
| ATOM | 4550 | CZ | TYR | 191 | 82.419 | -27.773 | 23.859 | 1.00 | 28.22 | L | C |
| ATOM | 4551 | OH | TYR | 191 | 81.097 | -27.419 | 23.745 | 1.00 | 30.91 | L | O |
| ATOM | 4552 | C | TYR | 191 | 88.295 | -30.381 | 23.010 | 1.00 | 28.07 | L | C |
| ATOM | 4553 | O | TYR | 191 | 88.946 | -30.821 | 23.960 | 1.00 | 29.13 | L | O |
| ATOM | 4554 | N | ALA | 192 | 88.837 | -30.159 | 21.822 | 1.00 | 17.93 | L | N |
| ATOM | 4555 | CA | ALA | 192 | 90.246 | -30.425 | 21.621 | 1.00 | 13.94 | L | C |
| ATOM | 4556 | CB | ALA | 192 | 90.424 | -31.850 | 21.160 | 1.00 | 12.32 | L | C |
| ATOM | 4557 | C | ALA | 192 | 90.921 | -29.489 | 20.640 | 1.00 | 14.27 | L | C |
| ATOM | 4558 | O | ALA | 192 | 90.271 | -28.885 | 19.784 | 1.00 | 14.89 | L | O |
| ATOM | 4559 | N | CYS | 193 | 92.234 | -29.362 | 20.787 | 1.00 | 20.91 | L | N |
| ATOM | 4560 | CA | CYS | 193 | 93.015 | -28.544 | 19.883 | 1.00 | 19.50 | L | C |
| ATOM | 4561 | C | CYS | 193 | 94.268 | -29.301 | 19.502 | 1.00 | 17.29 | L | C |
| ATOM | 4562 | O | CYS | 193 | 95.057 | -29.729 | 20.352 | 1.00 | 15.43 | L | O |
| ATOM | 4563 | CB | CYS | 193 | 93.361 | -27.183 | 20.490 | 1.00 | 44.80 | L | C |
| ATOM | 4564 | SG | CYS | 193 | 94.412 | -27.194 | 21.962 | 1.00 | 52.58 | L | S |
| ATOM | 4565 | N | GLU | 194 | 94.411 | -29.480 | 18.195 | 1.00 | 24.90 | L | N |
| ATOM | 4566 | CA | GLU | 194 | 95.522 | -30.193 | 17.600 | 1.00 | 25.90 | L | C |
| ATOM | 4567 | CB | GLU | 194 | 95.004 | -30.956 | 16.384 | 1.00 | 66.26 | L | C |
| ATOM | 4568 | CG | GLU | 194 | 95.979 | -31.887 | 15.718 | 1.00 | 77.97 | L | C |
| ATOM | 4569 | CD | GLU | 194 | 95.392 | -32.479 | 14.461 | 1.00 | 83.25 | L | C |
| ATOM | 4570 | OE1 | GLU | 194 | 95.276 | -31.738 | 13.462 | 1.00 | 80.00 | L | O |
| ATOM | 4571 | OE2 | GLU | 194 | 95.028 | -33.674 | 14.477 | 1.00 | 89.05 | L | O |
| ATOM | 4572 | C | GLU | 194 | 96.546 | -29.158 | 17.175 | 1.00 | 25.27 | L | C |
| ATOM | 4573 | O | GLU | 194 | 96.204 | -28.171 | 16.538 | 1.00 | 23.30 | L | O |
| ATOM | 4574 | N | VAL | 195 | 97.798 | -29.373 | 17.537 | 1.00 | 38.95 | L | N |
| ATOM | 4575 | CA | VAL | 195 | 98.850 | -28.443 | 17.168 | 1.00 | 34.83 | L | C |
| ATOM | 4576 | CB | VAL | 195 | 99.715 | -28.048 | 18.403 | 1.00 | 15.18 | L | C |
| ATOM | 4577 | CG1 | VAL | 195 | 100.911 | -27.210 | 17.971 | 1.00 | 11.26 | L | C |
| ATOM | 4578 | CG2 | VAL | 195 | 98.859 | -27.268 | 19.395 | 1.00 | 16.15 | L | C |
| ATOM | 4579 | C | VAL | 195 | 99.730 | -29.115 | 16.126 | 1.00 | 34.14 | L | C |
| ATOM | 4580 | O | VAL | 195 | 99.964 | -30.319 | 16.180 | 1.00 | 32.63 | L | O |
| ATOM | 4581 | N | THR | 196 | 100.190 | -28.340 | 15.157 | 1.00 | 43.12 | L | N |
| ATOM | 4582 | CA | THR | 196 | 101.063 | -28.876 | 14.135 | 1.00 | 42.44 | L | C |
| ATOM | 4583 | CB | THR | 196 | 100.411 | -28.867 | 12.764 | 1.00 | 26.65 | L | C |
| ATOM | 4584 | OG1 | THR | 196 | 99.001 | -28.673 | 12.909 | 1.00 | 36.35 | L | O |
| ATOM | 4585 | CG2 | THR | 196 | 100.671 | -30.180 | 12.067 | 1.00 | 28.65 | L | C |
| ATOM | 4586 | C | THR | 196 | 102.233 | -27.927 | 14.121 | 1.00 | 42.04 | L | C |
| ATOM | 4587 | O | THR | 196 | 102.049 | -26.710 | 14.053 | 1.00 | 37.83 | L | O |
| ATOM | 4588 | N | HIS | 197 | 103.437 | -28.479 | 14.186 | 1.00 | 32.41 | L | N |
| ATOM | 4589 | CA | HIS | 197 | 104.623 | -27.653 | 14.217 | 1.00 | 27.77 | L | C |
| ATOM | 4590 | CB | HIS | 197 | 104.867 | -27.172 | 15.651 | 1.00 | 21.71 | L | C |
| ATOM | 4591 | CG | HIS | 197 | 105.914 | -26.113 | 15.762 | 1.00 | 23.27 | L | C |
| ATOM | 4592 | CD2 | HIS | 197 | 105.817 | -24.761 | 15.753 | 1.00 | 17.64 | L | C |
| ATOM | 4593 | ND1 | HIS | 197 | 107.257 | -26.402 | 15.868 | 1.00 | 25.39 | L | N |
| ATOM | 4594 | CE1 | HIS | 197 | 107.944 | -25.274 | 15.923 | 1.00 | 22.67 | L | C |
| ATOM | 4595 | NE2 | HIS | 197 | 107.093 | -24.264 | 15.854 | 1.00 | 24.76 | L | N |
| ATOM | 4596 | C | HIS | 197 | 105.825 | -28.417 | 13.708 | 1.00 | 24.98 | L | C |
| ATOM | 4597 | O | HIS | 197 | 105.932 | -29.629 | 13.885 | 1.00 | 29.24 | L | O |
| ATOM | 4598 | N | GLN | 198 | 106.728 | -27.687 | 13.070 | 1.00 | 28.46 | L | N |
| ATOM | 4599 | CA | GLN | 198 | 107.944 | -28.252 | 12.515 | 1.00 | 26.49 | L | C |

Fig. 19: A-64

```
ATOM   4600  CB   GLN  198    108.840  -27.114  12.048  1.00  34.42  L  C
ATOM   4601  CG   GLN  198    110.091  -27.549  11.333  1.00  36.17  L  C
ATOM   4602  CD   GLN  198    110.868  -26.365  10.821  1.00  48.65  L  C
ATOM   4603  OE1  GLN  198    110.286  -25.414  10.299  1.00  57.22  L  O
ATOM   4604  NE2  GLN  198    112.185  -26.414  10.956  1.00  51.65  L  N
ATOM   4605  C    GLN  198    108.681  -29.107  13.541  1.00  29.43  L  C
ATOM   4606  O    GLN  198    109.331  -30.088  13.182  1.00  31.15  L  O
ATOM   4607  N    GLY  199    108.568  -28.728  14.815  1.00  31.39  L  N
ATOM   4608  CA   GLY  199    109.234  -29.452  15.887  1.00  36.65  L  C
ATOM   4609  C    GLY  199    108.465  -30.636  16.444  1.00  39.08  L  C
ATOM   4610  O    GLY  199    108.880  -31.244  17.425  1.00  43.81  L  O
ATOM   4611  N    LEU  200    107.339  -30.961  15.823  1.00  25.48  L  N
ATOM   4612  CA   LEU  200    106.510  -32.087  16.247  1.00  22.67  L  C
ATOM   4613  CB   LEU  200    105.094  -31.597  16.570  1.00  31.49  L  C
ATOM   4614  CG   LEU  200    104.868  -31.002  17.964  1.00  34.60  L  C
ATOM   4615  CD1  LEU  200    106.036  -30.149  18.361  1.00  37.97  L  C
ATOM   4616  CD2  LEU  200    103.592  -30.188  17.967  1.00  34.28  L  C
ATOM   4617  C    LEU  200    106.463  -33.152  15.144  1.00  23.29  L  C
ATOM   4618  O    LEU  200    106.089  -32.869  14.003  1.00  24.15  L  O
ATOM   4619  N    SER  201    106.860  -34.372  15.499  1.00  21.11  L  N
ATOM   4620  CA   SER  201    106.886  -35.503  14.570  1.00  24.08  L  C
ATOM   4621  CB   SER  201    107.367  -36.747  15.311  1.00  27.13  L  C
ATOM   4622  OG   SER  201    106.702  -36.875  16.561  1.00  28.99  L  O
ATOM   4623  C    SER  201    105.510  -35.761  13.957  1.00  24.14  L  C
ATOM   4624  O    SER  201    105.392  -36.267  12.835  1.00  25.49  L  O
ATOM   4625  N    SER  202    104.476  -35.405  14.717  1.00  17.09  L  N
ATOM   4626  CA   SER  202    103.086  -35.562  14.302  1.00  21.15  L  C
ATOM   4627  CB   SER  202    102.636  -37.010  14.522  1.00  43.22  L  C
ATOM   4628  OG   SER  202    103.011  -37.462  15.810  1.00  46.12  L  O
ATOM   4629  C    SER  202    102.265  -34.603  15.155  1.00  21.60  L  C
ATOM   4630  O    SER  202    102.656  -34.296  16.282  1.00  27.36  L  O
ATOM   4631  N    PRO  203    101.119  -34.121  14.636  1.00  22.94  L  N
ATOM   4632  CD   PRO  203    100.457  -34.478  13.368  1.00  32.35  L  C
ATOM   4633  CA   PRO  203    100.290  -33.187  15.407  1.00  18.89  L  C
ATOM   4634  CB   PRO  203     98.971  -33.177  14.643  1.00  26.47  L  C
ATOM   4635  CG   PRO  203     99.416  -33.370  13.223  1.00  29.48  L  C
ATOM   4636  C    PRO  203    100.128  -33.646  16.836  1.00  18.90  L  C
ATOM   4637  O    PRO  203    100.178  -34.842  17.100  1.00  21.86  L  O
ATOM   4638  N    VAL  204     99.980  -32.693  17.753  1.00  28.11  L  N
ATOM   4639  CA   VAL  204     99.794  -32.996  19.172  1.00  29.99  L  C
ATOM   4640  CB   VAL  204    100.759  -32.201  20.081  1.00  20.42  L  C
ATOM   4641  CG1  VAL  204    100.254  -32.204  21.512  1.00  20.30  L  C
ATOM   4642  CG2  VAL  204    102.141  -32.819  20.036  1.00  15.23  L  C
ATOM   4643  C    VAL  204     98.393  -32.574  19.514  1.00  33.93  L  C
ATOM   4644  O    VAL  204     97.887  -31.601  18.963  1.00  35.36  L  O
ATOM   4645  N    THR  205     97.755  -33.293  20.422  1.00  45.34  L  N
ATOM   4646  CA   THR  205     96.402  -32.933  20.787  1.00  46.97  L  C
ATOM   4647  CB   THR  205     95.386  -33.896  20.137  1.00  14.48  L  C
ATOM   4648  OG1  THR  205     95.275  -33.587  18.747  1.00  10.44  L  O
ATOM   4649  CG2  THR  205     94.013  -33.761  20.769  1.00  11.16  L  C
ATOM   4650  C    THR  205     96.169  -32.886  22.280  1.00  47.18  L  C
ATOM   4651  O    THR  205     96.596  -33.763  23.032  1.00  49.19  L  O
ATOM   4652  N    LYS  206     95.513  -31.822  22.709  1.00  22.09  L  N
ATOM   4653  CA   LYS  206     95.167  -31.681  24.108  1.00  26.52  L  C
ATOM   4654  CB   LYS  206     95.791  -30.422  24.710  1.00  41.06  L  C
ATOM   4655  CG   LYS  206     97.208  -30.641  25.215  1.00  44.88  L  C
ATOM   4656  CD   LYS  206     97.269  -31.688  26.312  1.00  47.36  L  C
ATOM   4657  CE   LYS  206     98.654  -31.760  26.957  1.00  49.27  L  C
ATOM   4658  NZ   LYS  206     99.723  -32.144  25.997  1.00  50.40  L  N
ATOM   4659  C    LYS  206     93.653  -31.602  24.100  1.00  29.29  L  C
ATOM   4660  O    LYS  206     93.063  -30.939  23.246  1.00  34.45  L  O
ATOM   4661  N    SER  207     93.026  -32.304  25.033  1.00  32.39  L  N
ATOM   4662  CA   SER  207     91.578  -32.324  25.083  1.00  29.18  L  C
ATOM   4663  CB   SER  207     91.046  -33.354  24.080  1.00  31.23  L  C
ATOM   4664  OG   SER  207     91.613  -34.655  24.294  1.00  31.62  L  O
ATOM   4665  C    SER  207     91.039  -32.624  26.476  1.00  28.78  L  C
ATOM   4666  O    SER  207     91.798  -32.938  27.397  1.00  29.47  L  O
ATOM   4667  N    PHE  208     89.719  -32.517  26.606  1.00  33.89  L  N
ATOM   4668  CA   PHE  208     89.013  -32.777  27.852  1.00  39.79  L  C
ATOM   4669  CB   PHE  208     89.217  -31.615  28.842  1.00  17.06  L  C
ATOM   4670  CG   PHE  208     88.662  -30.300  28.353  1.00  14.11  L  C
ATOM   4671  CD1  PHE  208     89.409  -29.482  27.499  1.00  18.84  L  C
ATOM   4672  CD2  PHE  208     87.376  -29.906  28.690  1.00  11.57  L  C
```

Fig. 19: A-65

```
ATOM   4673  CE1 PHE  208      88.879 -28.298  26.990  1.00  19.93      L  C
ATOM   4674  CE2 PHE  208      86.846 -28.729  28.182  1.00  14.34      L  C
ATOM   4675  CZ  PHE  208      87.602 -27.925  27.330  1.00  20.99      L  C
ATOM   4676  C   PHE  208      87.536 -32.873  27.472  1.00  45.59      L  C
ATOM   4677  O   PHE  208      87.168 -32.576  26.335  1.00  47.78      L  O
ATOM   4678  N   ASN  209      86.703 -33.293  28.420  1.00  24.67      L  N
ATOM   4679  CA  ASN  209      85.257 -33.398  28.213  1.00  28.33      L  C
ATOM   4680  CB  ASN  209      84.751 -34.785  28.623  1.00  27.05      L  C
ATOM   4681  CG  ASN  209      85.664 -35.913  28.172  1.00  33.97      L  C
ATOM   4682  OD1 ASN  209      85.777 -36.941  28.841  1.00  34.19      L  O
ATOM   4683  ND2 ASN  209      86.304 -35.732  27.031  1.00  37.01      L  N
ATOM   4684  C   ASN  209      84.630 -32.370  29.160  1.00  29.95      L  C
ATOM   4685  O   ASN  209      85.203 -32.108  30.218  1.00  31.18      L  O
ATOM   4686  N   ARG  210      83.473 -31.800  28.805  1.00  15.88      L  N
ATOM   4687  CA  ARG  210      82.810 -30.829  29.687  1.00  19.72      L  C
ATOM   4688  CB  ARG  210      81.337 -30.721  29.371  1.00  31.19      L  C
ATOM   4689  CG  ARG  210      81.027 -29.666  28.361  1.00  32.77      L  C
ATOM   4690  CD  ARG  210      79.655 -29.104  28.627  1.00  36.35      L  C
ATOM   4691  NE  ARG  210      78.656 -30.166  28.633  1.00  41.72      L  N
ATOM   4692  CZ  ARG  210      77.502 -30.095  29.282  1.00  45.49      L  C
ATOM   4693  NH1 ARG  210      77.204 -29.008  29.981  1.00  46.04      L  N
ATOM   4694  NH2 ARG  210      76.655 -31.112  29.232  1.00  47.73      L  N
ATOM   4695  C   ARG  210      82.964 -31.252  31.137  1.00  22.05      L  C
ATOM   4696  O   ARG  210      82.962 -32.440  31.428  1.00  23.93      L  O
ATOM   4697  N   GLY  211      83.096 -30.291  32.048  1.00  53.99      L  N
ATOM   4698  CA  GLY  211      83.297 -30.638  33.447  1.00  53.99      L  C
ATOM   4699  C   GLY  211      84.740 -31.088  33.630  1.00  53.99      L  C
ATOM   4700  O   GLY  211      85.665 -30.312  33.387  1.00  53.99      L  O
ATOM   4701  N   GLU  212      84.942 -32.336  34.046  1.00  80.95      L  N
ATOM   4702  CA  GLU  212      86.287 -32.890  34.236  1.00  80.95      L  C
ATOM   4703  CB  GLU  212      86.995 -33.004  32.871  1.00  34.07      L  C
ATOM   4704  CG  GLU  212      88.259 -33.888  32.849  1.00  34.07      L  C
ATOM   4705  CD  GLU  212      88.691 -34.311  31.435  1.00  34.07      L  C
ATOM   4706  OE1 GLU  212      89.803 -34.863  31.296  1.00  34.07      L  O
ATOM   4707  OE2 GLU  212      87.923 -34.113  30.468  1.00  34.07      L  O
ATOM   4708  C   GLU  212      87.134 -32.080  35.227  1.00  80.95      L  C
ATOM   4709  O   GLU  212      86.690 -31.043  35.732  1.00  80.95      L  O
ATOM   4710  N   CYS  213      88.341 -32.566  35.516  1.00  81.74      L  N
ATOM   4711  CA  CYS  213      89.243 -31.893  36.450  1.00  81.74      L  C
ATOM   4712  CB  CYS  213      88.990 -32.374  37.883  1.00  54.42      L  C
ATOM   4713  SG  CYS  213      87.479 -31.701  38.656  1.00  54.42      L  S
ATOM   4714  C   CYS  213      90.715 -32.123  36.095  1.00  81.74      L  C
ATOM   4715  O   CYS  213      90.996 -32.758  35.051  1.00  81.74      L  O
ATOM   4716  OXT CYS  213      91.581 -31.647  36.863  1.00  72.88      L  O
ATOM   4717  MN  MN   400     117.831  24.682   6.345  1.00  34.24      M
ATOM   4718  CB  THR  145     114.226  73.843  15.327  1.00  72.71      B  C
ATOM   4719  OG1 THR  145     113.673  74.174  16.611  1.00  72.71      B  O
ATOM   4720  CG2 THR  145     114.208  75.069  14.426  1.00  72.71      B  C
ATOM   4721  C   THR  145     113.665  71.399  15.485  1.00 109.74      B  C
ATOM   4722  O   THR  145     113.590  70.290  14.948  1.00 110.14      B  O
ATOM   4723  N   THR  145     111.957  72.996  14.632  1.00 108.12      B  N
ATOM   4724  CA  THR  145     113.414  72.677  14.686  1.00 107.72      B  C
ATOM   4725  N   GLN  146     113.963  71.561  16.769  1.00  79.22      B  N
ATOM   4726  CA  GLN  146     114.224  70.425  17.633  1.00  77.37      B  C
ATOM   4727  CB  GLN  146     115.554  70.620  18.378  1.00  80.28      B  C
ATOM   4728  CG  GLN  146     115.640  71.886  19.208  1.00  80.28      B  C
ATOM   4729  CD  GLN  146     116.952  72.001  19.955  1.00  80.28      B  C
ATOM   4730  OE1 GLN  146     117.150  72.929  20.742  1.00  80.28      B  O
ATOM   4731  NE2 GLN  146     117.858  71.059  19.712  1.00  80.28      B  N
ATOM   4732  C   GLN  146     113.077  70.200  18.620  1.00  77.79      B  C
ATOM   4733  O   GLN  146     112.818  71.018  19.511  1.00  79.65      B  O
ATOM   4734  N   LEU  147     112.383  69.081  18.432  1.00  43.47      B  N
ATOM   4735  CA  LEU  147     111.265  68.710  19.288  1.00  42.60      B  C
ATOM   4736  CB  LEU  147     109.936  68.755  18.525  1.00  51.95      B  C
ATOM   4737  CG  LEU  147     109.450  69.952  17.707  1.00  52.14      B  C
ATOM   4738  CD1 LEU  147     110.464  70.296  16.632  1.00  47.35      B  C
ATOM   4739  CD2 LEU  147     108.114  69.607  17.060  1.00  51.99      B  C
ATOM   4740  C   LEU  147     111.461  67.281  19.756  1.00  41.58      B  C
ATOM   4741  O   LEU  147     112.077  66.470  19.058  1.00  42.88      B  O
ATOM   4742  N   ASP  148     110.944  66.988  20.945  1.00  31.29      B  N
ATOM   4743  CA  ASP  148     110.974  65.640  21.493  1.00  28.75      B  C
ATOM   4744  CB  ASP  148     111.394  65.642  22.960  1.00  32.78      B  C
ATOM   4745  CG  ASP  148     112.897  65.718  23.133  1.00  32.40      B  C
```

Fig. 19: A-66

```
ATOM   4746  OD1 ASP  148    113.366  65.715  24.290  1.00  31.51  B  O
ATOM   4747  OD2 ASP  148    113.616  65.777  22.116  1.00  30.58  B  O
ATOM   4748  C   ASP  148    109.526  65.181  21.358  1.00  25.13  B  C
ATOM   4749  O   ASP  148    108.664  65.583  22.128  1.00  24.43  B  O
ATOM   4750  N   ILE  149    109.260  64.368  20.345  1.00  21.33  B  N
ATOM   4751  CA  ILE  149    107.918  63.885  20.105  1.00  20.27  B  C
ATOM   4752  CB  ILE  149    107.610  63.880  18.605  1.00  13.57  B  C
ATOM   4753  CG2 ILE  149    106.140  63.573  18.378  1.00   8.58  B  C
ATOM   4754  CG1 ILE  149    107.932  65.234  17.998  1.00   9.29  B  C
ATOM   4755  CD1 ILE  149    107.697  65.263  16.508  1.00  12.04  B  C
ATOM   4756  C   ILE  149    107.723  62.464  20.629  1.00  21.92  B  C
ATOM   4757  O   ILE  149    108.507  61.563  20.315  1.00  22.32  B  O
ATOM   4758  N   VAL  150    106.680  62.271  21.433  1.00  32.56  B  N
ATOM   4759  CA  VAL  150    106.357  60.950  21.956  1.00  34.12  B  C
ATOM   4760  CB  VAL  150    106.256  60.940  23.492  1.00  12.90  B  C
ATOM   4761  CG1 VAL  150    105.775  59.579  23.967  1.00  15.09  B  C
ATOM   4762  CG2 VAL  150    107.620  61.256  24.110  1.00  14.71  B  C
ATOM   4763  C   VAL  150    105.001  60.604  21.381  1.00  31.68  B  C
ATOM   4764  O   VAL  150    104.057  61.380  21.523  1.00  29.83  B  O
ATOM   4765  N   ILE  151    104.904  59.459  20.714  1.00  36.82  B  N
ATOM   4766  CA  ILE  151    103.640  59.037  20.115  1.00  35.62  B  C
ATOM   4767  CB  ILE  151    103.862  58.436  18.709  1.00  31.63  B  C
ATOM   4768  CG2 ILE  151    102.537  58.084  18.081  1.00  27.99  B  C
ATOM   4769  CG1 ILE  151    104.582  59.454  17.817  1.00  30.05  B  C
ATOM   4770  CD1 ILE  151    104.981  58.916  16.457  1.00  32.03  B  C
ATOM   4771  C   ILE  151    102.978  58.008  21.016  1.00  33.74  B  C
ATOM   4772  O   ILE  151    103.593  57.013  21.394  1.00  33.98  B  O
ATOM   4773  N   VAL  152    101.725  58.254  21.368  1.00  29.85  B  N
ATOM   4774  CA  VAL  152    100.996  57.347  22.243  1.00  30.70  B  C
ATOM   4775  CB  VAL  152    100.279  58.127  23.344  1.00  30.57  B  C
ATOM   4776  CG1 VAL  152     99.721  57.170  24.385  1.00  29.70  B  C
ATOM   4777  CG2 VAL  152    101.245  59.134  23.962  1.00  27.01  B  C
ATOM   4778  C   VAL  152     99.966  56.560  21.451  1.00  28.60  B  C
ATOM   4779  O   VAL  152     98.867  57.044  21.194  1.00  22.20  B  O
ATOM   4780  N   LEU  153    100.324  55.336  21.083  1.00  26.94  B  N
ATOM   4781  CA  LEU  153     99.451  54.479  20.289  1.00  27.05  B  C
ATOM   4782  CB  LEU  153    100.312  53.600  19.370  1.00  31.93  B  C
ATOM   4783  CG  LEU  153    100.518  54.010  17.910  1.00  33.71  B  C
ATOM   4784  CD1 LEU  153    100.287  55.490  17.732  1.00  34.22  B  C
ATOM   4785  CD2 LEU  153    101.914  53.616  17.481  1.00  36.25  B  C
ATOM   4786  C   LEU  153     98.475  53.597  21.058  1.00  28.11  B  C
ATOM   4787  O   LEU  153     98.837  52.930  22.035  1.00  27.11  B  O
ATOM   4788  N   ASP  154     97.228  53.602  20.604  1.00  33.48  B  N
ATOM   4789  CA  ASP  154     96.199  52.768  21.204  1.00  32.96  B  C
ATOM   4790  CB  ASP  154     94.809  53.341  20.911  1.00  34.05  B  C
ATOM   4791  CG  ASP  154     93.686  52.502  21.505  1.00  33.25  B  C
ATOM   4792  OD1 ASP  154     93.959  51.385  21.985  1.00  36.76  B  O
ATOM   4793  OD2 ASP  154     92.523  52.960  21.489  1.00  29.57  B  O
ATOM   4794  C   ASP  154     96.362  51.412  20.515  1.00  36.30  B  C
ATOM   4795  O   ASP  154     96.349  51.326  19.285  1.00  32.62  B  O
ATOM   4796  N   GLY  155     96.539  50.361  21.303  1.00  16.68  B  N
ATOM   4797  CA  GLY  155     96.700  49.039  20.732  1.00  18.75  B  C
ATOM   4798  C   GLY  155     95.706  48.058  21.321  1.00  20.01  B  C
ATOM   4799  O   GLY  155     95.856  46.845  21.177  1.00  22.50  B  O
ATOM   4800  N   SER  156     94.692  48.595  21.992  1.00  30.46  B  N
ATOM   4801  CA  SER  156     93.653  47.780  22.612  1.00  35.04  B  C
ATOM   4802  CB  SER  156     92.616  48.670  23.302  1.00  22.70  B  C
ATOM   4803  OG  SER  156     91.999  49.542  22.372  1.00  25.62  B  O
ATOM   4804  C   SER  156     92.962  46.891  21.584  1.00  32.03  B  C
ATOM   4805  O   SER  156     93.057  47.122  20.379  1.00  35.21  B  O
ATOM   4806  N   ASN  157     92.257  45.879  22.074  1.00  34.08  B  N
ATOM   4807  CA  ASN  157     91.565  44.927  21.216  1.00  31.16  B  C
ATOM   4808  CB  ASN  157     90.632  44.046  22.047  1.00  34.61  B  C
ATOM   4809  CG  ASN  157     91.378  42.971  22.811  1.00  36.10  B  C
ATOM   4810  OD1 ASN  157     90.795  42.270  23.638  1.00  33.17  B  O
ATOM   4811  ND2 ASN  157     92.672  42.832  22.536  1.00  33.38  B  N
ATOM   4812  C   ASN  157     90.783  45.529  20.069  1.00  29.13  B  C
ATOM   4813  O   ASN  157     90.806  45.003  18.956  1.00  27.11  B  O
ATOM   4814  N   SER  158     90.094  46.631  20.339  1.00  20.01  B  N
ATOM   4815  CA  SER  158     89.275  47.285  19.324  1.00  18.22  B  C
ATOM   4816  CB  SER  158     88.506  48.464  19.936  1.00  15.08  B  C
ATOM   4817  OG  SER  158     89.356  49.363  20.616  1.00  17.79  B  O
ATOM   4818  C   SER  158     90.035  47.739  18.087  1.00  18.99  B  C
```

Fig. 19: A-67

| ATOM | 4819 | O | SER | 158 | 89.527 | 47.602 | 16.984 | 1.00 | 16.16 | B | O |
|---|---|---|---|---|---|---|---|---|---|---|---|
| ATOM | 4820 | N | ILE | 159 | 91.245 | 48.269 | 18.257 | 1.00 | 19.55 | B | N |
| ATOM | 4821 | CA | ILE | 159 | 92.033 | 48.722 | 17.110 | 1.00 | 24.15 | B | C |
| ATOM | 4822 | CB | ILE | 159 | 93.423 | 49.203 | 17.541 | 1.00 | 21.45 | B | C |
| ATOM | 4823 | CG2 | ILE | 159 | 94.256 | 49.546 | 16.307 | 1.00 | 21.36 | B | C |
| ATOM | 4824 | CG1 | ILE | 159 | 93.293 | 50.411 | 18.471 | 1.00 | 26.23 | B | C |
| ATOM | 4825 | CD1 | ILE | 159 | 92.779 | 51.664 | 17.787 | 1.00 | 31.39 | B | C |
| ATOM | 4826 | C | ILE | 159 | 92.204 | 47.597 | 16.089 | 1.00 | 28.46 | B | C |
| ATOM | 4827 | O | ILE | 159 | 92.638 | 46.502 | 16.434 | 1.00 | 27.87 | B | O |
| ATOM | 4828 | N | TYR | 160 | 91.863 | 47.876 | 14.832 | 1.00 | 56.09 | B | N |
| ATOM | 4829 | CA | TYR | 160 | 91.959 | 46.886 | 13.756 | 1.00 | 58.22 | B | C |
| ATOM | 4830 | CB | TYR | 160 | 90.931 | 45.768 | 13.980 | 1.00 | 40.50 | B | C |
| ATOM | 4831 | CG | TYR | 160 | 90.932 | 44.654 | 12.939 | 1.00 | 37.26 | B | C |
| ATOM | 4832 | CD1 | TYR | 160 | 91.606 | 43.449 | 13.172 | 1.00 | 39.68 | B | C |
| ATOM | 4833 | CE1 | TYR | 160 | 91.602 | 42.423 | 12.225 | 1.00 | 37.28 | B | C |
| ATOM | 4834 | CD2 | TYR | 160 | 90.254 | 44.803 | 11.722 | 1.00 | 34.91 | B | C |
| ATOM | 4835 | CE2 | TYR | 160 | 90.251 | 43.782 | 10.770 | 1.00 | 38.62 | B | C |
| ATOM | 4836 | CZ | TYR | 160 | 90.926 | 42.598 | 11.030 | 1.00 | 37.97 | B | C |
| ATOM | 4837 | OH | TYR | 160 | 90.922 | 41.597 | 10.095 | 1.00 | 42.97 | B | O |
| ATOM | 4838 | C | TYR | 160 | 91.696 | 47.533 | 12.400 | 1.00 | 59.94 | B | C |
| ATOM | 4839 | O | TYR | 160 | 90.730 | 48.276 | 12.232 | 1.00 | 65.86 | B | O |
| ATOM | 4840 | N | PRO | 161 | 92.548 | 47.241 | 11.407 | 1.00 | 26.83 | B | N |
| ATOM | 4841 | CD | PRO | 161 | 92.182 | 47.499 | 10.002 | 1.00 | 24.03 | B | C |
| ATOM | 4842 | CA | PRO | 161 | 93.721 | 46.362 | 11.479 | 1.00 | 25.11 | B | C |
| ATOM | 4843 | CB | PRO | 161 | 93.784 | 45.785 | 10.075 | 1.00 | 28.41 | B | C |
| ATOM | 4844 | CG | PRO | 161 | 93.364 | 46.960 | 9.239 | 1.00 | 31.57 | B | C |
| ATOM | 4845 | C | PRO | 161 | 95.008 | 47.109 | 11.857 | 1.00 | 23.77 | B | C |
| ATOM | 4846 | O | PRO | 161 | 95.234 | 48.238 | 11.413 | 1.00 | 23.09 | B | O |
| ATOM | 4847 | N | TRP | 162 | 95.856 | 46.463 | 12.654 | 1.00 | 23.22 | B | N |
| ATOM | 4848 | CA | TRP | 162 | 97.108 | 47.062 | 13.111 | 1.00 | 24.29 | B | C |
| ATOM | 4849 | CB | TRP | 162 | 97.922 | 46.022 | 13.878 | 1.00 | 29.42 | B | C |
| ATOM | 4850 | CG | TRP | 162 | 99.067 | 46.586 | 14.670 | 1.00 | 29.94 | B | C |
| ATOM | 4851 | CD2 | TRP | 162 | 99.004 | 47.603 | 15.676 | 1.00 | 24.78 | B | C |
| ATOM | 4852 | CE2 | TRP | 162 | 100.308 | 47.769 | 16.185 | 1.00 | 28.33 | B | C |
| ATOM | 4853 | CE3 | TRP | 162 | 97.973 | 48.389 | 16.201 | 1.00 | 24.19 | B | C |
| ATOM | 4854 | CD1 | TRP | 162 | 100.369 | 46.192 | 14.611 | 1.00 | 29.13 | B | C |
| ATOM | 4855 | NE1 | TRP | 162 | 101.123 | 46.898 | 15.516 | 1.00 | 31.00 | B | N |
| ATOM | 4856 | CZ2 | TRP | 162 | 100.607 | 48.687 | 17.195 | 1.00 | 26.87 | B | C |
| ATOM | 4857 | CZ3 | TRP | 162 | 98.274 | 49.303 | 17.208 | 1.00 | 22.52 | B | C |
| ATOM | 4858 | CH2 | TRP | 162 | 99.580 | 49.441 | 17.691 | 1.00 | 27.43 | B | C |
| ATOM | 4859 | C | TRP | 162 | 97.961 | 47.663 | 11.988 | 1.00 | 26.07 | B | C |
| ATOM | 4860 | O | TRP | 162 | 98.554 | 48.734 | 12.161 | 1.00 | 25.22 | B | O |
| ATOM | 4861 | N | GLU | 163 | 98.010 | 46.979 | 10.843 | 1.00 | 39.64 | B | N |
| ATOM | 4862 | CA | GLU | 163 | 98.797 | 47.432 | 9.693 | 1.00 | 41.42 | B | C |
| ATOM | 4863 | CB | GLU | 163 | 98.585 | 46.509 | 8.485 | 1.00 | 121.98 | B | C |
| ATOM | 4864 | CG | GLU | 163 | 97.219 | 46.612 | 7.826 | 1.00 | 128.29 | B | C |
| ATOM | 4865 | CD | GLU | 163 | 97.206 | 46.043 | 6.418 | 1.00 | 130.43 | B | C |
| ATOM | 4866 | OE1 | GLU | 163 | 97.894 | 46.611 | 5.541 | 1.00 | 132.14 | B | O |
| ATOM | 4867 | OE2 | GLU | 163 | 96.512 | 45.029 | 6.187 | 1.00 | 129.39 | B | O |
| ATOM | 4868 | C | GLU | 163 | 98.491 | 48.867 | 9.280 | 1.00 | 41.08 | B | C |
| ATOM | 4869 | O | GLU | 163 | 99.390 | 49.609 | 8.881 | 1.00 | 37.25 | B | O |
| ATOM | 4870 | N | SER | 164 | 97.225 | 49.262 | 9.368 | 1.00 | 24.58 | B | N |
| ATOM | 4871 | CA | SER | 164 | 96.850 | 50.620 | 8.989 | 1.00 | 21.77 | B | C |
| ATOM | 4872 | CB | SER | 164 | 95.320 | 50.772 | 8.984 | 1.00 | 53.34 | B | C |
| ATOM | 4873 | OG | SER | 164 | 94.722 | 49.950 | 7.992 | 1.00 | 59.23 | B | O |
| ATOM | 4874 | C | SER | 164 | 97.484 | 51.619 | 9.956 | 1.00 | 22.53 | B | C |
| ATOM | 4875 | O | SER | 164 | 97.993 | 52.661 | 9.536 | 1.00 | 25.73 | B | O |
| ATOM | 4876 | N | VAL | 165 | 97.451 | 51.286 | 11.247 | 1.00 | 28.47 | B | N |
| ATOM | 4877 | CA | VAL | 165 | 98.027 | 52.137 | 12.280 | 1.00 | 27.86 | B | C |
| ATOM | 4878 | CB | VAL | 165 | 97.841 | 51.525 | 13.680 | 1.00 | 11.01 | B | C |
| ATOM | 4879 | CG1 | VAL | 165 | 98.722 | 52.245 | 14.697 | 1.00 | 12.40 | B | C |
| ATOM | 4880 | CG2 | VAL | 165 | 96.376 | 51.622 | 14.089 | 1.00 | 14.01 | B | C |
| ATOM | 4881 | C | VAL | 165 | 99.509 | 52.334 | 12.028 | 1.00 | 29.02 | B | C |
| ATOM | 4882 | O | VAL | 165 | 100.032 | 53.444 | 12.137 | 1.00 | 30.84 | B | O |
| ATOM | 4883 | N | ILE | 166 | 100.184 | 51.248 | 11.678 | 1.00 | 20.94 | B | N |
| ATOM | 4884 | CA | ILE | 166 | 101.613 | 51.305 | 11.400 | 1.00 | 20.26 | B | C |
| ATOM | 4885 | CB | ILE | 166 | 102.211 | 49.894 | 11.330 | 1.00 | 40.92 | B | C |
| ATOM | 4886 | CG2 | ILE | 166 | 103.697 | 49.962 | 10.986 | 1.00 | 40.13 | B | C |
| ATOM | 4887 | CG1 | ILE | 166 | 102.017 | 49.214 | 12.687 | 1.00 | 40.78 | B | C |
| ATOM | 4888 | CD1 | ILE | 166 | 102.580 | 47.823 | 12.762 | 1.00 | 37.18 | B | C |
| ATOM | 4889 | C | ILE | 166 | 101.920 | 52.073 | 10.121 | 1.00 | 19.71 | B | C |
| ATOM | 4890 | O | ILE | 166 | 102.909 | 52.792 | 10.059 | 1.00 | 21.46 | B | O |
| ATOM | 4891 | N | ALA | 167 | 101.076 | 51.927 | 9.106 | 1.00 | 22.08 | B | N |

Fig. 19: A-68

| ATOM | 4892 | CA  | ALA | 167 | 101.271 | 52.670 | 7.866  | 1.00 | 22.68  | B | C |
|------|------|-----|-----|-----|---------|--------|--------|------|--------|---|---|
| ATOM | 4893 | CB  | ALA | 167 | 100.207 | 52.309 | 6.859  | 1.00 | 1.87   | B | C |
| ATOM | 4894 | C   | ALA | 167 | 101.165 | 54.150 | 8.224  | 1.00 | 23.89  | B | C |
| ATOM | 4895 | O   | ALA | 167 | 101.881 | 54.989 | 7.684  | 1.00 | 20.49  | B | O |
| ATOM | 4896 | N   | PHE | 168 | 100.261 | 54.458 | 9.147  | 1.00 | 25.99  | B | N |
| ATOM | 4897 | CA  | PHE | 168 | 100.083 | 55.823 | 9.583  | 1.00 | 24.51  | B | C |
| ATOM | 4898 | CB  | PHE | 168 | 98.964  | 55.902 | 10.623 | 1.00 | 28.51  | B | C |
| ATOM | 4899 | CG  | PHE | 168 | 98.962  | 57.185 | 11.406 | 1.00 | 27.01  | B | C |
| ATOM | 4900 | CD1 | PHE | 168 | 99.549  | 57.240 | 12.671 | 1.00 | 28.61  | B | C |
| ATOM | 4901 | CD2 | PHE | 168 | 98.409  | 58.341 | 10.872 | 1.00 | 25.32  | B | C |
| ATOM | 4902 | CE1 | PHE | 168 | 99.587  | 58.424 | 13.392 | 1.00 | 27.09  | B | C |
| ATOM | 4903 | CE2 | PHE | 168 | 98.442  | 59.529 | 11.587 | 1.00 | 27.14  | B | C |
| ATOM | 4904 | CZ  | PHE | 168 | 99.034  | 59.570 | 12.853 | 1.00 | 29.63  | B | C |
| ATOM | 4905 | C   | PHE | 168 | 101.397 | 56.325 | 10.178 | 1.00 | 25.37  | B | C |
| ATOM | 4906 | O   | PHE | 168 | 101.832 | 57.446 | 9.908  | 1.00 | 21.81  | B | O |
| ATOM | 4907 | N   | LEU | 169 | 102.030 | 55.488 | 10.990 | 1.00 | 25.37  | B | N |
| ATOM | 4908 | CA  | LEU | 169 | 103.286 | 55.867 | 11.611 | 1.00 | 27.96  | B | C |
| ATOM | 4909 | CB  | LEU | 169 | 103.749 | 54.790 | 12.585 | 1.00 | 24.35  | B | C |
| ATOM | 4910 | CG  | LEU | 169 | 103.127 | 54.723 | 13.977 | 1.00 | 23.51  | B | C |
| ATOM | 4911 | CD1 | LEU | 169 | 103.983 | 53.810 | 14.831 | 1.00 | 19.97  | B | C |
| ATOM | 4912 | CD2 | LEU | 169 | 103.079 | 56.105 | 14.609 | 1.00 | 20.37  | B | C |
| ATOM | 4913 | C   | LEU | 169 | 104.357 | 56.081 | 10.555 | 1.00 | 30.26  | B | C |
| ATOM | 4914 | O   | LEU | 169 | 105.055 | 57.095 | 10.555 | 1.00 | 31.69  | B | O |
| ATOM | 4915 | N   | ASN | 170 | 104.488 | 55.115 | 9.655  | 1.00 | 28.40  | B | N |
| ATOM | 4916 | CA  | ASN | 170 | 105.470 | 55.208 | 8.591  | 1.00 | 25.53  | B | C |
| ATOM | 4917 | CB  | ASN | 170 | 105.243 | 54.077 | 7.580  | 1.00 | 72.75  | B | C |
| ATOM | 4918 | CG  | ASN | 170 | 106.484 | 53.768 | 6.747  | 1.00 | 76.17  | B | C |
| ATOM | 4919 | OD1 | ASN | 170 | 106.703 | 54.346 | 5.680  | 1.00 | 71.70  | B | O |
| ATOM | 4920 | ND2 | ASN | 170 | 107.307 | 52.854 | 7.242  | 1.00 | 74.08  | B | N |
| ATOM | 4921 | C   | ASN | 170 | 105.335 | 56.578 | 7.913  | 1.00 | 25.54  | B | C |
| ATOM | 4922 | O   | ASN | 170 | 106.242 | 57.408 | 7.992  | 1.00 | 25.75  | B | O |
| ATOM | 4923 | N   | ASP | 171 | 104.189 | 56.819 | 7.275  | 1.00 | 35.44  | B | N |
| ATOM | 4924 | CA  | ASP | 171 | 103.940 | 58.079 | 6.581  | 1.00 | 37.56  | B | C |
| ATOM | 4925 | CB  | ASP | 171 | 102.467 | 58.179 | 6.168  | 1.00 | 72.00  | B | C |
| ATOM | 4926 | CG  | ASP | 171 | 102.163 | 57.427 | 4.880  | 1.00 | 79.65  | B | C |
| ATOM | 4927 | OD1 | ASP | 171 | 102.448 | 56.213 | 4.805  | 1.00 | 81.87  | B | O |
| ATOM | 4928 | OD2 | ASP | 171 | 101.635 | 58.055 | 3.937  | 1.00 | 81.51  | B | O |
| ATOM | 4929 | C   | ASP | 171 | 104.309 | 59.289 | 7.418  | 1.00 | 39.05  | B | C |
| ATOM | 4930 | O   | ASP | 171 | 104.975 | 60.202 | 6.937  | 1.00 | 37.77  | B | O |
| ATOM | 4931 | N   | LEU | 172 | 103.881 | 59.289 | 8.674  | 1.00 | 36.54  | B | N |
| ATOM | 4932 | CA  | LEU | 172 | 104.152 | 60.403 | 9.570  | 1.00 | 37.22  | B | C |
| ATOM | 4933 | CB  | LEU | 172 | 103.410 | 60.204 | 10.891 | 1.00 | 36.27  | B | C |
| ATOM | 4934 | CG  | LEU | 172 | 102.901 | 61.423 | 11.674 | 1.00 | 35.76  | B | C |
| ATOM | 4935 | CD1 | LEU | 172 | 103.145 | 61.178 | 13.158 | 1.00 | 33.36  | B | C |
| ATOM | 4936 | CD2 | LEU | 172 | 103.593 | 62.706 | 11.237 | 1.00 | 33.93  | B | C |
| ATOM | 4937 | C   | LEU | 172 | 105.642 | 60.561 | 9.849  | 1.00 | 37.56  | B | C |
| ATOM | 4938 | O   | LEU | 172 | 106.212 | 61.628 | 9.627  | 1.00 | 37.55  | B | O |
| ATOM | 4939 | N   | LEU | 173 | 106.269 | 59.493 | 10.337 | 1.00 | 40.49  | B | N |
| ATOM | 4940 | CA  | LEU | 173 | 107.692 | 59.520 | 10.669 | 1.00 | 43.24  | B | C |
| ATOM | 4941 | CB  | LEU | 173 | 108.115 | 58.215 | 11.364 | 1.00 | 18.13  | B | C |
| ATOM | 4942 | CG  | LEU | 173 | 107.801 | 57.866 | 12.826 | 1.00 | 19.48  | B | C |
| ATOM | 4943 | CD1 | LEU | 173 | 108.033 | 59.060 | 13.729 | 1.00 | 23.00  | B | C |
| ATOM | 4944 | CD2 | LEU | 173 | 106.380 | 57.395 | 12.943 | 1.00 | 20.03  | B | C |
| ATOM | 4945 | C   | LEU | 173 | 108.650 | 59.772 | 9.503  | 1.00 | 44.67  | B | C |
| ATOM | 4946 | O   | LEU | 173 | 109.601 | 60.537 | 9.642  | 1.00 | 41.39  | B | O |
| ATOM | 4947 | N   | LYS | 174 | 108.409 | 59.135 | 8.360  | 1.00 | 37.56  | B | N |
| ATOM | 4948 | CA  | LYS | 174 | 109.304 | 59.291 | 7.221  | 1.00 | 37.78  | B | C |
| ATOM | 4949 | CB  | LYS | 174 | 108.836 | 58.421 | 6.047  | 1.00 | 42.14  | B | C |
| ATOM | 4950 | CG  | LYS | 174 | 107.739 | 58.988 | 5.169  | 1.00 | 42.47  | B | C |
| ATOM | 4951 | CD  | LYS | 174 | 107.472 | 58.022 | 4.008  | 1.00 | 41.72  | B | C |
| ATOM | 4952 | CE  | LYS | 174 | 106.689 | 58.660 | 2.852  | 1.00 | 36.97  | B | C |
| ATOM | 4953 | NZ  | LYS | 174 | 105.297 | 59.097 | 3.187  | 1.00 | 33.44  | B | N |
| ATOM | 4954 | C   | LYS | 174 | 109.511 | 60.738 | 6.774  | 1.00 | 36.14  | B | C |
| ATOM | 4955 | O   | LYS | 174 | 110.571 | 61.078 | 6.245  | 1.00 | 37.01  | B | O |
| ATOM | 4956 | N   | ARG | 175 | 108.514 | 61.589 | 7.004  | 1.00 | 41.42  | B | N |
| ATOM | 4957 | CA  | ARG | 175 | 108.587 | 63.006 | 6.635  | 1.00 | 43.65  | B | C |
| ATOM | 4958 | CB  | ARG | 175 | 107.182 | 63.634 | 6.654  | 1.00 | 108.28 | B | C |
| ATOM | 4959 | CG  | ARG | 175 | 106.189 | 63.149 | 5.589  | 1.00 | 115.21 | B | C |
| ATOM | 4960 | CD  | ARG | 175 | 104.762 | 63.613 | 5.939  | 1.00 | 119.49 | B | C |
| ATOM | 4961 | NE  | ARG | 175 | 103.895 | 63.818 | 4.775  | 1.00 | 124.39 | B | N |
| ATOM | 4962 | CZ  | ARG | 175 | 103.454 | 62.856 | 3.969  | 1.00 | 127.97 | B | C |
| ATOM | 4963 | NH1 | ARG | 175 | 103.793 | 61.593 | 4.182  | 1.00 | 128.17 | B | N |
| ATOM | 4964 | NH2 | ARG | 175 | 102.666 | 63.162 | 2.945  | 1.00 | 128.87 | B | N |

Fig. 19: A-69

| | | | | | | | | | | |
|---|---|---|---|---|---|---|---|---|---|---|
| ATOM | 4965 | C | ARG | 175 | 109.471 | 63.798 | 7.611 | 1.00 | 41.18 | B C |
| ATOM | 4966 | O | ARG | 175 | 109.696 | 64.986 | 7.411 | 1.00 | 41.02 | B O |
| ATOM | 4967 | N | MET | 176 | 109.970 | 63.145 | 8.660 | 1.00 | 47.15 | B N |
| ATOM | 4968 | CA | MET | 176 | 110.777 | 63.821 | 9.678 | 1.00 | 43.63 | B C |
| ATOM | 4969 | CB | MET | 176 | 110.320 | 63.383 | 11.065 | 1.00 | 33.29 | B C |
| ATOM | 4970 | CG | MET | 176 | 108.969 | 63.920 | 11.456 | 1.00 | 30.19 | B C |
| ATOM | 4971 | SD | MET | 176 | 108.444 | 63.366 | 13.073 | 1.00 | 34.33 | B S |
| ATOM | 4972 | CE | MET | 176 | 107.041 | 62.339 | 12.619 | 1.00 | 27.84 | B C |
| ATOM | 4973 | C | MET | 176 | 112.284 | 63.663 | 9.611 | 1.00 | 47.14 | B C |
| ATOM | 4974 | O | MET | 176 | 112.795 | 62.707 | 9.037 | 1.00 | 47.21 | B O |
| ATOM | 4975 | N | ASP | 177 | 112.991 | 64.617 | 10.213 | 1.00 | 51.06 | B N |
| ATOM | 4976 | CA | ASP | 177 | 114.451 | 64.590 | 10.276 | 1.00 | 53.55 | B C |
| ATOM | 4977 | CB | ASP | 177 | 115.047 | 65.944 | 9.881 | 1.00 | 101.95 | B C |
| ATOM | 4978 | CG | ASP | 177 | 115.065 | 66.158 | 8.381 | 1.00 | 104.90 | B C |
| ATOM | 4979 | OD1 | ASP | 177 | 115.635 | 67.174 | 7.934 | 1.00 | 104.57 | B O |
| ATOM | 4980 | OD2 | ASP | 177 | 114.511 | 65.310 | 7.647 | 1.00 | 106.55 | B O |
| ATOM | 4981 | C | ASP | 177 | 114.851 | 64.249 | 11.706 | 1.00 | 53.47 | B C |
| ATOM | 4982 | O | ASP | 177 | 115.107 | 65.133 | 12.519 | 1.00 | 53.19 | B O |
| ATOM | 4983 | N | ILE | 178 | 114.888 | 62.954 | 12.003 | 1.00 | 55.91 | B N |
| ATOM | 4984 | CA | ILE | 178 | 115.236 | 62.465 | 13.331 | 1.00 | 56.05 | B C |
| ATOM | 4985 | CB | ILE | 178 | 114.719 | 61.004 | 13.543 | 1.00 | 33.37 | B C |
| ATOM | 4986 | CG2 | ILE | 178 | 115.323 | 60.410 | 14.790 | 1.00 | 31.65 | B C |
| ATOM | 4987 | CG1 | ILE | 178 | 113.191 | 60.985 | 13.665 | 1.00 | 34.43 | B C |
| ATOM | 4988 | CD1 | ILE | 178 | 112.464 | 60.671 | 12.376 | 1.00 | 36.27 | B C |
| ATOM | 4989 | C | ILE | 178 | 116.743 | 62.502 | 13.583 | 1.00 | 55.19 | B C |
| ATOM | 4990 | O | ILE | 178 | 117.543 | 62.224 | 12.686 | 1.00 | 57.18 | B O |
| ATOM | 4991 | N | GLY | 179 | 117.117 | 62.846 | 14.812 | 1.00 | 23.09 | B N |
| ATOM | 4992 | CA | GLY | 179 | 118.521 | 62.912 | 15.178 | 1.00 | 22.81 | B C |
| ATOM | 4993 | C | GLY | 179 | 118.736 | 63.508 | 16.560 | 1.00 | 23.57 | B C |
| ATOM | 4994 | O | GLY | 179 | 117.931 | 64.325 | 17.012 | 1.00 | 21.72 | B O |
| ATOM | 4995 | N | PRO | 180 | 119.815 | 63.113 | 17.265 | 1.00 | 39.73 | B N |
| ATOM | 4996 | CD | PRO | 180 | 120.782 | 62.068 | 16.873 | 1.00 | 73.51 | B C |
| ATOM | 4997 | CA | PRO | 180 | 120.124 | 63.620 | 18.606 | 1.00 | 40.79 | B C |
| ATOM | 4998 | CB | PRO | 180 | 121.542 | 63.113 | 18.840 | 1.00 | 72.35 | B C |
| ATOM | 4999 | CG | PRO | 180 | 121.502 | 61.776 | 18.184 | 1.00 | 74.74 | B C |
| ATOM | 5000 | C | PRO | 180 | 120.019 | 65.135 | 18.697 | 1.00 | 42.57 | B C |
| ATOM | 5001 | O | PRO | 180 | 119.718 | 65.680 | 19.761 | 1.00 | 43.21 | B O |
| ATOM | 5002 | N | LYS | 181 | 120.268 | 65.810 | 17.578 | 1.00 | 56.97 | B N |
| ATOM | 5003 | CA | LYS | 181 | 120.186 | 67.265 | 17.534 | 1.00 | 57.39 | B C |
| ATOM | 5004 | CB | LYS | 181 | 121.522 | 67.867 | 17.092 | 1.00 | 83.43 | B C |
| ATOM | 5005 | CG | LYS | 181 | 122.677 | 67.613 | 18.052 | 1.00 | 84.03 | B C |
| ATOM | 5006 | CD | LYS | 181 | 122.430 | 68.205 | 19.442 | 1.00 | 82.89 | B C |
| ATOM | 5007 | CE | LYS | 181 | 123.580 | 67.868 | 20.394 | 1.00 | 85.41 | B C |
| ATOM | 5008 | NZ | LYS | 181 | 123.351 | 68.348 | 21.790 | 1.00 | 84.98 | B N |
| ATOM | 5009 | C | LYS | 181 | 119.070 | 67.736 | 16.597 | 1.00 | 56.74 | B C |
| ATOM | 5010 | O | LYS | 181 | 118.973 | 68.917 | 16.274 | 1.00 | 55.06 | B O |
| ATOM | 5011 | N | GLN | 182 | 118.225 | 66.804 | 16.167 | 1.00 | 33.36 | B N |
| ATOM | 5012 | CA | GLN | 182 | 117.112 | 67.117 | 15.279 | 1.00 | 32.02 | B C |
| ATOM | 5013 | CB | GLN | 182 | 117.152 | 66.219 | 14.044 | 1.00 | 74.94 | B C |
| ATOM | 5014 | CG | GLN | 182 | 118.512 | 66.050 | 13.424 | 1.00 | 76.22 | B C |
| ATOM | 5015 | CD | GLN | 182 | 119.037 | 67.334 | 12.850 | 1.00 | 77.84 | B C |
| ATOM | 5016 | OE1 | GLN | 182 | 119.266 | 68.305 | 13.573 | 1.00 | 78.68 | B O |
| ATOM | 5017 | NE2 | GLN | 182 | 119.230 | 67.356 | 11.537 | 1.00 | 79.20 | B N |
| ATOM | 5018 | C | GLN | 182 | 115.831 | 66.826 | 16.046 | 1.00 | 30.93 | B C |
| ATOM | 5019 | O | GLN | 182 | 115.638 | 67.278 | 17.173 | 1.00 | 35.26 | B O |
| ATOM | 5020 | N | THR | 183 | 114.961 | 66.046 | 15.419 | 1.00 | 29.87 | B N |
| ATOM | 5021 | CA | THR | 183 | 113.706 | 65.648 | 16.025 | 1.00 | 26.79 | B C |
| ATOM | 5022 | CB | THR | 183 | 112.612 | 65.493 | 14.962 | 1.00 | 31.40 | B C |
| ATOM | 5023 | OG1 | THR | 183 | 112.484 | 66.721 | 14.231 | 1.00 | 27.85 | B O |
| ATOM | 5024 | CG2 | THR | 183 | 111.285 | 65.127 | 15.610 | 1.00 | 29.08 | B C |
| ATOM | 5025 | C | THR | 183 | 113.957 | 64.288 | 16.666 | 1.00 | 26.45 | B C |
| ATOM | 5026 | O | THR | 183 | 114.624 | 63.428 | 16.077 | 1.00 | 24.98 | B O |
| ATOM | 5027 | N | GLN | 184 | 113.464 | 64.102 | 17.883 | 1.00 | 44.27 | B N |
| ATOM | 5028 | CA | GLN | 184 | 113.619 | 62.822 | 18.546 | 1.00 | 39.92 | B C |
| ATOM | 5029 | CB | GLN | 184 | 114.254 | 62.981 | 19.920 | 1.00 | 33.99 | B C |
| ATOM | 5030 | CG | GLN | 184 | 115.752 | 63.197 | 19.878 | 1.00 | 33.74 | B C |
| ATOM | 5031 | CD | GLN | 184 | 116.427 | 62.766 | 21.163 | 1.00 | 33.21 | B C |
| ATOM | 5032 | OE1 | GLN | 184 | 116.097 | 63.258 | 22.244 | 1.00 | 28.91 | B O |
| ATOM | 5033 | NE2 | GLN | 184 | 117.375 | 61.835 | 21.053 | 1.00 | 31.51 | B N |
| ATOM | 5034 | C | GLN | 184 | 112.227 | 62.240 | 18.670 | 1.00 | 40.30 | B C |
| ATOM | 5035 | O | GLN | 184 | 111.249 | 62.978 | 18.834 | 1.00 | 37.69 | B O |
| ATOM | 5036 | N | VAL | 185 | 112.131 | 60.918 | 18.574 | 1.00 | 24.17 | B N |
| ATOM | 5037 | CA | VAL | 185 | 110.837 | 60.255 | 18.649 | 1.00 | 22.54 | B C |

Fig. 19: A-70

| | | | | | | | | | | | |
|---|---|---|---|---|---|---|---|---|---|---|---|
| ATOM | 5038 | CB | VAL | 185 | 110.345 | 59.858 | 17.235 | 1.00 | 12.44 | B | C |
| ATOM | 5039 | CG1 | VAL | 185 | 109.105 | 58.990 | 17.335 | 1.00 | 12.43 | B | C |
| ATOM | 5040 | CG2 | VAL | 185 | 110.052 | 61.103 | 16.425 | 1.00 | 1.87 | B | C |
| ATOM | 5041 | C | VAL | 185 | 110.840 | 59.025 | 19.536 | 1.00 | 23.13 | B | C |
| ATOM | 5042 | O | VAL | 185 | 111.756 | 58.206 | 19.510 | 1.00 | 20.28 | B | O |
| ATOM | 5043 | N | GLY | 186 | 109.789 | 58.914 | 20.328 | 1.00 | 27.91 | B | N |
| ATOM | 5044 | CA | GLY | 186 | 109.630 | 57.782 | 21.213 | 1.00 | 29.54 | B | C |
| ATOM | 5045 | C | GLY | 186 | 108.200 | 57.319 | 21.045 | 1.00 | 27.52 | B | C |
| ATOM | 5046 | O | GLY | 186 | 107.308 | 58.138 | 20.839 | 1.00 | 32.88 | B | O |
| ATOM | 5047 | N | ILE | 187 | 107.970 | 56.017 | 21.105 | 1.00 | 20.77 | B | N |
| ATOM | 5048 | CA | ILE | 187 | 106.617 | 55.519 | 20.958 | 1.00 | 19.36 | B | C |
| ATOM | 5049 | CB | ILE | 187 | 106.460 | 54.729 | 19.642 | 1.00 | 17.70 | B | C |
| ATOM | 5050 | CG2 | ILE | 187 | 105.081 | 54.079 | 19.577 | 1.00 | 15.03 | B | C |
| ATOM | 5051 | CG1 | ILE | 187 | 106.639 | 55.676 | 18.454 | 1.00 | 18.22 | B | C |
| ATOM | 5052 | CD1 | ILE | 187 | 106.437 | 55.033 | 17.100 | 1.00 | 19.27 | B | C |
| ATOM | 5053 | C | ILE | 187 | 106.160 | 54.674 | 22.143 | 1.00 | 18.65 | B | C |
| ATOM | 5054 | O | ILE | 187 | 106.852 | 53.763 | 22.590 | 1.00 | 17.55 | B | O |
| ATOM | 5055 | N | VAL | 188 | 104.984 | 55.015 | 22.649 | 1.00 | 23.72 | B | N |
| ATOM | 5056 | CA | VAL | 188 | 104.370 | 54.332 | 23.774 | 1.00 | 23.39 | B | C |
| ATOM | 5057 | CB | VAL | 188 | 104.053 | 55.333 | 24.911 | 1.00 | 24.28 | B | C |
| ATOM | 5058 | CG1 | VAL | 188 | 103.055 | 54.728 | 25.896 | 1.00 | 19.55 | B | C |
| ATOM | 5059 | CG2 | VAL | 188 | 105.320 | 55.715 | 25.625 | 1.00 | 24.70 | B | C |
| ATOM | 5060 | C | VAL | 188 | 103.055 | 53.702 | 23.303 | 1.00 | 21.93 | B | C |
| ATOM | 5061 | O | VAL | 188 | 102.274 | 54.341 | 22.591 | 1.00 | 21.34 | B | O |
| ATOM | 5062 | N | GLN | 189 | 102.815 | 52.453 | 23.686 | 1.00 | 21.90 | B | N |
| ATOM | 5063 | CA | GLN | 189 | 101.580 | 51.785 | 23.312 | 1.00 | 21.58 | B | C |
| ATOM | 5064 | CB | GLN | 189 | 101.857 | 50.545 | 22.463 | 1.00 | 19.75 | B | C |
| ATOM | 5065 | CG | GLN | 189 | 100.577 | 49.784 | 22.128 | 1.00 | 17.26 | B | C |
| ATOM | 5066 | CD | GLN | 189 | 100.819 | 48.495 | 21.377 | 1.00 | 17.97 | B | C |
| ATOM | 5067 | OE1 | GLN | 189 | 99.930 | 47.647 | 21.283 | 1.00 | 19.19 | B | O |
| ATOM | 5068 | NE2 | GLN | 189 | 102.022 | 48.340 | 20.831 | 1.00 | 19.01 | B | N |
| ATOM | 5069 | C | GLN | 189 | 100.820 | 51.386 | 24.572 | 1.00 | 18.57 | B | C |
| ATOM | 5070 | O | GLN | 189 | 101.423 | 50.980 | 25.567 | 1.00 | 16.93 | B | O |
| ATOM | 5071 | N | TYR | 190 | 99.494 | 51.500 | 24.524 | 1.00 | 20.56 | B | N |
| ATOM | 5072 | CA | TYR | 190 | 98.671 | 51.159 | 25.680 | 1.00 | 24.08 | B | C |
| ATOM | 5073 | CB | TYR | 190 | 98.255 | 52.432 | 26.418 | 1.00 | 22.72 | B | C |
| ATOM | 5074 | CG | TYR | 190 | 97.213 | 53.255 | 25.687 | 1.00 | 17.37 | B | C |
| ATOM | 5075 | CD1 | TYR | 190 | 95.849 | 53.072 | 25.929 | 1.00 | 15.48 | B | C |
| ATOM | 5076 | CE1 | TYR | 190 | 94.882 | 53.820 | 25.244 | 1.00 | 17.37 | B | C |
| ATOM | 5077 | CD2 | TYR | 190 | 97.586 | 54.207 | 24.739 | 1.00 | 13.48 | B | C |
| ATOM | 5078 | CE2 | TYR | 190 | 96.624 | 54.957 | 24.051 | 1.00 | 14.90 | B | C |
| ATOM | 5079 | CZ | TYR | 190 | 95.279 | 54.760 | 24.311 | 1.00 | 15.79 | B | C |
| ATOM | 5080 | OH | TYR | 190 | 94.340 | 55.527 | 23.663 | 1.00 | 14.38 | B | O |
| ATOM | 5081 | C | TYR | 190 | 97.428 | 50.342 | 25.344 | 1.00 | 25.93 | B | C |
| ATOM | 5082 | O | TYR | 190 | 97.000 | 50.260 | 24.195 | 1.00 | 26.01 | B | O |
| ATOM | 5083 | N | GLY | 191 | 96.860 | 49.746 | 26.385 | 1.00 | 24.69 | B | N |
| ATOM | 5084 | CA | GLY | 191 | 95.675 | 48.920 | 26.270 | 1.00 | 22.44 | B | C |
| ATOM | 5085 | C | GLY | 191 | 95.277 | 48.649 | 27.701 | 1.00 | 23.88 | B | C |
| ATOM | 5086 | O | GLY | 191 | 94.720 | 49.532 | 28.348 | 1.00 | 27.26 | B | O |
| ATOM | 5087 | N | GLU | 192 | 95.572 | 47.446 | 28.197 | 1.00 | 23.59 | B | N |
| ATOM | 5088 | CA | GLU | 192 | 95.284 | 47.084 | 29.584 | 1.00 | 25.60 | B | C |
| ATOM | 5089 | CB | GLU | 192 | 95.232 | 45.574 | 29.758 | 1.00 | 40.14 | B | C |
| ATOM | 5090 | CG | GLU | 192 | 94.135 | 44.871 | 29.002 | 1.00 | 40.52 | B | C |
| ATOM | 5091 | CD | GLU | 192 | 94.134 | 43.382 | 29.273 | 1.00 | 40.71 | B | C |
| ATOM | 5092 | OE1 | GLU | 192 | 93.230 | 42.690 | 28.759 | 1.00 | 43.60 | B | O |
| ATOM | 5093 | OE2 | GLU | 192 | 95.038 | 42.906 | 29.999 | 1.00 | 38.58 | B | O |
| ATOM | 5094 | C | GLU | 192 | 96.465 | 47.608 | 30.390 | 1.00 | 25.41 | B | C |
| ATOM | 5095 | O | GLU | 192 | 96.325 | 48.027 | 31.536 | 1.00 | 26.78 | B | O |
| ATOM | 5096 | N | ASN | 193 | 97.637 | 47.569 | 29.770 | 1.00 | 17.36 | B | N |
| ATOM | 5097 | CA | ASN | 193 | 98.862 | 48.041 | 30.395 | 1.00 | 18.57 | B | C |
| ATOM | 5098 | CB | ASN | 193 | 99.814 | 46.877 | 30.653 | 1.00 | 57.60 | B | C |
| ATOM | 5099 | CG | ASN | 193 | 99.159 | 45.755 | 31.418 | 1.00 | 60.77 | B | C |
| ATOM | 5100 | OD1 | ASN | 193 | 98.225 | 45.115 | 30.933 | 1.00 | 64.88 | B | O |
| ATOM | 5101 | ND2 | ASN | 193 | 99.644 | 45.509 | 32.626 | 1.00 | 62.88 | B | N |
| ATOM | 5102 | C | ASN | 193 | 99.510 | 49.007 | 29.425 | 1.00 | 16.75 | B | C |
| ATOM | 5103 | O | ASN | 193 | 98.917 | 49.360 | 28.413 | 1.00 | 17.75 | B | O |
| ATOM | 5104 | N | VAL | 194 | 100.735 | 49.418 | 29.728 | 1.00 | 23.63 | B | N |
| ATOM | 5105 | CA | VAL | 194 | 101.454 | 50.346 | 28.866 | 1.00 | 25.97 | B | C |
| ATOM | 5106 | CB | VAL | 194 | 101.516 | 51.750 | 29.490 | 1.00 | 24.85 | B | C |
| ATOM | 5107 | CG1 | VAL | 194 | 102.014 | 52.745 | 28.459 | 1.00 | 25.88 | B | C |
| ATOM | 5108 | CG2 | VAL | 194 | 100.153 | 52.147 | 30.032 | 1.00 | 22.12 | B | C |
| ATOM | 5109 | C | VAL | 194 | 102.887 | 49.864 | 28.661 | 1.00 | 23.74 | B | C |
| ATOM | 5110 | O | VAL | 194 | 103.535 | 49.384 | 29.597 | 1.00 | 21.86 | B | O |

Fig. 19: A-71

| | | | | | | | | | | |
|---|---|---|---|---|---|---|---|---|---|---|
| ATOM | 5111 | N | THR | 195 | 103.397 | 49.986 | 27.444 | 1.00 | 25.03 | B | N |
| ATOM | 5112 | CA | THR | 195 | 104.758 | 49.552 | 27.197 | 1.00 | 26.21 | B | C |
| ATOM | 5113 | CB | THR | 195 | 104.797 | 48.182 | 26.450 | 1.00 | 38.61 | B | C |
| ATOM | 5114 | OG1 | THR | 195 | 104.420 | 48.360 | 25.081 | 1.00 | 42.62 | B | O |
| ATOM | 5115 | CG2 | THR | 195 | 103.828 | 47.195 | 27.087 | 1.00 | 40.24 | B | C |
| ATOM | 5116 | C | THR | 195 | 105.511 | 50.599 | 26.391 | 1.00 | 27.05 | B | C |
| ATOM | 5117 | O | THR | 195 | 104.944 | 51.254 | 25.514 | 1.00 | 29.64 | B | O |
| ATOM | 5118 | N | HIS | 196 | 106.791 | 50.765 | 26.716 | 1.00 | 33.64 | B | N |
| ATOM | 5119 | CA | HIS | 196 | 107.656 | 51.713 | 26.029 | 1.00 | 33.74 | B | C |
| ATOM | 5120 | CB | HIS | 196 | 108.815 | 52.119 | 26.942 | 1.00 | 34.91 | B | C |
| ATOM | 5121 | CG | HIS | 196 | 108.417 | 53.011 | 28.079 | 1.00 | 31.41 | B | C |
| ATOM | 5122 | CD2 | HIS | 196 | 108.084 | 52.725 | 29.360 | 1.00 | 32.04 | B | C |
| ATOM | 5123 | ND1 | HIS | 196 | 108.322 | 54.382 | 27.955 | 1.00 | 30.06 | B | N |
| ATOM | 5124 | CE1 | HIS | 196 | 107.949 | 54.901 | 29.111 | 1.00 | 26.78 | B | C |
| ATOM | 5125 | NE2 | HIS | 196 | 107.797 | 53.918 | 29.979 | 1.00 | 24.99 | B | N |
| ATOM | 5126 | C | HIS | 196 | 108.219 | 51.017 | 24.806 | 1.00 | 33.60 | B | C |
| ATOM | 5127 | O | HIS | 196 | 109.201 | 50.289 | 24.932 | 1.00 | 32.26 | B | O |
| ATOM | 5128 | N | GLU | 197 | 107.609 | 51.216 | 23.636 | 1.00 | 34.73 | B | N |
| ATOM | 5129 | CA | GLU | 197 | 108.123 | 50.583 | 22.417 | 1.00 | 32.06 | B | C |
| ATOM | 5130 | CB | GLU | 197 | 107.313 | 50.999 | 21.193 | 1.00 | 45.57 | B | C |
| ATOM | 5131 | CG | GLU | 197 | 105.913 | 50.386 | 21.130 | 1.00 | 45.91 | B | C |
| ATOM | 5132 | CD | GLU | 197 | 105.911 | 48.876 | 21.303 | 1.00 | 44.98 | B | C |
| ATOM | 5133 | OE1 | GLU | 197 | 106.869 | 48.228 | 20.834 | 1.00 | 43.56 | B | O |
| ATOM | 5134 | OE2 | GLU | 197 | 104.949 | 48.331 | 21.892 | 1.00 | 46.64 | B | O |
| ATOM | 5135 | C | GLU | 197 | 109.595 | 50.958 | 22.245 | 1.00 | 29.53 | B | C |
| ATOM | 5136 | O | GLU | 197 | 110.447 | 50.081 | 22.151 | 1.00 | 34.73 | B | O |
| ATOM | 5137 | N | PHE | 198 | 109.898 | 52.254 | 22.203 | 1.00 | 32.40 | B | N |
| ATOM | 5138 | CA | PHE | 198 | 111.293 | 52.691 | 22.126 | 1.00 | 34.20 | B | C |
| ATOM | 5139 | CB | PHE | 198 | 111.881 | 52.501 | 20.714 | 1.00 | 23.77 | B | C |
| ATOM | 5140 | CG | PHE | 198 | 111.239 | 53.331 | 19.636 | 1.00 | 22.02 | B | C |
| ATOM | 5141 | CD1 | PHE | 198 | 111.379 | 54.711 | 19.614 | 1.00 | 28.16 | B | C |
| ATOM | 5142 | CD2 | PHE | 198 | 110.539 | 52.715 | 18.597 | 1.00 | 16.76 | B | C |
| ATOM | 5143 | CE1 | PHE | 198 | 110.837 | 55.468 | 18.571 | 1.00 | 24.19 | B | C |
| ATOM | 5144 | CE2 | PHE | 198 | 109.990 | 53.460 | 17.548 | 1.00 | 22.67 | B | C |
| ATOM | 5145 | CZ | PHE | 198 | 110.140 | 54.838 | 17.536 | 1.00 | 26.47 | B | C |
| ATOM | 5146 | C | PHE | 198 | 111.471 | 54.120 | 22.642 | 1.00 | 36.88 | B | C |
| ATOM | 5147 | O | PHE | 198 | 110.631 | 54.973 | 22.398 | 1.00 | 38.17 | B | O |
| ATOM | 5148 | N | ASN | 199 | 112.552 | 54.366 | 23.386 | 1.00 | 21.75 | B | N |
| ATOM | 5149 | CA | ASN | 199 | 112.810 | 55.686 | 23.971 | 1.00 | 22.04 | B | C |
| ATOM | 5150 | CB | ASN | 199 | 113.924 | 55.613 | 25.007 | 1.00 | 33.57 | B | C |
| ATOM | 5151 | CG | ASN | 199 | 113.636 | 54.633 | 26.105 | 1.00 | 34.83 | B | C |
| ATOM | 5152 | OD1 | ASN | 199 | 112.614 | 54.717 | 26.785 | 1.00 | 36.36 | B | O |
| ATOM | 5153 | ND2 | ASN | 199 | 114.549 | 53.688 | 26.295 | 1.00 | 33.71 | B | N |
| ATOM | 5154 | C | ASN | 199 | 113.159 | 56.792 | 22.996 | 1.00 | 24.50 | B | C |
| ATOM | 5155 | O | ASN | 199 | 113.569 | 56.546 | 21.862 | 1.00 | 22.31 | B | O |
| ATOM | 5156 | N | LEU | 200 | 113.004 | 58.023 | 23.473 | 1.00 | 27.41 | B | N |
| ATOM | 5157 | CA | LEU | 200 | 113.286 | 59.215 | 22.685 | 1.00 | 29.37 | B | C |
| ATOM | 5158 | CB | LEU | 200 | 113.094 | 60.467 | 23.542 | 1.00 | 22.93 | B | C |
| ATOM | 5159 | CG | LEU | 200 | 111.694 | 61.088 | 23.545 | 1.00 | 20.78 | B | C |
| ATOM | 5160 | CD1 | LEU | 200 | 111.613 | 62.208 | 24.578 | 1.00 | 25.90 | B | C |
| ATOM | 5161 | CD2 | LEU | 200 | 111.375 | 61.607 | 22.140 | 1.00 | 21.95 | B | C |
| ATOM | 5162 | C | LEU | 200 | 114.685 | 59.223 | 22.104 | 1.00 | 29.77 | B | C |
| ATOM | 5163 | O | LEU | 200 | 114.899 | 59.698 | 20.992 | 1.00 | 30.79 | B | O |
| ATOM | 5164 | N | ASN | 201 | 115.635 | 58.685 | 22.856 | 1.00 | 32.06 | B | N |
| ATOM | 5165 | CA | ASN | 201 | 117.027 | 58.660 | 22.426 | 1.00 | 33.91 | B | C |
| ATOM | 5166 | CB | ASN | 201 | 117.920 | 59.105 | 23.578 | 1.00 | 34.75 | B | C |
| ATOM | 5167 | CG | ASN | 201 | 117.838 | 58.168 | 24.769 | 1.00 | 37.03 | B | C |
| ATOM | 5168 | OD1 | ASN | 201 | 118.389 | 58.443 | 25.832 | 1.00 | 37.17 | B | O |
| ATOM | 5169 | ND2 | ASN | 201 | 117.147 | 57.052 | 24.592 | 1.00 | 34.87 | B | N |
| ATOM | 5170 | C | ASN | 201 | 117.517 | 57.309 | 21.936 | 1.00 | 33.96 | B | C |
| ATOM | 5171 | O | ASN | 201 | 118.723 | 57.111 | 21.825 | 1.00 | 29.86 | B | O |
| ATOM | 5172 | N | LYS | 202 | 116.603 | 56.382 | 21.653 | 1.00 | 35.80 | B | N |
| ATOM | 5173 | CA | LYS | 202 | 116.990 | 55.051 | 21.183 | 1.00 | 35.92 | B | C |
| ATOM | 5174 | CB | LYS | 202 | 115.786 | 54.107 | 21.160 | 1.00 | 34.30 | B | C |
| ATOM | 5175 | CG | LYS | 202 | 116.107 | 52.652 | 20.788 | 1.00 | 35.84 | B | C |
| ATOM | 5176 | CD | LYS | 202 | 116.841 | 51.929 | 21.898 | 1.00 | 37.75 | B | C |
| ATOM | 5177 | CE | LYS | 202 | 116.185 | 52.179 | 23.273 | 1.00 | 43.50 | B | C |
| ATOM | 5178 | NZ | LYS | 202 | 114.729 | 51.801 | 23.388 | 1.00 | 42.52 | B | N |
| ATOM | 5179 | C | LYS | 202 | 117.617 | 55.071 | 19.800 | 1.00 | 34.79 | B | C |
| ATOM | 5180 | O | LYS | 202 | 118.667 | 54.472 | 19.589 | 1.00 | 32.07 | B | O |
| ATOM | 5181 | N | TYR | 203 | 116.977 | 55.747 | 18.852 | 1.00 | 23.81 | B | N |
| ATOM | 5182 | CA | TYR | 203 | 117.509 | 55.815 | 17.491 | 1.00 | 23.49 | B | C |
| ATOM | 5183 | CB | TYR | 203 | 116.466 | 55.300 | 16.499 | 1.00 | 32.41 | B | C |

Fig. 19: A-72

| | | | | | | | | | | |
|---|---|---|---|---|---|---|---|---|---|---|
| ATOM | 5184 | CG | TYR | 203 | 115.907 | 53.951 | 16.886 | 1.00 | 31.08 | B C |
| ATOM | 5185 | CD1 | TYR | 203 | 114.665 | 53.844 | 17.509 | 1.00 | 31.69 | B C |
| ATOM | 5186 | CE1 | TYR | 203 | 114.179 | 52.613 | 17.930 | 1.00 | 28.16 | B C |
| ATOM | 5187 | CD2 | TYR | 203 | 116.649 | 52.784 | 16.689 | 1.00 | 33.97 | B C |
| ATOM | 5188 | CE2 | TYR | 203 | 116.173 | 51.550 | 17.109 | 1.00 | 36.72 | B C |
| ATOM | 5189 | CZ | TYR | 203 | 114.940 | 51.474 | 17.730 | 1.00 | 36.34 | B C |
| ATOM | 5190 | OH | TYR | 203 | 114.466 | 50.262 | 18.169 | 1.00 | 41.34 | B O |
| ATOM | 5191 | C | TYR | 203 | 117.957 | 57.230 | 17.114 | 1.00 | 24.13 | B C |
| ATOM | 5192 | O | TYR | 203 | 117.268 | 58.211 | 17.387 | 1.00 | 22.30 | B O |
| ATOM | 5193 | N | SER | 204 | 119.122 | 57.323 | 16.484 | 1.00 | 32.64 | B N |
| ATOM | 5194 | CA | SER | 204 | 119.693 | 58.608 | 16.089 | 1.00 | 34.49 | B C |
| ATOM | 5195 | CB | SER | 204 | 121.199 | 58.588 | 16.320 | 1.00 | 50.27 | B C |
| ATOM | 5196 | OG | SER | 204 | 121.780 | 57.499 | 15.621 | 1.00 | 52.10 | B O |
| ATOM | 5197 | C | SER | 204 | 119.432 | 58.924 | 14.632 | 1.00 | 37.07 | B C |
| ATOM | 5198 | O | SER | 204 | 119.922 | 59.919 | 14.113 | 1.00 | 37.58 | B O |
| ATOM | 5199 | N | SER | 205 | 118.657 | 58.082 | 13.966 | 1.00 | 56.25 | B N |
| ATOM | 5200 | CA | SER | 205 | 118.379 | 58.289 | 12.558 | 1.00 | 55.91 | B C |
| ATOM | 5201 | CB | SER | 205 | 119.256 | 57.357 | 11.734 | 1.00 | 30.45 | B C |
| ATOM | 5202 | OG | SER | 205 | 118.818 | 57.302 | 10.393 | 1.00 | 35.94 | B O |
| ATOM | 5203 | C | SER | 205 | 116.918 | 58.067 | 12.195 | 1.00 | 54.04 | B C |
| ATOM | 5204 | O | SER | 205 | 116.208 | 57.320 | 12.866 | 1.00 | 50.30 | B O |
| ATOM | 5205 | N | THR | 206 | 116.477 | 58.718 | 11.122 | 1.00 | 22.26 | B N |
| ATOM | 5206 | CA | THR | 206 | 115.105 | 58.589 | 10.661 | 1.00 | 23.61 | B C |
| ATOM | 5207 | CB | THR | 206 | 114.799 | 59.611 | 9.560 | 1.00 | 36.04 | B C |
| ATOM | 5208 | OG1 | THR | 206 | 114.968 | 60.935 | 10.086 | 1.00 | 34.85 | B O |
| ATOM | 5209 | CG2 | THR | 206 | 113.364 | 59.438 | 9.047 | 1.00 | 34.41 | B C |
| ATOM | 5210 | C | THR | 206 | 114.780 | 57.188 | 10.144 | 1.00 | 24.20 | B C |
| ATOM | 5211 | O | THR | 206 | 113.676 | 56.683 | 10.363 | 1.00 | 26.99 | B O |
| ATOM | 5212 | N | GLU | 207 | 115.719 | 56.554 | 9.447 | 1.00 | 31.43 | B N |
| ATOM | 5213 | CA | GLU | 207 | 115.444 | 55.210 | 8.964 | 1.00 | 30.59 | B C |
| ATOM | 5214 | CB | GLU | 207 | 116.448 | 54.791 | 7.893 | 1.00 | 74.76 | B C |
| ATOM | 5215 | CG | GLU | 207 | 117.897 | 54.985 | 8.248 | 1.00 | 75.48 | B C |
| ATOM | 5216 | CD | GLU | 207 | 118.817 | 54.402 | 7.189 | 1.00 | 76.89 | B C |
| ATOM | 5217 | OE1 | GLU | 207 | 118.595 | 54.668 | 5.982 | 1.00 | 76.12 | B O |
| ATOM | 5218 | OE2 | GLU | 207 | 119.765 | 53.679 | 7.565 | 1.00 | 75.79 | B O |
| ATOM | 5219 | C | GLU | 207 | 115.462 | 54.237 | 10.141 | 1.00 | 31.09 | B C |
| ATOM | 5220 | O | GLU | 207 | 114.647 | 53.315 | 10.194 | 1.00 | 31.04 | B O |
| ATOM | 5221 | N | GLU | 208 | 116.373 | 54.449 | 11.093 | 1.00 | 40.73 | B N |
| ATOM | 5222 | CA | GLU | 208 | 116.441 | 53.594 | 12.267 | 1.00 | 42.46 | B C |
| ATOM | 5223 | CB | GLU | 208 | 117.542 | 54.038 | 13.230 | 1.00 | 57.02 | B C |
| ATOM | 5224 | CG | GLU | 208 | 118.951 | 53.899 | 12.682 | 1.00 | 54.49 | B C |
| ATOM | 5225 | CD | GLU | 208 | 120.022 | 54.254 | 13.703 | 1.00 | 54.01 | B C |
| ATOM | 5226 | OE1 | GLU | 208 | 121.217 | 54.253 | 13.333 | 1.00 | 59.78 | B O |
| ATOM | 5227 | OE2 | GLU | 208 | 119.669 | 54.533 | 14.873 | 1.00 | 52.73 | B O |
| ATOM | 5228 | C | GLU | 208 | 115.100 | 53.611 | 12.991 | 1.00 | 43.16 | B C |
| ATOM | 5229 | O | GLU | 208 | 114.637 | 52.584 | 13.489 | 1.00 | 44.16 | B O |
| ATOM | 5230 | N | VAL | 209 | 114.478 | 54.787 | 13.046 | 1.00 | 30.06 | B N |
| ATOM | 5231 | CA | VAL | 209 | 113.190 | 54.922 | 13.709 | 1.00 | 28.98 | B C |
| ATOM | 5232 | CB | VAL | 209 | 112.879 | 56.399 | 14.058 | 1.00 | 17.77 | B C |
| ATOM | 5233 | CG1 | VAL | 209 | 111.379 | 56.612 | 14.232 | 1.00 | 18.10 | B C |
| ATOM | 5234 | CG2 | VAL | 209 | 113.575 | 56.762 | 15.349 | 1.00 | 18.79 | B C |
| ATOM | 5235 | C | VAL | 209 | 112.098 | 54.359 | 12.820 | 1.00 | 27.00 | B C |
| ATOM | 5236 | O | VAL | 209 | 111.198 | 53.660 | 13.296 | 1.00 | 25.96 | B O |
| ATOM | 5237 | N | LEU | 210 | 112.187 | 54.655 | 11.529 | 1.00 | 33.19 | B N |
| ATOM | 5238 | CA | LEU | 210 | 111.207 | 54.164 | 10.570 | 1.00 | 33.52 | B C |
| ATOM | 5239 | CB | LEU | 210 | 111.557 | 54.643 | 9.168 | 1.00 | 15.67 | B C |
| ATOM | 5240 | CG | LEU | 210 | 110.629 | 55.672 | 8.535 | 1.00 | 15.91 | B C |
| ATOM | 5241 | CD1 | LEU | 210 | 111.182 | 55.981 | 7.171 | 1.00 | 12.46 | B C |
| ATOM | 5242 | CD2 | LEU | 210 | 109.191 | 55.157 | 8.437 | 1.00 | 9.36 | B C |
| ATOM | 5243 | C | LEU | 210 | 111.152 | 52.639 | 10.571 | 1.00 | 31.78 | B C |
| ATOM | 5244 | O | LEU | 210 | 110.090 | 52.042 | 10.382 | 1.00 | 32.55 | B O |
| ATOM | 5245 | N | VAL | 211 | 112.307 | 52.017 | 10.779 | 1.00 | 24.37 | B N |
| ATOM | 5246 | CA | VAL | 211 | 112.404 | 50.569 | 10.809 | 1.00 | 24.13 | B C |
| ATOM | 5247 | CB | VAL | 211 | 113.852 | 50.123 | 10.575 | 1.00 | 20.01 | B C |
| ATOM | 5248 | CG1 | VAL | 211 | 114.002 | 48.647 | 10.897 | 1.00 | 22.19 | B C |
| ATOM | 5249 | CG2 | VAL | 211 | 114.239 | 50.405 | 9.118 | 1.00 | 20.62 | B C |
| ATOM | 5250 | C | VAL | 211 | 111.913 | 49.997 | 12.129 | 1.00 | 23.38 | B C |
| ATOM | 5251 | O | VAL | 211 | 111.260 | 48.958 | 12.164 | 1.00 | 24.06 | B O |
| ATOM | 5252 | N | ALA | 212 | 112.230 | 50.674 | 13.221 | 1.00 | 40.83 | B N |
| ATOM | 5253 | CA | ALA | 212 | 111.803 | 50.203 | 14.526 | 1.00 | 39.81 | B C |
| ATOM | 5254 | CB | ALA | 212 | 112.489 | 51.000 | 15.612 | 1.00 | 28.52 | B C |
| ATOM | 5255 | C | ALA | 212 | 110.295 | 50.339 | 14.650 | 1.00 | 37.62 | B C |
| ATOM | 5256 | O | ALA | 212 | 109.626 | 49.493 | 15.256 | 1.00 | 37.56 | B O |

Fig. 19: A-73

| ATOM | 5257 | N   | ALA | 213 | 109.759 | 51.408 | 14.069 | 1.00 | 31.97 | B | N |
|------|------|-----|-----|-----|---------|--------|--------|------|-------|---|---|
| ATOM | 5258 | CA  | ALA | 213 | 108.324 | 51.658 | 14.122 | 1.00 | 33.14 | B | C |
| ATOM | 5259 | CB  | ALA | 213 | 107.999 | 52.998 | 13.459 | 1.00 | 19.99 | B | C |
| ATOM | 5260 | C   | ALA | 213 | 107.530 | 50.535 | 13.458 | 1.00 | 31.94 | B | C |
| ATOM | 5261 | O   | ALA | 213 | 106.556 | 50.029 | 14.025 | 1.00 | 29.57 | B | O |
| ATOM | 5262 | N   | ASN | 214 | 107.954 | 50.142 | 12.258 | 1.00 | 35.89 | B | N |
| ATOM | 5263 | CA  | ASN | 214 | 107.264 | 49.091 | 11.524 | 1.00 | 39.76 | B | C |
| ATOM | 5264 | CB  | ASN | 214 | 107.804 | 48.970 | 10.100 | 1.00 | 79.46 | B | C |
| ATOM | 5265 | CG  | ASN | 214 | 107.278 | 50.049 | 9.190  | 1.00 | 81.19 | B | C |
| ATOM | 5266 | OD1 | ASN | 214 | 107.666 | 51.210 | 9.296  | 1.00 | 83.12 | B | O |
| ATOM | 5267 | ND2 | ASN | 214 | 106.379 | 49.676 | 8.289  | 1.00 | 81.61 | B | N |
| ATOM | 5268 | C   | ASN | 214 | 107.348 | 47.738 | 12.207 | 1.00 | 42.15 | B | C |
| ATOM | 5269 | O   | ASN | 214 | 106.583 | 46.829 | 11.891 | 1.00 | 42.87 | B | O |
| ATOM | 5270 | N   | LYS | 215 | 108.271 | 47.596 | 13.148 | 1.00 | 30.37 | B | N |
| ATOM | 5271 | CA  | LYS | 215 | 108.418 | 46.326 | 13.856 | 1.00 | 30.81 | B | C |
| ATOM | 5272 | CB  | LYS | 215 | 109.892 | 46.059 | 14.209 | 1.00 | 46.54 | B | C |
| ATOM | 5273 | CG  | LYS | 215 | 110.791 | 45.922 | 12.978 | 1.00 | 54.12 | B | C |
| ATOM | 5274 | CD  | LYS | 215 | 112.062 | 45.124 | 13.256 | 1.00 | 57.66 | B | C |
| ATOM | 5275 | CE  | LYS | 215 | 112.950 | 45.778 | 14.311 | 1.00 | 61.12 | B | C |
| ATOM | 5276 | NZ  | LYS | 215 | 114.249 | 45.057 | 14.483 | 1.00 | 62.11 | B | N |
| ATOM | 5277 | C   | LYS | 215 | 107.560 | 46.274 | 15.113 | 1.00 | 28.94 | B | C |
| ATOM | 5278 | O   | LYS | 215 | 107.568 | 45.277 | 15.832 | 1.00 | 30.16 | B | O |
| ATOM | 5279 | N   | ILE | 216 | 106.809 | 47.341 | 15.377 | 1.00 | 44.32 | B | N |
| ATOM | 5280 | CA  | ILE | 216 | 105.945 | 47.362 | 16.553 | 1.00 | 41.14 | B | C |
| ATOM | 5281 | CB  | ILE | 216 | 105.443 | 48.776 | 16.874 | 1.00 | 15.33 | B | C |
| ATOM | 5282 | CG2 | ILE | 216 | 104.492 | 48.730 | 18.038 | 1.00 | 12.11 | B | C |
| ATOM | 5283 | CG1 | ILE | 216 | 106.616 | 49.674 | 17.243 | 1.00 | 12.01 | B | C |
| ATOM | 5284 | CD1 | ILE | 216 | 106.191 | 51.073 | 17.602 | 1.00 | 10.70 | B | C |
| ATOM | 5285 | C   | ILE | 216 | 104.740 | 46.447 | 16.369 | 1.00 | 39.58 | B | C |
| ATOM | 5286 | O   | ILE | 216 | 104.035 | 46.498 | 15.361 | 1.00 | 40.28 | B | O |
| ATOM | 5287 | N   | VAL | 217 | 104.524 | 45.611 | 17.372 | 1.00 | 36.13 | B | N |
| ATOM | 5288 | CA  | VAL | 217 | 103.436 | 44.647 | 17.392 | 1.00 | 37.90 | B | C |
| ATOM | 5289 | CB  | VAL | 217 | 103.949 | 43.284 | 17.887 | 1.00 | 59.95 | B | C |
| ATOM | 5290 | CG1 | VAL | 217 | 102.793 | 42.367 | 18.217 | 1.00 | 59.95 | B | C |
| ATOM | 5291 | CG2 | VAL | 217 | 104.837 | 42.666 | 16.829 | 1.00 | 59.95 | B | C |
| ATOM | 5292 | C   | VAL | 217 | 102.316 | 45.111 | 18.311 | 1.00 | 39.06 | B | C |
| ATOM | 5293 | O   | VAL | 217 | 102.565 | 45.725 | 19.352 | 1.00 | 38.52 | B | O |
| ATOM | 5294 | N   | GLN | 218 | 101.084 | 44.809 | 17.914 | 1.00 | 32.14 | B | N |
| ATOM | 5295 | CA  | GLN | 218 | 99.907  | 45.181 | 18.687 | 1.00 | 32.80 | B | C |
| ATOM | 5296 | CB  | GLN | 218 | 98.646  | 44.976 | 17.850 | 1.00 | 28.44 | B | C |
| ATOM | 5297 | CG  | GLN | 218 | 97.378  | 45.433 | 18.528 | 1.00 | 28.44 | B | C |
| ATOM | 5298 | CD  | GLN | 218 | 96.153  | 45.273 | 17.644 | 1.00 | 28.44 | B | C |
| ATOM | 5299 | OE1 | GLN | 218 | 95.096  | 45.843 | 17.928 | 1.00 | 28.44 | B | O |
| ATOM | 5300 | NE2 | GLN | 218 | 96.283  | 44.490 | 16.571 | 1.00 | 28.44 | B | N |
| ATOM | 5301 | C   | GLN | 218 | 99.856  | 44.288 | 19.913 | 1.00 | 32.25 | B | C |
| ATOM | 5302 | O   | GLN | 218 | 99.948  | 43.079 | 19.792 | 1.00 | 36.00 | B | O |
| ATOM | 5303 | N   | ARG | 219 | 99.709  | 44.883 | 21.091 | 1.00 | 14.17 | B | N |
| ATOM | 5304 | CA  | ARG | 219 | 99.664  | 44.114 | 22.330 | 1.00 | 13.82 | B | C |
| ATOM | 5305 | CB  | ARG | 219 | 100.490 | 44.828 | 23.394 | 1.00 | 43.11 | B | C |
| ATOM | 5306 | CG  | ARG | 219 | 101.627 | 45.640 | 22.823 | 1.00 | 43.11 | B | C |
| ATOM | 5307 | CD  | ARG | 219 | 102.594 | 46.039 | 23.901 | 1.00 | 43.11 | B | C |
| ATOM | 5308 | NE  | ARG | 219 | 103.597 | 45.007 | 24.124 | 1.00 | 43.11 | B | N |
| ATOM | 5309 | CZ  | ARG | 219 | 104.694 | 44.867 | 23.384 | 1.00 | 43.11 | B | C |
| ATOM | 5310 | NH1 | ARG | 219 | 104.921 | 45.705 | 22.369 | 1.00 | 43.11 | B | N |
| ATOM | 5311 | NH2 | ARG | 219 | 105.566 | 43.900 | 23.661 | 1.00 | 43.11 | B | N |
| ATOM | 5312 | C   | ARG | 219 | 98.221  | 43.910 | 22.821 | 1.00 | 15.03 | B | C |
| ATOM | 5313 | O   | ARG | 219 | 97.976  | 43.309 | 23.871 | 1.00 | 15.04 | B | O |
| ATOM | 5314 | N   | GLY | 220 | 97.269  | 44.423 | 22.048 | 1.00 | 30.91 | B | N |
| ATOM | 5315 | CA  | GLY | 220 | 95.868  | 44.283 | 22.402 | 1.00 | 30.52 | B | C |
| ATOM | 5316 | C   | GLY | 220 | 95.495  | 44.884 | 23.742 | 1.00 | 30.19 | B | C |
| ATOM | 5317 | O   | GLY | 220 | 96.246  | 45.674 | 24.327 | 1.00 | 28.53 | B | O |
| ATOM | 5318 | N   | GLY | 221 | 94.316  | 44.511 | 24.222 | 1.00 | 22.15 | B | N |
| ATOM | 5319 | CA  | GLY | 221 | 93.852  | 45.009 | 25.500 | 1.00 | 20.72 | B | C |
| ATOM | 5320 | C   | GLY | 221 | 92.348  | 44.902 | 25.652 | 1.00 | 21.14 | B | C |
| ATOM | 5321 | O   | GLY | 221 | 91.598  | 45.328 | 24.776 | 1.00 | 17.94 | B | O |
| ATOM | 5322 | N   | ARG | 222 | 91.897  | 44.327 | 26.760 | 1.00 | 28.36 | B | N |
| ATOM | 5323 | CA  | ARG | 222 | 90.467  | 44.199 | 27.011 | 1.00 | 29.07 | B | C |
| ATOM | 5324 | CB  | ARG | 222 | 90.204  | 43.114 | 28.053 | 1.00 | 26.86 | B | C |
| ATOM | 5325 | CG  | ARG | 222 | 90.365  | 41.713 | 27.491 | 1.00 | 26.86 | B | C |
| ATOM | 5326 | CD  | ARG | 222 | 90.427  | 40.663 | 28.578 | 1.00 | 26.86 | B | C |
| ATOM | 5327 | NE  | ARG | 222 | 91.679  | 40.734 | 29.316 | 1.00 | 26.86 | B | N |
| ATOM | 5328 | CZ  | ARG | 222 | 92.021  | 39.885 | 30.274 | 1.00 | 26.86 | B | C |
| ATOM | 5329 | NH1 | ARG | 222 | 91.201  | 38.895 | 30.612 | 1.00 | 26.86 | B | N |

Fig. 19: A-74

```
ATOM   5330  NH2 ARG  222     93.184  40.027  30.893  1.00  26.86  B  N
ATOM   5331  C   ARG  222     89.899  45.529  27.482  1.00  29.12  B  C
ATOM   5332  O   ARG  222     88.686  45.686  27.599  1.00  29.89  B  O
ATOM   5333  N   GLN  223     90.792  46.477  27.756  1.00  34.74  B  N
ATOM   5334  CA  GLN  223     90.423  47.826  28.182  1.00  33.03  B  C
ATOM   5335  CB  GLN  223     90.700  48.050  29.677  1.00  36.16  B  C
ATOM   5336  CG  GLN  223     89.723  47.394  30.641  1.00  37.60  B  C
ATOM   5337  CD  GLN  223     90.065  45.957  30.915  1.00  38.01  B  C
ATOM   5338  OE1 GLN  223     91.209  45.635  31.230  1.00  38.41  B  O
ATOM   5339  NE2 GLN  223     89.075  45.080  30.811  1.00  38.45  B  N
ATOM   5340  C   GLN  223     91.221  48.849  27.372  1.00  33.77  B  C
ATOM   5341  O   GLN  223     92.122  48.487  26.619  1.00  33.25  B  O
ATOM   5342  N   THR  224     90.893  50.126  27.535  1.00  56.95  B  N
ATOM   5343  CA  THR  224     91.572  51.197  26.820  1.00  54.83  B  C
ATOM   5344  CB  THR  224     90.628  51.834  25.793  1.00   7.14  B  C
ATOM   5345  OG1 THR  224     90.118  50.811  24.930  1.00   7.13  B  O
ATOM   5346  CG2 THR  224     91.357  52.895  24.965  1.00   4.73  B  C
ATOM   5347  C   THR  224     92.002  52.252  27.829  1.00  51.84  B  C
ATOM   5348  O   THR  224     91.290  53.221  28.067  1.00  48.33  B  O
ATOM   5349  N   MET  225     93.175  52.061  28.419  1.00  27.08  B  N
ATOM   5350  CA  MET  225     93.679  52.980  29.426  1.00  27.97  B  C
ATOM   5351  CB  MET  225     94.712  52.269  30.301  1.00  32.79  B  C
ATOM   5352  CG  MET  225     94.280  50.904  30.804  1.00  30.22  B  C
ATOM   5353  SD  MET  225     92.971  50.963  31.995  1.00  37.96  B  S
ATOM   5354  CE  MET  225     93.153  49.343  32.760  1.00  34.54  B  C
ATOM   5355  C   MET  225     94.304  54.237  28.846  1.00  29.00  B  C
ATOM   5356  O   MET  225     95.442  54.561  29.180  1.00  30.46  B  O
ATOM   5357  N   THR  226     93.571  54.953  27.997  1.00  32.08  B  N
ATOM   5358  CA  THR  226     94.102  56.178  27.393  1.00  31.55  B  C
ATOM   5359  CB  THR  226     93.013  56.963  26.655  1.00  28.80  B  C
ATOM   5360  OG1 THR  226     92.395  56.132  25.665  1.00  30.82  B  O
ATOM   5361  CG2 THR  226     93.620  58.170  25.976  1.00  26.52  B  C
ATOM   5362  C   THR  226     94.735  57.104  28.438  1.00  30.15  B  C
ATOM   5363  O   THR  226     95.804  57.672  28.216  1.00  24.84  B  O
ATOM   5364  N   ALA  227     94.075  57.249  29.581  1.00  17.95  B  N
ATOM   5365  CA  ALA  227     94.594  58.094  30.645  1.00  16.89  B  C
ATOM   5366  CB  ALA  227     93.655  58.069  31.829  1.00  18.36  B  C
ATOM   5367  C   ALA  227     95.975  57.633  31.076  1.00  17.55  B  C
ATOM   5368  O   ALA  227     96.898  58.439  31.199  1.00  18.35  B  O
ATOM   5369  N   LEU  228     96.111  56.331  31.307  1.00  19.16  B  N
ATOM   5370  CA  LEU  228     97.384  55.752  31.728  1.00  17.60  B  C
ATOM   5371  CB  LEU  228     97.206  54.252  32.017  1.00   6.84  B  C
ATOM   5372  CG  LEU  228     98.453  53.498  32.483  1.00  14.73  B  C
ATOM   5373  CD1 LEU  228     99.020  54.157  33.734  1.00  12.32  B  C
ATOM   5374  CD2 LEU  228     98.097  52.064  32.732  1.00  11.78  B  C
ATOM   5375  C   LEU  228     98.463  55.955  30.662  1.00  16.78  B  C
ATOM   5376  O   LEU  228     99.605  56.321  30.971  1.00  19.76  B  O
ATOM   5377  N   GLY  229     98.094  55.713  29.408  1.00  21.79  B  N
ATOM   5378  CA  GLY  229     99.033  55.877  28.318  1.00  24.15  B  C
ATOM   5379  C   GLY  229     99.620  57.267  28.293  1.00  26.71  B  C
ATOM   5380  O   GLY  229    100.843  57.422  28.296  1.00  27.30  B  O
ATOM   5381  N   ILE  230     98.756  58.281  28.280  1.00  20.54  B  N
ATOM   5382  CA  ILE  230     99.216  59.666  28.259  1.00  21.87  B  C
ATOM   5383  CB  ILE  230     98.039  60.677  28.160  1.00  18.79  B  C
ATOM   5384  CG2 ILE  230     98.595  62.090  28.034  1.00  18.79  B  C
ATOM   5385  CG1 ILE  230     97.174  60.370  26.933  1.00  18.79  B  C
ATOM   5386  CD1 ILE  230     95.945  61.225  26.807  1.00  18.79  B  C
ATOM   5387  C   ILE  230    100.042  60.007  29.505  1.00  22.13  B  C
ATOM   5388  O   ILE  230    101.101  60.634  29.402  1.00  20.06  B  O
ATOM   5389  N   ASP  231     99.566  59.595  30.677  1.00  30.92  B  N
ATOM   5390  CA  ASP  231    100.286  59.876  31.916  1.00  29.32  B  C
ATOM   5391  CB  ASP  231     99.494  59.354  33.116  1.00  27.91  B  C
ATOM   5392  CG  ASP  231     99.993  59.917  34.442  1.00  34.91  B  C
ATOM   5393  OD1 ASP  231     99.939  61.155  34.644  1.00  33.67  B  O
ATOM   5394  OD2 ASP  231    100.432  59.112  35.288  1.00  38.45  B  O
ATOM   5395  C   ASP  231    101.676  59.231  31.884  1.00  30.30  B  C
ATOM   5396  O   ASP  231    102.669  59.838  32.318  1.00  27.52  B  O
ATOM   5397  N   THR  232    101.741  58.007  31.361  1.00  43.37  B  N
ATOM   5398  CA  THR  232    102.998  57.276  31.260  1.00  42.16  B  C
ATOM   5399  CB  THR  232    102.768  55.830  30.801  1.00  59.43  B  C
ATOM   5400  OG1 THR  232    101.963  55.148  31.771  1.00  57.94  B  O
ATOM   5401  CG2 THR  232    104.097  55.098  30.645  1.00  52.97  B  C
ATOM   5402  C   THR  232    103.939  57.959  30.274  1.00  42.79  B  C
```

Fig. 19: A-75

```
ATOM   5403  O    THR  232     105.153  58.050  30.509  1.00  42.96  B  O
ATOM   5404  N    ALA  233     103.383  58.427  29.161  1.00  22.02  B  N
ATOM   5405  CA   ALA  233     104.202  59.116  28.179  1.00  24.67  B  C
ATOM   5406  CB   ALA  233     103.373  59.472  26.961  1.00  49.88  B  C
ATOM   5407  C    ALA  233     104.752  60.385  28.836  1.00  26.98  B  C
ATOM   5408  O    ALA  233     105.862  60.834  28.532  1.00  28.89  B  O
ATOM   5409  N    ARG  234     103.967  60.947  29.751  1.00  50.27  B  N
ATOM   5410  CA   ARG  234     104.361  62.165  30.431  1.00  53.37  B  C
ATOM   5411  CB   ARG  234     103.146  62.842  31.077  1.00  50.29  B  C
ATOM   5412  CG   ARG  234     103.377  64.312  31.390  1.00  50.29  B  C
ATOM   5413  CD   ARG  234     102.536  64.816  32.561  1.00  50.29  B  C
ATOM   5414  NE   ARG  234     103.103  64.432  33.852  1.00  50.29  B  N
ATOM   5415  CZ   ARG  234     102.668  63.418  34.592  1.00  50.29  B  C
ATOM   5416  NH1  ARG  234     101.650  62.682  34.172  1.00  50.29  B  N
ATOM   5417  NH2  ARG  234     103.258  63.135  35.744  1.00  50.29  B  N
ATOM   5418  C    ARG  234     105.406  61.904  31.498  1.00  55.50  B  C
ATOM   5419  O    ARG  234     106.556  62.316  31.368  1.00  55.55  B  O
ATOM   5420  N    LYS  235     105.009  61.196  32.547  1.00  27.28  B  N
ATOM   5421  CA   LYS  235     105.914  60.939  33.660  1.00  27.23  B  C
ATOM   5422  CB   LYS  235     105.129  60.356  34.848  1.00  39.45  B  C
ATOM   5423  CG   LYS  235     104.888  58.857  34.831  1.00  40.60  B  C
ATOM   5424  CD   LYS  235     104.027  58.450  36.030  1.00  40.42  B  C
ATOM   5425  CE   LYS  235     104.119  56.955  36.346  1.00  41.22  B  C
ATOM   5426  NZ   LYS  235     103.715  56.073  35.205  1.00  41.98  B  N
ATOM   5427  C    LYS  235     107.149  60.078  33.375  1.00  27.37  B  C
ATOM   5428  O    LYS  235     108.112  60.118  34.130  1.00  27.71  B  O
ATOM   5429  N    GLU  236     107.133  59.313  32.290  1.00  28.33  B  N
ATOM   5430  CA   GLU  236     108.264  58.454  31.964  1.00  29.95  B  C
ATOM   5431  CB   GLU  236     107.803  56.992  31.884  1.00  47.54  B  C
ATOM   5432  CG   GLU  236     107.861  56.249  33.216  1.00  50.31  B  C
ATOM   5433  CD   GLU  236     107.031  54.965  33.245  1.00  52.79  B  C
ATOM   5434  OE1  GLU  236     107.194  54.118  32.342  1.00  52.88  B  O
ATOM   5435  OE2  GLU  236     106.219  54.797  34.184  1.00  52.63  B  O
ATOM   5436  C    GLU  236     108.966  58.840  30.670  1.00  28.50  B  C
ATOM   5437  O    GLU  236     110.092  59.336  30.684  1.00  29.93  B  O
ATOM   5438  N    ALA  237     108.287  58.617  29.552  1.00  22.73  B  N
ATOM   5439  CA   ALA  237     108.860  58.901  28.248  1.00  20.20  B  C
ATOM   5440  CB   ALA  237     107.783  58.831  27.180  1.00  41.37  B  C
ATOM   5441  C    ALA  237     109.562  60.233  28.187  1.00  19.04  B  C
ATOM   5442  O    ALA  237     110.636  60.344  27.589  1.00  17.46  B  O
ATOM   5443  N    PHE  238     108.962  61.242  28.810  1.00  29.57  B  N
ATOM   5444  CA   PHE  238     109.530  62.580  28.795  1.00  29.00  B  C
ATOM   5445  CB   PHE  238     108.419  63.620  28.752  1.00  35.30  B  C
ATOM   5446  CG   PHE  238     107.856  63.854  27.381  1.00  34.33  B  C
ATOM   5447  CD1  PHE  238     106.531  63.532  27.101  1.00  35.56  B  C
ATOM   5448  CD2  PHE  238     108.635  64.429  26.380  1.00  31.93  B  C
ATOM   5449  CE1  PHE  238     105.985  63.780  25.841  1.00  33.36  B  C
ATOM   5450  CE2  PHE  238     108.106  64.682  25.124  1.00  38.24  B  C
ATOM   5451  CZ   PHE  238     106.778  64.359  24.850  1.00  39.66  B  C
ATOM   5452  C    PHE  238     110.468  62.908  29.943  1.00  30.85  B  C
ATOM   5453  O    PHE  238     110.433  64.012  30.479  1.00  30.95  B  O
ATOM   5454  N    THR  239     111.303  61.951  30.325  1.00  29.27  B  N
ATOM   5455  CA   THR  239     112.266  62.182  31.391  1.00  33.21  B  C
ATOM   5456  CB   THR  239     112.113  61.150  32.520  1.00  23.55  B  C
ATOM   5457  OG1  THR  239     112.276  59.840  31.989  1.00  21.51  B  O
ATOM   5458  CG2  THR  239     110.745  61.242  33.153  1.00  26.46  B  C
ATOM   5459  C    THR  239     113.660  62.084  30.770  1.00  33.47  B  C
ATOM   5460  O    THR  239     113.930  61.177  29.980  1.00  33.97  B  O
ATOM   5461  N    GLU  240     114.531  63.030  31.117  1.00  17.24  B  N
ATOM   5462  CA   GLU  240     115.890  63.085  30.580  1.00  17.49  B  C
ATOM   5463  CB   GLU  240     116.748  64.003  31.444  1.00  74.12  B  C
ATOM   5464  CG   GLU  240     118.007  64.483  30.758  1.00  78.76  B  C
ATOM   5465  CD   GLU  240     118.634  65.654  31.479  1.00  81.67  B  C
ATOM   5466  OE1  GLU  240     117.904  66.627  31.774  1.00  81.77  B  O
ATOM   5467  OE2  GLU  240     119.853  65.605  31.746  1.00  81.74  B  O
ATOM   5468  C    GLU  240     116.555  61.712  30.465  1.00  18.84  B  C
ATOM   5469  O    GLU  240     117.323  61.444  29.530  1.00  20.05  B  O
ATOM   5470  N    ALA  241     116.234  60.839  31.415  1.00  54.75  B  N
ATOM   5471  CA   ALA  241     116.784  59.491  31.446  1.00  55.60  B  C
ATOM   5472  CB   ALA  241     116.331  58.783  32.723  1.00  26.00  B  C
ATOM   5473  C    ALA  241     116.387  58.678  30.212  1.00  55.07  B  C
ATOM   5474  O    ALA  241     117.093  57.751  29.823  1.00  56.53  B  O
ATOM   5475  N    ARG  242     115.259  59.024  29.598  1.00  25.17  B  N
```

Fig. 19: A-76

```
ATOM   5476  CA   ARG  242    114.805  58.305  28.417  1.00   24.91  B  C
ATOM   5477  CB   ARG  242    113.337  57.917  28.570  1.00   45.62  B  C
ATOM   5478  CG   ARG  242    113.136  56.644  29.392  1.00   45.82  B  C
ATOM   5479  CD   ARG  242    111.684  56.188  29.334  1.00   46.68  B  C
ATOM   5480  NE   ARG  242    111.525  54.733  29.424  1.00   47.88  B  N
ATOM   5481  CZ   ARG  242    111.348  54.055  30.557  1.00   47.08  B  C
ATOM   5482  NH1  ARG  242    111.307  54.695  31.721  1.00   46.13  B  N
ATOM   5483  NH2  ARG  242    111.187  52.738  30.526  1.00   49.10  B  N
ATOM   5484  C    ARG  242    115.039  59.088  27.120  1.00   26.11  B  C
ATOM   5485  O    ARG  242    114.450  58.796  26.076  1.00   29.12  B  O
ATOM   5486  N    GLY  243    115.919  60.078  27.194  1.00   41.48  B  N
ATOM   5487  CA   GLY  243    116.226  60.863  26.014  1.00   39.63  B  C
ATOM   5488  C    GLY  243    115.497  62.187  25.893  1.00   37.91  B  C
ATOM   5489  O    GLY  243    115.454  62.774  24.810  1.00   37.53  B  O
ATOM   5490  N    ALA  244    114.913  62.665  26.986  1.00   32.61  B  N
ATOM   5491  CA   ALA  244    114.209  63.941  26.939  1.00   30.61  B  C
ATOM   5492  CB   ALA  244    113.253  64.074  28.124  1.00    2.29  B  C
ATOM   5493  C    ALA  244    115.262  65.033  26.984  1.00   32.49  B  C
ATOM   5494  O    ALA  244    115.867  65.266  28.021  1.00   31.95  B  O
ATOM   5495  N    ARG  245    115.491  65.690  25.854  1.00   46.01  B  N
ATOM   5496  CA   ARG  245    116.482  66.760  25.768  1.00   46.93  B  C
ATOM   5497  CB   ARG  245    116.690  67.163  24.309  1.00   24.44  B  C
ATOM   5498  CG   ARG  245    117.460  66.126  23.503  1.00   26.91  B  C
ATOM   5499  CD   ARG  245    117.553  66.517  22.054  1.00   27.12  B  C
ATOM   5500  NE   ARG  245    116.229  66.560  21.457  1.00   21.54  B  N
ATOM   5501  CZ   ARG  245    115.999  66.826  20.179  1.00   21.36  B  C
ATOM   5502  NH1  ARG  245    117.016  67.074  19.370  1.00   20.56  B  N
ATOM   5503  NH2  ARG  245    114.756  66.834  19.708  1.00   18.65  B  N
ATOM   5504  C    ARG  245    116.101  67.986  26.585  1.00   45.30  B  C
ATOM   5505  O    ARG  245    114.975  68.480  26.496  1.00   41.41  B  O
ATOM   5506  N    ARG  246    117.051  68.476  27.376  1.00   48.54  B  N
ATOM   5507  CA   ARG  246    116.830  69.640  28.229  1.00   51.33  B  C
ATOM   5508  CB   ARG  246    118.096  69.982  29.012  1.00   83.48  B  C
ATOM   5509  CG   ARG  246    117.975  71.269  29.811  1.00   88.84  B  C
ATOM   5510  CD   ARG  246    119.295  71.647  30.449  1.00   94.76  B  C
ATOM   5511  NE   ARG  246    119.896  70.525  31.165  1.00   97.67  B  N
ATOM   5512  CZ   ARG  246    119.288  69.828  32.123  1.00  100.78  B  C
ATOM   5513  NH1  ARG  246    118.047  70.132  32.491  1.00  100.47  B  N
ATOM   5514  NH2  ARG  246    119.923  68.825  32.717  1.00  101.56  B  N
ATOM   5515  C    ARG  246    116.415  70.871  27.448  1.00   49.15  B  C
ATOM   5516  O    ARG  246    117.082  71.246  26.489  1.00   51.78  B  O
ATOM   5517  N    GLY  247    115.311  71.489  27.868  1.00   46.59  B  N
ATOM   5518  CA   GLY  247    114.825  72.705  27.233  1.00   49.17  B  C
ATOM   5519  C    GLY  247    114.381  72.609  25.787  1.00   49.24  B  C
ATOM   5520  O    GLY  247    114.531  73.560  25.019  1.00   52.20  B  O
ATOM   5521  N    VAL  248    113.836  71.462  25.407  1.00   57.57  B  N
ATOM   5522  CA   VAL  248    113.357  71.266  24.049  1.00   55.58  B  C
ATOM   5523  CB   VAL  248    114.012  70.043  23.407  1.00   22.85  B  C
ATOM   5524  CG1  VAL  248    113.384  69.765  22.056  1.00   20.50  B  C
ATOM   5525  CG2  VAL  248    115.499  70.287  23.266  1.00   14.62  B  C
ATOM   5526  C    VAL  248    111.855  71.056  24.094  1.00   58.60  B  C
ATOM   5527  O    VAL  248    111.343  70.403  25.005  1.00   62.65  B  O
ATOM   5528  N    LYS  249    111.147  71.607  23.115  1.00   37.34  B  N
ATOM   5529  CA   LYS  249    109.698  71.464  23.086  1.00   38.25  B  C
ATOM   5530  CB   LYS  249    109.115  72.122  21.832  1.00   57.29  B  C
ATOM   5531  CG   LYS  249    107.594  72.204  21.869  1.00   62.81  B  C
ATOM   5532  CD   LYS  249    107.103  72.892  23.155  1.00   63.88  B  C
ATOM   5533  CE   LYS  249    105.634  72.579  23.450  1.00   66.24  B  C
ATOM   5534  NZ   LYS  249    105.067  73.292  24.636  1.00   69.06  B  N
ATOM   5535  C    LYS  249    109.244  69.998  23.173  1.00   36.91  B  C
ATOM   5536  O    LYS  249    109.790  69.112  22.505  1.00   36.73  B  O
ATOM   5537  N    LYS  250    108.238  69.755  24.009  1.00   33.42  B  N
ATOM   5538  CA   LYS  250    107.706  68.419  24.208  1.00   33.07  B  C
ATOM   5539  CB   LYS  250    107.603  68.147  25.710  1.00   46.37  B  C
ATOM   5540  CG   LYS  250    108.970  68.151  26.374  1.00   44.97  B  C
ATOM   5541  CD   LYS  250    108.918  68.429  27.872  1.00   46.52  B  C
ATOM   5542  CE   LYS  250    108.389  67.256  28.686  1.00   45.68  B  C
ATOM   5543  NZ   LYS  250    108.578  67.474  30.157  1.00   47.50  B  N
ATOM   5544  C    LYS  250    106.355  68.263  23.506  1.00   32.42  B  C
ATOM   5545  O    LYS  250    105.380  68.931  23.842  1.00   32.10  B  O
ATOM   5546  N    VAL  251    106.320  67.372  22.519  1.00   37.83  B  N
ATOM   5547  CA   VAL  251    105.121  67.115  21.730  1.00   37.74  B  C
ATOM   5548  CB   VAL  251    105.403  67.373  20.248  1.00   28.71  B  C
```

Fig. 19: A-77

| ATOM | 5549 | CG1 | VAL | 251 | 104.180 | 67.017 | 19.410 | 1.00 | 26.86 | B | C |
|------|------|-----|-----|-----|---------|--------|--------|------|-------|---|---|
| ATOM | 5550 | CG2 | VAL | 251 | 105.819 | 68.822 | 20.057 | 1.00 | 29.92 | B | C |
| ATOM | 5551 | C   | VAL | 251 | 104.591 | 65.689 | 21.866 | 1.00 | 36.22 | B | C |
| ATOM | 5552 | O   | VAL | 251 | 105.339 | 64.715 | 21.714 | 1.00 | 32.22 | B | O |
| ATOM | 5553 | N   | MET | 252 | 103.289 | 65.572 | 22.122 | 1.00 | 42.57 | B | N |
| ATOM | 5554 | CA  | MET | 252 | 102.651 | 64.269 | 22.275 | 1.00 | 43.55 | B | C |
| ATOM | 5555 | CB  | MET | 252 | 102.013 | 64.160 | 23.660 | 1.00 | 27.32 | B | C |
| ATOM | 5556 | CG  | MET | 252 | 101.440 | 62.787 | 23.998 | 1.00 | 26.01 | B | C |
| ATOM | 5557 | SD  | MET | 252 | 100.740 | 62.725 | 25.675 | 1.00 | 30.06 | B | S |
| ATOM | 5558 | CE  | MET | 252 | 102.222 | 63.011 | 26.691 | 1.00 | 21.37 | B | C |
| ATOM | 5559 | C   | MET | 252 | 101.583 | 64.060 | 21.217 | 1.00 | 42.57 | B | C |
| ATOM | 5560 | O   | MET | 252 | 100.761 | 64.937 | 20.982 | 1.00 | 44.94 | B | O |
| ATOM | 5561 | N   | VAL | 253 | 101.604 | 62.900 | 20.573 | 1.00 | 21.89 | B | N |
| ATOM | 5562 | CA  | VAL | 253 | 100.607 | 62.580 | 19.558 | 1.00 | 23.04 | B | C |
| ATOM | 5563 | CB  | VAL | 253 | 101.267 | 62.281 | 18.187 | 1.00 | 9.79  | B | C |
| ATOM | 5564 | CG1 | VAL | 253 | 100.191 | 61.900 | 17.168 | 1.00 | 11.21 | B | C |
| ATOM | 5565 | CG2 | VAL | 253 | 102.044 | 63.490 | 17.701 | 1.00 | 9.43  | B | C |
| ATOM | 5566 | C   | VAL | 253 | 99.819  | 61.353 | 20.015 | 1.00 | 22.61 | B | C |
| ATOM | 5567 | O   | VAL | 253 | 100.383 | 60.276 | 20.161 | 1.00 | 21.05 | B | O |
| ATOM | 5568 | N   | ILE | 254 | 98.522  | 61.516 | 20.252 | 1.00 | 29.50 | B | N |
| ATOM | 5569 | CA  | ILE | 254 | 97.692  | 60.403 | 20.701 | 1.00 | 26.40 | B | C |
| ATOM | 5570 | CB  | ILE | 254 | 96.820  | 60.777 | 21.925 | 1.00 | 25.01 | B | C |
| ATOM | 5571 | CG2 | ILE | 254 | 96.017  | 59.564 | 22.369 | 1.00 | 21.48 | B | C |
| ATOM | 5572 | CG1 | ILE | 254 | 97.697  | 61.256 | 23.089 | 1.00 | 23.59 | B | C |
| ATOM | 5573 | CD1 | ILE | 254 | 98.231  | 62.661 | 22.921 | 1.00 | 23.22 | B | C |
| ATOM | 5574 | C   | ILE | 254 | 96.757  | 59.905 | 19.611 | 1.00 | 24.49 | B | C |
| ATOM | 5575 | O   | ILE | 254 | 96.163  | 60.692 | 18.876 | 1.00 | 26.36 | B | O |
| ATOM | 5576 | N   | VAL | 255 | 96.628  | 58.587 | 19.516 | 1.00 | 26.63 | B | N |
| ATOM | 5577 | CA  | VAL | 255 | 95.758  | 57.981 | 18.521 | 1.00 | 25.37 | B | C |
| ATOM | 5578 | CB  | VAL | 255 | 96.553  | 57.259 | 17.428 | 1.00 | 15.78 | B | C |
| ATOM | 5579 | CG1 | VAL | 255 | 95.672  | 57.064 | 16.198 | 1.00 | 14.23 | B | C |
| ATOM | 5580 | CG2 | VAL | 255 | 97.805  | 58.036 | 17.089 | 1.00 | 16.42 | B | C |
| ATOM | 5581 | C   | VAL | 255 | 94.907  | 56.947 | 19.221 | 1.00 | 23.12 | B | C |
| ATOM | 5582 | O   | VAL | 255 | 95.444  | 56.089 | 19.916 | 1.00 | 25.12 | B | O |
| ATOM | 5583 | N   | THR | 256 | 93.591  | 57.012 | 19.036 | 1.00 | 8.41  | B | N |
| ATOM | 5584 | CA  | THR | 256 | 92.709  | 56.052 | 19.689 | 1.00 | 8.83  | B | C |
| ATOM | 5585 | CB  | THR | 256 | 92.529  | 56.416 | 21.189 | 1.00 | 19.33 | B | C |
| ATOM | 5586 | OG1 | THR | 256 | 91.459  | 55.645 | 21.755 | 1.00 | 15.37 | B | O |
| ATOM | 5587 | CG2 | THR | 256 | 92.255  | 57.908 | 21.344 | 1.00 | 18.18 | B | C |
| ATOM | 5588 | C   | THR | 256 | 91.353  | 55.955 | 18.992 | 1.00 | 12.31 | B | C |
| ATOM | 5589 | O   | THR | 256 | 90.941  | 56.881 | 18.308 | 1.00 | 8.47  | B | O |
| ATOM | 5590 | N   | ASP | 257 | 90.673  | 54.824 | 19.162 | 1.00 | 17.26 | B | N |
| ATOM | 5591 | CA  | ASP | 257 | 89.375  | 54.601 | 18.530 | 1.00 | 17.64 | B | C |
| ATOM | 5592 | CB  | ASP | 257 | 89.491  | 53.474 | 17.491 | 1.00 | 29.20 | B | C |
| ATOM | 5593 | CG  | ASP | 257 | 89.534  | 52.074 | 18.122 | 1.00 | 34.56 | B | C |
| ATOM | 5594 | OD1 | ASP | 257 | 89.894  | 51.957 | 19.313 | 1.00 | 35.03 | B | O |
| ATOM | 5595 | OD2 | ASP | 257 | 89.220  | 51.084 | 17.421 | 1.00 | 39.83 | B | O |
| ATOM | 5596 | C   | ASP | 257 | 88.267  | 54.259 | 19.535 | 1.00 | 14.23 | B | C |
| ATOM | 5597 | O   | ASP | 257 | 87.243  | 53.660 | 19.169 | 1.00 | 13.47 | B | O |
| ATOM | 5598 | N   | GLY | 258 | 88.462  | 54.634 | 20.798 | 1.00 | 26.33 | B | N |
| ATOM | 5599 | CA  | GLY | 258 | 87.450  | 54.331 | 21.793 | 1.00 | 28.75 | B | C |
| ATOM | 5600 | C   | GLY | 258 | 87.546  | 55.109 | 23.088 | 1.00 | 32.57 | B | C |
| ATOM | 5601 | O   | GLY | 258 | 88.615  | 55.601 | 23.476 | 1.00 | 28.29 | B | O |
| ATOM | 5602 | N   | GLU | 259 | 86.404  | 55.231 | 23.755 | 1.00 | 39.52 | B | N |
| ATOM | 5603 | CA  | GLU | 259 | 86.335  | 55.931 | 25.025 | 1.00 | 41.40 | B | C |
| ATOM | 5604 | CB  | GLU | 259 | 84.905  | 55.925 | 25.555 | 1.00 | 36.52 | B | C |
| ATOM | 5605 | CG  | GLU | 259 | 83.950  | 56.783 | 24.749 | 1.00 | 44.30 | B | C |
| ATOM | 5606 | CD  | GLU | 259 | 82.509  | 56.415 | 24.994 | 1.00 | 48.11 | B | C |
| ATOM | 5607 | OE1 | GLU | 259 | 81.625  | 57.175 | 24.546 | 1.00 | 54.86 | B | O |
| ATOM | 5608 | OE2 | GLU | 259 | 82.262  | 55.360 | 25.626 | 1.00 | 48.13 | B | O |
| ATOM | 5609 | C   | GLU | 259 | 87.240  | 55.210 | 26.003 | 1.00 | 40.26 | B | C |
| ATOM | 5610 | O   | GLU | 259 | 87.125  | 53.999 | 26.194 | 1.00 | 37.43 | B | O |
| ATOM | 5611 | N   | SER | 260 | 88.155  | 55.953 | 26.610 | 1.00 | 34.06 | B | N |
| ATOM | 5612 | CA  | SER | 260 | 89.067  | 55.369 | 27.576 | 1.00 | 37.22 | B | C |
| ATOM | 5613 | CB  | SER | 260 | 90.041  | 56.432 | 28.083 | 1.00 | 50.00 | B | C |
| ATOM | 5614 | OG  | SER | 260 | 89.341  | 57.516 | 28.666 | 1.00 | 50.51 | B | O |
| ATOM | 5615 | C   | SER | 260 | 88.261  | 54.814 | 28.740 | 1.00 | 37.12 | B | C |
| ATOM | 5616 | O   | SER | 260 | 87.177  | 55.300 | 29.043 | 1.00 | 33.15 | B | O |
| ATOM | 5617 | N   | HIS | 261 | 88.781  | 53.787 | 29.392 | 1.00 | 36.47 | B | N |
| ATOM | 5618 | CA  | HIS | 261 | 88.084  | 53.212 | 30.527 | 1.00 | 40.82 | B | C |
| ATOM | 5619 | CB  | HIS | 261 | 88.509  | 51.755 | 30.728 | 1.00 | 21.13 | B | C |
| ATOM | 5620 | CG  | HIS | 261 | 87.908  | 50.809 | 29.732 | 1.00 | 24.33 | B | C |
| ATOM | 5621 | CD2 | HIS | 261 | 88.345  | 50.398 | 28.519 | 1.00 | 23.44 | B | C |

Fig. 19: A-78

| | | | | | | | | | | |
|---|---|---|---|---|---|---|---|---|---|---|
| ATOM | 5622 | ND1 | HIS | 261 | 86.688 | 50.197 | 29.925 | 1.00 | 25.81 | B N |
| ATOM | 5623 | CE1 | HIS | 261 | 86.400 | 49.448 | 28.876 | 1.00 | 25.88 | B C |
| ATOM | 5624 | NE2 | HIS | 261 | 87.390 | 49.554 | 28.009 | 1.00 | 23.15 | B N |
| ATOM | 5625 | C | HIS | 261 | 88.394 | 54.045 | 31.761 | 1.00 | 41.88 | B C |
| ATOM | 5626 | O | HIS | 261 | 87.711 | 53.940 | 32.779 | 1.00 | 39.10 | B O |
| ATOM | 5627 | N | ASP | 262 | 89.425 | 54.880 | 31.657 | 1.00 | 49.36 | B N |
| ATOM | 5628 | CA | ASP | 262 | 89.825 | 55.758 | 32.753 | 1.00 | 54.33 | B C |
| ATOM | 5629 | CB | ASP | 262 | 91.343 | 55.676 | 32.985 | 1.00 | 33.92 | B C |
| ATOM | 5630 | CG | ASP | 262 | 92.124 | 55.281 | 31.733 | 1.00 | 33.92 | B C |
| ATOM | 5631 | OD1 | ASP | 262 | 91.724 | 55.659 | 30.611 | 1.00 | 33.92 | B O |
| ATOM | 5632 | OD2 | ASP | 262 | 93.162 | 54.600 | 31.875 | 1.00 | 33.92 | B O |
| ATOM | 5633 | C | ASP | 262 | 89.418 | 57.218 | 32.507 | 1.00 | 54.38 | B C |
| ATOM | 5634 | O | ASP | 262 | 90.221 | 58.134 | 32.700 | 1.00 | 54.24 | B O |
| ATOM | 5635 | N | ASN | 263 | 88.171 | 57.424 | 32.085 | 1.00 | 68.10 | B N |
| ATOM | 5636 | CA | ASN | 263 | 87.646 | 58.765 | 31.813 | 1.00 | 69.27 | B C |
| ATOM | 5637 | CB | ASN | 263 | 86.123 | 58.734 | 31.630 | 1.00 | 82.52 | B C |
| ATOM | 5638 | CG | ASN | 263 | 85.660 | 57.631 | 30.707 | 1.00 | 86.89 | B C |
| ATOM | 5639 | OD1 | ASN | 263 | 85.981 | 57.626 | 29.519 | 1.00 | 88.39 | B O |
| ATOM | 5640 | ND2 | ASN | 263 | 84.893 | 56.686 | 31.249 | 1.00 | 81.39 | B N |
| ATOM | 5641 | C | ASN | 263 | 87.948 | 59.670 | 32.998 | 1.00 | 69.91 | B C |
| ATOM | 5642 | O | ASN | 263 | 88.360 | 60.822 | 32.841 | 1.00 | 68.81 | B O |
| ATOM | 5643 | N | TYR | 264 | 87.732 | 59.122 | 34.187 | 1.00 | 59.82 | B N |
| ATOM | 5644 | CA | TYR | 264 | 87.925 | 59.837 | 35.432 | 1.00 | 57.67 | B C |
| ATOM | 5645 | CB | TYR | 264 | 87.914 | 58.853 | 36.590 | 1.00 | 108.49 | B C |
| ATOM | 5646 | CG | TYR | 264 | 86.626 | 58.083 | 36.660 | 1.00 | 108.49 | B C |
| ATOM | 5647 | CD1 | TYR | 264 | 86.284 | 57.171 | 35.663 | 1.00 | 108.49 | B C |
| ATOM | 5648 | CE1 | TYR | 264 | 85.074 | 56.490 | 35.698 | 1.00 | 108.49 | B C |
| ATOM | 5649 | CD2 | TYR | 264 | 85.723 | 58.292 | 37.699 | 1.00 | 108.49 | B C |
| ATOM | 5650 | CE2 | TYR | 264 | 84.509 | 57.615 | 37.744 | 1.00 | 108.49 | B C |
| ATOM | 5651 | CZ | TYR | 264 | 84.190 | 56.717 | 36.741 | 1.00 | 108.49 | B C |
| ATOM | 5652 | OH | TYR | 264 | 82.987 | 56.052 | 36.783 | 1.00 | 108.49 | B O |
| ATOM | 5653 | C | TYR | 264 | 89.156 | 60.710 | 35.512 | 1.00 | 56.32 | B C |
| ATOM | 5654 | O | TYR | 264 | 89.047 | 61.935 | 35.549 | 1.00 | 53.45 | B O |
| ATOM | 5655 | N | ARG | 265 | 90.331 | 60.098 | 35.527 | 1.00 | 41.74 | B N |
| ATOM | 5656 | CA | ARG | 265 | 91.544 | 60.892 | 35.641 | 1.00 | 40.64 | B C |
| ATOM | 5657 | CB | ARG | 265 | 92.610 | 60.127 | 36.427 | 1.00 | 58.89 | B C |
| ATOM | 5658 | CG | ARG | 265 | 93.152 | 58.875 | 35.779 | 1.00 | 59.34 | B C |
| ATOM | 5659 | CD | ARG | 265 | 94.501 | 58.614 | 36.400 | 1.00 | 61.17 | B C |
| ATOM | 5660 | NE | ARG | 265 | 95.183 | 57.456 | 35.851 | 1.00 | 66.56 | B N |
| ATOM | 5661 | CZ | ARG | 265 | 96.506 | 57.349 | 35.784 | 1.00 | 66.73 | B C |
| ATOM | 5662 | NH1 | ARG | 265 | 97.281 | 58.334 | 36.227 | 1.00 | 71.36 | B N |
| ATOM | 5663 | NH2 | ARG | 265 | 97.059 | 56.256 | 35.280 | 1.00 | 70.70 | B N |
| ATOM | 5664 | C | ARG | 265 | 92.147 | 61.423 | 34.347 | 1.00 | 39.89 | B C |
| ATOM | 5665 | O | ARG | 265 | 93.311 | 61.833 | 34.319 | 1.00 | 41.20 | B O |
| ATOM | 5666 | N | LEU | 266 | 91.360 | 61.433 | 33.278 | 1.00 | 45.12 | B N |
| ATOM | 5667 | CA | LEU | 266 | 91.855 | 61.947 | 32.007 | 1.00 | 46.69 | B C |
| ATOM | 5668 | CB | LEU | 266 | 90.885 | 61.580 | 30.886 | 1.00 | 30.69 | B C |
| ATOM | 5669 | CG | LEU | 266 | 91.357 | 61.919 | 29.480 | 1.00 | 29.90 | B C |
| ATOM | 5670 | CD1 | LEU | 266 | 92.760 | 61.369 | 29.232 | 1.00 | 32.24 | B C |
| ATOM | 5671 | CD2 | LEU | 266 | 90.347 | 61.344 | 28.500 | 1.00 | 26.36 | B C |
| ATOM | 5672 | C | LEU | 266 | 91.989 | 63.466 | 32.139 | 1.00 | 49.51 | B C |
| ATOM | 5673 | O | LEU | 266 | 92.861 | 64.093 | 31.541 | 1.00 | 49.39 | B O |
| ATOM | 5674 | N | LYS | 267 | 91.107 | 64.041 | 32.945 | 1.00 | 50.12 | B N |
| ATOM | 5675 | CA | LYS | 267 | 91.097 | 65.473 | 33.206 | 1.00 | 52.43 | B C |
| ATOM | 5676 | CB | LYS | 267 | 89.927 | 65.807 | 34.136 | 1.00 | 99.33 | B C |
| ATOM | 5677 | CG | LYS | 267 | 89.719 | 67.279 | 34.431 | 1.00 | 99.33 | B C |
| ATOM | 5678 | CD | LYS | 267 | 88.623 | 67.863 | 33.558 | 1.00 | 99.33 | B C |
| ATOM | 5679 | CE | LYS | 267 | 88.211 | 69.242 | 34.049 | 1.00 | 99.33 | B C |
| ATOM | 5680 | NZ | LYS | 267 | 87.044 | 69.788 | 33.293 | 1.00 | 99.33 | B N |
| ATOM | 5681 | C | LYS | 267 | 92.417 | 65.835 | 33.882 | 1.00 | 51.92 | B C |
| ATOM | 5682 | O | LYS | 267 | 93.126 | 66.738 | 33.440 | 1.00 | 51.44 | B O |
| ATOM | 5683 | N | GLN | 268 | 92.736 | 65.115 | 34.956 | 1.00 | 36.69 | B N |
| ATOM | 5684 | CA | GLN | 268 | 93.968 | 65.338 | 35.709 | 1.00 | 35.66 | B C |
| ATOM | 5685 | CB | GLN | 268 | 94.098 | 64.324 | 36.841 | 1.00 | 127.61 | B C |
| ATOM | 5686 | CG | GLN | 268 | 93.032 | 64.387 | 37.906 | 1.00 | 127.61 | B C |
| ATOM | 5687 | CD | GLN | 268 | 93.203 | 63.286 | 38.941 | 1.00 | 127.61 | B C |
| ATOM | 5688 | OE1 | GLN | 268 | 92.487 | 63.236 | 39.939 | 1.00 | 127.61 | B O |
| ATOM | 5689 | NE2 | GLN | 268 | 94.158 | 62.392 | 38.702 | 1.00 | 127.61 | B N |
| ATOM | 5690 | C | GLN | 268 | 95.203 | 65.210 | 34.824 | 1.00 | 31.41 | B C |
| ATOM | 5691 | O | GLN | 268 | 96.044 | 66.108 | 34.788 | 1.00 | 32.59 | B O |
| ATOM | 5692 | N | VAL | 269 | 95.308 | 64.085 | 34.114 | 1.00 | 29.89 | B N |
| ATOM | 5693 | CA | VAL | 269 | 96.457 | 63.831 | 33.256 | 1.00 | 27.64 | B C |
| ATOM | 5694 | CB | VAL | 269 | 96.321 | 62.467 | 32.516 | 1.00 | 26.10 | B C |

Fig. 19: A-79

| ATOM | 5695 | CG1 | VAL | 269 | 97.551 | 62.215 | 31.663 | 1.00 | 21.75 | B | C |
| --- | --- | --- | --- | --- | --- | --- | --- | --- | --- | --- | --- |
| ATOM | 5696 | CG2 | VAL | 269 | 96.161 | 61.338 | 33.520 | 1.00 | 23.96 | B | C |
| ATOM | 5697 | C | VAL | 269 | 96.683 | 64.956 | 32.246 | 1.00 | 27.23 | B | C |
| ATOM | 5698 | O | VAL | 269 | 97.784 | 65.502 | 32.174 | 1.00 | 30.07 | B | O |
| ATOM | 5699 | N | ILE | 270 | 95.658 | 65.306 | 31.471 | 1.00 | 16.50 | B | N |
| ATOM | 5700 | CA | ILE | 270 | 95.797 | 66.379 | 30.487 | 1.00 | 17.12 | B | C |
| ATOM | 5701 | CB | ILE | 270 | 94.459 | 66.696 | 29.777 | 1.00 | 35.19 | B | C |
| ATOM | 5702 | CG2 | ILE | 270 | 94.594 | 67.973 | 28.937 | 1.00 | 29.81 | B | C |
| ATOM | 5703 | CG1 | ILE | 270 | 94.060 | 65.520 | 28.885 | 1.00 | 32.75 | B | C |
| ATOM | 5704 | CD1 | ILE | 270 | 95.062 | 65.231 | 27.778 | 1.00 | 33.87 | B | C |
| ATOM | 5705 | C | ILE | 270 | 96.275 | 67.631 | 31.210 | 1.00 | 20.99 | B | C |
| ATOM | 5706 | O | ILE | 270 | 97.060 | 68.413 | 30.670 | 1.00 | 19.77 | B | O |
| ATOM | 5707 | N | GLN | 271 | 95.802 | 67.796 | 32.444 | 1.00 | 57.05 | B | N |
| ATOM | 5708 | CA | GLN | 271 | 96.169 | 68.935 | 33.269 | 1.00 | 59.11 | B | C |
| ATOM | 5709 | CB | GLN | 271 | 95.440 | 68.865 | 34.610 | 1.00 | 85.78 | B | C |
| ATOM | 5710 | CG | GLN | 271 | 95.525 | 70.134 | 35.439 | 1.00 | 87.68 | B | C |
| ATOM | 5711 | CD | GLN | 271 | 94.967 | 71.338 | 34.708 | 1.00 | 90.18 | B | C |
| ATOM | 5712 | OE1 | GLN | 271 | 95.614 | 71.898 | 33.822 | 1.00 | 90.51 | B | O |
| ATOM | 5713 | NE2 | GLN | 271 | 93.752 | 71.735 | 35.065 | 1.00 | 91.75 | B | N |
| ATOM | 5714 | C | GLN | 271 | 97.673 | 68.932 | 33.495 | 1.00 | 61.57 | B | C |
| ATOM | 5715 | O | GLN | 271 | 98.359 | 69.896 | 33.172 | 1.00 | 64.26 | B | O |
| ATOM | 5716 | N | ASP | 272 | 98.184 | 67.837 | 34.042 | 1.00 | 39.03 | B | N |
| ATOM | 5717 | CA | ASP | 272 | 99.612 | 67.716 | 34.304 | 1.00 | 40.31 | B | C |
| ATOM | 5718 | CB | ASP | 272 | 99.922 | 66.338 | 34.890 | 1.00 | 54.12 | B | C |
| ATOM | 5719 | CG | ASP | 272 | 99.275 | 66.122 | 36.255 | 1.00 | 55.74 | B | C |
| ATOM | 5720 | OD1 | ASP | 272 | 99.087 | 64.949 | 36.647 | 1.00 | 57.81 | B | O |
| ATOM | 5721 | OD2 | ASP | 272 | 98.961 | 67.123 | 36.939 | 1.00 | 62.00 | B | O |
| ATOM | 5722 | C | ASP | 272 | 100.420 | 67.937 | 33.033 | 1.00 | 41.11 | B | C |
| ATOM | 5723 | O | ASP | 272 | 101.550 | 68.418 | 33.083 | 1.00 | 38.56 | B | O |
| ATOM | 5724 | N | CYS | 273 | 99.843 | 67.587 | 31.891 | 1.00 | 49.56 | B | N |
| ATOM | 5725 | CA | CYS | 273 | 100.538 | 67.776 | 30.629 | 1.00 | 47.99 | B | C |
| ATOM | 5726 | CB | CYS | 273 | 99.824 | 67.028 | 29.503 | 1.00 | 39.07 | B | C |
| ATOM | 5727 | SG | CYS | 273 | 100.050 | 65.235 | 29.538 | 1.00 | 37.17 | B | S |
| ATOM | 5728 | C | CYS | 273 | 100.628 | 69.257 | 30.291 | 1.00 | 48.36 | B | C |
| ATOM | 5729 | O | CYS | 273 | 101.602 | 69.695 | 29.686 | 1.00 | 42.67 | B | O |
| ATOM | 5730 | N | GLU | 274 | 99.609 | 70.022 | 30.682 | 1.00 | 40.12 | B | N |
| ATOM | 5731 | CA | GLU | 274 | 99.584 | 71.467 | 30.425 | 1.00 | 42.92 | B | C |
| ATOM | 5732 | CB | GLU | 274 | 98.187 | 72.055 | 30.703 | 1.00 | 40.77 | B | C |
| ATOM | 5733 | CG | GLU | 274 | 97.285 | 72.151 | 29.470 | 1.00 | 45.89 | B | C |
| ATOM | 5734 | CD | GLU | 274 | 97.830 | 73.108 | 28.405 | 1.00 | 51.00 | B | C |
| ATOM | 5735 | OE1 | GLU | 274 | 97.269 | 73.155 | 27.284 | 1.00 | 52.87 | B | O |
| ATOM | 5736 | OE2 | GLU | 274 | 98.816 | 73.818 | 28.691 | 1.00 | 55.56 | B | O |
| ATOM | 5737 | C | GLU | 274 | 100.615 | 72.172 | 31.293 | 1.00 | 45.34 | B | C |
| ATOM | 5738 | O | GLU | 274 | 101.309 | 73.081 | 30.842 | 1.00 | 47.54 | B | O |
| ATOM | 5739 | N | ASP | 275 | 100.711 | 71.735 | 32.542 | 1.00 | 77.40 | B | N |
| ATOM | 5740 | CA | ASP | 275 | 101.656 | 72.302 | 33.495 | 1.00 | 76.14 | B | C |
| ATOM | 5741 | CB | ASP | 275 | 101.456 | 71.665 | 34.871 | 1.00 | 72.98 | B | C |
| ATOM | 5742 | CG | ASP | 275 | 100.070 | 71.900 | 35.432 | 1.00 | 74.25 | B | C |
| ATOM | 5743 | OD1 | ASP | 275 | 99.160 | 72.258 | 34.656 | 1.00 | 77.95 | B | O |
| ATOM | 5744 | OD2 | ASP | 275 | 99.887 | 71.712 | 36.652 | 1.00 | 75.91 | B | O |
| ATOM | 5745 | C | ASP | 275 | 103.093 | 72.050 | 33.046 | 1.00 | 75.13 | B | C |
| ATOM | 5746 | O | ASP | 275 | 104.021 | 72.707 | 33.512 | 1.00 | 70.68 | B | O |
| ATOM | 5747 | N | GLU | 276 | 103.275 | 71.091 | 32.146 | 1.00 | 44.46 | B | N |
| ATOM | 5748 | CA | GLU | 276 | 104.606 | 70.757 | 31.668 | 1.00 | 44.11 | B | C |
| ATOM | 5749 | CB | GLU | 276 | 104.846 | 69.258 | 31.847 | 1.00 | 54.99 | B | C |
| ATOM | 5750 | CG | GLU | 276 | 104.556 | 68.799 | 33.266 | 1.00 | 54.86 | B | C |
| ATOM | 5751 | CD | GLU | 276 | 105.018 | 67.383 | 33.547 | 1.00 | 55.96 | B | C |
| ATOM | 5752 | OE1 | GLU | 276 | 104.861 | 66.934 | 34.705 | 1.00 | 56.67 | B | O |
| ATOM | 5753 | OE2 | GLU | 276 | 105.538 | 66.724 | 32.616 | 1.00 | 52.90 | B | O |
| ATOM | 5754 | C | GLU | 276 | 104.843 | 71.175 | 30.222 | 1.00 | 42.94 | B | C |
| ATOM | 5755 | O | GLU | 276 | 105.823 | 70.759 | 29.597 | 1.00 | 44.05 | B | O |
| ATOM | 5756 | N | ASN | 277 | 103.938 | 71.997 | 29.700 | 1.00 | 43.81 | B | N |
| ATOM | 5757 | CA | ASN | 277 | 104.043 | 72.505 | 28.338 | 1.00 | 43.78 | B | C |
| ATOM | 5758 | CB | ASN | 277 | 105.229 | 73.464 | 28.233 | 1.00 | 55.27 | B | C |
| ATOM | 5759 | CG | ASN | 277 | 105.219 | 74.514 | 29.311 | 1.00 | 60.19 | B | C |
| ATOM | 5760 | OD1 | ASN | 277 | 104.288 | 75.315 | 29.403 | 1.00 | 60.01 | B | O |
| ATOM | 5761 | ND2 | ASN | 277 | 106.256 | 74.518 | 30.145 | 1.00 | 59.15 | B | N |
| ATOM | 5762 | C | ASN | 277 | 104.188 | 71.428 | 27.261 | 1.00 | 40.13 | B | C |
| ATOM | 5763 | O | ASN | 277 | 105.083 | 71.515 | 26.416 | 1.00 | 41.11 | B | O |
| ATOM | 5764 | N | ILE | 278 | 103.309 | 70.427 | 27.278 | 1.00 | 17.87 | B | N |
| ATOM | 5765 | CA | ILE | 278 | 103.366 | 69.361 | 26.289 | 1.00 | 18.32 | B | C |
| ATOM | 5766 | CB | ILE | 278 | 103.110 | 67.975 | 26.928 | 1.00 | 22.06 | B | C |
| ATOM | 5767 | CG2 | ILE | 278 | 103.120 | 66.897 | 25.854 | 1.00 | 23.45 | B | C |

Fig. 19: A-80

| | | | | | | | | | | |
|---|---|---|---|---|---|---|---|---|---|---|
| ATOM | 5768 | CG1 | ILE | 278 | 104.172 | 67.675 | 27.987 | 1.00 | 19.51 | B C |
| ATOM | 5769 | CD1 | ILE | 278 | 103.941 | 66.373 | 28.707 | 1.00 | 21.79 | B C |
| ATOM | 5770 | C | ILE | 278 | 102.316 | 69.579 | 25.213 | 1.00 | 18.92 | B C |
| ATOM | 5771 | O | ILE | 278 | 101.132 | 69.378 | 25.463 | 1.00 | 19.26 | B O |
| ATOM | 5772 | N | GLN | 279 | 102.749 | 69.994 | 24.024 | 1.00 | 49.21 | B N |
| ATOM | 5773 | CA | GLN | 279 | 101.831 | 70.198 | 22.908 | 1.00 | 48.81 | B C |
| ATOM | 5774 | CB | GLN | 279 | 102.579 | 70.633 | 21.652 | 1.00 | 63.04 | B C |
| ATOM | 5775 | CG | GLN | 279 | 103.187 | 71.998 | 21.752 | 1.00 | 68.82 | B C |
| ATOM | 5776 | CD | GLN | 279 | 102.173 | 73.043 | 22.155 | 1.00 | 72.74 | B C |
| ATOM | 5777 | OE1 | GLN | 279 | 101.233 | 73.328 | 21.410 | 1.00 | 66.98 | B O |
| ATOM | 5778 | NE2 | GLN | 279 | 102.352 | 73.618 | 23.345 | 1.00 | 72.33 | B N |
| ATOM | 5779 | C | GLN | 279 | 101.175 | 68.864 | 22.640 | 1.00 | 46.68 | B C |
| ATOM | 5780 | O | GLN | 279 | 101.861 | 67.859 | 22.467 | 1.00 | 43.60 | B O |
| ATOM | 5781 | N | ARG | 280 | 99.851 | 68.848 | 22.595 | 1.00 | 28.30 | B N |
| ATOM | 5782 | CA | ARG | 280 | 99.138 | 67.605 | 22.363 | 1.00 | 29.82 | B C |
| ATOM | 5783 | CB | ARG | 280 | 98.276 | 67.277 | 23.575 | 1.00 | 38.67 | B C |
| ATOM | 5784 | CG | ARG | 280 | 99.036 | 67.225 | 24.874 | 1.00 | 37.30 | B C |
| ATOM | 5785 | CD | ARG | 280 | 98.068 | 67.012 | 26.018 | 1.00 | 36.97 | B C |
| ATOM | 5786 | NE | ARG | 280 | 97.070 | 68.075 | 26.073 | 1.00 | 34.02 | B N |
| ATOM | 5787 | CZ | ARG | 280 | 97.288 | 69.298 | 26.557 | 1.00 | 37.93 | B C |
| ATOM | 5788 | NH1 | ARG | 280 | 98.483 | 69.627 | 27.041 | 1.00 | 40.85 | B N |
| ATOM | 5789 | NH2 | ARG | 280 | 96.307 | 70.192 | 26.554 | 1.00 | 42.87 | B N |
| ATOM | 5790 | C | ARG | 280 | 98.264 | 67.579 | 21.111 | 1.00 | 29.48 | B C |
| ATOM | 5791 | O | ARG | 280 | 97.406 | 68.437 | 20.912 | 1.00 | 29.21 | B O |
| ATOM | 5792 | N | PHE | 281 | 98.501 | 66.582 | 20.266 | 1.00 | 31.71 | B N |
| ATOM | 5793 | CA | PHE | 281 | 97.713 | 66.392 | 19.066 | 1.00 | 33.70 | B C |
| ATOM | 5794 | CB | PHE | 281 | 98.594 | 66.335 | 17.826 | 1.00 | 18.70 | B C |
| ATOM | 5795 | CG | PHE | 281 | 99.324 | 67.604 | 17.555 | 1.00 | 21.73 | B C |
| ATOM | 5796 | CD1 | PHE | 281 | 100.438 | 67.950 | 18.308 | 1.00 | 25.58 | B C |
| ATOM | 5797 | CD2 | PHE | 281 | 98.887 | 68.469 | 16.551 | 1.00 | 23.46 | B C |
| ATOM | 5798 | CE1 | PHE | 281 | 101.111 | 69.136 | 18.070 | 1.00 | 25.64 | B C |
| ATOM | 5799 | CE2 | PHE | 281 | 99.554 | 69.665 | 16.301 | 1.00 | 21.19 | B C |
| ATOM | 5800 | CZ | PHE | 281 | 100.669 | 69.999 | 17.064 | 1.00 | 22.62 | B C |
| ATOM | 5801 | C | PHE | 281 | 97.025 | 65.060 | 19.266 | 1.00 | 34.41 | B C |
| ATOM | 5802 | O | PHE | 281 | 97.677 | 64.053 | 19.509 | 1.00 | 36.78 | B O |
| ATOM | 5803 | N | SER | 282 | 95.704 | 65.061 | 19.202 | 1.00 | 16.00 | B N |
| ATOM | 5804 | CA | SER | 282 | 94.962 | 63.835 | 19.374 | 1.00 | 17.85 | B C |
| ATOM | 5805 | CB | SER | 282 | 93.973 | 63.973 | 20.528 | 1.00 | 14.79 | B C |
| ATOM | 5806 | OG | SER | 282 | 93.036 | 64.997 | 20.286 | 1.00 | 11.34 | B O |
| ATOM | 5807 | C | SER | 282 | 94.231 | 63.507 | 18.093 | 1.00 | 19.73 | B C |
| ATOM | 5808 | O | SER | 282 | 93.909 | 64.389 | 17.306 | 1.00 | 23.59 | B O |
| ATOM | 5809 | N | ILE | 283 | 93.986 | 62.224 | 17.881 | 1.00 | 19.27 | B N |
| ATOM | 5810 | CA | ILE | 283 | 93.288 | 61.779 | 16.693 | 1.00 | 17.19 | B C |
| ATOM | 5811 | CB | ILE | 283 | 94.245 | 61.146 | 15.697 | 1.00 | 9.92 | B C |
| ATOM | 5812 | CG2 | ILE | 283 | 93.501 | 60.806 | 14.425 | 1.00 | 10.73 | B C |
| ATOM | 5813 | CG1 | ILE | 283 | 95.377 | 62.118 | 15.383 | 1.00 | 6.39 | B C |
| ATOM | 5814 | CD1 | ILE | 283 | 96.630 | 61.446 | 14.894 | 1.00 | 9.95 | B C |
| ATOM | 5815 | C | ILE | 283 | 92.278 | 60.748 | 17.127 | 1.00 | 16.26 | B C |
| ATOM | 5816 | O | ILE | 283 | 92.574 | 59.886 | 17.947 | 1.00 | 16.12 | B O |
| ATOM | 5817 | N | ALA | 284 | 91.078 | 60.836 | 16.584 | 1.00 | 18.66 | B N |
| ATOM | 5818 | CA | ALA | 284 | 90.050 | 59.896 | 16.955 | 1.00 | 18.68 | B C |
| ATOM | 5819 | CB | ALA | 284 | 88.903 | 60.627 | 17.622 | 1.00 | 45.12 | B C |
| ATOM | 5820 | C | ALA | 284 | 89.542 | 59.107 | 15.759 | 1.00 | 16.81 | B C |
| ATOM | 5821 | O | ALA | 284 | 89.045 | 59.681 | 14.792 | 1.00 | 15.47 | B O |
| ATOM | 5822 | N | ILE | 285 | 89.691 | 57.788 | 15.826 | 1.00 | 23.61 | B N |
| ATOM | 5823 | CA | ILE | 285 | 89.205 | 56.922 | 14.772 | 1.00 | 17.81 | B C |
| ATOM | 5824 | CB | ILE | 285 | 89.960 | 55.564 | 14.741 | 1.00 | 12.20 | B C |
| ATOM | 5825 | CG2 | ILE | 285 | 89.210 | 54.576 | 13.862 | 1.00 | 7.02 | B C |
| ATOM | 5826 | CG1 | ILE | 285 | 91.380 | 55.738 | 14.204 | 1.00 | 7.53 | B C |
| ATOM | 5827 | CD1 | ILE | 285 | 92.342 | 56.334 | 15.179 | 1.00 | 8.67 | B C |
| ATOM | 5828 | C | ILE | 285 | 87.745 | 56.678 | 15.148 | 1.00 | 21.13 | B C |
| ATOM | 5829 | O | ILE | 285 | 87.466 | 56.108 | 16.201 | 1.00 | 22.87 | B O |
| ATOM | 5830 | N | LEU | 286 | 86.820 | 57.112 | 14.297 | 1.00 | 18.22 | B N |
| ATOM | 5831 | CA | LEU | 286 | 85.399 | 56.937 | 14.581 | 1.00 | 18.70 | B C |
| ATOM | 5832 | CB | LEU | 286 | 84.615 | 58.129 | 14.039 | 1.00 | 27.86 | B C |
| ATOM | 5833 | CG | LEU | 286 | 85.105 | 59.512 | 14.456 | 1.00 | 30.68 | B C |
| ATOM | 5834 | CD1 | LEU | 286 | 84.112 | 60.536 | 13.961 | 1.00 | 33.24 | B C |
| ATOM | 5835 | CD2 | LEU | 286 | 85.249 | 59.599 | 15.963 | 1.00 | 32.35 | B C |
| ATOM | 5836 | C | LEU | 286 | 84.774 | 55.645 | 14.044 | 1.00 | 19.15 | B C |
| ATOM | 5837 | O | LEU | 286 | 83.552 | 55.458 | 14.122 | 1.00 | 19.99 | B O |
| ATOM | 5838 | N | GLY | 287 | 85.609 | 54.752 | 13.520 | 1.00 | 37.37 | B N |
| ATOM | 5839 | CA | GLY | 287 | 85.115 | 53.501 | 12.967 | 1.00 | 36.15 | B C |
| ATOM | 5840 | C | GLY | 287 | 84.059 | 52.745 | 13.760 | 1.00 | 33.73 | B C |

Fig. 19: A-81

```
ATOM   5841  O    GLY  287      82.899   52.681   13.367  1.00   37.83      B   O
ATOM   5842  N    HIS  288      84.464   52.162   14.878  1.00   34.79      B   N
ATOM   5843  CA   HIS  288      83.563   51.376   15.700  1.00   32.75      B   C
ATOM   5844  CB   HIS  288      84.272   51.016   16.996  1.00   68.63      B   C
ATOM   5845  CG   HIS  288      85.486   50.181   16.763  1.00   70.54      B   C
ATOM   5846  CD2  HIS  288      85.781   48.912   17.123  1.00   66.91      B   C
ATOM   5847  ND1  HIS  288      86.520   50.600   15.955  1.00   65.20      B   N
ATOM   5848  CE1  HIS  288      87.397   49.623   15.821  1.00   65.56      B   C
ATOM   5849  NE2  HIS  288      86.972   48.586   16.519  1.00   64.05      B   N
ATOM   5850  C    HIS  288      82.214   52.006   15.968  1.00   30.23      B   C
ATOM   5851  O    HIS  288      81.180   51.398   15.711  1.00   29.80      B   O
ATOM   5852  N    TYR  289      82.219   53.233   16.461  1.00   26.66      B   N
ATOM   5853  CA   TYR  289      80.982   53.912   16.754  1.00   27.59      B   C
ATOM   5854  CB   TYR  289      81.287   55.288   17.309  1.00   20.91      B   C
ATOM   5855  CG   TYR  289      81.803   55.203   18.717  1.00   23.71      B   C
ATOM   5856  CD1  TYR  289      83.163   55.293   18.997  1.00   24.30      B   C
ATOM   5857  CE1  TYR  289      83.633   55.127   20.281  1.00   27.49      B   C
ATOM   5858  CD2  TYR  289      80.928   54.947   19.764  1.00   26.60      B   C
ATOM   5859  CE2  TYR  289      81.381   54.776   21.047  1.00   21.41      B   C
ATOM   5860  CZ   TYR  289      82.733   54.866   21.303  1.00   23.14      B   C
ATOM   5861  OH   TYR  289      83.166   54.686   22.597  1.00   27.79      B   O
ATOM   5862  C    TYR  289      80.039   54.015   15.572  1.00   29.36      B   C
ATOM   5863  O    TYR  289      78.849   53.720   15.692  1.00   28.55      B   O
ATOM   5864  N    ASN  290      80.551   54.414   14.419  1.00   30.33      B   N
ATOM   5865  CA   ASN  290      79.681   54.538   13.264  1.00   29.82      B   C
ATOM   5866  CB   ASN  290      80.390   55.290   12.141  1.00   19.88      B   C
ATOM   5867  CG   ASN  290      80.582   56.750   12.466  1.00   23.09      B   C
ATOM   5868  OD1  ASN  290      79.681   57.395   13.005  1.00   24.51      B   O
ATOM   5869  ND2  ASN  290      81.748   57.286   12.133  1.00   26.61      B   N
ATOM   5870  C    ASN  290      79.142   53.214   12.746  1.00   28.65      B   C
ATOM   5871  O    ASN  290      78.008   53.153   12.264  1.00   35.25      B   O
ATOM   5872  N    ARG  291      79.944   52.155   12.842  1.00   46.80      B   N
ATOM   5873  CA   ARG  291      79.513   50.850   12.362  1.00   46.11      B   C
ATOM   5874  CB   ARG  291      80.694   49.867   12.337  1.00   45.84      B   C
ATOM   5875  CG   ARG  291      81.661   50.063   11.152  1.00   50.80      B   C
ATOM   5876  CD   ARG  291      82.722   48.943   11.054  1.00   54.88      B   C
ATOM   5877  NE   ARG  291      83.916   49.157   11.883  1.00   47.06      B   N
ATOM   5878  CZ   ARG  291      84.884   50.030   11.603  1.00   56.55      B   C
ATOM   5879  NH1  ARG  291      84.813   50.787   10.515  1.00   55.39      B   N
ATOM   5880  NH2  ARG  291      85.936   50.131   12.401  1.00   53.31      B   N
ATOM   5881  C    ARG  291      78.367   50.296   13.207  1.00   43.91      B   C
ATOM   5882  O    ARG  291      77.338   49.876   12.676  1.00   47.17      B   O
ATOM   5883  N    GLY  292      78.531   50.306   14.523  1.00   18.83      B   N
ATOM   5884  CA   GLY  292      77.476   49.795   15.374  1.00   19.08      B   C
ATOM   5885  C    GLY  292      76.427   50.857   15.628  1.00   25.45      B   C
ATOM   5886  O    GLY  292      75.874   50.947   16.722  1.00   32.58      B   O
ATOM   5887  N    ASN  293      76.151   51.664   14.610  1.00   32.56      B   N
ATOM   5888  CA   ASN  293      75.177   52.740   14.724  1.00   34.89      B   C
ATOM   5889  CB   ASN  293      73.785   52.239   14.339  1.00   18.98      B   C
ATOM   5890  CG   ASN  293      73.623   52.066   12.846  1.00   25.56      B   C
ATOM   5891  OD1  ASN  293      74.249   52.776   12.063  1.00   27.19      B   O
ATOM   5892  ND2  ASN  293      72.757   51.132   12.440  1.00   26.33      B   N
ATOM   5893  C    ASN  293      75.116   53.389   16.111  1.00   36.22      B   C
ATOM   5894  O    ASN  293      74.054   53.448   16.722  1.00   31.70      B   O
ATOM   5895  N    LEU  294      76.247   53.875   16.614  1.00   40.17      B   N
ATOM   5896  CA   LEU  294      76.260   54.525   17.921  1.00   39.32      B   C
ATOM   5897  CB   LEU  294      77.141   53.737   18.901  1.00   27.66      B   C
ATOM   5898  CG   LEU  294      76.633   52.343   19.291  1.00   26.48      B   C
ATOM   5899  CD1  LEU  294      77.463   51.781   20.440  1.00   27.02      B   C
ATOM   5900  CD2  LEU  294      75.175   52.437   19.714  1.00   27.39      B   C
ATOM   5901  C    LEU  294      76.730   55.985   17.823  1.00   41.69      B   C
ATOM   5902  O    LEU  294      77.579   56.314   16.984  1.00   40.35      B   O
ATOM   5903  N    SER  295      76.158   56.860   18.656  1.00   29.47      B   N
ATOM   5904  CA   SER  295      76.534   58.272   18.644  1.00   29.33      B   C
ATOM   5905  CB   SER  295      75.802   59.063   19.740  1.00   35.11      B   C
ATOM   5906  OG   SER  295      76.336   60.371   19.894  1.00   41.79      B   O
ATOM   5907  C    SER  295      78.022   58.329   18.890  1.00   25.45      B   C
ATOM   5908  O    SER  295      78.583   57.444   19.533  1.00   22.32      B   O
ATOM   5909  N    THR  296      78.661   59.379   18.401  1.00   28.05      B   N
ATOM   5910  CA   THR  296      80.096   59.500   18.559  1.00   28.09      B   C
ATOM   5911  CB   THR  296      80.786   59.452   17.191  1.00   44.94      B   C
ATOM   5912  OG1  THR  296      80.305   60.534   16.383  1.00   50.00      B   O
ATOM   5913  CG2  THR  296      80.485   58.150   16.487  1.00   44.81      B   C
```

Fig. 19: A-82

```
ATOM   5914  C    THR  296     80.519  60.792  19.227  1.00   29.07      B  C
ATOM   5915  O    THR  296     81.695  60.971  19.535  1.00   27.88      B  O
ATOM   5916  N    GLU  297     79.581  61.705  19.451  1.00   50.64      B  N
ATOM   5917  CA   GLU  297     79.970  62.978  20.038  1.00   54.10      B  C
ATOM   5918  CB   GLU  297     78.781  63.943  20.111  1.00   93.12      B  C
ATOM   5919  CG   GLU  297     77.787  63.695  21.213  1.00  100.15      B  C
ATOM   5920  CD   GLU  297     77.036  64.960  21.569  1.00  101.40      B  C
ATOM   5921  OE1  GLU  297     76.160  64.911  22.455  1.00  104.84      B  O
ATOM   5922  OE2  GLU  297     77.333  66.010  20.964  1.00  102.89      B  O
ATOM   5923  C    GLU  297     80.639  62.849  21.399  1.00   52.14      B  C
ATOM   5924  O    GLU  297     81.715  63.406  21.612  1.00   51.64      B  O
ATOM   5925  N    LYS  298     80.029  62.104  22.315  1.00   35.40      B  N
ATOM   5926  CA   LYS  298     80.622  61.942  23.636  1.00   35.40      B  C
ATOM   5927  CB   LYS  298     79.837  60.916  24.443  1.00   37.32      B  C
ATOM   5928  CG   LYS  298     80.199  60.902  25.910  1.00   46.03      B  C
ATOM   5929  CD   LYS  298     79.201  60.085  26.727  1.00   47.75      B  C
ATOM   5930  CE   LYS  298     77.777  60.625  26.578  1.00   51.57      B  C
ATOM   5931  NZ   LYS  298     77.676  62.075  26.908  1.00   55.89      B  N
ATOM   5932  C    LYS  298     82.087  61.518  23.514  1.00   33.00      B  C
ATOM   5933  O    LYS  298     82.939  61.933  24.310  1.00   33.88      B  O
ATOM   5934  N    PHE  299     82.371  60.699  22.505  1.00   29.00      B  N
ATOM   5935  CA   PHE  299     83.729  60.226  22.244  1.00   27.24      B  C
ATOM   5936  CB   PHE  299     83.701  59.054  21.263  1.00   39.15      B  C
ATOM   5937  CG   PHE  299     85.065  58.571  20.851  1.00   31.59      B  C
ATOM   5938  CD1  PHE  299     86.020  58.237  21.806  1.00   28.04      B  C
ATOM   5939  CD2  PHE  299     85.396  58.435  19.505  1.00   29.32      B  C
ATOM   5940  CE1  PHE  299     87.284  57.776  21.422  1.00   27.45      B  C
ATOM   5941  CE2  PHE  299     86.667  57.970  19.119  1.00   23.73      B  C
ATOM   5942  CZ   PHE  299     87.603  57.643  20.078  1.00   22.24      B  C
ATOM   5943  C    PHE  299     84.562  61.361  21.662  1.00   27.59      B  C
ATOM   5944  O    PHE  299     85.625  61.702  22.183  1.00   23.40      B  O
ATOM   5945  N    VAL  300     84.077  61.946  20.576  1.00   13.78      B  N
ATOM   5946  CA   VAL  300     84.791  63.050  19.944  1.00   18.73      B  C
ATOM   5947  CB   VAL  300     83.954  63.701  18.822  1.00   24.12      B  C
ATOM   5948  CG1  VAL  300     84.616  64.979  18.363  1.00   27.69      B  C
ATOM   5949  CG2  VAL  300     83.814  62.731  17.646  1.00   28.13      B  C
ATOM   5950  C    VAL  300     85.142  64.119  20.966  1.00   17.37      B  C
ATOM   5951  O    VAL  300     86.209  64.715  20.906  1.00   17.87      B  O
ATOM   5952  N    GLU  301     84.248  64.359  21.914  1.00   33.19      B  N
ATOM   5953  CA   GLU  301     84.520  65.377  22.915  1.00   33.85      B  C
ATOM   5954  CB   GLU  301     83.255  65.707  23.706  1.00  133.49      B  C
ATOM   5955  CG   GLU  301     83.426  66.851  24.703  1.00  135.76      B  C
ATOM   5956  CD   GLU  301     84.115  68.077  24.108  1.00  141.57      B  C
ATOM   5957  OE1  GLU  301     83.669  68.566  23.046  1.00  141.12      B  O
ATOM   5958  OE2  GLU  301     85.102  68.555  24.713  1.00  143.84      B  O
ATOM   5959  C    GLU  301     85.634  64.925  23.847  1.00   32.42      B  C
ATOM   5960  O    GLU  301     86.495  65.723  24.239  1.00   30.50      B  O
ATOM   5961  N    GLU  302     85.628  63.642  24.190  1.00   18.71      B  N
ATOM   5962  CA   GLU  302     86.663  63.091  25.060  1.00   18.52      B  C
ATOM   5963  CB   GLU  302     86.420  61.596  25.293  1.00   49.27      B  C
ATOM   5964  CG   GLU  302     87.438  60.934  26.207  1.00   49.02      B  C
ATOM   5965  CD   GLU  302     87.100  59.486  26.491  1.00   45.95      B  C
ATOM   5966  OE1  GLU  302     86.051  59.237  27.118  1.00   45.93      B  O
ATOM   5967  OE2  GLU  302     87.875  58.594  26.084  1.00   50.37      B  O
ATOM   5968  C    GLU  302     88.046  63.301  24.456  1.00   21.59      B  C
ATOM   5969  O    GLU  302     88.964  63.720  25.150  1.00   20.85      B  O
ATOM   5970  N    ILE  303     88.188  63.031  23.159  1.00   30.73      B  N
ATOM   5971  CA   ILE  303     89.479  63.175  22.472  1.00   30.78      B  C
ATOM   5972  CB   ILE  303     89.470  62.431  21.112  1.00   21.11      B  C
ATOM   5973  CG2  ILE  303     90.865  62.406  20.518  1.00   16.29      B  C
ATOM   5974  CG1  ILE  303     88.932  61.003  21.306  1.00   18.71      B  C
ATOM   5975  CD1  ILE  303     89.501  60.262  22.515  1.00   15.17      B  C
ATOM   5976  C    ILE  303     89.922  64.625  22.242  1.00   32.81      B  C
ATOM   5977  O    ILE  303     91.097  64.955  22.415  1.00   35.30      B  O
ATOM   5978  N    LYS  304     88.989  65.485  21.847  1.00   41.13      B  N
ATOM   5979  CA   LYS  304     89.321  66.881  21.624  1.00   41.93      B  C
ATOM   5980  CB   LYS  304     88.087  67.695  21.239  1.00   34.23      B  C
ATOM   5981  CG   LYS  304     87.578  67.484  19.837  1.00   40.90      B  C
ATOM   5982  CD   LYS  304     86.491  68.498  19.526  1.00   42.43      B  C
ATOM   5983  CE   LYS  304     85.937  68.312  18.122  1.00   45.16      B  C
ATOM   5984  NZ   LYS  304     84.893  69.323  17.799  1.00   47.34      B  N
ATOM   5985  C    LYS  304     89.892  67.455  22.906  1.00   38.02      B  C
ATOM   5986  O    LYS  304     90.833  68.240  22.871  1.00   42.10      B  O
```

Fig. 19: A-83

```
ATOM   5987  N    SER  305      89.322  67.066  24.043  1.00  21.53   B  N
ATOM   5988  CA   SER  305      89.788  67.571  25.335  1.00  18.69   B  C
ATOM   5989  CB   SER  305      88.872  67.096  26.460  1.00  39.18   B  C
ATOM   5990  OG   SER  305      89.039  65.715  26.696  1.00  35.86   B  O
ATOM   5991  C    SER  305      91.223  67.134  25.622  1.00  19.21   B  C
ATOM   5992  O    SER  305      91.935  67.754  26.418  1.00  21.78   B  O
ATOM   5993  N    ILE  306      91.652  66.063  24.969  1.00  47.39   B  N
ATOM   5994  CA   ILE  306      93.005  65.582  25.158  1.00  44.14   B  C
ATOM   5995  CB   ILE  306      93.129  64.131  24.682  1.00  20.56   B  C
ATOM   5996  CG2  ILE  306      94.584  63.769  24.454  1.00  21.29   B  C
ATOM   5997  CG1  ILE  306      92.479  63.210  25.713  1.00  23.19   B  C
ATOM   5998  CD1  ILE  306      92.459  61.762  25.302  1.00  20.90   B  C
ATOM   5999  C    ILE  306      93.966  66.469  24.378  1.00  41.90   B  C
ATOM   6000  O    ILE  306      95.146  66.583  24.717  1.00  42.43   B  O
ATOM   6001  N    ALA  307      93.445  67.103  23.334  1.00  47.34   B  N
ATOM   6002  CA   ALA  307      94.247  67.979  22.497  1.00  49.53   B  C
ATOM   6003  CB   ALA  307      93.538  68.236  21.181  1.00  34.34   B  C
ATOM   6004  C    ALA  307      94.526  69.296  23.200  1.00  49.19   B  C
ATOM   6005  O    ALA  307      93.952  69.595  24.253  1.00  48.18   B  O
ATOM   6006  N    SER  308      95.415  70.078  22.604  1.00  31.36   B  N
ATOM   6007  CA   SER  308      95.801  71.367  23.141  1.00  34.29   B  C
ATOM   6008  CB   SER  308      97.299  71.580  22.943  1.00   9.08   B  C
ATOM   6009  OG   SER  308      98.040  70.819  23.867  1.00  12.47   B  O
ATOM   6010  C    SER  308      95.054  72.489  22.446  1.00  37.94   B  C
ATOM   6011  O    SER  308      94.703  72.373  21.272  1.00  35.28   B  O
ATOM   6012  N    GLU  309      94.813  73.575  23.178  1.00  31.30   B  N
ATOM   6013  CA   GLU  309      94.137  74.735  22.614  1.00  34.79   B  C
ATOM   6014  CB   GLU  309      93.786  75.736  23.721  1.00  74.37   B  C
ATOM   6015  CG   GLU  309      92.834  75.203  24.787  1.00  79.74   B  C
ATOM   6016  CD   GLU  309      91.461  74.845  24.234  1.00  82.50   B  C
ATOM   6017  OE1  GLU  309      90.533  74.518  25.043  1.00  84.83   B  O
ATOM   6018  OE2  GLU  309      91.307  74.784  22.995  1.00  86.65   B  O
ATOM   6019  C    GLU  309      95.138  75.359  21.642  1.00  35.54   B  C
ATOM   6020  O    GLU  309      96.321  75.480  21.971  1.00  37.19   B  O
ATOM   6021  N    PRO  310      94.685  75.762  20.435  1.00  19.46   B  N
ATOM   6022  CD   PRO  310      95.588  76.399  19.457  1.00  19.32   B  C
ATOM   6023  CA   PRO  310      93.324  75.694  19.890  1.00  19.65   B  C
ATOM   6024  CB   PRO  310      93.362  76.729  18.770  1.00  21.15   B  C
ATOM   6025  CG   PRO  310      94.715  76.515  18.203  1.00  20.71   B  C
ATOM   6026  C    PRO  310      92.884  74.312  19.384  1.00  20.14   B  C
ATOM   6027  O    PRO  310      93.368  73.816  18.374  1.00  16.93   B  O
ATOM   6028  N    THR  311      91.945  73.714  20.101  1.00  34.98   B  N
ATOM   6029  CA   THR  311      91.410  72.410  19.764  1.00  35.85   B  C
ATOM   6030  CB   THR  311      89.985  72.276  20.321  1.00  54.06   B  C
ATOM   6031  OG1  THR  311      89.327  71.159  19.711  1.00  58.22   B  O
ATOM   6032  CG2  THR  311      89.195  73.556  20.052  1.00  57.14   B  C
ATOM   6033  C    THR  311      91.390  72.103  18.265  1.00  37.72   B  C
ATOM   6034  O    THR  311      91.801  71.022  17.847  1.00  38.89   B  O
ATOM   6035  N    GLU  312      90.929  73.049  17.451  1.00  45.13   B  N
ATOM   6036  CA   GLU  312      90.842  72.825  16.004  1.00  43.75   B  C
ATOM   6037  CB   GLU  312      90.160  74.008  15.309  1.00  94.13   B  C
ATOM   6038  CG   GLU  312      90.848  75.342  15.528  1.00  95.89   B  C
ATOM   6039  CD   GLU  312      90.633  76.309  14.376  1.00  95.00   B  C
ATOM   6040  OE1  GLU  312      90.998  77.496  14.516  1.00  98.35   B  O
ATOM   6041  OE2  GLU  312      90.109  75.880  13.327  1.00  95.87   B  O
ATOM   6042  C    GLU  312      92.168  72.547  15.310  1.00  42.37   B  C
ATOM   6043  O    GLU  312      92.219  71.771  14.367  1.00  42.33   B  O
ATOM   6044  N    LYS  313      93.240  73.180  15.763  1.00  62.67   B  N
ATOM   6045  CA   LYS  313      94.537  72.966  15.141  1.00  61.87   B  C
ATOM   6046  CB   LYS  313      95.368  74.255  15.192  1.00  80.35   B  C
ATOM   6047  CG   LYS  313      94.954  75.308  14.167  1.00  80.23   B  C
ATOM   6048  CD   LYS  313      95.351  74.917  12.745  1.00  76.53   B  C
ATOM   6049  CE   LYS  313      96.790  75.307  12.430  1.00  78.57   B  C
ATOM   6050  NZ   LYS  313      97.781  74.730  13.383  1.00  83.05   B  N
ATOM   6051  C    LYS  313      95.308  71.832  15.800  1.00  63.02   B  C
ATOM   6052  O    LYS  313      96.473  71.610  15.491  1.00  65.34   B  O
ATOM   6053  N    HIS  314      94.656  71.103  16.697  1.00  42.28   B  N
ATOM   6054  CA   HIS  314      95.326  70.011  17.391  1.00  43.13   B  C
ATOM   6055  CB   HIS  314      95.631  70.426  18.828  1.00  51.27   B  C
ATOM   6056  CG   HIS  314      96.611  71.551  18.938  1.00  48.13   B  C
ATOM   6057  CD2  HIS  314      96.423  72.880  19.111  1.00  47.60   B  C
ATOM   6058  ND1  HIS  314      97.973  71.364  18.847  1.00  47.71   B  N
ATOM   6059  CE1  HIS  314      98.582  72.530  18.960  1.00  47.00   B  C
```

Fig. 19: A-84

| | | | | | | | | | |
|---|---|---|---|---|---|---|---|---|---|
| ATOM | 6060 | NE2 | HIS | 314 | 97.664 | 73.466 | 19.121 | 1.00 | 47.39 | B | N |
| ATOM | 6061 | C | HIS | 314 | 94.540 | 68.706 | 17.405 | 1.00 | 43.26 | B | C |
| ATOM | 6062 | O | HIS | 314 | 95.034 | 67.690 | 17.896 | 1.00 | 46.66 | B | O |
| ATOM | 6063 | N | PHE | 315 | 93.324 | 68.732 | 16.868 | 1.00 | 55.79 | B | N |
| ATOM | 6064 | CA | PHE | 315 | 92.475 | 67.546 | 16.835 | 1.00 | 55.59 | B | C |
| ATOM | 6065 | CB | PHE | 315 | 91.175 | 67.834 | 17.578 | 1.00 | 29.85 | B | C |
| ATOM | 6066 | CG | PHE | 315 | 90.175 | 66.731 | 17.499 | 1.00 | 24.83 | B | C |
| ATOM | 6067 | CD1 | PHE | 315 | 90.445 | 65.490 | 18.057 | 1.00 | 26.67 | B | C |
| ATOM | 6068 | CD2 | PHE | 315 | 88.944 | 66.942 | 16.890 | 1.00 | 22.91 | B | C |
| ATOM | 6069 | CE1 | PHE | 315 | 89.503 | 64.473 | 18.016 | 1.00 | 21.62 | B | C |
| ATOM | 6070 | CE2 | PHE | 315 | 87.989 | 65.939 | 16.838 | 1.00 | 23.61 | B | C |
| ATOM | 6071 | CZ | PHE | 315 | 88.268 | 64.700 | 17.404 | 1.00 | 25.28 | B | C |
| ATOM | 6072 | C | PHE | 315 | 92.172 | 67.086 | 15.412 | 1.00 | 56.31 | B | C |
| ATOM | 6073 | O | PHE | 315 | 91.948 | 67.903 | 14.516 | 1.00 | 57.71 | B | O |
| ATOM | 6074 | N | PHE | 316 | 92.170 | 65.772 | 15.212 | 1.00 | 44.89 | B | N |
| ATOM | 6075 | CA | PHE | 316 | 91.898 | 65.200 | 13.899 | 1.00 | 41.94 | B | C |
| ATOM | 6076 | CB | PHE | 316 | 93.175 | 64.621 | 13.282 | 1.00 | 20.23 | B | C |
| ATOM | 6077 | CG | PHE | 316 | 94.195 | 65.652 | 12.900 | 1.00 | 23.85 | B | C |
| ATOM | 6078 | CD1 | PHE | 316 | 95.118 | 66.114 | 13.828 | 1.00 | 19.44 | B | C |
| ATOM | 6079 | CD2 | PHE | 316 | 94.229 | 66.165 | 11.605 | 1.00 | 20.70 | B | C |
| ATOM | 6080 | CE1 | PHE | 316 | 96.066 | 67.074 | 13.475 | 1.00 | 22.01 | B | C |
| ATOM | 6081 | CE2 | PHE | 316 | 95.171 | 67.125 | 11.242 | 1.00 | 23.81 | B | C |
| ATOM | 6082 | CZ | PHE | 316 | 96.092 | 67.580 | 12.180 | 1.00 | 24.04 | B | C |
| ATOM | 6083 | C | PHE | 316 | 90.841 | 64.107 | 13.990 | 1.00 | 39.87 | B | C |
| ATOM | 6084 | O | PHE | 316 | 90.845 | 63.302 | 14.910 | 1.00 | 39.11 | B | O |
| ATOM | 6085 | N | ASN | 317 | 89.938 | 64.088 | 13.020 | 1.00 | 36.72 | B | N |
| ATOM | 6086 | CA | ASN | 317 | 88.863 | 63.110 | 12.978 | 1.00 | 37.94 | B | C |
| ATOM | 6087 | CB | ASN | 317 | 87.538 | 63.826 | 12.746 | 1.00 | 58.19 | B | C |
| ATOM | 6088 | CG | ASN | 317 | 86.496 | 63.443 | 13.752 | 1.00 | 61.18 | B | C |
| ATOM | 6089 | OD1 | ASN | 317 | 86.408 | 62.284 | 14.144 | 1.00 | 63.11 | B | O |
| ATOM | 6090 | ND2 | ASN | 317 | 85.688 | 64.411 | 14.176 | 1.00 | 59.44 | B | N |
| ATOM | 6091 | C | ASN | 317 | 89.102 | 62.140 | 11.831 | 1.00 | 38.90 | B | C |
| ATOM | 6092 | O | ASN | 317 | 89.519 | 62.549 | 10.757 | 1.00 | 39.76 | B | O |
| ATOM | 6093 | N | VAL | 318 | 88.840 | 60.858 | 12.045 | 1.00 | 40.86 | B | N |
| ATOM | 6094 | CA | VAL | 318 | 89.027 | 59.872 | 10.981 | 1.00 | 39.49 | B | C |
| ATOM | 6095 | CB | VAL | 318 | 90.348 | 59.096 | 11.156 | 1.00 | 59.32 | B | C |
| ATOM | 6096 | CG1 | VAL | 318 | 90.497 | 58.075 | 10.065 | 1.00 | 59.45 | B | C |
| ATOM | 6097 | CG2 | VAL | 318 | 91.519 | 60.052 | 11.111 | 1.00 | 59.30 | B | C |
| ATOM | 6098 | C | VAL | 318 | 87.861 | 58.894 | 10.987 | 1.00 | 34.64 | B | C |
| ATOM | 6099 | O | VAL | 318 | 87.363 | 58.523 | 12.050 | 1.00 | 35.31 | B | O |
| ATOM | 6100 | N | SER | 319 | 87.417 | 58.482 | 9.803 | 1.00 | 25.74 | B | N |
| ATOM | 6101 | CA | SER | 319 | 86.300 | 57.557 | 9.711 | 1.00 | 25.00 | B | C |
| ATOM | 6102 | CB | SER | 319 | 85.769 | 57.502 | 8.275 | 1.00 | 46.83 | B | C |
| ATOM | 6103 | OG | SER | 319 | 86.801 | 57.222 | 7.348 | 1.00 | 58.78 | B | O |
| ATOM | 6104 | C | SER | 319 | 86.672 | 56.161 | 10.195 | 1.00 | 23.60 | B | C |
| ATOM | 6105 | O | SER | 319 | 85.877 | 55.513 | 10.876 | 1.00 | 21.67 | B | O |
| ATOM | 6106 | N | ASP | 320 | 87.875 | 55.702 | 9.855 | 1.00 | 29.04 | B | N |
| ATOM | 6107 | CA | ASP | 320 | 88.342 | 54.377 | 10.272 | 1.00 | 29.02 | B | C |
| ATOM | 6108 | CB | ASP | 320 | 87.700 | 53.292 | 9.391 | 1.00 | 54.50 | B | C |
| ATOM | 6109 | CG | ASP | 320 | 88.036 | 53.455 | 7.907 | 1.00 | 52.95 | B | C |
| ATOM | 6110 | OD1 | ASP | 320 | 87.708 | 54.505 | 7.318 | 1.00 | 51.63 | B | O |
| ATOM | 6111 | OD2 | ASP | 320 | 88.628 | 52.525 | 7.324 | 1.00 | 53.50 | B | O |
| ATOM | 6112 | C | ASP | 320 | 89.878 | 54.249 | 10.227 | 1.00 | 27.39 | B | C |
| ATOM | 6113 | O | ASP | 320 | 90.574 | 55.142 | 9.734 | 1.00 | 27.17 | B | O |
| ATOM | 6114 | N | GLU | 321 | 90.403 | 53.140 | 10.745 | 1.00 | 32.71 | B | N |
| ATOM | 6115 | CA | GLU | 321 | 91.845 | 52.909 | 10.748 | 1.00 | 33.69 | B | C |
| ATOM | 6116 | CB | GLU | 321 | 92.152 | 51.430 | 11.018 | 1.00 | 76.40 | B | C |
| ATOM | 6117 | CG | GLU | 321 | 92.439 | 51.066 | 12.469 | 1.00 | 70.24 | B | C |
| ATOM | 6118 | CD | GLU | 321 | 91.229 | 51.194 | 13.373 | 1.00 | 69.99 | B | C |
| ATOM | 6119 | OE1 | GLU | 321 | 90.159 | 50.621 | 13.053 | 1.00 | 71.42 | B | O |
| ATOM | 6120 | OE2 | GLU | 321 | 91.357 | 51.862 | 14.418 | 1.00 | 74.03 | B | O |
| ATOM | 6121 | C | GLU | 321 | 92.476 | 53.300 | 9.412 | 1.00 | 37.68 | B | C |
| ATOM | 6122 | O | GLU | 321 | 93.529 | 53.943 | 9.369 | 1.00 | 34.44 | B | O |
| ATOM | 6123 | N | LEU | 322 | 91.820 | 52.905 | 8.323 | 1.00 | 34.24 | B | N |
| ATOM | 6124 | CA | LEU | 322 | 92.310 | 53.175 | 6.971 | 1.00 | 36.93 | B | C |
| ATOM | 6125 | CB | LEU | 322 | 91.345 | 52.598 | 5.937 | 1.00 | 67.00 | B | C |
| ATOM | 6126 | CG | LEU | 322 | 91.361 | 51.081 | 5.743 | 1.00 | 65.63 | B | C |
| ATOM | 6127 | CD1 | LEU | 322 | 92.716 | 50.681 | 5.198 | 1.00 | 67.37 | B | C |
| ATOM | 6128 | CD2 | LEU | 322 | 91.058 | 50.353 | 7.063 | 1.00 | 70.68 | B | C |
| ATOM | 6129 | C | LEU | 322 | 92.566 | 54.632 | 6.643 | 1.00 | 38.52 | B | C |
| ATOM | 6130 | O | LEU | 322 | 93.607 | 54.971 | 6.097 | 1.00 | 41.87 | B | O |
| ATOM | 6131 | N | ALA | 323 | 91.617 | 55.492 | 6.974 | 1.00 | 34.22 | B | N |
| ATOM | 6132 | CA | ALA | 323 | 91.759 | 56.908 | 6.687 | 1.00 | 34.65 | B | C |

Fig. 19: A-85

| | | | | | | | | | | |
|---|---|---|---|---|---|---|---|---|---|---|
| ATOM | 6133 | CB | ALA | 323 | 90.420 | 57.600 | 6.897 | 1.00 | 1.87 | B C |
| ATOM | 6134 | C | ALA | 323 | 92.859 | 57.644 | 7.476 | 1.00 | 35.06 | B C |
| ATOM | 6135 | O | ALA | 323 | 93.171 | 58.804 | 7.181 | 1.00 | 35.08 | B O |
| ATOM | 6136 | N | LEU | 324 | 93.447 | 56.995 | 8.476 | 1.00 | 26.80 | B N |
| ATOM | 6137 | CA | LEU | 324 | 94.492 | 57.652 | 9.256 | 1.00 | 25.28 | B C |
| ATOM | 6138 | CB | LEU | 324 | 95.221 | 56.640 | 10.146 | 1.00 | 29.36 | B C |
| ATOM | 6139 | CG | LEU | 324 | 94.590 | 56.344 | 11.516 | 1.00 | 28.09 | B C |
| ATOM | 6140 | CD1 | LEU | 324 | 95.288 | 55.158 | 12.170 | 1.00 | 27.23 | B C |
| ATOM | 6141 | CD2 | LEU | 324 | 94.676 | 57.580 | 12.406 | 1.00 | 26.02 | B C |
| ATOM | 6142 | C | LEU | 324 | 95.495 | 58.366 | 8.354 | 1.00 | 28.81 | B C |
| ATOM | 6143 | O | LEU | 324 | 95.822 | 59.521 | 8.588 | 1.00 | 25.35 | B O |
| ATOM | 6144 | N | VAL | 325 | 95.966 | 57.679 | 7.317 | 1.00 | 52.77 | B N |
| ATOM | 6145 | CA | VAL | 325 | 96.934 | 58.246 | 6.378 | 1.00 | 56.30 | B C |
| ATOM | 6146 | CB | VAL | 325 | 97.153 | 57.321 | 5.185 | 1.00 | 36.74 | B C |
| ATOM | 6147 | CG1 | VAL | 325 | 97.936 | 56.099 | 5.614 | 1.00 | 36.85 | B C |
| ATOM | 6148 | CG2 | VAL | 325 | 95.810 | 56.923 | 4.599 | 1.00 | 40.13 | B C |
| ATOM | 6149 | C | VAL | 325 | 96.524 | 59.598 | 5.818 | 1.00 | 59.12 | B C |
| ATOM | 6150 | O | VAL | 325 | 97.324 | 60.529 | 5.761 | 1.00 | 61.18 | B O |
| ATOM | 6151 | N | THR | 326 | 95.277 | 59.694 | 5.384 | 1.00 | 40.34 | B N |
| ATOM | 6152 | CA | THR | 326 | 94.743 | 60.925 | 4.818 | 1.00 | 41.75 | B C |
| ATOM | 6153 | CB | THR | 326 | 93.298 | 60.706 | 4.344 | 1.00 | 81.94 | B C |
| ATOM | 6154 | OG1 | THR | 326 | 92.430 | 60.600 | 5.481 | 1.00 | 83.85 | B O |
| ATOM | 6155 | CG2 | THR | 326 | 93.206 | 59.417 | 3.534 | 1.00 | 84.31 | B C |
| ATOM | 6156 | C | THR | 326 | 94.744 | 62.070 | 5.836 | 1.00 | 41.76 | B C |
| ATOM | 6157 | O | THR | 326 | 93.885 | 62.952 | 5.785 | 1.00 | 40.58 | B O |
| ATOM | 6158 | N | ILE | 327 | 95.705 | 62.052 | 6.755 | 1.00 | 36.65 | B N |
| ATOM | 6159 | CA | ILE | 327 | 95.812 | 63.075 | 7.792 | 1.00 | 36.84 | B C |
| ATOM | 6160 | CB | ILE | 327 | 95.078 | 62.604 | 9.085 | 1.00 | 16.25 | B C |
| ATOM | 6161 | CG2 | ILE | 327 | 95.934 | 62.757 | 10.328 | 1.00 | 17.02 | B C |
| ATOM | 6162 | CG1 | ILE | 327 | 93.807 | 63.408 | 9.260 | 1.00 | 16.61 | B C |
| ATOM | 6163 | CD1 | ILE | 327 | 92.943 | 62.878 | 10.372 | 1.00 | 16.28 | B C |
| ATOM | 6164 | C | ILE | 327 | 97.272 | 63.402 | 8.093 | 1.00 | 37.35 | B C |
| ATOM | 6165 | O | ILE | 327 | 97.590 | 64.494 | 8.559 | 1.00 | 37.60 | B O |
| ATOM | 6166 | N | VAL | 328 | 98.158 | 62.455 | 7.804 | 1.00 | 43.89 | B N |
| ATOM | 6167 | CA | VAL | 328 | 99.575 | 62.643 | 8.060 | 1.00 | 46.03 | B C |
| ATOM | 6168 | CB | VAL | 328 | 100.407 | 61.469 | 7.510 | 1.00 | 54.81 | B C |
| ATOM | 6169 | CG1 | VAL | 328 | 99.871 | 60.157 | 8.061 | 1.00 | 56.76 | B C |
| ATOM | 6170 | CG2 | VAL | 328 | 100.381 | 61.480 | 5.997 | 1.00 | 56.08 | B C |
| ATOM | 6171 | C | VAL | 328 | 100.121 | 63.943 | 7.481 | 1.00 | 45.95 | B C |
| ATOM | 6172 | O | VAL | 328 | 100.998 | 64.563 | 8.075 | 1.00 | 45.23 | B O |
| ATOM | 6173 | N | LYS | 329 | 99.611 | 64.366 | 6.331 | 1.00 | 44.51 | B N |
| ATOM | 6174 | CA | LYS | 329 | 100.097 | 65.609 | 5.732 | 1.00 | 43.72 | B C |
| ATOM | 6175 | CB | LYS | 329 | 99.471 | 65.824 | 4.356 | 1.00 | 45.34 | B C |
| ATOM | 6176 | CG | LYS | 329 | 100.174 | 66.880 | 3.520 | 1.00 | 46.89 | B C |
| ATOM | 6177 | CD | LYS | 329 | 99.423 | 67.129 | 2.220 | 1.00 | 49.21 | B C |
| ATOM | 6178 | CE | LYS | 329 | 100.179 | 68.074 | 1.298 | 1.00 | 52.25 | B C |
| ATOM | 6179 | NZ | LYS | 329 | 101.450 | 67.466 | 0.831 | 1.00 | 55.93 | B N |
| ATOM | 6180 | C | LYS | 329 | 99.762 | 66.797 | 6.640 | 1.00 | 41.89 | B C |
| ATOM | 6181 | O | LYS | 329 | 100.640 | 67.552 | 7.056 | 1.00 | 43.10 | B O |
| ATOM | 6182 | N | ALA | 330 | 98.483 | 66.957 | 6.952 | 1.00 | 14.46 | B N |
| ATOM | 6183 | CA | ALA | 330 | 98.053 | 68.043 | 7.814 | 1.00 | 14.49 | B C |
| ATOM | 6184 | CB | ALA | 330 | 96.538 | 68.052 | 7.906 | 1.00 | 26.19 | B C |
| ATOM | 6185 | C | ALA | 330 | 98.657 | 67.910 | 9.210 | 1.00 | 15.64 | B C |
| ATOM | 6186 | O | ALA | 330 | 99.090 | 68.896 | 9.796 | 1.00 | 15.54 | B O |
| ATOM | 6187 | N | LEU | 331 | 98.666 | 66.688 | 9.745 | 1.00 | 29.61 | B N |
| ATOM | 6188 | CA | LEU | 331 | 99.200 | 66.447 | 11.078 | 1.00 | 27.25 | B C |
| ATOM | 6189 | CB | LEU | 331 | 99.108 | 64.969 | 11.454 | 1.00 | 20.84 | B C |
| ATOM | 6190 | CG | LEU | 331 | 99.086 | 64.642 | 12.958 | 1.00 | 17.26 | B C |
| ATOM | 6191 | CD1 | LEU | 331 | 99.332 | 63.152 | 13.131 | 1.00 | 18.89 | B C |
| ATOM | 6192 | CD2 | LEU | 331 | 100.130 | 65.436 | 13.722 | 1.00 | 12.95 | B C |
| ATOM | 6193 | C | LEU | 331 | 100.647 | 66.860 | 11.070 | 1.00 | 27.28 | B C |
| ATOM | 6194 | O | LEU | 331 | 101.090 | 67.613 | 11.931 | 1.00 | 26.63 | B O |
| ATOM | 6195 | N | GLY | 332 | 101.374 | 66.358 | 10.079 | 1.00 | 36.12 | B N |
| ATOM | 6196 | CA | GLY | 332 | 102.784 | 66.666 | 9.949 | 1.00 | 37.22 | B C |
| ATOM | 6197 | C | GLY | 332 | 103.089 | 68.150 | 9.917 | 1.00 | 37.48 | B C |
| ATOM | 6198 | O | GLY | 332 | 103.940 | 68.628 | 10.670 | 1.00 | 41.35 | B O |
| ATOM | 6199 | N | GLU | 333 | 102.398 | 68.892 | 9.058 | 1.00 | 41.72 | B N |
| ATOM | 6200 | CA | GLU | 333 | 102.653 | 70.317 | 8.967 | 1.00 | 39.78 | B C |
| ATOM | 6201 | CB | GLU | 333 | 102.052 | 70.889 | 7.683 | 1.00 | 98.89 | B C |
| ATOM | 6202 | CG | GLU | 333 | 100.546 | 70.988 | 7.678 | 1.00 | 97.26 | B C |
| ATOM | 6203 | CD | GLU | 333 | 100.018 | 71.598 | 6.400 | 1.00 | 97.28 | B C |
| ATOM | 6204 | OE1 | GLU | 333 | 98.795 | 71.849 | 6.322 | 1.00 | 99.33 | B O |
| ATOM | 6205 | OE2 | GLU | 333 | 100.824 | 71.823 | 5.472 | 1.00 | 91.40 | B O |

Fig. 19: A-86

| | | | | | | | | | | |
|---|---|---|---|---|---|---|---|---|---|---|
| ATOM | 6206 | C | GLU | 333 | 102.120 | 71.069 | 10.179 | 1.00 | 38.76 | B C |
| ATOM | 6207 | O | GLU | 333 | 102.747 | 72.010 | 10.650 | 1.00 | 38.38 | B O |
| ATOM | 6208 | N | ARG | 334 | 100.969 | 70.659 | 10.695 | 1.00 | 43.09 | B N |
| ATOM | 6209 | CA | ARG | 334 | 100.398 | 71.340 | 11.847 | 1.00 | 46.47 | B C |
| ATOM | 6210 | CB | ARG | 334 | 99.089 | 70.667 | 12.265 | 1.00 | 41.05 | B C |
| ATOM | 6211 | CG | ARG | 334 | 98.167 | 71.568 | 13.056 | 1.00 | 40.34 | B C |
| ATOM | 6212 | CD | ARG | 334 | 96.722 | 71.432 | 12.592 | 1.00 | 39.10 | B C |
| ATOM | 6213 | NE | ARG | 334 | 96.544 | 71.911 | 11.222 | 1.00 | 34.65 | B N |
| ATOM | 6214 | CZ | ARG | 334 | 95.446 | 71.721 | 10.488 | 1.00 | 38.74 | B C |
| ATOM | 6215 | NH1 | ARG | 334 | 94.407 | 71.052 | 10.987 | 1.00 | 35.48 | B N |
| ATOM | 6216 | NH2 | ARG | 334 | 95.388 | 72.197 | 9.246 | 1.00 | 44.88 | B N |
| ATOM | 6217 | C | ARG | 334 | 101.419 | 71.321 | 12.980 | 1.00 | 47.77 | B C |
| ATOM | 6218 | O | ARG | 334 | 101.633 | 72.329 | 13.643 | 1.00 | 44.69 | B O |
| ATOM | 6219 | N | ILE | 335 | 102.060 | 70.177 | 13.192 | 1.00 | 95.68 | B N |
| ATOM | 6220 | CA | ILE | 335 | 103.084 | 70.066 | 14.227 | 1.00 | 95.61 | B C |
| ATOM | 6221 | CB | ILE | 335 | 103.349 | 68.565 | 14.599 | 1.00 | 69.44 | B C |
| ATOM | 6222 | CG2 | ILE | 335 | 103.371 | 67.701 | 13.359 | 1.00 | 72.22 | B C |
| ATOM | 6223 | CG1 | ILE | 335 | 104.671 | 68.420 | 15.350 | 1.00 | 70.66 | B C |
| ATOM | 6224 | CD1 | ILE | 335 | 105.043 | 66.983 | 15.628 | 1.00 | 73.45 | B C |
| ATOM | 6225 | C | ILE | 335 | 104.346 | 70.716 | 13.653 | 1.00 | 93.90 | B C |
| ATOM | 6226 | O | ILE | 335 | 105.317 | 70.979 | 14.364 | 1.00 | 96.50 | B O |
| ATOM | 6227 | N | PHE | 336 | 104.273 | 71.011 | 12.356 | 1.00 | 144.26 | B N |
| ATOM | 6228 | CA | PHE | 336 | 105.347 | 71.604 | 11.560 | 1.00 | 143.89 | B C |
| ATOM | 6229 | CB | PHE | 336 | 105.336 | 73.156 | 11.625 | 1.00 | 83.50 | B C |
| ATOM | 6230 | CG | PHE | 336 | 105.600 | 73.748 | 12.992 | 1.00 | 79.82 | B C |
| ATOM | 6231 | CD1 | PHE | 336 | 106.696 | 73.355 | 13.760 | 1.00 | 79.24 | B C |
| ATOM | 6232 | CD2 | PHE | 336 | 104.783 | 74.762 | 13.479 | 1.00 | 77.77 | B C |
| ATOM | 6233 | CE1 | PHE | 336 | 106.973 | 73.966 | 14.988 | 1.00 | 69.57 | B C |
| ATOM | 6234 | CE2 | PHE | 336 | 105.053 | 75.377 | 14.702 | 1.00 | 72.13 | B C |
| ATOM | 6235 | CZ | PHE | 336 | 106.152 | 74.977 | 15.457 | 1.00 | 72.59 | B C |
| ATOM | 6236 | C | PHE | 336 | 106.737 | 71.068 | 11.853 | 1.00 | 143.92 | B C |
| ATOM | 6237 | O | PHE | 336 | 106.889 | 70.255 | 12.788 | 1.00 | 123.54 | B O |
| ATOM | 6238 | OXT | PHE | 336 | 107.658 | 71.461 | 11.111 | 1.00 | 66.99 | B O |
| ATOM | 6239 | CB | GLU | 1 | 68.990 | 38.972 | 10.337 | 1.00 | 143.47 | X C |
| ATOM | 6240 | CG | GLU | 1 | 68.785 | 37.653 | 11.053 | 1.00 | 143.47 | X C |
| ATOM | 6241 | CD | GLU | 1 | 68.300 | 36.572 | 10.118 | 1.00 | 143.47 | X C |
| ATOM | 6242 | OE1 | GLU | 1 | 69.012 | 36.278 | 9.134 | 1.00 | 143.47 | X O |
| ATOM | 6243 | OE2 | GLU | 1 | 67.209 | 36.019 | 10.363 | 1.00 | 143.47 | X O |
| ATOM | 6244 | C | GLU | 1 | 71.024 | 39.462 | 11.710 | 1.00 | 74.19 | X C |
| ATOM | 6245 | O | GLU | 1 | 71.492 | 38.415 | 11.265 | 1.00 | 74.19 | X O |
| ATOM | 6246 | N | GLU | 1 | 69.921 | 41.257 | 10.328 | 1.00 | 74.19 | X N |
| ATOM | 6247 | CA | GLU | 1 | 69.711 | 40.037 | 11.162 | 1.00 | 74.19 | X C |
| ATOM | 6248 | N | VAL | 2 | 71.613 | 40.151 | 12.681 | 1.00 | 55.61 | X N |
| ATOM | 6249 | CA | VAL | 2 | 72.858 | 39.694 | 13.284 | 1.00 | 55.61 | X C |
| ATOM | 6250 | CB | VAL | 2 | 73.533 | 40.812 | 14.089 | 1.00 | 66.95 | X C |
| ATOM | 6251 | CG1 | VAL | 2 | 74.850 | 40.323 | 14.647 | 1.00 | 66.95 | X C |
| ATOM | 6252 | CG2 | VAL | 2 | 73.752 | 42.021 | 13.210 | 1.00 | 66.95 | X C |
| ATOM | 6253 | C | VAL | 2 | 72.566 | 38.543 | 14.232 | 1.00 | 55.61 | X C |
| ATOM | 6254 | O | VAL | 2 | 71.728 | 38.673 | 15.127 | 1.00 | 55.61 | X O |
| ATOM | 6255 | N | GLN | 3 | 73.258 | 37.421 | 14.045 | 1.00 | 39.72 | X N |
| ATOM | 6256 | CA | GLN | 3 | 73.044 | 36.261 | 14.908 | 1.00 | 39.72 | X C |
| ATOM | 6257 | CB | GLN | 3 | 71.807 | 35.502 | 14.455 | 1.00 | 102.66 | X C |
| ATOM | 6258 | CG | GLN | 3 | 71.852 | 35.144 | 13.002 | 1.00 | 102.66 | X C |
| ATOM | 6259 | CD | GLN | 3 | 70.688 | 34.291 | 12.604 | 1.00 | 102.66 | X C |
| ATOM | 6260 | OE1 | GLN | 3 | 69.537 | 34.635 | 12.873 | 1.00 | 102.66 | X O |
| ATOM | 6261 | NE2 | GLN | 3 | 70.972 | 33.168 | 11.955 | 1.00 | 102.66 | X N |
| ATOM | 6262 | C | GLN | 3 | 74.213 | 35.288 | 15.002 | 1.00 | 39.72 | X C |
| ATOM | 6263 | O | GLN | 3 | 75.064 | 35.207 | 14.108 | 1.00 | 39.72 | X O |
| ATOM | 6264 | N | LEU | 4 | 74.231 | 34.553 | 16.109 | 1.00 | 34.59 | X N |
| ATOM | 6265 | CA | LEU | 4 | 75.260 | 33.555 | 16.389 | 1.00 | 34.59 | X C |
| ATOM | 6266 | CB | LEU | 4 | 76.043 | 33.931 | 17.653 | 1.00 | 34.08 | X C |
| ATOM | 6267 | CG | LEU | 4 | 77.107 | 35.040 | 17.665 | 1.00 | 34.08 | X C |
| ATOM | 6268 | CD1 | LEU | 4 | 77.119 | 35.820 | 16.353 | 1.00 | 34.08 | X C |
| ATOM | 6269 | CD2 | LEU | 4 | 76.844 | 35.950 | 18.863 | 1.00 | 34.08 | X C |
| ATOM | 6270 | C | LEU | 4 | 74.581 | 32.212 | 16.615 | 1.00 | 34.59 | X C |
| ATOM | 6271 | O | LEU | 4 | 73.737 | 32.080 | 17.503 | 1.00 | 34.59 | X O |
| ATOM | 6272 | N | VAL | 5 | 74.933 | 31.218 | 15.806 | 1.00 | 36.99 | X N |
| ATOM | 6273 | CA | VAL | 5 | 74.350 | 29.889 | 15.961 | 1.00 | 36.99 | X C |
| ATOM | 6274 | CB | VAL | 5 | 73.536 | 29.456 | 14.698 | 1.00 | 37.13 | X C |
| ATOM | 6275 | CG1 | VAL | 5 | 74.285 | 29.815 | 13.430 | 1.00 | 37.13 | X C |
| ATOM | 6276 | CG2 | VAL | 5 | 73.264 | 27.963 | 14.744 | 1.00 | 37.13 | X C |
| ATOM | 6277 | C | VAL | 5 | 75.429 | 28.861 | 16.277 | 1.00 | 36.99 | X C |
| ATOM | 6278 | O | VAL | 5 | 76.163 | 28.404 | 15.398 | 1.00 | 36.99 | X O |

Fig. 19: A-87

```
ATOM   6279  N    GLU   6      75.519  28.517  17.555  1.00  44.32      X   N
ATOM   6280  CA   GLU   6      76.499  27.550  18.020  1.00  44.32      X   C
ATOM   6281  CB   GLU   6      76.924  27.884  19.457  1.00  53.96      X   C
ATOM   6282  CG   GLU   6      75.844  28.531  20.292  1.00  53.96      X   C
ATOM   6283  CD   GLU   6      76.340  28.943  21.659  1.00  53.96      X   C
ATOM   6284  OE1  GLU   6      75.590  29.646  22.368  1.00  53.96      X   O
ATOM   6285  OE2  GLU   6      77.472  28.561  22.028  1.00  53.96      X   O
ATOM   6286  C    GLU   6      76.029  26.095  17.930  1.00  44.32      X   C
ATOM   6287  O    GLU   6      74.856  25.813  17.668  1.00  44.32      X   O
ATOM   6288  N    SER   7      76.980  25.185  18.135  1.00  42.31      X   N
ATOM   6289  CA   SER   7      76.758  23.745  18.091  1.00  42.31      X   C
ATOM   6290  CB   SER   7      76.762  23.261  16.642  1.00  44.31      X   C
ATOM   6291  OG   SER   7      77.832  23.845  15.922  1.00  44.31      X   O
ATOM   6292  C    SER   7      77.919  23.123  18.848  1.00  42.31      X   C
ATOM   6293  O    SER   7      78.889  23.813  19.138  1.00  42.31      X   O
ATOM   6294  N    GLY   8      77.822  21.838  19.178  1.00  39.85      X   N
ATOM   6295  CA   GLY   8      78.908  21.177  19.893  1.00  39.85      X   C
ATOM   6296  C    GLY   8      78.569  20.747  21.313  1.00  39.85      X   C
ATOM   6297  O    GLY   8      79.330  20.016  21.962  1.00  39.85      X   O
ATOM   6298  N    GLY   9      77.417  21.199  21.795  1.00  54.13      X   N
ATOM   6299  CA   GLY   9      76.998  20.852  23.138  1.00  54.13      X   C
ATOM   6300  C    GLY   9      76.467  19.439  23.283  1.00  54.13      X   C
ATOM   6301  O    GLY   9      75.390  19.102  22.783  1.00  54.13      X   O
ATOM   6302  N    GLY  10      77.235  18.606  23.972  1.00  51.55      X   N
ATOM   6303  CA   GLY  10      76.825  17.236  24.195  1.00  51.55      X   C
ATOM   6304  C    GLY  10      77.359  16.807  25.544  1.00  51.55      X   C
ATOM   6305  O    GLY  10      77.723  17.651  26.370  1.00  51.55      X   O
ATOM   6306  N    LEU  11      77.409  15.500  25.776  1.00  54.73      X   N
ATOM   6307  CA   LEU  11      77.930  14.981  27.032  1.00  54.73      X   C
ATOM   6308  CB   LEU  11      76.994  13.903  27.583  1.00  40.69      X   C
ATOM   6309  CG   LEU  11      77.583  13.086  28.735  1.00  40.69      X   C
ATOM   6310  CD1  LEU  11      78.170  14.011  29.795  1.00  40.69      X   C
ATOM   6311  CD2  LEU  11      76.508  12.198  29.317  1.00  40.69      X   C
ATOM   6312  C    LEU  11      79.341  14.412  26.852  1.00  54.73      X   C
ATOM   6313  O    LEU  11      79.654  13.853  25.806  1.00  54.73      X   O
ATOM   6314  N    VAL  12      80.177  14.576  27.872  1.00  43.40      X   N
ATOM   6315  CA   VAL  12      81.552  14.079  27.848  1.00  43.40      X   C
ATOM   6316  CB   VAL  12      82.538  15.118  27.273  1.00  57.73      X   C
ATOM   6317  CG1  VAL  12      82.222  15.388  25.812  1.00  57.73      X   C
ATOM   6318  CG2  VAL  12      82.473  16.404  28.086  1.00  57.73      X   C
ATOM   6319  C    VAL  12      81.991  13.753  29.269  1.00  43.40      X   C
ATOM   6320  O    VAL  12      81.490  14.344  30.230  1.00  43.40      X   O
ATOM   6321  N    GLN  13      82.931  12.821  29.403  1.00  46.11      X   N
ATOM   6322  CA   GLN  13      83.404  12.420  30.720  1.00  46.11      X   C
ATOM   6323  CB   GLN  13      83.873  10.965  30.676  1.00 148.60      X   C
ATOM   6324  CG   GLN  13      82.843  10.015  30.094  1.00 148.60      X   C
ATOM   6325  CD   GLN  13      83.232   8.560  30.263  1.00 148.60      X   C
ATOM   6326  OE1  GLN  13      84.322   8.145  29.868  1.00 148.60      X   O
ATOM   6327  NE2  GLN  13      82.337   7.774  30.852  1.00 148.60      X   N
ATOM   6328  C    GLN  13      84.532  13.311  31.234  1.00  46.11      X   C
ATOM   6329  O    GLN  13      85.186  14.002  30.454  1.00  46.11      X   O
ATOM   6330  N    PRO  14      84.763  13.319  32.563  1.00  39.23      X   N
ATOM   6331  CD   PRO  14      83.989  12.657  33.630  1.00  55.62      X   C
ATOM   6332  CA   PRO  14      85.831  14.141  33.141  1.00  39.23      X   C
ATOM   6333  CB   PRO  14      85.902  13.648  34.581  1.00  55.62      X   C
ATOM   6334  CG   PRO  14      84.474  13.374  34.887  1.00  55.62      X   C
ATOM   6335  C    PRO  14      87.122  13.905  32.392  1.00  39.23      X   C
ATOM   6336  O    PRO  14      87.357  12.810  31.885  1.00  39.23      X   O
ATOM   6337  N    GLY  15      87.954  14.935  32.320  1.00  28.04      X   N
ATOM   6338  CA   GLY  15      89.220  14.816  31.616  1.00  28.04      X   C
ATOM   6339  C    GLY  15      89.037  14.807  30.109  1.00  28.04      X   C
ATOM   6340  O    GLY  15      89.990  14.979  29.352  1.00  28.04      X   O
ATOM   6341  N    GLY  16      87.801  14.613  29.672  1.00  22.75      X   N
ATOM   6342  CA   GLY  16      87.529  14.583  28.250  1.00  22.75      X   C
ATOM   6343  C    GLY  16      87.705  15.912  27.539  1.00  22.75      X   C
ATOM   6344  O    GLY  16      87.887  16.969  28.155  1.00  22.75      X   O
ATOM   6345  N    SER  17      87.633  15.845  26.217  1.00  36.95      X   N
ATOM   6346  CA   SER  17      87.789  17.014  25.371  1.00  36.95      X   C
ATOM   6347  CB   SER  17      88.962  16.795  24.417  1.00  47.78      X   C
ATOM   6348  OG   SER  17      89.203  17.952  23.645  1.00  47.78      X   O
ATOM   6349  C    SER  17      86.509  17.311  24.581  1.00  36.95      X   C
ATOM   6350  O    SER  17      85.817  16.402  24.106  1.00  36.95      X   O
ATOM   6351  N    LEU  18      86.199  18.593  24.429  1.00  50.75      X   N
```

Fig. 19: A-88

| | | | | | | | | | | |
|---|---|---|---|---|---|---|---|---|---|---|
| ATOM | 6352 | CA | LEU | 18 | 84.995 | 18.978 | 23.719 | 1.00 | 50.75 | X | C |
| ATOM | 6353 | CB | LEU | 18 | 83.833 | 18.944 | 24.701 | 1.00 | 37.38 | X | C |
| ATOM | 6354 | CG | LEU | 18 | 82.463 | 19.285 | 24.146 | 1.00 | 37.38 | X | C |
| ATOM | 6355 | CD1 | LEU | 18 | 82.177 | 18.476 | 22.874 | 1.00 | 37.38 | X | C |
| ATOM | 6356 | CD2 | LEU | 18 | 81.442 | 19.012 | 25.239 | 1.00 | 37.38 | X | C |
| ATOM | 6357 | C | LEU | 18 | 85.107 | 20.355 | 23.069 | 1.00 | 50.75 | X | C |
| ATOM | 6358 | O | LEU | 18 | 85.530 | 21.313 | 23.714 | 1.00 | 50.75 | X | O |
| ATOM | 6359 | N | ARG | 19 | 84.737 | 20.454 | 21.792 | 1.00 | 27.07 | X | N |
| ATOM | 6360 | CA | ARG | 19 | 84.805 | 21.739 | 21.097 | 1.00 | 27.07 | X | C |
| ATOM | 6361 | CB | ARG | 19 | 85.774 | 21.708 | 19.924 | 1.00 | 43.18 | X | C |
| ATOM | 6362 | CG | ARG | 19 | 85.825 | 23.068 | 19.238 | 1.00 | 43.18 | X | C |
| ATOM | 6363 | CD | ARG | 19 | 86.689 | 23.075 | 18.015 | 1.00 | 43.18 | X | C |
| ATOM | 6364 | NE | ARG | 19 | 86.060 | 22.389 | 16.896 | 1.00 | 43.18 | X | N |
| ATOM | 6365 | CZ | ARG | 19 | 86.564 | 22.371 | 15.666 | 1.00 | 43.18 | X | C |
| ATOM | 6366 | NH1 | ARG | 19 | 87.708 | 23.006 | 15.407 | 1.00 | 43.18 | X | N |
| ATOM | 6367 | NH2 | ARG | 19 | 85.924 | 21.725 | 14.696 | 1.00 | 43.18 | X | N |
| ATOM | 6368 | C | ARG | 19 | 83.501 | 22.302 | 20.558 | 1.00 | 27.07 | X | C |
| ATOM | 6369 | O | ARG | 19 | 82.895 | 21.745 | 19.625 | 1.00 | 27.07 | X | O |
| ATOM | 6370 | N | LEU | 20 | 83.109 | 23.438 | 21.135 | 1.00 | 30.57 | X | N |
| ATOM | 6371 | CA | LEU | 20 | 81.908 | 24.150 | 20.731 | 1.00 | 30.57 | X | C |
| ATOM | 6372 | CB | LEU | 20 | 81.354 | 24.965 | 21.896 | 1.00 | 36.53 | X | C |
| ATOM | 6373 | CG | LEU | 20 | 80.981 | 24.196 | 23.159 | 1.00 | 36.53 | X | C |
| ATOM | 6374 | CD1 | LEU | 20 | 80.415 | 25.142 | 24.218 | 1.00 | 36.53 | X | C |
| ATOM | 6375 | CD2 | LEU | 20 | 79.964 | 23.135 | 22.802 | 1.00 | 36.53 | X | C |
| ATOM | 6376 | C | LEU | 20 | 82.304 | 25.098 | 19.618 | 1.00 | 30.57 | X | C |
| ATOM | 6377 | O | LEU | 20 | 83.313 | 25.784 | 19.723 | 1.00 | 30.57 | X | O |
| ATOM | 6378 | N | SER | 21 | 81.527 | 25.122 | 18.544 | 1.00 | 31.77 | X | N |
| ATOM | 6379 | CA | SER | 21 | 81.789 | 26.024 | 17.426 | 1.00 | 31.77 | X | C |
| ATOM | 6380 | CB | SER | 21 | 81.876 | 25.252 | 16.117 | 1.00 | 32.65 | X | C |
| ATOM | 6381 | OG | SER | 21 | 80.580 | 24.896 | 15.682 | 1.00 | 32.65 | X | O |
| ATOM | 6382 | C | SER | 21 | 80.593 | 26.971 | 17.383 | 1.00 | 31.77 | X | C |
| ATOM | 6383 | O | SER | 21 | 79.591 | 26.738 | 18.057 | 1.00 | 31.77 | X | O |
| ATOM | 6384 | N | CYS | 22 | 80.673 | 28.024 | 16.585 | 1.00 | 49.03 | X | N |
| ATOM | 6385 | CA | CYS | 22 | 79.580 | 28.981 | 16.526 | 1.00 | 49.03 | X | C |
| ATOM | 6386 | C | CYS | 22 | 79.725 | 29.812 | 15.272 | 1.00 | 49.03 | X | C |
| ATOM | 6387 | O | CYS | 22 | 80.743 | 30.484 | 15.096 | 1.00 | 49.03 | X | O |
| ATOM | 6388 | CB | CYS | 22 | 79.643 | 29.849 | 17.788 | 1.00 | 49.62 | X | C |
| ATOM | 6389 | SG | CYS | 22 | 78.993 | 31.555 | 17.774 | 1.00 | 49.62 | X | S |
| ATOM | 6390 | N | ALA | 23 | 78.724 | 29.744 | 14.389 | 1.00 | 43.82 | X | N |
| ATOM | 6391 | CA | ALA | 23 | 78.742 | 30.509 | 13.136 | 1.00 | 43.82 | X | C |
| ATOM | 6392 | CB | ALA | 23 | 78.022 | 29.768 | 12.021 | 1.00 | 1.87 | X | C |
| ATOM | 6393 | C | ALA | 23 | 78.093 | 31.854 | 13.329 | 1.00 | 43.82 | X | C |
| ATOM | 6394 | O | ALA | 23 | 77.118 | 31.999 | 14.070 | 1.00 | 43.82 | X | O |
| ATOM | 6395 | N | ALA | 24 | 78.644 | 32.843 | 12.645 | 1.00 | 28.70 | X | N |
| ATOM | 6396 | CA | ALA | 24 | 78.129 | 34.190 | 12.735 | 1.00 | 28.70 | X | C |
| ATOM | 6397 | CB | ALA | 24 | 79.199 | 35.129 | 13.323 | 1.00 | 18.49 | X | C |
| ATOM | 6398 | C | ALA | 24 | 77.725 | 34.659 | 11.356 | 1.00 | 28.70 | X | C |
| ATOM | 6399 | O | ALA | 24 | 78.213 | 34.160 | 10.345 | 1.00 | 28.70 | X | O |
| ATOM | 6400 | N | SER | 25 | 76.816 | 35.620 | 11.338 | 1.00 | 39.45 | X | N |
| ATOM | 6401 | CA | SER | 25 | 76.338 | 36.218 | 10.108 | 1.00 | 39.45 | X | C |
| ATOM | 6402 | CB | SER | 25 | 75.279 | 35.322 | 9.443 | 1.00 | 48.28 | X | C |
| ATOM | 6403 | OG | SER | 25 | 74.163 | 35.090 | 10.287 | 1.00 | 48.28 | X | O |
| ATOM | 6404 | C | SER | 25 | 75.751 | 37.575 | 10.486 | 1.00 | 39.45 | X | C |
| ATOM | 6405 | O | SER | 25 | 75.425 | 37.819 | 11.656 | 1.00 | 39.45 | X | O |
| ATOM | 6406 | N | GLY | 26 | 75.651 | 38.464 | 9.506 | 1.00 | 15.13 | X | N |
| ATOM | 6407 | CA | GLY | 26 | 75.093 | 39.773 | 9.767 | 1.00 | 15.13 | X | C |
| ATOM | 6408 | C | GLY | 26 | 76.061 | 40.808 | 10.313 | 1.00 | 15.13 | X | C |
| ATOM | 6409 | O | GLY | 26 | 75.650 | 41.692 | 11.070 | 1.00 | 15.13 | X | O |
| ATOM | 6410 | N | PHE | 27 | 77.336 | 40.697 | 9.941 | 1.00 | 51.25 | X | N |
| ATOM | 6411 | CA | PHE | 27 | 78.375 | 41.638 | 10.358 | 1.00 | 51.25 | X | C |
| ATOM | 6412 | CB | PHE | 27 | 78.322 | 41.921 | 11.860 | 1.00 | 33.43 | X | C |
| ATOM | 6413 | CG | PHE | 27 | 78.647 | 40.736 | 12.720 | 1.00 | 33.43 | X | C |
| ATOM | 6414 | CD1 | PHE | 27 | 77.696 | 39.749 | 12.958 | 1.00 | 33.43 | X | C |
| ATOM | 6415 | CD2 | PHE | 27 | 79.891 | 40.629 | 13.337 | 1.00 | 33.43 | X | C |
| ATOM | 6416 | CE1 | PHE | 27 | 77.978 | 38.673 | 13.810 | 1.00 | 33.43 | X | C |
| ATOM | 6417 | CE2 | PHE | 27 | 80.186 | 39.558 | 14.190 | 1.00 | 33.43 | X | C |
| ATOM | 6418 | CZ | PHE | 27 | 79.227 | 38.581 | 14.428 | 1.00 | 33.43 | X | C |
| ATOM | 6419 | C | PHE | 27 | 79.748 | 41.100 | 10.012 | 1.00 | 51.25 | X | C |
| ATOM | 6420 | O | PHE | 27 | 79.966 | 39.894 | 10.027 | 1.00 | 51.25 | X | O |
| ATOM | 6421 | N | THR | 28 | 80.671 | 42.006 | 9.707 | 1.00 | 31.93 | X | N |
| ATOM | 6422 | CA | THR | 28 | 82.031 | 41.637 | 9.348 | 1.00 | 31.93 | X | C |
| ATOM | 6423 | CB | THR | 28 | 82.821 | 42.872 | 8.910 | 1.00 | 48.89 | X | C |
| ATOM | 6424 | OG1 | THR | 28 | 82.126 | 43.520 | 7.836 | 1.00 | 48.89 | X | O |

Fig. 19: A-89

```
ATOM   6425  CG2 THR  28      84.212  42.474   8.454  1.00  48.89      X    C
ATOM   6426  C   THR  28      82.744  40.981  10.519  1.00  31.93      X    C
ATOM   6427  O   THR  28      83.431  41.640  11.286  1.00  31.93      X    O
ATOM   6428  N   PHE  29      82.576  39.671  10.636  1.00  37.68      X    N
ATOM   6429  CA  PHE  29      83.166  38.876  11.712  1.00  37.68      X    C
ATOM   6430  CB  PHE  29      83.068  37.386  11.352  1.00  38.41      X    C
ATOM   6431  CG  PHE  29      83.484  36.454  12.462  1.00  38.41      X    C
ATOM   6432  CD1 PHE  29      82.795  36.440  13.676  1.00  38.41      X    C
ATOM   6433  CD2 PHE  29      84.570  35.587  12.296  1.00  38.41      X    C
ATOM   6434  CE1 PHE  29      83.183  35.577  14.709  1.00  38.41      X    C
ATOM   6435  CE2 PHE  29      84.967  34.718  13.324  1.00  38.41      X    C
ATOM   6436  CZ  PHE  29      84.272  34.715  14.530  1.00  38.41      X    C
ATOM   6437  C   PHE  29      84.616  39.225  12.021  1.00  37.68      X    C
ATOM   6438  O   PHE  29      84.958  39.552  13.160  1.00  37.68      X    O
ATOM   6439  N   SER  30      85.462  39.160  10.998  1.00  22.05      X    N
ATOM   6440  CA  SER  30      86.890  39.421  11.157  1.00  22.05      X    C
ATOM   6441  CB  SER  30      87.553  39.545   9.783  1.00  37.79      X    C
ATOM   6442  OG  SER  30      86.886  40.481   8.959  1.00  37.79      X    O
ATOM   6443  C   SER  30      87.270  40.622  12.014  1.00  22.05      X    C
ATOM   6444  O   SER  30      88.326  40.634  12.639  1.00  22.05      X    O
ATOM   6445  N   ARG  31      86.395  41.615  12.063  1.00  29.69      X    N
ATOM   6446  CA  ARG  31      86.651  42.846  12.801  1.00  29.69      X    C
ATOM   6447  CB  ARG  31      85.819  43.956  12.162  1.00  51.15      X    C
ATOM   6448  CG  ARG  31      86.068  45.323  12.719  1.00  51.15      X    C
ATOM   6449  CD  ARG  31      84.999  46.281  12.231  1.00  51.15      X    C
ATOM   6450  NE  ARG  31      84.964  46.383  10.772  1.00  51.15      X    N
ATOM   6451  CZ  ARG  31      85.899  46.974  10.038  1.00  51.15      X    C
ATOM   6452  NH1 ARG  31      86.959  47.523  10.621  1.00  51.15      X    N
ATOM   6453  NH2 ARG  31      85.764  47.027   8.722  1.00  51.15      X    N
ATOM   6454  C   ARG  31      86.425  42.833  14.329  1.00  29.69      X    C
ATOM   6455  O   ARG  31      87.226  43.399  15.080  1.00  29.69      X    O
ATOM   6456  N   TYR  32      85.352  42.185  14.785  1.00  39.46      X    N
ATOM   6457  CA  TYR  32      85.009  42.144  16.217  1.00  39.46      X    C
ATOM   6458  CB  TYR  32      83.506  41.880  16.409  1.00  51.56      X    C
ATOM   6459  CG  TYR  32      82.601  42.689  15.516  1.00  51.56      X    C
ATOM   6460  CD1 TYR  32      82.540  42.437  14.148  1.00  51.56      X    C
ATOM   6461  CE1 TYR  32      81.721  43.181  13.316  1.00  51.56      X    C
ATOM   6462  CD2 TYR  32      81.811  43.714  16.034  1.00  51.56      X    C
ATOM   6463  CE2 TYR  32      80.985  44.467  15.209  1.00  51.56      X    C
ATOM   6464  CZ  TYR  32      80.946  44.193  13.851  1.00  51.56      X    C
ATOM   6465  OH  TYR  32      80.135  44.929  13.015  1.00  51.56      X    O
ATOM   6466  C   TYR  32      85.761  41.108  17.037  1.00  39.46      X    C
ATOM   6467  O   TYR  32      86.159  40.072  16.515  1.00  39.46      X    O
ATOM   6468  N   THR  33      85.943  41.386  18.328  1.00  29.44      X    N
ATOM   6469  CA  THR  33      86.611  40.421  19.191  1.00  29.44      X    C
ATOM   6470  CB  THR  33      87.510  41.080  20.315  1.00  20.65      X    C
ATOM   6471  OG1 THR  33      86.749  41.242  21.514  1.00  20.65      X    O
ATOM   6472  CG2 THR  33      88.072  42.437  19.866  1.00  20.65      X    C
ATOM   6473  C   THR  33      85.483  39.614  19.835  1.00  29.44      X    C
ATOM   6474  O   THR  33      84.632  40.167  20.536  1.00  29.44      X    O
ATOM   6475  N   MET  34      85.484  38.307  19.568  1.00  30.35      X    N
ATOM   6476  CA  MET  34      84.474  37.391  20.084  1.00  30.35      X    C
ATOM   6477  CB  MET  34      84.235  36.284  19.067  1.00  43.39      X    C
ATOM   6478  CG  MET  34      84.070  36.798  17.652  1.00  43.39      X    C
ATOM   6479  SD  MET  34      82.775  38.029  17.525  1.00  43.39      X    S
ATOM   6480  CE  MET  34      81.376  37.024  17.198  1.00  43.39      X    C
ATOM   6481  C   MET  34      84.867  36.785  21.430  1.00  30.35      X    C
ATOM   6482  O   MET  34      86.049  36.761  21.790  1.00  30.35      X    O
ATOM   6483  N   SER  35      83.866  36.293  22.164  1.00  35.95      X    N
ATOM   6484  CA  SER  35      84.073  35.701  23.487  1.00  35.95      X    C
ATOM   6485  CB  SER  35      83.875  36.765  24.580  1.00  34.42      X    C
ATOM   6486  OG  SER  35      84.740  37.878  24.420  1.00  34.42      X    O
ATOM   6487  C   SER  35      83.105  34.548  23.761  1.00  35.95      X    C
ATOM   6488  O   SER  35      82.191  34.290  22.978  1.00  35.95      X    O
ATOM   6489  N   TRP  36      83.323  33.856  24.879  1.00  43.17      X    N
ATOM   6490  CA  TRP  36      82.457  32.758  25.309  1.00  43.17      X    C
ATOM   6491  CB  TRP  36      83.159  31.383  25.200  1.00  32.84      X    C
ATOM   6492  CG  TRP  36      83.355  30.875  23.782  1.00  32.84      X    C
ATOM   6493  CD2 TRP  36      82.419  30.118  22.998  1.00  32.84      X    C
ATOM   6494  CE2 TRP  36      82.982  29.957  21.711  1.00  32.84      X    C
ATOM   6495  CE3 TRP  36      81.153  29.564  23.257  1.00  32.84      X    C
ATOM   6496  CD1 TRP  36      84.419  31.124  22.962  1.00  32.84      X    C
ATOM   6497  NE1 TRP  36      84.201  30.579  21.716  1.00  32.84      X    N
```

Fig. 19: A-90

| | | | | | | | | | | |
|---|---|---|---|---|---|---|---|---|---|---|
| ATOM | 6498 | CZ2 | TRP | 36 | 82.324 | 29.267 | 20.681 | 1.00 | 32.84 | X C |
| ATOM | 6499 | CZ3 | TRP | 36 | 80.495 | 28.877 | 22.228 | 1.00 | 32.84 | X C |
| ATOM | 6500 | CH2 | TRP | 36 | 81.086 | 28.738 | 20.957 | 1.00 | 32.84 | X C |
| ATOM | 6501 | C | TRP | 36 | 82.056 | 33.022 | 26.764 | 1.00 | 43.17 | X C |
| ATOM | 6502 | O | TRP | 36 | 82.908 | 33.298 | 27.615 | 1.00 | 43.17 | X O |
| ATOM | 6503 | N | VAL | 37 | 80.751 | 32.958 | 27.026 | 1.00 | 29.19 | X N |
| ATOM | 6504 | CA | VAL | 37 | 80.177 | 33.175 | 28.360 | 1.00 | 29.19 | X C |
| ATOM | 6505 | CB | VAL | 37 | 79.213 | 34.419 | 28.353 | 1.00 | 8.00 | X C |
| ATOM | 6506 | CG1 | VAL | 37 | 78.350 | 34.467 | 29.621 | 1.00 | 8.00 | X C |
| ATOM | 6507 | CG2 | VAL | 37 | 80.026 | 35.689 | 28.240 | 1.00 | 8.00 | X C |
| ATOM | 6508 | C | VAL | 37 | 79.412 | 31.907 | 28.760 | 1.00 | 29.19 | X C |
| ATOM | 6509 | O | VAL | 37 | 78.629 | 31.381 | 27.971 | 1.00 | 29.19 | X O |
| ATOM | 6510 | N | ARG | 38 | 79.651 | 31.415 | 29.974 | 1.00 | 61.80 | X N |
| ATOM | 6511 | CA | ARG | 38 | 78.992 | 30.198 | 30.454 | 1.00 | 61.80 | X C |
| ATOM | 6512 | CB | ARG | 38 | 80.036 | 29.167 | 30.899 | 1.00 | 27.50 | X C |
| ATOM | 6513 | CG | ARG | 38 | 80.926 | 29.688 | 32.011 | 1.00 | 27.50 | X C |
| ATOM | 6514 | CD | ARG | 38 | 81.370 | 28.603 | 32.965 | 1.00 | 27.50 | X C |
| ATOM | 6515 | NE | ARG | 38 | 82.222 | 27.579 | 32.364 | 1.00 | 27.50 | X N |
| ATOM | 6516 | CZ | ARG | 38 | 83.391 | 27.181 | 32.874 | 1.00 | 27.50 | X C |
| ATOM | 6517 | NH1 | ARG | 38 | 83.862 | 27.725 | 33.992 | 1.00 | 27.50 | X N |
| ATOM | 6518 | NH2 | ARG | 38 | 84.087 | 26.217 | 32.281 | 1.00 | 27.50 | X N |
| ATOM | 6519 | C | ARG | 38 | 78.053 | 30.468 | 31.628 | 1.00 | 61.80 | X C |
| ATOM | 6520 | O | ARG | 38 | 78.104 | 31.528 | 32.245 | 1.00 | 61.80 | X O |
| ATOM | 6521 | N | GLN | 39 | 77.204 | 29.491 | 31.934 | 1.00 | 39.46 | X N |
| ATOM | 6522 | CA | GLN | 39 | 76.269 | 29.597 | 33.049 | 1.00 | 39.46 | X C |
| ATOM | 6523 | CB | GLN | 39 | 74.982 | 30.269 | 32.588 | 1.00 | 44.48 | X C |
| ATOM | 6524 | CG | GLN | 39 | 73.997 | 30.530 | 33.708 | 1.00 | 44.48 | X C |
| ATOM | 6525 | CD | GLN | 39 | 72.916 | 31.497 | 33.294 | 1.00 | 44.48 | X C |
| ATOM | 6526 | OE1 | GLN | 39 | 72.269 | 31.320 | 32.252 | 1.00 | 44.48 | X O |
| ATOM | 6527 | NE2 | GLN | 39 | 72.709 | 32.532 | 34.106 | 1.00 | 44.48 | X N |
| ATOM | 6528 | C | GLN | 39 | 75.955 | 28.224 | 33.663 | 1.00 | 39.46 | X C |
| ATOM | 6529 | O | GLN | 39 | 75.233 | 27.404 | 33.076 | 1.00 | 39.46 | X O |
| ATOM | 6530 | N | ALA | 40 | 76.514 | 27.984 | 34.846 | 1.00 | 47.11 | X N |
| ATOM | 6531 | CA | ALA | 40 | 76.324 | 26.727 | 35.558 | 1.00 | 47.11 | X C |
| ATOM | 6532 | CB | ALA | 40 | 77.241 | 26.678 | 36.773 | 1.00 | 19.87 | X C |
| ATOM | 6533 | C | ALA | 40 | 74.875 | 26.592 | 35.995 | 1.00 | 47.11 | X C |
| ATOM | 6534 | O | ALA | 40 | 74.296 | 27.542 | 36.512 | 1.00 | 47.11 | X O |
| ATOM | 6535 | N | PRO | 41 | 74.271 | 25.403 | 35.802 | 1.00 | 63.91 | X N |
| ATOM | 6536 | CD | PRO | 41 | 74.879 | 24.157 | 35.299 | 1.00 | 66.56 | X C |
| ATOM | 6537 | CA | PRO | 41 | 72.875 | 25.168 | 36.187 | 1.00 | 63.91 | X C |
| ATOM | 6538 | CB | PRO | 41 | 72.793 | 23.649 | 36.244 | 1.00 | 66.56 | X C |
| ATOM | 6539 | CG | PRO | 41 | 73.667 | 23.254 | 35.115 | 1.00 | 66.56 | X C |
| ATOM | 6540 | C | PRO | 41 | 72.507 | 25.826 | 37.508 | 1.00 | 63.91 | X C |
| ATOM | 6541 | O | PRO | 41 | 73.186 | 25.637 | 38.522 | 1.00 | 63.91 | X O |
| ATOM | 6542 | N | GLY | 42 | 71.432 | 26.608 | 37.478 | 1.00 | 63.56 | X N |
| ATOM | 6543 | CA | GLY | 42 | 70.979 | 27.297 | 38.671 | 1.00 | 63.56 | X C |
| ATOM | 6544 | C | GLY | 42 | 71.963 | 28.342 | 39.165 | 1.00 | 63.56 | X C |
| ATOM | 6545 | O | GLY | 42 | 71.920 | 28.732 | 40.334 | 1.00 | 63.56 | X O |
| ATOM | 6546 | N | LYS | 43 | 72.846 | 28.793 | 38.276 | 1.00 | 103.79 | X N |
| ATOM | 6547 | CA | LYS | 43 | 73.852 | 29.802 | 38.607 | 1.00 | 103.79 | X C |
| ATOM | 6548 | CB | LYS | 43 | 75.248 | 29.168 | 38.641 | 1.00 | 95.84 | X C |
| ATOM | 6549 | CG | LYS | 43 | 75.752 | 28.830 | 40.037 | 1.00 | 95.84 | X C |
| ATOM | 6550 | CD | LYS | 43 | 74.840 | 27.853 | 40.755 | 1.00 | 95.84 | X C |
| ATOM | 6551 | CE | LYS | 43 | 75.225 | 27.734 | 42.222 | 1.00 | 95.84 | X C |
| ATOM | 6552 | NZ | LYS | 43 | 75.138 | 29.048 | 42.920 | 1.00 | 95.84 | X N |
| ATOM | 6553 | C | LYS | 43 | 73.848 | 30.984 | 37.634 | 1.00 | 103.79 | X C |
| ATOM | 6554 | O | LYS | 43 | 73.085 | 31.013 | 36.668 | 1.00 | 103.79 | X O |
| ATOM | 6555 | N | GLY | 44 | 74.714 | 31.956 | 37.899 | 1.00 | 36.05 | X N |
| ATOM | 6556 | CA | GLY | 44 | 74.796 | 33.131 | 37.055 | 1.00 | 36.05 | X C |
| ATOM | 6557 | C | GLY | 44 | 75.710 | 33.025 | 35.845 | 1.00 | 36.05 | X C |
| ATOM | 6558 | O | GLY | 44 | 76.150 | 31.931 | 35.477 | 1.00 | 36.05 | X O |
| ATOM | 6559 | N | LEU | 45 | 76.003 | 34.186 | 35.249 | 1.00 | 24.14 | X N |
| ATOM | 6560 | CA | LEU | 45 | 76.832 | 34.316 | 34.046 | 1.00 | 24.14 | X C |
| ATOM | 6561 | CB | LEU | 45 | 76.343 | 35.504 | 33.214 | 1.00 | 15.59 | X C |
| ATOM | 6562 | CG | LEU | 45 | 74.932 | 35.346 | 32.638 | 1.00 | 15.59 | X C |
| ATOM | 6563 | CD1 | LEU | 45 | 74.470 | 36.606 | 31.917 | 1.00 | 15.59 | X C |
| ATOM | 6564 | CD2 | LEU | 45 | 74.942 | 34.179 | 31.677 | 1.00 | 15.59 | X C |
| ATOM | 6565 | C | LEU | 45 | 78.316 | 34.474 | 34.311 | 1.00 | 24.14 | X C |
| ATOM | 6566 | O | LEU | 45 | 78.732 | 35.324 | 35.095 | 1.00 | 24.14 | X O |
| ATOM | 6567 | N | GLU | 46 | 79.110 | 33.661 | 33.624 | 1.00 | 56.59 | X N |
| ATOM | 6568 | CA | GLU | 46 | 80.557 | 33.686 | 33.774 | 1.00 | 56.59 | X C |
| ATOM | 6569 | CB | GLU | 46 | 81.034 | 32.373 | 34.412 | 1.00 | 46.99 | X C |
| ATOM | 6570 | CG | GLU | 46 | 82.536 | 32.308 | 34.666 | 1.00 | 46.99 | X C |

Fig. 19: A-91

| ATOM | 6571 | CD | GLU | 46 | 82.953 | 31.066 | 35.438 | 1.00 | 46.99 | X | C |
|------|------|-----|-----|----|--------|--------|--------|------|-------|---|---|
| ATOM | 6572 | OE1 | GLU | 46 | 82.642 | 29.952 | 34.970 | 1.00 | 46.99 | X | O |
| ATOM | 6573 | OE2 | GLU | 46 | 83.594 | 31.201 | 36.508 | 1.00 | 46.99 | X | O |
| ATOM | 6574 | C | GLU | 46 | 81.272 | 33.904 | 32.439 | 1.00 | 56.59 | X | C |
| ATOM | 6575 | O | GLU | 46 | 80.821 | 33.433 | 31.393 | 1.00 | 56.59 | X | O |
| ATOM | 6576 | N | TRP | 47 | 82.385 | 34.632 | 32.489 | 1.00 | 30.60 | X | N |
| ATOM | 6577 | CA | TRP | 47 | 83.188 | 34.910 | 31.300 | 1.00 | 30.60 | X | C |
| ATOM | 6578 | CB | TRP | 47 | 83.889 | 36.273 | 31.426 | 1.00 | 23.41 | X | C |
| ATOM | 6579 | CG | TRP | 47 | 84.944 | 36.481 | 30.385 | 1.00 | 23.41 | X | C |
| ATOM | 6580 | CD2 | TRP | 47 | 86.358 | 36.500 | 30.601 | 1.00 | 23.41 | X | C |
| ATOM | 6581 | CE2 | TRP | 47 | 86.971 | 36.591 | 29.328 | 1.00 | 23.41 | X | C |
| ATOM | 6582 | CE3 | TRP | 47 | 87.170 | 36.441 | 31.746 | 1.00 | 23.41 | X | C |
| ATOM | 6583 | CD1 | TRP | 47 | 84.759 | 36.570 | 29.031 | 1.00 | 23.41 | X | C |
| ATOM | 6584 | NE1 | TRP | 47 | 85.969 | 36.633 | 28.392 | 1.00 | 23.41 | X | N |
| ATOM | 6585 | CZ2 | TRP | 47 | 88.365 | 36.622 | 29.165 | 1.00 | 23.41 | X | C |
| ATOM | 6586 | CZ3 | TRP | 47 | 88.553 | 36.470 | 31.587 | 1.00 | 23.41 | X | C |
| ATOM | 6587 | CH2 | TRP | 47 | 89.137 | 36.560 | 30.304 | 1.00 | 23.41 | X | C |
| ATOM | 6588 | C | TRP | 47 | 84.231 | 33.810 | 31.153 | 1.00 | 30.60 | X | C |
| ATOM | 6589 | O | TRP | 47 | 84.965 | 33.516 | 32.097 | 1.00 | 30.60 | X | O |
| ATOM | 6590 | N | VAL | 48 | 84.317 | 33.219 | 29.967 | 1.00 | 24.17 | X | N |
| ATOM | 6591 | CA | VAL | 48 | 85.270 | 32.128 | 29.755 | 1.00 | 24.17 | X | C |
| ATOM | 6592 | CB | VAL | 48 | 84.589 | 30.924 | 29.011 | 1.00 | 22.03 | X | C |
| ATOM | 6593 | CG1 | VAL | 48 | 85.589 | 29.786 | 28.790 | 1.00 | 22.03 | X | C |
| ATOM | 6594 | CG2 | VAL | 48 | 83.408 | 30.436 | 29.805 | 1.00 | 22.03 | X | C |
| ATOM | 6595 | C | VAL | 48 | 86.550 | 32.490 | 29.006 | 1.00 | 24.17 | X | C |
| ATOM | 6596 | O | VAL | 48 | 87.640 | 32.477 | 29.579 | 1.00 | 24.17 | X | O |
| ATOM | 6597 | N | ALA | 49 | 86.407 | 32.800 | 27.724 | 1.00 | 21.43 | X | N |
| ATOM | 6598 | CA | ALA | 49 | 87.550 | 33.118 | 26.885 | 1.00 | 21.43 | X | C |
| ATOM | 6599 | CB | ALA | 49 | 87.953 | 31.884 | 26.094 | 1.00 | 38.48 | X | C |
| ATOM | 6600 | C | ALA | 49 | 87.228 | 34.257 | 25.934 | 1.00 | 21.43 | X | C |
| ATOM | 6601 | O | ALA | 49 | 86.066 | 34.661 | 25.825 | 1.00 | 21.43 | X | O |
| ATOM | 6602 | N | THR | 50 | 88.257 | 34.745 | 25.235 | 1.00 | 24.70 | X | N |
| ATOM | 6603 | CA | THR | 50 | 88.115 | 35.856 | 24.286 | 1.00 | 24.70 | X | C |
| ATOM | 6604 | CB | THR | 50 | 87.952 | 37.202 | 25.048 | 1.00 | 38.80 | X | C |
| ATOM | 6605 | OG1 | THR | 50 | 86.711 | 37.215 | 25.763 | 1.00 | 38.80 | X | O |
| ATOM | 6606 | CG2 | THR | 50 | 87.981 | 38.369 | 24.087 | 1.00 | 38.80 | X | C |
| ATOM | 6607 | C | THR | 50 | 89.298 | 36.039 | 23.324 | 1.00 | 24.70 | X | C |
| ATOM | 6608 | O | THR | 50 | 90.456 | 35.935 | 23.738 | 1.00 | 24.70 | X | O |
| ATOM | 6609 | N | ILE | 51 | 89.010 | 36.300 | 22.047 | 1.00 | 32.54 | X | N |
| ATOM | 6610 | CA | ILE | 51 | 90.075 | 36.599 | 21.074 | 1.00 | 32.54 | X | C |
| ATOM | 6611 | CB | ILE | 51 | 90.333 | 35.495 | 19.998 | 1.00 | 54.98 | X | C |
| ATOM | 6612 | CG2 | ILE | 51 | 90.567 | 34.178 | 20.661 | 1.00 | 54.98 | X | C |
| ATOM | 6613 | CG1 | ILE | 51 | 89.180 | 35.415 | 18.997 | 1.00 | 54.98 | X | C |
| ATOM | 6614 | CD1 | ILE | 51 | 87.893 | 34.921 | 19.582 | 1.00 | 54.98 | X | C |
| ATOM | 6615 | C | ILE | 51 | 89.674 | 37.865 | 20.335 | 1.00 | 32.54 | X | C |
| ATOM | 6616 | O | ILE | 51 | 88.516 | 38.024 | 19.937 | 1.00 | 32.54 | X | O |
| ATOM | 6617 | N | SER | 52 | 90.628 | 38.774 | 20.167 | 1.00 | 43.61 | X | N |
| ATOM | 6618 | CA | SER | 52 | 90.361 | 40.024 | 19.477 | 1.00 | 43.61 | X | C |
| ATOM | 6619 | CB | SER | 52 | 91.374 | 41.081 | 19.910 | 1.00 | 24.33 | X | C |
| ATOM | 6620 | OG | SER | 52 | 92.684 | 40.702 | 19.528 | 1.00 | 24.33 | X | O |
| ATOM | 6621 | C | SER | 52 | 90.450 | 39.789 | 17.973 | 1.00 | 43.61 | X | C |
| ATOM | 6622 | O | SER | 52 | 90.677 | 38.663 | 17.533 | 1.00 | 43.61 | X | O |
| ATOM | 6623 | N | GLY | 53 | 90.243 | 40.843 | 17.187 | 1.00 | 34.59 | X | N |
| ATOM | 6624 | CA | GLY | 53 | 90.336 | 40.707 | 15.747 | 1.00 | 34.59 | X | C |
| ATOM | 6625 | C | GLY | 53 | 91.800 | 40.559 | 15.381 | 1.00 | 34.59 | X | C |
| ATOM | 6626 | O | GLY | 53 | 92.152 | 40.020 | 14.332 | 1.00 | 34.59 | X | O |
| ATOM | 6627 | N | GLY | 54 | 92.658 | 41.047 | 16.266 | 1.00 | 29.30 | X | N |
| ATOM | 6628 | CA | GLY | 54 | 94.079 | 40.949 | 16.033 | 1.00 | 29.30 | X | C |
| ATOM | 6629 | C | GLY | 54 | 94.555 | 39.550 | 16.359 | 1.00 | 29.30 | X | C |
| ATOM | 6630 | O | GLY | 54 | 95.642 | 39.135 | 15.954 | 1.00 | 29.30 | X | O |
| ATOM | 6631 | N | GLY | 55 | 93.747 | 38.811 | 17.103 | 1.00 | 15.27 | X | N |
| ATOM | 6632 | CA | GLY | 55 | 94.139 | 37.465 | 17.437 | 1.00 | 15.27 | X | C |
| ATOM | 6633 | C | GLY | 55 | 94.596 | 37.254 | 18.867 | 1.00 | 15.27 | X | C |
| ATOM | 6634 | O | GLY | 55 | 94.878 | 36.105 | 19.231 | 1.00 | 15.27 | X | O |
| ATOM | 6635 | N | HIS | 56 | 94.676 | 38.319 | 19.675 | 1.00 | 13.76 | X | N |
| ATOM | 6636 | CA | HIS | 56 | 95.101 | 38.181 | 21.076 | 1.00 | 13.76 | X | C |
| ATOM | 6637 | CB | HIS | 56 | 95.268 | 39.543 | 21.741 | 1.00 | 60.58 | X | C |
| ATOM | 6638 | CG | HIS | 56 | 96.115 | 40.490 | 20.957 | 1.00 | 60.58 | X | C |
| ATOM | 6639 | CD2 | HIS | 56 | 97.417 | 40.838 | 21.087 | 1.00 | 60.58 | X | C |
| ATOM | 6640 | ND1 | HIS | 56 | 95.638 | 41.180 | 19.862 | 1.00 | 60.58 | X | N |
| ATOM | 6641 | CE1 | HIS | 56 | 96.611 | 41.913 | 19.351 | 1.00 | 60.58 | X | C |
| ATOM | 6642 | NE2 | HIS | 56 | 97.701 | 41.724 | 20.075 | 1.00 | 60.58 | X | N |
| ATOM | 6643 | C | HIS | 56 | 94.071 | 37.383 | 21.857 | 1.00 | 13.76 | X | C |

Fig. 19: A-92

| ATOM | 6644 | O   | HIS | 56 | 92.864 | 37.621 | 21.736 | 1.00 | 13.76 | X | O |
|------|------|-----|-----|----|--------|--------|--------|------|-------|---|---|
| ATOM | 6645 | N   | THR | 57 | 94.529 | 36.438 | 22.671 | 1.00 | 20.05 | X | N |
| ATOM | 6646 | CA  | THR | 57 | 93.583 | 35.632 | 23.436 | 1.00 | 20.05 | X | C |
| ATOM | 6647 | CB  | THR | 57 | 93.759 | 34.123 | 23.096 | 1.00 | 15.53 | X | C |
| ATOM | 6648 | OG1 | THR | 57 | 95.015 | 33.651 | 23.587 | 1.00 | 15.53 | X | O |
| ATOM | 6649 | CG2 | THR | 57 | 93.734 | 33.929 | 21.593 | 1.00 | 15.53 | X | C |
| ATOM | 6650 | C   | THR | 57 | 93.655 | 35.876 | 24.952 | 1.00 | 20.05 | X | C |
| ATOM | 6651 | O   | THR | 57 | 94.716 | 36.142 | 25.512 | 1.00 | 20.05 | X | O |
| ATOM | 6652 | N   | TYR | 58 | 92.500 | 35.808 | 25.603 | 1.00 | 19.06 | X | N |
| ATOM | 6653 | CA  | TYR | 58 | 92.410 | 36.037 | 27.040 | 1.00 | 19.06 | X | C |
| ATOM | 6654 | CB  | TYR | 58 | 91.829 | 37.428 | 27.304 | 1.00 | 22.48 | X | C |
| ATOM | 6655 | CG  | TYR | 58 | 92.614 | 38.542 | 26.661 | 1.00 | 22.48 | X | C |
| ATOM | 6656 | CD1 | TYR | 58 | 93.565 | 39.252 | 27.384 | 1.00 | 22.48 | X | C |
| ATOM | 6657 | CE1 | TYR | 58 | 94.308 | 40.265 | 26.788 | 1.00 | 22.48 | X | C |
| ATOM | 6658 | CD2 | TYR | 58 | 92.423 | 38.871 | 25.316 | 1.00 | 22.48 | X | C |
| ATOM | 6659 | CE2 | TYR | 58 | 93.167 | 39.886 | 24.703 | 1.00 | 22.48 | X | C |
| ATOM | 6660 | CZ  | TYR | 58 | 94.105 | 40.580 | 25.447 | 1.00 | 22.48 | X | C |
| ATOM | 6661 | OH  | TYR | 58 | 94.828 | 41.611 | 24.876 | 1.00 | 22.48 | X | O |
| ATOM | 6662 | C   | TYR | 58 | 91.513 | 34.973 | 27.656 | 1.00 | 19.06 | X | C |
| ATOM | 6663 | O   | TYR | 58 | 90.442 | 34.660 | 27.123 | 1.00 | 19.06 | X | O |
| ATOM | 6664 | N   | TYR | 59 | 91.945 | 34.437 | 28.792 | 1.00 | 29.06 | X | N |
| ATOM | 6665 | CA  | TYR | 59 | 91.199 | 33.378 | 29.456 | 1.00 | 29.06 | X | C |
| ATOM | 6666 | CB  | TYR | 59 | 91.988 | 32.080 | 29.371 | 1.00 | 21.37 | X | C |
| ATOM | 6667 | CG  | TYR | 59 | 92.252 | 31.641 | 27.969 | 1.00 | 21.37 | X | C |
| ATOM | 6668 | CD1 | TYR | 59 | 91.352 | 30.813 | 27.303 | 1.00 | 21.37 | X | C |
| ATOM | 6669 | CE1 | TYR | 59 | 91.573 | 30.428 | 25.988 | 1.00 | 21.37 | X | C |
| ATOM | 6670 | CD2 | TYR | 59 | 93.382 | 32.076 | 27.286 | 1.00 | 21.37 | X | C |
| ATOM | 6671 | CE2 | TYR | 59 | 93.608 | 31.698 | 25.968 | 1.00 | 21.37 | X | C |
| ATOM | 6672 | CZ  | TYR | 59 | 92.697 | 30.874 | 25.330 | 1.00 | 21.37 | X | C |
| ATOM | 6673 | OH  | TYR | 59 | 92.897 | 30.495 | 24.027 | 1.00 | 21.37 | X | O |
| ATOM | 6674 | C   | TYR | 59 | 90.857 | 33.605 | 30.910 | 1.00 | 29.06 | X | C |
| ATOM | 6675 | O   | TYR | 59 | 91.575 | 34.287 | 31.648 | 1.00 | 29.06 | X | O |
| ATOM | 6676 | N   | LEU | 60 | 89.745 | 33.002 | 31.308 | 1.00 | 26.45 | X | N |
| ATOM | 6677 | CA  | LEU | 60 | 89.309 | 33.048 | 32.689 | 1.00 | 26.45 | X | C |
| ATOM | 6678 | CB  | LEU | 60 | 87.927 | 32.397 | 32.826 | 1.00 | 24.21 | X | C |
| ATOM | 6679 | CG  | LEU | 60 | 87.411 | 32.193 | 34.252 | 1.00 | 24.21 | X | C |
| ATOM | 6680 | CD1 | LEU | 60 | 87.173 | 33.538 | 34.911 | 1.00 | 24.21 | X | C |
| ATOM | 6681 | CD2 | LEU | 60 | 86.135 | 31.380 | 34.223 | 1.00 | 24.21 | X | C |
| ATOM | 6682 | C   | LEU | 60 | 90.382 | 32.189 | 33.360 | 1.00 | 26.45 | X | C |
| ATOM | 6683 | O   | LEU | 60 | 90.822 | 31.191 | 32.781 | 1.00 | 26.45 | X | O |
| ATOM | 6684 | N   | ASP | 61 | 90.822 | 32.570 | 34.553 | 1.00 | 64.06 | X | N |
| ATOM | 6685 | CA  | ASP | 61 | 91.865 | 31.810 | 35.240 | 1.00 | 64.06 | X | C |
| ATOM | 6686 | CB  | ASP | 61 | 92.297 | 32.556 | 36.502 | 1.00 | 60.41 | X | C |
| ATOM | 6687 | CG  | ASP | 61 | 92.984 | 33.865 | 36.183 | 1.00 | 60.41 | X | C |
| ATOM | 6688 | OD1 | ASP | 61 | 93.262 | 34.650 | 37.114 | 1.00 | 60.41 | X | O |
| ATOM | 6689 | OD2 | ASP | 61 | 93.250 | 34.106 | 34.986 | 1.00 | 60.41 | X | O |
| ATOM | 6690 | C   | ASP | 61 | 91.477 | 30.371 | 35.576 | 1.00 | 64.06 | X | C |
| ATOM | 6691 | O   | ASP | 61 | 92.337 | 29.503 | 35.701 | 1.00 | 64.06 | X | O |
| ATOM | 6692 | N   | SER | 62 | 90.181 | 30.122 | 35.707 | 1.00 | 57.78 | X | N |
| ATOM | 6693 | CA  | SER | 62 | 89.681 | 28.791 | 36.028 | 1.00 | 57.78 | X | C |
| ATOM | 6694 | CB  | SER | 62 | 88.196 | 28.868 | 36.386 | 1.00 | 42.55 | X | C |
| ATOM | 6695 | OG  | SER | 62 | 87.643 | 27.575 | 36.556 | 1.00 | 42.55 | X | O |
| ATOM | 6696 | C   | SER | 62 | 89.872 | 27.787 | 34.894 | 1.00 | 57.78 | X | C |
| ATOM | 6697 | O   | SER | 62 | 90.000 | 26.590 | 35.142 | 1.00 | 57.78 | X | O |
| ATOM | 6698 | N   | VAL | 63 | 89.890 | 28.269 | 33.655 | 1.00 | 47.11 | X | N |
| ATOM | 6699 | CA  | VAL | 63 | 90.047 | 27.383 | 32.504 | 1.00 | 47.11 | X | C |
| ATOM | 6700 | CB  | VAL | 63 | 88.796 | 27.464 | 31.555 | 1.00 | 39.29 | X | C |
| ATOM | 6701 | CG1 | VAL | 63 | 87.513 | 27.472 | 32.375 | 1.00 | 39.29 | X | C |
| ATOM | 6702 | CG2 | VAL | 63 | 88.863 | 28.700 | 30.679 | 1.00 | 39.29 | X | C |
| ATOM | 6703 | C   | VAL | 63 | 91.318 | 27.660 | 31.686 | 1.00 | 47.11 | X | C |
| ATOM | 6704 | O   | VAL | 63 | 91.504 | 27.093 | 30.603 | 1.00 | 47.11 | X | O |
| ATOM | 6705 | N   | LYS | 64 | 92.200 | 28.511 | 32.208 | 1.00 | 47.01 | X | N |
| ATOM | 6706 | CA  | LYS | 64 | 93.424 | 28.843 | 31.483 | 1.00 | 47.01 | X | C |
| ATOM | 6707 | CB  | LYS | 64 | 94.116 | 30.063 | 32.107 | 1.00 | 84.46 | X | C |
| ATOM | 6708 | CG  | LYS | 64 | 95.038 | 30.797 | 31.135 | 1.00 | 84.46 | X | C |
| ATOM | 6709 | CD  | LYS | 64 | 95.670 | 32.025 | 31.766 | 1.00 | 84.46 | X | C |
| ATOM | 6710 | CE  | LYS | 64 | 96.370 | 32.907 | 30.725 | 1.00 | 84.46 | X | C |
| ATOM | 6711 | NZ  | LYS | 64 | 95.419 | 33.654 | 29.833 | 1.00 | 84.46 | X | N |
| ATOM | 6712 | C   | LYS | 64 | 94.388 | 27.666 | 31.441 | 1.00 | 47.01 | X | C |
| ATOM | 6713 | O   | LYS | 64 | 94.757 | 27.113 | 32.479 | 1.00 | 47.01 | X | O |
| ATOM | 6714 | N   | GLY | 65 | 94.795 | 27.289 | 30.231 | 1.00 | 35.35 | X | N |
| ATOM | 6715 | CA  | GLY | 65 | 95.704 | 26.167 | 30.073 | 1.00 | 35.35 | X | C |
| ATOM | 6716 | C   | GLY | 65 | 94.953 | 24.919 | 29.652 | 1.00 | 35.35 | X | C |

Fig. 19: A-93

```
ATOM   6717  O    GLY  65      95.547  23.945  29.195  1.00  35.35      X   O
ATOM   6718  N    ARG  66      93.634  24.956  29.809  1.00  33.32      X   N
ATOM   6719  CA   ARG  66      92.791  23.833  29.450  1.00  33.32      X   C
ATOM   6720  CB   ARG  66      91.881  23.470  30.616  1.00  43.17      X   C
ATOM   6721  CG   ARG  66      92.594  23.386  31.958  1.00  43.17      X   C
ATOM   6722  CD   ARG  66      91.684  22.813  33.050  1.00  43.17      X   C
ATOM   6723  NE   ARG  66      90.548  23.679  33.367  1.00  43.17      X   N
ATOM   6724  CZ   ARG  66      89.277  23.296  33.305  1.00  43.17      X   C
ATOM   6725  NH1  ARG  66      88.973  22.061  32.932  1.00  43.17      X   N
ATOM   6726  NH2  ARG  66      88.309  24.144  33.630  1.00  43.17      X   N
ATOM   6727  C    ARG  66      91.945  24.169  28.232  1.00  33.32      X   C
ATOM   6728  O    ARG  66      91.775  23.336  27.346  1.00  33.32      X   O
ATOM   6729  N    PHE  67      91.411  25.389  28.191  1.00  33.69      X   N
ATOM   6730  CA   PHE  67      90.567  25.834  27.074  1.00  33.69      X   C
ATOM   6731  CB   PHE  67      89.444  26.750  27.587  1.00  42.44      X   C
ATOM   6732  CG   PHE  67      88.346  26.030  28.330  1.00  42.44      X   C
ATOM   6733  CD1  PHE  67      88.573  24.802  28.943  1.00  42.44      X   C
ATOM   6734  CD2  PHE  67      87.074  26.594  28.426  1.00  42.44      X   C
ATOM   6735  CE1  PHE  67      87.547  24.145  29.637  1.00  42.44      X   C
ATOM   6736  CE2  PHE  67      86.038  25.940  29.122  1.00  42.44      X   C
ATOM   6737  CZ   PHE  67      86.278  24.717  29.724  1.00  42.44      X   C
ATOM   6738  C    PHE  67      91.393  26.578  26.027  1.00  33.69      X   C
ATOM   6739  O    PHE  67      92.405  27.194  26.344  1.00  33.69      X   O
ATOM   6740  N    THR  68      90.949  26.526  24.779  1.00  56.59      X   N
ATOM   6741  CA   THR  68      91.646  27.201  23.689  1.00  56.59      X   C
ATOM   6742  CB   THR  68      92.454  26.193  22.846  1.00  46.98      X   C
ATOM   6743  OG1  THR  68      93.611  25.781  23.578  1.00  46.98      X   O
ATOM   6744  CG2  THR  68      92.870  26.808  21.512  1.00  46.98      X   C
ATOM   6745  C    THR  68      90.661  27.913  22.768  1.00  56.59      X   C
ATOM   6746  O    THR  68      89.899  27.270  22.047  1.00  56.59      X   O
ATOM   6747  N    ILE  69      90.672  29.239  22.781  1.00  20.15      X   N
ATOM   6748  CA   ILE  69      89.760  29.975  21.918  1.00  20.15      X   C
ATOM   6749  CB   ILE  69      89.287  31.289  22.607  1.00  31.46      X   C
ATOM   6750  CG2  ILE  69      90.480  32.153  22.953  1.00  31.46      X   C
ATOM   6751  CG1  ILE  69      88.283  32.028  21.722  1.00  31.46      X   C
ATOM   6752  CD1  ILE  69      87.574  33.159  22.446  1.00  31.46      X   C
ATOM   6753  C    ILE  69      90.464  30.262  20.591  1.00  20.15      X   C
ATOM   6754  O    ILE  69      91.672  30.481  20.559  1.00  20.15      X   O
ATOM   6755  N    SER  70      89.724  30.223  19.489  1.00  21.14      X   N
ATOM   6756  CA   SER  70      90.319  30.482  18.182  1.00  21.14      X   C
ATOM   6757  CB   SER  70      91.105  29.263  17.693  1.00  37.41      X   C
ATOM   6758  OG   SER  70      90.228  28.236  17.253  1.00  37.41      X   O
ATOM   6759  C    SER  70      89.242  30.824  17.163  1.00  21.14      X   C
ATOM   6760  O    SER  70      88.045  30.637  17.413  1.00  21.14      X   O
ATOM   6761  N    ARG  71      89.673  31.322  16.009  1.00  30.73      X   N
ATOM   6762  CA   ARG  71      88.734  31.687  14.966  1.00  30.73      X   C
ATOM   6763  CB   ARG  71      88.369  33.178  15.073  1.00  24.51      X   C
ATOM   6764  CG   ARG  71      89.546  34.139  14.901  1.00  24.51      X   C
ATOM   6765  CD   ARG  71      89.071  35.503  14.453  1.00  24.51      X   C
ATOM   6766  NE   ARG  71      88.464  36.278  15.534  1.00  24.51      X   N
ATOM   6767  CZ   ARG  71      87.604  37.283  15.351  1.00  24.51      X   C
ATOM   6768  NH1  ARG  71      87.229  37.643  14.131  1.00  24.51      X   N
ATOM   6769  NH2  ARG  71      87.132  37.948  16.391  1.00  24.51      X   N
ATOM   6770  C    ARG  71      89.259  31.393  13.560  1.00  30.73      X   C
ATOM   6771  O    ARG  71      90.464  31.415  13.301  1.00  30.73      X   O
ATOM   6772  N    ASP  72      88.326  31.106  12.663  1.00  55.72      X   N
ATOM   6773  CA   ASP  72      88.619  30.836  11.268  1.00  55.72      X   C
ATOM   6774  CB   ASP  72      88.219  29.405  10.902  1.00  83.09      X   C
ATOM   6775  CG   ASP  72      88.255  29.153   9.409  1.00  83.09      X   C
ATOM   6776  OD1  ASP  72      89.282  29.466   8.773  1.00  83.09      X   O
ATOM   6777  OD2  ASP  72      87.256  28.637   8.870  1.00  83.09      X   O
ATOM   6778  C    ASP  72      87.749  31.837  10.528  1.00  55.72      X   C
ATOM   6779  O    ASP  72      86.613  31.539  10.162  1.00  55.72      X   O
ATOM   6780  N    ASN  73      88.284  33.036  10.340  1.00  57.89      X   N
ATOM   6781  CA   ASN  73      87.552  34.098   9.673  1.00  57.89      X   C
ATOM   6782  CB   ASN  73      88.426  35.345   9.558  1.00  43.96      X   C
ATOM   6783  CG   ASN  73      88.777  35.928  10.912  1.00  43.96      X   C
ATOM   6784  OD1  ASN  73      88.021  35.794  11.879  1.00  43.96      X   O
ATOM   6785  ND2  ASN  73      89.919  36.593  10.986  1.00  43.96      X   N
ATOM   6786  C    ASN  73      87.020  33.715   8.306  1.00  57.89      X   C
ATOM   6787  O    ASN  73      85.949  34.173   7.903  1.00  57.89      X   O
ATOM   6788  N    SER  74      87.756  32.870   7.594  1.00  50.09      X   N
ATOM   6789  CA   SER  74      87.324  32.451   6.268  1.00  50.09      X   C
```

Fig. 19: A-94

| | | | | | | | | | | | |
|---|---|---|---|---|---|---|---|---|---|---|---|
| ATOM | 6790 | CB | SER | 74 | 88.277 | 31.398 | 5.705 | 1.00 | 34.87 | X | C |
| ATOM | 6791 | OG | SER | 74 | 88.179 | 30.197 | 6.441 | 1.00 | 34.87 | X | O |
| ATOM | 6792 | C | SER | 74 | 85.910 | 31.880 | 6.303 | 1.00 | 50.09 | X | C |
| ATOM | 6793 | O | SER | 74 | 85.141 | 32.050 | 5.356 | 1.00 | 50.09 | X | O |
| ATOM | 6794 | N | LYS | 75 | 85.572 | 31.209 | 7.400 | 1.00 | 50.16 | X | N |
| ATOM | 6795 | CA | LYS | 75 | 84.257 | 30.597 | 7.551 | 1.00 | 50.16 | X | C |
| ATOM | 6796 | CB | LYS | 75 | 84.418 | 29.097 | 7.814 | 1.00 | 60.89 | X | C |
| ATOM | 6797 | CG | LYS | 75 | 85.206 | 28.372 | 6.729 | 1.00 | 60.89 | X | C |
| ATOM | 6798 | CD | LYS | 75 | 85.356 | 26.884 | 7.009 | 1.00 | 60.89 | X | C |
| ATOM | 6799 | CE | LYS | 75 | 86.046 | 26.195 | 5.840 | 1.00 | 60.89 | X | C |
| ATOM | 6800 | NZ | LYS | 75 | 85.341 | 26.459 | 4.551 | 1.00 | 60.89 | X | N |
| ATOM | 6801 | C | LYS | 75 | 83.423 | 31.226 | 8.663 | 1.00 | 50.16 | X | C |
| ATOM | 6802 | O | LYS | 75 | 82.470 | 30.618 | 9.142 | 1.00 | 50.16 | X | O |
| ATOM | 6803 | N | ASN | 76 | 83.786 | 32.441 | 9.066 | 1.00 | 54.49 | X | N |
| ATOM | 6804 | CA | ASN | 76 | 83.075 | 33.165 | 10.117 | 1.00 | 54.49 | X | C |
| ATOM | 6805 | CB | ASN | 76 | 81.812 | 33.818 | 9.559 | 1.00 | 41.29 | X | C |
| ATOM | 6806 | CG | ASN | 76 | 82.116 | 34.956 | 8.620 | 1.00 | 41.29 | X | C |
| ATOM | 6807 | OD1 | ASN | 76 | 81.399 | 35.956 | 8.592 | 1.00 | 41.29 | X | O |
| ATOM | 6808 | ND2 | ASN | 76 | 83.181 | 34.812 | 7.839 | 1.00 | 41.29 | X | N |
| ATOM | 6809 | C | ASN | 76 | 82.684 | 32.285 | 11.286 | 1.00 | 54.49 | X | C |
| ATOM | 6810 | O | ASN | 76 | 81.523 | 32.278 | 11.706 | 1.00 | 54.49 | X | O |
| ATOM | 6811 | N | THR | 77 | 83.645 | 31.550 | 11.827 | 1.00 | 48.88 | X | N |
| ATOM | 6812 | CA | THR | 77 | 83.325 | 30.675 | 12.938 | 1.00 | 48.88 | X | C |
| ATOM | 6813 | CB | THR | 77 | 83.321 | 29.215 | 12.481 | 1.00 | 67.62 | X | C |
| ATOM | 6814 | OG1 | THR | 77 | 82.318 | 29.048 | 11.469 | 1.00 | 67.62 | X | O |
| ATOM | 6815 | CG2 | THR | 77 | 83.028 | 28.284 | 13.653 | 1.00 | 67.62 | X | C |
| ATOM | 6816 | C | THR | 77 | 84.245 | 30.817 | 14.132 | 1.00 | 48.88 | X | C |
| ATOM | 6817 | O | THR | 77 | 85.463 | 30.858 | 13.990 | 1.00 | 48.88 | X | O |
| ATOM | 6818 | N | LEU | 78 | 83.641 | 30.900 | 15.313 | 1.00 | 25.08 | X | N |
| ATOM | 6819 | CA | LEU | 78 | 84.387 | 31.014 | 16.562 | 1.00 | 25.08 | X | C |
| ATOM | 6820 | CB | LEU | 78 | 83.739 | 32.047 | 17.488 | 1.00 | 24.57 | X | C |
| ATOM | 6821 | CG | LEU | 78 | 84.362 | 32.022 | 18.881 | 1.00 | 24.57 | X | C |
| ATOM | 6822 | CD1 | LEU | 78 | 85.757 | 32.625 | 18.789 | 1.00 | 24.57 | X | C |
| ATOM | 6823 | CD2 | LEU | 78 | 83.507 | 32.770 | 19.868 | 1.00 | 24.57 | X | C |
| ATOM | 6824 | C | LEU | 78 | 84.370 | 29.653 | 17.250 | 1.00 | 25.08 | X | C |
| ATOM | 6825 | O | LEU | 78 | 83.312 | 29.041 | 17.389 | 1.00 | 25.08 | X | O |
| ATOM | 6826 | N | TYR | 79 | 85.530 | 29.179 | 17.687 | 1.00 | 41.94 | X | N |
| ATOM | 6827 | CA | TYR | 79 | 85.595 | 27.880 | 18.344 | 1.00 | 41.94 | X | C |
| ATOM | 6828 | CB | TYR | 79 | 86.608 | 26.963 | 17.657 | 1.00 | 47.62 | X | C |
| ATOM | 6829 | CG | TYR | 79 | 86.328 | 26.619 | 16.226 | 1.00 | 47.62 | X | C |
| ATOM | 6830 | CD1 | TYR | 79 | 85.264 | 25.794 | 15.887 | 1.00 | 47.62 | X | C |
| ATOM | 6831 | CE1 | TYR | 79 | 85.008 | 25.460 | 14.559 | 1.00 | 47.62 | X | C |
| ATOM | 6832 | CD2 | TYR | 79 | 87.139 | 27.108 | 15.207 | 1.00 | 47.62 | X | C |
| ATOM | 6833 | CE2 | TYR | 79 | 86.896 | 26.784 | 13.878 | 1.00 | 47.62 | X | C |
| ATOM | 6834 | CZ | TYR | 79 | 85.826 | 25.959 | 13.559 | 1.00 | 47.62 | X | C |
| ATOM | 6835 | OH | TYR | 79 | 85.564 | 25.640 | 12.245 | 1.00 | 47.62 | X | O |
| ATOM | 6836 | C | TYR | 79 | 86.043 | 27.991 | 19.779 | 1.00 | 41.94 | X | C |
| ATOM | 6837 | O | TYR | 79 | 86.890 | 28.824 | 20.100 | 1.00 | 41.94 | X | O |
| ATOM | 6838 | N | LEU | 80 | 85.470 | 27.160 | 20.642 | 1.00 | 19.15 | X | N |
| ATOM | 6839 | CA | LEU | 80 | 85.917 | 27.110 | 22.022 | 1.00 | 19.15 | X | C |
| ATOM | 6840 | CB | LEU | 80 | 84.809 | 27.382 | 23.047 | 1.00 | 21.08 | X | C |
| ATOM | 6841 | CG | LEU | 80 | 85.271 | 27.127 | 24.510 | 1.00 | 21.08 | X | C |
| ATOM | 6842 | CD1 | LEU | 80 | 86.500 | 27.981 | 24.840 | 1.00 | 21.08 | X | C |
| ATOM | 6843 | CD2 | LEU | 80 | 84.142 | 27.412 | 25.503 | 1.00 | 21.08 | X | C |
| ATOM | 6844 | C | LEU | 80 | 86.342 | 25.671 | 22.129 | 1.00 | 19.15 | X | C |
| ATOM | 6845 | O | LEU | 80 | 85.517 | 24.769 | 21.941 | 1.00 | 19.15 | X | O |
| ATOM | 6846 | N | GLN | 81 | 87.631 | 25.455 | 22.395 | 1.00 | 31.28 | X | N |
| ATOM | 6847 | CA | GLN | 81 | 88.193 | 24.111 | 22.530 | 1.00 | 31.28 | X | C |
| ATOM | 6848 | CB | GLN | 81 | 89.497 | 24.015 | 21.738 | 1.00 | 68.87 | X | C |
| ATOM | 6849 | CG | GLN | 81 | 90.141 | 22.647 | 21.783 | 1.00 | 68.87 | X | C |
| ATOM | 6850 | CD | GLN | 81 | 89.318 | 21.580 | 21.075 | 1.00 | 68.87 | X | C |
| ATOM | 6851 | OE1 | GLN | 81 | 89.101 | 21.648 | 19.864 | 1.00 | 68.87 | X | O |
| ATOM | 6852 | NE2 | GLN | 81 | 88.857 | 20.588 | 21.831 | 1.00 | 68.87 | X | N |
| ATOM | 6853 | C | GLN | 81 | 88.448 | 23.775 | 24.001 | 1.00 | 31.28 | X | C |
| ATOM | 6854 | O | GLN | 81 | 89.402 | 24.260 | 24.604 | 1.00 | 31.28 | X | O |
| ATOM | 6855 | N | MET | 82 | 87.589 | 22.935 | 24.569 | 1.00 | 32.50 | X | N |
| ATOM | 6856 | CA | MET | 82 | 87.701 | 22.541 | 25.975 | 1.00 | 32.50 | X | C |
| ATOM | 6857 | CB | MET | 82 | 86.297 | 22.429 | 26.589 | 1.00 | 41.50 | X | C |
| ATOM | 6858 | CG | MET | 82 | 85.537 | 23.752 | 26.653 | 1.00 | 41.50 | X | C |
| ATOM | 6859 | SD | MET | 82 | 83.790 | 23.594 | 27.062 | 1.00 | 41.50 | X | S |
| ATOM | 6860 | CE | MET | 82 | 83.088 | 23.391 | 25.452 | 1.00 | 41.50 | X | C |
| ATOM | 6861 | C | MET | 82 | 88.463 | 21.230 | 26.188 | 1.00 | 32.50 | X | C |
| ATOM | 6862 | O | MET | 82 | 88.239 | 20.250 | 25.487 | 1.00 | 32.50 | X | O |

Fig. 19: A-95

```
ATOM   6863  N    ASN   83      89.369  21.224  27.160  1.00  43.69      X   N
ATOM   6864  CA   ASN   83      90.155  20.032  27.459  1.00  43.69      X   C
ATOM   6865  CB   ASN   83      91.574  20.157  26.883  1.00  34.50      X   C
ATOM   6866  CG   ASN   83      91.574  20.391  25.383  1.00  34.50      X   C
ATOM   6867  OD1  ASN   83      90.920  19.670  24.636  1.00  34.50      X   O
ATOM   6868  ND2  ASN   83      92.313  21.401  24.937  1.00  34.50      X   N
ATOM   6869  C    ASN   83      90.225  19.855  28.967  1.00  43.69      X   C
ATOM   6870  O    ASN   83      90.054  20.822  29.705  1.00  43.69      X   O
ATOM   6871  N    SER   84      90.480  18.625  29.416  1.00  47.01      X   N
ATOM   6872  CA   SER   84      90.560  18.322  30.843  1.00  47.01      X   C
ATOM   6873  CB   SER   84      91.748  19.045  31.482  1.00  36.84      X   C
ATOM   6874  OG   SER   84      92.963  18.623  30.892  1.00  36.84      X   O
ATOM   6875  C    SER   84      89.270  18.757  31.516  1.00  47.01      X   C
ATOM   6876  O    SER   84      89.272  19.261  32.644  1.00  47.01      X   O
ATOM   6877  N    LEU   85      88.170  18.548  30.804  1.00  35.88      X   N
ATOM   6878  CA   LEU   85      86.842  18.920  31.273  1.00  35.88      X   C
ATOM   6879  CB   LEU   85      85.800  18.466  30.250  1.00  45.16      X   C
ATOM   6880  CG   LEU   85      85.854  19.211  28.921  1.00  45.16      X   C
ATOM   6881  CD1  LEU   85      84.875  18.608  27.936  1.00  45.16      X   C
ATOM   6882  CD2  LEU   85      85.536  20.672  29.178  1.00  45.16      X   C
ATOM   6883  C    LEU   85      86.450  18.396  32.652  1.00  35.88      X   C
ATOM   6884  O    LEU   85      86.175  17.208  32.818  1.00  35.88      X   O
ATOM   6885  N    ARG   86      86.415  19.290  33.636  1.00  55.90      X   N
ATOM   6886  CA   ARG   86      86.022  18.907  34.985  1.00  55.90      X   C
ATOM   6887  CB   ARG   86      86.606  19.864  36.023  1.00  50.18      X   C
ATOM   6888  CG   ARG   86      88.108  20.015  35.994  1.00  50.18      X   C
ATOM   6889  CD   ARG   86      88.620  20.357  37.385  1.00  50.18      X   C
ATOM   6890  NE   ARG   86      89.970  20.904  37.355  1.00  50.18      X   N
ATOM   6891  CZ   ARG   86      90.256  22.185  37.133  1.00  50.18      X   C
ATOM   6892  NH1  ARG   86      89.280  23.066  36.926  1.00  50.18      X   N
ATOM   6893  NH2  ARG   86      91.524  22.587  37.109  1.00  50.18      X   N
ATOM   6894  C    ARG   86      84.501  18.954  35.069  1.00  55.90      X   C
ATOM   6895  O    ARG   86      83.818  19.086  34.055  1.00  55.90      X   O
ATOM   6896  N    ALA   87      83.974  18.856  36.282  1.00  39.09      X   N
ATOM   6897  CA   ALA   87      82.533  18.893  36.485  1.00  39.09      X   C
ATOM   6898  CB   ALA   87      82.164  18.133  37.750  1.00  69.79      X   C
ATOM   6899  C    ALA   87      82.028  20.325  36.578  1.00  39.09      X   C
ATOM   6900  O    ALA   87      80.885  20.607  36.219  1.00  39.09      X   O
ATOM   6901  N    GLU   88      82.876  21.228  37.066  1.00  49.44      X   N
ATOM   6902  CA   GLU   88      82.492  22.628  37.197  1.00  49.44      X   C
ATOM   6903  CB   GLU   88      83.586  23.435  37.899  1.00  57.40      X   C
ATOM   6904  CG   GLU   88      84.189  22.765  39.107  1.00  57.40      X   C
ATOM   6905  CD   GLU   88      85.178  21.691  38.724  1.00  57.40      X   C
ATOM   6906  OE1  GLU   88      86.227  22.035  38.146  1.00  57.40      X   O
ATOM   6907  OE2  GLU   88      84.906  20.504  38.993  1.00  57.40      X   O
ATOM   6908  C    GLU   88      82.242  23.242  35.824  1.00  49.44      X   C
ATOM   6909  O    GLU   88      81.474  24.195  35.687  1.00  49.44      X   O
ATOM   6910  N    ASP   89      82.892  22.698  34.803  1.00  49.12      X   N
ATOM   6911  CA   ASP   89      82.720  23.229  33.464  1.00  49.12      X   C
ATOM   6912  CB   ASP   89      83.818  22.698  32.549  1.00  52.75      X   C
ATOM   6913  CG   ASP   89      85.194  22.903  33.124  1.00  52.75      X   C
ATOM   6914  OD1  ASP   89      85.430  23.960  33.752  1.00  52.75      X   O
ATOM   6915  OD2  ASP   89      86.043  22.011  32.936  1.00  52.75      X   O
ATOM   6916  C    ASP   89      81.348  22.914  32.871  1.00  49.12      X   C
ATOM   6917  O    ASP   89      80.981  23.459  31.834  1.00  49.12      X   O
ATOM   6918  N    THR   90      80.590  22.034  33.517  1.00  33.14      X   N
ATOM   6919  CA   THR   90      79.265  21.686  33.012  1.00  33.14      X   C
ATOM   6920  CB   THR   90      78.652  20.480  33.766  1.00  40.77      X   C
ATOM   6921  OG1  THR   90      78.585  20.770  35.162  1.00  40.77      X   O
ATOM   6922  CG2  THR   90      79.498  19.257  33.590  1.00  40.77      X   C
ATOM   6923  C    THR   90      78.361  22.899  33.174  1.00  33.14      X   C
ATOM   6924  O    THR   90      78.260  23.486  34.263  1.00  33.14      X   O
ATOM   6925  N    ALA   91      77.718  23.276  32.076  1.00  55.37      X   N
ATOM   6926  CA   ALA   91      76.832  24.428  32.058  1.00  55.37      X   C
ATOM   6927  CB   ALA   91      77.527  25.625  32.692  1.00   7.95      X   C
ATOM   6928  C    ALA   91      76.504  24.732  30.609  1.00  55.37      X   C
ATOM   6929  O    ALA   91      77.073  24.128  29.698  1.00  55.37      X   O
ATOM   6930  N    VAL   92      75.579  25.656  30.387  1.00  44.83      X   N
ATOM   6931  CA   VAL   92      75.243  26.017  29.021  1.00  44.83      X   C
ATOM   6932  CB   VAL   92      73.747  26.429  28.878  1.00  41.51      X   C
ATOM   6933  CG1  VAL   92      73.210  26.967  30.198  1.00  41.51      X   C
ATOM   6934  CG2  VAL   92      73.596  27.460  27.769  1.00  41.51      X   C
ATOM   6935  C    VAL   92      76.182  27.145  28.591  1.00  44.83      X   C
```

Fig. 19: A-96

| ATOM | 6936 | O   | VAL | 92  | 76.446 | 28.085 | 29.354 | 1.00 | 44.83 | X | O |
|------|------|-----|-----|-----|--------|--------|--------|------|-------|---|---|
| ATOM | 6937 | N   | TYR | 93  | 76.701 | 27.019 | 27.371 | 1.00 | 51.76 | X | N |
| ATOM | 6938 | CA  | TYR | 93  | 77.642 | 27.978 | 26.811 | 1.00 | 51.76 | X | C |
| ATOM | 6939 | CB  | TYR | 93  | 78.838 | 27.241 | 26.227 | 1.00 | 15.58 | X | C |
| ATOM | 6940 | CG  | TYR | 93  | 79.743 | 26.693 | 27.287 | 1.00 | 15.58 | X | C |
| ATOM | 6941 | CD1 | TYR | 93  | 79.520 | 25.443 | 27.841 | 1.00 | 15.58 | X | C |
| ATOM | 6942 | CE1 | TYR | 93  | 80.339 | 24.959 | 28.860 | 1.00 | 15.58 | X | C |
| ATOM | 6943 | CD2 | TYR | 93  | 80.802 | 27.454 | 27.777 | 1.00 | 15.58 | X | C |
| ATOM | 6944 | CE2 | TYR | 93  | 81.618 | 26.983 | 28.797 | 1.00 | 15.58 | X | C |
| ATOM | 6945 | CZ  | TYR | 93  | 81.384 | 25.735 | 29.328 | 1.00 | 15.58 | X | C |
| ATOM | 6946 | OH  | TYR | 93  | 82.223 | 25.253 | 30.297 | 1.00 | 15.58 | X | O |
| ATOM | 6947 | C   | TYR | 93  | 77.091 | 28.908 | 25.757 | 1.00 | 51.76 | X | C |
| ATOM | 6948 | O   | TYR | 93  | 76.223 | 28.534 | 24.972 | 1.00 | 51.76 | X | O |
| ATOM | 6949 | N   | TYR | 94  | 77.633 | 30.121 | 25.729 | 1.00 | 29.82 | X | N |
| ATOM | 6950 | CA  | TYR | 94  | 77.210 | 31.143 | 24.774 | 1.00 | 29.82 | X | C |
| ATOM | 6951 | CB  | TYR | 94  | 76.448 | 32.267 | 25.489 | 1.00 | 45.66 | X | C |
| ATOM | 6952 | CG  | TYR | 94  | 75.282 | 31.829 | 26.343 | 1.00 | 45.66 | X | C |
| ATOM | 6953 | CD1 | TYR | 94  | 74.053 | 31.494 | 25.771 | 1.00 | 45.66 | X | C |
| ATOM | 6954 | CE1 | TYR | 94  | 72.979 | 31.108 | 26.564 | 1.00 | 45.66 | X | C |
| ATOM | 6955 | CD2 | TYR | 94  | 75.405 | 31.763 | 27.733 | 1.00 | 45.66 | X | C |
| ATOM | 6956 | CE2 | TYR | 94  | 74.342 | 31.376 | 28.532 | 1.00 | 45.66 | X | C |
| ATOM | 6957 | CZ  | TYR | 94  | 73.132 | 31.051 | 27.943 | 1.00 | 45.66 | X | C |
| ATOM | 6958 | OH  | TYR | 94  | 72.082 | 30.665 | 28.743 | 1.00 | 45.66 | X | O |
| ATOM | 6959 | C   | TYR | 94  | 78.389 | 31.799 | 24.074 | 1.00 | 29.82 | X | C |
| ATOM | 6960 | O   | TYR | 94  | 79.360 | 32.174 | 24.727 | 1.00 | 29.82 | X | O |
| ATOM | 6961 | N   | CYS | 95  | 78.332 | 31.923 | 22.752 | 1.00 | 22.64 | X | N |
| ATOM | 6962 | CA  | CYS | 95  | 79.394 | 32.659 | 22.091 | 1.00 | 22.64 | X | C |
| ATOM | 6963 | C   | CYS | 95  | 78.871 | 34.094 | 22.103 | 1.00 | 22.64 | X | C |
| ATOM | 6964 | O   | CYS | 95  | 77.656 | 34.337 | 22.170 | 1.00 | 22.64 | X | O |
| ATOM | 6965 | CB  | CYS | 95  | 79.660 | 32.185 | 20.660 | 1.00 | 55.79 | X | C |
| ATOM | 6966 | SG  | CYS | 95  | 78.222 | 31.748 | 19.650 | 1.00 | 55.79 | X | S |
| ATOM | 6967 | N   | THR | 96  | 79.778 | 35.057 | 22.067 | 1.00 | 43.77 | X | N |
| ATOM | 6968 | CA  | THR | 96  | 79.337 | 36.435 | 22.107 | 1.00 | 43.77 | X | C |
| ATOM | 6969 | CB  | THR | 96  | 79.387 | 36.985 | 23.556 | 1.00 | 38.47 | X | C |
| ATOM | 6970 | OG1 | THR | 96  | 80.723 | 36.865 | 24.069 | 1.00 | 38.47 | X | O |
| ATOM | 6971 | CG2 | THR | 96  | 78.421 | 36.220 | 24.453 | 1.00 | 38.47 | X | C |
| ATOM | 6972 | C   | THR | 96  | 80.130 | 37.370 | 21.220 | 1.00 | 43.77 | X | C |
| ATOM | 6973 | O   | THR | 96  | 81.328 | 37.174 | 20.987 | 1.00 | 43.77 | X | O |
| ATOM | 6974 | N   | ARG | 97  | 79.432 | 38.379 | 20.709 | 1.00 | 52.60 | X | N |
| ATOM | 6975 | CA  | ARG | 97  | 80.068 | 39.400 | 19.899 | 1.00 | 52.60 | X | C |
| ATOM | 6976 | CB  | ARG | 97  | 79.237 | 39.799 | 18.689 | 1.00 | 26.06 | X | C |
| ATOM | 6977 | CG  | ARG | 97  | 80.052 | 40.645 | 17.733 | 1.00 | 26.06 | X | C |
| ATOM | 6978 | CD  | ARG | 97  | 79.235 | 41.249 | 16.624 | 1.00 | 26.06 | X | C |
| ATOM | 6979 | NE  | ARG | 97  | 78.494 | 42.412 | 17.074 | 1.00 | 26.06 | X | N |
| ATOM | 6980 | CZ  | ARG | 97  | 77.853 | 43.231 | 16.255 | 1.00 | 26.06 | X | C |
| ATOM | 6981 | NH1 | ARG | 97  | 77.873 | 43.004 | 14.948 | 1.00 | 26.06 | X | N |
| ATOM | 6982 | NH2 | ARG | 97  | 77.187 | 44.271 | 16.742 | 1.00 | 26.06 | X | N |
| ATOM | 6983 | C   | ARG | 97  | 80.142 | 40.590 | 20.820 | 1.00 | 52.60 | X | C |
| ATOM | 6984 | O   | ARG | 97  | 79.116 | 41.100 | 21.260 | 1.00 | 52.60 | X | O |
| ATOM | 6985 | N   | GLY | 98  | 81.353 | 41.020 | 21.129 | 1.00 | 31.82 | X | N |
| ATOM | 6986 | CA  | GLY | 98  | 81.505 | 42.162 | 22.004 | 1.00 | 31.82 | X | C |
| ATOM | 6987 | C   | GLY | 98  | 81.635 | 43.450 | 21.225 | 1.00 | 31.82 | X | C |
| ATOM | 6988 | O   | GLY | 98  | 81.903 | 43.452 | 20.020 | 1.00 | 31.82 | X | O |
| ATOM | 6989 | N   | PHE | 99  | 81.416 | 44.558 | 21.913 | 1.00 | 20.36 | X | N |
| ATOM | 6990 | CA  | PHE | 99  | 81.554 | 45.859 | 21.289 | 1.00 | 20.36 | X | C |
| ATOM | 6991 | CB  | PHE | 99  | 80.358 | 46.753 | 21.621 | 1.00 | 37.93 | X | C |
| ATOM | 6992 | CG  | PHE | 99  | 80.633 | 48.214 | 21.431 | 1.00 | 37.93 | X | C |
| ATOM | 6993 | CD1 | PHE | 99  | 80.968 | 49.015 | 22.517 | 1.00 | 37.93 | X | C |
| ATOM | 6994 | CD2 | PHE | 99  | 80.606 | 48.783 | 20.158 | 1.00 | 37.93 | X | C |
| ATOM | 6995 | CE1 | PHE | 99  | 81.276 | 50.355 | 22.339 | 1.00 | 37.93 | X | C |
| ATOM | 6996 | CE2 | PHE | 99  | 80.913 | 50.127 | 19.967 | 1.00 | 37.93 | X | C |
| ATOM | 6997 | CZ  | PHE | 99  | 81.250 | 50.914 | 21.058 | 1.00 | 37.93 | X | C |
| ATOM | 6998 | C   | PHE | 99  | 82.836 | 46.468 | 21.835 | 1.00 | 20.36 | X | C |
| ATOM | 6999 | O   | PHE | 99  | 83.239 | 46.164 | 22.969 | 1.00 | 20.36 | X | O |
| ATOM | 7000 | N   | GLY | 100 | 83.480 | 47.309 | 21.030 | 1.00 | 25.28 | X | N |
| ATOM | 7001 | CA  | GLY | 100 | 84.704 | 47.954 | 21.469 | 1.00 | 25.28 | X | C |
| ATOM | 7002 | C   | GLY | 100 | 85.850 | 46.983 | 21.672 | 1.00 | 25.28 | X | C |
| ATOM | 7003 | O   | GLY | 100 | 86.390 | 46.466 | 20.700 | 1.00 | 25.28 | X | O |
| ATOM | 7004 | N   | ASP | 101 | 86.231 | 46.744 | 22.926 | 1.00 | 27.39 | X | N |
| ATOM | 7005 | CA  | ASP | 101 | 87.315 | 45.814 | 23.233 | 1.00 | 27.39 | X | C |
| ATOM | 7006 | CB  | ASP | 101 | 88.175 | 46.338 | 24.396 | 1.00 | 32.17 | X | C |
| ATOM | 7007 | CG  | ASP | 101 | 89.037 | 47.540 | 24.013 | 1.00 | 32.17 | X | C |
| ATOM | 7008 | OD1 | ASP | 101 | 89.287 | 47.744 | 22.812 | 1.00 | 32.17 | X | O |

Fig. 19: A-97

| | | | | | | | | | | | |
|---|---|---|---|---|---|---|---|---|---|---|---|
| ATOM | 7009 | CD2 | ASP | 101 | 89.483 | 48.274 | 24.920 | 1.00 | 32.17 | X | O |
| ATOM | 7010 | C   | ASP | 101 | 86.773 | 44.418 | 23.596 | 1.00 | 27.39 | X | C |
| ATOM | 7011 | O   | ASP | 101 | 87.549 | 43.518 | 23.929 | 1.00 | 27.39 | X | O |
| ATOM | 7012 | N   | GLY | 102 | 85.449 | 44.250 | 23.538 | 1.00 | 18.22 | X | N |
| ATOM | 7013 | CA  | GLY | 102 | 84.822 | 42.973 | 23.861 | 1.00 | 18.22 | X | C |
| ATOM | 7014 | C   | GLY | 102 | 83.925 | 42.948 | 25.100 | 1.00 | 18.22 | X | C |
| ATOM | 7015 | O   | GLY | 102 | 83.031 | 42.113 | 25.198 | 1.00 | 18.22 | X | O |
| ATOM | 7016 | N   | GLY | 103 | 84.147 | 43.870 | 26.034 | 1.00 | 34.16 | X | N |
| ATOM | 7017 | CA  | GLY | 103 | 83.370 | 43.915 | 27.268 | 1.00 | 34.16 | X | C |
| ATOM | 7018 | C   | GLY | 103 | 81.850 | 43.964 | 27.216 | 1.00 | 34.16 | X | C |
| ATOM | 7019 | O   | GLY | 103 | 81.182 | 43.416 | 28.087 | 1.00 | 34.16 | X | O |
| ATOM | 7020 | N   | TYR | 104 | 81.290 | 44.649 | 26.230 | 1.00 | 25.31 | X | N |
| ATOM | 7021 | CA  | TYR | 104 | 79.839 | 44.732 | 26.096 | 1.00 | 25.31 | X | C |
| ATOM | 7022 | CB  | TYR | 104 | 79.433 | 46.131 | 25.639 | 1.00 | 26.21 | X | C |
| ATOM | 7023 | CG  | TYR | 104 | 77.989 | 46.260 | 25.234 | 1.00 | 26.21 | X | C |
| ATOM | 7024 | CD1 | TYR | 104 | 77.635 | 46.980 | 24.087 | 1.00 | 26.21 | X | C |
| ATOM | 7025 | CE1 | TYR | 104 | 76.309 | 47.079 | 23.677 | 1.00 | 26.21 | X | C |
| ATOM | 7026 | CD2 | TYR | 104 | 76.972 | 45.646 | 25.972 | 1.00 | 26.21 | X | C |
| ATOM | 7027 | CE2 | TYR | 104 | 75.639 | 45.742 | 25.573 | 1.00 | 26.21 | X | C |
| ATOM | 7028 | CZ  | TYR | 104 | 75.323 | 46.456 | 24.422 | 1.00 | 26.21 | X | C |
| ATOM | 7029 | OH  | TYR | 104 | 74.025 | 46.523 | 23.995 | 1.00 | 26.21 | X | O |
| ATOM | 7030 | C   | TYR | 104 | 79.484 | 43.700 | 25.037 | 1.00 | 25.31 | X | C |
| ATOM | 7031 | O   | TYR | 104 | 79.905 | 43.810 | 23.886 | 1.00 | 25.31 | X | O |
| ATOM | 7032 | N   | PHE | 105 | 78.728 | 42.686 | 25.432 | 1.00 | 17.54 | X | N |
| ATOM | 7033 | CA  | PHE | 105 | 78.354 | 41.616 | 24.518 | 1.00 | 17.54 | X | C |
| ATOM | 7034 | CB  | PHE | 105 | 78.088 | 40.337 | 25.309 | 1.00 | 20.12 | X | C |
| ATOM | 7035 | CG  | PHE | 105 | 79.154 | 40.010 | 26.312 | 1.00 | 20.12 | X | C |
| ATOM | 7036 | CD1 | PHE | 105 | 80.478 | 39.817 | 25.908 | 1.00 | 20.12 | X | C |
| ATOM | 7037 | CD2 | PHE | 105 | 78.832 | 39.891 | 27.661 | 1.00 | 20.12 | X | C |
| ATOM | 7038 | CE1 | PHE | 105 | 81.472 | 39.511 | 26.836 | 1.00 | 20.12 | X | C |
| ATOM | 7039 | CE2 | PHE | 105 | 79.808 | 39.586 | 28.594 | 1.00 | 20.12 | X | C |
| ATOM | 7040 | CZ  | PHE | 105 | 81.136 | 39.395 | 28.183 | 1.00 | 20.12 | X | C |
| ATOM | 7041 | C   | PHE | 105 | 77.127 | 41.938 | 23.669 | 1.00 | 17.54 | X | C |
| ATOM | 7042 | O   | PHE | 105 | 75.989 | 41.689 | 24.080 | 1.00 | 17.54 | X | O |
| ATOM | 7043 | N   | ASP | 106 | 77.376 | 42.488 | 22.482 | 1.00 | 46.21 | X | N |
| ATOM | 7044 | CA  | ASP | 106 | 76.327 | 42.840 | 21.532 | 1.00 | 46.21 | X | C |
| ATOM | 7045 | CB  | ASP | 106 | 76.908 | 43.074 | 20.143 | 1.00 | 54.80 | X | C |
| ATOM | 7046 | CG  | ASP | 106 | 77.456 | 44.442 | 19.976 | 1.00 | 54.80 | X | C |
| ATOM | 7047 | OD1 | ASP | 106 | 76.774 | 45.384 | 20.429 | 1.00 | 54.80 | X | O |
| ATOM | 7048 | OD2 | ASP | 106 | 78.552 | 44.576 | 19.387 | 1.00 | 54.80 | X | O |
| ATOM | 7049 | C   | ASP | 106 | 75.355 | 41.705 | 21.399 | 1.00 | 46.21 | X | C |
| ATOM | 7050 | O   | ASP | 106 | 74.281 | 41.707 | 21.974 | 1.00 | 46.21 | X | O |
| ATOM | 7051 | N   | VAL | 107 | 75.769 | 40.732 | 20.603 | 1.00 | 33.04 | X | N |
| ATOM | 7052 | CA  | VAL | 107 | 74.979 | 39.559 | 20.312 | 1.00 | 33.04 | X | C |
| ATOM | 7053 | CB  | VAL | 107 | 75.180 | 39.152 | 18.858 | 1.00 | 31.62 | X | C |
| ATOM | 7054 | CG1 | VAL | 107 | 74.156 | 38.100 | 18.457 | 1.00 | 31.62 | X | C |
| ATOM | 7055 | CG2 | VAL | 107 | 75.092 | 40.388 | 17.980 | 1.00 | 31.62 | X | C |
| ATOM | 7056 | C   | VAL | 107 | 75.322 | 38.379 | 21.197 | 1.00 | 33.04 | X | C |
| ATOM | 7057 | O   | VAL | 107 | 76.413 | 38.296 | 21.763 | 1.00 | 33.04 | X | O |
| ATOM | 7058 | N   | TRP | 108 | 74.359 | 37.474 | 21.306 | 1.00 | 37.95 | X | N |
| ATOM | 7059 | CA  | TRP | 108 | 74.501 | 36.266 | 22.092 | 1.00 | 37.95 | X | C |
| ATOM | 7060 | CB  | TRP | 108 | 73.674 | 36.351 | 23.372 | 1.00 | 32.89 | X | C |
| ATOM | 7061 | CG  | TRP | 108 | 74.212 | 37.315 | 24.368 | 1.00 | 32.89 | X | C |
| ATOM | 7062 | CD2 | TRP | 108 | 74.712 | 37.004 | 25.668 | 1.00 | 32.89 | X | C |
| ATOM | 7063 | CE2 | TRP | 108 | 75.114 | 38.216 | 26.261 | 1.00 | 32.89 | X | C |
| ATOM | 7064 | CE3 | TRP | 108 | 74.861 | 35.816 | 26.390 | 1.00 | 32.89 | X | C |
| ATOM | 7065 | CD1 | TRP | 108 | 74.327 | 38.664 | 24.225 | 1.00 | 32.89 | X | C |
| ATOM | 7066 | NE1 | TRP | 108 | 74.867 | 39.216 | 25.358 | 1.00 | 32.89 | X | N |
| ATOM | 7067 | CZ2 | TRP | 108 | 75.655 | 38.278 | 27.543 | 1.00 | 32.89 | X | C |
| ATOM | 7068 | CZ3 | TRP | 108 | 75.402 | 35.878 | 27.670 | 1.00 | 32.89 | X | C |
| ATOM | 7069 | CH2 | TRP | 108 | 75.792 | 37.103 | 28.231 | 1.00 | 32.89 | X | C |
| ATOM | 7070 | C   | TRP | 108 | 73.984 | 35.119 | 21.260 | 1.00 | 37.95 | X | C |
| ATOM | 7071 | O   | TRP | 108 | 73.067 | 35.296 | 20.451 | 1.00 | 37.95 | X | O |
| ATOM | 7072 | N   | GLY | 109 | 74.568 | 33.942 | 21.460 | 1.00 | 75.91 | X | N |
| ATOM | 7073 | CA  | GLY | 109 | 74.124 | 32.770 | 20.732 | 1.00 | 75.91 | X | C |
| ATOM | 7074 | C   | GLY | 109 | 72.791 | 32.307 | 21.288 | 1.00 | 75.91 | X | C |
| ATOM | 7075 | O   | GLY | 109 | 71.997 | 33.114 | 21.780 | 1.00 | 75.91 | X | O |
| ATOM | 7076 | N   | GLN | 110 | 72.537 | 31.007 | 21.207 | 1.00 | 35.37 | X | N |
| ATOM | 7077 | CA  | GLN | 110 | 71.291 | 30.457 | 21.724 | 1.00 | 35.37 | X | C |
| ATOM | 7078 | CB  | GLN | 110 | 70.652 | 29.498 | 20.714 | 1.00 | 98.79 | X | C |
| ATOM | 7079 | CG  | GLN | 110 | 71.443 | 28.228 | 20.442 | 1.00 | 98.79 | X | C |
| ATOM | 7080 | CD  | GLN | 110 | 72.597 | 28.441 | 19.485 | 1.00 | 98.79 | X | C |
| ATOM | 7081 | OE1 | GLN | 110 | 73.318 | 27.502 | 19.152 | 1.00 | 98.79 | X | O |

Fig. 19: A-98

| ATOM | 7082 | NE2 | GLN | 110 | 72.775 | 29.675 | 19.031 | 1.00 | 98.79 | X | N |
|---|---|---|---|---|---|---|---|---|---|---|---|
| ATOM | 7083 | C | GLN | 110 | 71.610 | 29.708 | 23.004 | 1.00 | 35.37 | X | C |
| ATOM | 7084 | O | GLN | 110 | 70.793 | 29.626 | 23.918 | 1.00 | 35.37 | X | O |
| ATOM | 7085 | N | GLY | 111 | 72.831 | 29.194 | 23.067 | 1.00 | 45.85 | X | N |
| ATOM | 7086 | CA | GLY | 111 | 73.257 | 28.430 | 24.219 | 1.00 | 45.85 | X | C |
| ATOM | 7087 | C | GLY | 111 | 73.349 | 26.981 | 23.781 | 1.00 | 45.85 | X | C |
| ATOM | 7088 | O | GLY | 111 | 72.596 | 26.540 | 22.913 | 1.00 | 45.85 | X | O |
| ATOM | 7089 | N | THR | 112 | 74.281 | 26.243 | 24.369 | 1.00 | 30.06 | X | N |
| ATOM | 7090 | CA | THR | 112 | 74.480 | 24.840 | 24.040 | 1.00 | 30.06 | X | C |
| ATOM | 7091 | CB | THR | 112 | 75.550 | 24.696 | 22.962 | 1.00 | 24.67 | X | C |
| ATOM | 7092 | OG1 | THR | 112 | 75.636 | 23.327 | 22.562 | 1.00 | 24.67 | X | O |
| ATOM | 7093 | CG2 | THR | 112 | 76.903 | 25.177 | 23.487 | 1.00 | 24.67 | X | C |
| ATOM | 7094 | C | THR | 112 | 74.944 | 24.184 | 25.328 | 1.00 | 30.06 | X | C |
| ATOM | 7095 | O | THR | 112 | 75.883 | 24.658 | 25.960 | 1.00 | 30.06 | X | O |
| ATOM | 7096 | N | LEU | 113 | 74.292 | 23.102 | 25.725 | 1.00 | 42.99 | X | N |
| ATOM | 7097 | CA | LEU | 113 | 74.646 | 22.449 | 26.981 | 1.00 | 42.99 | X | C |
| ATOM | 7098 | CB | LEU | 113 | 73.434 | 21.652 | 27.499 | 1.00 | 32.90 | X | C |
| ATOM | 7099 | CG | LEU | 113 | 73.366 | 21.006 | 28.896 | 1.00 | 32.90 | X | C |
| ATOM | 7100 | CD1 | LEU | 113 | 73.914 | 19.580 | 28.860 | 1.00 | 32.90 | X | C |
| ATOM | 7101 | CD2 | LEU | 113 | 74.109 | 21.884 | 29.889 | 1.00 | 32.90 | X | C |
| ATOM | 7102 | C | LEU | 113 | 75.890 | 21.560 | 26.932 | 1.00 | 42.99 | X | C |
| ATOM | 7103 | O | LEU | 113 | 76.190 | 20.899 | 25.929 | 1.00 | 42.99 | X | O |
| ATOM | 7104 | N | VAL | 114 | 76.621 | 21.561 | 28.037 | 1.00 | 35.21 | X | N |
| ATOM | 7105 | CA | VAL | 114 | 77.815 | 20.754 | 28.141 | 1.00 | 35.21 | X | C |
| ATOM | 7106 | CB | VAL | 114 | 79.070 | 21.592 | 27.837 | 1.00 | 43.74 | X | C |
| ATOM | 7107 | CG1 | VAL | 114 | 80.324 | 20.909 | 28.384 | 1.00 | 43.74 | X | C |
| ATOM | 7108 | CG2 | VAL | 114 | 79.189 | 21.774 | 26.331 | 1.00 | 43.74 | X | C |
| ATOM | 7109 | C | VAL | 114 | 77.906 | 20.141 | 29.529 | 1.00 | 35.21 | X | C |
| ATOM | 7110 | O | VAL | 114 | 78.064 | 20.845 | 30.529 | 1.00 | 35.21 | X | O |
| ATOM | 7111 | N | THR | 115 | 77.788 | 18.819 | 29.575 | 1.00 | 58.81 | X | N |
| ATOM | 7112 | CA | THR | 115 | 77.855 | 18.099 | 30.829 | 1.00 | 58.81 | X | C |
| ATOM | 7113 | CB | THR | 115 | 76.717 | 17.098 | 30.956 | 1.00 | 63.66 | X | C |
| ATOM | 7114 | OG1 | THR | 115 | 75.549 | 17.620 | 30.311 | 1.00 | 63.66 | X | O |
| ATOM | 7115 | CG2 | THR | 115 | 76.412 | 16.849 | 32.422 | 1.00 | 63.66 | X | C |
| ATOM | 7116 | C | THR | 115 | 79.161 | 17.337 | 30.903 | 1.00 | 58.81 | X | C |
| ATOM | 7117 | O | THR | 115 | 79.831 | 17.121 | 29.893 | 1.00 | 58.81 | X | O |
| ATOM | 7118 | N | VAL | 116 | 79.516 | 16.933 | 32.114 | 1.00 | 73.79 | X | N |
| ATOM | 7119 | CA | VAL | 116 | 80.741 | 16.191 | 32.352 | 1.00 | 73.79 | X | C |
| ATOM | 7120 | CB | VAL | 116 | 81.899 | 17.135 | 32.747 | 1.00 | 46.90 | X | C |
| ATOM | 7121 | CG1 | VAL | 116 | 83.172 | 16.339 | 32.941 | 1.00 | 46.90 | X | C |
| ATOM | 7122 | CG2 | VAL | 116 | 82.101 | 18.194 | 31.667 | 1.00 | 46.90 | X | C |
| ATOM | 7123 | C | VAL | 116 | 80.478 | 15.202 | 33.482 | 1.00 | 73.79 | X | C |
| ATOM | 7124 | O | VAL | 116 | 80.382 | 15.584 | 34.649 | 1.00 | 73.79 | X | O |
| ATOM | 7125 | N | SER | 117 | 80.349 | 13.931 | 33.114 | 1.00 | 65.98 | X | N |
| ATOM | 7126 | CA | SER | 117 | 80.088 | 12.858 | 34.066 | 1.00 | 65.98 | X | C |
| ATOM | 7127 | CB | SER | 117 | 78.608 | 12.861 | 34.458 | 1.00 | 62.16 | X | C |
| ATOM | 7128 | OG | SER | 117 | 77.776 | 12.825 | 33.308 | 1.00 | 62.16 | X | O |
| ATOM | 7129 | C | SER | 117 | 80.454 | 11.521 | 33.427 | 1.00 | 65.98 | X | C |
| ATOM | 7130 | O | SER | 117 | 81.498 | 11.396 | 32.789 | 1.00 | 65.98 | X | O |
| ATOM | 7131 | N | SER | 118 | 79.587 | 10.524 | 33.594 | 1.00 | 80.64 | X | N |
| ATOM | 7132 | CA | SER | 118 | 79.828 | 9.208 | 33.014 | 1.00 | 80.64 | X | C |
| ATOM | 7133 | CB | SER | 118 | 80.556 | 8.329 | 34.031 | 1.00 | 66.12 | X | C |
| ATOM | 7134 | OG | SER | 118 | 81.771 | 8.944 | 34.438 | 1.00 | 66.12 | X | O |
| ATOM | 7135 | C | SER | 118 | 78.524 | 8.543 | 32.563 | 1.00 | 80.64 | X | C |
| ATOM | 7136 | O | SER | 118 | 77.445 | 9.021 | 32.973 | 1.00 | 79.69 | X | O |
| ATOM | 7137 | OXT | SER | 118 | 78.594 | 7.553 | 31.804 | 1.00 | 65.17 | X | O |
| ATOM | 7138 | CB | ILE | 2 | 85.629 | 44.767 | 39.417 | 1.00 | 24.34 | Y | C |
| ATOM | 7139 | CG2 | ILE | 2 | 84.329 | 45.456 | 39.830 | 1.00 | 24.34 | Y | C |
| ATOM | 7140 | CG1 | ILE | 2 | 86.754 | 45.793 | 39.275 | 1.00 | 24.34 | Y | C |
| ATOM | 7141 | CD1 | ILE | 2 | 86.473 | 46.861 | 38.237 | 1.00 | 24.34 | Y | C |
| ATOM | 7142 | C | ILE | 2 | 84.812 | 42.776 | 40.634 | 1.00 | 29.24 | Y | C |
| ATOM | 7143 | O | ILE | 2 | 84.508 | 41.962 | 39.756 | 1.00 | 29.24 | Y | O |
| ATOM | 7144 | N | ILE | 2 | 87.254 | 42.972 | 40.068 | 1.00 | 29.24 | Y | N |
| ATOM | 7145 | CA | ILE | 2 | 86.011 | 43.705 | 40.462 | 1.00 | 29.24 | Y | C |
| ATOM | 7146 | N | GLN | 3 | 84.122 | 42.926 | 41.761 | 1.00 | 42.94 | Y | N |
| ATOM | 7147 | CA | GLN | 3 | 82.960 | 42.107 | 42.070 | 1.00 | 42.94 | Y | C |
| ATOM | 7148 | CB | GLN | 3 | 83.156 | 41.435 | 43.434 | 1.00 | 85.86 | Y | C |
| ATOM | 7149 | CG | GLN | 3 | 82.045 | 40.492 | 43.850 | 1.00 | 85.86 | Y | C |
| ATOM | 7150 | CD | GLN | 3 | 82.371 | 39.747 | 45.131 | 1.00 | 85.86 | Y | C |
| ATOM | 7151 | OE1 | GLN | 3 | 81.534 | 39.028 | 45.670 | 1.00 | 85.86 | Y | O |
| ATOM | 7152 | NE2 | GLN | 3 | 83.597 | 39.911 | 45.621 | 1.00 | 85.86 | Y | N |
| ATOM | 7153 | C | GLN | 3 | 81.684 | 42.943 | 42.059 | 1.00 | 42.94 | Y | C |
| ATOM | 7154 | O | GLN | 3 | 81.626 | 44.026 | 42.645 | 1.00 | 42.94 | Y | O |

Fig. 19: A-99

| | | | | | | | | | | |
|---|---|---|---|---|---|---|---|---|---|---|
| ATOM | 7155 | N | LEU | 4 | 80.666 | 42.426 | 41.380 | 1.00 | 33.35 | Y N |
| ATOM | 7156 | CA | LEU | 4 | 79.378 | 43.098 | 41.269 | 1.00 | 33.35 | Y C |
| ATOM | 7157 | CB | LEU | 4 | 78.954 | 43.160 | 39.800 | 1.00 | 47.12 | Y C |
| ATOM | 7158 | CG | LEU | 4 | 79.344 | 44.389 | 38.979 | 1.00 | 47.12 | Y C |
| ATOM | 7159 | CD1 | LEU | 4 | 80.683 | 44.945 | 39.443 | 1.00 | 47.12 | Y C |
| ATOM | 7160 | CD2 | LEU | 4 | 79.370 | 44.008 | 37.512 | 1.00 | 47.12 | Y C |
| ATOM | 7161 | C | LEU | 4 | 78.296 | 42.395 | 42.073 | 1.00 | 33.35 | Y C |
| ATOM | 7162 | O | LEU | 4 | 78.012 | 41.215 | 41.852 | 1.00 | 33.35 | Y O |
| ATOM | 7163 | N | THR | 5 | 77.691 | 43.129 | 43.001 | 1.00 | 42.53 | Y N |
| ATOM | 7164 | CA | THR | 5 | 76.628 | 42.586 | 43.833 | 1.00 | 42.53 | Y C |
| ATOM | 7165 | CB | THR | 5 | 77.100 | 42.482 | 45.315 | 1.00 | 37.95 | Y C |
| ATOM | 7166 | OG1 | THR | 5 | 75.992 | 42.697 | 46.196 | 1.00 | 37.95 | Y O |
| ATOM | 7167 | CG2 | THR | 5 | 78.209 | 43.479 | 45.604 | 1.00 | 37.95 | Y C |
| ATOM | 7168 | C | THR | 5 | 75.348 | 43.426 | 43.699 | 1.00 | 42.53 | Y C |
| ATOM | 7169 | O | THR | 5 | 75.306 | 44.593 | 44.089 | 1.00 | 42.53 | Y O |
| ATOM | 7170 | N | GLN | 6 | 74.318 | 42.806 | 43.119 | 1.00 | 44.79 | Y N |
| ATOM | 7171 | CA | GLN | 6 | 73.009 | 43.423 | 42.877 | 1.00 | 44.79 | Y C |
| ATOM | 7172 | CB | GLN | 6 | 72.340 | 42.791 | 41.641 | 1.00 | 23.30 | Y C |
| ATOM | 7173 | CG | GLN | 6 | 73.239 | 42.643 | 40.421 | 1.00 | 23.30 | Y C |
| ATOM | 7174 | CD | GLN | 6 | 72.520 | 42.055 | 39.195 | 1.00 | 23.30 | Y C |
| ATOM | 7175 | OE1 | GLN | 6 | 73.163 | 41.628 | 38.231 | 1.00 | 23.30 | Y O |
| ATOM | 7176 | NE2 | GLN | 6 | 71.193 | 42.046 | 39.226 | 1.00 | 23.30 | Y N |
| ATOM | 7177 | C | GLN | 6 | 72.050 | 43.274 | 44.061 | 1.00 | 44.79 | Y C |
| ATOM | 7178 | O | GLN | 6 | 72.195 | 42.370 | 44.883 | 1.00 | 44.79 | Y O |
| ATOM | 7179 | N | SER | 7 | 71.057 | 44.156 | 44.128 | 1.00 | 78.31 | Y N |
| ATOM | 7180 | CA | SER | 7 | 70.069 | 44.113 | 45.201 | 1.00 | 78.31 | Y C |
| ATOM | 7181 | CB | SER | 7 | 70.640 | 44.715 | 46.480 | 1.00 | 85.46 | Y C |
| ATOM | 7182 | OG | SER | 7 | 71.028 | 46.058 | 46.262 | 1.00 | 85.46 | Y O |
| ATOM | 7183 | C | SER | 7 | 68.797 | 44.855 | 44.824 | 1.00 | 78.31 | Y C |
| ATOM | 7184 | O | SER | 7 | 68.847 | 45.923 | 44.220 | 1.00 | 78.31 | Y O |
| ATOM | 7185 | N | PRO | 8 | 67.633 | 44.283 | 45.165 | 1.00 | 83.70 | Y N |
| ATOM | 7186 | CD | PRO | 8 | 66.277 | 44.777 | 44.863 | 1.00 | 54.81 | Y C |
| ATOM | 7187 | CA | PRO | 8 | 67.571 | 43.000 | 45.865 | 1.00 | 83.70 | Y C |
| ATOM | 7188 | CB | PRO | 8 | 66.097 | 42.880 | 46.226 | 1.00 | 54.81 | Y C |
| ATOM | 7189 | CG | PRO | 8 | 65.427 | 43.534 | 45.054 | 1.00 | 54.81 | Y C |
| ATOM | 7190 | C | PRO | 8 | 68.015 | 41.895 | 44.925 | 1.00 | 83.70 | Y C |
| ATOM | 7191 | O | PRO | 8 | 68.274 | 42.136 | 43.745 | 1.00 | 83.70 | Y O |
| ATOM | 7192 | N | SER | 9 | 68.111 | 40.685 | 45.455 | 1.00 | 47.38 | Y N |
| ATOM | 7193 | CA | SER | 9 | 68.504 | 39.541 | 44.651 | 1.00 | 47.38 | Y C |
| ATOM | 7194 | CB | SER | 9 | 69.145 | 38.481 | 45.543 | 1.00 | 74.91 | Y C |
| ATOM | 7195 | OG | SER | 9 | 70.214 | 39.045 | 46.283 | 1.00 | 74.91 | Y O |
| ATOM | 7196 | C | SER | 9 | 67.232 | 39.002 | 44.025 | 1.00 | 47.38 | Y C |
| ATOM | 7197 | O | SER | 9 | 67.237 | 38.434 | 42.936 | 1.00 | 47.38 | Y O |
| ATOM | 7198 | N | SER | 10 | 66.134 | 39.214 | 44.736 | 1.00 | 60.45 | Y N |
| ATOM | 7199 | CA | SER | 10 | 64.819 | 38.770 | 44.305 | 1.00 | 60.45 | Y C |
| ATOM | 7200 | CB | SER | 10 | 64.476 | 37.449 | 44.991 | 1.00 | 51.82 | Y C |
| ATOM | 7201 | OG | SER | 10 | 63.252 | 36.935 | 44.504 | 1.00 | 51.82 | Y O |
| ATOM | 7202 | C | SER | 10 | 63.797 | 39.840 | 44.691 | 1.00 | 60.45 | Y C |
| ATOM | 7203 | O | SER | 10 | 63.976 | 40.552 | 45.683 | 1.00 | 60.45 | Y O |
| ATOM | 7204 | N | LEU | 11 | 62.730 | 39.964 | 43.910 | 1.00 | 65.48 | Y N |
| ATOM | 7205 | CA | LEU | 11 | 61.710 | 40.964 | 44.206 | 1.00 | 65.48 | Y C |
| ATOM | 7206 | CB | LEU | 11 | 62.206 | 42.366 | 43.830 | 1.00 | 51.28 | Y C |
| ATOM | 7207 | CG | LEU | 11 | 62.310 | 42.727 | 42.342 | 1.00 | 51.28 | Y C |
| ATOM | 7208 | CD1 | LEU | 11 | 60.949 | 43.139 | 41.803 | 1.00 | 51.28 | Y C |
| ATOM | 7209 | CD2 | LEU | 11 | 63.294 | 43.877 | 42.168 | 1.00 | 51.28 | Y C |
| ATOM | 7210 | C | LEU | 11 | 60.413 | 40.680 | 43.473 | 1.00 | 65.48 | Y C |
| ATOM | 7211 | O | LEU | 11 | 60.412 | 40.363 | 42.282 | 1.00 | 65.48 | Y O |
| ATOM | 7212 | N | SER | 12 | 59.305 | 40.803 | 44.189 | 1.00 | 84.56 | Y N |
| ATOM | 7213 | CA | SER | 12 | 58.004 | 40.567 | 43.595 | 1.00 | 84.56 | Y C |
| ATOM | 7214 | CB | SER | 12 | 57.209 | 39.578 | 44.445 | 1.00 | 71.89 | Y C |
| ATOM | 7215 | OG | SER | 12 | 56.137 | 39.026 | 43.705 | 1.00 | 71.89 | Y O |
| ATOM | 7216 | C | SER | 12 | 57.273 | 41.902 | 43.507 | 1.00 | 84.56 | Y C |
| ATOM | 7217 | O | SER | 12 | 57.232 | 42.666 | 44.471 | 1.00 | 84.56 | Y O |
| ATOM | 7218 | N | ALA | 13 | 56.713 | 42.192 | 42.341 | 1.00 | 109.71 | Y N |
| ATOM | 7219 | CA | ALA | 13 | 55.997 | 43.442 | 42.152 | 1.00 | 109.71 | Y C |
| ATOM | 7220 | CB | ALA | 13 | 56.947 | 44.509 | 41.632 | 1.00 | 88.46 | Y C |
| ATOM | 7221 | C | ALA | 13 | 54.838 | 43.244 | 41.186 | 1.00 | 109.71 | Y C |
| ATOM | 7222 | O | ALA | 13 | 54.869 | 42.347 | 40.341 | 1.00 | 109.71 | Y O |
| ATOM | 7223 | N | SER | 14 | 53.816 | 44.084 | 41.315 | 1.00 | 66.55 | Y N |
| ATOM | 7224 | CA | SER | 14 | 52.632 | 44.000 | 40.461 | 1.00 | 66.55 | Y C |
| ATOM | 7225 | CB | SER | 14 | 51.370 | 44.265 | 41.290 | 1.00 | 62.23 | Y C |
| ATOM | 7226 | OG | SER | 14 | 51.506 | 45.449 | 42.059 | 1.00 | 62.23 | Y O |
| ATOM | 7227 | C | SER | 14 | 52.699 | 44.984 | 39.299 | 1.00 | 66.55 | Y C |

Fig. 19: A-100

| | | | | | | | | | | |
|---|---|---|---|---|---|---|---|---|---|---|
| ATOM | 7228 | O | SER | 14 | 53.362 | 46.015 | 39.394 | 1.00 | 66.55 | Y | O |
| ATOM | 7229 | N | VAL | 15 | 52.018 | 44.660 | 38.202 | 1.00 | 56.27 | Y | N |
| ATOM | 7230 | CA | VAL | 15 | 52.017 | 45.540 | 37.037 | 1.00 | 56.27 | Y | C |
| ATOM | 7231 | CB | VAL | 15 | 50.922 | 45.156 | 36.016 | 1.00 | 42.35 | Y | C |
| ATOM | 7232 | CG1 | VAL | 15 | 51.449 | 44.089 | 35.066 | 1.00 | 42.35 | Y | C |
| ATOM | 7233 | CG2 | VAL | 15 | 49.679 | 44.644 | 36.750 | 1.00 | 42.35 | Y | C |
| ATOM | 7234 | C | VAL | 15 | 51.773 | 46.964 | 37.492 | 1.00 | 56.27 | Y | C |
| ATOM | 7235 | O | VAL | 15 | 50.948 | 47.208 | 38.369 | 1.00 | 56.27 | Y | O |
| ATOM | 7236 | N | GLY | 16 | 52.509 | 47.903 | 36.911 | 1.00 | 54.44 | Y | N |
| ATOM | 7237 | CA | GLY | 16 | 52.343 | 49.296 | 37.280 | 1.00 | 54.44 | Y | C |
| ATOM | 7238 | C | GLY | 16 | 53.284 | 49.795 | 38.359 | 1.00 | 54.44 | Y | C |
| ATOM | 7239 | O | GLY | 16 | 53.419 | 51.000 | 38.542 | 1.00 | 54.44 | Y | O |
| ATOM | 7240 | N | ASP | 17 | 53.931 | 48.885 | 39.082 | 1.00 | 75.77 | Y | N |
| ATOM | 7241 | CA | ASP | 17 | 54.863 | 49.283 | 40.134 | 1.00 | 75.77 | Y | C |
| ATOM | 7242 | CB | ASP | 17 | 55.212 | 48.091 | 41.034 | 1.00 | 114.73 | Y | C |
| ATOM | 7243 | CG | ASP | 17 | 54.035 | 47.608 | 41.849 | 1.00 | 114.73 | Y | C |
| ATOM | 7244 | OD1 | ASP | 17 | 54.208 | 46.639 | 42.623 | 1.00 | 114.73 | Y | O |
| ATOM | 7245 | OD2 | ASP | 17 | 52.942 | 48.198 | 41.716 | 1.00 | 114.73 | Y | O |
| ATOM | 7246 | C | ASP | 17 | 56.149 | 49.824 | 39.525 | 1.00 | 75.77 | Y | C |
| ATOM | 7247 | O | ASP | 17 | 56.476 | 49.533 | 38.373 | 1.00 | 75.77 | Y | O |
| ATOM | 7248 | N | ARG | 18 | 56.873 | 50.616 | 40.304 | 1.00 | 69.15 | Y | N |
| ATOM | 7249 | CA | ARG | 18 | 58.139 | 51.161 | 39.844 | 1.00 | 69.15 | Y | C |
| ATOM | 7250 | CB | ARG | 18 | 58.263 | 52.634 | 40.225 | 1.00 | 52.23 | Y | C |
| ATOM | 7251 | CG | ARG | 18 | 59.557 | 53.291 | 39.779 | 1.00 | 52.23 | Y | C |
| ATOM | 7252 | CD | ARG | 18 | 59.365 | 54.788 | 39.625 | 1.00 | 52.23 | Y | C |
| ATOM | 7253 | NE | ARG | 18 | 60.622 | 55.478 | 39.370 | 1.00 | 52.23 | Y | N |
| ATOM | 7254 | CZ | ARG | 18 | 61.621 | 55.550 | 40.246 | 1.00 | 52.23 | Y | C |
| ATOM | 7255 | NH1 | ARG | 18 | 61.506 | 54.968 | 41.436 | 1.00 | 52.23 | Y | N |
| ATOM | 7256 | NH2 | ARG | 18 | 62.733 | 56.209 | 39.933 | 1.00 | 52.23 | Y | N |
| ATOM | 7257 | C | ARG | 18 | 59.232 | 50.346 | 40.514 | 1.00 | 69.15 | Y | C |
| ATOM | 7258 | O | ARG | 18 | 59.318 | 50.293 | 41.744 | 1.00 | 69.15 | Y | O |
| ATOM | 7259 | N | VAL | 19 | 60.064 | 49.706 | 39.701 | 1.00 | 58.62 | Y | N |
| ATOM | 7260 | CA | VAL | 19 | 61.132 | 48.871 | 40.221 | 1.00 | 58.62 | Y | C |
| ATOM | 7261 | CB | VAL | 19 | 61.068 | 47.477 | 39.567 | 1.00 | 74.00 | Y | C |
| ATOM | 7262 | CG1 | VAL | 19 | 62.050 | 46.531 | 40.235 | 1.00 | 74.00 | Y | C |
| ATOM | 7263 | CG2 | VAL | 19 | 59.651 | 46.938 | 39.664 | 1.00 | 74.00 | Y | C |
| ATOM | 7264 | C | VAL | 19 | 62.518 | 49.477 | 40.003 | 1.00 | 58.62 | Y | C |
| ATOM | 7265 | O | VAL | 19 | 62.782 | 50.096 | 38.975 | 1.00 | 58.62 | Y | O |
| ATOM | 7266 | N | THR | 20 | 63.399 | 49.297 | 40.978 | 1.00 | 54.75 | Y | N |
| ATOM | 7267 | CA | THR | 20 | 64.753 | 49.815 | 40.878 | 1.00 | 54.75 | Y | C |
| ATOM | 7268 | CB | THR | 20 | 64.883 | 51.148 | 41.639 | 1.00 | 56.43 | Y | C |
| ATOM | 7269 | OG1 | THR | 20 | 64.132 | 52.154 | 40.955 | 1.00 | 56.43 | Y | O |
| ATOM | 7270 | CG2 | THR | 20 | 66.337 | 51.586 | 41.726 | 1.00 | 56.43 | Y | C |
| ATOM | 7271 | C | THR | 20 | 65.806 | 48.834 | 41.401 | 1.00 | 54.75 | Y | C |
| ATOM | 7272 | O | THR | 20 | 65.963 | 48.663 | 42.611 | 1.00 | 54.75 | Y | O |
| ATOM | 7273 | N | ILE | 21 | 66.526 | 48.194 | 40.484 | 1.00 | 38.23 | Y | N |
| ATOM | 7274 | CA | ILE | 21 | 67.572 | 47.250 | 40.855 | 1.00 | 38.23 | Y | C |
| ATOM | 7275 | CB | ILE | 21 | 67.775 | 46.182 | 39.765 | 1.00 | 34.57 | Y | C |
| ATOM | 7276 | CG2 | ILE | 21 | 68.753 | 45.112 | 40.252 | 1.00 | 34.57 | Y | C |
| ATOM | 7277 | CG1 | ILE | 21 | 66.427 | 45.547 | 39.426 | 1.00 | 34.57 | Y | C |
| ATOM | 7278 | CD1 | ILE | 21 | 66.496 | 44.426 | 38.415 | 1.00 | 34.57 | Y | C |
| ATOM | 7279 | C | ILE | 21 | 68.877 | 48.006 | 41.047 | 1.00 | 38.23 | Y | C |
| ATOM | 7280 | O | ILE | 21 | 69.215 | 48.885 | 40.256 | 1.00 | 38.23 | Y | O |
| ATOM | 7281 | N | THR | 22 | 69.610 | 47.660 | 42.100 | 1.00 | 41.70 | Y | N |
| ATOM | 7282 | CA | THR | 22 | 70.880 | 48.312 | 42.396 | 1.00 | 41.70 | Y | C |
| ATOM | 7283 | CB | THR | 22 | 70.919 | 48.826 | 43.856 | 1.00 | 62.77 | Y | C |
| ATOM | 7284 | OG1 | THR | 22 | 69.986 | 49.903 | 44.017 | 1.00 | 62.77 | Y | O |
| ATOM | 7285 | CG2 | THR | 22 | 72.322 | 49.303 | 44.222 | 1.00 | 62.77 | Y | C |
| ATOM | 7286 | C | THR | 22 | 72.052 | 47.370 | 42.199 | 1.00 | 41.70 | Y | C |
| ATOM | 7287 | O | THR | 22 | 72.028 | 46.237 | 42.674 | 1.00 | 41.70 | Y | O |
| ATOM | 7288 | N | CYS | 23 | 73.077 | 47.852 | 41.500 | 1.00 | 52.46 | Y | N |
| ATOM | 7289 | CA | CYS | 23 | 74.289 | 47.076 | 41.247 | 1.00 | 52.46 | Y | C |
| ATOM | 7290 | C | CYS | 23 | 75.446 | 47.833 | 41.875 | 1.00 | 52.46 | Y | C |
| ATOM | 7291 | O | CYS | 23 | 75.749 | 48.957 | 41.476 | 1.00 | 52.46 | Y | O |
| ATOM | 7292 | CB | CYS | 23 | 74.522 | 46.938 | 39.744 | 1.00 | 61.15 | Y | C |
| ATOM | 7293 | SG | CYS | 23 | 75.983 | 45.982 | 39.184 | 1.00 | 61.15 | Y | S |
| ATOM | 7294 | N | SER | 24 | 76.079 | 47.219 | 42.866 | 1.00 | 43.95 | Y | N |
| ATOM | 7295 | CA | SER | 24 | 77.200 | 47.837 | 43.556 | 1.00 | 43.95 | Y | C |
| ATOM | 7296 | CB | SER | 24 | 76.992 | 47.751 | 45.072 | 1.00 | 58.07 | Y | C |
| ATOM | 7297 | OG | SER | 24 | 75.782 | 48.379 | 45.462 | 1.00 | 58.07 | Y | O |
| ATOM | 7298 | C | SER | 24 | 78.495 | 47.138 | 43.177 | 1.00 | 43.95 | Y | C |
| ATOM | 7299 | O | SER | 24 | 78.582 | 45.912 | 43.222 | 1.00 | 43.95 | Y | O |
| ATOM | 7300 | N | ALA | 25 | 79.503 | 47.924 | 42.814 | 1.00 | 35.63 | Y | N |

Fig. 19: A-101

```
ATOM   7301  CA   ALA   25      80.796  47.373  42.427  1.00  35.63  Y  C
ATOM   7302  CB   ALA   25      81.214  47.920  41.068  1.00  50.18  Y  C
ATOM   7303  C    ALA   25      81.894  47.635  43.454  1.00  35.63  Y  C
ATOM   7304  O    ALA   25      82.050  48.754  43.959  1.00  35.63  Y  O
ATOM   7305  N    SER   26      82.650  46.579  43.742  1.00  37.44  Y  N
ATOM   7306  CA   SER   26      83.746  46.616  44.697  1.00  37.44  Y  C
ATOM   7307  CB   SER   26      84.492  45.280  44.672  1.00  31.41  Y  C
ATOM   7308  OG   SER   26      85.018  45.005  43.381  1.00  31.41  Y  O
ATOM   7309  C    SER   26      84.718  47.745  44.393  1.00  37.44  Y  C
ATOM   7310  O    SER   26      85.358  48.286  45.297  1.00  37.44  Y  O
ATOM   7311  N    SER   27      84.835  48.088  43.116  1.00  70.39  Y  N
ATOM   7312  CA   SER   27      85.726  49.157  42.687  1.00  70.39  Y  C
ATOM   7313  CB   SER   27      86.941  48.581  41.954  1.00  53.81  Y  C
ATOM   7314  OG   SER   27      87.574  47.567  42.716  1.00  53.81  Y  O
ATOM   7315  C    SER   27      84.922  50.023  41.736  1.00  70.39  Y  C
ATOM   7316  O    SER   27      83.960  49.545  41.139  1.00  70.39  Y  O
ATOM   7317  N    SER   28      85.306  51.290  41.595  1.00  30.73  Y  N
ATOM   7318  CA   SER   28      84.598  52.194  40.695  1.00  30.73  Y  C
ATOM   7319  CB   SER   28      85.060  53.628  40.920  1.00  55.81  Y  C
ATOM   7320  OG   SER   28      86.448  53.723  40.688  1.00  55.81  Y  O
ATOM   7321  C    SER   28      84.824  51.813  39.230  1.00  30.73  Y  C
ATOM   7322  O    SER   28      85.873  51.287  38.863  1.00  30.73  Y  O
ATOM   7323  N    VAL   29      83.832  52.092  38.398  1.00  34.83  Y  N
ATOM   7324  CA   VAL   29      83.909  51.780  36.983  1.00  34.83  Y  C
ATOM   7325  CB   VAL   29      83.173  50.443  36.682  1.00  24.96  Y  C
ATOM   7326  CG1  VAL   29      83.891  49.286  37.382  1.00  24.96  Y  C
ATOM   7327  CG2  VAL   29      81.717  50.518  37.153  1.00  24.96  Y  C
ATOM   7328  C    VAL   29      83.267  52.929  36.208  1.00  34.83  Y  C
ATOM   7329  O    VAL   29      82.397  53.621  36.738  1.00  34.83  Y  O
ATOM   7330  N    ASN   30      83.689  53.134  34.963  1.00  19.83  Y  N
ATOM   7331  CA   ASN   30      83.152  54.225  34.145  1.00  19.83  Y  C
ATOM   7332  CB   ASN   30      84.086  54.517  32.963  1.00  44.92  Y  C
ATOM   7333  CG   ASN   30      84.524  53.261  32.254  1.00  44.92  Y  C
ATOM   7334  OD1  ASN   30      85.235  52.431  32.832  1.00  44.92  Y  O
ATOM   7335  ND2  ASN   30      84.097  53.099  31.001  1.00  44.92  Y  N
ATOM   7336  C    ASN   30      81.740  53.976  33.634  1.00  19.83  Y  C
ATOM   7337  O    ASN   30      80.998  54.926  33.381  1.00  19.83  Y  O
ATOM   7338  N    HIS   31      81.367  52.708  33.475  1.00  24.55  Y  N
ATOM   7339  CA   HIS   31      80.031  52.373  32.991  1.00  24.55  Y  C
ATOM   7340  CB   HIS   31      80.003  52.259  31.459  1.00  41.70  Y  C
ATOM   7341  CG   HIS   31      80.061  53.572  30.737  1.00  41.70  Y  C
ATOM   7342  CD2  HIS   31      79.124  54.233  30.016  1.00  41.70  Y  C
ATOM   7343  ND1  HIS   31      81.196  54.351  30.692  1.00  41.70  Y  N
ATOM   7344  CE1  HIS   31      80.958  55.435  29.973  1.00  41.70  Y  C
ATOM   7345  NE2  HIS   31      79.708  55.387  29.551  1.00  41.70  Y  N
ATOM   7346  C    HIS   31      79.548  51.058  33.567  1.00  24.55  Y  C
ATOM   7347  O    HIS   31      80.274  50.392  34.305  1.00  24.55  Y  O
ATOM   7348  N    MET   32      78.312  50.698  33.227  1.00  16.59  Y  N
ATOM   7349  CA   MET   32      77.719  49.440  33.664  1.00  16.59  Y  C
ATOM   7350  CB   MET   32      76.944  49.624  34.971  1.00  29.77  Y  C
ATOM   7351  CG   MET   32      76.606  48.310  35.684  1.00  29.77  Y  C
ATOM   7352  SD   MET   32      78.097  47.369  36.143  1.00  29.77  Y  S
ATOM   7353  CE   MET   32      78.855  48.463  37.337  1.00  29.77  Y  C
ATOM   7354  C    MET   32      76.779  48.941  32.563  1.00  16.59  Y  C
ATOM   7355  O    MET   32      76.138  49.734  31.871  1.00  16.59  Y  O
ATOM   7356  N    PHE   33      76.706  47.629  32.383  1.00  41.04  Y  N
ATOM   7357  CA   PHE   33      75.830  47.089  31.358  1.00  41.04  Y  C
ATOM   7358  CB   PHE   33      76.639  46.329  30.315  1.00  16.08  Y  C
ATOM   7359  CG   PHE   33      77.695  47.161  29.657  1.00  16.08  Y  C
ATOM   7360  CD1  PHE   33      78.846  47.528  30.354  1.00  16.08  Y  C
ATOM   7361  CD2  PHE   33      77.524  47.609  28.350  1.00  16.08  Y  C
ATOM   7362  CE1  PHE   33      79.810  48.328  29.763  1.00  16.08  Y  C
ATOM   7363  CE2  PHE   33      78.484  48.414  27.745  1.00  16.08  Y  C
ATOM   7364  CZ   PHE   33      79.634  48.776  28.456  1.00  16.08  Y  C
ATOM   7365  C    PHE   33      74.803  46.175  31.985  1.00  41.04  Y  C
ATOM   7366  O    PHE   33      75.036  45.622  33.057  1.00  41.04  Y  O
ATOM   7367  N    TRP   34      73.664  46.020  31.322  1.00  26.10  Y  N
ATOM   7368  CA   TRP   34      72.604  45.168  31.843  1.00  26.10  Y  C
ATOM   7369  CB   TRP   34      71.438  46.009  32.364  1.00  47.27  Y  C
ATOM   7370  CG   TRP   34      71.807  46.935  33.466  1.00  47.27  Y  C
ATOM   7371  CD2  TRP   34      71.660  46.692  34.868  1.00  47.27  Y  C
ATOM   7372  CE2  TRP   34      72.145  47.836  35.542  1.00  47.27  Y  C
ATOM   7373  CE3  TRP   34      71.167  45.621  35.622  1.00  47.27  Y  C
```

Fig. 19: A-102

```
ATOM   7374  CD1 TRP    34      72.360  48.175  33.346  1.00   47.27    Y  C
ATOM   7375  NE1 TRP    34      72.567  48.725  34.589  1.00   47.27    Y  N
ATOM   7376  CZ2 TRP    34      72.150  47.939  36.940  1.00   47.27    Y  C
ATOM   7377  CZ3 TRP    34      71.172  45.725  37.013  1.00   47.27    Y  C
ATOM   7378  CH2 TRP    34      71.661  46.879  37.655  1.00   47.27    Y  C
ATOM   7379  C   TRP    34      72.067  44.187  30.812  1.00   26.10    Y  C
ATOM   7380  O   TRP    34      71.904  44.513  29.630  1.00   26.10    Y  O
ATOM   7381  N   TYR    35      71.793  42.972  31.267  1.00   43.42    Y  N
ATOM   7382  CA  TYR    35      71.248  41.964  30.381  1.00   43.42    Y  C
ATOM   7383  CB  TYR    35      72.230  40.808  30.189  1.00   22.29    Y  C
ATOM   7384  CG  TYR    35      73.549  41.240  29.596  1.00   22.29    Y  C
ATOM   7385  CD1 TYR    35      74.645  41.535  30.417  1.00   22.29    Y  C
ATOM   7386  CE1 TYR    35      75.841  41.962  29.881  1.00   22.29    Y  C
ATOM   7387  CD2 TYR    35      73.697  41.385  28.216  1.00   22.29    Y  C
ATOM   7388  CE2 TYR    35      74.898  41.808  27.670  1.00   22.29    Y  C
ATOM   7389  CZ  TYR    35      75.960  42.094  28.510  1.00   22.29    Y  C
ATOM   7390  OH  TYR    35      77.148  42.516  27.972  1.00   22.29    Y  O
ATOM   7391  C   TYR    35      69.966  41.449  30.991  1.00   43.42    Y  C
ATOM   7392  O   TYR    35      69.826  41.393  32.214  1.00   43.42    Y  O
ATOM   7393  N   GLN    36      69.015  41.107  30.136  1.00   45.64    Y  N
ATOM   7394  CA  GLN    36      67.760  40.567  30.607  1.00   45.64    Y  C
ATOM   7395  CB  GLN    36      66.574  41.346  30.054  1.00   37.71    Y  C
ATOM   7396  CG  GLN    36      65.259  40.610  30.277  1.00   37.71    Y  C
ATOM   7397  CD  GLN    36      64.189  41.002  29.287  1.00   37.71    Y  C
ATOM   7398  OE1 GLN    36      63.601  42.072  29.391  1.00   37.71    Y  O
ATOM   7399  NE2 GLN    36      63.936  40.137  28.314  1.00   37.71    Y  N
ATOM   7400  C   GLN    36      67.664  39.138  30.118  1.00   45.64    Y  C
ATOM   7401  O   GLN    36      67.725  38.881  28.910  1.00   45.64    Y  O
ATOM   7402  N   GLN    37      67.522  38.205  31.050  1.00   50.28    Y  N
ATOM   7403  CA  GLN    37      67.390  36.809  30.670  1.00   50.28    Y  C
ATOM   7404  CB  GLN    37      68.522  35.961  31.265  1.00   34.85    Y  C
ATOM   7405  CG  GLN    37      68.392  34.487  30.904  1.00   34.85    Y  C
ATOM   7406  CD  GLN    37      69.543  33.645  31.388  1.00   34.85    Y  C
ATOM   7407  OE1 GLN    37      69.925  33.699  32.565  1.00   34.85    Y  O
ATOM   7408  NE2 GLN    37      70.098  32.842  30.484  1.00   34.85    Y  N
ATOM   7409  C   GLN    37      66.042  36.248  31.108  1.00   50.28    Y  C
ATOM   7410  O   GLN    37      65.690  36.272  32.293  1.00   50.28    Y  O
ATOM   7411  N   LYS    38      65.284  35.763  30.133  1.00   68.24    Y  N
ATOM   7412  CA  LYS    38      63.983  35.175  30.403  1.00   68.24    Y  C
ATOM   7413  CB  LYS    38      62.991  35.530  29.291  1.00   55.54    Y  C
ATOM   7414  CG  LYS    38      62.893  37.031  29.023  1.00   55.54    Y  C
ATOM   7415  CD  LYS    38      61.764  37.382  28.056  1.00   55.54    Y  C
ATOM   7416  CE  LYS    38      60.394  37.298  28.726  1.00   55.54    Y  C
ATOM   7417  NZ  LYS    38      60.290  38.166  29.943  1.00   55.54    Y  N
ATOM   7418  C   LYS    38      64.198  33.667  30.473  1.00   68.24    Y  C
ATOM   7419  O   LYS    38      64.971  33.104  29.696  1.00   68.24    Y  O
ATOM   7420  N   PRO    39      63.520  32.994  31.412  1.00   67.87    Y  N
ATOM   7421  CD  PRO    39      62.478  33.563  32.282  1.00   58.47    Y  C
ATOM   7422  CA  PRO    39      63.621  31.546  31.614  1.00   67.87    Y  C
ATOM   7423  CB  PRO    39      62.368  31.234  32.417  1.00   58.47    Y  C
ATOM   7424  CG  PRO    39      62.247  32.446  33.271  1.00   58.47    Y  C
ATOM   7425  C   PRO    39      63.717  30.714  30.338  1.00   67.87    Y  C
ATOM   7426  O   PRO    39      62.898  30.859  29.425  1.00   67.87    Y  O
ATOM   7427  N   GLY    40      64.730  29.847  30.288  1.00   54.98    Y  N
ATOM   7428  CA  GLY    40      64.925  28.977  29.137  1.00   54.98    Y  C
ATOM   7429  C   GLY    40      65.488  29.625  27.882  1.00   54.98    Y  C
ATOM   7430  O   GLY    40      65.625  28.957  26.855  1.00   54.98    Y  O
ATOM   7431  N   LYS    41      65.801  30.918  27.955  1.00   83.28    Y  N
ATOM   7432  CA  LYS    41      66.364  31.641  26.816  1.00   83.28    Y  C
ATOM   7433  CB  LYS    41      65.414  32.754  26.354  1.00   72.06    Y  C
ATOM   7434  CG  LYS    41      64.045  32.271  25.882  1.00   72.06    Y  C
ATOM   7435  CD  LYS    41      63.316  33.311  25.008  1.00   72.06    Y  C
ATOM   7436  CE  LYS    41      63.035  34.642  25.726  1.00   72.06    Y  C
ATOM   7437  NZ  LYS    41      64.229  35.536  25.855  1.00   72.06    Y  N
ATOM   7438  C   LYS    41      67.727  32.245  27.160  1.00   83.28    Y  C
ATOM   7439  O   LYS    41      68.110  32.327  28.331  1.00   83.28    Y  O
ATOM   7440  N   ALA    42      68.458  32.666  26.133  1.00   55.60    Y  N
ATOM   7441  CA  ALA    42      69.776  33.261  26.326  1.00   55.60    Y  C
ATOM   7442  CB  ALA    42      70.561  33.194  25.041  1.00    1.87    Y  C
ATOM   7443  C   ALA    42      69.623  34.707  26.754  1.00   55.60    Y  C
ATOM   7444  O   ALA    42      68.607  35.337  26.462  1.00   55.60    Y  O
ATOM   7445  N   PRO    43      70.628  35.259  27.455  1.00   54.21    Y  N
ATOM   7446  CD  PRO    43      71.849  34.627  27.983  1.00   18.24    Y  C
```

Fig. 19: A-103

```
ATOM   7447  CA   PRO  43      70.537  36.656  27.889  1.00  54.21  Y  C
ATOM   7448  CB   PRO  43      71.875  36.890  28.594  1.00  18.24  Y  C
ATOM   7449  CG   PRO  43      72.202  35.544  29.149  1.00  18.24  Y  C
ATOM   7450  C    PRO  43      70.349  37.584  26.689  1.00  54.21  Y  C
ATOM   7451  O    PRO  43      70.660  37.219  25.555  1.00  54.21  Y  O
ATOM   7452  N    LYS  44      69.837  38.782  26.946  1.00  55.44  Y  N
ATOM   7453  CA   LYS  44      69.618  39.764  25.892  1.00  55.44  Y  C
ATOM   7454  CB   LYS  44      68.120  39.894  25.601  1.00  46.11  Y  C
ATOM   7455  CG   LYS  44      67.705  39.473  24.199  1.00  46.11  Y  C
ATOM   7456  CD   LYS  44      66.189  39.520  24.018  1.00  46.11  Y  C
ATOM   7457  CE   LYS  44      65.457  38.464  24.865  1.00  46.11  Y  C
ATOM   7458  NZ   LYS  44      65.564  38.665  26.354  1.00  46.11  Y  N
ATOM   7459  C    LYS  44      70.172  41.117  26.328  1.00  55.44  Y  C
ATOM   7460  O    LYS  44      69.930  41.554  27.454  1.00  55.44  Y  O
ATOM   7461  N    PRO  45      70.946  41.785  25.451  1.00  21.39  Y  N
ATOM   7462  CD   PRO  45      71.303  41.365  24.085  1.00  11.37  Y  C
ATOM   7463  CA   PRO  45      71.523  43.103  25.772  1.00  21.39  Y  C
ATOM   7464  CB   PRO  45      72.159  43.539  24.457  1.00  11.37  Y  C
ATOM   7465  CG   PRO  45      72.485  42.234  23.795  1.00  11.37  Y  C
ATOM   7466  C    PRO  45      70.361  44.010  26.138  1.00  21.39  Y  C
ATOM   7467  O    PRO  45      69.407  44.103  25.383  1.00  21.39  Y  O
ATOM   7468  N    TRP  46      70.434  44.676  27.281  1.00  48.64  Y  N
ATOM   7469  CA   TRP  46      69.333  45.532  27.704  1.00  48.64  Y  C
ATOM   7470  CB   TRP  46      68.783  45.038  29.043  1.00  23.18  Y  C
ATOM   7471  CG   TRP  46      67.316  45.220  29.143  1.00  23.18  Y  C
ATOM   7472  CD2  TRP  46      66.330  44.620  28.299  1.00  23.18  Y  C
ATOM   7473  CE2  TRP  46      65.070  45.075  28.739  1.00  23.18  Y  C
ATOM   7474  CE3  TRP  46      66.391  43.736  27.206  1.00  23.18  Y  C
ATOM   7475  CD1  TRP  46      66.637  45.997  30.038  1.00  23.18  Y  C
ATOM   7476  NE1  TRP  46      65.282  45.914  29.803  1.00  23.18  Y  N
ATOM   7477  CZ2  TRP  46      63.881  44.679  28.126  1.00  23.18  Y  C
ATOM   7478  CZ3  TRP  46      65.212  43.342  26.599  1.00  23.18  Y  C
ATOM   7479  CH2  TRP  46      63.973  43.814  27.059  1.00  23.18  Y  C
ATOM   7480  C    TRP  46      69.694  47.007  27.826  1.00  48.64  Y  C
ATOM   7481  O    TRP  46      68.986  47.877  27.324  1.00  48.64  Y  O
ATOM   7482  N    ILE  47      70.785  47.283  28.523  1.00  42.06  Y  N
ATOM   7483  CA   ILE  47      71.238  48.644  28.717  1.00  42.06  Y  C
ATOM   7484  CB   ILE  47      70.801  49.172  30.099  1.00  37.03  Y  C
ATOM   7485  CG2  ILE  47      71.345  50.580  30.325  1.00  37.03  Y  C
ATOM   7486  CG1  ILE  47      69.275  49.168  30.198  1.00  37.03  Y  C
ATOM   7487  CD1  ILE  47      68.749  49.670  31.538  1.00  37.03  Y  C
ATOM   7488  C    ILE  47      72.758  48.641  28.638  1.00  42.06  Y  C
ATOM   7489  O    ILE  47      73.417  47.951  29.414  1.00  42.06  Y  O
ATOM   7490  N    TYR  48      73.310  49.387  27.684  1.00  17.47  Y  N
ATOM   7491  CA   TYR  48      74.753  49.467  27.532  1.00  17.47  Y  C
ATOM   7492  CB   TYR  48      75.189  49.145  26.106  1.00  20.64  Y  C
ATOM   7493  CG   TYR  48      74.613  50.048  25.046  1.00  20.64  Y  C
ATOM   7494  CD1  TYR  48      73.267  49.988  24.710  1.00  20.64  Y  C
ATOM   7495  CE1  TYR  48      72.743  50.792  23.704  1.00  20.64  Y  C
ATOM   7496  CD2  TYR  48      75.425  50.940  24.353  1.00  20.64  Y  C
ATOM   7497  CE2  TYR  48      74.916  51.750  23.347  1.00  20.64  Y  C
ATOM   7498  CZ   TYR  48      73.573  51.671  23.028  1.00  20.64  Y  C
ATOM   7499  OH   TYR  48      73.051  52.476  22.045  1.00  20.64  Y  O
ATOM   7500  C    TYR  48      75.193  50.861  27.892  1.00  17.47  Y  C
ATOM   7501  O    TYR  48      74.365  51.754  28.021  1.00  17.47  Y  O
ATOM   7502  N    LEU  49      76.497  51.044  28.054  1.00  31.07  Y  N
ATOM   7503  CA   LEU  49      77.042  52.337  28.429  1.00  31.07  Y  C
ATOM   7504  CB   LEU  49      77.200  53.247  27.205  1.00  20.44  Y  C
ATOM   7505  CG   LEU  49      78.368  53.044  26.236  1.00  20.44  Y  C
ATOM   7506  CD1  LEU  49      79.662  52.870  27.019  1.00  20.44  Y  C
ATOM   7507  CD2  LEU  49      78.121  51.836  25.385  1.00  20.44  Y  C
ATOM   7508  C    LEU  49      76.173  53.037  29.475  1.00  31.07  Y  C
ATOM   7509  O    LEU  49      75.769  54.178  29.293  1.00  31.07  Y  O
ATOM   7510  N    THR  50      75.861  52.329  30.555  1.00  28.24  Y  N
ATOM   7511  CA   THR  50      75.083  52.870  31.670  1.00  28.24  Y  C
ATOM   7512  CB   THR  50      75.754  54.128  32.230  1.00  41.62  Y  C
ATOM   7513  OG1  THR  50      77.134  53.847  32.495  1.00  41.62  Y  O
ATOM   7514  CG2  THR  50      75.066  54.568  33.522  1.00  41.62  Y  C
ATOM   7515  C    THR  50      73.605  53.187  31.485  1.00  28.24  Y  C
ATOM   7516  O    THR  50      72.761  52.603  32.158  1.00  28.24  Y  O
ATOM   7517  N    SER  51      73.283  54.114  30.595  1.00  28.33  Y  N
ATOM   7518  CA   SER  51      71.889  54.496  30.402  1.00  28.33  Y  C
ATOM   7519  CB   SER  51      71.729  55.981  30.714  1.00  81.44  Y  C
```

Fig. 19: A-104

```
ATOM   7520  OG   SER   51      72.714  56.738  30.034  1.00  81.44      Y  O
ATOM   7521  C    SER   51      71.312  54.190  29.019  1.00  28.33      Y  C
ATOM   7522  O    SER   51      70.092  54.174  28.831  1.00  28.33      Y  O
ATOM   7523  N    ASN   52      72.184  53.941  28.053  1.00  27.44      Y  N
ATOM   7524  CA   ASN   52      71.736  53.648  26.704  1.00  27.44      Y  C
ATOM   7525  CB   ASN   52      72.942  53.523  25.779  1.00  42.81      Y  C
ATOM   7526  CG   ASN   52      73.623  54.849  25.546  1.00  42.81      Y  C
ATOM   7527  OD1  ASN   52      73.059  55.733  24.907  1.00  42.81      Y  O
ATOM   7528  ND2  ASN   52      74.829  55.006  26.076  1.00  42.81      Y  N
ATOM   7529  C    ASN   52      70.896  52.390  26.623  1.00  27.44      Y  C
ATOM   7530  O    ASN   52      71.336  51.320  27.027  1.00  27.44      Y  O
ATOM   7531  N    LEU   53      69.682  52.519  26.100  1.00  46.42      Y  N
ATOM   7532  CA   LEU   53      68.805  51.367  25.954  1.00  46.42      Y  C
ATOM   7533  CB   LEU   53      67.349  51.803  25.887  1.00  19.90      Y  C
ATOM   7534  CG   LEU   53      66.763  52.595  27.051  1.00  19.90      Y  C
ATOM   7535  CD1  LEU   53      65.255  52.685  26.846  1.00  19.90      Y  C
ATOM   7536  CD2  LEU   53      67.071  51.918  28.382  1.00  19.90      Y  C
ATOM   7537  C    LEU   53      69.136  50.610  24.676  1.00  46.42      Y  C
ATOM   7538  O    LEU   53      69.414  51.220  23.644  1.00  46.42      Y  O
ATOM   7539  N    ALA   54      69.101  49.281  24.744  1.00  35.05      Y  N
ATOM   7540  CA   ALA   54      69.378  48.447  23.583  1.00  35.05      Y  C
ATOM   7541  CB   ALA   54      69.220  46.994  23.930  1.00  27.54      Y  C
ATOM   7542  C    ALA   54      68.373  48.829  22.530  1.00  35.05      Y  C
ATOM   7543  O    ALA   54      67.680  49.834  22.666  1.00  35.05      Y  O
ATOM   7544  N    SER   55      68.259  48.026  21.486  1.00  47.40      Y  N
ATOM   7545  CA   SER   55      67.319  48.376  20.443  1.00  47.40      Y  C
ATOM   7546  CB   SER   55      67.689  47.681  19.140  1.00  36.06      Y  C
ATOM   7547  OG   SER   55      67.083  48.359  18.051  1.00  36.06      Y  O
ATOM   7548  C    SER   55      65.866  48.073  20.801  1.00  47.40      Y  C
ATOM   7549  O    SER   55      64.993  48.921  20.631  1.00  47.40      Y  O
ATOM   7550  N    GLY   56      65.599  46.878  21.312  1.00  54.09      Y  N
ATOM   7551  CA   GLY   56      64.225  46.531  21.647  1.00  54.09      Y  C
ATOM   7552  C    GLY   56      63.650  47.071  22.948  1.00  54.09      Y  C
ATOM   7553  O    GLY   56      62.457  47.370  23.025  1.00  54.09      Y  O
ATOM   7554  N    VAL   57      64.497  47.197  23.965  1.00  63.10      Y  N
ATOM   7555  CA   VAL   57      64.082  47.667  25.282  1.00  63.10      Y  C
ATOM   7556  CB   VAL   57      65.311  48.113  26.120  1.00  46.15      Y  C
ATOM   7557  CG1  VAL   57      64.923  48.248  27.588  1.00  46.15      Y  C
ATOM   7558  CG2  VAL   57      66.446  47.118  25.961  1.00  46.15      Y  C
ATOM   7559  C    VAL   57      63.071  48.817  25.251  1.00  63.10      Y  C
ATOM   7560  O    VAL   57      63.363  49.898  24.747  1.00  63.10      Y  O
ATOM   7561  N    PRO   58      61.862  48.594  25.791  1.00  51.01      Y  N
ATOM   7562  CD   PRO   58      61.362  47.365  26.426  1.00  31.12      Y  C
ATOM   7563  CA   PRO   58      60.834  49.639  25.815  1.00  51.01      Y  C
ATOM   7564  CB   PRO   58      59.634  48.929  26.433  1.00  31.12      Y  C
ATOM   7565  CG   PRO   58      60.258  47.899  27.300  1.00  31.12      Y  C
ATOM   7566  C    PRO   58      61.305  50.829  26.643  1.00  51.01      Y  C
ATOM   7567  O    PRO   58      61.992  50.660  27.653  1.00  51.01      Y  O
ATOM   7568  N    SER   59      60.918  52.027  26.216  1.00  33.61      Y  N
ATOM   7569  CA   SER   59      61.330  53.267  26.874  1.00  33.61      Y  C
ATOM   7570  CB   SER   59      60.780  54.482  26.113  1.00  61.12      Y  C
ATOM   7571  OG   SER   59      59.368  54.481  26.096  1.00  61.12      Y  O
ATOM   7572  C    SER   59      61.023  53.411  28.359  1.00  33.61      Y  C
ATOM   7573  O    SER   59      61.495  54.353  28.990  1.00  33.61      Y  O
ATOM   7574  N    ARG   60      60.244  52.500  28.928  1.00  39.70      Y  N
ATOM   7575  CA   ARG   60      59.963  52.599  30.359  1.00  39.70      Y  C
ATOM   7576  CB   ARG   60      58.764  51.731  30.751  1.00  42.51      Y  C
ATOM   7577  CG   ARG   60      58.846  50.293  30.287  1.00  42.51      Y  C
ATOM   7578  CD   ARG   60      57.798  49.425  30.971  1.00  42.51      Y  C
ATOM   7579  NE   ARG   60      57.683  48.120  30.333  1.00  42.51      Y  N
ATOM   7580  CZ   ARG   60      57.277  47.939  29.079  1.00  42.51      Y  C
ATOM   7581  NH1  ARG   60      56.943  48.979  28.324  1.00  42.51      Y  N
ATOM   7582  NH2  ARG   60      57.210  46.718  28.569  1.00  42.51      Y  N
ATOM   7583  C    ARG   60      61.202  52.180  31.158  1.00  39.70      Y  C
ATOM   7584  O    ARG   60      61.311  52.451  32.357  1.00  39.70      Y  O
ATOM   7585  N    PHE   61      62.136  51.522  30.480  1.00  40.60      Y  N
ATOM   7586  CA   PHE   61      63.372  51.086  31.109  1.00  40.60      Y  C
ATOM   7587  CB   PHE   61      63.965  49.886  30.370  1.00  38.42      Y  C
ATOM   7588  CG   PHE   61      63.416  48.563  30.811  1.00  38.42      Y  C
ATOM   7589  CD1  PHE   61      62.493  47.881  30.028  1.00  38.42      Y  C
ATOM   7590  CD2  PHE   61      63.830  47.997  32.010  1.00  38.42      Y  C
ATOM   7591  CE1  PHE   61      61.990  46.652  30.434  1.00  38.42      Y  C
ATOM   7592  CE2  PHE   61      63.332  46.770  32.423  1.00  38.42      Y  C
```

Fig. 19: A-105

| ATOM | 7593 | CZ | PHE | 61 | 62.410 | 46.096 | 31.634 | 1.00 | 38.42 | Y | C |
|------|------|-----|-----|----|--------|--------|--------|------|-------|---|---|
| ATOM | 7594 | C | PHE | 61 | 64.399 | 52.209 | 31.097 | 1.00 | 40.60 | Y | C |
| ATOM | 7595 | O | PHE | 61 | 64.470 | 52.989 | 30.144 | 1.00 | 40.60 | Y | O |
| ATOM | 7596 | N | SER | 62 | 65.202 | 52.284 | 32.152 | 1.00 | 26.58 | Y | N |
| ATOM | 7597 | CA | SER | 62 | 66.238 | 53.306 | 32.247 | 1.00 | 26.58 | Y | C |
| ATOM | 7598 | CB | SER | 62 | 65.658 | 54.604 | 32.802 | 1.00 | 47.08 | Y | C |
| ATOM | 7599 | OG | SER | 62 | 65.071 | 54.395 | 34.076 | 1.00 | 47.08 | Y | O |
| ATOM | 7600 | C | SER | 62 | 67.376 | 52.828 | 33.145 | 1.00 | 26.58 | Y | C |
| ATOM | 7601 | O | SER | 62 | 67.160 | 52.123 | 34.125 | 1.00 | 26.58 | Y | O |
| ATOM | 7602 | N | GLY | 63 | 68.595 | 53.208 | 32.797 | 1.00 | 30.78 | Y | N |
| ATOM | 7603 | CA | GLY | 63 | 69.738 | 52.810 | 33.591 | 1.00 | 30.78 | Y | C |
| ATOM | 7604 | C | GLY | 63 | 70.426 | 54.067 | 34.056 | 1.00 | 30.78 | Y | C |
| ATOM | 7605 | O | GLY | 63 | 70.266 | 55.122 | 33.442 | 1.00 | 30.78 | Y | O |
| ATOM | 7606 | N | SER | 64 | 71.195 | 53.964 | 35.130 | 1.00 | 54.48 | Y | N |
| ATOM | 7607 | CA | SER | 64 | 71.884 | 55.130 | 35.652 | 1.00 | 54.48 | Y | C |
| ATOM | 7608 | CB | SER | 64 | 70.869 | 56.075 | 36.290 | 1.00 | 25.06 | Y | C |
| ATOM | 7609 | OG | SER | 64 | 71.519 | 57.204 | 36.839 | 1.00 | 25.06 | Y | O |
| ATOM | 7610 | C | SER | 64 | 72.947 | 54.763 | 36.675 | 1.00 | 54.48 | Y | C |
| ATOM | 7611 | O | SER | 64 | 73.000 | 53.632 | 37.154 | 1.00 | 54.48 | Y | O |
| ATOM | 7612 | N | GLY | 65 | 73.793 | 55.732 | 37.007 | 1.00 | 43.76 | Y | N |
| ATOM | 7613 | CA | GLY | 65 | 74.836 | 55.494 | 37.984 | 1.00 | 43.76 | Y | C |
| ATOM | 7614 | C | GLY | 65 | 76.218 | 56.023 | 37.637 | 1.00 | 43.76 | Y | C |
| ATOM | 7615 | O | GLY | 65 | 76.431 | 56.698 | 36.622 | 1.00 | 43.76 | Y | O |
| ATOM | 7616 | N | SER | 66 | 77.167 | 55.703 | 38.508 | 1.00 | 27.01 | Y | N |
| ATOM | 7617 | CA | SER | 66 | 78.546 | 56.110 | 38.339 | 1.00 | 27.01 | Y | C |
| ATOM | 7618 | CB | SER | 66 | 78.641 | 57.635 | 38.286 | 1.00 | 58.01 | Y | C |
| ATOM | 7619 | OG | SER | 66 | 77.927 | 58.229 | 39.355 | 1.00 | 58.01 | Y | O |
| ATOM | 7620 | C | SER | 66 | 79.367 | 55.563 | 39.498 | 1.00 | 27.01 | Y | C |
| ATOM | 7621 | O | SER | 66 | 78.817 | 55.039 | 40.464 | 1.00 | 27.01 | Y | O |
| ATOM | 7622 | N | GLY | 67 | 80.685 | 55.668 | 39.385 | 1.00 | 73.15 | Y | N |
| ATOM | 7623 | CA | GLY | 67 | 81.555 | 55.179 | 40.436 | 1.00 | 73.15 | Y | C |
| ATOM | 7624 | C | GLY | 67 | 81.312 | 53.733 | 40.822 | 1.00 | 73.15 | Y | C |
| ATOM | 7625 | O | GLY | 67 | 81.609 | 52.814 | 40.056 | 1.00 | 73.15 | Y | O |
| ATOM | 7626 | N | THR | 68 | 80.758 | 53.530 | 42.011 | 1.00 | 44.05 | Y | N |
| ATOM | 7627 | CA | THR | 68 | 80.506 | 52.186 | 42.506 | 1.00 | 44.05 | Y | C |
| ATOM | 7628 | CB | THR | 68 | 81.118 | 52.003 | 43.894 | 1.00 | 42.61 | Y | C |
| ATOM | 7629 | OG1 | THR | 68 | 80.524 | 52.945 | 44.793 | 1.00 | 42.61 | Y | O |
| ATOM | 7630 | CG2 | THR | 68 | 82.627 | 52.225 | 43.845 | 1.00 | 42.61 | Y | C |
| ATOM | 7631 | C | THR | 68 | 79.042 | 51.786 | 42.592 | 1.00 | 44.05 | Y | C |
| ATOM | 7632 | O | THR | 68 | 78.743 | 50.632 | 42.879 | 1.00 | 44.05 | Y | O |
| ATOM | 7633 | N | ASP | 69 | 78.128 | 52.720 | 42.352 | 1.00 | 35.15 | Y | N |
| ATOM | 7634 | CA | ASP | 69 | 76.708 | 52.392 | 42.424 | 1.00 | 35.15 | Y | C |
| ATOM | 7635 | CB | ASP | 69 | 76.066 | 53.103 | 43.617 | 1.00 | 108.02 | Y | C |
| ATOM | 7636 | CG | ASP | 69 | 76.592 | 52.591 | 44.946 | 1.00 | 108.02 | Y | C |
| ATOM | 7637 | OD1 | ASP | 69 | 76.357 | 51.406 | 45.268 | 1.00 | 108.02 | Y | O |
| ATOM | 7638 | OD2 | ASP | 69 | 77.249 | 53.370 | 45.667 | 1.00 | 108.02 | Y | O |
| ATOM | 7639 | C | ASP | 69 | 75.942 | 52.705 | 41.139 | 1.00 | 35.15 | Y | C |
| ATOM | 7640 | O | ASP | 69 | 75.884 | 53.850 | 40.693 | 1.00 | 35.15 | Y | O |
| ATOM | 7641 | N | TYR | 70 | 75.359 | 51.664 | 40.551 | 1.00 | 27.55 | Y | N |
| ATOM | 7642 | CA | TYR | 70 | 74.599 | 51.787 | 39.317 | 1.00 | 27.55 | Y | C |
| ATOM | 7643 | CB | TYR | 70 | 75.315 | 51.016 | 38.191 | 1.00 | 25.09 | Y | C |
| ATOM | 7644 | CG | TYR | 70 | 76.543 | 51.737 | 37.662 | 1.00 | 25.09 | Y | C |
| ATOM | 7645 | CD1 | TYR | 70 | 76.447 | 52.637 | 36.596 | 1.00 | 25.09 | Y | C |
| ATOM | 7646 | CE1 | TYR | 70 | 77.562 | 53.365 | 36.158 | 1.00 | 25.09 | Y | C |
| ATOM | 7647 | CD2 | TYR | 70 | 77.787 | 51.577 | 38.275 | 1.00 | 25.09 | Y | C |
| ATOM | 7648 | CE2 | TYR | 70 | 78.906 | 52.299 | 37.848 | 1.00 | 25.09 | Y | C |
| ATOM | 7649 | CZ | TYR | 70 | 78.785 | 53.194 | 36.790 | 1.00 | 25.09 | Y | C |
| ATOM | 7650 | OH | TYR | 70 | 79.873 | 53.933 | 36.382 | 1.00 | 25.09 | Y | O |
| ATOM | 7651 | C | TYR | 70 | 73.184 | 51.267 | 39.523 | 1.00 | 27.55 | Y | C |
| ATOM | 7652 | O | TYR | 70 | 72.920 | 50.545 | 40.488 | 1.00 | 27.55 | Y | O |
| ATOM | 7653 | N | THR | 71 | 72.270 | 51.635 | 38.627 | 1.00 | 38.36 | Y | N |
| ATOM | 7654 | CA | THR | 71 | 70.893 | 51.184 | 38.767 | 1.00 | 38.36 | Y | C |
| ATOM | 7655 | CB | THR | 71 | 70.074 | 52.152 | 39.657 | 1.00 | 44.65 | Y | C |
| ATOM | 7656 | OG1 | THR | 71 | 69.921 | 53.403 | 38.978 | 1.00 | 44.65 | Y | O |
| ATOM | 7657 | CG2 | THR | 71 | 70.770 | 52.394 | 40.989 | 1.00 | 44.65 | Y | C |
| ATOM | 7658 | C | THR | 71 | 70.099 | 50.991 | 37.473 | 1.00 | 38.36 | Y | C |
| ATOM | 7659 | O | THR | 71 | 70.281 | 51.707 | 36.485 | 1.00 | 38.36 | Y | O |
| ATOM | 7660 | N | LEU | 72 | 69.216 | 50.001 | 37.499 | 1.00 | 32.67 | Y | N |
| ATOM | 7661 | CA | LEU | 72 | 68.324 | 49.718 | 36.385 | 1.00 | 32.67 | Y | C |
| ATOM | 7662 | CB | LEU | 72 | 68.392 | 48.238 | 35.985 | 1.00 | 53.11 | Y | C |
| ATOM | 7663 | CG | LEU | 72 | 67.283 | 47.694 | 35.073 | 1.00 | 53.11 | Y | C |
| ATOM | 7664 | CD1 | LEU | 72 | 66.871 | 48.731 | 34.059 | 1.00 | 53.11 | Y | C |
| ATOM | 7665 | CD2 | LEU | 72 | 67.769 | 46.444 | 34.372 | 1.00 | 53.11 | Y | C |

Fig. 19: A-106

```
ATOM   7666  C    LEU   72      66.958  50.056  36.972  1.00   32.67      Y  C
ATOM   7667  O    LEU   72      66.688  49.738  38.129  1.00   32.67      Y  O
ATOM   7668  N    THR   73      66.106  50.715  36.195  1.00   42.60      Y  N
ATOM   7669  CA   THR   73      64.795  51.100  36.700  1.00   42.60      Y  C
ATOM   7670  CB   THR   73      64.780  52.597  37.094  1.00   57.15      Y  C
ATOM   7671  OG1  THR   73      66.018  52.943  37.730  1.00   57.15      Y  O
ATOM   7672  CG2  THR   73      63.639  52.879  38.058  1.00   57.15      Y  C
ATOM   7673  C    THR   73      63.665  50.854  35.708  1.00   42.60      Y  C
ATOM   7674  O    THR   73      63.791  51.132  34.516  1.00   42.60      Y  O
ATOM   7675  N    ILE   74      62.564  50.316  36.212  1.00   51.99      Y  N
ATOM   7676  CA   ILE   74      61.396  50.068  35.386  1.00   51.99      Y  C
ATOM   7677  CB   ILE   74      60.934  48.597  35.455  1.00   52.44      Y  C
ATOM   7678  CG2  ILE   74      60.081  48.271  34.231  1.00   52.44      Y  C
ATOM   7679  CG1  ILE   74      62.138  47.656  35.471  1.00   52.44      Y  C
ATOM   7680  CD1  ILE   74      61.757  46.182  35.513  1.00   52.44      Y  C
ATOM   7681  C    ILE   74      60.314  50.963  35.988  1.00   51.99      Y  C
ATOM   7682  O    ILE   74      59.739  50.639  37.030  1.00   51.99      Y  O
ATOM   7683  N    SER   75      60.058  52.094  35.335  1.00   41.67      Y  N
ATOM   7684  CA   SER   75      59.069  53.066  35.801  1.00   41.67      Y  C
ATOM   7685  CB   SER   75      59.090  54.291  34.889  1.00   51.63      Y  C
ATOM   7686  OG   SER   75      58.934  53.909  33.535  1.00   51.63      Y  O
ATOM   7687  C    SER   75      57.644  52.524  35.901  1.00   41.67      Y  C
ATOM   7688  O    SER   75      56.885  52.924  36.777  1.00   41.67      Y  O
ATOM   7689  N    SER   76      57.280  51.627  34.993  1.00   62.86      Y  N
ATOM   7690  CA   SER   76      55.950  51.032  34.996  1.00   62.86      Y  C
ATOM   7691  CB   SER   76      55.045  51.724  33.980  1.00   71.45      Y  C
ATOM   7692  OG   SER   76      53.779  51.086  33.932  1.00   71.45      Y  O
ATOM   7693  C    SER   76      56.056  49.558  34.649  1.00   62.86      Y  C
ATOM   7694  O    SER   76      55.970  49.176  33.480  1.00   62.86      Y  O
ATOM   7695  N    LEU   77      56.237  48.734  35.675  1.00   53.25      Y  N
ATOM   7696  CA   LEU   77      56.380  47.298  35.490  1.00   53.25      Y  C
ATOM   7697  CB   LEU   77      56.342  46.596  36.841  1.00   41.03      Y  C
ATOM   7698  CG   LEU   77      57.317  45.433  37.008  1.00   41.03      Y  C
ATOM   7699  CD1  LEU   77      56.911  44.632  38.239  1.00   41.03      Y  C
ATOM   7700  CD2  LEU   77      57.310  44.548  35.766  1.00   41.03      Y  C
ATOM   7701  C    LEU   77      55.303  46.703  34.590  1.00   53.25      Y  C
ATOM   7702  O    LEU   77      54.114  46.944  34.787  1.00   53.25      Y  O
ATOM   7703  N    GLN   78      55.723  45.921  33.602  1.00   82.27      Y  N
ATOM   7704  CA   GLN   78      54.781  45.285  32.691  1.00   82.27      Y  C
ATOM   7705  CB   GLN   78      55.094  45.667  31.243  1.00   41.92      Y  C
ATOM   7706  CG   GLN   78      54.907  47.148  30.956  1.00   41.92      Y  C
ATOM   7707  CD   GLN   78      53.508  47.627  31.288  1.00   41.92      Y  C
ATOM   7708  OE1  GLN   78      52.520  47.033  30.852  1.00   41.92      Y  O
ATOM   7709  NE2  GLN   78      53.416  48.711  32.056  1.00   41.92      Y  N
ATOM   7710  C    GLN   78      54.830  43.774  32.852  1.00   82.27      Y  C
ATOM   7711  O    GLN   78      55.851  43.213  33.244  1.00   82.27      Y  O
ATOM   7712  N    PRO   79      53.718  43.093  32.549  1.00   81.12      Y  N
ATOM   7713  CD   PRO   79      52.505  43.636  31.915  1.00   80.96      Y  C
ATOM   7714  CA   PRO   79      53.632  41.636  32.660  1.00   81.12      Y  C
ATOM   7715  CB   PRO   79      52.198  41.351  32.225  1.00   80.96      Y  C
ATOM   7716  CG   PRO   79      51.949  42.426  31.213  1.00   80.96      Y  C
ATOM   7717  C    PRO   79      54.663  40.914  31.792  1.00   81.12      Y  C
ATOM   7718  O    PRO   79      54.865  39.708  31.914  1.00   81.12      Y  O
ATOM   7719  N    GLU   80      55.316  41.670  30.921  1.00   44.20      Y  N
ATOM   7720  CA   GLU   80      56.316  41.120  30.021  1.00   44.20      Y  C
ATOM   7721  CB   GLU   80      56.117  41.729  28.636  1.00  102.65      Y  C
ATOM   7722  CG   GLU   80      55.853  43.217  28.678  1.00  102.65      Y  C
ATOM   7723  CD   GLU   80      55.814  43.833  27.301  1.00  102.65      Y  C
ATOM   7724  OE1  GLU   80      56.717  43.528  26.494  1.00  102.65      Y  O
ATOM   7725  OE2  GLU   80      54.891  44.629  27.026  1.00  102.65      Y  O
ATOM   7726  C    GLU   80      57.742  41.368  30.520  1.00   44.20      Y  C
ATOM   7727  O    GLU   80      58.672  40.652  30.145  1.00   44.20      Y  O
ATOM   7728  N    ASP   81      57.902  42.380  31.371  1.00   52.34      Y  N
ATOM   7729  CA   ASP   81      59.206  42.733  31.931  1.00   52.34      Y  C
ATOM   7730  CB   ASP   81      59.167  44.111  32.593  1.00   55.47      Y  C
ATOM   7731  CG   ASP   81      58.700  45.195  31.663  1.00   55.47      Y  C
ATOM   7732  OD1  ASP   81      58.950  45.085  30.446  1.00   55.47      Y  O
ATOM   7733  OD2  ASP   81      58.099  46.171  32.156  1.00   55.47      Y  O
ATOM   7734  C    ASP   81      59.641  41.740  32.991  1.00   52.34      Y  C
ATOM   7735  O    ASP   81      60.649  41.946  33.673  1.00   52.34      Y  O
ATOM   7736  N    PHE   82      58.884  40.664  33.138  1.00   63.15      Y  N
ATOM   7737  CA   PHE   82      59.207  39.685  34.158  1.00   63.15      Y  C
ATOM   7738  CB   PHE   82      57.917  39.041  34.647  1.00  168.46      Y  C
```

Fig. 19: A-107

| ATOM | 7739 | CG | PHE | 82 | 57.024 | 40.004 | 35.381 | 1.00 | 168.46 | Y | C |
|---|---|---|---|---|---|---|---|---|---|---|---|
| ATOM | 7740 | CD1 | PHE | 82 | 57.371 | 40.454 | 36.650 | 1.00 | 168.46 | Y | C |
| ATOM | 7741 | CD2 | PHE | 82 | 55.866 | 40.498 | 34.791 | 1.00 | 168.46 | Y | C |
| ATOM | 7742 | CE1 | PHE | 82 | 56.579 | 41.384 | 37.321 | 1.00 | 168.46 | Y | C |
| ATOM | 7743 | CE2 | PHE | 82 | 55.067 | 41.430 | 35.458 | 1.00 | 168.46 | Y | C |
| ATOM | 7744 | CZ | PHE | 82 | 55.425 | 41.872 | 36.724 | 1.00 | 168.46 | Y | C |
| ATOM | 7745 | C | PHE | 82 | 60.238 | 38.657 | 33.742 | 1.00 | 63.15 | Y | C |
| ATOM | 7746 | O | PHE | 82 | 59.960 | 37.733 | 32.979 | 1.00 | 63.15 | Y | O |
| ATOM | 7747 | N | ALA | 83 | 61.447 | 38.867 | 34.256 | 1.00 | 34.42 | Y | N |
| ATOM | 7748 | CA | ALA | 83 | 62.601 | 38.015 | 34.000 | 1.00 | 34.42 | Y | C |
| ATOM | 7749 | CB | ALA | 83 | 63.138 | 38.260 | 32.595 | 1.00 | 53.93 | Y | C |
| ATOM | 7750 | C | ALA | 83 | 63.669 | 38.353 | 35.036 | 1.00 | 34.42 | Y | C |
| ATOM | 7751 | O | ALA | 83 | 63.389 | 39.033 | 36.025 | 1.00 | 34.42 | Y | O |
| ATOM | 7752 | N | THR | 84 | 64.890 | 37.877 | 34.821 | 1.00 | 50.51 | Y | N |
| ATOM | 7753 | CA | THR | 84 | 65.968 | 38.161 | 35.758 | 1.00 | 50.51 | Y | C |
| ATOM | 7754 | CB | THR | 84 | 66.566 | 36.849 | 36.323 | 1.00 | 63.35 | Y | C |
| ATOM | 7755 | OG1 | THR | 84 | 67.888 | 37.096 | 36.819 | 1.00 | 63.35 | Y | O |
| ATOM | 7756 | CG2 | THR | 84 | 66.584 | 35.766 | 35.260 | 1.00 | 63.35 | Y | C |
| ATOM | 7757 | C | THR | 84 | 67.028 | 39.021 | 35.065 | 1.00 | 50.51 | Y | C |
| ATOM | 7758 | O | THR | 84 | 67.474 | 38.708 | 33.959 | 1.00 | 50.51 | Y | O |
| ATOM | 7759 | N | TYR | 85 | 67.401 | 40.119 | 35.723 | 1.00 | 40.66 | Y | N |
| ATOM | 7760 | CA | TYR | 85 | 68.364 | 41.076 | 35.187 | 1.00 | 40.66 | Y | C |
| ATOM | 7761 | CB | TYR | 85 | 67.819 | 42.503 | 35.330 | 1.00 | 42.00 | Y | C |
| ATOM | 7762 | CG | TYR | 85 | 66.476 | 42.693 | 34.668 | 1.00 | 42.00 | Y | C |
| ATOM | 7763 | CD1 | TYR | 85 | 65.330 | 42.084 | 35.185 | 1.00 | 42.00 | Y | C |
| ATOM | 7764 | CE1 | TYR | 85 | 64.110 | 42.163 | 34.521 | 1.00 | 42.00 | Y | C |
| ATOM | 7765 | CD2 | TYR | 85 | 66.363 | 43.401 | 33.472 | 1.00 | 42.00 | Y | C |
| ATOM | 7766 | CE2 | TYR | 85 | 65.148 | 43.486 | 32.800 | 1.00 | 42.00 | Y | C |
| ATOM | 7767 | CZ | TYR | 85 | 64.028 | 42.860 | 33.327 | 1.00 | 42.00 | Y | C |
| ATOM | 7768 | OH | TYR | 85 | 62.841 | 42.889 | 32.633 | 1.00 | 42.00 | Y | O |
| ATOM | 7769 | C | TYR | 85 | 69.746 | 41.012 | 35.816 | 1.00 | 40.66 | Y | C |
| ATOM | 7770 | O | TYR | 85 | 69.891 | 40.982 | 37.042 | 1.00 | 40.66 | Y | O |
| ATOM | 7771 | N | TYR | 86 | 70.756 | 41.016 | 34.949 | 1.00 | 43.34 | Y | N |
| ATOM | 7772 | CA | TYR | 86 | 72.159 | 40.970 | 35.349 | 1.00 | 43.34 | Y | C |
| ATOM | 7773 | CB | TYR | 86 | 72.890 | 39.833 | 34.633 | 1.00 | 34.52 | Y | C |
| ATOM | 7774 | CG | TYR | 86 | 72.406 | 38.441 | 34.941 | 1.00 | 34.52 | Y | C |
| ATOM | 7775 | CD1 | TYR | 86 | 72.902 | 37.731 | 36.040 | 1.00 | 34.52 | Y | C |
| ATOM | 7776 | CE1 | TYR | 86 | 72.472 | 36.433 | 36.303 | 1.00 | 34.52 | Y | C |
| ATOM | 7777 | CD2 | TYR | 86 | 71.466 | 37.820 | 34.118 | 1.00 | 34.52 | Y | C |
| ATOM | 7778 | CE2 | TYR | 86 | 71.031 | 36.530 | 34.375 | 1.00 | 34.52 | Y | C |
| ATOM | 7779 | CZ | TYR | 86 | 71.538 | 35.841 | 35.462 | 1.00 | 34.52 | Y | C |
| ATOM | 7780 | OH | TYR | 86 | 71.124 | 34.549 | 35.683 | 1.00 | 34.52 | Y | O |
| ATOM | 7781 | C | TYR | 86 | 72.873 | 42.259 | 34.957 | 1.00 | 43.34 | Y | C |
| ATOM | 7782 | O | TYR | 86 | 72.662 | 42.780 | 33.851 | 1.00 | 43.34 | Y | O |
| ATOM | 7783 | N | CYS | 87 | 73.706 | 42.773 | 35.862 | 1.00 | 31.05 | Y | N |
| ATOM | 7784 | CA | CYS | 87 | 74.499 | 43.945 | 35.548 | 1.00 | 31.05 | Y | C |
| ATOM | 7785 | C | CYS | 87 | 75.857 | 43.346 | 35.237 | 1.00 | 31.05 | Y | C |
| ATOM | 7786 | O | CYS | 87 | 76.171 | 42.248 | 35.707 | 1.00 | 31.05 | Y | O |
| ATOM | 7787 | CB | CYS | 87 | 74.587 | 44.922 | 36.721 | 1.00 | 63.19 | Y | C |
| ATOM | 7788 | SG | CYS | 87 | 75.151 | 44.318 | 38.354 | 1.00 | 63.19 | Y | S |
| ATOM | 7789 | N | GLN | 88 | 76.653 | 44.040 | 34.431 | 1.00 | 35.54 | Y | N |
| ATOM | 7790 | CA | GLN | 88 | 77.964 | 43.536 | 34.058 | 1.00 | 35.54 | Y | C |
| ATOM | 7791 | CB | GLN | 88 | 77.834 | 42.732 | 32.769 | 1.00 | 42.46 | Y | C |
| ATOM | 7792 | CG | GLN | 88 | 79.114 | 42.125 | 32.259 | 1.00 | 42.46 | Y | C |
| ATOM | 7793 | CD | GLN | 88 | 79.594 | 42.783 | 30.983 | 1.00 | 42.46 | Y | C |
| ATOM | 7794 | OE1 | GLN | 88 | 78.834 | 42.928 | 30.019 | 1.00 | 42.46 | Y | O |
| ATOM | 7795 | NE2 | GLN | 88 | 80.863 | 43.183 | 30.965 | 1.00 | 42.46 | Y | N |
| ATOM | 7796 | C | GLN | 88 | 78.930 | 44.691 | 33.873 | 1.00 | 35.54 | Y | C |
| ATOM | 7797 | O | GLN | 88 | 78.530 | 45.774 | 33.436 | 1.00 | 35.54 | Y | O |
| ATOM | 7798 | N | GLN | 89 | 80.195 | 44.465 | 34.216 | 1.00 | 24.85 | Y | N |
| ATOM | 7799 | CA | GLN | 89 | 81.208 | 45.502 | 34.082 | 1.00 | 24.85 | Y | C |
| ATOM | 7800 | CB | GLN | 89 | 81.794 | 45.851 | 35.458 | 1.00 | 29.69 | Y | C |
| ATOM | 7801 | CG | GLN | 89 | 82.481 | 44.722 | 36.182 | 1.00 | 29.69 | Y | C |
| ATOM | 7802 | CD | GLN | 89 | 83.903 | 44.496 | 35.696 | 1.00 | 29.69 | Y | C |
| ATOM | 7803 | OE1 | GLN | 89 | 84.676 | 45.442 | 35.535 | 1.00 | 29.69 | Y | O |
| ATOM | 7804 | NE2 | GLN | 89 | 84.261 | 43.238 | 35.476 | 1.00 | 29.69 | Y | N |
| ATOM | 7805 | C | GLN | 89 | 82.294 | 45.043 | 33.128 | 1.00 | 24.85 | Y | C |
| ATOM | 7806 | O | GLN | 89 | 82.527 | 43.853 | 32.990 | 1.00 | 24.85 | Y | O |
| ATOM | 7807 | N | TRP | 90 | 82.943 | 45.993 | 32.460 | 1.00 | 39.13 | Y | N |
| ATOM | 7808 | CA | TRP | 90 | 84.008 | 45.672 | 31.510 | 1.00 | 39.13 | Y | C |
| ATOM | 7809 | CB | TRP | 90 | 83.529 | 45.955 | 30.069 | 1.00 | 30.35 | Y | C |
| ATOM | 7810 | CG | TRP | 90 | 83.422 | 47.437 | 29.678 | 1.00 | 30.35 | Y | C |
| ATOM | 7811 | CD2 | TRP | 90 | 83.088 | 47.967 | 28.385 | 1.00 | 30.35 | Y | C |

Fig. 19: A-108

```
ATOM   7812  CE2 TRP    90      83.122  49.375  28.486  1.00  30.35      Y    C
ATOM   7813  CE3 TRP    90      82.762  47.389  27.152  1.00  30.35      Y    C
ATOM   7814  CD1 TRP    90      83.635  48.523  30.484  1.00  30.35      Y    C
ATOM   7815  NE1 TRP    90      83.460  49.686  29.776  1.00  30.35      Y    N
ATOM   7816  CZ2 TRP    90      82.840  50.217  27.398  1.00  30.35      Y    C
ATOM   7817  CZ3 TRP    90      82.480  48.232  26.063  1.00  30.35      Y    C
ATOM   7818  CH2 TRP    90      82.522  49.627  26.199  1.00  30.35      Y    C
ATOM   7819  C   TRP    90      85.290  46.457  31.816  1.00  39.13      Y    C
ATOM   7820  O   TRP    90      86.293  46.339  31.115  1.00  39.13      Y    O
ATOM   7821  N   SER    91      85.251  47.254  32.876  1.00  18.51      Y    N
ATOM   7822  CA  SER    91      86.395  48.067  33.257  1.00  18.51      Y    C
ATOM   7823  CB  SER    91      85.948  49.152  34.237  1.00  45.24      Y    C
ATOM   7824  OG  SER    91      84.909  49.937  33.686  1.00  45.24      Y    O
ATOM   7825  C   SER    91      87.555  47.267  33.866  1.00  18.51      Y    C
ATOM   7826  O   SER    91      88.717  47.649  33.739  1.00  18.51      Y    O
ATOM   7827  N   GLY    92      87.241  46.166  34.534  1.00  40.34      Y    N
ATOM   7828  CA  GLY    92      88.282  45.360  35.146  1.00  40.34      Y    C
ATOM   7829  C   GLY    92      88.273  43.910  34.687  1.00  40.34      Y    C
ATOM   7830  O   GLY    92      87.248  43.386  34.244  1.00  40.34      Y    O
ATOM   7831  N   ASN    93      89.420  43.249  34.801  1.00  37.36      Y    N
ATOM   7832  CA  ASN    93      89.544  41.863  34.380  1.00  37.36      Y    C
ATOM   7833  CB  ASN    93      90.765  41.702  33.492  1.00  14.59      Y    C
ATOM   7834  CG  ASN    93      90.634  42.451  32.208  1.00  14.59      Y    C
ATOM   7835  OD1 ASN    93      91.556  43.159  31.796  1.00  14.59      Y    O
ATOM   7836  ND2 ASN    93      89.482  42.305  31.552  1.00  14.59      Y    N
ATOM   7837  C   ASN    93      89.668  40.944  35.574  1.00  37.36      Y    C
ATOM   7838  O   ASN    93      90.346  41.265  36.539  1.00  37.36      Y    O
ATOM   7839  N   PRO    94      89.005  39.783  35.525  1.00  28.71      Y    N
ATOM   7840  CD  PRO    94      88.990  38.808  36.629  1.00   9.29      Y    C
ATOM   7841  CA  PRO    94      88.167  39.322  34.412  1.00  28.71      Y    C
ATOM   7842  CB  PRO    94      87.940  37.858  34.745  1.00   9.29      Y    C
ATOM   7843  CG  PRO    94      87.823  37.904  36.251  1.00   9.29      Y    C
ATOM   7844  C   PRO    94      86.845  40.076  34.372  1.00  28.71      Y    C
ATOM   7845  O   PRO    94      86.418  40.640  35.384  1.00  28.71      Y    O
ATOM   7846  N   TRP    95      86.200  40.084  33.206  1.00  37.86      Y    N
ATOM   7847  CA  TRP    95      84.910  40.743  33.082  1.00  37.86      Y    C
ATOM   7848  CB  TRP    95      84.428  40.762  31.629  1.00  24.14      Y    C
ATOM   7849  CG  TRP    95      85.220  41.665  30.744  1.00  24.14      Y    C
ATOM   7850  CD2 TRP    95      85.537  41.458  29.359  1.00  24.14      Y    C
ATOM   7851  CE2 TRP    95      86.285  42.575  28.929  1.00  24.14      Y    C
ATOM   7852  CE3 TRP    95      85.264  40.437  28.440  1.00  24.14      Y    C
ATOM   7853  CD1 TRP    95      85.770  42.867  31.085  1.00  24.14      Y    C
ATOM   7854  NE1 TRP    95      86.411  43.419  30.000  1.00  24.14      Y    N
ATOM   7855  CZ2 TRP    95      86.765  42.697  27.624  1.00  24.14      Y    C
ATOM   7856  CZ3 TRP    95      85.748  40.566  27.133  1.00  24.14      Y    C
ATOM   7857  CH2 TRP    95      86.487  41.685  26.744  1.00  24.14      Y    C
ATOM   7858  C   TRP    95      83.959  39.922  33.941  1.00  37.86      Y    C
ATOM   7859  O   TRP    95      83.997  38.688  33.920  1.00  37.86      Y    O
ATOM   7860  N   THR    96      83.105  40.605  34.695  1.00  19.88      Y    N
ATOM   7861  CA  THR    96      82.192  39.913  35.582  1.00  19.88      Y    C
ATOM   7862  CB  THR    96      82.692  40.028  37.038  1.00  22.31      Y    C
ATOM   7863  OG1 THR    96      82.747  41.408  37.404  1.00  22.31      Y    O
ATOM   7864  CG2 THR    96      84.091  39.443  37.186  1.00  22.31      Y    C
ATOM   7865  C   THR    96      80.759  40.413  35.508  1.00  19.88      Y    C
ATOM   7866  O   THR    96      80.500  41.491  34.998  1.00  19.88      Y    O
ATOM   7867  N   PHE    97      79.839  39.596  36.015  1.00  20.15      Y    N
ATOM   7868  CA  PHE    97      78.420  39.912  36.073  1.00  20.15      Y    C
ATOM   7869  CB  PHE    97      77.580  38.827  35.397  1.00  25.28      Y    C
ATOM   7870  CG  PHE    97      77.890  38.613  33.946  1.00  25.28      Y    C
ATOM   7871  CD1 PHE    97      79.062  37.994  33.554  1.00  25.28      Y    C
ATOM   7872  CD2 PHE    97      76.979  38.990  32.969  1.00  25.28      Y    C
ATOM   7873  CE1 PHE    97      79.322  37.750  32.204  1.00  25.28      Y    C
ATOM   7874  CE2 PHE    97      77.234  38.748  31.611  1.00  25.28      Y    C
ATOM   7875  CZ  PHE    97      78.404  38.128  31.233  1.00  25.28      Y    C
ATOM   7876  C   PHE    97      78.054  39.931  37.557  1.00  20.15      Y    C
ATOM   7877  O   PHE    97      78.841  39.487  38.394  1.00  20.15      Y    O
ATOM   7878  N   GLY    98      76.875  40.460  37.879  1.00  30.22      Y    N
ATOM   7879  CA  GLY    98      76.412  40.488  39.256  1.00  30.22      Y    C
ATOM   7880  C   GLY    98      75.676  39.178  39.406  1.00  30.22      Y    C
ATOM   7881  O   GLY    98      75.506  38.478  38.405  1.00  30.22      Y    O
ATOM   7882  N   GLN    99      75.235  38.819  40.608  1.00  24.51      Y    N
ATOM   7883  CA  GLN    99      74.537  37.541  40.755  1.00  24.51      Y    C
ATOM   7884  CB  GLN    99      74.350  37.163  42.231  1.00  60.71      Y    C
```

Fig. 19: A-109

| | | | | | | | | | | |
|---|---|---|---|---|---|---|---|---|---|---|
| ATOM | 7885 | CG | GLN | 99 | 74.599 | 38.274 | 43.209 | 1.00 | 60.71 | Y C |
| ATOM | 7886 | CD | GLN | 99 | 73.728 | 39.464 | 42.945 | 1.00 | 60.71 | Y C |
| ATOM | 7887 | OE1 | GLN | 99 | 72.510 | 39.411 | 43.113 | 1.00 | 60.71 | Y O |
| ATOM | 7888 | NE2 | GLN | 99 | 74.346 | 40.551 | 42.515 | 1.00 | 60.71 | Y N |
| ATOM | 7889 | C | GLN | 99 | 73.189 | 37.507 | 40.043 | 1.00 | 24.51 | Y C |
| ATOM | 7890 | O | GLN | 99 | 72.587 | 36.443 | 39.894 | 1.00 | 24.51 | Y O |
| ATOM | 7891 | N | GLY | 100 | 72.730 | 38.666 | 39.586 | 1.00 | 42.40 | Y N |
| ATOM | 7892 | CA | GLY | 100 | 71.455 | 38.725 | 38.900 | 1.00 | 42.40 | Y C |
| ATOM | 7893 | C | GLY | 100 | 70.355 | 39.043 | 39.886 | 1.00 | 42.40 | Y C |
| ATOM | 7894 | O | GLY | 100 | 70.483 | 38.749 | 41.074 | 1.00 | 42.40 | Y O |
| ATOM | 7895 | N | THR | 101 | 69.283 | 39.662 | 39.399 | 1.00 | 27.30 | Y N |
| ATOM | 7896 | CA | THR | 101 | 68.144 | 40.021 | 40.236 | 1.00 | 27.30 | Y C |
| ATOM | 7897 | CB | THR | 101 | 68.024 | 41.538 | 40.401 | 1.00 | 28.79 | Y C |
| ATOM | 7898 | OG1 | THR | 101 | 69.008 | 41.995 | 41.336 | 1.00 | 28.79 | Y O |
| ATOM | 7899 | CG2 | THR | 101 | 66.646 | 41.907 | 40.892 | 1.00 | 28.79 | Y C |
| ATOM | 7900 | C | THR | 101 | 66.903 | 39.492 | 39.551 | 1.00 | 27.30 | Y C |
| ATOM | 7901 | O | THR | 101 | 66.619 | 39.845 | 38.408 | 1.00 | 27.30 | Y O |
| ATOM | 7902 | N | LYS | 102 | 66.166 | 38.635 | 40.240 | 1.00 | 67.88 | Y N |
| ATOM | 7903 | CA | LYS | 102 | 64.978 | 38.064 | 39.642 | 1.00 | 67.88 | Y C |
| ATOM | 7904 | CB | LYS | 102 | 64.806 | 36.618 | 40.106 | 1.00 | 117.75 | Y C |
| ATOM | 7905 | CG | LYS | 102 | 63.920 | 35.785 | 39.198 | 1.00 | 117.75 | Y C |
| ATOM | 7906 | CD | LYS | 102 | 63.925 | 34.321 | 39.608 | 1.00 | 117.75 | Y C |
| ATOM | 7907 | CE | LYS | 102 | 63.094 | 33.485 | 38.651 | 1.00 | 117.75 | Y C |
| ATOM | 7908 | NZ | LYS | 102 | 63.586 | 33.621 | 37.250 | 1.00 | 117.75 | Y N |
| ATOM | 7909 | C | LYS | 102 | 63.749 | 38.885 | 39.996 | 1.00 | 67.88 | Y C |
| ATOM | 7910 | O | LYS | 102 | 63.560 | 39.262 | 41.155 | 1.00 | 67.88 | Y O |
| ATOM | 7911 | N | VAL | 103 | 62.926 | 39.176 | 38.989 | 1.00 | 55.50 | Y N |
| ATOM | 7912 | CA | VAL | 103 | 61.706 | 39.941 | 39.208 | 1.00 | 55.50 | Y C |
| ATOM | 7913 | CB | VAL | 103 | 61.779 | 41.349 | 38.510 | 1.00 | 68.46 | Y C |
| ATOM | 7914 | CG1 | VAL | 103 | 63.207 | 41.865 | 38.530 | 1.00 | 68.46 | Y C |
| ATOM | 7915 | CG2 | VAL | 103 | 61.258 | 41.290 | 37.084 | 1.00 | 68.46 | Y C |
| ATOM | 7916 | C | VAL | 103 | 60.489 | 39.141 | 38.709 | 1.00 | 55.50 | Y C |
| ATOM | 7917 | O | VAL | 103 | 60.378 | 38.828 | 37.517 | 1.00 | 55.50 | Y O |
| ATOM | 7918 | N | GLU | 104 | 59.597 | 38.779 | 39.633 | 1.00 | 70.95 | Y N |
| ATOM | 7919 | CA | GLU | 104 | 58.395 | 38.025 | 39.281 | 1.00 | 70.95 | Y C |
| ATOM | 7920 | CB | GLU | 104 | 58.243 | 36.764 | 40.145 | 1.00 | 145.77 | Y C |
| ATOM | 7921 | CG | GLU | 104 | 57.957 | 37.019 | 41.616 | 1.00 | 145.77 | Y C |
| ATOM | 7922 | CD | GLU | 104 | 59.215 | 37.263 | 42.418 | 1.00 | 145.77 | Y C |
| ATOM | 7923 | OE1 | GLU | 104 | 59.106 | 37.542 | 43.631 | 1.00 | 145.77 | Y O |
| ATOM | 7924 | OE2 | GLU | 104 | 60.315 | 37.167 | 41.839 | 1.00 | 145.77 | Y O |
| ATOM | 7925 | C | GLU | 104 | 57.157 | 38.897 | 39.443 | 1.00 | 70.95 | Y C |
| ATOM | 7926 | O | GLU | 104 | 57.197 | 39.939 | 40.108 | 1.00 | 70.95 | Y O |
| ATOM | 7927 | N | ILE | 105 | 56.058 | 38.459 | 38.834 | 1.00 | 139.77 | Y N |
| ATOM | 7928 | CA | ILE | 105 | 54.791 | 39.184 | 38.876 | 1.00 | 139.77 | Y C |
| ATOM | 7929 | CB | ILE | 105 | 53.838 | 38.730 | 37.757 | 1.00 | 105.35 | Y C |
| ATOM | 7930 | CG2 | ILE | 105 | 52.923 | 39.875 | 37.373 | 1.00 | 105.35 | Y C |
| ATOM | 7931 | CG1 | ILE | 105 | 54.633 | 38.232 | 36.553 | 1.00 | 105.35 | Y C |
| ATOM | 7932 | CD1 | ILE | 105 | 53.775 | 37.746 | 35.397 | 1.00 | 105.35 | Y C |
| ATOM | 7933 | C | ILE | 105 | 54.047 | 38.952 | 40.180 | 1.00 | 139.77 | Y C |
| ATOM | 7934 | O | ILE | 105 | 53.763 | 37.810 | 40.533 | 1.00 | 139.77 | Y O |
| ATOM | 7935 | N | LYS | 106 | 53.706 | 40.031 | 40.880 | 1.00 | 101.75 | Y N |
| ATOM | 7936 | CA | LYS | 106 | 52.969 | 39.916 | 42.135 | 1.00 | 101.75 | Y C |
| ATOM | 7937 | CB | LYS | 106 | 53.545 | 40.870 | 43.189 | 1.00 | 95.13 | Y C |
| ATOM | 7938 | CG | LYS | 106 | 52.954 | 40.690 | 44.584 | 1.00 | 95.13 | Y C |
| ATOM | 7939 | CD | LYS | 106 | 53.556 | 41.665 | 45.586 | 1.00 | 95.13 | Y C |
| ATOM | 7940 | CE | LYS | 106 | 52.939 | 41.482 | 46.965 | 1.00 | 95.13 | Y C |
| ATOM | 7941 | NZ | LYS | 106 | 53.446 | 42.478 | 47.948 | 1.00 | 95.13 | Y N |
| ATOM | 7942 | C | LYS | 106 | 51.492 | 40.235 | 41.897 | 1.00 | 101.75 | Y C |
| ATOM | 7943 | O | LYS | 106 | 51.148 | 40.637 | 40.765 | 1.00 | 100.80 | Y O |
| ATOM | 7944 | OXT | LYS | 106 | 50.694 | 40.080 | 42.844 | 1.00 | 94.18 | Y O |
| ATOM | 7945 | MN | MN | 400 | 89.864 | 50.249 | 22.621 | 1.00 | 34.24 | N |

END

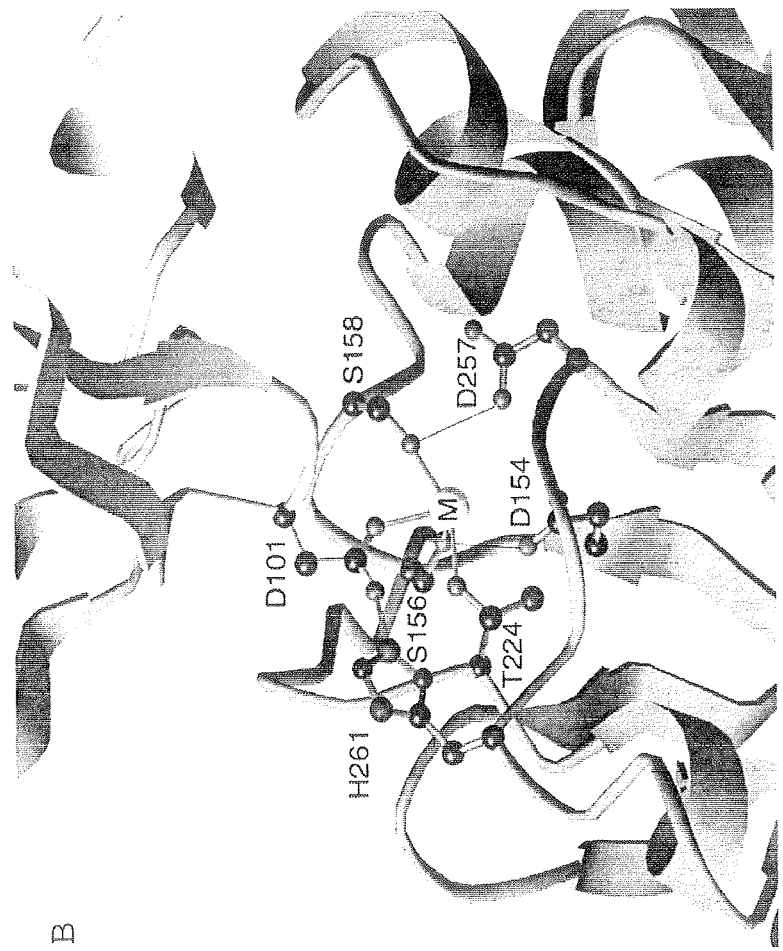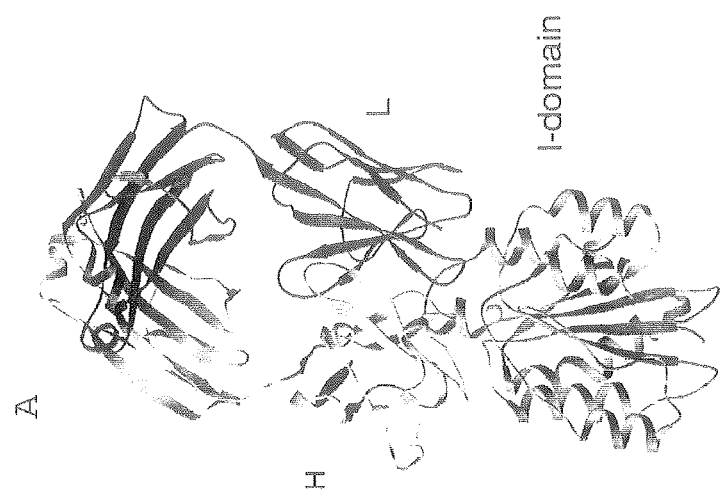
Fig. 20

# ANTIBODIES TO VLA-1

CROSS-REFERENCE TO RELATED APPLICATIONS

This application is a divisional application of U.S. application Ser. No. 10/474,832, filed Oct. 14, 2003 (which issued as U.S. Pat. No. 7,358,054 on Apr. 15, 2008), which is the National Stage filing under 35 U.S.C. §371 of International Application No. PCT/US02/11521, filed Apr. 12, 2002, which claims benefit under 35 U.S.C. §119(e) of U.S. provisional application Nos. 60/283,794, filed Apr. 13, 2001, and 60/303,689, filed Jul. 6, 2001.

FIELD OF THE INVENTION

This invention relates to antibodies to VLA-1 integrin and the use of these antibodies in treating inflammatory diseases and other immunological disorders.

This invention also relates to the crystal structure of the complex between one such antibody and the α1-I domain of VLA-1, and to the use of this structural information for computational drug design.

BACKGROUND OF THE INVENTION

Integrins are a superfamily of cell surface receptors that mediate cell-cell and cell-matrix adhesion. These proteins are known to provide anchorage as well as signals for cellular growth, migration and differentiation during development and tissue repair. They have been implicated in immune and inflammatory processes.

Integrins are heterodimeric proteins composed of two non-covalently linked polypeptide chains, α and β. The amino terminus of each chain forms a globular head that contributes to interchain linking and to ligand binding. The globular heads are connected to the transmembrane segments by stalks. The cytoplasmic tails are usually less than 50 amino acid residues long. Integrin subfamilies were originally defined on the basis of which β subunit was used to form the heterodimers. The β1-containing integrins are also called VLA molecules referring to "very late activation" antigens. VLA-1 to VLA-6 refer to β1 subfamily members containing α1 to α6 (i.e., CD49a to CD49f), respectively. For general review, see *Cellular and Molecular Immunology*, eds. Abul K. Abbas et al., W.B. Saunders Company, Philadelphia, Pa., 2000.

Collagen (both types I and IV) and laminin are known ligands of α1β1 integrin (i.e., VLA-1). VLA-1 has been implicated in cell adhesion and migration on collagen (Keely et al., 1995, *J. Cell Sci.* 108:595-607; and Gotwals et al., 1996, *J. Clin. Invest.* 97:2469-2477); in promoting contraction and reorganization of collagen matrices, a critical component of wound healing (Gotwals et al., supra; and Chiro, 1991, *Cell* 67:403-410); and in regulating the expression of genes involved in extracellular matrix remodeling (Riikonen et al., 1995, *J. Biol. Chem.* 270:1-5; and Langholz et al., 1995, *J. Cell Biol.* 131:1903-1915). Thus, improper regulation of VLA-1 may result in certain pathological conditions such as fibrosis.

Moreover, it has been suggested that VLA-1 may play a role in T cell/monocyte-driven diseases. Anti-VLA-1 antibodies block T-cell dependent cytokine expression (Miyake et al., 1993, *J. Exp. Med.* 177:863-868). Expression of VLA-1 is increased in persistently activated, 2 to 4 week old cultured T cells (Hemler et al., 1985, *Eur. J. Immunol.* 15:502-508). VLA-1 is also expressed on a high percentage of T cells isolated from the synovium of patients with rheumatoid arthritis (Hemler et al., 1986, *J. Clin. Invest.* 78:692-702).

Several crystal structures of integrin α subunits have been determined, including the structures of the α2-I domain of α2β1 (PDB accession code 1aox; Emsley et al., 1997, *J. Biol. Chem.* 272:28512-28517); the α1-I domain of rat α1β1 (PDB accession number 1ck4; Nolte et al., 1999, *FEBS Lett.* 452: 379-385; WO 00/20459); the α1 subunit of human α1β1 (PDB accession code 1qc5; Rich et al., 1999, *J. Biol. Chem.* 274:24906-24913); the αL-I and αM-I domains; and vWF-A3 (Lee et al., 1995, *Cell* 80:631-635; Lee et al., 1995, *Structure* 3:1333-1340; Qu et al., 1995, *Proc. Natl. Acad. Sci. USA* 92:10277-10281; Qu et al., 1996, *Structure* 4:931-942). The α2β1 structure revealed a helix (i.e., the C-helix) that created a trench or groove on one face of the protein at the metal-ion binding site (Emsley et al., supra). The crystal structure of the α2-I domain complexed to a short collagen-based triple helical peptide revealed that the collagen-based peptide was bound to that trench, where the α2-I amino acids that made intermolecular or metal contacts included Asp151, Asn154, Tyr157, Gln215, Asp219, Leu220, Thr221, Asp254, Glu256, His258, Tyr285, Leu286, Asn289, Leu291, Asn295, and Lys298 (PDB accession code 1dzi; Emsley et al., 2000, *Cell* 101:47-56; WO 01/73444). The amino acid numbering immediately above is based on PDB accession code 1dzi and herein referred to as "crystal numbering." The crystal structures of the rat and human α1-I domains revealed a similar trench.

SUMMARY OF THE INVENTION

The present invention provides anti-VLA-1 antibodies and methods of using these antibodies to treat a variety of inflammatory and immunological disorders.

Specifically, the invention embraces an antibody that specifically binds to VLA-1 (e.g., human VLA-1). This antibody contains light chain complementarity determining regions ("CDR"s) defined by amino acid residues 24 to 33, 49 to 55, and 88 to 96 of SEQ ID NO:1, and/or heavy chain complementarity determining regions defined by amino acid residues 31 to 35, 50 to 65, and 98 to 107 of SEQ ID NO:2. These CDRs may contain mutations (e.g., deletions, insertions and/or substitutions) in the non-antigen-contacting portions, as determined from the crystal structure disclosed herein, without affecting the VLA-1-binding activity of the antibody. Exemplary mutations are S24N, G92S and D101A in the light chain CDRs, and G55 S in the heavy chain CDR2. In one embodiment, the antibody of this invention contains a light chain variable domain sequence of SEQ ID NO:1 and/or a heavy chain variable domain sequence of SEQ ID NO:2.

In a related embodiment, the antibody of this invention contains the same heavy and light chain polypeptide sequences as an antibody produced by hybridoma mAQC2, deposited on Apr. 18, 2001 at the American Type Culture Collection ("ATCC"), 10801 University Boulevard, Manassas, Va. 20110-2209 and having ATCC accession number PTA3273. (All ATCC deposits recited herein were made under the Budapest Treaty). This antibody can be produced by, for example, hybridoma mAQC2, or cells containing nucleic acid sequences isolated from that hybridoma that encode the heavy and light chains of the mAQC2 monoclonal antibody.

In another embodiment, the antibody is a humanized antibody comprising at least one (e.g., 2, 3, 4, or 5) of the following residues in its light chain: Q1, L4, P46, W47 and Y71; or at least one (e.g., 2, 3, 4, 5, 6 or 7) of the following residues in its heavy chain: D1, V12, S28, F29, A49, T93, R94 (Kabat numbering convention). For instance, the antibody comprises Q1, L4 and Y71 in the light chain; and/or (i) F29, A49, T93 and R94, or (ii) A49 and T93, in the heavy chain.

The humanized antibody of this invention may contain a light chain variable domain sequence defined by amino acid residues 1 to 106 of SEQ ID NO:3, and/or a heavy chain variable domain sequence defined by amino acid residues 1 to 118 of SEQ ID NO:4. The humanized antibody may comprise the same heavy and/or light chain polypeptide sequences as an antibody produced by cell line hAQC2 (ATCC accession number PTA3275; deposited on Apr. 18, 2001).

In another embodiment, the humanized antibody of this invention may contain a mutation (e.g., deletion, substitution or addition) at one or more (e.g., 2, 3, 4, 5, 6, 7 or 8) of certain positions in the heavy chain such that an effector function of the antibody (e.g., the ability of the antibody to bind to a Fc receptor or a complement factor) is altered without affecting the antibody's ability to bind to VLA-1 (U.S. Pat. No. 5,648, 260). These heavy chain positions include, without limitation, residues 234, 235, 236, 237, 297, 318, 320 and 322 (EU numbering system). The humanized antibody can, for instance, contain the mutations L234A (i.e., replacing leucine at position 234 of an unmodified antibody with alanine) and L235A (EU numbering system) in its heavy chain. In one related embodiment, the antibody comprises the same heavy chain polypeptide sequence as an antibody produced by cell line hsAQC2 (ATCC accession number PTA3356; deposited on May 4, 2001).

In yet another embodiment, the humanized antibody of this invention may contain a mutation (e.g., deletion or substitution) at an amino acid residue that is a site for glycosylation, such that the glycosylation site is eliminated. Such an antibody may be clinically beneficial for having reduced effector functions or other undesired functions while retaining its VLA-1 binding affinity. Mutations of glycosylation sites can also be beneficial for process development (e.g., protein expression and purification). For instance, the heavy chain of the antibody may contain the mutation N297Q (EU numbering system) such that the heavy chain can no longer be glycosylated at this site. In one related embodiment, the humanized antibody may comprise the same heavy chain polypeptide sequence as an antibody produced by cell line haAQC2 (ATCC accession number PTA3274; deposited on Apr. 18, 2001).

In still other embodiments, the heavy and/or light chains of the antibody of this invention contain mutations that increase affinity for binding to VLA-1 and thereby increase potency for treating VLA-1-mediated disorders.

Embraced in this invention are also a composition containing an antibody of the invention and a pharmaceutically acceptable carrier; an isolated nucleic acid containing a coding sequence for SEQ ID NO:1; an isolated nucleic acid containing a coding sequence for SEQ ID NO:2; an isolated nucleic acid containing a coding sequence for the light chain of an antibody produced by hybridoma mAQC2; an isolated nucleic acid containing a coding sequence for the heavy chain of an antibody produced by hybridoma mAQC2; an isolated nucleic acid containing a coding sequence for the light chain of an antibody produced by cell line hAQC2; an isolated nucleic acid containing a coding sequence for the heavy chain of an antibody produced by cell line hAQC2; an isolated nucleic acid containing a coding sequence for the heavy chain of an antibody produced by cell line haAQC2; an isolated nucleic acid containing a coding sequence for the heavy chain of an antibody produced by cell line hsAQC2; an isolated nucleic acid containing a coding sequence for residues 1 to 106 of SEQ ID NO:3; an isolated nucleic acid containing a coding sequence for residues 1 to 118 of SEQ ID NO:4; cells of hybridoma mAQC2; cells from cell line hAQC2; cells from cell line haAQC2; and cells from cell line hsAQC2.

The present invention also provides a method of treating a subject with an immunological disorder mediated by VLA-1, including administering to the subject an effective amount of an antibody of this invention. For instance, this method is used to treat a human subject to palliate, ameliorate, stabilize, reverse, prevent, slow or delay progression of the disorder. Alternatively, this method is used prophylactically to treat a human subject at risk for developing this immunological disorder so as to prevent or delay the onset of the disorder. An "effective amount" of the composition can be administered in one or more dosages.

VLA-1 mediated immunological disorders include, but are not limited to, disorders in which the VLA-1 activity level is elevated in one or more tissues as compared to a normal subject. Examples of such disorders are skin related conditions (e.g., psoriasis, eczema, burns, dermatitis, and abnormal proliferation of hair follicle cells), fibrosis (e.g., kidney or lung fibrosis), allergic rhinitis, respiratory distress syndrome, asthma, bronchitis, tendinitis, bursitis, fever, migraine headaches, gastrointestinal conditions (e.g., inflammatory bowel disease, Crohn's disease, gastritis, irritable bowel syndrome, colitis and colorectal cancer), vascular diseases (e.g., atherosclerosis), periarteritis nodosa, thyroiditis, aplastic anemia, Hodgkin's Disease, rheumatic fever, osteoarthritis, autoimmune diseases (e.g., type I diabetes, myasthenia gravis, rheumatoid arthritis, systemic lupus erythematosus, and multiple sclerosis), sarcoidosis, nephrotic syndrome, renal failure, Bechet's Syndrome, polymyositis, gingivitis, hypersensitivity (e.g., delayed type hypersensitivity or immediate hypersensitivity), graft and transplant rejections, graft versus host disease (GVHD), conjunctivitis, swelling occurring after injury, myocardial ischemia, and endotoxin shock syndrome.

The present invention also provides a method of determining the level of VLA-1 in a tissue (e.g., tissue specimen and body fluid) comprising contacting the tissue (e.g., in vivo or in vitro) with the antibody of the invention, and then detecting the binding of the antibody to the tissue, thereby determining the level of VLA-1 in the tissue.

As used herein, the antibody of this invention can be, for instance, a murine antibody, a humanized antibody, or a chimeric antibody. It can be a whole antibody (i.e., with two full length light chains and two full length heavy chains) of any isotype and subtypes (e.g., IgM, IgD, IgG$_1$, IgG$_2$, IgG$_3$, IgG$_4$, IgE, IgA, and IgA$_2$; with either kappa or lambda light chain). Alternatively, the antibody of this invention refers to an antigen-binding fragment (e.g., Fab, F(ab')$_2$, and single chain Fv) of a whole antibody.

The present invention further provides crystallizable compositions and crystals of complexes formed by a rat-human chimeric α1-I domain (mutant RΔH) and a hAQC2 Fab fragment, and methods for using such compositions and crystals. This invention also provides the structure coordinates and binding sites of the chimeric domain and the hAQC2 Fab fragment. The atomic coordinates derived from the crystal structure described herein provide a structural basis for the biological activities of hAQC2 as well as a basis for rational design of VLA-1 agonists or antagonists with predicted biological activities (e.g., small molecule compounds or antibodies such as hAQC2 variants).

The crystal structure disclosed herein is the first crystal structure of an α1-I domain of an α1β1 integrin/Fab complex. This structure shows the residues critical for Fab binding by α1-I domain. In addition, the Fab binds in the putative collagen-binding site and inhibits collagen binding. Amino acid residues found in the binding site on the α1-I domain include Asp154, Ser156, Asn157, Ser158, Tyr160, Glu192, Glu218, Arg219, Gly220, Gly221, Arg222, Gln223, Thr224, Asp257, His261, Asn263, Arg291, and Leu294 (crystal numbering). Residues on the Fab fragment found to bind to the α1-I domain include light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering).

This invention also provides a computer for producing a three-dimensional representation of a molecular complex, where the molecular complex is defined by the set of structure coordinates of a complex of a chimeric I domain of an α1β1 integrin RΔH and humanized antibody hAQC2, according to FIG. 19; or a homologue of the molecular complex, the homologue having a root mean square deviation from the backbone atoms of the amino acids of not more than 0.65 Å. The computer includes a machine-readable data storage medium including a data storage material encoded with machine-readable data, where the data contains at least a portion of the structure coordinates of the complex according to FIG. 19; a working memory for storing instructions for processing the machine-readable data; a central processing unit coupled to the working memory and to the machine-readable data storage medium for processing the machine readable data into the three-dimensional representations; and a display coupled to the central-processing unit for displaying the three-dimensional representation.

This invention further provides a computer for producing a three-dimensional representation of a molecule or molecular complex including a binding site defined by structure coordinates of hAQC2 amino acids including at least seven (e.g., 7, 8, 9, 10, 11, 12, 13, 14, 15, or 16) of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering), according to FIG. 19; or a homologue of the molecule or molecular complex, where the homologue includes a binding site that has a root mean square deviation from the backbone atoms of the hAQC2 amino acids of not more than 1.10 Å. This invention also provides a computer for producing a three-dimensional representation of: a binding site defined by structure coordinates of hAQC2 amino acids including at least seven (e.g., 7, 8, 9, 10, 11, 12, 13, 14, 15, or 16) of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering), according to FIG. 19; a binding site of a homologue that has a root mean square deviation from the backbone atoms of the hAQC2 amino acids of not more than 1.10 Å.

This invention also provides a method for identifying an inhibitor of an I domain of an integrin including the steps of using structure coordinates of hAQC2 amino acids including at least seven (e.g., 7, 8, 9, 10, 11, 12, 13, 14, 15, or 16) of light chain residues Asn30, Tyr48, Trp90, Ser91, Asn93 and Trp95, and heavy chain residues Ser30, Arg39, Trp47, Ser52, Gly53, His56, Tyr58, Phe99, Gly100 and Asp101 (crystal numbering), according to FIG. 19 or ± a root mean square deviation from the backbone atoms of the hAQC2 amino acids not more than 1.10 Å, to generate a three-dimensional structure of a binding site; employing the three-dimensional structure to design or select a potential antagonist; synthesizing the potential antagonist; and contacting the potential antagonist with hAQC2 to determine the ability of the potential antagonist to interact with hAQC2, where the ability of the potential antagonist to interact with hAQC2 indicates that the potential antagonist is an inhibitor of the I domain. This invention further provides an inhibitor of I domain of integrin identified by this method.

This invention also provides a computer for producing a three-dimensional representation of a molecule or molecular complex including: a binding site defined by structure coordinates of I domain amino acid residues Asp 154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19; or a homologue of the molecule or molecular complex, where the homologue includes a second binding site that has a root mean square deviation from the backbone atoms of the I domain amino acids not more than 0.65 Å. This invention also provides a computer for producing a three-dimensional representation of: a first binding site defined by structure coordinates of I domain amino acids residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19; or a binding site of a homologue that has a root mean square deviation from the backbone atoms of the I domain amino acids not more than 0.65 Å.

This invention also provides a computer for producing a three-dimensional representation of a molecule or molecular complex including: a binding site defined by structure coordinates of I domain amino acids including at least three of residues Glu192, Gln218, Arg219, Gly220, and Gly221 (crystal numbering), according to FIG. 19; or a homologue of the molecule or molecular complex, where the homologue includes a second binding site that has a root mean square deviation from the backbone atoms of the I domain amino acids not more than 1.0 Å. The invention further provides a computer for producing a three-dimensional representation of a binding site defined by structure coordinates of I domain amino acids including at least three of residues Glu192, Gln218, Arg219, Gly220, and Gly221 (crystal numbering), according to FIG. 19; or a binding site of a homologue that has a root mean square deviation from the backbone atoms of the I domain amino acids not more than 1.0 Å.

This invention further provides methods for using these three-dimensional representations to design chemical entities that associate with the chimeric domain or the hAQC2 Fab fragment, or portions thereof; and act as potential inhibitors of the chimeric domain or the hAQC2 Fab fragment, or portions thereof. This invention also relates to compositions including chemical entities, such as inhibitors and variants of the chimeric domain or variants of the hAQC2 Fab fragment, where such chemical entities and variants are rationally designed by means of the structure coordinates of the chimeric domain or the hAQC2 Fab fragment, or binding sites. The invention further relates to use of the above-identified chemical entities to treat or prevent conditions associated with inappropriate or abnormal α1β1 activity in a subject.

This invention further provides a method for identifying an inhibitor of an I domain of an integrin including the steps of using the structure coordinates of I domain amino acids residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19, to generate a three-dimensional structure of a binding site; employing the three-dimensional structure to design or select a potential antagonist; synthesizing the potential antagonist; and contacting the potential antagonist with I domain to determine the ability of the potential antagonist to interact with I domain, where the ability of the potential antagonist to interact with the I domain indicates that the potential antagonist is an inhibitor of the I domain.

This invention also provides a method for identifying an inhibitor of an I domain of an integrin including the steps of using the structure coordinates of at least three of I domain amino acids including residues Glu192, Gln218, Arg219, Gly220, and Gly221 (crystal numbering), according to FIG. 19, or ± a root mean square deviation from the backbone atoms of the I domain amino acids not more than 0.65 Å, to generate a three-dimensional structure of a binding site; employing the three-dimensional structure to design or select a potential antagonist; synthesizing the potential antagonist; and contacting the potential antagonist with I domain to determine the ability of the potential antagonist to interact with I domain of integrin, where the ability of the potential antagonist to interact with the I domain indicates that the potential antagonist is an inhibitor of the I domain. This invention also provides an inhibitor of I domain of integrin identified by this method.

Other features and advantages of the invention will be apparent from the following detailed description, and from the claims.

Arthritis was apparent by day 6 and continued for several weeks. Mice were treated i.p. with mAbs (250 µg) or Ig fusion protein (200 µg) every 3$^{rd}$ day starting on day 4. Mice received either mAb (Ha4/8 isotype control or Ha31/8 anti-α1), Ig fusion protein (Isotype control Ig or TNF-R55-Ig) or a combination of both (250 ug Ha31/8 and 200 ug T —R55-Ig). Each limb was evaluated and scored on a 0 to 4 scale every 3$^{rd}$ day. Results are expressed as the mean arthritic score per limb (maximum score of 4). Groups of 4 mice per condition were used.

FIG. 11. Location of the Epitope for the anti-α1 I domain Blocking mAbs. A. Amino acid sequence of the rat (top; SEQ ID NO:63) and human (below; residues of SEQ ID NO:64, which are different from rat are shown) α1-I domain. The residues that comprise the MIDAS (metal ion dependent adhesion site) motif are shown in bold. The human amino acids that replaced the corresponding rat residues (RΔH) are shown below the rat sequence in the boxed region. For clarity, residue numbering in the text refers to this figure, unless otherwise designated, e.g., as crystal numbering. B. Increasing concentrations of mAb AJH10 (ATCC No. PTA-3580; deposited under the Budapest Treaty with the American Type Culture Collection, Manassas, Va., USA on Aug. 2, 2001) were bound to plates coated with 30 µg/mL human (circles), rat (triangles) or RΔH (squares) α1-I domain. Data shown is representative of three experiments.

Figure 12:
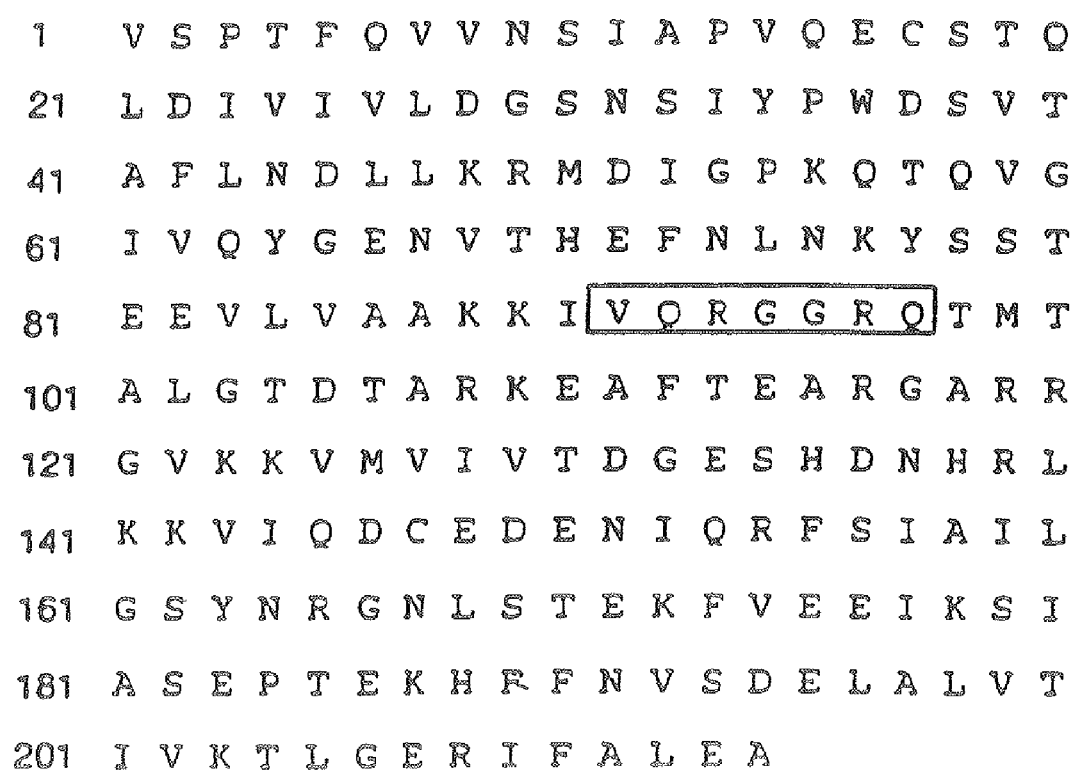

FIG. 12. Amino acid sequence of the human α1-I domain (SEQ ID NO:64).

Figure 13A:
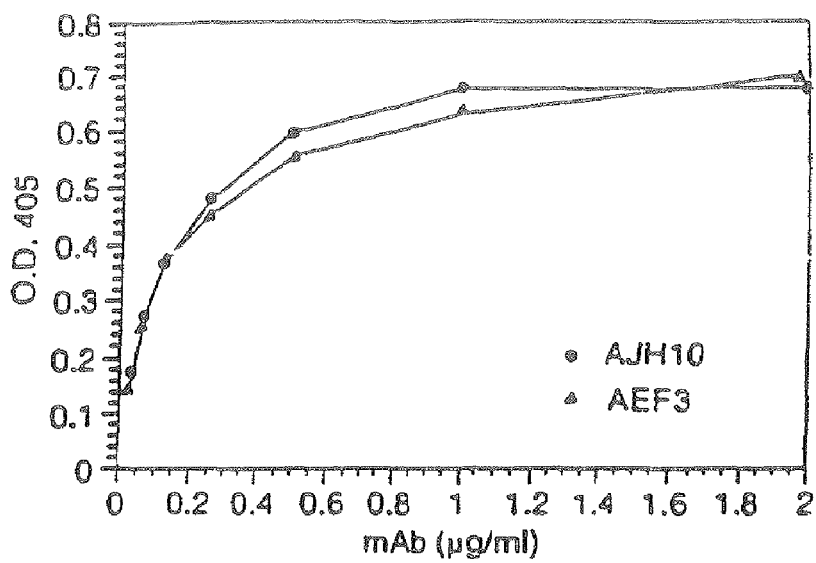
Figure 13B:
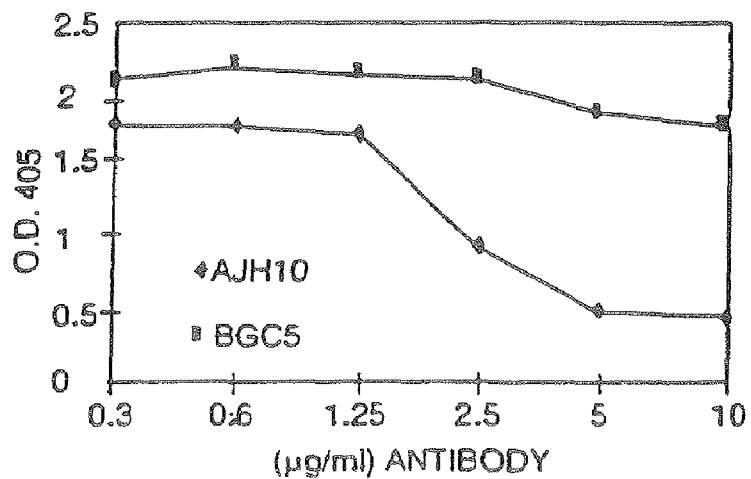
Figure 13C:
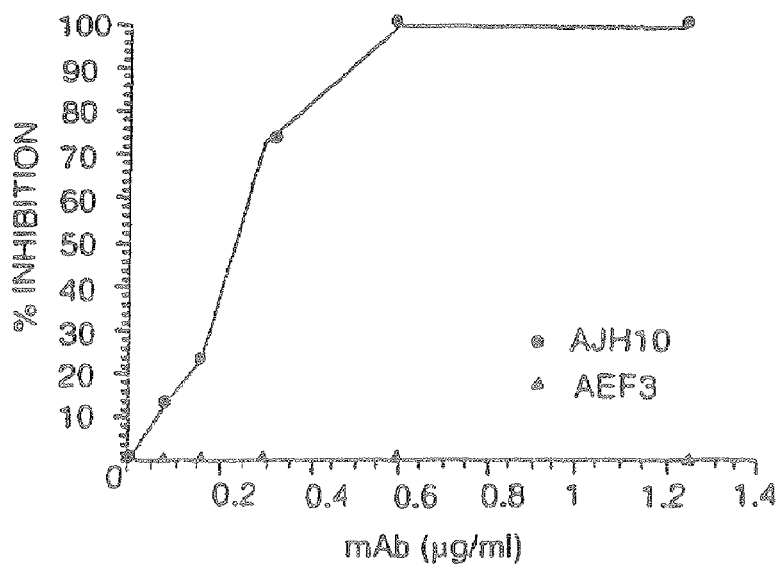

FIG. 13. Identification of a blocking mAb to the α1-I domain. A. Increasing concentration of mAbs AEF3 (triangles) or AJH10 (circles) were bound to plates coated with 30 µg/ml α1-I domain. B. The α1-I domain was treated with increasing concentrations of mAb AJH10 (diamonds) or mAb BGC5 (squares) and bound collagen IV (2 µg/ml) coated plates. C. K562-α1 cell were treated with increasing concentration of mAbs AEF3 (triangles) or AJH10 (circles) and bound to collagen IV (5 µg/ml) coated plates. 45-50% of cells added to each well adhered to collagen IV. Data shown is representative of three independent experiments.

Figure 14:
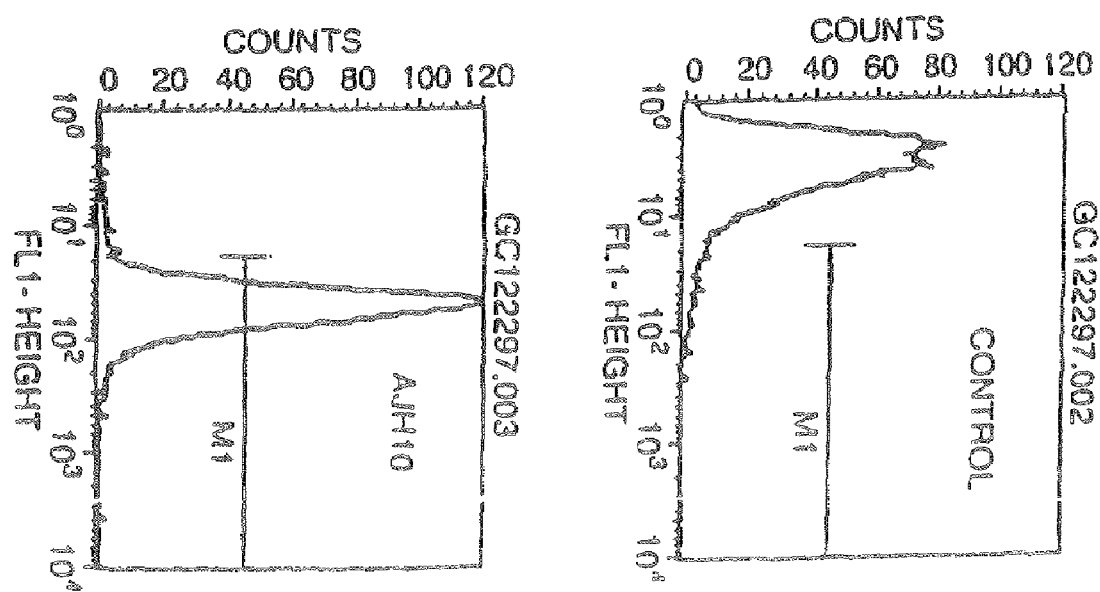

FIG. 14. Species Cross-reactivity of the blocking mAbs analyzed by fluorescence activated cell sorter (FACS). Rabbit vascular smooth muscle cells were incubated with either mAb AJH10 (bottom) or murine IgG control (top) and analyzed by fluorescence activated cell sorter (FACS).

FIG. 15. The α1-I domain binds collagen. A. Increasing concentrations of the human α1-I domain were bound to plates previously coated with 1 µg/ml collagen I (squares) or collagen IV (circles). Values shown have been corrected for background binding to BSA. B. 2 µg/ml human α1-I domain was mixed with increasing concentration of an anti-human α1-I integrin antibody 5E8D9 (squares) or an anti-human α2-integrin antibody A2IIE10 (circles), and then bound to plates previously coated with 1 µg/ml collagen IV. C. Plates were coated with 1 µg/ml collagen TV or 3% BSA. α1-I domain (2 µg/ml) was subsequently bound to coated plates in the presence of 1 mM Mn$^{2+}$, 1 mM Mg$^{2+}$, or 5 mM EDTA. Data shown is representative of three independent experiments.

FIG. 16. Characterization of Humanized AQC2 Forms. mAQC2 (triangles), chAQC2 (circles), hAQC2 (inverted triangles) and hAQC2' (squares) were evaluated.

A. Inhibition of VLA-1 binding to type IV collagen.
B. Inhibition of α1-I domain binding to type IV collagen.
C. Binding to immobilized α1-I domain.
D. Competition with biotinylated mAQC2 for binding to immobilized α1-I domain.

Figure 17:
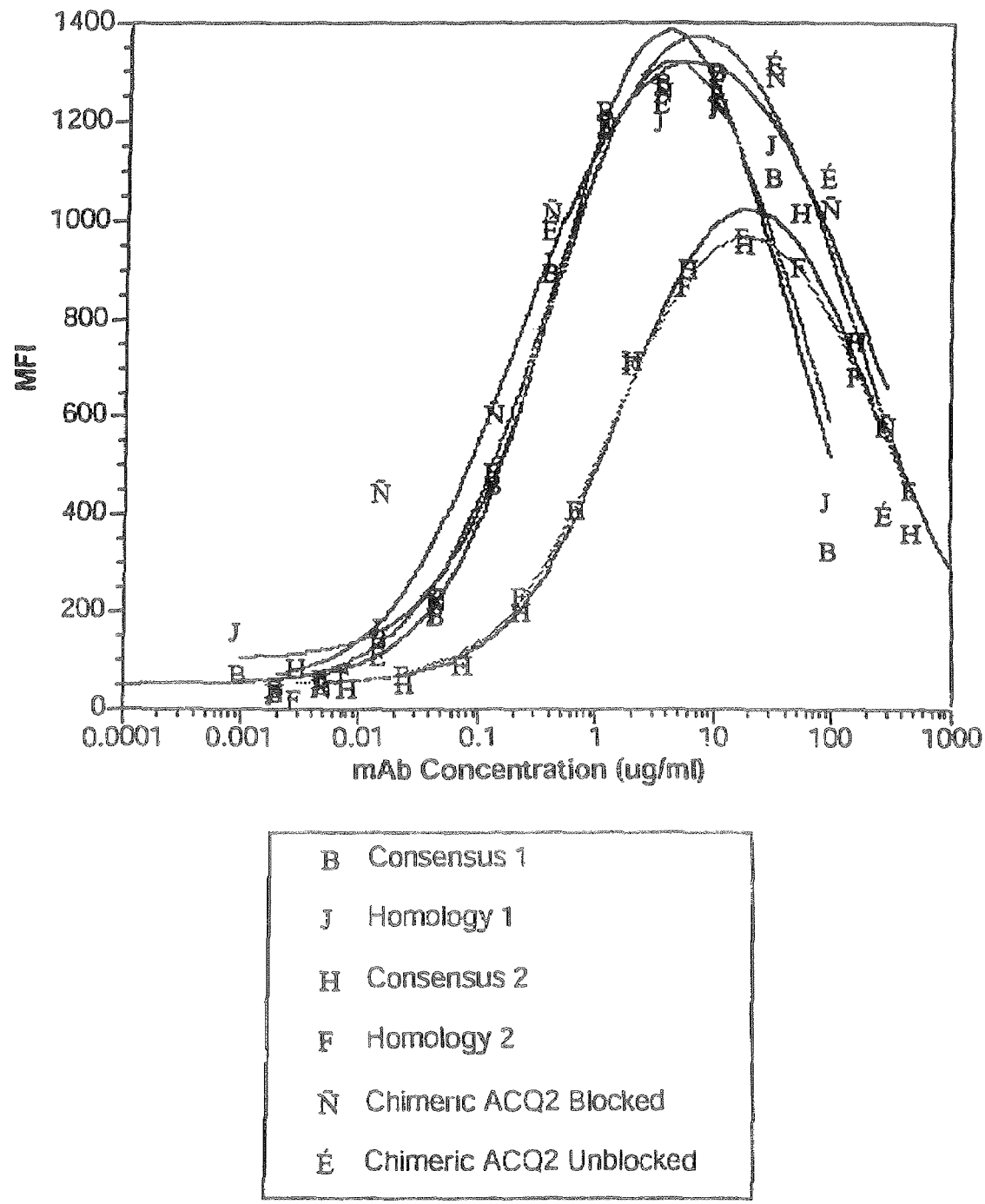

FIG. 17. Characterization of Humanized AQC2 Forms by FACS.

Figure 18:
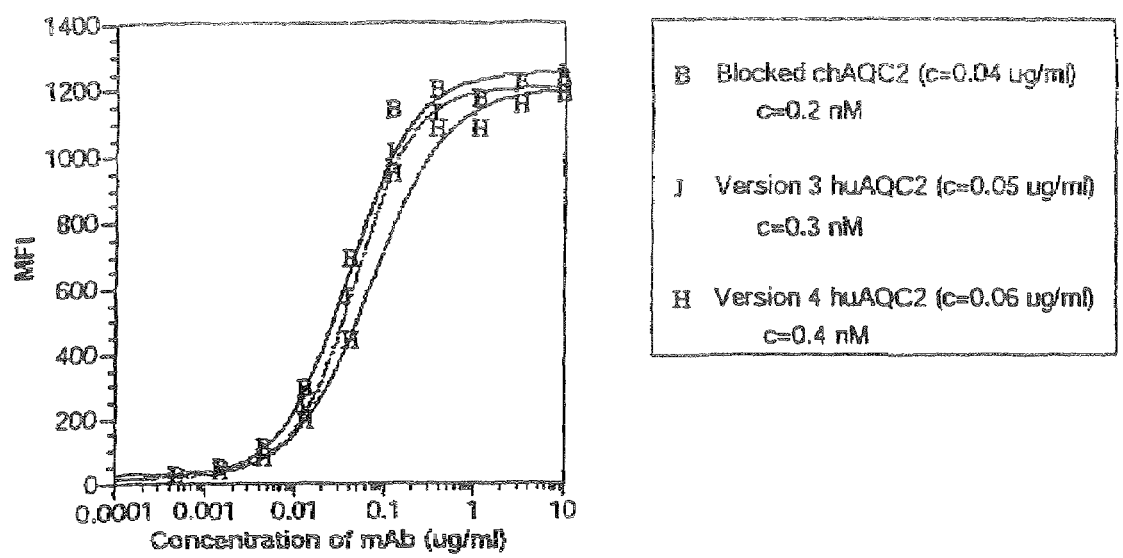

FIG. 18. Characterization of Humanized AQC2 Forms by FACS.

FIG. 19. Atomic structure coordinates for the α1-I domain/Fab complex, as derived by X-ray crystallography from crystals of that complex in Protein Data Bank (PDB) format. The coordinates of the two complexes in the asymmetric unit are listed as follows.

Complex 1: molecule A=I domain of integrin
　molecule H=heavy chain of hAQC2 Fab
　molecule L=light chain of hAQC2 Fab
　molecule M=Mn$^{+2}$
Complex 2: molecule B=I domain of integrin
　molecule X=heavy chain of hAQC2 Fab
　molecule Y=light chain of hAQC2 Fab
　molecule M=Mn$^{+2}$ FIG. 20. I domain-Fab complex. A. Ribbon diagram of the I domain-Fab complex. The I domain and the antibody heavy and light chain are labeled. The Mn$^{+2}$ ion is shown as a sphere. B. Close-up of the MIDAS (Metal-Ion-Dependent-Adhesion Site) site showing the coordination of the metal ion (sphere) by Asp101 (crystal numbering). The protein backbones are shown as ribbon diagrams and the side chains in the ball-and-stick representation. The cylinders represent interactions between the metal ion and protein atoms. The thin lines represent H-bonds. FIG. 20 was made with the software program RIBBONS (Carson, 1991, *J. Appl. Cryst.* 24:958-961).

Figure 21:
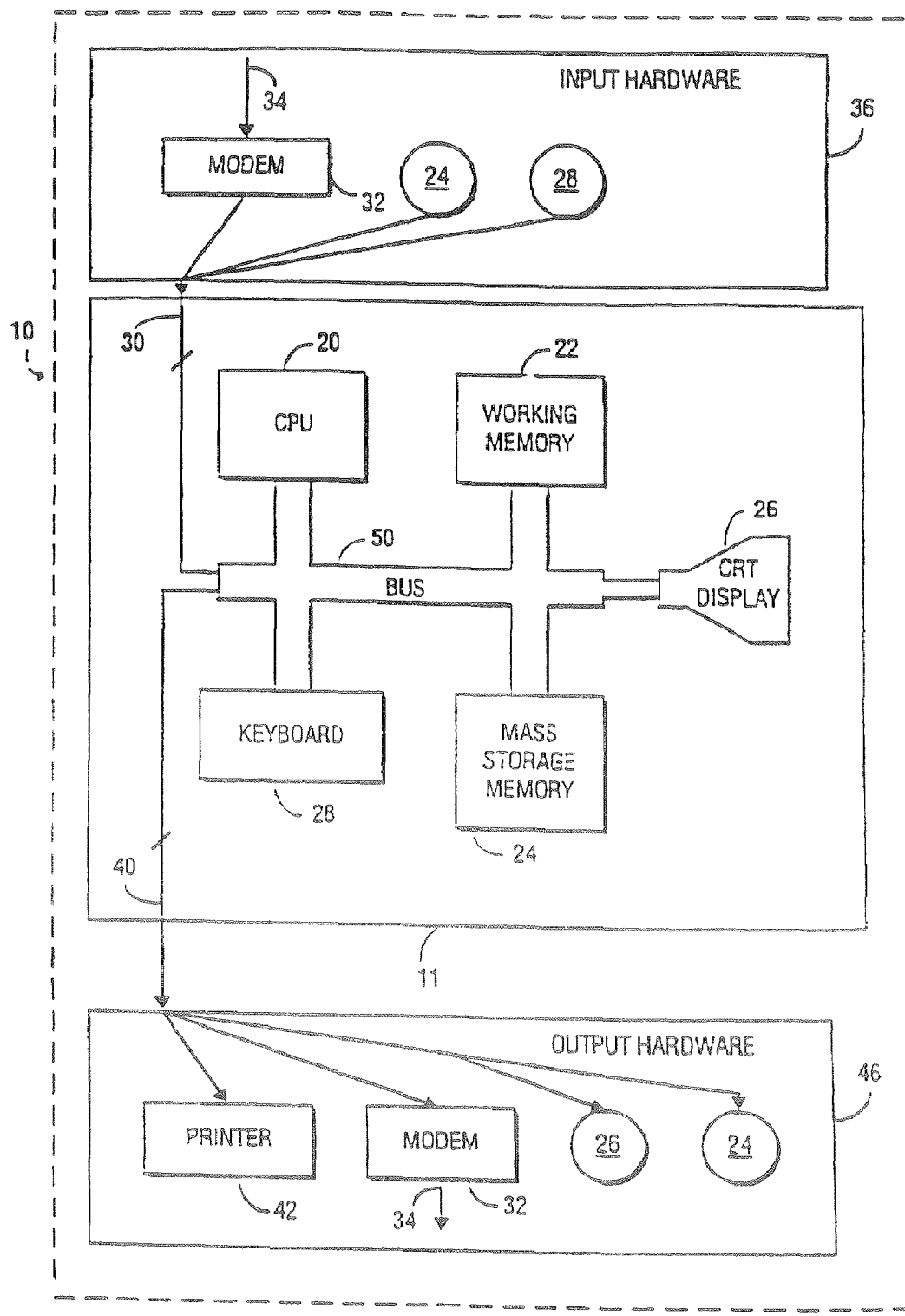

FIG. 21. A diagram of a system used to carry out the instructions encoded by the storage medium of FIGS. 22 and 23.

Figure 22:
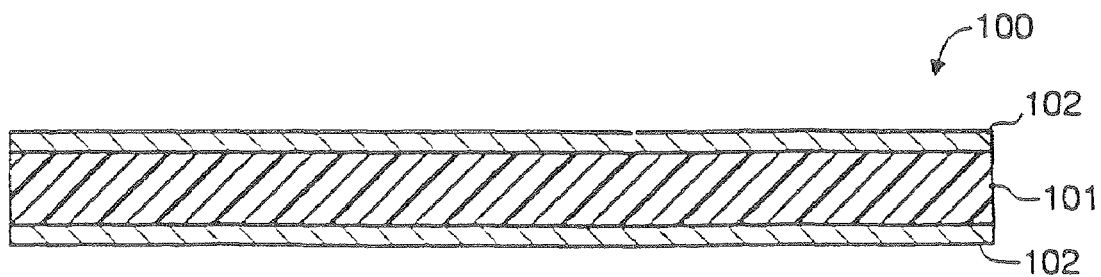

FIG. 22. A cross section of a magnetic storage medium.

Figure 23:
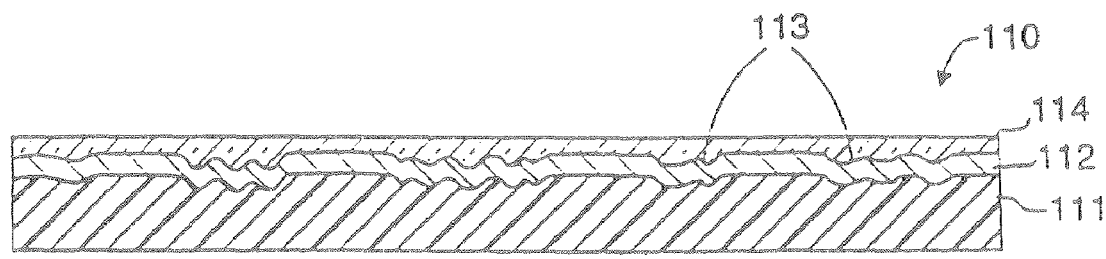

FIG. 23. A cross section of an optically-readable data storage medium.

DETAILED DESCRIPTION OF THE INVENTION

It is a discovery of the present invention that an antibody to an integrin (e.g., VLA-1) and fragment thereof, particularly, an α1-integrin subunit, can block the interaction of pro-inflammatory leukocytes with components of the extracellular matrix including, but not limited to collagens, laminin and fibronectin. This discovery illustrates the importance of adhesion molecules of the integrin family, particularly α1β1, in the peripheral tissue environment during conditions related to inflammation. It also extends the role of integrins family and fragments thereof in inflammation beyond leukocyte attachment and extravasation at the endothelial interface by highlighting the importance of the matrix-rich peripheral tissue environment to immune responses and it reveals peripheral tissues as a new point of intervention for adhesion based therapies.

I. Anti-Integrin Antibodies

The methods of the present invention contemplate the use of antibodies to integrins where the integrins contemplated include molecules which comprise a β chain, including but not limited to β1, β2, β3, β4, β5, β6, β7, β8, noncovalently bound to an α chain, including but not limited to α1, α2, α3, α4, α5, α6, α7, α8, α9, α10, αV, αL, αM, αX, αD, αE, αIIb. Examples of the various integrins contemplated for use in the invention include, but are not limited to:

α1β1, α2β1, α3β1, α4β1, α5β1, α6β1, α7β1, α8β1, α9β1, α10β1, αVβ1, αLβ1, αMβ1, αXβ1, αDβ1, αIIbβ1, αEβ1;

α1β2, α2β2, α3β2, α4β2, α5β2, α6β2, α7β2, α8β2, α9β2, α10β2, αVβ2, αLβ2, αMβ2, αXβ2, αDβ2, αIIbβ2, αEβ2;

α1β3, α2β3, α3β3, α4β3, α5β3, α6β3, α7β3, α8β3, α9β3, α10β3, αVβ3, αLβ3, αMβ3, αXβ3, αDβ3, αIIbβ3, αEβ3;

α1β4, α2β4, α3β4, α4β4, α5β4, α6β4, α7β4, α8β4, α9β4, α10β4, αVβ4, αLβ4, αMβ4, αXβ4, αDβ4, αIIbβ4, αEβ4;

α1β5, α2β5, α3β5, α4β5, α5β5, α6β5, α7β5, α8β5, α9β5, α10β5, αVβ5, αLβ5, αMβ5, αXβ5, αDβ5, αIIbβ5, αEβ5;

α1β6, α2β6, α3β6, α4β6, α5β6, α6β6, α7β6, α8β6, α9β6, α10β6, αVβ6, αLβ6, αMβ6, αXβ6, αDβ6, αIIbβ6, αEβ6;

α1β7, α2β7, α3β7, α4β7, α5β7, α6β7, α7β7, α8β7, α9β7, α10β7, αVβ7, αLβ7, αMβ7, αXβ7, αDβ7, αIIbβ7, αEβ7;

α1β8, α2β8, α3β8, α4β8, α5β8, α6β8, α7β8, α8β8, α9β8, α10β8, αVβ8, αLβ8, αMβ8, αXβ8, αDβ8, αIIbβ8, αEβ8;

The methods of the present invention also contemplate the use of antibodies to integrin fragments including for example antibodies to a β chain alone, including but not limited to β1, β2, β3, β4, β5, β6, β7, β8, as well as an α chain alone, including but not limited to α1, α2, α3, α4, α5, α6, α7, α8, α9, α10, αV, αL, αM, αX, αD, αE, αIIb. In addition, the methods of the present invention further contemplate the use of antibodies to integrin fragments including for example antibodies to the I domain of the α chain, including but not limited to the I domain from α1β1 (Briesewitz et al., 1993, *J. Biol. Chem.* 268:2989); α2β1 (Takada and Hemler, 1989, *J Cell Biol* 109:397), αLβ2 (Larson et al., 1989, *J Cell Biol* 108:703), αMβ2 (Corbi et al., 1988, *J Biol Chem* 263:12403), αXβ2 (Corbi et al., 1987, *EMBO J* 6:4023), αDβ2 (Grayson et al., 1988, *J Exp Med* 188:2187), αEβ7 (Shaw et al., 1994, *J Biol Chem* 269:6016). In one embodiment, the α1-I domain antigenic determinant includes an amino acid sequence of at least 6 contiguous amino acids, wherein the contiguous sequence is found within the sequence of FIG. 12. In a related embodiment, the contiguous sequence is Val-Gln-Arg-Gly-Gly-Arg (residues 91-96 of SEQ ID NO:64).

Methods for producing integrins for use in the present invention are known to those of skill in the art (see, e.g., Springer et al., 1990, *Nature* 346:425-434).

Embodiments of the present invention further include anti-integrin polyclonal and monoclonal antibodies. Embodiments of the present invention include a monoclonal antibody such an anti-α1 monoclonal antibody. Antibodies for treatment, in particular for human treatment, include human antibodies, humanized antibodies, chimeric antibodies, and antigen-binding fragments of whole antibodies such as Fab, Fab', F(ab')2 and F(v) antibody fragments. Some antibodies of this invention may also include proteins containing one or more immunoglobulin light chains and/or heavy chains, such as monomers and homo-or hetero-multimers (e.g., dimers or trimers) of these chains, where these chains are optionally disulfide-bonded or otherwise cross-linked. These antibodies may be capable of binding to one or more antigens (e.g., α1, α2, α6 or alpha-I domain containing integrin subunits).

An α1β1 function blocking antibody as used herein refers to an antibody that binds to the α1-I domain, for example, residues 91-97 of FIG. 12, and blocks α1β1 function as tested, for example, by their ability to inhibit K562-α1 dependent adhesion to Collagen IV (see Example 15).

The following describes the various methods of making the antibodies of this invention. Methods that are known in the art but not specifically described herein are also within the scope of this invention. For instance, antibodies of this invention can also be identified using phage-displayed antibody libraries, such as those described in Smith, 1985, *Science* 228:1315-7; U.S. Pat. Nos. 5,565,332, 5,733,743, 6,291,650, and 6,303,313. Additional antibodies of this invention can be made by coupling the heavy chains identified herein with a noncognate light chain, e.g., a light chain identified by phage display technology.

II. Non-Human Hybridoma Antibodies

The monoclonal antibodies of this invention can be generated by well known hybridoma technology. For instance, $\beta_1$ −/− animals (e.g., mice, rats or rabbits) can be immunized with purified or crude $\alpha_1\beta_1$ preparations, cells transfected with cDNA constructs encoding $\alpha_1$, $\beta_1$ or both antigens, cells that constitutively express $\alpha_1\beta_1$, and the like. The antigen can be delivered as purified protein, protein expressed on cells, protein fragment or peptide thereof, or as naked DNA or viral vectors encoding the protein, protein fragment, or peptide. Sera of the immunized animals are then tested for the presence of anti-$\alpha_1\beta_1$ antibodies. B cells are isolated from animals that test positive, and hybridomas are made with these B cells.

Antibodies secreted by the hybridomas are screened for their ability to bind specifically to VLA-1 (e.g., binding to $\alpha_1$-transfected cells and not to untransfected parent cells) and for any other desired features, e.g., having the desired CDR consensus sequences, inhibiting (or not inhibiting in the case of nonblockers) the binding between collagen and VLA-1.

Hybridoma cells that test positive in the screening assays are cultured in a nutrient medium under conditions that allow the cells to secrete the monoclonal antibodies into the culture medium. The conditioned hybridoma culture supernatant is then collected and antibodies contained in the supernatant are purified. Alternatively, the desired antibody may be produced by injecting the hybridoma cells into the peritoneal cavity of an unimmunized animal (e.g., a mouse). The hybridoma cells proliferate in the peritoneal cavity, secreting the antibody which accumulates as ascites fluid. The antibody may then be harvested by withdrawing the ascites fluid from the peritoneal cavity with a syringe.

The monoclonal antibodies can also be generated by isolating the antibody-coding cDNAs from the desired hybridomas, transfecting mammalian host cells (e.g., CHO or NSO cells) with the cDNAs, culturing the transfected host cells, and recovering the antibody from the culture medium.

III. Chimeric Antibodies

The monoclonal antibodies of this invention can also be generated by engineering a cognate hybridoma (e.g., murine, rat or rabbit) antibody. For instance, a cognate antibody can be altered by recombinant DNA technology such that part or all of the hinge and/or constant regions of the heavy and/or light chains are replaced with the corresponding components of an antibody from another species (e.g., human). Generally, the variable domains of the engineered antibody remain identical or substantially so to the variable domains of the cognate antibody. Such an engineered antibody is called a chimeric antibody and is less antigenic than the cognate antibody when administered to an individual of the species from which the hinge and/or constant region is derived (e.g., a human). Methods of making chimeric antibodies are well known in the art. Human constant regions include those derived from IgG1 and IgG4.

IV. Fully Human Antibodies

The monoclonal antibodies of this invention also include fully human antibodies. They may be prepared using in vitro-primed human splenocytes, as described by Boerner et al., 1991, *J. Immunol.* 147:8695, or using phage-displayed antibody libraries, as described in, e.g., U.S. Pat. No. 6,300,064.

Alternatively, fully human antibodies may be prepared by repertoire cloning as described by Persson et al., 1991, *Proc. Nat. Acad. Sci. USA* 88: 2432-2436; and Huang and Stollar, 1991, *J. Immunol, Methods* 141: 227-236. In addition, U.S. Pat. No. 5,798,230 (Aug. 25, 1998) describes preparation of human monoclonal antibodies from human B cells, wherein human antibody-producing B cells are immortalized by infection with an Epstein-Barr virus, or a derivative thereof, that expresses Epstein Barr virus nuclear antigen 2 (EBNA2), a protein required for immortalization. The EBNA2 function is subsequently shut off, resulting in an increase in antibody production.

Some other methods for producing fully human antibodies involve the use of nonhuman animals that have inactivated endogenous Ig loci and are transgenic for un-rearranged human antibody heavy chain and light chain genes. Such transgenic animals can be immunized with $\alpha_1\beta_1$ and hybridomas are then made from B cells derived therefrom. These methods are described in, e.g., the various GenPharm/Medarex (Palo Alto, Calif.) publications/patents concerning transgenic mice containing human Ig miniloci (e.g., Lonberg U.S. Pat. No. 5,789,650); the various Abgenix (Fremont, Calif.) publications/patents with respect to XENOMICE (e.g., Kucherlapati U.S. Pat. Nos. 6,075,181, 6,150,584 and 6,162,963; Green et al., 1994, *Nature Genetics* 7:13-21; and Mendez et al., 1997, *Nature Genetics* 15(2):146-56); and the various Kirin (Japan) publications/patents concerning "transomic" mice (e.g., EP 843 961, and Tomizuka et al., 1997, *Nature Genetics* 16:133-1443).

V. Humanized Antibodies

The monoclonal antibodies of this invention also include humanized versions of cognate anti-$\alpha_1\beta_1$ antibodies derived from other species. A humanized antibody is an antibody produced by recombinant DNA technology, in which some or all of the amino acids of a human immunoglobulin light or heavy chain that are not required for antigen binding (e.g., the constant regions and the framework regions of the variable domains) are used to substitute for the corresponding amino acids from the light or heavy chain of the cognate, nonhuman antibody. By way of example, a humanized version of a murine antibody to a given antigen has on both of its heavy and light chains (1) constant regions of a human antibody; (2) framework regions from the variable domains of a human antibody; and (3) CDRs from the murine antibody. When necessary, one or more residues in the human framework regions can be changed to residues at the corresponding positions in the murine antibody so as to preserve the binding affinity of the humanized antibody to the antigen. This change is sometimes called "back mutation." Humanized antibodies generally are less likely to elicit an immune response in humans as compared to chimeric human antibodies because the former contain considerably fewer nonhuman components.

The methods for making humanized antibodies are described in, e.g., Winter EP 239 400; Jones et al., 1986, *Nature* 321:522-525; Riechmann et al., 1988, *Nature* 332: 323-327 (1988); Verhoeyen et al., 1988, *Science* 239:1534-1536; Queen et al., 1989, *Proc. Nat. Acad. Sci. USA* 86:10029; U.S. Pat. No. 6,180,370; and Orlandi et al., 1989, *Proc. Natl. Acad. Sci. USA* 86:3833. Generally, the transplantation of murine (or other non-human) CDRs onto a human antibody is achieved as follows. The cDNAs encoding heavy and light chain variable domains are isolated from a hybridoma. The DNA sequences of the variable domains, including the CDRs, are determined by sequencing. The DNAs encoding the CDRs are transferred to the corresponding regions of a human antibody heavy or light chain variable domain coding sequence by site directed mutagenesis. Then human constant region gene segments of a desired isotype (e.g, γ1 for CH and k for CL) are added. The humanized heavy and light chain genes are co-expressed in mammalian host cells (e.g., CHO or NSO cells) to produce soluble humanized antibody. To facilitate large scale production of antibodies, it is often desirable to produce such humanized antibodies in bioreactors containing the antibody-expressing cells, or to produce transgenic mammals (e.g., goats, cows, or sheep) that express the antibody in milk (see, e.g., U.S. Pat. No. 5,827,690).

At times, direct transfer of CDRs to a human framework leads to a loss of antigen-binding affinity of the resultant antibody. This is because in some cognate antibodies, certain amino acids within the framework regions interact with the CDRs and thus influence the overall antigen binding affinity of the antibody. In such cases, it would be critical to introduce "back mutations" (supra) in the framework regions of the acceptor antibody in order to retain the antigen-binding activity of the cognate antibody.

The general approach of making back mutations is known in the art. For instance, Queen et al. (supra), Co et al., 1991, *Proc. Nat. Acad. Sci. USA* 88:2869-2873, and WO 90/07861 (Protein Design Labs Inc.) describe an approach that involves two key steps. First, the human V framework regions are chosen by computer analysis for optimal protein sequence homology to the V region framework of the cognate murine antibody. Then, the tertiary structure of the murine V region is modeled by computer in order to visualize framework amino acid residues that are likely to interact with the murine CDRs, and these murine amino acid residues are then superimposed on the homologous human framework.

Under this two-step approach, there are several criteria for designing humanized antibodies. The first criterion is to use as the human acceptor the framework from a particular human immunoglobulin that is usually homologous to the nonhuman donor immunoglobulin, or to use a consensus framework from many human antibodies. The second criterion is to use the donor amino acid rather than the acceptor if the human acceptor residue is unusual and the donor residue is typical for human sequences at a specific residue of the framework. The third criterion is to use the donor framework amino acid residue rather than the acceptor at positions immediately adjacent to the CDRs.

One may also use a different approach as described in, e.g., Tempest, 1991, *Biotechnology* 9: 266-271. Under this approach, the V region frameworks derived from NEWM and REI heavy and light chains, respectively, are used for CDR-grafting without radical introduction of mouse residues. An advantage of using this approach is that the three-dimensional structures of NEWM and REI variable regions are known from X-ray crystallography and thus specific interactions between CDRs and V region framework residues can be readily modeled.

VI. Other Moieties

The monoclonal antibodies of this invention may further include other moieties to effect the desired functions. For instance, the antibodies may include a toxin moiety (e.g., tetanus toxoid or ricin) or a radionuclide (e.g., $^{111}$In or $^{90}$Y)

for killing of cells targeted by the antibodies (see, e.g., U.S. Pat. No. 6,307,026). The antibodies may include a moiety (e.g., biotin, fluorescent moieties, radioactive moieties, histidine tag or other peptide tags) for easy isolation or detection. The antibodies may also include a moiety that can prolong their serum half life, for example, a polyethylene glycol (PEG) moiety, and a member of the immunoglobulin super family or fragment thereof (e.g., a portion of human IgG1 heavy chain constant region such as the hinge, CH2 and CH3 regions).

VII. Crystallizable Compositions and Crystals

This invention also provides a crystallizable composition containing a complex of: (1) a rat-human chimeric α1-I domain (e.g., mutant RΔH), or a portion thereof (e.g., a polypeptide including 135 to 336 amino acids of the rat-human chimeric α1-I domain); and (2) a Fab fragment of hAQC2, or a portion thereof (e.g., a polypeptide including 3 to 213 amino acids of the light chain and/or a polypeptide including 3 to 219 amino acids of the heavy chain). An exemplary complex is shown in FIG. 20. The RΔH α1-I domain can include, e.g., amino acid residues 145 to 336 (crystal numbering) (SEQ ID NO:59, infra) of the rat α1 subunit. The hAQC2 Fab fragments may include light chain amino acid residues 1 to 106 (e.g., 1213) of SEQ ID NO:3 and heavy chain amino acid residues 1 to 118 (e.g., 1-219) of SEQ ID NO:4. The hAQC2 Fab fragments may be obtained by papain digestion of the whole antibody or made by recombinant methods. The Fab fragments include at least an antigen-binding portion of the variable domains of the light chain and/or the heavy chains of hAQC2.

```
                                              (SEQ ID NO: 59)
145 TQLDIV

151 IVLDGSNSIY PWESVIAFLN DLLKRMDIGP KQTQVGIVQY

191 GENVTHEFNL NKYSSTEEVL VAANKIVQRG GRQTMTALGI

231 DTARKEAFTE ARGARRGVKK VMVIVTDGES HDNYRLKQVI

271 QDCEDENIQR FSIAILGHYN RGNLSTEKFV EEIKSIASEP

311 TEKHPENVSD ELALVTIVKA LGERIF
```

Some crystallizable compositions and crystals of this invention may contain a molecule or molecular complex that is homologous to the α1-I domain and/or the hAQC2 Fab fragment by amino acid sequence or by three-dimensional structure. Examples of homologues include, but are not limited to: the α1-I domain and/or the hAQC2 Fab fragment with mutations, such as conservative substitutions, additions, deletions or a combination thereof. "Conservative substitutions" refer to replacement residues that are physically similar in size, shape, hydrophobicity, charge, and/or chemical properties to the corresponding reference residues. Methods for identifying a "corresponding" amino acid are known in the art and are based upon sequence, structural alignment, its functional position or a combination thereof as compared to the crystal structure solved in the present invention. For example, corresponding amino acids may be identified by superimposing the backbone atoms of the amino acids in the α1-I domain/hAQC2 complex and a α1-I domain and/or hAQC2 homologue using well known software applications, such as QUANTA (Molecular Simulations, Inc., San Diego, Calif. ©1998, 2000). The corresponding amino acids may also be identified using sequence alignment programs such as the "bestfit" program available from the Genetics Computer Group, which uses the local homology algorithm described by Smith and Waterman in *Adv. Appl. Math.* 2:482 (1981).

Crystallizable compositions of this invention may further include one or more components that promote crystallization and/or is compatible with crystallization conditions. Such components may include, but are not limited to, buffer, salts, precipitating agents and other reagents. One component can be 30% weight/volume Polyethylene Glycol 1500 (PEG1500).

The instant invention also provides methods of making crystals from crystallizable compositions including a complex of α1-I domain and an antigen-binding portion of hAQC2 (e.g., Fab, Fab' or other fragments, supra). Various techniques of crystallization can be used in the claimed invention, including, but not limited to, vapor-diffusion, dialysis, microbatch, batch, and liquid-liquid diffusion. Vapor diffusion methods include, but are not limited too, sitting-drop, hanging-drop and sandwich-drop techniques. Vapor-diffusion methods can use techniques to control the rate of crystallization, such as the addition of oils on the drops or reservoir solution. Crystallization methods can include mixing a reservoir solution containing precipitating agent with an aqueous solution of a complex of α1-I domain and an antigen-binding portion of hAQC2 to produce a crystallizable composition. The mixture or crystallizable composition may then be crystallized using the various above-listed techniques. The crystallizable composition of this invention may be an aqueous solution of a complex of α1-I domain and an antigen-binding portion of hAQC2 containing the complex at a concentration of about 1 to 50 mg per mL, such as a concentration of about 5 to 115 mg per mL (e.g., 11 mg per mL).

VIII. Crystal Structures and Structure Coordinates

This invention further provides the three-dimensional structure of a crystal including a complex of mutant RΔH, and a hAQC2 Fab fragment at 2.8 Å resolution (Example 24, infra). The three-dimensional structures of other related crystals may also be determined using techniques described herein and those known in the art. The three-dimensional structure of this complex is defined by a set of structure coordinates set forth in FIG. 19. These structure coordinates are Cartesian atomic coordinates derived from mathematical equations related to the patterns obtained from diffraction of a monochromatic beam of X-rays by the atoms or scattering centers of the crystalline complex of the α1-I domain and the hAQC2 Fab fragment. Diffraction data are first used to calculate an electron density map of the repeating unit of the crystal. The electron density map is then used to establish the positions of individual atoms of the complex.

This invention provides a molecule or a molecular complex defined by all or part of the structure coordinates of all amino acids set forth in FIG. 19, as well as a homologue of the molecule or molecular complex, where the homologue has a root mean square deviation from the backbone atoms of these amino acids between 0.00 Å and 0.65 Å, such as between 0.00 Å and 0.60 Å (e.g., between 0.00 Å and 0.50 Å). The term "root mean square deviation" or "r.m.s. deviation" means the square root of the arithmetic mean of the squares of the deviations from the mean. It is a way to express the deviation or variation from a trend or object. For purposes of this invention, the "root mean square deviation" or "r.m.s. positional deviation" defines the variation in the backbone of a protein from the relevant portion of the backbone of the polypeptide as defined by the structure coordinates described herein.

A molecule or a molecular complex of this invention may also include a binding site defined by structure coordinates of at least seven amino acids of the hAQC2 Fab fragment selected from the group including of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering) according to FIG. 19; or a homologue of the molecule or molecular complex, where the homologue includes a binding site that has a root mean square deviation from the backbone atoms of one or more of these amino acids between 0.00 Å and 1.10 Å, such as between 0.00 Å and 1.00 Å (e.g., between 0.00 Å and 0.50 Å). The term "binding site" as used herein, refers to a region of a molecule or molecular complex that, as a result of its shape and charge, favorably associates with another chemical entity. The term "site" includes, but is not limited to, trench, cleft, channel or pocket. For instance, binding sites on the α1-I domain may include a collagen-binding site (Emsley et al., 1997, supra), an antibody-binding site, and an allosteric (or IDAS) binding site (Huth et al., 2000, *Proc. Natl. Acad. Sci. U.S.A.* 97:5231-5236). The term "chemical entity" includes, but is not limited to, any molecule, molecular complex, compound or fragment thereof. The term "associate with" refers to an association or binding in a condition of proximity between a chemical entity, or portions thereof, and a binding pocket or binding site on a protein. The association may be non-covalent—where the juxtaposition is energetically favored by hydrogen bonding or van der Waals or electrostatic interactions—or it may be covalent.

A molecule or molecular complex of this invention can include a binding site defined by structure coordinates of α1-I domain amino acids selected from the group consisting of residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19, or a homologue of the molecule or molecular complex, where the homologue includes a binding site that has a root mean square deviation from the backbone atoms of the α1-I domain amino acids between 0.00 Å and 0.92 Å.

A molecule or molecular complex of this invention also may include a binding site defined by structure coordinates of α1-I domain amino acids selected from the group consisting of residues Glu192, Gln218, Arg219, Gly220, and Gly221 (crystal numbering), according to FIG. 19; or a homologue of the molecule or molecular complex, where the homologue includes a binding site that has a root mean square deviation from the backbone atoms of the α1-I domain amino acids between 0.00 Å and 0.30 Å.

Those of skill in the art will understand that a set of structure coordinates for a polypeptide is a relative set of points that define a shape in three dimensions. Thus, it is possible that an entirely different set of coordinates that define a similar or identical shape could be generated using mathematical manipulations of the structure coordinates in FIG. 19. For example, the structure coordinates could be manipulated by crystallographic permutations of the structure coordinates, fractionalization of the structure coordinates, integer additions or subtractions to sets of the structure coordinates, inversion of the structure coordinates, or any combination thereof. Moreover, slight variations in the individual coordinates will have little effect on overall shape.

Alternatively, modification in the crystal structure due to mutations, such as additions, substitutions, and/or deletions of amino acids, or other changes in any of the polypeptide components (e.g., a hAQC2 Fab fragment or a α1-I domain) that make up the crystal can also account for variations in structure coordinates. If such variations are within an acceptable standard error as compared to the original coordinates, the resulting three-dimensional shape is considered to be the same as that of the unmodified crystal.

It is therefore necessary to determine whether an entity is sufficiently similar to all or parts of the structure described herein as to be considered the same. Such analyses may be carried out using current software applications, such as QUANTA (Accelrys, Inc. and Molecular Simulations, Inc., San Diego, Calif. ©1998, 2000) and O (Jones et al., 1991, *Acta Cryst.* A47:110-119), and accompanying User Guides. The Molecular Similarity application of QUANTA and the LSQ application of O permit comparisons between different structures, different conformations of the same structure, and different parts of the same structure. The general procedure used in both applications is to input the structures to be compared, define the equivalent atomic positions in these structures, perform a fitting operation, and analyze the results.

When each structure is input into the application, it is given a name. and identified as the fixed structure or a moving structures. Atom equivalency is usually defined by equivalent atoms such as protein backbone atoms (N, Cα, C and O) for all conserved residues between the two structures being compared. The moving structure is translated and rotated to obtain an optimum or least-squares fit with the fixed structure. The root mean square difference of the fit over the specified pairs of equivalent atom is reported by both programs in angstroms.

For the purpose of this invention, any molecular complex that has a root mean square deviation of conserved residue backbone atoms (N, Cα, C, 0) between 0.00 Å and 1.50 Å, such as between 0.00 Å and 1.00 Å (e.g., between 0.00 Å and 0.50 Å), when superimposed on the relevant backbone atoms described by structure coordinates listed in FIG. 19 are considered identical.

IX. Determining Other Crystal Structures

The structure coordinates set forth in FIG. 19 can also be used to aid in obtaining structural information about another crystallized molecular entity, such as another hAQC2 containing amino acid substitutions in one of its CDRs. This may be achieved by any well-known techniques, including molecular replacement, an especially useful method for determining the structures of mutants and homologues of α1-I domain/Fab.

The structure coordinates set forth in FIG. 19 can also be used for determining at least a portion of the three-dimensional structure of molecular entities that contain at least some structural features similar to at least a portion of the α1-I domain or the hAQC2 Fab. Therefore, another embodiment of this invention provides a method of utilizing molecular replacement to obtain structural information about a crystallized molecule or molecular complex with unknown structure including the steps of: (a) generating an X-ray diffraction pattern from the crystallized molecule or molecular complex; and (b) applying at least a portion of the structure coordinates set forth in FIG. 19 to the X-ray diffraction pattern to generate a three-dimensional electron density map of the molecule or molecular complex with unknown structure.

By using molecular replacement, all or part of the structure coordinates set forth in FIG. 19 can be used to determine the unknown structure of a crystallized molecular entity more rapidly and efficiently than attempting to determine such information ab initio. Molecular replacement provides an accurate estimation of the phases for an unknown structure. Phases are a factor in equations used to solve crystal structures that cannot be determined directly. Obtaining accurate values for the phases, by methods other than molecular replacement, can often be a time-consuming process that involves iterative cycles of approximations and refinements and greatly hinders the solution of crystal structures. However, when the crystal structure of a protein containing at least a homologous portion has been solved, the phases from the known structure can often provide a satisfactory estimate of the phases for the unknown structure.

Thus, molecular replacement involves generating a preliminary model of a molecule or molecular complex whose structure coordinates are unknown, by orienting and positioning the relevant portion of the complex according to FIG. 19 within the unit cell of the crystal of the unknown molecule or molecular complex, so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (Lattman, 1985, *Meth. Enzymol.* 115:55-77; Rossmann, ed., "The Molecular Replacement Method", Int. Sci. Rev. Ser., No. 13, Gordon & Breach, New York, 1972). The structure of any portion of any crystallized molecule or molecular complex that is sufficiently homologous to any portion of the α1-I domain and/or the hAQC2 Fab fragment (according to FIG. 19) can be solved by this method.

X. Computer and Storage Medium

To use the structure coordinates of this invention, e.g., those set forth in FIG. 19, it is usually necessary to convert the coordinates into a three-dimensional representation or shape. Commercially available graphical software programs including, but not limited to, O (Jones et al., 1991, *Acta Cryst.* A47:110-119) and ISIGHTII (© Accelrys, Inc. and Molecular Simulations, Inc., San Diego, Calif.) are capable of generating three-dimensional representations of molecules or molecular complexes, or portions thereof, from a set of structure coordinates.

In accordance with the present invention, the structure coordinates of the molecular entities of this invention are stored in a storage medium readable by machine (e.g., a computer). Using a computer and appropriate software, such data may be used for a variety of purposes, such as drug discovery and X-ray crystallographic analysis of other protein crystals.

Accordingly, a machine-readable data storage medium may include a data storage material encoded with machine-readable data including at least a portion of the structure coordinates set forth in FIG. 19. The computer may further include instructions to produce three-dimensional representations of the molecular complexes of α1-I domain and the hAQC2 Fab fragment by processing the machine-readable data of this invention. The computer of this invention may also include a display, a graphical interface for displaying, or an input device for moving and manipulating the three-dimensional graphical representation of the structure coordinates.

This invention also provides a computer for determining at least a portion of the structure coordinates corresponding to X-ray diffraction data obtained from a molecular complex of α1β1 integrin and the Fab fragment of hAQC2 antibody, where the computer includes a machine-readable data storage medium including a data storage material encoded with machine-readable data, where the data includes at least a portion of the structure coordinates of the molecular complex of α1-I domain and the hAQC2 Fab fragment according to FIG. 19, or X-ray diffraction data obtained from the crystalline molecular complex. The computer further includes instructions for performing a Fourier transform of the machine readable coordinate data, and instructions for processing this machine readable diffraction data into structure coordinates. This computer may further include: a working memory for storing instructions for processing the machine-readable data; a central-processing unit coupled to the working memory and to the machine-readable data; and optionally a graphical interface or display coupled to the central-processing unit for displaying the three-dimensional graphical representation of the structure coordinates of the molecule or molecular complex.

This invention further provides a computer for producing a three-dimensional representation of: a molecule or a molecular complex defined by at least a portion or all of the structure coordinates of all the α1-I domain and the AQC2 Fab fragment amino acids set forth in FIG. 19, or a homologue of the molecule or molecular complex, where the homologue has a root mean square deviation from the backbone atoms of the amino acids of between 0.00 Å than 1.50 Å, such as between 0.00 Å and 1.00 Å, (e.g., between 0.00 Å and 0.50 Å). Further in this invention the computer includes: a machine-readable data storage medium including a data storage material encoded with machine-readable data, where the data includes at least a portion or all of the structure coordinates of all of the α1-I domain and the Fab hAQC2 fragment amino acids set forth in FIG. 19.

A computer of this invention may also produce a three-dimensional representation of a molecule or molecular complex including a binding site. The binding site may be defined by structure coordinates of at least seven amino acids of: the hAQC2 Fab fragment selected from the group including light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering) according to FIG. 19; or a homologue of the molecule or molecular complex, where the homologue includes a binding site that has a root mean square deviation from the backbone atoms of the at least one amino acid of the hAQC2 Fab fragment of between 0.00 Å and 1.10 Å, such as between 0.00 Å and 1.00 Å, (e.g., between 0.00 Å and 0.50 Å). Further, the computer of this invention includes: a machine-readable data storage medium including a data storage material encoded with machine-readable data, where the data includes the structure coordinates of at least seven amino acids of the hAQC2 Fab fragment selected from the group consisting of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering) according to FIG. 19.

This invention also provides a computer for producing a three-dimensional representation of: a molecule or molecular complex including a binding site defined by structure coordinates I domain amino acids selected from the group consisting of residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19; or a homologue of the molecule or molecular complex, where the homologue includes a binding site that has a root mean square deviation from the backbone atoms of the I domain amino acids between 0.00 Å and 0.92 Å. Further in this invention, the computer includes: a machine-readable data storage medium including a data storage material encoded with machine-readable data, where the data includes the structure coordinates of I domain amino acids selected from the group consisting of residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19.

This invention also provides a computer for producing a three-dimensional representation of a molecule or molecular complex including a binding site defined by structure coordinates of I domain amino acids selected from the group consisting of residues Glu192, Gln218, Arg219, Gly220, and Gly221 (crystal numbering), according to FIG. 19; or a homologue of the molecule or molecular complex, where the homologue includes a binding site that has a root mean square deviation from the backbone atoms of I domain amino acids between 0.00 Å and 0.30 Å. Further in this invention the computer includes: a machine-readable data storage medium including a data storage material encoded with machine-readable data, where the data includes the structure coordinates I domain amino acids selected from the group consisting of residues Glu192, Gln218, Arg219, Gly220, and Gly221 (crystal numbering), according to FIG. 19.

FIG. 21 demonstrates one such embodiment. System 10 includes a computer 11 including a central-processing unit ("CPU") 20, a working memory 22 which may be, e.g., Ram (random-access memory) or "core" memory, mass storage memory 24 (such as one or more disk or tape drives or CD-ROM or DVD-ROM drives), one or more cathode-ray tube ("CRT") display terminals 26, one or more keyboards 28, one or more input lines 30, and one or more output lines 40, all of which are interconnected by a conventional bidirectional system bus 50.

Input hardware 36, coupled to computer 11 by input lines 30, may be implemented in a variety of ways. Machine-readable data of this invention may be inputted via the use of a modem or modems 32 connected by a telephone line or dedicated data line 34. Alternatively or additionally, the input hardware 36 may include CD-ROM or DVD-ROM drives or tape or disk drives 24. In conjunction with display terminal 26, keyboard 28 may also be used as an input device.

Output hardware 46, coupled to computer 11 by output lines 40, may similarly be implemented by conventional devices. By way of example, output hardware 46 may include CRT display terminal 26 for displaying a graphical representation of a binding site of this invention using a program such as QUANTA as described herein. Output hardware might also include a printer 42, so that hard copy output may be produced, or a disk drive 24, to store system output for later use.

In operation, CPU 20 coordinates the use of the various input and output devices 36, 46, coordinates data accesses from mass storage 24 and accesses to and from working memory 22, and determines the sequence of data processing steps. A number of programs may be used to process the machine-readable data of this invention. Such programs are discussed in reference to the computational methods of drug discovery as described herein. Specific references to components of the hardware system 10 are included as appropriate throughout the following description of the data storage medium.

FIG. 22 shows a cross-section of a magnetic data storage medium 100 which can be encoded with machine-readable data that can be carried out by a system such as system 10 of FIG. 21. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening (not shown) for receiving the spindle of a disk drive or other data storage device 24.

The magnetic domains of coating 102 of medium 100 are polarized or oriented so as to encode in manner which may be conventional, machine readable data such as that described herein, for execution by a system such as system 11 of FIG. 21.

FIG. 23 shows a cross-section of an optically-readable data storage medium 110 which also can be encoded with such machine-readable data, or a set of instructions, which can be carried out by a system such as system 10 of FIG. 21. Medium 110 can be a conventional compact disk or DVD disk read only memory (CD-ROM or DVD-ROM) or a rewritable medium, such as a magneto-optical disk which is optically readable and magneto-optically writable. Medium 100 has a suitable substrate 111, which may be conventional, and a suitable coating 112, which may be conventional, usually of one side of substrate 111.

In the case of CD-ROM, as is well known, coating 112 is reflective and is impressed with a plurality of pits 113 to encode the machine-readable data. The arrangement of pits is read by reflecting laser light off the surface of coating 112. A protective coating 114, which is substantially transparent, is provided on top of coating 112.

In the case of a magneto-optical disk, as is well known, coating 112 has no pits 113, but has a plurality of magnetic domains whose polarity or orientation can be changed magnetically when heated above a certain temperature, as by a laser (not shown). The orientation of the domains can be read by measuring the polarization of laser light reflected from coating 112. The arrangement of the domains encodes the data as described above.

XI. Rational Drug Design

The present invention permits the use of structure-based and rational drug design techniques to design, select, and synthesize or isolate chemical entities, such as inhibitors of the α1-I domain and to improve known inhibitors of this domain. These inhibitors may be capable of blocking the collagen-binding site of VLA-1. This invention also permits the use of structure-based and rational drug design techniques to design variants that may act as inhibitors of collagen binding.

The three-dimensional representation of this invention can be used experimentally or computationally to design potential inhibitors, other chemical entities, variants of the Fab fragment or combinations of chemical entities that may bind to and effect the biological functions of the hAQC2 Fab fragment or the chimeric α1-I domain of the current invention.

One skilled in the art can use one of several methods to screen chemical entities for their ability to associate with the complex of the hAQC2 Fab fragment or the chimeric α1-I domain of the current invention and more particularly with a binding site of either the I domain or the Fab fragment. This process may begin by visual inspection of, for example, the binding site for either the I domain or the Fab fragment on the computer screen, based on the coordinates of the complex in FIG. 19. Selected chemical entities may then be positioned in a variety of orientations, or docked, within an individual binding site of either the I domain or the Fab fragment. Docking may be accomplished using software such as QUANTA, followed by energy minimization and molecular dynamics with standard molecular mechanics forcefields, such as CHARMM (Molecular Simulations, Inc., Burlington, Mass. ©1994) and AMBER (P. A. Kollman, University of California at San Francisco, ©1994).

Specialized computer programs may also assist in the process of selecting chemical entities. These include, inter alia:
1. GRID (Goodford, P. J., 1985, *J. Med. Chem.* 28:849-857). GRID is available from Oxford University, Oxford, UK.
2. MCSS (Miranker, A. and M. Karplus, 1991, *Proteins: Structure, Function and Genetics* 11:29-34). MCSS is available from Molecular Simulations, Burlington, Mass.
3. AUTODOCK (Goodsell, D. S, and A. J. Olsen, 1990, *Proteins: Structure, Function, and Genetics* 8:195-202). AUTODOCK is available from Scripps Research Institute, La Jolla, Calif.
4. DOCK (Kuntz, I. D. et al., 1982, *J. Mol. Biol.* 161:269-288). DOCK is available from University of California, San Francisco, Calif.

Once suitable chemical entities have been selected, they can be assembled into a single compound. Assembly may proceed by visual inspection of the relationship of the entities to each other on the three-dimensional image displayed on a computer screen in relation to the structure coordinates of the complex of hAQC2 Fab fragment and the chimeric α1-I domain. This is followed by manual model building using software such as Quanta or Sybyl.

The above-described evaluation process for chemical entities may be performed in a similar fashion for compounds or for variants that may bind the α1-I domain.

Useful programs to aid one of skill in the art in connecting the individual chemical entities include:

1. CAVEAT (Bartlett, P. A. et al, "CAVEAT: A Program to Facilitate the Structure-Derived Design of Biologically Active Molecules". In "Molecular Recognition in Chemical and Biological Problems", Special Pub., 1989, Royal Chem. Soc., 78:182-196). CAVEAT is available from the University of California, Berkeley, Calif.
2. 3D Database systems such as MACCS-3D (MDL Information Systems, San Leandro, Calif.). This area is reviewed in Martin, Y. C., 1992, *J. Med. Chem.* 35:2145-2154.
3. HOOK (available from Molecular Simulations, Burlington, Mass.).

Instead of proceeding to build an inhibitor or binding compound in a step-wise fashion one chemical entity at a time, as described above, binding compounds may be designed as a whole or "de novo" using either an empty binding site (such as a binding site of the α1-I domain or the hAQC2 Fab fragment) or optionally including some portion(s) of a known α1-I domain or the hAQC2 Fab fragment binding compound. These methods include:

1. LUDI (Bohm, H.-J., 1992, *J. Comp. Aid. Molec. Design* 6:61-78). LUDI is available from Biosym Technologies, San Diego, Calif.
2. LEGEND (Nishibata, Y. and A. Itai, 1991, *Tetrahedron* 47:8985). LEGEND is available from Molecular Simulations, Burlington, Mass.
3. LeapFrog (available from Tripos Associates, St. Louis, Mo.).

Other molecular modeling techniques may also be employed in accordance with this invention. See, e.g., Cohen, N. C. et al., 1990, *J. Med. Chem.* 33:883-894. See also Navia, M. A. and M. A. Murcko, 1992, *Curr. Opin. Struct. Biol.* 2:202-210.

Once an entity has been designed or selected by the above methods, the efficiency with which that entity may bind to the α1-I domain or the hAQC2 Fab fragment can be tested and optimized by computational evaluation. For example, a compound that has been designed or selected to function as α1-I domain binding compound can traverse a volume not overlapping that occupied by the binding site when it is bound to the chimeric α1-I domain. An effective α1-I domain binding compound can demonstrate a relatively small difference in energy between its bound and free states (i.e., a small deformation energy of binding). Thus, the most efficient α1-I domain binding compound should be designed with a deformation energy of binding of not greater than about 10 kcal/mole, e.g., not greater than 7 kcal/mole. α1-I domain binding compounds may interact with the α1-I domain in more than one conformation that is similar in overall binding energy. In those cases, the deformation energy of binding is taken to be the difference between the energy of the free compound and the average energy of the conformations observed when the compound binds to the protein.

A compound designed or selected as binding to α1-I domain may be further computationally optimized so that in its bound state it would lack repulsive electrostatic interaction with the target protein. Such non-complementary (e.g., electrostatic) interactions include repulsive charge-charge, dipole-dipole and charge-dipole interactions. Specifically, the sum of all electrostatic interactions between the compound and the protein when the compound is bound to α1-I domain, should make a neutral or favorable contribution to the enthalpy of binding.

Specific computer software is available in the art to evaluate compound deformation energy and electrostatic interaction. Examples of programs designed for such uses include: Gaussian 92, revision C (M. J. Frisch, Gaussian, Inc., Pittsburgh, Pa. ©1992); AMBER, version 4.0 (P. A. Kollman, University of California at San Francisco, ©1994); QUANTA/CHARMM (Molecular Simulations, Inc., Burlington, Mass. ©1994); and Insight II/Discover (Biosysm Technologies Inc., San Diego, Calif. ©1994). These programs may be implemented, for instance, using a Silicon Graphics workstation. Other hardware systems and software packages will be known to those skilled in the alt.

One other useful drug design technique enabled by this invention is iterative drug design. Iterative drug design is a method for optimizing associations between a protein and a compound (that compound includes an antibody) by determining and evaluating the three-dimensional structures of successive sets of protein/compound complexes. In iterative drug design, a series of crystals of a protein complexed with entities that bind the protein are obtained and then the three-dimensional structure of each molecular complex is solved. Such an approach provides insight into the associations between the proteins and other entities of each complex. This is accomplished by selecting chemical entities with inhibitory activity, obtaining crystals of these new complexes, solving the three-dimensional structure of the complexes, and comparing the associations between the new complexes and the previously solved complex. Associations within a complex can be optimized by observing how changes in the components of the complex affect associations.

In some cases, iterative drug design is carried out by forming successive complexes and then crystallizing each new complex. Alternatively, a pre-formed protein crystal is soaked in the presence of another chemical entity, thereby forming a complex and obviating the need to crystallize each individual complex.

XII. Pharmaceutical Compositions

The pharmaceutical compositions of this invention contains one or more VLA-1 antagonists of the present invention (e.g., anti-VLA-1 antibodies and the small molecular VLA-1 antagonists identified by the above-described rational drug design methods), or pharmaceutically acceptable derivatives thereof. The compositions may further contain a pharmaceutically acceptable carrier, such as an adjuvant, a vehicle, a buffer, and a stabilizer.

The pharmaceutical compositions of this invention may be given orally, topically, intravenously, subcutaneously, intraperitoneally, intramuscularly, intramedullarily, intraarterially, intra-articularly, intra-synovially, intrasternally, intrathecally, intrahepatically, intraspinally, intracranially as desired, or just locally at sites of inflammation or tumor growth. The pharmaceutical compositions of this invention may also be administered by inhalation through the use of, e.g., a nebulizer, a dry powder inhaler or a metered dose inhaler, or by implantation of an infusion pump or a biocompatible sustained release implant into the subject.

The pharmaceutical compositions may be in the form of a sterile injectable preparation, for example a sterile injectable aqueous or oleaginous suspension. This suspension may be formulated according to techniques known in the art using suitable dispersing, wetting, and suspending agents. If given orally, the pharmaceutical compositions can be administered in form of capsules, tablets, aqueous suspensions or solutions. For topical applications, the pharmaceutical compositions may be formulated in a suitable ointment.

The dosage and dose rate of the VLA-1 antagonists of this invention effective to produce the desired effects will depend on a variety of factors, such as the nature of the disease to be treated, the size of the subject, the goal of the treatment, the specific pharmaceutical composition used, and the judgment of the treating physician. Dosage levels of between about 0.001 and about 100 mg/kg body weight per day, for example between about 0.1 and about 50 mg/kg body weight per day, of the active ingredient compound are useful. For instance, antibody of the invention will be administered at a dose ranging between about 0.01 mg/kg body weight/day and about 20 mg/kg body weight/day, e.g., ranging between about 0.1 mg/kg body weight/day and about 10 mg/kg body weight/day, and at intervals of every one to fourteen days. In another embodiment, the antibody is administered at a dose of about 0.3 to 1 mg/kg body weight when administered intraperitoneally. In yet another embodiment, the antibody is administered at a dose of about 5 to 12.5 mg/kg body weight when administered intravenously. In one embodiment, an antibody composition is administered in an amount effective to provide a plasma level of antibody of at least 1 mg/ml.

XIII. Diseased Conditions and Animal Models

The VLA-1 antagonists of the invention are useful in the treatment, including prevention, of $\alpha_1\beta_1$-mediated diseases such as those enumerated above. The treatments of this invention are effective on both human and animal subjects afflicted with these conditions. Animal subjects to which the invention is applicable extend to both domestic animals and livestock, raised either as pets or for commercial purposes. Examples are dogs, cats, cattle, horses, sheep, hogs and goats.

The efficacy of the VLA-1 antagonists of the invention can be tested in various animal models. For instance, useful psoriasis and arthritis models include those described in WO 00/72881. Kidney fibrosis models include those described in WO 99/61040, the Alport's syndrome kidney model described in Cosgove et al., 2000, *Am. J. Path.* 157:1649-1659, and the SNF1 mouse model of lupus nephritis described in Kalled et al., 2001, *Lupus* 10:9-22. Vascular fibrosis models for restenosis include a rat carotid balloon injury model described in Smith et al., 1999, *Circ. Res.* 84:1212-1222. Lung fibrosis models for idiopathic pulmonary fibrosis and scleroderma-associated pulmonary fibrosis include a bleomycin-induced pulmonary fibrosis model described in Wang et al., 1999, *Thorax* 54:805-812. Liver cirrhosis models for hepatitis C- or alcohol-induced cirrhosis include the bile duct ligation model described in George et al., 1999, *Proc. Natl. Acad. Sci. USA* 96:12719-12724 and the CCL4-induced liver fibrosis model described in Shi et al., 1997, *Proc. Natl. Acad. Sci. USA* 94:10663-10668.

The efficacy of the treatments of this invention may be measured by a number of available diagnostic tools, including physical examination, blood tests, proteinuria measurements, creatinine levels and creatinine clearance, pulmonary function tests, chest X-rays, bronchoscopy, bronchioalveolar lavage, lung biopsy, plasma blood urea nitrogen (BUN) levels, observation and scoring of scarring or fibrotic lesions, deposition of extracellular matrix such as collagen, smooth muscle actin and fibronectin, kidney function tests, ultrasound, magnetic resonance imaging (MRI), and CT scan.

XIV. Diagnostic Methods

The antibodies of this invention can be used to diagnose diseased conditions associated with altered $\alpha_1\beta_1$ expression levels. A tissue sample from a subject, such as a tissue biopsy, body fluid sample or lavage (e.g., alveolar lavage), can be tested in an antigen capture assay, ELISA, immunohistochemistry assay, and the like using the antibodies. A tissue sample from a normal individual is used as control.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, *Molecular Cloning: A Laboratory Manual*, 2nd edition (Sambrook et al., Eds.), 1989; *Oligonucleotide Synthesis*, (M. J. Gait, Ed.), 1984; U.S. Pat. No. 4,683,195 to Mullis et al.; *Nucleic Acid Hybridization*, (B. D. Hames and S. J. Higgins), 1984; *Transcription and Translation*, (B. D. Hames and S. J. Higgins), 1984; *Culture of Animal Cells* (R. I. Freshney, Ed.), 1987; *Immobilized Cells and Enzymes*, IRL Press, 1986; *A Practical Guide to Molecular Cloning* (B. Perbal), 1984; *Methods in Enzymology*, Volumes 154 and 155 (Wu et al., Eds.), Academic Press, New York; *Gene Transfer Vectors for Mammalian Cells* (J. H. Miller and M. P. Calos, Eds.), 1987; *Immunochemical Methods in Cell and Molecular Biology* (Mayer and Walker, Eds.), 1987; *Handbook of Experiment Immunology*, Volumes I-IV (D. M. Weir and C. C. Blackwell, Eds.), 1986; *Manipulating the Mouse Embryo*, 1986.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting. Throughout this specification and claims, the word "comprise," or variations such as "comprises" or "comprising" will be understood to imply the inclusion of a stated integer or group of integers but not the exclusion of any other integer or group of integers.

The following Examples are provided to illustrate the present invention, and should not be construed as limiting thereof.

EXAMPLES

Chemical Reagents

Fluorescein isothiocyanate (FITC) was purchased from Sigma Chemical Co. (St. Louis, Mo.). Croton oil was purchased from ICN Biochemicals (Aurora, Ohio). Whole sheep blood in Alsevers solution was obtained from East Acres Biologicals (Southbridge, Mass.). Type I rat tail collagen and type IV mouse collagen were purchased from Collaborative Research Inc. (Bedford, Mass.) and Gibco (Gaithersburg, Md.), respectively.

Balb/c female mice of 6-8 weeks of age were purchased from Taconic (Germantown, N.Y.) and the α1β1 integrin-deficient mice on a Balb/c background were as previously described (3).

Example 1

Monoclonal Antibodies. Function-blocking mAbs to murine antigens were prepared in an azide-free and low endotoxin format: Ha31/8 (hamster anti-CD49a; integrin oil) (Mendrick et al. 1995. *Lab. Invest.* 72:367-375), Ha1/29 (hamster anti-CD49b; integrin α2)(β1) (Mendrick et al. 1995. *Lab. Invest.* 72:367-375; Mendrick, D. L. and D. M. Kelly 1993 *Lab. Invest.* 69:690-702), hamster group II control mAb Ha4/8 (hamster anti-KLH) (Mendrick, D. L. and D. M. Kelly 1993 *Lab. Invest.* 69:690-702), and PS/2 (rat anti-CD49d; integrin α4β1 chain) (Miyake et al. 1991 *J. Exp. Med.* 173: 599-607). In addition, the following function-blocking mAbs to murine antigens were purchased as no-azide/low endotoxin preparations from Pharmingen (San Diego, Calif.): HMβ1-1 (hamster anti-CD29; integrin β1 chain) (Noto et al. 1995 *Int. Immunol.* 7:835-842), Ha2/5 (hamster anti-CD29; integrin β1 chain) (Mendrick, D. L. and D. M. Kelly 1993 *Lab. Invest.* 69:690-702), 3E2 (hamster anti-CD54, ICAM-1)(Scheynius et al. 1993 J. Immunol. 150:655-663), 5H10-27 (rat anti-CD49e; integrin α5)(Kinashi, T., and T. A. Springer. 1994. *Blood Cells.* 20:25-44), GoH3 (rat anti-CD49f; integrin α6) (Sonnenberg et al. 1987 *J. Biol. Chem.* 262:10376-10383), and the rat isotype control mAbs R35-95 (rat IgG2a) and R35-38 (rat IgG2b).

Adhesion Assay. Splenocytes from Balb/c mice were cultured with 20 ng/ml IL-2 for 7-12 d. Adhesion of cells to type I and type IV collagen was as previously described (Gotwals et al. 1996 *J. Clin. Invest.* 97:2469-2477). Briefly, 96-well Maxisorp plates (Nunc, Napierville, Ill.) were coated with either 10 μg/ml type IV or 5 μg/ml type I collagen and non-specific sites blocked with 1% BSA. IL-2 activated splenocytes were labeled with 2 μM BCECF [2',7'-bis(carboxyethyl)-5(6) carboxyl fluorescein penta acetoxymethylester] (Molecular Probes, Eugene, Oreg.) and incubated with 10 μg/ml of indicated mAbs for 15 min. $10^5$ cells in 0.25% BSA in RPMI were then added to coated wells and incubated for 60 min at 37° C. Unbound cells were removed by washing three times with 0.25% BSA in RPMI. Adhesion was quantified using a CytoFluor 2350 fluorescent plate reader (Millipore, Bedford, Mass.). The ratio of bound cells to input cells was measured and percent adhesion relative to control mAb-treated cells (normalized to 100%) calculated. Background values due to cell adhesion on wells coated with BSA alone were subtracted.

Figure 1A:
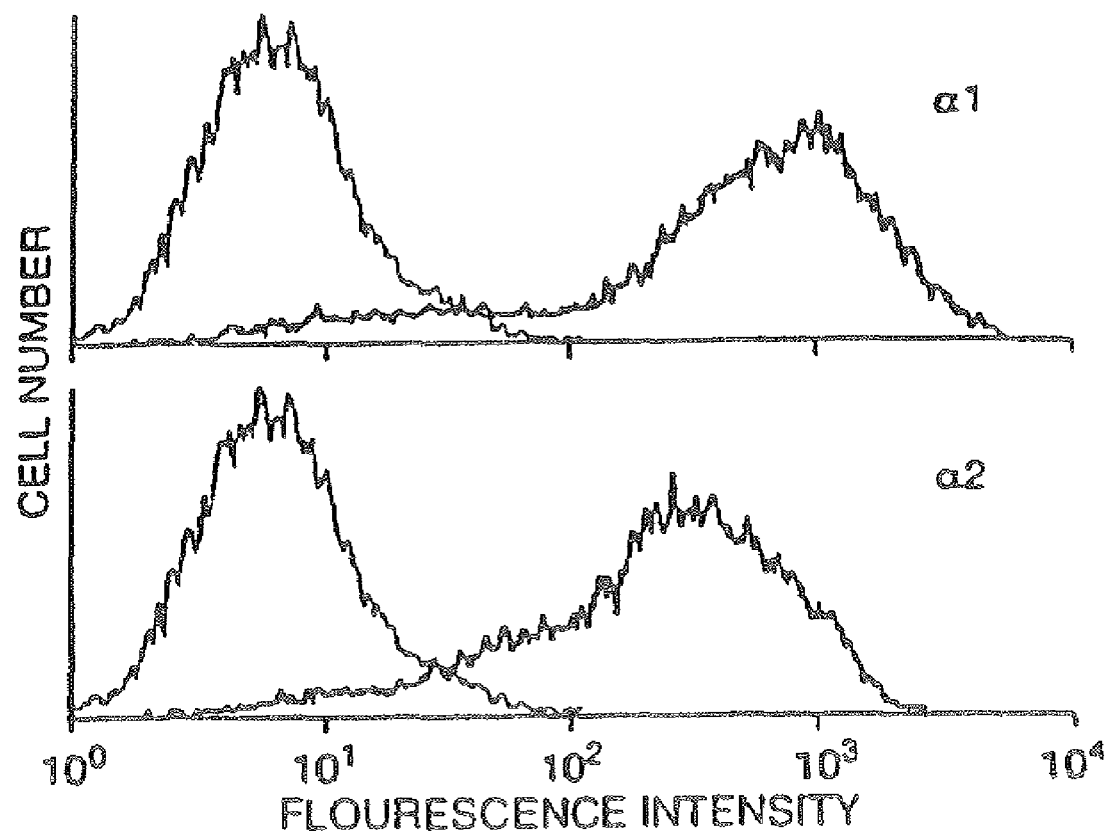
FIG. 1. Collagen-binding integrins α1β1 and α2β1 on activated leukocytes. (A). Flow cytometric analysis of α1 and α2β1 integrin expression on IL-2-activated splenocytes (d 11). Cells were labeled with either anti-α1 mAb, anti-α2 mAb, or non-binding control mAb (grey lines), and followed by FITC-anti-hamster immunoglobulin. (B) Effect of anti-α1 and anti-α2 mAbs on leukocyte adhesion to collagen. $10^5$ IL-2 activated splenocytes were treated with indicated mAbs for 15 min before plating onto either type IV or type I collagen-coated wells for 1 h at 37° C. Adhesion was calculated as illustrated in Example 1, and expressed as % adhesion relative to control mAb-treated cells. Adhesion assays were done in triplicate, and at least three independent experiments were performed. One representative experiment is shown.
Figure 1B:
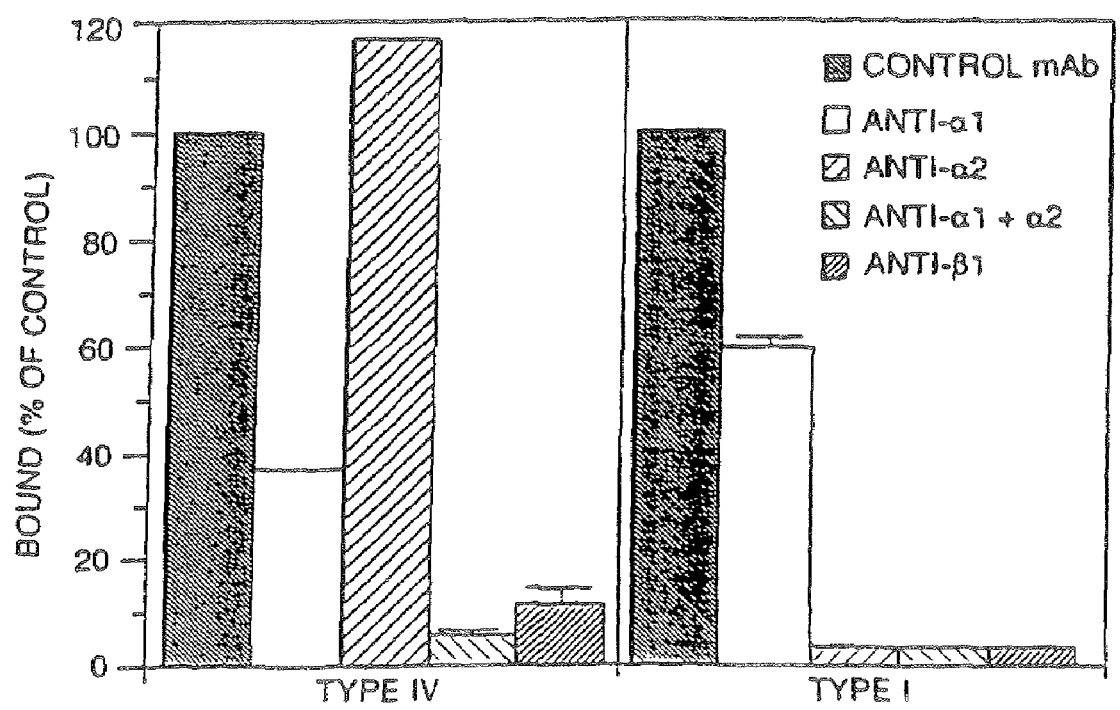

Expression and functional blockade of α1β1 and α2β1 on activated leukocytes. Given the key role leukocytes play in inflammation, we decided to test whether anti-α1 and anti-α2 mAbs were capable of blocking leukocyte adhesion to collagens. In order to obtain leukocytes expressing high levels of both α1 and α2, murine T cells were stimulated in vitro with IL-2 for 7-12 d. These cells expressed high levels of both α1 and α2 (FIG. 1A), and bound well to both collagen type IV and type I-coated surfaces (FIG. 1B). Adhesion to type IV collagen was partially inhibited by anti-α1 mAb alone and was not inhibited by anti-α2 mAb alone. In contrast, adhesion to type I collagen was completely inhibited by anti-α2 mAb and anti-α1 mAb alone showed only partial inhibition. Both anti-β1 mAb and the combination of anti-α1 and anti-α2 mAbs completely inhibited adhesion to types I and IV collagen. Having demonstrated that the α1β1 and α2β1 integrins are expressed on activated T cells and that anti-α1 and α2 mAbs are able to functionally block leukocyte adhesion to collagens, we used these mAbs to investigate the in vivo role of these integrins in animal models of inflammatory disorders.

Example 2

Inhibition of DTH responses by anti-integrin mAbs. SRBC-induced delayed type hypersensitivity (DTH) responses were adapted from a previously published protocol (Hurtrel et al., 1992, *Cell. Immunol.* 142:252-263). Briefly, mice were immunized s.c. in the back with $2\times10^7$ SRBC in 100 ul PBS on d 0. The mice were challenged on d 5 by injecting $1\times10^8$ SRBC in 25 ul PBS s.c into the right hind footpad. Footpad thickness was measured with an engineer's caliper (Mitutoyo/MTI, Paramus, N.J.) 20 h after antigen challenge, and the degree of footpad swelling calculated. Results are reported as the mean percent increase footpad thickness±SEM and calculated as % increase=[1=(Right footpad thickness 20 h after antigen challenge/Uninjected left footpad thickness 20 h after antigen challenge)]×100. To block the effector phase of the SRBC-induced DTH response, therapeutic or control mAb (100 ug), which were prepared according to the methods described in Example 1, was given i.p. 1 h prior to antigen challenge on d 5.

Figure 2:
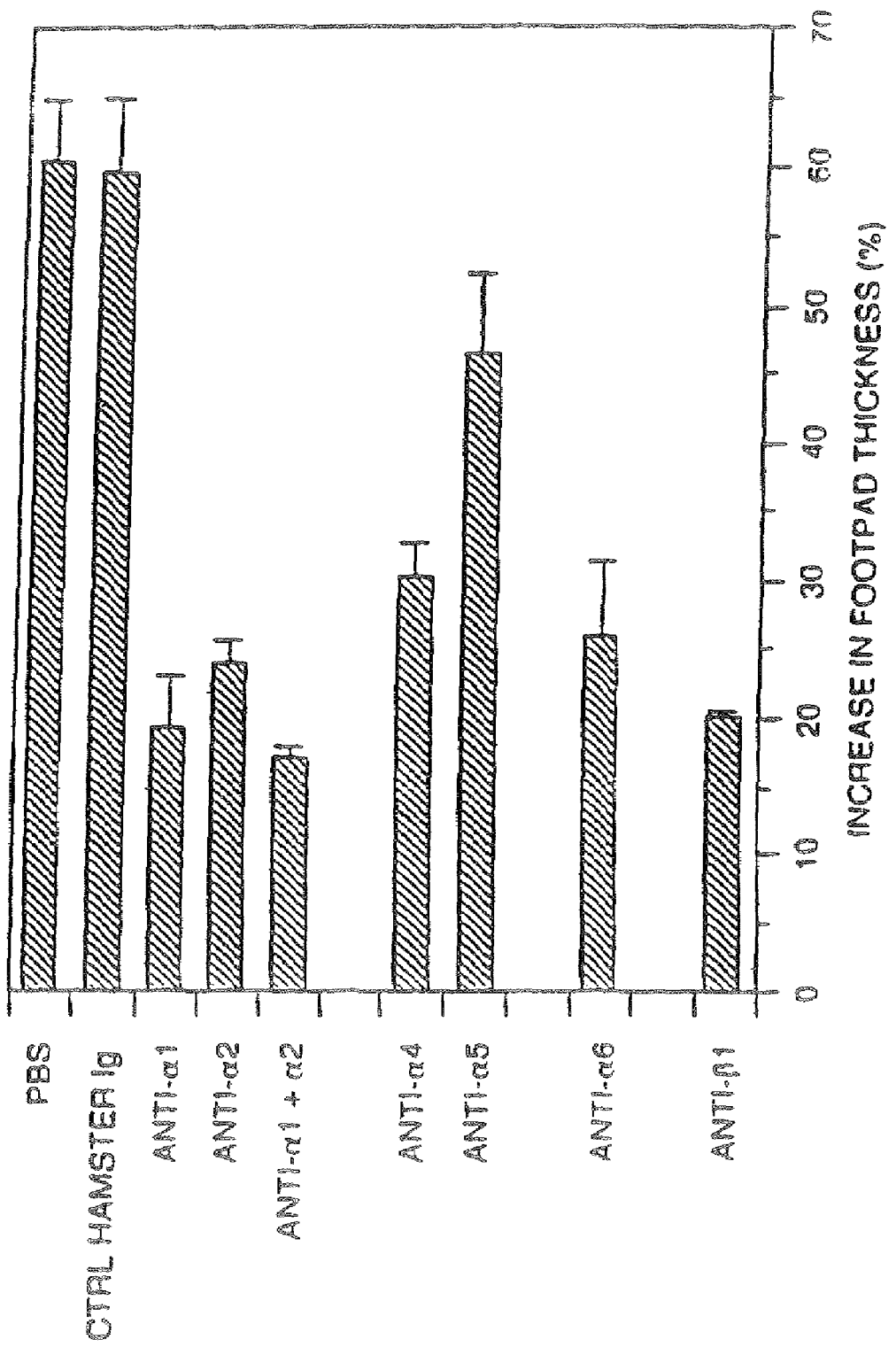
FIG. 2. Effect of anti-integrin mAbs on the effector phase of delayed-type hypersensitivity. SRBC-sensitized mice were injected i.p. with the indicated mAbs 1 h prior to SRBC challenge, Footpad thickness was measured 20 h after antigen challenge, and results shown as % increase in footpad thickness±SEM as illustrated in Example 2. These data represent a summary of eight experiments with n=79 (PBS), 68 (control hamster Ig), 68 (anti-α1), 29 (anti-α2), 18 (anti-α1+ anti-α2), 45 (anti-α4), 18 (anti-α5), 20 (anti-α6), and 10 (anti-β1). The mAbs used were: Ha4/8 (control hamster Ig group 2), Ha31/8 (anti-α1), Ha1/29 (anti-α2), PS/2 (anti-α4), 5H10-27 (anti-α5), GoH3 (anti-α6), and HMβ1-1 (anti-β1).

SRBC-induced DTH is a well characterized in vivo model of inflammation, and in particular psoriasis, that has been used to demonstrate the importance of a variety of cytokines and adhesion molecules in inflammation (Tedder et al., 1995, *J. Exp. Med.* 181:2259-2264, Terashita et al., 1996, *J Immunol* 156:4638-4643). SRBC-sensitized mice received anti-integrin mAbs 1 h prior to footpad antigen challenge and inflammation was assessed 20 h later as measured by increased footpad thickness. PBS and control hamster Ig-treated mice showed a 60-70% increase in footpad thickness 20 h after antigen challenge (FIG. 2). Compared to control hamster Ig treatment, anti-α1 or anti-α2 mAbs resulted in a 68% and 60% inhibition in footpad thickness, respectively. The combination of anti-α1 and α2 mAbs resulted in 71% inhibition, demonstrating little additive effect over anti-α1 or anti-α2 mAbs alone. Treatment with other anti-integrin mAbs was also effective at inhibiting DTH effector response. The degree of inhibition seen with the various mAb treatments was 49% (anti-α4), 23% (anti-α5), and 57% (anti-α6). Lastly, mAb blockade of the common β1 integrin subunit (mAb HMBI-1) inhibited the effector DTH response by 67%.

Example 3

Inhibition of CHS effector responses by anti-integrin mAbs. Contact hypersensitivity (CHS) to FITC was assayed as previously described (Gaspari et al., 1991, In Current Protocols in Immunology. J. E. Coligan, A. M. Kruisbeek, D. H. Margulies, E. M. Shevach, and W. Strober, editors. John Wiley & Sons, New York. Section 4.2:1). Briefly, mice were sensitized by painting 100 ul 0.5% FITC in 1:1 acetone/dibutylphthalate onto the shaved back on d 0.10 d later, animals were challenged by applying 5 ul 0.5% FITC onto both sides of each ear. Ear swelling response was determined by ear thickness measured with an engineer's caliper (Mitutoyo/MTI, Paramus, N.J.) at the time of antigen challenge (d 10) and 24 h later, and the results reported as mean percent increase in baseline ear thickness±SEM. Increase in ear thickness was calculated as % increase=[1=(Ear thickness 24 h after antigen challenge/Ear thickness at the time of antigen challenge)]×100. To block the effector phase of the CHS response, therapeutic or control in mAb (250 ug) was given i.p. 4 h prior to antigen challenge on d 10. Mice that were antigen-sensitized and ear challenged with vehicle only (vehicle control) or mice that were ear challenged without prior sensitization (irritant control) served as negative controls (never exceeded 2% increase in ear thickness).

Figure 3:
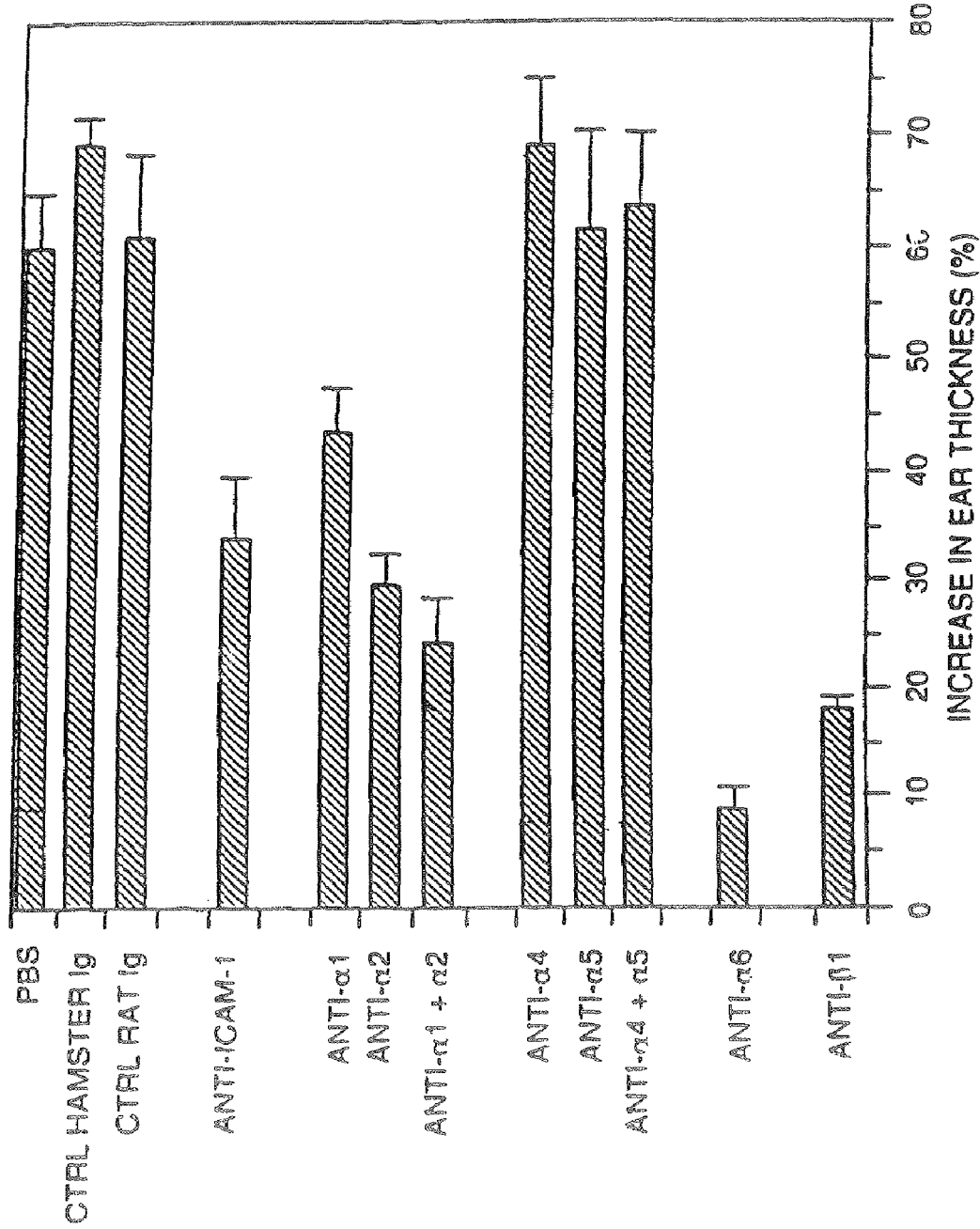
FIG. 3. Effect of anti-integrin mAbs on the effector phase of contact hypersensitivity. FITC-sensitized mice were injected i.p. with the indicated mAbs 4 h prior to FITC challenge. Ear thickness was measured at baseline and 24 h later, and results shown as % increase in ear thickness ±SEM as illustrated in Example 3. These data represent a summary of nine experiments with n=74 (PBS), 60 (control hamster Ig), 26 (anti-ICAM-1), 44 (anti-α1), 44 (anti-α2), 38 (anti-α1+ anti-α2), 36 (anti-α4), 16 (anti-α5), 26 (anti-α4+anti-α5), 24 (anti-α6), and 22 (anti-β1). The hamster mAbs used were: Ha4/8 (control hamster Ig group 2), Ha31/8 (anti-α1), Ha1/29 (anti-α2), HMβ1-1 (anti-β1), 3E2 (anti-ICAM-1); the rat mAbs used were: R35-95 and R35-38 (control rat IgG2a and rat IgG2b, respectively), PS/2 (anti-α4), 5H10-27 (anti-α5), GoH3 (anti-α6).

Given that CHS is mechanistically distinct from DTH and involves different effector cells, we investigated what effect anti-integrin mAbs had on the effector phase of the CHS response. Mice were hapten-sensitized using FITC applied to their shaved backs, followed 10 d later with FITC challenge to the ear resulting in an inflammatory response the next day. FITC-sensitized mice demonstrated a 60-70% increase in thickness 24 h after antigen challenge (FIG. 3). Consistent with published results (Scheynius et al., *J. Immunol.* 150:655-663), anti-ICAM-1 mAb treatment resulted in 51% inhibition of ear swelling. Compared to control hamster mAb, treatment of mice with anti-α1 or anti-α2 mAb 4 h prior to antigen challenge resulted in 37% and 57% inhibition in ear swelling, respectively (FIG. 3). The combination of anti-α1 and anti-α2 mAbs resulted in slightly greater inhibition of ear swelling (65%). Treatment with other mAbs to β1 integrins revealed that while anti-α4 and anti-α5 mAbs resulted in no inhibition of FITC-induced CHS effector response when compared to control rat mAb, treatment with anti-α6 mAb resulted in an 86% inhibition of effector responses. Lastly, mAb blockade of the common β1 integrin subunit inhibited CHS effector responses by 74%. Similar CHS results were obtained using different strains of mice (C57/BL6, 129/Sv) and a different sensitizing agent (oxazolone) (data not shown). Similar to the results seen in the SRBC-induced DTH model, histologic analysis of inflamed ears revealed that both edema formation and leukocytic infiltration were inhibited by anti-α1 and anti-α2 mAb treatment.

Consistent with the finding that α1β1 and α2β1 can be expressed on IL-2-activated splenocytes, analysis of lymph nodes from antigen-sensitized mice (FITC or oxazolone) revealed of α1β1 and α2β1 to be expressed exclusively on CD44$^{hi}$ LFA-1$^{hi}$ activated CD4+ and CD8+ T cells (data not shown). Treatment of mice with anti-α1 and anti-α2 mAbs did not result in deletion of these cells, as the numbers of activated T cells in both spleen and lymph nodes seen in response to antigen sensitization in the CHS model was unaffected. In addition, effector cells were not functionally deleted as prolonged treatment of antigen-sensitized mice with anti-α1 and anti-α2 mAbs (d 10-16) did not affect the inflammatory response of mice challenged with antigen at d 20 (data not shown).

Example 4

Figure 4:
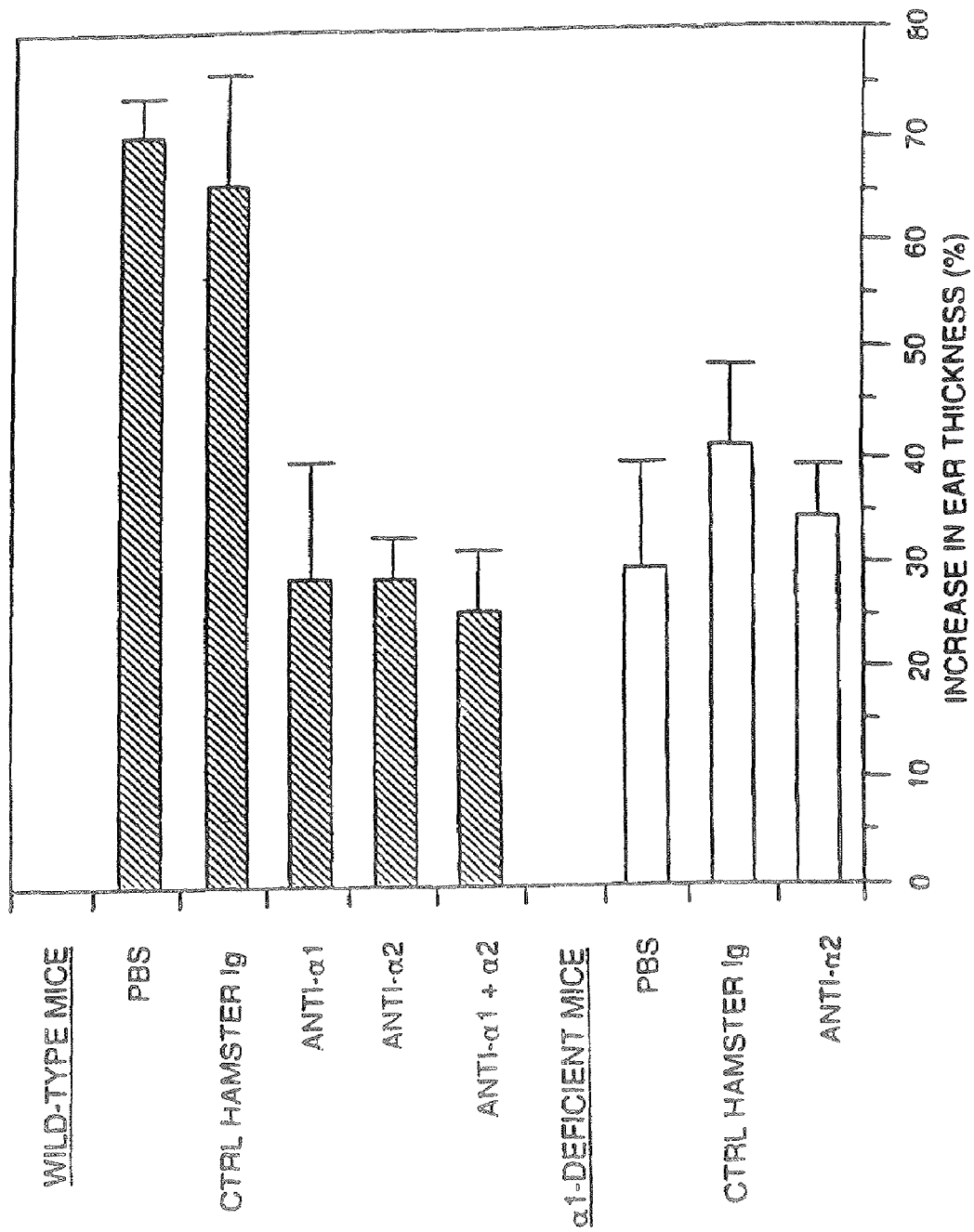
FIG. 4. Contact hypersensitivity responses in α1-deficient mice compared to wild-type mice. FITC-sensitized mice were injected i.p. with indicated mAbs 4 h prior to FITC challenge. Ear thickness was measured at baseline and 24 h later, and results shown as % increase in ear thickness±SEM as illustrated in Example 4. Groups of four to five mice per condition were used, and all experiments were performed a minimum of three times. One representative experiment is shown.

CHS effector responses are decreased in α1≈1-deficient mice. To exclude the possibility that the inhibitory role of α1β1 in the effector response of FITC-mediated CHS was mAb-mediated, experiments were carried out in wild-type and α1β1 integrin deficient mice (FIG. 4). MAb inhibition of the effector phase in wild-type mice was consistent with previous results with 56% inhibition in ear thickness seen with anti-α1, 56% with anti-α2 and 62% with a combination of anti-α1 and anti-α2. The effector phase of CHS was significantly reduced in untreated α1β1-deficient mice as compared to untreated wild-type mice (30% vs 71% increase in ear thickness, respectively). As expected, the level of ear swelling in untreated α1β1-deficient mice was equivalent to the level of ear swelling seen in anti-α1 mAb-treated wild-type mice. Lastly, mAb blockade of α2β1 in the α1β1-deficient mice resulted in only slightly increased inhibition of ear swelling, consistent with the results seen in wild-type mice treated with a combination of anti-α1 and anti-α2 mAbs.

Example 5

To further exclude the possibility that the inhibitory effect of the anti-integrin mAbs seen in both the DTH and CHS models of inflammation is caused by a general anti-inflammatory effect mediated by the anti-α1 and anti-α2 mAbs, the effect of these mAbs on irritant dermatitis was studied.

To assess irritant dermatitis, mice were painted with 5 ul of 0.8% croton oil in acetone on both sides of each ear. Therapeutic or control antibodies were given 4 h prior to the application of the irritant. Ear swelling was measured 24 h later as described above and compared to ear thickness prior to croton oil application. Results are reported as mean percent increase in baseline ear thickness±SEM as described above. Mice painted with acetone only (vehicle control) served as a negative control.

Figure 5:
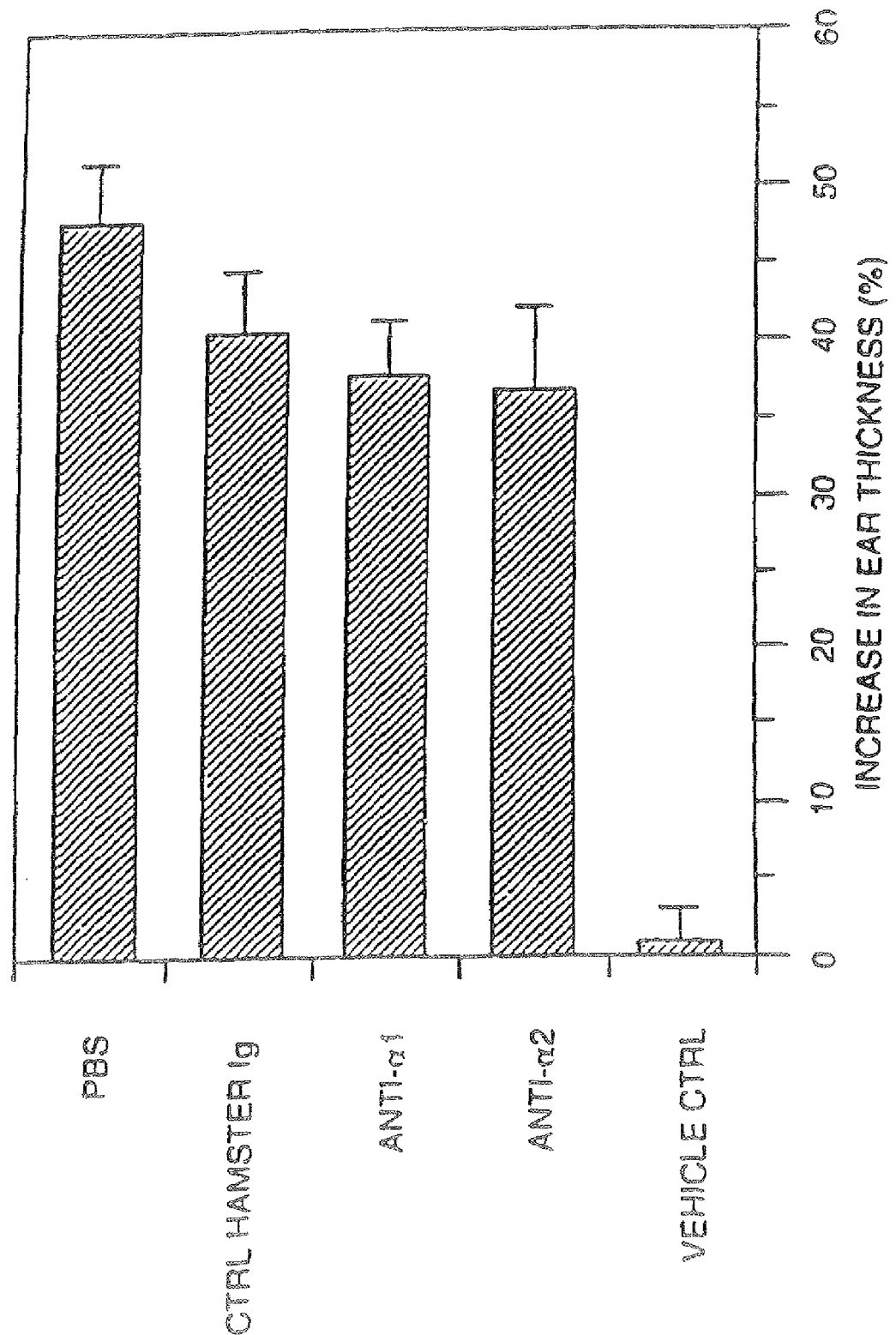
FIG. 5. Effect of anti-α1 and anti-α2 mAbs on croton oil-induced non-specific inflammation. Mice were injected i.p. with indicated mAbs 4 h prior to ear painting with croton oil. Ear thickness was measured at baseline and 24 h later, and results shown as % increase in ear thickness±SEM as illustrated in Example 5. Groups of four to five mice per condition were used, and all experiments were performed a minimum of three times. One representative experiment is shown.

24 h later, ears of mice treated with croton oil showed a significant increase in ear thickness (48%), when compared to mice receiving vehicle only (acetone). Toxic ear swelling caused by croton oil was not significantly affected in mice pretreated with anti-α1 or anti-α2 mAbs when compared to either PBS or control mAb-treated animals (FIG. 5). Histologic examination of the croton oil-treated ears revealed no differences in numbers or types of infiltrating cells or edema formation in mice treated with anti-α1 or anti-α2 mAbs, as compared to control mAb-treated mice or PBS-treated mice (data not shown).

Example 6

Inhibition of arthritis bar α1β1 and α2β1. As α1β1 is well expressed on infiltrating cells in the synovium of arthritis patients, we decided to examine whether anti-α1 or anti-α2 mAbs would be inhibitory in an accelerated model of arthritis previously described (Terato et al., 1992, *J. Immunol.* 148: 2103-2108; Terato et al., 1995, *Autoimmunity* 22:137-147).

Arthrogen-CIA Antibody kits were purchased from Stratagene (La Jolla, Calif.) and arthritis induced using a well established protocol (Terato et al., 1992, *J. Immunol.* 148: 2103-2108; Terato et al., 1995, *Autoimmunity* 22:137-147). Briefly, arthritis was induced through i.p. injection of a cocktail of 4 anti-collagen type II mAbs (1 mg each) on d 0, followed by i.p. injection of 50 ug LPS on d 3. Over the course of the next 3-4 d, the mice developed swollen wrists, ankles and digits. Therapeutic or control mAb (250 ug) was administered i.p. 4 h prior to injection of the anti-collagen mAbs on d 0, and again 4 h prior to LPS administration on d 3, and then continuing every 3$^{rd}$ day for the length of the experiment. Beginning on d 3, mice were evaluated for the development of arthritis. Severity of arthritis in each limb was scored using a four point system. 0=normal; 1=mild redness, slight swelling of ankle or wrist; 2=moderate swelling of ankle or wrist; 3=severe swelling including some digits, ankle, and foot; 4=maximally inflamed.

Figure 6:
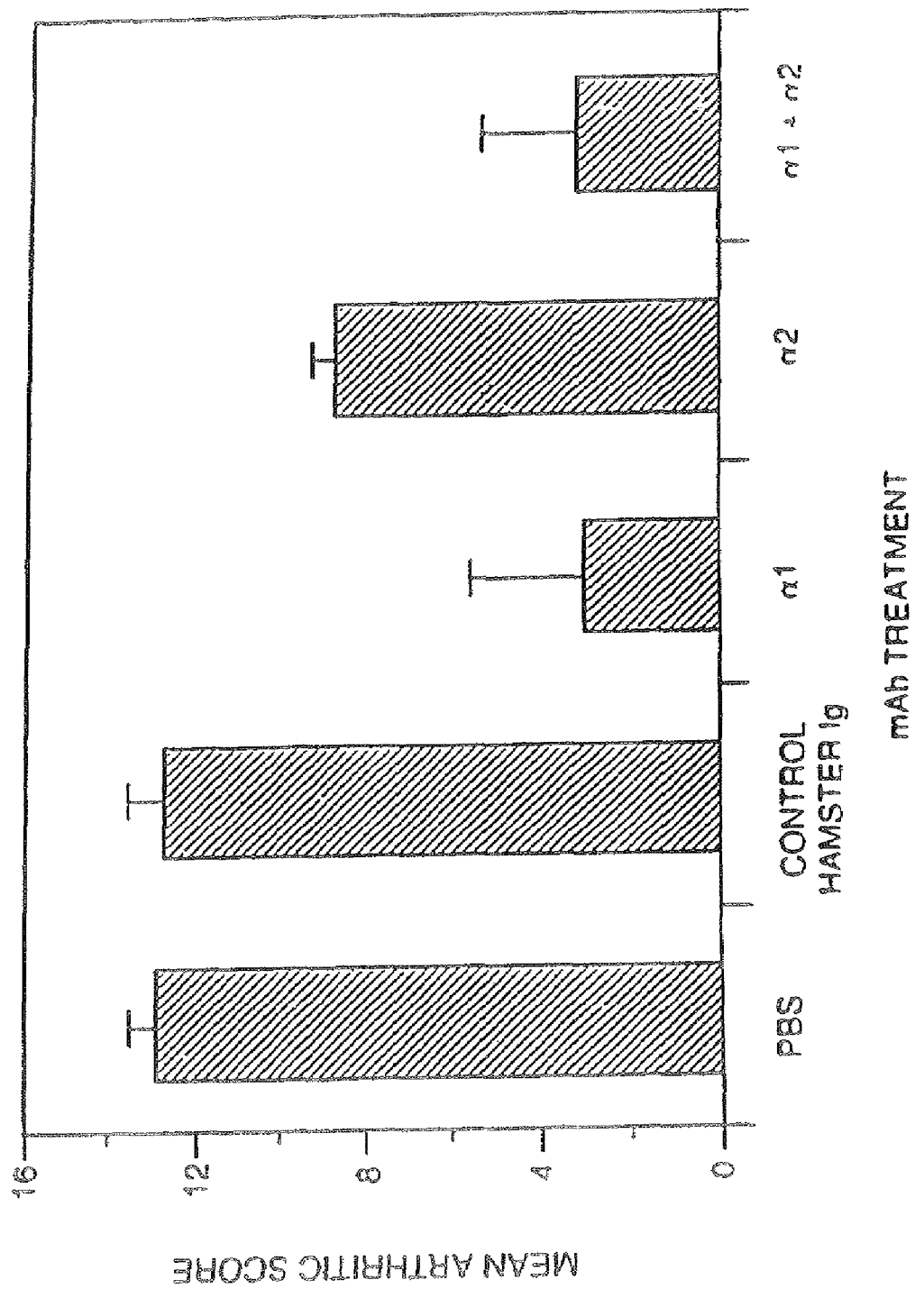
FIG. 6. Effect of anti-α1 and α2 mAbs in collagen mAb-induced arthritis. Mice were injected i.p. with anti-collagen mAbs at d 0, followed by LPS on day 3. Mice were injected i.p. with indicated mAbs every $3^{rd}$ day starting on d 0. Clinical arthritis was apparent 2-3 d following LPS injection and continued for several weeks. Each limb was evaluated on a 0 to 4 scale every $3^{rd}$ day as illustrated in Example 6 and results are expressed as the mean arthritic score between d 9 and d 15 (±SEM) of all four limbs. These data represent a summary of four experiments with each experiment consisting of groups of three to four mice per condition.

Severe arthritis in Balb/c mice developed within 72 h after LPS injection and persisted for more than 3 weeks. Neither injection of anti-collagen mAbs alone nor LPS alone induced arthritis. Mice receiving control mAb treatment displayed equally severe arthritis as than seen in PBS-treated mice (FIG. 6). In contrast, treatment with anti-α1 mAb alone resulted in a marked reduction (78%) in arthritis, lasting the duration of the experiment. Treatment with anti-α2 mAb alone also had a beneficial effect, resulting in a 32% decrease in the arthritic score as compared to control b-treated mice. The combination of anti-α1 and anti-α2 mAbs resulted in a similar degree of inhibition as seen with anti-α1 mAb alone.

Example 7

Histological analysis of effect of anti-α1 and anti-α2 mAb treatment on the inflammatory cellular infiltrate. Further histological analysis of the SRBC-induced DTH response confirmed the ability of anti-α1 and anti-α2 mAb treatment to modulate the elicited inflammatory response. An unchallenged footpad from an SRBC-sensitized mouse showed virtually no inflammatory cellular infiltrate when compared to an SRBC-challenged footpad from the same mouse. Treatment of SRBC-sensitized mice with anti-α1 and anti-α2 mAbs either alone or combined greatly reduced the number of these infiltrating cells found in SRBC-challenged footpads when compared to control mAb-treated mice. Closer examination of the infiltrating cells revealed most cells to be composed of neutrophils, with some monocytes and lymphocytes present, and confirmed that anti-α1 and anti-α2 mAb treatment greatly decreased the numbers of these cells.

Example 8

Immunohistochemical demonstration of α1-expressing cells in the inflammatory cellular infiltrate. Immunohistochemistry was performed to more precisely determine the nature of the infiltrating cells and whether they express collagen-binding integrins. Infiltrating cells from an inflamed footpad of an untreated mouse were examined for expression of α1β1 integrin and cell lineage markers. α1β1 integrin was found to be expressed on many infiltrating leukocytes. Dual immunohistochemistry was utilized to identify the nature of the infiltrating cells and the distribution of α1β1 expression. Using cell lineage markers, the infiltrate was found to be composed largely of granulocyte/monocytes (Mac-1+), with many of these cells being neutrophils (Gr1+), along with a smaller number of T lymphocytes (CD3+). Expression of α1β1 integrin was found among all three subsets of cells, with α1 expressed on a subset of Mac-1+ granulocyte/monocytes, a subset of Gr1+ neutrophils, and on the majority of infiltrating CD3+ T lymphocytes. Detailed immunohistochemical analysis revealed that although anti-α1 and anti-α2 mAb treatment reduced the numbers of infiltrating cells, no change in the cellular composition of the infiltrate was seen (data not shown). Immunohistochemistry staining with a FITC anti-hamster mAb confirmed the ability of the anti-α1 and antis α2 mAb to localize to the inflamed footpad (data not shown).

Example 9

Figure 7:
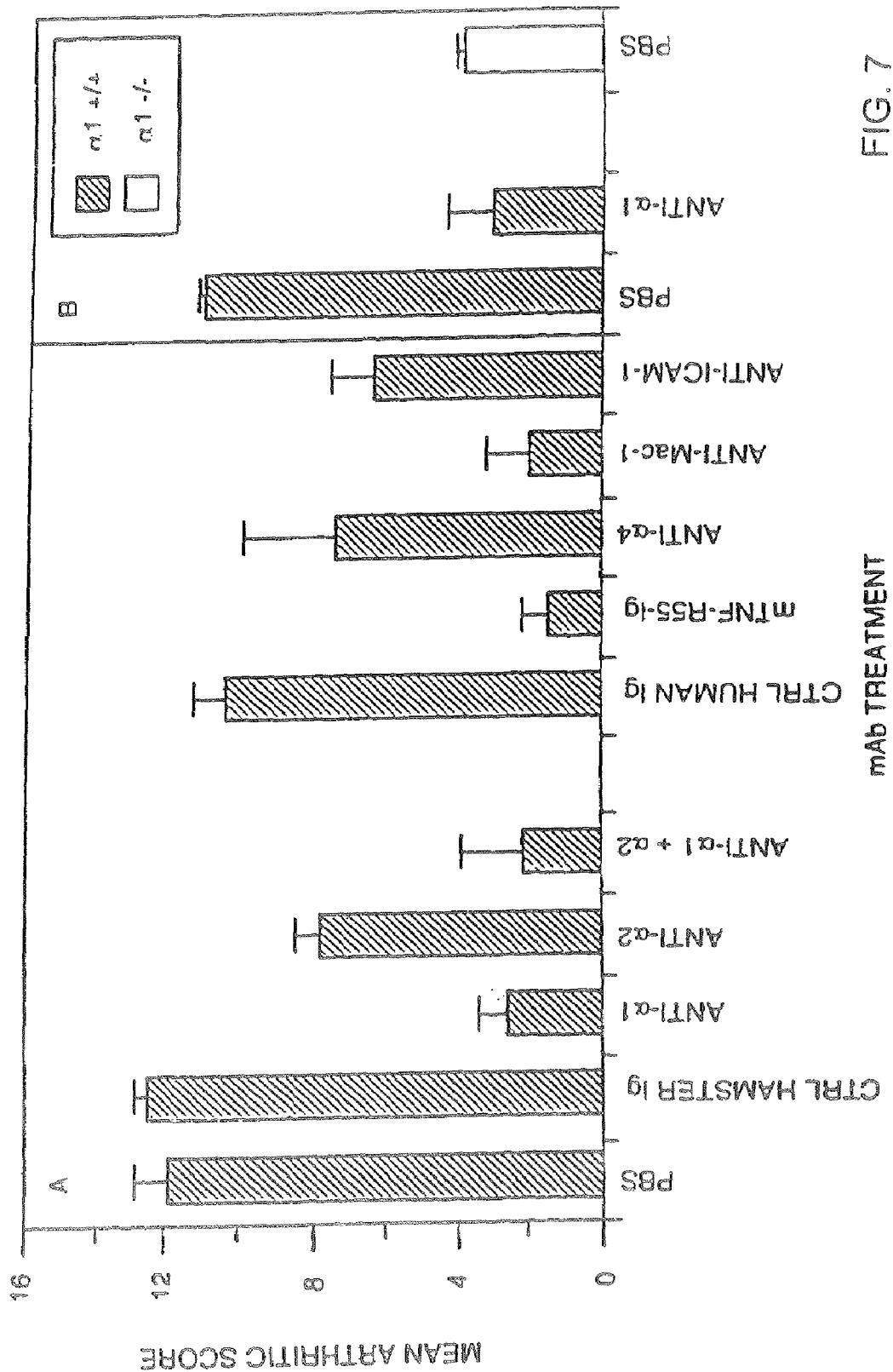
FIG. 7. Effect of anti-α1 and α2 mAbs in collagen mAb-induced arthritis. A. Preventative treatment of mice with either anti-α1 or anti-α2 mAb decreases arthritic score. Mice were treated with anti-collagen mAbs at d 0, followed by LPS on d 3. Arthritis was apparent by d 6 and continued for several weeks. Mice were treated with the indicated mAbs every $3^{rd}$ day starting on d 0. Each limb was evaluated and scored on a 0 to 4 scale every $3^{rd}$ day. Results are expressed as the mean arthritic score between d 9 and d 15 (±SEM) of all four limbs (maximum score of 16). Groups of 4 mice per condition were used; the average of 12 experiments is shown. B. α1-deficient mice have a reduced arthritic score comparable to anti-α1 mAb-treated wild-type mice. Experimental details and scoring are as outlined above. Groups of 4 mice per condition were used; the average of 2 experiments is shown.

Inhibition of arthritis by mAbs to α1β1 and α2β1 and in α1-deficient mice. As α1β1 is well expressed on infiltrating cells in the synovium of arthritis patients, we decided to examine whether anti-α1 or anti-α2 mAbs would be inhibitory in an accelerated model of arthritis previously described (Terato et al., 1992, *J. Immunol* 148:2103-2108; Terato et al., 1995, *Autoimmunity* 22:137-147). This model involves injection of a cocktail of anti-collagen type II mAbs into mice, followed later by LPS administration, resulting in the development of arthritis over the next 3-7 d. Mice were given mAb every $3^{rd}$ day starting at d 0, and scored for the development of arthritis every $3^{rd}$ day. Severe arthritis developed in all mice within 72 h after LPS injection and persisted for more than 3 weeks. Neither injection of anti-collagen mAbs alone nor LPS alone induced arthritis. Mice receiving control mAb treatment displayed equally severe arthritis as than seen in PBS-treated mice (FIG. 7). In contrast, treatment with anti-α1 mAb alone resulted in a marked reduction (79% and higher) in arthritis, lasting the duration of the experiment. Treatment with anti-α2 mAb alone also had a beneficial effect, resulting in a 37% decrease in the arthritic score as compared to control mAb-treated mice. The combination of anti-α1 and anti-α2 mAbs resulted in a similar degree of inhibition as seen with anti-α1 mAb alone. Reduction of arthritic score with anti-α1 mAb treatment was seen in all mice and compares favorably with several other mAb-based treatments for arthritis such as soluble TNF receptor Ig fusion protein (Mori et al., 1996, *J. Immunol.* 157:3178-3182), anti-Mac-1 (Taylor et al., 1996, *Immunology.* 88:315-321), anti-α4 (Seiffge, 1996, *J. Rheumatol.* 23:2086-2091), and anti-ICAM-1 (Kakimoto et al., 1992, *Cell Immunol.* 142:326-337). In agreement with mAb-based data showing an important role for α1β1 in arthritis, untreated i-deficient mice showed significant reduction in arthritic score when compared to wild-type mice.

Example 10

Effect of anti-α1 mAb treatment on the immunopathology of arthritic joints. Joints from wild-type arthritic mice (day 8) receiving either control mAb or anti-α1 mAb treatment were compared visually and histologically to joints from a normal untreated mouse. Visually, joints from control mAb-treated mice demonstrated redness and swelling of the entire foot including digits, while anti-α1 mAb-treated mice showed little if any signs of inflammation in either joints or digits. Histologic examination showed severe changes in control mAb-treated arthritic joints, with extensive infiltration of the subsynovial tissue with inflammatory cells, adherence of cells to the joint surface, and marked cartilage destruction as evidenced by proteoglycan loss. Consistent with previous reports (Terato et al., 1992, *J. Immunol* 148:2103-2108; Terato et al., 1995, *Autoimmunity* 22:137-147), the majority of the infiltrating cells in this model are neutrophils. Anti-α1 mAb treatment of mice dramatically reduced the amount of inflammatory infiltrate and the degree of cartilage destruction.

Example 11

Figure 8:
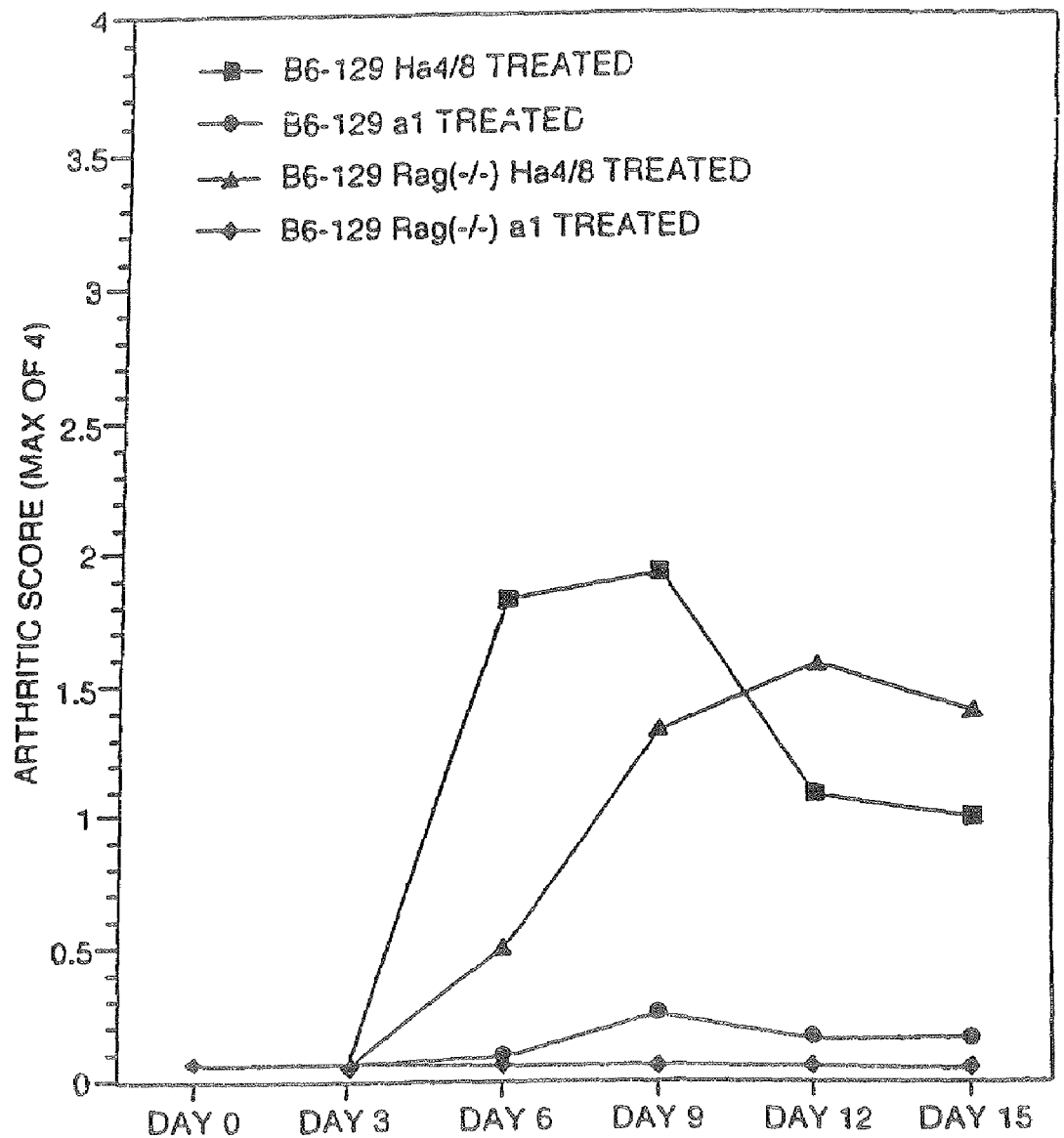
FIG. 8. Development of arthritis is delayed in the absence of lymphocytes and inhibition of arthritis by anti-α1 mAb occurs in the absence of lymphocytes. Wild-type B6,129 or RAG-1-deficient B6,129 mice were treated with anti-collagen mAbs at day 0, followed by LPS on day 3. Arthritis was apparent by day 6 and continued for several weeks. Mice were treated with the indicated mAbs every $3^{rd}$ day starting on day 0. Each limb was evaluated and scored on a 0 to 4 scale every $3^{rd}$ day. Results are expressed as the mean arthritic score per limb (maximum score of 4). Groups of 4 mice per condition were used.

Development of arthritis is delayed in the absence of lymphocytes and inhibition of arthritis by anti-α1 mAb occurs in the absence of lymphocytes. To determine what cell types might be important in the collagen mAb-induced arthritis model we compared the ability of wild-type B6-129 mice and RAG-1-deficient B6-129 mice to develop arthritis (FIG. 8). Genetic deletion of the RAG-1 (recombination activating gene-1) gene results in a complete loss of mature T and B lymphocytes (Mombaerts et al., 1992, *Cell* 68:869-877).

Both the wild-type and RAG-1-deficient mice developed arthritis, though the kinetics of induction in the RAG-1-deficient mice is significantly slower (FIG. 8). These results suggest that while lymphocytes are involved in this model of arthritis, they are not required for the development and progression of the disease. Published reports examining the effect of the RAG-1-deficient mice in other models of arthritis also found that loss of T and B lymphocytes delayed the onset of arthritis (Plows et al., 1999, *J. Immunol.* 162:1018-1023). Treatment of either wild-type or RAG-1-deficient mice with anti-α1 mAb completely inhibited arthritis (FIG. 8). These results demonstrate that the effectiveness of anti-α1 mAb in this model is not dependent on the presence of lymphocytes, and that as suggested by previous experiments (FIG. 7), the efficacy of anti-α1 mAb in preventing disease may be through its action on other α1-expressing cells, such as macrophages and neutrophils.

Example 12

Figure 9:
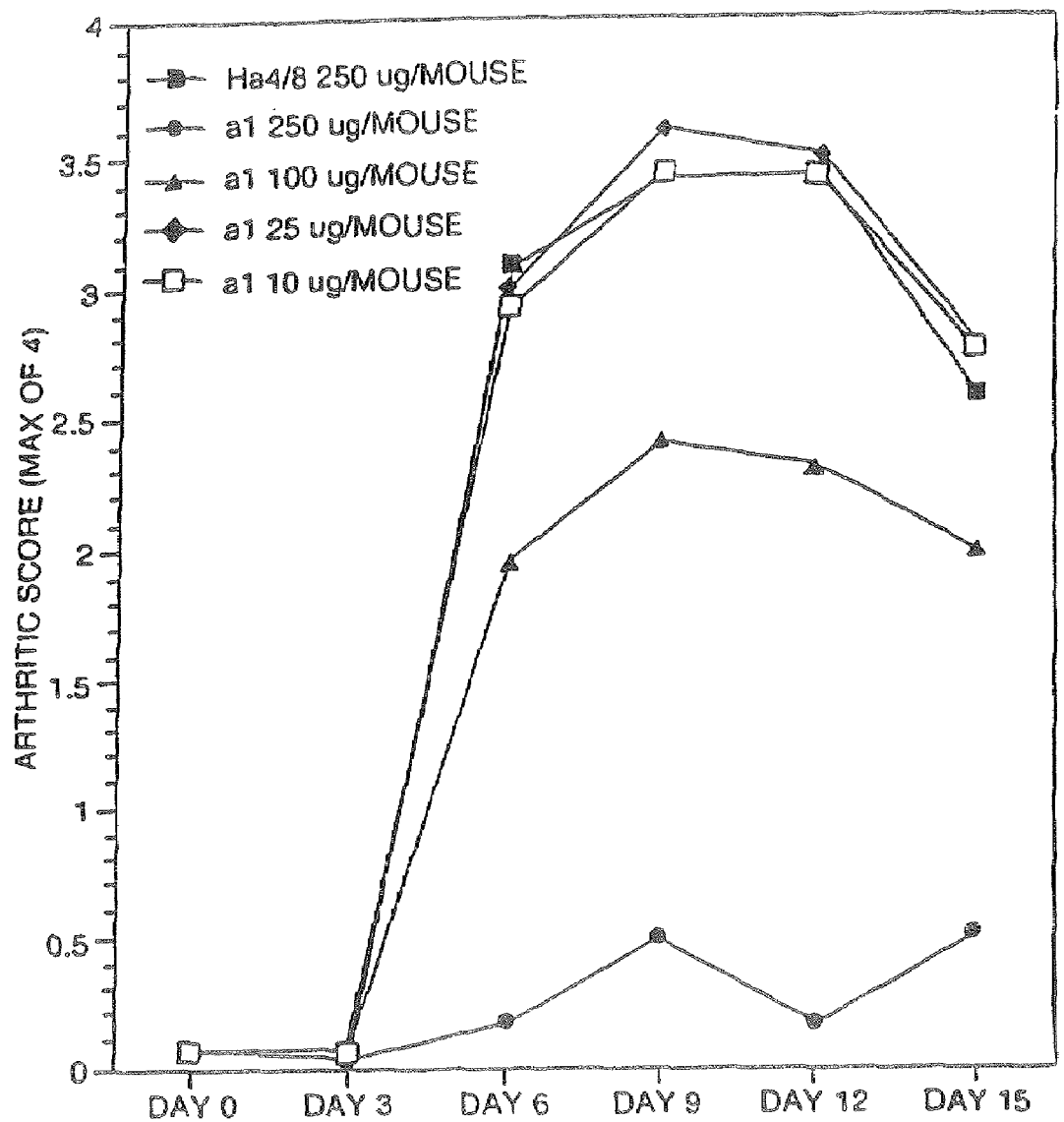
FIG. 9. Dose response of anti-α1 mAb inhibition of arthritis. Wild-type Balb/c mice were treated with anti-collagen mAbs at day 0, followed by LPS on day 3. Arthritis was apparent by day 6 and continued for several weeks. Mice were treated i.p. with the indicated dose of either Ha4/8 (isotype control) or Ha31/8 (anti-α1) mAbs every $3^{rd}$ day starting on day 0. Each limb was evaluated and scored on a 0 to 4 scale every $3^{rd}$ day. Results are expressed as the mean arthritic score per limb (maximum score of 4). Groups of 4 mice per condition were used.

Dose response of anti-α1 mAb inhibition of arthritis. Given the striking effects of anti-α1 mAb treatment on preventing arthritis, we extended these studies to include a dose response analysis (FIG. 9). Different doses of mAb were administered i.p. every $3^{rd}$ day starting at day 0. In agreement with earlier data, a 250 ug dose of anti-α1 mAb resulted in near complete prevention of arthritis. A lower dose of 100 ug of anti-α1 mAb was partially effective at preventing arthritis in this model, while lower doses did not have any discernable effect on arthritic score (FIG. 9).

Example 13

Figure 10:
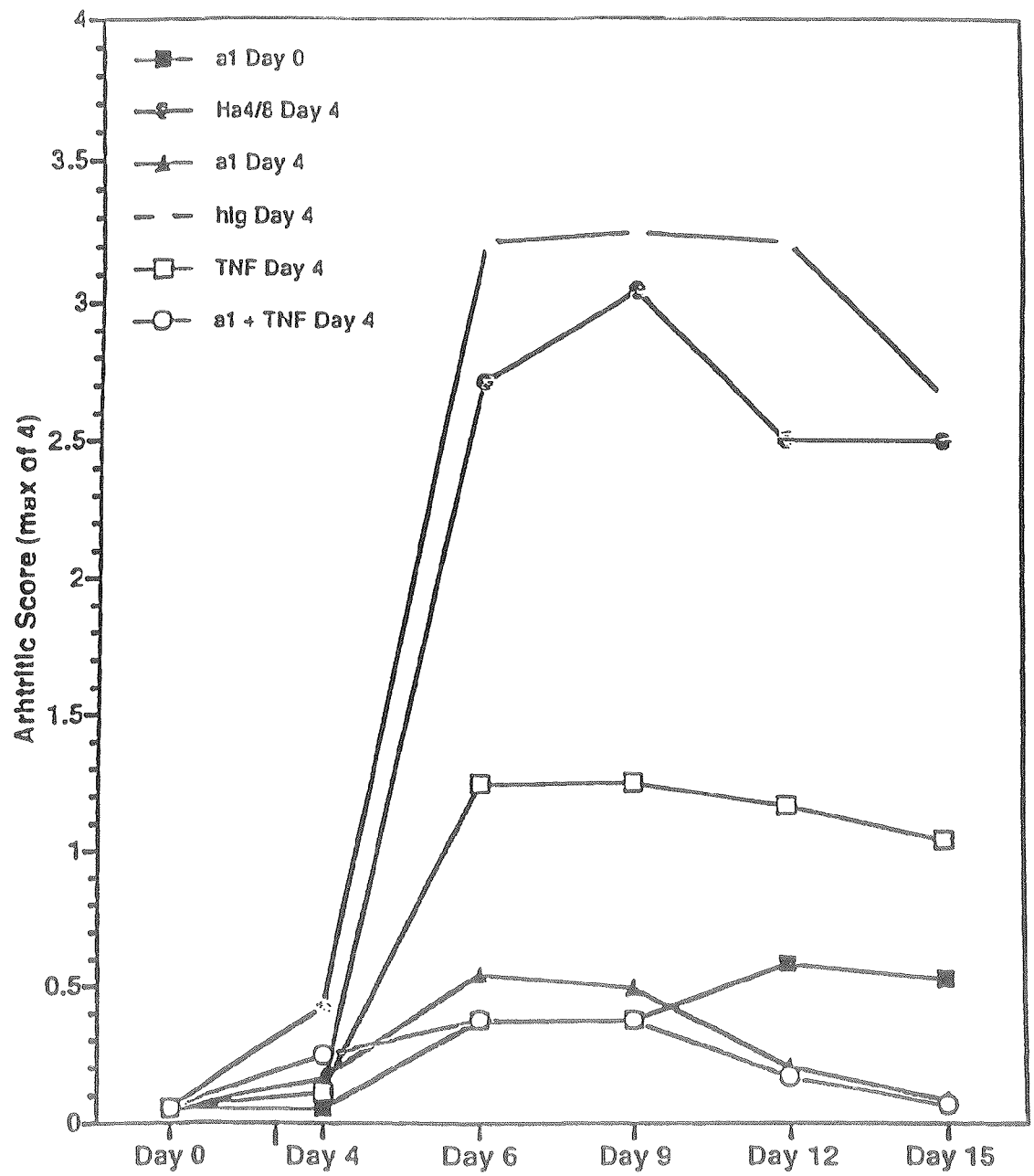
FIG. 10. Therapeutic treatment with anti-α1 mAb can decrease arthritic score. Wild-type Balb/c mice were treated with anti-collagen mAbs at day 0, followed by LPS on day 3.

Therapeutic treatment with anti-α1 mAb can decrease arthritic score. Given the effectiveness of anti-α1 mAb in preventing arthritis, we attempted to treat mice that are on their way to develop disease. Arthritis was induced in mice by injection of a cocktail of anti-collagen type II mAbs on day 0, followed by LPS administration on day 3. Mice were then treated with either anti-α1 mAb or a soluble TNF receptor Ig fusion protein starting on day 4. Progression of arthritis was completely blocked in mice receiving anti-α1 mAb starting at day 4, when compared to mice receiving control hamster mAb starting at day 4 (FIG. 10). The degree of inhibition seen with therapeutic administration of anti-α1 mAb was complete and was equal to that seen with preventative treatment of anti-α1 mAb (started at day 0) (FIG. 10). In comparison, treatment with TN receptor Ig fusion protein from day 4 onwards resulted in only a 60-70% inhibition in arthritic score when compared to control Ig fusion protein (FIG. 10). Combined treatment of anti-α1 mAb and TNF receptor Ig fusion together was effective at completely inhibiting arthritic score, which is not surprising given the complete effectiveness of anti-α1 mAb treatment alone in suppressing arthritis. In summary, these results indicate that therapeutic treatment with anti-α1 mAb is effective at inhibiting arthritic score, and compares favorably to therapeutic treatment with a TNF antagonist.

Example 14

Cloning and mutagenesis of the α1-I domain. Human and rat α1β1 integrin I domain sequences were amplified from full length cDNAs (Kem, et al., 1994, *J. Biol. Chem.* 269, 22811-22816; Ignatius et al., 1990, *J. Cell Biol.* 111, 709-720) by the polymerase chain reaction (PCR) (PCR CORE Kit; Boehringer Mannheim, GmbH Germany), using either human specific primers, 5'-CAGGATCCGTCAGCCCCA-CATTTCAA-3' [forward] (SEQ ED NO:7), and 5'-TCCTC-GAGGGCTTGCAGGGCAAATAT-3' [reverse] (SEQ ID NO:8), or rat specific primers, 5'-CAGGATCCGTCAGTC-CTACATTTCAA-3' [forward] (SEQ ID NO:9), and 5'-TC-CTCGAGCGCTTCCAAAGCGAATAT-3' [reverse] (SEQ ID NO:10).

The resulting PCR amplified products were purified, ligated into pGEX4t-i (Pharmacia), and transformed into competent DH5α cells (Life Technologies). Ampicillin resistant colonies were screened for the expression of the ~45 kDa glutathione S-transferase-I domain fusion protein. The sequences from inserts of plasmid DNA of clones that were selected for further characterization were confirmed by DNA sequencing.

A rat/human chimeric α1-I domain (RΔH) was generated (MORPH Mutagenesis kit; 5 Prime—3 prime), exchanging the rat residues G91, R92, Q93, and L96 (FIG. 11) for the corresponding human residues, V, Q, R, and R, respectively. Clones harboring the RΔH I domain were identified by the loss of a diagnostic Stu 1 restriction enzyme site, and the inserts confirmed by DNA sequencing. The amino acid sequence of the human α1-I domain is shown in FIG. 12.

Example 15

Generation of mAbs specific to the α1-I domain. Monoclonal antibodies have proved to be very useful probes in studying the relationship between structure and function of integrin subunits. For example, mAbs were used extensively to study regions of the β1 subunit associated with an activated conformation (Qu, A., and Leahy, D. J. (1996) *Structure* 4, 931-942). Thus, to identify potential probes for conformational changes of the α1-I domain, we generated a panel of mAbs to the human α1-I domain.

Generation of anti-α1 I domain Monoclonal Antibodies. Female Robertsonian mice (Jackson Labs) were immunized intraperitoneally (i.p.) with 25 μg of purified human α1β1 (Edwards et al., 1995, *J. Biol. Chem.* 270, 12635-12640; Gotwals et al., 1999, *Biochemistry* 38:8280-8) emulsified with complete Freund's adjuvant (LifeTechnologies). They were boosted three times i.p. with 25 μg of α1β1 emulsified with incomplete Freund's adjuvant (LifeTechnologies). The mouse with the highest anti-α1-I domain titer was boosted i.p. with 100 μg of α1β1 three days prior to fusion, and intravenously with 50 μg of α1β1 one day prior to fusion. Spleen cells were fused with FL653 myeloma cells at a 1:6 ratio and were plated at 100,000 and 33,000 per well into 96 well tissue culture plates.

Supernatants were assessed for binding to the α1β1 integrin by single color FACS. Prior to FACS analysis, supernatants were incubated with untransfected K562 cells to eliminate IgG that bound solely to the D subunit. Subsequently, 3-5×10⁴ K562 cells transfected with the α1 integrin subunit (K562-α1) suspended in FACS buffer (1% fetal calf serum (FCS) in PBS containing 0.5% $NaN_3$) were incubated with supernatant for 45 minutes at 4° C., washed and incubated with antis mouse IgG conjugated to phycoerythrin. After washing twice with FACS buffer, cells were analyzed in a Becton Dickinson Flow Cytometer.

Supernatants from the resulting hybridomas were screened for binding to the α1-I domain. Briefly, 50 μl of 30 μg/ml human α1-I-domain-(GST fusion in PBS was coated onto wells of a 96-well plate (Nunc) overnight at 4° C. The plates were washed with PBS, blocked with 1% BSA in PBS and the hybridoma supernatant was incubated with the I domain at room temperature for 1 hour. After extensive washing with PBS containing 0.03% Tween 20, alkaline phosphatase linked anti-mouse IgG (Jackson ImmunoResearch) was added for an additional hour. After a final wash, 1 mg/ml p-nitrophenylphosphate (pNPP) in 0.1 M glycine, 1 mM $ZnCl_2$, and 1 mM $MgCl_2$ was added for 30 minutes at room temperature, and the plates were read at O.D. 405.

Selected supernatants were tested for their ability to inhibit K562-α1 dependent adhesion to Collagen IV. K562-α1 cells were labeled with 2 mM 2',7' (bis-2-carboxyethyl-5 and 6) carboxyfluorescein penta acetoxymethylester (BCECF; Molecular Probes) in DMEM containing 0.25% BSA at 37° C. for 30 minutes. Labeled cells were washed with binding buffer (10 mM Hepes, pH 7.4; 0.9% NaCl; and 2% glucose) and resuspended in binding buffer plus 5 mM $MgCl_2$ at a final concentration of $1 \times 10^6$ cells/mL. 50 μl of supernatant was incubated with an equal volume of $2 \times 10^5$ K562-α1 cells in wells of a 96 well plate. The plate was then centrifuged and the supernatants removed. Cells were resuspended in binding buffer and transferred to wells of a collagen-coated plate and incubated for 1 hour at 37° C. Following incubation, the non-adherent cells were removed by washing three times with binding buffer. Attached cells were analyzed on a Cytofluor (Millipore).

We initially identified 19 hybridomas, the supernatants of which bound to human leukemia K562 cells expressing the α1β1 integrin (K562-α1) and to the α1-I domain. The immunoglobulins were purified from each of these hybridomas and tested for the ability to block either K562-α1 or α1-I domain binding to collagen IV. The mAbs fall into two classes: those that block and those that do not block α1β1 function. For example, while the mAbs produced by clones AEF3, BGC5, AQC2 and AJH10 bind the α1-I domain (FIG. 13A, data not shown for BGC5), only mAbs AJH10 and AQC2 inhibit α1-I domain-dependent (FIG. 13B; FIG. 16B) or K562-α1 (FIG. 13C; FIG. 16C) adhesion to collagen IV.

Sequencing of the Complementarity Determining Regions. To establish the clonal origin of this panel of mAbs, we amplified by PCR and sequenced the CDRs from 12 of the 19 antibodies (data not shown).

2 μg of mRNA, isolated from $10^7$ hybridomas (FastTrack mRNA isolation kit, Invitrogen), was reverse transcribed (Ready-To-Go You Prime First Strand Kit, Pharmacia Biotech) using 25 pM each of the following primers: heavy chain VH1FOR-2 (Michishita et al., 1993, *Cell* 72:857-867); light chain, VK4FOR, which defines four separate oligos (Kern et al., 1994, *J. Biol. Chem.* 269:22811-22816). For each hybridoma, heavy and light chains were amplified in four separate PCR reactions using various combination of the following oligos: 1) Heavy chain: VH1FR1K (Kamata et al., 1995, *J. of Biol. Chem.* 270:12531-12535), VH1BACK, VH1BACK (Baldwin et al. (1998) *Structure* 6, 923-935), $V_H$fr1a, $V_H$fr1b, $V_H$fr1e, $V_H$fr1f, $V_H$fr1g (Ignatius et al. (1990) *J. Cell Biol.* 111, 709-720), or VH1FOR-2 (Michishita, M., Videm, V., and Arnaout, M. A. (1993) *Cell* 72, 857-867); 2) Light chain: VK1BACK (Baldwin et al. (1998) *Structure* 6, 923-935), VK4FOR, VK2BACK oligos (Kern et al. (1994) *J. Biol. Chem.* 269, 22811-22816), or $V_K$fr1a, $V_H$fr1c, $V_H$fr1e, $V_H$fr1f (Ignatius et al. (1990) *J. Cell Biol.* 111, 709-720). Products were amplified (5 min at 95° C., 50 cycles of 1 min at 94° C., 2 min at 55° C., 2 min at 72° C., and a final cycle of 10 min at 72° C.), gel purified (QIAquick, Qiagen), and sequenced directly using various of the listed oligos on an ABI 377 Sequencer.

Sequences from clones producing function-blocking mAbs were nearly identical across all the complementarity-determining regions (CDRs) and the intervening framework regions suggesting that these hybridomas are clonally related.

Example 16

Immunoblotting and FACS Analysis. Sequences of the variable regions of the non-blocking antibodies were markedly different from the clonally related family of sequences found for the blocking antibodies. As the blocking antibodies appear to originate from a single clone, we chose two (AJH10 and AQC2) to characterize further.

Immunoblotting The smooth muscle cell layer dissected from sheep aorta, and K562-α1 cells were extracted with 1% Triton X-100 in 50 mM Hepes, pH 7.5, 150 mM NaCl, 10 mM phenylmethylsulfonyl flouride (PMSF), 20 μg/ml aprotinin, 10 μg/ml leupeptin, 10 mM ethylenediaminetetraacetic acid (EDTA). Samples were subjected to 4-20% gradient SDS-PAGE, and electroblotted onto nitrocellulose membranes. The blots were blocked with 5% dry milk in TBS; washed in TBS containing 0.03% Tween-20, and incubated with antibodies in blocking buffer containing 0.05% $NaN_3$ for 2 hours. Blots were then washed as before, incubated with horseradish peroxidase conjugated anti-mouse IgG for one hour, washed again and then treated with ECL reagent (Amersham). Blots were then exposed to film (Kodak) for 30 to 60 seconds, and developed.

Immunoblotting and FACS analysis (FIG. 14) demonstrate that AJH10 reacts with human, rabbit, and sheep, but not rat α1β1 integrin suggesting that the blocking mAbs bind to an evolutionarily conserved, linear epitope. The non-blocking mAbs were neither efficient at immunoblotting nor did they react with species other than human.

Example 17

Binding of the α1-I Domain to Collagen is Divalent Cation-dependent

A. Purification of the α1-I Domains.

The α1-I domains were expressed in *E. coli* as GST (glutathione-S-transferase) fusion proteins containing a thrombin cleavage site at the junction of the sequences. The clarified supernatant from cells lysed in PBS was loaded onto a glutathione Sepharose 4B column (Pharmacia) which was washed extensively with PBS. The α1-I domain-GST fusion protein was eluted with 50 mM Tris-HCl, pH 8.0, 5 mM glutathione (reduced). For denaturation studies, the I domain was cleaved with thrombin in 50 mM Tris, pH 7.5, and purified from the GST fusion partner. DTT was added to 2 mM and the sample was loaded on a glutathione Sepharose 4B column. The flow-through and wash fractions were pooled and loaded onto a Q Sepharose FF column (Pharmacia). The α1-I domain was eluted with 50 mM Tris HCl, pH 7.5, 10 mM 2-mercaptoethanol, 75 mM NaCl. The purified I domain displayed its predicted mass (Lee et al. (1995) *Structure* 3, 1333-1340, 871 Da) by electrospray ionization-mass spectrometry (ESI-MS), migrated as a single band by SDS-PAGE, and the protein eluted as a single peak of appropriate size by size exclusion chromotography on a Superose 6 FPLC column (Pharmacia).

B. Functional Analysis 96 well plates were coated overnight at 4° C. with 1 μg/ml collagen IV (Sigma) or collagen Type I (Collaborative Biomedical), washed with Triton buffer (0.1% Triton X-100; 1 mM $MnCl_2$; 25 mM Tris-HCl; 150 mM NaCl), and blocked with 3% bovine serum albumin (BSA) in 25 mM Tris-HCl; 150 mM NaCl (TBS). Serial dilutions of the α1-I domain-GST fusion protein in TBS containing 1 mM $MnCl_2$ and 3% BSA were incubated on the coated plates at room temperature for 1 hour, and washed in Triton buffer. Bound α1-I domain was detected with serial additions of 10 μg/ml biotinylated anti-GST polyclonal antibody (Pharmacia); ExtrAvidin-horseradish peroxidase (Sigma) diluted 1:3000 in TBS containing 1 mM $MnCl_2$ and 3% BSA, and 1-Step ABTS (2,2'-Azine-di[3-ethylbenzthiazoline sulfonate]; Pierce). Plates were read at O.D. 405 on a microplate reader (Molecular Devices).

Results.

Figure 15C:
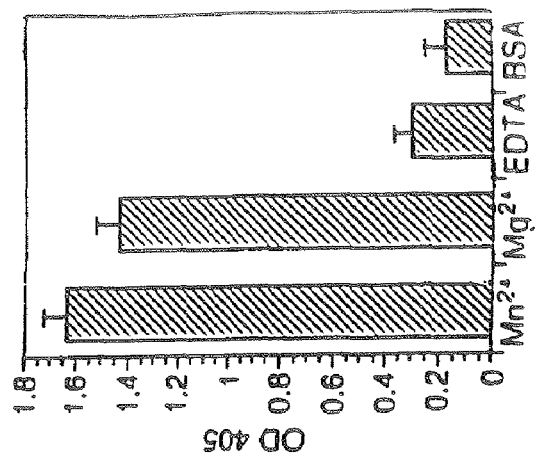
Figure 15B:
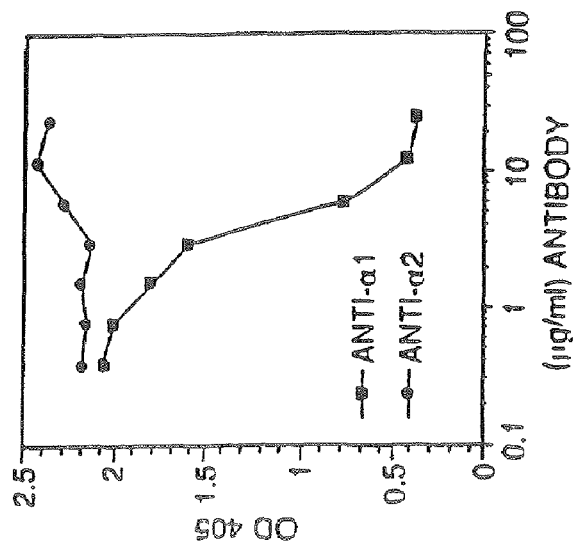
Figure 15A:
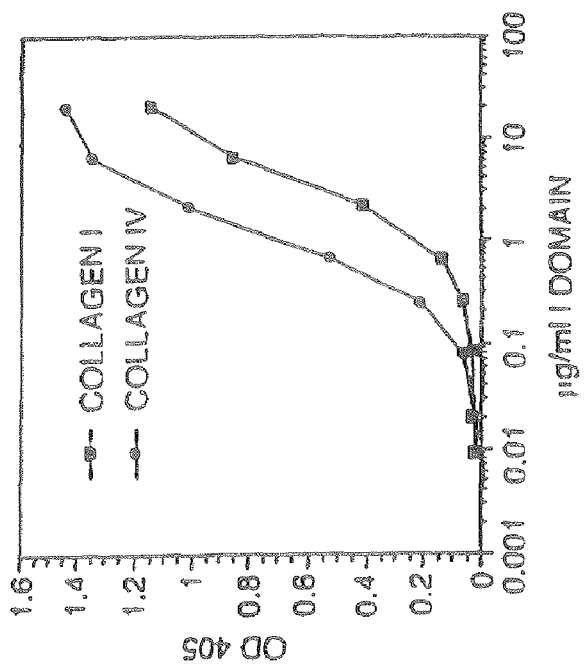

The human and rat (95% identity to human) α1-I domains were expressed in E. coli as GST-fusion proteins and purified over glutathione sepharose. Both proteins were examined for binding to collagen I and IV using a variation of an ELISA-based assay previously described (Qu, A., and Leahy, D. J. (1995) Proc. Natl. Acad. Sci. USA 92, 10277-10281). The human α1-I domain binds collagen IV with better efficiency than collagen I (FIG. 15A). An antibody specific to the α1-I domain, but not an antibody specific to the α2-I domain (FIG. 15B) abrogated binding to both ligands (data for collagen I is not shown). Both $Mn^{2+}$ and $Mg^{2+}$ stimulated binding, and EDTA reduced binding to background levels (FIG. 15C). No measurable differences in ligand binding were detected between the human and rat α1-I domains suggesting that the sequence differences between species are not functionally relevant (data not shown). Thus, the α1-I domain, specifically, require cation for efficient ligand binding.

Example 18

Figures 11A, 11B:
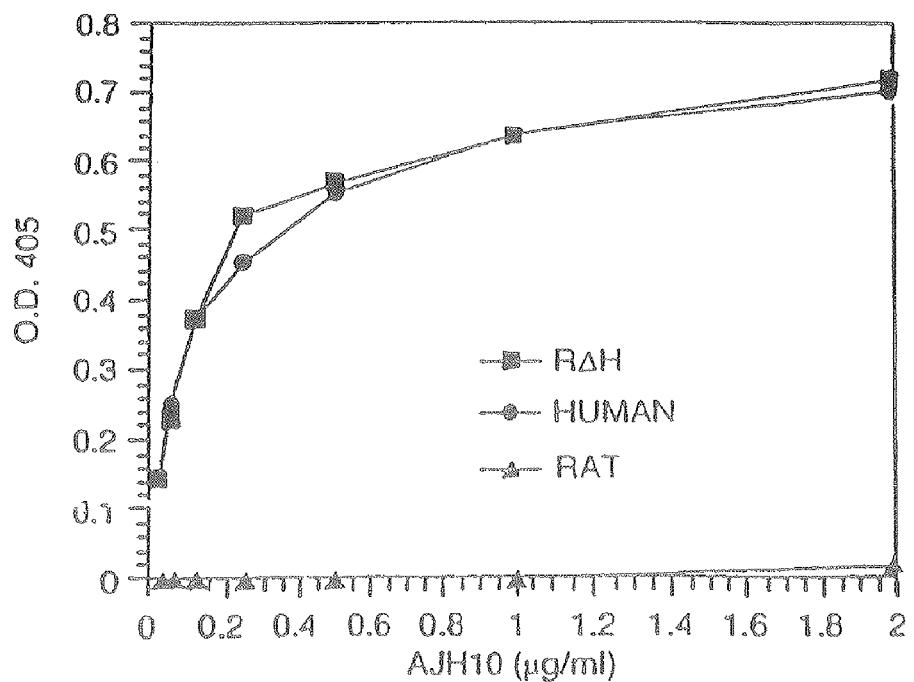

A Cation-Dependent Epitope Resides near the MIDAS motif. We exploited the observation that AJH10 recognizes the human, but not the rat α1-I domain sequences to map the epitope for the α1β1 function-blocking mAbs. The human and rat sequences differ by only 12 amino acids, 4 of which lie in a stretch of 6 amino acids (aa 92-97, FIG. 11A) adjacent to the critical threonine (FIG. 11A, aa 98) within the MIDAS motif. To test the hypothesis that the 6 amino acid residues, Val-Gln-Arg-Gly-Gly-Arg (residues 91-96 of SEQ ID NO:64), comprise the epitope for the blocking mAbs, we constructed a chimeric I domain (RΔH), exchanging the rat residues G91, R92, Q93, and L96 for the corresponding human residues, V, Q, R, and R, respectively. AJH10, along with all the function-blocking mAbs, recognizes the chimeric I domain (RΔH; FIG. 11B).

To orient these residues with respect to the MIDAS domain in the tertiary structure of the α1-I domain, we modeled the α1-I domain using the coordinates of the crystal structure of the α2 I domain.

A homology model of the human α2 I-domain was built using the X ray crystal structure of the human α2 I-domain (Ward et al. (1989) Nature 341, 544-546). The model was built using the homology modeling module of Insight II (version 2.3.5; Biosym Technologies). The program CHARMM (Clackson et al. (1991) Nature 352, 624-628) was used with the all-hydrogen parameter set 22 with a distant dependent dielectric constant of two times the atom separation distance. We first did 1000 steps of steepest descent minimization with mass-weighted harmonic positional constraints of 1 kcal/(mol Å$^2$) on all atoms of the α1-I domain. This minimization was followed by another 1000 steps of steepest descent and 5000 steps of Adopted-Basis Newton Raphson with constraints of 0.1 kcal/(mol Å$^2$) on the C-α atoms of the α1-I domain to avoid significant deviations from the α2-I domain X-ray crystal structure.

The α1β1 and α2β1 integrin sequences exhibit 51% identity with no insertions or deletions, suggesting that the overall structure of the two I domains will be similar. The metal coordination site is predicted to be the same in the α1-I domain as in the α2-I domain, and the residues that comprise the epitope for the blocking mAbs lie on a loop between helix α3 and helix α4 which contains the threonine within the MIDAS motif critical for cation binding. The α1-I domain model predicts that the amide nitrogen of Q92 (FIG. 11A) hydrogen bonds with the carbonyl group of I33, the residue adjacent to S32. Thus, the loop that contains the epitope may play a functional role in stabilizing the MIDAS region.

Example 19

Monoclonal antibody AQC2 (i.e., mAQC2; "m" for murine) (Example 15, supra) is an $IgG_1$, kappa antibody. To identify the nucleotide sequences encoding the heavy and light chains of this antibody, total cellular RNA from AQC2 murine hybridoma cells was obtained by using a QIAGEN RNEASY midi kit in accordance with the manufacturer's instructions. Then cDNAs encoding the variable regions of the heavy and light chains were cloned by RT-PCR from total cellular RNA using a GIBCO BRL SUPERSCRIPT Preamplification System for First Strand cDNA Synthesis following the manufacturer's recommended protocol. Random hexamers were used for priming.

The heavy chain variable domain of mAQC2 was amplified by PCR from the first strand cDNA with the primers: 5' TGA GGA GAC GGT GAC CGT GGC CCT TGG CCC C 3' (SEQ ID NO:11) and 5' AGG TSM ARC TGC AGS AGT CWG G 3' (S=C/G, M=A/C, R=A/G, and W=A/T) (SEQ ID NO:12). The PCR was subjected to 30 cycles using Clontech's Advantage Taq polymerase: denature 30 sec at 94° C., anneal 1 min at 50° C., and elongate 1.5 min at 68° C. The mAQC2 light chain with its signal sequence was amplified by PCR using the primers: 5' ACT AGT CGA CAT GGA TTT WCA GGT GCA GAT TWT CAG CTT C 3' (W=A/T) (SEQ ID NO:13) and 5' ACT GGA TGG TGG GAA GAT GGA 3' (SEQ ID NO:14). The PCR was subjected to 30 cycles using Stratagene's cloned Pfu polymerase: denature 1 min at 94° C., anneal 1 min at 50° C., and elongate 2 min at 72° C. The PCR products for the heavy and light chains were gel-purified using a QIAGEN QIAQUICK gel extraction kit following the manufacturer's recommended protocol.

Purified heavy chain product was subcloned into Invitrogen's pCR2.1-TOPO TA vector using its TOPO TA cloning kit. Purified light chain was subcloned into Invitrogen's pCR-bluntIITOPO vector using its Zero blunt TOPO cloning kit following the manufacturer's recommended protocol. Inserts from multiple independent subclones were sequenced. With the exception of degenerate positions within the PCR primers, the insert sequences of the independent subclones were identical.

The polypeptide sequences of mAQC2 were deduced from their coding sequences. The N-terminal amino acid sequence for the mature light chain predicted by the cDNA sequence from the PCR product amplified with a signal sequence exactly matched the N-terminal sequence of purified mAQC2 light chain derived from Edman degradation (DVKVVESGG; SEQ ID NO:15). BLAST analyses of the variable domain sequences confirmed their immunoglobulin identity.

The polypeptide sequence of the light chain variable domain of mAQC2 is shown below:

```
                                              (SEQ ID NO: 1)
  1  QIVLTQFPAL MSASPGEKVT MTCSASSSVN HMFWYQQKPK

41  SSPKPWIYLT SNLASGVPAR FSGSGSGTSY SLTISSMEAE

81  DAATYYCQQW SGNPWTFGGG TKLEIK 106
```

The CDRs are shown in boldface. The CDRs are defined according to Kabat et al., Sequences of Proteins of Immunological Interest, 5th Edition, The United States Department of Health and Human Services, The United States Government Printing Office, 1991. Using the Kabat numbering system, SEQ ID NO:1 is represented as follows, where a dash denotes the absence of an amino acid:

```
  1  QIVLTQFPAL MSASPGEKVT MTCSASS-SV NHMFWYQQKP

41  KSSPKPWIYL TSNLASGVPA RFSGSGSGTS YSLTISSMEA

81  EDAATYYCQQ WSGNPWTFGG GTKLEIK 107
```

The polypeptide sequence of the heavy chain variable domain of mAQC2 is:

```
                                            (SEQ ID NO: 2)
  1  DVKVVESGGG LVKPGGSLKL ACAASGFSFS RYTMSWVRQI

41  PEKRLEWVAT ISGGGHTYYL DSVKGRFTIS RDNAKNTLYL

81  QMSSLRSEDT AMYYCTRGFG DGGYFDVWGQ GTTVTVSS
```

The CDRs are shown in boldface. Using the Kabat numbering system, SEQ ID NO:2 is represented as follows, where positions numbers are consecutive numerals unless otherwise indicated:

```
   1    DVKVVESGGG LVKPGGSLKL ACAASGFSFS RYTMSWVRQI

41    PEKRLEWVAT ISGGGHTYYL DSVKGRFTIS RDNAKNTLYL

81    QM 82a-c  SSL

83    RSEDTAMY YCTRGFGDGG 100a-b  YF

101    DVWGQGTTVT VSS 113
```

As used herein, residue position numbers of variable domains are designated in accordance with the Kabat numbering system unless otherwise indicated.

Example 20

This example describes the generation of a murine-human chimeric antibody, chAQC2.

The cDNAs encoding the variable regions of the mAQC2 heavy and light chains were used to construct chAQC2 expression vectors, in which the mAQC2 variable regions were linked to human IgG$_1$ and kappa constant regions.

The heavy chain chimera was constructed as follows. A 0.33 kb PstI-BstEII fragment from the mAQC2 heavy chain plasmid pAND083 was subcloned into the phosphatased 2.82 kb PstI-BstEU vector fragment from the 5a8 heavy chain plasmid pLCB7, so as to add a murine heavy chain signal-encoding sequence and a murine splice donor site to the cDNA of the mAQC2 heavy chain variable region. 5a8 is a molecularly cloned CD4-specific mAb (see, e.g., Boon et al., 2002, *Toxicology* 172:191-203). In the mature heavy chain encoded by the resultant plasmid (pAND092), the N-terminus differed by five residues from the N-terminus (DVKVVE; SEQ ID NO:16) of the cognate mAQC2 heavy chain.

To correct the heavy chain N-terminus, pAND092 was subjected to unique site elimination (USE) mutagenesis using an USE mutagenesis kit (Amersham Pharmacia Biotech) following the manufacturer's recommended protocol. The Q1D, Q3K, L4V, Q5V, Q6E substitutions were encoded by the mutagenic primer 5' GCA CCA GGT GCC CAC TCC GAC GTC AAG GTG GTG GAG TCA GGG GGA GGC TTA GTG 3' (SEQ ID NO:17). Mutated plasmid clones were identified by their new AatII and HinfI sites and eliminated PstI site. The heavy chain coding sequence was then confirmed by DNA sequencing. The correctly mutated plasmid was called pAND094. The 0.43 kb NotI-HindIII fragment from pAND094 and the 1.21 kb HindIII-NotI fragment from the plasmid pEAG964 (containing a coding sequence for a human IgG$_1$ constant region) were subcloned into the NotI site of pCH269, a plasmid derived from the pCEP4 EBV expression vector (Invitrogen). The resultant plasmid was named pAND099.

The light chain chimera was generated as follows. A 0.46 kb EcoRI fragment from the mAQC2 light chain variable domain plasmid pAND081 was subcloned into the phosphatased 2.7 kb vector fragment of the pUC-derived pNN09 cloning vector, to add a 5' NotI site. The resulting plasmid, pAND091, was subjected to mutagenesis using the Amersham USE kit (supra) to introduce a BglII site at the 3' end of the coding sequence. The mutagenic primer had the sequence 5' GGA GGC ACC AAG CTG GAG ATC TAA CGG GCT GAT GCT GC 3' (SEQ TD NO: 18). The correctly mutated plasmid was identified by its BglII and BstYI site changes. The light chain coding sequence in the resultant plasmid pAND093 was confirmed by DNA sequencing. Then the 0.44 kb NotI-BglII light chain variable domain fragment from pAND093 and the 0.68 kb BclI-NotI fragment from the plasmid pEAG963 (containing a coding sequence for a human kappa light chain constant domain) were subcloned into the NotI site of pCH269 (supra), producing plasmid pAND102. To create an unblocked kappa light chain (Q1E), pAND093 was subjected to USE mutagenesis with the mutagenic primer 5' CAT MT GTC CAG GGG AGA AAT TGT TCT CAC CCA G 3' (SEQ ID NO:19), to introduce an XmnI site. The mutated plasmid was identified by screening for an XmnI site change. The light chain sequence in the resultant plasmid pAND097 was confirmed by DNA sequencing. The 0.44 kb NotI-BglII light chain variable domain fragment from pAND097 and the 0.68 kb BclI-NotI fragment from the plasmid pEAG963 (containing a human kappa light chain constant domain) were subcloned into the NotI site of pCH269, producing plasmid pAND098.

To generate chAQC2 antibodies, expression vectors (chAQC2 heavy chain vector pAND099+chAQC2 light chain vector pAND102, and chAQC2 heavy chain vector pAND099+chAQC2 unblocked light chain vector pAND098) were co-transfected into 293-EBNA cells. The transfectants were tested for antibody secretion and specificity. The controls were cells transfected with the corresponding vectors without an insert or with DNA constructs encoding ch5c8 (a molecularly cloned CD154-specific mAb described in, e.g., Elster et al., 2001, *Transplantation* 72:1473-1478) or chCBE11 (a molecularly cloned LTβR-specific mAb described in, e.g., Browning et al., 1996, *J. Biol. Chem.* 271:24934-24938).

Then transfectants with the desired antibody secretion were lysed, and protein A immunoprecipitation was performed on the lysates and conditioned medium. Western blot analysis of the precipitates performed with anti-human heavy and light chain antibodies indicated that chAQC2-transfected cells synthesized and efficiently secreted heavy and light chains at levels similar to ch5c8-transfected and chCBE11-transfected cells. Further, huVLA-1-expressing K562α1 cells were stained with the conditioned medium from the transfected cells, and FACS analysis was performed on the stained cells. The results indicated that the chAQC2 antibody produced staining patterns similar to those of mAQC2, while conditioned media from mock-transfected and ch5c8-transfected cells failed to stain K562α1 cells. Chimeric AQC2 produced from scaled-up transient transfection was purified and shown to bind to VLA-1 by FACS titration. Chimeric AQC2 with either a wildtype or a genetically unblocked light chain bound to VLA-1. See also FIGS. 16A-D (discussed below).

Example 21

This example describes a method of humanizing the mAQC2 monoclonal antibody.

Analysis of the mAQC2 variable domains. The variable domains in the light and heavy chains of mAQC2 were compared with the consensus sequences for mouse and human subgroups (Kabat et al, supra) using the software program FASTA. The light chain variable domain was found to be a member of mouse subgroup VI with 89% identity in a 109 amino acid overlap. This domain also corresponded to human subgroup I with 72% identity in a 113 amino acid overlap. The heavy chain variable domain was found to be a member of mouse subgroup IIId with 86% identity in a 129 amino acid overlap. This heavy chain variable domain also corresponded to human subgroup III with 79% identity in a 130 amino acid overlap.

The CDRs were categorized into canonical classes according to Chothia et al., *Nature* 342, pp. 877-883 (1989). The key residues defining each canonical class determine to a large extent the structural conformation of the CDR loop, and thus should be retained in the reshaped antibody. The L1 loop of mAQC2 fell into canonical class 1 (10 residue loop), L2 into class 1 (7 residue loop) and L3 into class 1 (9 residue loop). The H1 loop fell into class 1 (5 residue loop) and the H2 loop into class 1 (16 residue loop) residues. The H3 loop did not seem to belong to any canonical class. The canonical residues important for these classes were all included in the humanized antibodies.

Unusual framework residues in mAQC2 were determined by analyzing all mouse and human variable chain sequences in the September 1999 version of the Kabat database. It was believed that mAQC2-specific differences might indicate somatic mutations that enhance binding affinity if these differences were close to the binding site. Unusual mAQC2 residues further away from the binding site and unusual human framework residues were removed in case they would create immunogenic epitopes in the humanized antibody. Unusual framework residues found in mAQC2 were 7(F), 10(L), and 41(K) in the light chain; and 4(V), 21(A), and 40(I) in the heavy chain. None of these unusual mouse framework residues were retained the humanized antibodies.

Modeling the structure of the variable regions. The light and heavy chains of mAQC2 were aligned against a nonredundant database to determine which structural frames to use to construct three-dimensional models of the mAQC2 light and heavy chains. Using FASTA, the light chain was found to have 82% sequence identity to monoclonal murine antibody ab57 (1CLOL), whereas the heavy chain was found to have 76% sequence identity to murine 6d9 Fab fragment (1HYY). Using the molecular modeling software package SYBYL (Tripos Inc.), the approximate three dimensional structures of the mAQC2 light and heavy chains were built using the light chain of ab57 and the heavy chain of 6d9, respectively. The structural integrity of the models was assessed at the console and was found to be reasonable.

Design of the reshaped variable regions. Two approaches were used to choose human acceptor frameworks to "accept" mAQC2's CDRs. The first approach was by homology matching and the other by using consensus human Ig sequences. Under the homology approach, the Kabat database, the nonredundant database from NCBI, ENTREZ (The National Institutes of Health), and the Incyte database were searched using the software programs FASTA and BLAST. The choice of human acceptor frameworks was made based on sequence identity between mAQC2 frameworks and human frameworks (excluding frameworks from previously humanized antibodies) and the source of the antibody.

The frameworks from an immunoglobulin variable region gene having a GENBANK accession number of gi:587330 (human kappa subgroup I Vκ-1c147) were eventually chosen for the light chain of the humanized antibody (Welschof et al., *J. Immunol. Meth.* 179:203-14 (1995)). The frameworks from Amulc11 (Kabat ED 044469; human subgroup III) were chosen for the heavy chain of the humanized antibody (Huang et al., *J. Immunol.* 151:5290-300 (1993)).

Back mutations of the human frameworks. Strategies for determining which back mutations to make are available on the Humanization bY Design web sites under mirrored urls on the worldwide web at mathbio.nimr.mrc.ac.uk/jsaldan and cryst.bbk.ac.uk/~ubcg07s. Previous experiments have shown that it is important to retain canonical residues, interface packing residues and unusual murine residues that are close to the binding site. In addition, residues in the "Vernier Zone," which forms a platform on which the CDRs rest (Foote et al., *J. Mol. Biol.* 224, p. 487 (1992)) and those close to CDR H3 should be considered.

Four reshaped versions were designed for each of the variable light and heavy chains, as shown in Table 1. Two of the four versions for each chain were designed by homology matching (designated huAQC2-h1 and -h2) and the other two versions by consensus matching (huAQC2-c1 and c2). It should be noted that the sequences for huAQC-h1 heavy chain and huAQC-c1 heavy chain are identical.

TABLE 1

Sequences of mAQC2, huAQC2, and human frameworks

LIGHT CHAIN:

|  | FR1 |  |
|---|---|---|
| Vk-1c147 | D--M--S-SSL---V-DR--I--* | |
| hUAQC2-h2 | ------S-SSL---V-DR--I-- | |
| huAQC2-h1 | ------S-SSL---V-DR--I-- | |
| mAQC2 | QIVLTQFPALMSASPGEKVTMTC | |
| huAQC2-c1 | --Q---S-SSL---V-DR--I-- | |
| huAQC2-c2 | --Q---S-SSL---V-DR--I-- | |

|  | CDR1 | FR2 |
|---|---|---|
| Vk-1c147 | R--Q-ISYLN | ------GKA--LL-- |
| huAQC2-h2 | ---------- | ------GKA--LL-- |
| huAQC2-h1 | ---------- | ------GKA------ |
| mAQC2 | SASSSVNHMF | WYQQKPKSSPKPWIY |
| huAQC2-c1 | ---------- | ------GKA------ |
| huAQC2-c2 | ---------- | ------GKA--LL-- |

TABLE 1-continued

Sequences of mAQC2, huAQC2, and human frameworks

|  | CDR2 | FR3 |  |
|---|---|---|---|
| Vk-1c147 | AA-S-Q- | ---S---------DFT-----LQP--F----- |  |
| huAQC2-h2 | ------- | ---S---------D-T-----LQP--F----- |  |
| huAQC2-h1 | ------- | ---S---------D-T-----LQP--F----- |  |
| mAQC2 | LTSNLAS | GVPARFSGSGSGTSYSLTISSMEAEDAATYYC |  |
| huAQC2-c1 | ------- | ---S---------D-T-----LQP--F----- |  |
| hUAQC2-c2 | ------- | ---S---------D-T-----LQP--F----- |  |

|  | CDR3 | FR4 | Framework changes |
|---|---|---|---|
| Vk-1c147 | --SYST-L- | ------V--- | 25 |
| huAQC2-h2 | --------- | ------V--- | 21 |
| huAQC2-h1 | --------- | ------V--- | 19 |
| mAQC2 | QQWSGNPWT | FGGGTKLEIK** | 0 |
| huAQC2-c1 | --------- | --Q---V--- | 21 |
| huAQC2-c2 | --------- | --Q---V--- | 23 |

SEQ ID NOs: 65, 51, 49, 1, 66, and 54, respectively, in order of appearance.

HEAVY CHAIN:

|  | FR1 | CDR1 |
|---|---|---|
| AMU1C11 | E-QL-------IQ-----R-S------TV- | SNY-- |
| huAQC2-h2 | E-QL-------IQ-----R-S------T-- | ----- |
| huAQC2-h1 | --QL-------Q-----R-S--------- | ----- |
| mAQC2 | DVKVVESGGGLVKPGGSLKLACAASGFSFS | RYTMS |
| huAQC2-c1 | E-QL-------Q-----R-S------T-- | ----- |
| huAQC2-c2 | E-QL-------Q-----R-S------T-- | ----- |

|  | FR2 | CDR2 |
|---|---|---|
| AMU1C11 | ----A-G-G----S | V-YS--S---A----- |
| huAQC2-h2 | ----A-G-G----- | ---------------- |
| hUAQC2-h1 | ----A-G-G----- | ---------------- |
| mAQC2 | WVRQIPEKRLEWVA | TISGGGHTYYLDSVKG |
| huAQC2-c1 | ----A-G-G----- | ---------------- |
| huAQC2-c2 | ----A-G-G----- | ---------------- |

|  | FR3 | CDR3 |
|---|---|---|
| AMU1C11 | --------S---------N---A----V---AS | IRFLEWS--Y |
| huAQC2-h2 | --------S---------N---A----V----- | ---------- |
| hUAQC2-h1 | --------S---------N---A----V----- | ---------- |
| mAQC2 | RFTISRDNAKNTLYLQMSSLRSEDTAMYYCTR | GFGDGGYFDV |
| huAQC2-c1 | --------S---------N---A----V----- | ---------- |
| huAQC2-c2 | --------S---------N---A----V----- | ---------- |

|  | FR4 | Framework changes |
|---|---|---|
| AMU1C11 | -----L----- | 20 |
| huAQC2-h2 | -----L----- | 16 |
| huAQC2-h1 | -----L----- | 13 |
| mAQC2 | WGQGTTVTVSS*** | 0 |
| huAQC2-c1 | -----L----- | 13 |
| huAQC2-c2 | -----L----- | 15 |

*Dashes indicate identity with the mAQC2 amino acid sequence.
**Part of SEQ ID NO: 1.
***Part of SEQ ID NO: 2.
SEQ ID NOs: 67, 44, 42, 2, 42 and 68, respectively, in order of appearance.

Some of the back mutations are discussed below.

(1) Light Chain:
1 D->Q This mutation was made in all versions since previous reshaping experiments (e.g. Kolbinger et al, Protein Eng. 6, p. 971 (1993)) suggested its importance for antigen binding.
4 M->L This is a vernier residue and was retained in all versions,
46 L->P This residue is both an interfacial and vernier residue and was retained only in h1 and c1.
47 L->W This is a vernier residue and was retained only in h1 and c1.
71 F->Y This residue is in an important canonical position and was retained in all versions.

(2) Heavy Chain:
1 E->D This back mutation was made in h1 (i.e., c1) only.
12 I->V The residue I is unusual in human and was retained in the h2 only.
28 T->S This is a vernier residue and was retained in h1 only.
29 V->F This is a canonical residue and was retained in all versions.
49 S->A This is a vernier residue and was retained in all versions.
93 A->T This is a vernier residue and interfacial and was retained in all versions.
94 S->R This is a canonical residue and was retained in both versions.

The huAQC2 variable regions were made by USE mutagenesis as described above, using the chAQC2 variable domain plasmids as starting templates. The human acceptor framework ("FR") cDNA sequences were Kabat #Z37334 for the light chain and Kabat #U00490 for the heavy chain. To facilitate identification of mutated plasmids, silent mutations were introduced to change restriction sites. Mutated plasmids were identified by the restriction site changes. The variable region cDNA sequences in the resultant plasmids were confirmed by DNA sequencing.

The h1 and c1 versions of heavy chain (which were identical) were made by using plasmid pAND094 as template. The mutagenic primers were: FR1 primer 5'GGT GCC CAC TCC GAC GTC CAG CTG GTC GAG TCA GGG GGA GGC TTA GTC CAC CCT GGA GGG TCC CTG AGA CTC TCC TGT GCA GCC TCT GGA TTC 3' (SEQ ID NO:20), which introduced TaqI and PvuII sites, and eliminated a DdeI site; FR2 primer 5' ATG TCT TGG GTT CGC CAG GCT CCG GGG AAG GGG CTG GAG TGG GTC GCA ACC 3' (SEQ ID NO:21), which introduced a NciI site, and eliminated BspEI and EarI sites; FR3 primer 5' TTC ACC ATC TCC AGA GAC AAT TCC AAG AAC ACC CTG TAC CTG CAG ATG AAC AGT CTG AGG GCC GAG GAC ACA GCC GTG TAT TAC TGT ACA AGA 3' (SEQ ID NO:22), which introduced PstI and DdeI sites; and FR4 primer 5' TGG GGC CAA GGT ACC CTG GTC ACC GTC TCC TCA GGT GAG 3' (SEQ ID NO:23), which introduced KpnI and Eco0109I sites. The resultant h1 (i.e., c1) heavy chain plasmid was designated pAND104.

The c2 version of heavy chain were made by using pAND104 as template with the following mutagenic primers: FR1 primer 5' TCC TGT GCA GCC TCT GGA TTC ACC TTC AGT AGG TAT ACT ATG TCT TGG GTT 3' (SEQ ID NO:24), which introduced an AccI site; and FR1 primer 5' GCA CCA GGT GCG CAC TCC GAG GTC CAG CTG GTC GAG TCA 3' (SEQ ID NO:25), which introduced an FspI site and eliminated an AatII site. The resultant c2 heavy chain plasmid was designated pAND115.

The h2 version of heavy chain were made by using pAND115 as template with the following primer: FR1 primer 5' GAG TCA GGG GGA GGC TTA ATC CAG CCT GGA GGG TCC CTG 3' (SEQ ID NO:26), which eliminated a DdeI site. The resultant h2 heavy chain plasmid was designated pAND113.

To generate expression vectors for the huAQC2 heavy chains, the 0.43 kb NotI-HindIII heavy chain variable domain fragment from pAND104, pAND115, or pAND113, and the 1.21 kb HindIII-NotI fragment from pEAG964 (supra) were subcloned into the NotI site of pCH269 (supra). The resultant heavy chain expression plasmids were designated pAND114 (h1), pAND121 (c2), and pAND124 (h2), respectively.

The h1 version of light chain were made by using plasmid pAND093 as template. The mutagenic primers were: FR1 primer 5' CAA ATT GTT CTC ACC CAG TCT CCA TCC TCC CTG TCT GCG TCT GTA GGG GAC AGA GTC ACC ATC ACA TGC AGT GCC AGC TCA 3' (SEQ ID NO:27), which removed BstEII and PstI sites; FR2 primer 5' TTC TGG TAT CAG CAG AAG CCC GGG AAA GCC CCC AAA CCC TGG ATT 3' (SEQ D NO:28), which introduced an NciI site; FR3 primer 5 GCT TCT GGA GTC CCT TCA CGC TTC AGT GGC AGT GGG TCT GGG ACA GAT TAC ACT CTC ACA ATC AGC AGC CTG CAA CCT GAA GAT TTT GCC ACT TAT TAC TGC CAG 3' (SEQ ID NO:29), which introduced a DdeI site and eliminated EcoO109I and AvaII sites; and FR4 primer 5' GGT GGA GGC ACT AAG GTG GAG ATC TAA CGG GCT 3' (SEQ ID NO:30), which introduced DdeI and StyI sites. The resultant h1 light chain plasmid was designated pAND103.

The h2 version of light chain were made by using pAND103 as template with the following primer: FR2 primer 5' CCC GGG AAA GCG CCC AAA CTC CTG ATT TAT CTC ACA TCC 3' (SEQ ID NO:31), which introduced Hay and Headi sites. The resultant h2 light chain plasmid was designated pAND116.

The c1 version of light chain used plasmid pAND103 template with the following primers: FR1 primer 5' GCC TCA GTC ATA ATG TCC CGG GGA CAA ATT CAG CTC ACC CAG TCT CCA TCC 3' (SEQ ID NO:32), which introduced SamI, NciI, and HpaII sites; FR4 primer 5' GGT AAC CCG TGG ACG TTC GGT CAG GGC ACT AAG GTG GAG ATC TAA CGG GCT 3' (SEQ ID NO:33), which introduced a Bsp1286I site. The resultant c1 light chain plasmid was designated pAND118.

The c2 version of light chain were made by using plasmid pAND116 template with the following primers: FR1 primer 5' GCC TCA GTC ATA ATG TCC CGG GGA CAA ATT CAG CTC ACC CAG TCT CCA TCC 3' (SEQ ID NO:34), which introduced SamI, NciI, and HpaII sites; FR4 primer 5' GGT AAC CCG TGG ACG TTC GGT CAG GGC ACT AAG GTG GAG ATC TAA CGG GCT 3' (SEQ ID NO:35), which introduced a BP1286I site. The resultant c2 light chain plasmid was designated pAND119.

To generate expression vectors for the huAQC2 light chains, the 0.44 kb NotI-BglII light chain variable domain fragment from pAND103, pAND116, pAND118, or pAND119, and the 0.68 kb BclI-NotI fragment from pEAG963 (supra) were subcloned into the NotI site of pCH269 (supra). The resultant light chain expression vectors were designated pAND117 (h1), pAND120 (h2), pAND122 (c1), and pAND123 (c2), respectively.

The expression vectors were co-transfected into 293-EBNA cells, and transfected cells were tested for antibody secretion and specificity. Cells transfected with an empty vector served as negative control. The whole cell lysates and the conditioned medium were immuno-precipitated with protein A. Western blot analysis of the precipitates (developed with anti-human heavy and light chain antibodies) indicated that huAQC2-transfected cells synthesized and efficiently secreted heavy and light chains at levels similar to chAQC2-transfected cells.

FACS analysis of VLA-1 expressing K 562α1 cells stained with conditioned medium from the transfected cells was then performed, To do so, the K562α1 cells were incubated with the conditioned medium on ice for 120 min. The cells were then washed three times with a FACS buffer (PBS with 5% FBS and 0.05% sodium azide). The washed cells were resuspended in the buffer and incubated with PE-conjugated anti-human IgG (H+L) (Jackson ImmunoResearch Laboratories, Inc.) on ice for 30 min on ice. After the incubation, the cells were washed three times with the FACS buffer, and resuspended in the FACS buffer for analysis. The data are shown in Table 2, in which HuAQC2-h1 refers to an mAb consisting of the h1 version of the huAQC2 heavy chain (HC) and the h1 version of the huAQC2 light chain (LC) (see Table 1). Likewise, huAQC-h2 is an mAb consisting of the h2 versions of the heavy and light chains, huAQC2-c1 the c1 versions, and huAQC2-c2 the c2 versions. In the table, relative MFI refers to mean MFI normalized to that observed for chAQC2 blocked. Data shown represents the average from two independent transfections. These data indicated that the huAQC2-h2 and -c2 mAbs bound less well than huAQC2-h1 and -c1 relative to chAQC2.

TABLE 2

FACS staining of K562α1 cells by chAQC2 and huAQC2

|  | Light chain | Heavy chain | Relative MFI |
|---|---|---|---|
| chAQC2 | pAND102 | pAND099 | 1.00 |
| huAQC2-h1 | pAND117 | pAND114 | 1.50 |
| huAQC2-h2 | pAND120 | pAND124 | 0.64 |
| huAQC2-c1 | pAND122 | pAND114 | 1.50 |
| huAQC2-c2 | pAND123 | pAND121 | 0.68 |
| huAQC2 LC c1/HC c2 | pAND122 | pAND121 | 2.21 |
| huAQC2 LC c2/HC c1 | pAND123 | pAND114 | 0.76 |
| huAQC2 LC unblocked c1/HC c2 | pAND150* | pAND121 | 0.75 |
| huAQC2 LC L46P c2/HC c2 | pAND133** | pAND121 | 1.50 |
| huAQC2 LC L47W c2/HC c2 | pAND132*** | pAND121 | 1.00 |

*It encodes huAQC2 LC c1 with an unblocked N-terminus Q1D.
**It encodes huAQC2 LC c2 with L46P.
***It encodes huAQC2 LC c2 with L47W.

Co-transfections of 293-EBNA cells with chAQC2 and huAQC2h1, -h2, -c1 and -c2 were scaled up. Antibodies in the conditioned media were purified with Protein A-Sepharose. Purified mAbs were assayed by FACS for activity. The protocol as follows.

1. Count cells from flask that was split 1:4 on the day prior to the assay.
2. Pellet cells and resuspend at 2.5e5 cells/ml in FACS buffer (5% FBS in PBS with 0.02% NaAzide).
3. Pipette 100 µl of cells into the wells of a 96 well V bottom plate.
4. Prepare 1:3 serial dilutions of AQC2 starting at 3 µg/ml in FACS buffer.
5. Pellet the cells for 5 minutes at 800×g and flick plate to remove buffer.
6. Resuspend the cells in 100 µl of the diluted antibody series.
7. Incubate for 2 hours on ice.
8. Wash plate. Pellet the cells for 3 minutes at 800×g and flick plate to remove buffer.
9. Resuspend the cells in 100 µl of secondary antibody (diluted 1:100 in FACS buffer).
10. Incubate for 30 minutes on ice.
11. Wash plate (see above).
12. Resuspend cells in 25 µl of FACS buffer.
13. Centrifuge the FACS tubes briefly to ensure that the 50 µl is in the bottom of the tubes.
14. Vortex each tube vigorously and collect 5000 events.

The data are shown in FIG. 17. These data confirmed that huAQC2-h2 and -c2 bound less well than huAQC2-h1 and c1 relative to chAQC2.

The consensus versions of huAQC2 were studied further because they would be less immunogenic when used to treat patients with chronic indications. Mix-and-match cotransfections were performed to identify whether a single chain was responsible for the apparent decrease in binding seen with huAQC2-c2. The co-transfections suggested that the reduction could be attributed to the c2 light chain (encoded by pAND123), which differed from the c1 light chain (encoded by pAND122) at only two residues in the FR region: P46L and W47L.

To examine the individual contributions of each of these two changes, new c2 light chain expression vectors were constructed. Plasmid pAND125, the L47W variant of the c2 light chain was made using pAND119 as a template with the following mutagenic primer: FR2 primer 5' GGG AAA GCA CCC AAA CTC TGG ATC TAT CTC ACA TCC AAC 3' (SEQ ID NO:36), which introduced HhaI and HaeII sites. Plasmid pAND126, the L46P variant of the c2 light chain, was made by using pAND119 as a template with the following mutagenic primer: FR2 primer 5' AAG CCC GGG AAG GCG CCC AAA CCC CTG ATT TAT CTC ACA TCC AAC 3' (SEQ ID NO:37), which introduced BsaHI, BanI, and NarI sites. Expression vectors for these new huAQC2 light chains were made by subcloning the 0.44 kb NotI-BglII light chain variable domain fragment from pAND125 or pAND126, and the 0.68 kb BclI-NotI fragment from pEAG963 (supra) into the NotI site of pCH269 (supra). The resultant plasmids were designated pAND132 (c2 with L47W) (SEQ ID NO:47), and pAND133 (c2 with L46P) (SEQ ID NO:70), respectively.

Co-transfections of the new light chain plasmids with each of the huAQC2 heavy chain plasmids were performed. VLA-1 binding was examined by FACS. The data demonstrate that the L47W back mutation failed to improve binding. The L46P mutation improved the peak of the binding curve, but the EC50 was still right-shifted relative to the behavior of huAQC2 version 1 (Table 2, supra). These results suggested that both back mutations were needed for full binding activity.

A genetically unblocked c1 light chain was also made, since the Q1D variant would be one residue more "humanized." The Q1D mutant, designated pAND148, was made with the template pAND118 with the following mutagenic primer: FR1 primer 5' GTC ATA ATG TCC CGG GGA GAT ATC CAG CTC ACC CAG TCT 3' (SEQ ID NO:38), which introduced a new EcoRI site and removed an ApoI site. An expression vector for this last variant of the huAQC2 light chain was made by subcloning the 0.44 kb NotI-BglII light chain variable domain fragment from pAND148 and the 0.68 kb BclI-NotI fragment from pEAG963 into the NotI site of pCH269, producing the light chain expression vector pAND150 (c1 with unblocked N-terminus Q1D). Co-expression of the genetically unblocked light chain with the c2 heavy chain (i.e., "huAQC2 LC c1 unblocked/HC c2"; designated huAQC2c4) was equivalent to that of "huAQC2 LC c1/HC c2" (designated as huAQC2-c3). VLA-1 binding was confirmed by FACS on VLA1-expressing K562α1 cells (Table 2).

Co-transfections of 293EBNA cells with chAQC2 and huAQC2h1, -h2, -c1, -c2, -c3, and -c4 Antibodies in the conditioned media were purified on Protein A-Sepharose. The purified mAbs were assayed for activity (FIGS. 17 and 18). HuAQC2-c3 was chosen as the drug candidate, since its properties were more similar to chAQC2. Vectors were then designed for stable expression of huAQC2-c3 in CHO cells. The vectors contained a cDNA for the huAQC2 c1 LC or c2 HC, with the 5' and 3' UTRs eliminated and the heavy chain C-terminal lysine genetically deleted to ensure product homogeneity. The final vectors were pAND162 (light chain), pAND160 (heavy chain). As used herein, huAQC2-c3 is also called hAQC2.

The full polypeptide sequences of hAQC2 are as follows.

Light Chain (Plasmid: pAND162)
(SEQ ID NO: 3)

```
  1 QIQLTQSPSS LSASVGDRVT ITCSASSSVN HMFWYQQKPG

KAPKPWIYLT

51 SNLASGVPSR FSGSGSGTDY TLTISSLQPE DFATYYCQQW

SGNPWTFGQG

101 TKVEIKRTVA APSVFIFPPS DEQLKSGTAS VVCLLNNFYP

REAKVQWKVD

151 NALQSGNSQE SVTEQDSKDS TYSLSSTLTL SKADYEKHKV

YACEVTHQGL

201 SSPVTKSNR GEC
```

Heavy Chain (Plasmid: pAND160)
(SEQ ID NO: 4)

```
  1 EVQLVFSGGG LVQPGGSLRL SCAASGFTFS RYTMSWVRQA

PGKGLEWVAT

51 ISGGGHTYYL DSVKGRFTIS RDNSKNTLYL QMNSLRAEDT

AVYYCTRGFG

101 DGGYFDVWGQ GTLVTVSSAS TKGPSVFPLA PSSKSTSGGT

AALGCLVKDY

151 FPEPVTVSWN SGALTSGVHT PPAVLQSSGL YSLSSVVTVP

SSSLGTQTYI

201 CNVNHKPSNT KVDKKVEPKS CDKTHTCPPC PAPELLGGPS

VFLFPPKPKD

251 TLMISRTPEV TCVVVDVSHE DPEVKFNWYV DGVEVHNAKT

KPREEQYNST

301 YRVVSVLTVL HQDWLNGKEY KCKVSNKALP APIEKTISKA

KGQPREPQVY

351 TLPPSRDELT KNQVSLTCLV KGFYPSDIAV EWESNGQPEN

NYKTTPPVLD

401 SDGSFFLYSK LTVDKSRWQQ GNVFSCSVMH EALHNHYTQK

SLSLSPG
```

Other heavy and light chain polypeptide and nucleotide sequences are shown below.

A. chAQC2 heavy chain (Pand099) (SEQ ID NOs: 39 and 40.
The former No refers to the nucleotide sequence and the
latter to the polypeptide sequence. The same order is
used in the following numbering.)
```
  1 GACGTCAAGGTGGTGGAGTCAGGGGGAGGCTTAGTGAAGCCTGGAGGGTCCCTGAAACTC
    D   V   K   V   V   E   S   G   G   G   L   V   K   P   G   G   S   L   K   L 61 GCCTGTGCAGCCTCTGGATTCAGTTTCAGTAGATATACTATGTCTTGGGTTCGCCAGATT
    A   C   A   A   S   G   F   S   F   S   R   Y   T   M   S   W   V   R   Q   I 121 CCGGAGAAGAGGCTGGAGTGGGTCGCAACCATTAGTGGTGGTGGTCACACCTACTATCTA
    P   E   K   R   L   E   W   V   A   T   I   S   G   G   G   H   T   Y   Y   L 181 GACAGTGTGAAGGGCCGATTCACCATCTCCAGAGACAATGCCAAGAACACCCTGTACCTG
    D   S   V   K   G   R   F   T   I   S   R   D   N   A   K   N   T   L   Y   L 241 CAAATGAGCAGTCTGAGGTCTGAGGACACAGCCATGTATTACTGTACAAGAGGTTTTGGA
    Q   M   S   S   L   R   S   E   D   T   A   M   Y   Y   C   T   R   G   F   G 301 GACGGGGGGTACTTCGATGTCTGGGGCCAAGGGACCACGGTCACCGTCTCCTCA
    D   G   G   Y   F   D   V   W   G   Q   G   T   T   V   T   V   S   S
```

B. hAQC2 HC h1 and c1 (pAND114) (SEQ ID NOs: 41 and 42)
```
  1 GACGTCCAGCTGGTCGACTCAGGGGGAGGCTTAGTCCAGCCTGGAGGGTCCCTGAGACTC
    D   V   Q   L   V   E   S   G   G   G   L   V   Q   P   G   G   S   L   R   L 61 TCCTGTGCACCCTCTGGATTCAGTTTCAGTAGATATACTATGTCTTGGGTTCGCCAGGCT
    S   C   A   A   S   G   F   S   F   S   R   Y   T   M   S   W   V   R   Q   A 121 CCGGGGAAGGGGCTGGAGTGGGTCGCAACCATTAGTGGTGGTGGTCACACCTACTATCTA
    P   G   K   G   L   E   W   V   A   T   I   S   G   G   G   H   T   Y   Y   L 181 GACAGTGTGAAGGGCCGATTCACCATCTCCAGAGACAATTCCAAGAACACCCTGTACCTG
    D   S   V   K   G   R   F   T   I   S   R   D   N   S   K   N   T   L   Y   L 241 CAGATGAACAGTCTGAGGGCCGAGGACACAGCCGTGTATTACTGTACAAGAGGTTTTGGA
    Q   M   N   S   L   R   A   E   D   T   A   V   Y   Y   C   T   R   G   F   G 301 GACGGGGGGTACTTCGATGTCTGGGGCCAAGGTACCCTGGTCACCGTCTCCTCA
    D   G   G   Y   F   D   V   W   G   Q   G   T   L   V   T   V   S   S
```

C. hAQC2 h2 heavy chain (pAND124) (SEQ ID NOs: 43 and 44)
```
  1 GAGGTCCAGCTGGTCGAGTCAGGGGGAGGCTTAATCCAGCCTGGAGGGTCCCTGAGACTC
    E   V   Q   L   V   E   S   G   G   G   L   I   Q   P   G   G   S   L   R   L 61 TCCTGTGCAGCCTCTGGATTCACCTTCAGTAGGTATACTATGTCTTGGGTTCGCCAGGCT
    S   C   A   A   S   G   F   T   F   S   R   Y   T   M   S   W   V   R   Q   A 121 CCGGGGAAGGGGCTGGAGTGGGTCGCAACCATTAGTGGTGGTGGTCACACCTACTATCTA
    P   G   K   G   L   E   W   V   A   T   I   S   G   G   G   H   T   Y   Y   L 181 GACAGTGTGAAGGGCCGATTCACCATCTCCAGAGACAATTCCAAGAACACCCTGTACCTG
    D   S   V   K   G   R   F   T   I   S   R   D   N   S   K   N   T   L   Y   L 241 CAGATGAACAGTCTGAGGGCCGAGGACACAGCCGTGTATTACTGTACAAGAGGTTTTGGA
    Q   M   N   S   L   R   A   E   D   T   A   V   Y   Y   C   T   R   G   F   G 301 GACGGGGGGTACTTCGATGTCTGGGGCCAAGGTACCCTGGTCACCGTCTCCTCAGG
    D   G   G   Y   F   D   V   W   G   Q   G   T   L   V   T   V   S   S
```

D. hAQC2 c2 heavy chain (pAND121) (SEQ ID NOs: 45 AND 68)
```
  1 GAGGTCCAGCTGGTCGAGTCAGGGGGAGGCTTAGTCCAGCCTGGAGGGTCCCTGAGACTC
    E   V   Q   L   V   E   S   G   G   G   L   V   Q   P   G   G   S   L   R   L 61 TCCTGTGCAGCCTCTGGATTCACCTTCAGTAGGTATACTATGTCTTGGGTTCGCCAGGCT
    S   C   A   A   S   G   F   T   F   S   R   Y   T   M   S   W   V   R   Q   A 121 CCGGGGAAGGGGCTGGAGTGGGTCGCAACCATTAGTGGTGGTGGTCACACCTACTATCTA
    P   G   K   G   L   E   W   V   A   T   I   S   G   G   G   H   T   Y   Y   L 181 GACAGTGTGAAGGGCCGATTCACCATCTCCAGAGACAATTCCAAGAACACCCTGTACCTG
    D   S   V   K   G   R   F   T   I   S   R   D   N   S   K   N   T   L   Y   L 241 CAGATGAACAGTCTGAGGGCCGAGGACACAGCCGTGTATTACTGTACAAGAGGTTTTGGA
    Q   M   N   S   L   R   A   E   D   T   A   V   Y   Y   C   T   R   G   F   G 301 GACGGGGGGTACTTCGATGTCTGGGGCCAAGGTACCCTGGTCACCGTCTCCTCAGG
    D   G   G   Y   F   D   V   W   G   Q   G   T   L   V   T   V   S   S
```

-continued

E. chAQC2 blocked light chain (Pand102) (SEQ ID NOs: 46 and 1)
```
  1 CAAATTGTTCTCACCCAGTTTCCAGCACTCATGTCTGCGTCTCCAGGGGAGAAGCTCACC
    Q   I   V   L   T   Q   F   P   A   L   M   S   A   S   P   G   E   K   V   T 61 ATGACCTGCAGTGCCAGCTCAAGTGTAAATCACATGTTCTGGTATCAGCAGAAGCCAAAA
    M   T   C   S   A   S   S   S   V   N   H   M   F   W   Y   Q   Q   K   P   K 121 TCCTCCCCCAAACCCTGGATTTATCTCACATCCAACCTGGCTTCTGGAGTCCCTGCTCGC
    S   S   P   K   P   W   I   Y   L   T   S   N   L   A   S   G   V   P   A   R 181 TTCAGTGGCAGTGGGTCTGGGACCTCTTACTCTCTCACAATCAGCAGCATGGAGGCTGAA
    F   S   G   S   G   S   G   T   S   Y   S   L   T   I   S   S   M   E   A   E 241 GATGCTGCCACTTATTACTGCCAGCAGTGGAGTGGTAACCCGTGGACGTTCGGTGGAGGC
    D   A   A   T   Y   Y   C   Q   Q   W   S   G   N   P   W   T   F   G   G   G

301 ACCAAGCTGGAGATCAAA
    T   K   L   E   I   K
```

F. hAQC2 h1 light chain (pAND117) (SEQ ID NOs: 48 and 49)
```
  1 CAAATTGTTCTCACCCAGTCTCCATCCTCCCTGTCTGCGTCTGTAGGGGACAGAGTCACC
    Q   I   V   L   T   Q   S   P   S   S   L   S   A   S   V   G   D   R   V   T 61 ATCACATGCAGTGCCAGCTCAAGTGTAAATCACATGTTCTGGTATCAGCAGAAGCCCGGG
    I   T   C   S   A   S   S   S   V   N   H   M   F   W   Y   Q   Q   K   P   G 121 AAAGCCCCCAAACCCTGGATTTATCTCACATCCAACCTGGCTTCTGGAGTCCCTTCACGC
    K   A   P   K   P   W   I   Y   L   T   S   N   L   A   S   G   V   P   S   R 181 TTCAGTGGCAGTGGGTCTGGGACAGATTACACTCTCACAATCAGCAGCCTGCAACCTGAA
    F   S   G   S   G   S   G   T   D   Y   T   L   T   I   S   S   L   Q   P   E 241 GATTTTGCCACTTATTACTGCCAGCAGTGGAGTGGTAACCCGTGGACGTTCGGTGGAGGC
    D   F   A   T   Y   Y   C   Q   Q   W   S   G   N   P   W   T   F   G   G   G

301 ACTAAGGTGGAGATCAAA
    T   K   V   E   I   K
```

G. hAQC2 h2 light chain (pAND120) (SEQ ID NOs: 50 and 51)
```
  1 CAAATTGTTCTCACCCAGTCTCCATCCTCCCTGTCTGCGTCTGTAGGGGACAGAGTCACC
    Q   I   V   L   T   Q   S   P   S   S   L   S   A   S   V   G   D   R   V   T 61 ATCACATGCAGTGCCAGCTCAAGTGTAAATCACATGTTCTGGTATCAGCAGAAGCCCGGG
    I   T   C   S   A   S   S   S   V   N   H   M   F   W   Y   Q   Q   K   P   G 121 AAAGCGCCCAAACTCCTGATTTATCTCACATCCAACCTGGCTTCTGGAGTCCCTTCACGC
    K   A   P   K   L   L   I   Y   L   T   S   N   L   A   S   G   V   P   S   R 181 TTCAGTGGCAGTGGGTCTGGGACAGATTACACTCTCACAATCAGCAGCCTGCAACCTGAA
    F   S   G   S   G   S   G   T   D   Y   T   L   T   I   S   S   L   Q   P   E 241 GATTTTGCCACTTATTACTGCCAGCAGTGGAGTGGTAACCCGTGGACGTTCGGTGGAGGC
    D   F   A   T   Y   Y   C   Q   Q   W   S   G   N   P   W   T   F   G   G   G

301 ACTAAGGTGGAGATCAAA
    T   K   V   E   I   K
```

H. hAQC2 c1 light chain (pAND122) (SEQ ID NOs: 52 and 66)
```
  1 CAAATTCAGCTCACCCAGTCTCCATCCTCCCTGTCTGCGTCTGTAGGGGACAGAGTCACC
    Q   I   Q   L   T   Q   S   P   S   S   L   S   A   S   V   G   D   R   V   T 61 ATCACATGCAGTGCCAGCTCAAGTGTAAATCACATGTTCTGGTATCAGCAGAAGCCCGGG
    I   T   C   S   A   S   S   S   V   N   H   M   F   W   Y   Q   Q   K   P   G 121 AAAGCCCCCAAACCCTGGATTTATCTCACATCCAACCTGGCTTCTGGAGTCCCTTCACGC
    K   A   P   K   P   W   I   Y   L   T   S   N   L   A   S   G   V   P   S   R 181 TTCACTGGCAGTGGGTCTGGGACAGATTACACTCTCACAATCAGCAGCCTGCAACCTGAA
    F   S   G   S   G   S   G   T   D   Y   T   L   T   I   S   S   L   Q   P   E 241 GATTTTGCCACTTATTACTGCCAGCAGTGGAGTGGTAACCCGTGGACGTTCGGTCAGGGC
    D   F   A   T   Y   Y   C   Q   Q   W   S   G   N   P   W   T   F   G   Q   G

301 ACTAAGGTGGAGATCAAA
    T   K   V   E   I   K
```

-continued

I. hAQC2 c2 light chain (pAND123) (SEQ ID NOs: 53 and 54)
```
  1 CAAATTCAGCTCACCCAGTCTCCATCCTCCCTGTCTGCGTCTGTAGGGGACAGAGTCACC
    Q   I   Q   L   T   Q   S   P   S   S   L   S   A   S   V   G   D   R   V   T 61 ATCACATGCAGTGCCAGCTCAAGTGTAAATCACATGTTCTGGTATCAGCAGAAGCCCGGG
    I   T   C   S   A   S   S   S   V   N   H   M   F   W   Y   Q   Q   K   P   G 121 AAAGCGCCCAAACTCCTGATTTATCTCACATCCAACCTGGCTTCTGGAGTCCCTTCACGC
    K   A   P   K   L   L   I   Y   L   T   S   N   L   A   S   G   V   P   S   R 181 TTCAGTGGCAGTGGGTCTGGGACAGATTACACTCTCACAATCAGCAGCCTGCAACCTGAA
    F   S   G   S   G   S   G   T   D   Y   T   L   T   I   S   S   L   Q   P   E 241 GATTTTGCCACTTATTACTGCCAGCAGTGGAGTGGTAACCCGTGGACGTTCGGTCAGGGC
    D   F   A   T   Y   Y   C   Q   Q   W   S   G   N   P   W   T   F   G   Q   G

301 ACTAAGGTGGAGATCAAA
    T   K   V   E   I   K
```

J. chAQC2 unblocked light chain (pAND098) (SEQ ID NOs: 55 and 56)
```
  1 GAAATTGTTCTCACCCAGTTTCCAGCACTCATGTCTGCGTCTCCAGGGGAGAAGGTCACC
    E   I   V   L   T   Q   F   P   A   L   M   S   A   S   P   G   E   K   V   T 61 ATGACCTGCAGTGCCAGCTCAAGTGTAAATCACATGTTCTGGTATCAGCAGAAGCCAAAA
    M   T   C   S   A   S   S   S   V   N   H   M   F   W   Y   Q   Q   K   P   K 121 TCCTCCCCCAAACCCTGGATTTATCTCACATCCAACCTGGCTTCTGGAGTCCCTGCTCGC
    S   S   P   K   P   W   I   Y   L   T   S   N   L   A   S   G   V   P   A   R 181 TTCAGTGGCAGTGGGTCTGGGACCTCTTACTCTCTCACAATCAGCAGCATGGAGGCTGAA
    F   S   G   S   G   S   G   T   S   Y   S   L   T   I   S   S   M   E   A   E 241 GATGCTGCCACTTATTACTGCCAGCAGTGGAGTGGTAACCCGTGGACGTTCGGTGGAGGC
    D   A   A   T   Y   Y   C   Q   Q   W   S   G   N   P   W   T   F   G   G   G

301 ACCAAGCTGGAGATCAAA
    T   K   L   E   I   K
```

K. huAQC2 unblocked c1 light chain (pAND150) (SEQ ID NOs: 57 and 58)
```
  1 GATATCCAGCTCACCCAGTCTCCATCCTCCCTGTCTGCGTCTGTAGGGGACAGAGTCACC
    D   I   Q   L   T   Q   S   P   S   S   L   S   A   S   V   G   D   R   V   T 61 ATCACATGCAGTGCCAGCTCAAGTGTAAATCACATGTTCTGGTATCAGCAGAAGCCCGGG
    I   T   C   S   A   S   S   S   V   N   H   M   F   W   Y   Q   Q   K   P   G 121 AAAGCCCCCAAACCCTGGATTTATCTCACATCCAACCTGGCTTCTGGAGTCCCTTCACGC
    K   A   P   K   P   W   I   Y   L   T   S   N   L   A   S   G   V   P   S   R 181 TTCAGTGGCAGTGGGTCTGGGACAGATTACACTCTCACAATCAGCAGCCTGCAACCTGAA
    F   S   G   S   G   S   G   T   D   Y   T   L   T   I   S   S   L   Q   P   E 241 GATTTTGCCACTTATTACTGCCAGCAGTGGAGTGGTAACCCGTGGACGTTCGGTCAGGGC
    D   F   A   T   Y   Y   C   Q   Q   W   S   G   N   P   W   T   F   G   Q   G

301 ACTAAGGTGGAGATCAAA
    T   K   V   E   I   K
```

Example 22

This example describes the characterization of various AQC2 antibodies of the invention.

Solid-phase assay for α1 I domain binding. Fifty µl of 10 mg/ml α1 I domain-GST fusion protein was added to a CORNING COSTAR EASY WASH polystyrene 96-well plate (Gotwals et al., *Biochemistry*, 38, 8280-8 (1999)). Following incubation at 4° C. for 16 hrs, the plate was washed four times with 350 µl of 0.1% Tween-20 in PBS in a plate washer. The plate was blocked by addition of 180 µl of 3% BSA in TBS at 25° C. for 60 min, and then washed as above. Dilutions of antibodies (50 µl/well) in TBS containing 1 mg/ml BSA (assay buffer) were prepared in a 96-well round-bottom plate, transferred to the α1 I domain-coated plate, and incubated for 60 min at 25° C. Following a final wash, 100 µl/well of TMB reagent (Pierce) was added. After 10 min, 100 µl of 1 M sulfuric acid was added, and the absorbance at 450 nm was read on a UV-Vis 96-well spectrophotometer.

Electrochemiluminescence assays for binding of α1β1 integrin or α1 I domain to collagen. Tosyl-activated DYNA-BEADS M-280 (Dynal, Inc.) were coated with 100 µg/ml type IV collagen (Sigma) according to the manufacturer's instructions. Cell lysates from α1-transfected K562 cells were prepared as follows. Cells were collected by centrifugation, resuspended at $10^8$ cells/ml in a lysis buffer containing 25 mM Tris, pH 7.4, 1% NP-40, 1 mM $CaCl_2$, 1 mM $MnCl_2$, 1 mM $MgCl_2$, 2% BSA, and 1 mM PMSF, and incubated at 4° C. for 60 ruin. Cell debris was removed by centrifugation at 12,000 rpm for 30 min and the resulting supernatant was used in subsequent experiments. Anti-β1 activating antibody TS2/16 and polyclonal anti-GST antibody (Pharmacia) were labeled with TAG-NHS ester (IGEN International, Inc., Gaithersburg, Md.) according to the manufacturer's instructions, Labeled antibodies were purified by gel filtration chromatography on SEPHADEX G25M (Pharmacia).

To carry out the binding assay, collagen-coated beads (1 mg/ml) were blocked for 5 min with 8% Lewis rat plasma in an assay buffer containing 50 mM HEPES, pH 7.5, 150 mM NaCl, and 0.1% Triton X-100. For the α1β1 binding assay, serial dilutions of antibodies were incubated with 10 μg of beads, cell lysate prepared from $10^5$ α1-transfected K562 cells (supra), and 0.1 μg/ml of TAG-TS2/16 in an assay buffer containing 1 mM $MnCl_2$. For the α1 I domain binding assay, the antibodies were incubated with 10 μg of beads, 0.1 μg/ml α1 I domain GST fusion protein, and 1 μg/ml of TAG-anti-GST in an assay buffer containing 1 mM $MnCl_2$. After one to two hours of agitation at room temperature, 200 μl of the assay buffer was added and the samples were read on an ORIGEN 1.5 electrochemiluminescence detector (IGEN). Plots are presented with arbitrary electrochemiluminescence units (ECL) on the ordinate axis.

Biotinylated mAQC2 competition assay. A 96-well plate was coated with 50 μl of 5 μg/ml α1 I domain GST fusion protein and blocked with 3% BSA in TBS as described above. Dilutions of antibodies (60 μl/well) in the assay buffer were prepared in a 96-well roundbottom plate, and 60 μl of 0.1 μg/ml biotinylated murine AQC2 in the assay buffer was added. Fifty microliters from each well was transferred to the coated plate and incubated for 3 hrs at 25° C. The plate was then washed as above, 50 μl of 1 μg/ml peroxidase-conjugated EXTRAVIDIN (Sigma) was added, and the plate was incubated another 2 hrs at 25° C. After a final wash, 100 μl/well of TMB reagent (Pierce) was added. After 10 min, 100 μl of 1 M sulfuric acid was added, and the absorbance at 450 nm was read on a UV-Vis 96-well spectrophotometer.

Experimental results. The experimental results are shown in FIGS. 16A-D and Table 3. The ability of mAQC2, chAQC2, hAQC2, and hAQC2' (i.e., huAQC2-c4; differing from hAQC2 only in that residue 1 of the hAQC2' light chain was D instead of Q) to (1) bind to human α1-transfected K562 cells (by FACS); (2) bind to immobilized α1-I domain (by ELISA); (3) compete with mAQC2 for binding to α1-I domain (ELISA); (4) block α1β1 domain binding to collagen (Electrochemiluminescence assay); or (5) block a α1β1 integrin binding to collagen (Electrochemiluminescence assay) was determined. The results are shown in FIGS. 16A-D, and calculated IC50 (for inhibition) or EC50 (for binding) values are given in Table 3. In each assay, each of the humanized AQC2 forms showed a similar ability to either bind VLA1 (or the α1 domain) or block binding to collagen (Note that in panel C, the observed difference in intensity between mAQC2 and the humanized forms derives from the use of an anti-murine-IgG secondary antibody, instead of an anti-human-IgG).

TABLE 3

Summary of assay results (all values in nM)

| Antibody | FACS (EC50) | VLA1 Inhibition (IC50) | α1I Inhibition (IC50) | ELISA (EC50) | Competition with biotin-AQC2 (IC50) |
|---|---|---|---|---|---|
| mAQC2 | n.d. | 0.0726 (±0.014) | 0.029 (±0.011) | 0.061 (±0.015) | 38 (±8.7) |
| Chimera | 0.25 | 0.071 (±0.002) | 0.027 (±0.007) | 0.176 (±0.058) | 30 (±6.9) |
| hAQC2 | 0.29 | 0.129 (±0.005) | 0.035 (±0.005) | 0.190 (±0.010) | 65 (±2.2) |

TABLE 3-continued

Summary of assay results (all values in nM)

| Antibody | FACS (EC50) | VLA1 Inhibition (IC50) | α1I Inhibition (IC50) | ELISA (EC50) | Competition with biotin-AQC2 (IC50) |
|---|---|---|---|---|---|
| hAQC2' | 0.43 | 0.125 (±0.018) | 0.037 (±0.001) | 0.313 (±0.072) | 69 (±25.7) |

We next tested whether changes at certain conservative residues in the CDRs could preserve the VLA-1 binding activity of hAQC2, DNA constructs encoding variants of hAQC2 with the following mutations were made by site-directed mutagenesis: (1) G55S in the heavy chain CDR2; (2) S24N in the light chain CDR1 (introducing an occupied N-linked glycosylation site); (3) G92S in the light chain CDR3; (4) a combination of (1) and (2); and (5) a combination of (1) and (3). The DNA constructs encoding both the heavy and light chains were then co-transfected into 293-EBNA cells, and the conditioned medium of the transfectants was assayed for antibody expression by Western blot and ELISA. The results indicated that the hAQC2 variants were expressed as efficiently as cognate h-AQC2. FACS analysis using VLA-1-expressing K562 cells further showed that the VLA-1 binding activities of these variants were similar to hAQC2 itself. In sum, the amino acid substitutions did not alter the VLA-1 binding activity of hAQC2. Indeed, X-ray crystal structure of the RΔH/hAQC2 Fab complex (infra) shows that S24 and G92 of the light chain and G55 of the heavy chain are not in the binding pocket that is in contact with the α1-I domain.

Example 23

The effector functions of an immunoglobulin couple the immunoglobulin's antigen-binding activity to the inflammatory, cytotoxic and stimulatory arms of the immune system. Effector functions may impair the safety and efficacy of an immunoglobulin therapeutic product. To reduce the potential effector functions of hAQC2, mutations of L234A and L235A were made to its heavy chain to generate hsAQC2. For the same reason, a single mutation of N298Q (numbering according to SEQ ID NO:5) was made in the heavy chain of hAQC2 to generate an aglycosylated form of hAQC2, named haAQC2. Studies can be done to compare their efficacy, residual effector function, stability and immunogenicity to cognate hAQC2. Unless otherwise indicated, residue position numbers in constant regions as used herein are designated in accordance with the EU numbering convention.

The heavy chain polypeptide sequence of haAQC2 is as follows

```
(Plasmid: pAND161):
                                        (SEQ ID NO: 5)
  1  EVQLVESGGG LVQPGGSLRL SCAASGFTFS RYTMSWVRQA
     PGKGLEWVAT
 51  ISGGGHTYYL DSVKGRFTIS RDNSKNTLYL QMNSLRAEDT
     AVYYCTRGFG
101  DGGYFDVWGQ GTLVTVSSAS TKGPSVFPLA PSSKSTSGGT
     AALGCLVKDY
```

-continued

```
151 FPEPVTVSWN SGALTSGVHT FPAVLQSSGL YSLSSVVTVP
    SSSLGTQTYI
201 CNVNHKPSNT KVDKKVEPKS CDKTHTCPPC PAPELLGGPS
    VFLFPPKPKD
251 TLMISRTPEV TCVVVDVSHE DPEVKFNWYV DGVEVHNAKT
    KPREEQYQST
301 YRVVSVLTVL HQDWLNGKEY KCKVSNKALP APIEKTISKA
    KGQPREPQVY
351 TLPPSRDELT KNQVSLTCLV KGFYPSDIAV EWESNGQPEN
    NYKTTPPVLD
401 SDGSFFLYSK LTVDKSRWQQ GNVFSCSVMH EALHNHYTQK
    SLSLSPG
```

The heavy chain polypeptide sequence of hsAQC2 is as follows (Plasmid: pAND171):
(SEQ ID NO: 6)
```
  1 EVQLVESGGG LVQPGGSLRL SCAASGFTFS RYTMSWVRQA
    PGKGLEWVAT
 51 ISGGGHTYYL DSVKGRFTIS RDNSKNTLYL QMNSLRAEDT
    AVYYCTRGFG
101 DGGYPDVWGQ GTLVTVSSAS TKGPSVFPLA PSSKSTSGGT
    AALGCLVKDY
151 FPEPVTVSWN SGALTSGVHT FPAVLQSSGL YSLSSVVTVP
    SSSLGTQTYI
201 CNVNHKPSNT KVDKKVEPKS CDKTHTCPPC PAPEAAGGPS
    VFLFPPKPKD
251 TLMISRTPEV TCVVVDVSHE DPEVKFNWYV DGVEVHNAKT
    KPREEQYNST
301 YRVVSVLTVL HQDWLNGKEY KCKVSNKALP APIEKTISKA
    KGQPREPQVY
351 TLPPSRDELT KNQVSLTCLV KGFYPLDIAV EWESNGQPEN
    NYKTTPPVLD
401 SDGSFFLYSK LTVDKSRWQQ GNVFSCSVMH EALHNHYTQK
    SLSLSPG
```

Example 24

This example describes a method for determining the crystal structure of the complex of a rat/human chimeric α1-I domain of the α1β1 integrin and the hAQC2 Fab fragment.

Preparation of the Protein Complex

The hAQC2 Fab fragment was prepared from hAQC2 antibody using a variation of the procedure of the IMMUNOPURE® Fab preparation kit (Cat# 44885, Pierce, Rockford, Ill.). The intact hAQC2 antibody was concentrated to 12 mg/ml in a buffer containing 20 mM phosphate, 10 mM EDTA and 25 mM cysteine (pH 7.0). Immobilized papain was added at an enzyme to substrate ratio of 1:50, and digestion was allowed to occur overnight at 37° C. The immobilized papain was removed and the crude digest was dialyzed against 20 mM sodium acetate buffer (pH 4.5). The Fab fragment was separated from residual intact antibody, dimeric Fab fragment, and Fc fragment by cation exchange chromatography using a S-column (Poros HS/M, PERSEPTIVE Biosystems #PO42M26) with a shallow salt gradient. The Fab fragment was then exchanged into 0.1 M Hepes buffer (pH 8.0).

The chimeric α1-I domain used in the present invention is a rat/human chimeric I domain construct (mutant RΔH) containing residues Thr145-Phe336 of the rat α1 integrin chain, where residues Gly217, Arg218, Gln219 and Leu222 (crystal numbering) have been substituted with equivalent human residues Val, Gln, Arg and Arg, respectively, in order to restore antibody binding. The amino acid sequences of chimeric RΔH, rat, and human α1-I domains are given below in SEQ ID NOs:59, 60 and 61, respectively. Recombinant α1-I domain was expressed in *E. coli* as a GST-fusion protein. The RΔH α1-I domain was cleaved with thrombin and purified from a *Pichia pastoris* clone as described previously (Gotwals et al., 1999, *Biochemistry* 38:8280-8288).

(SEQ ID NO: 59)
```
145 TQLDIV
151 IVLDGSNSIY PWESVIAFLN DLLKRMDIGP KQTQVGIVQY
191 GENVTHEFNL NKYSSTEEVL VAANKIVQRG GRQTMTALGI
231 DTARKEAFTE ARGARRGVKK VMVIVTDGES HDNYRLKQVI
271 QDCEDENIQR FSIAILGHYN RGNLSTEKFV EEIKSIASEP
311 TEKHFFNVSD ELALVTIVKA LGERIF
```

(SEQ ID NO: 60)
```
145 TQLDIV
151 IVLDGSNSIY PWESVIAFLN DLLKRMDIGP KQTQVGIVQY
191 GENVTHEFNL NKYSSTEEVL VAANKIGRQG GLQTMTALGI
231 DTARKEAFTE ARGARRGVKK VMVIVTDGES HDNYRLKQVI
271 QDCEDENIQR FSIAILGHYN RGNLSTEKFV EEIKSIASEP
311 TEKHFFNVSD ELALVTIVKA LGERIF
```

(SEQ ID NO: 61)
```
145 TQLDIV
151 IVLDGSNSIY PWDSVTAFLN DLLKRMDIGP KQTQVGIVQY
191 GENVTHEFNL NKYSSTEEVL VAAKKIVQRG GRQTMTALGI
231 DTARKEAFTE ARGARRGVKK VMVIVTDGES HDNHRLKKVI
271 QDCEDENIQR FSIAILGSYN RGNLSTEKFV EEIKSIASEP
311 TEKHFFNVSD EIALVTIVKT LGERIF
```

The hAQC2 Fab fragment was mixed with excess chimeric α1-I domain and incubated at 37° C. for 15 minutes. The saturated a1/Fab complexes were separated from uncomplexed α1-I domain by size exclusion chromatography using a S200 Sephacryl column (Pharmacia, Gibco). The complex was further concentrated to 11 mg/ml in a 20 mM Tris (pH 7.4) 150 mM NaCl 1 mM MnCl$_2$, 5 mM β-mercaptoethanol.

Preparation of Crystals

Crystallization conditions were found using the CRYSTAL SCREEN™KITs from Hampton Research (Laguna Niguel, Calif.), Crystals of the complex described above were grown at 20° C. by vapor diffusion using an equal amount of protein complex solution and a 20-30% PEG 1500 reservoir solution. Typically, 2 μL of protein complex was added to 2 μL of well solution to yield drops of 4 μL. Crystals grew in two to seven days as hexagonal rods with dimensions 0.8× 0.05×0.05 mm$^3$. The presence of the α1-I domain and hAQC2 Fab fragment was confirmed by SDS-PAGE analysis of dissolved crystals. In order to reduce the inherent radiation damage during data collection, X-ray diffraction data was collected at approximately 100 K. To prepare the crystals for data collection at this low temperature, crystals were gradually equilibrated into a cryoprotectant solution containing 25% PEG 400 and 30% PEG 1500, and flash cooled in liquid nitrogen.

Structure Determination

Native X-ray diffraction data to 2.8 Å resolution were collected from a single crystal at about 100 K using an ADSC Quantum 4 charged-coupled device detector at beamline X4A of the Brookhaven National Laboratory (BNL) National Synchrotron Light Source (NSLS). Data was processed using the software programs DENZO and SCALEPACK (Otwinowski & Minor, 1997, *Methods in Enzymol.* 276:307-326). Crystals belonged to the space group P6$_1$ or its enantiomorph P6$_5$, with unit cell dimensions a=b=255.09 Å, c=38.64 Å. The data set was 96.6% complete and had an R-merge of 8.3%. The Matthews coefficient (Matthews, 1968, *J. Mol. Biol.* 33:491-497) was 2.59 Å$^3$ Da$^{-1}$ with a solvent content of 52.1%, which indicated that there were two complexes in the asymmetric unit. The two complexes in the asymmetric unit were related by non-crystallographic 2-fold symmetry. Data statistics are shown in Table 4.

Molecular replacement searches were done with the program AMoRe (Navaza, 1994, *Acta Cryst. A*50:157-163) from the CCP4 program package (Collaborative Computational Project No. 4. The CCP4 Suite: programs for protein crystallography. 1994, *Acta Cryst. D*50:760-763), and molecular graphics manipulations were done with the program QUANTA. A single α1-I domain from the structure of the rat α1-I domain of α1β1 integrin (Protein Data Bank (PDB) accession number 1ck4; Nolte et al., 1999, *FEBS Lett.* 452: 379-385) was used as a model or probe for rotation and translation searches. The translation function search indicated that the 1$^{st}$ and 9$^{th}$ highest peaks of the rotation function corresponded to the correct solutions for the two α1-I domains in the asymmetric unit (correlation coefficient (cc) =21.1%, R=53.1%) and that the space group was P6$_5$. Subsequently, searches for the hAQC2 Fab fragments were done, keeping the I domain solutions fixed and using a model of the Fv domain of the hAQC2 Fab as a search probe. A clear solution was found for one of the two Fv domains (cc=22.1%, R=52.6%), but the second Fv could not be located. The position of the second Fv was derived using the non-crystallographic 2-fold symmetry. Rigid body refinement of the two I domains and two Fv domains reduced the R-factor to 43.6% (R-free=42.7%). An 2Fo-Fc electron density map showed clear electron density for the constant domain (Fconst) of the first Fab fragment, but no density for the Fconst domain of the second Fab fragment. A model of the Fconst domain of the first Fab was manually fit in the observed electron density. Subsequent rigid body refinement with the software program CNX (Accelrys Inc., San Diego, Calif. ©2000; Brunger, 1998, *Acta Cryst.* D54:905-921), using data in the 500-2.8 Å resolution range, optimized the position of all domains, reducing the R-factor to 39.7% (R-free=38.9%).

All subsequent refinement steps were carried out with the CNX program. To reduce model bias, partial models were used for 2Fo-Fc map calculation and model refinement. The initial partial model, was subjected to simulated annealing and grouped B-factor refinement with non-crystallographic symmetry restraints. The R-working and R-free factors dropped to 28.3% and 32.9%, respectively. Several cycles consisting of iterative model building, maximum likelihood positional refinement and B-factor refinement followed. Only model adjustments that resulted in a drop in the K-free factor were accepted. A bulk-solvent correction was employed after the complete model was built. The R-working and K-free factors of the final model are 21.3% and 27.2%, respectively for the data (F>2σ) in the 500-2.8 Å resolution range.

The final 2Fo-Fc electron density map is of good quality for most of the complex with the exception of amino acid residues 288-295 of one I domain fragment (molecule A in FIG. 19) that are associated with weak electron density and have not been included in the model. In addition, the entire constant domain of one Fab fragment has no visible electron density, which indicates that it is disordered. This appears to be consequence of the absence of crystal contacts for the constant domain of the Fab fragment due to its position within a large solvent channel. This domain was also not included in the final model that consists of 1030 amino acid residues, constituting 6 polypeptide chains, and 2 manganese ions. The r.m.s. positional deviation between equivalent residues from the two complexes in the asymmetric unit is small (0.37 Å for 1660 equivalent main chain atoms). Stereochemistry statistics were calculated with the software programs PROCHECK (Laskowski et al., 1993, *J. Appl. Cryst.* 26:283-291; Morris et al., 1992, *Proteins* 12:345-364) and CNX. Hydrogen bonds (<3.6 Å) were found with the program CONTACT (Tadeusz Skarzvnski, Imperial College, London, Jan. 12, 1988; Collaborative Computational Project No. 4. The CCP4 Suite: programs for protein crystallography. 1994, *Acta Cryst. D*50, 760-763). All non-glycine residues (except residue Thr50 of the L chain that will be discussed below) are in the allowed regions of the Ramachandran diagram and 86% of the residues are in the most favored regions. The average B-factor of the main chain atoms is 38.5 Å$^2$. Crystallographic analysis data are in Table 4.

TABLE 4

Summary of Data Statistics and Crystallographic Analysis

| Data collection | |
|---|---|
| Cell dimensions a, b, c (Å) | 255.09, 255.09, 38.64 |
| Space group | P6$_5$ |
| Resolution (Å) | 500-2.8 (2.9-2.8)† |
| Unique reflections | 35275 |
| Completeness (%) | 96.6 (87.7)† |
| Average I/s | 11.92 (2.29)† |
| Rmerge* (%) | 8.3 (30.9)† |
| Model | |
| Number of non-H atoms | 7950 |
| Number of protein residues | 1030 |
| Contents of asymmetric unit | 2 I domains, 1 Fab fragment, 1 Fv domain |
| Average B-factor (Å$^2$) | 38.5 |
| Refinement | |
| Resolution range used (F > 2σ) | 500-2.8 |
| R-factor (R-working) (%) | 21.3 |
| R-free†† (%) | 27.2 |

TABLE 4-continued

Summary of Data Statistics and Crystallographic Analysis

| Stereochemistry RMS deviations | |
|---|---|
| Bond lengths (Å) | 0.007 |
| Angles (°) | 1.43 |

*Rmerge = $\Sigma_h \Sigma_i |I_{hi} - I_h|/\Sigma_{hi} I_{hi}$
†Values for the highest resolution shell given in parenthesis.
††8% of the data were allocated for the calculation of R-free factor.

Example 25

This example describes the crystal structure of the complex of a rat/human chimeric α1-I domain of the α1β1 integrin and the hAQC2 Fab fragment.

Architecture of Crystal Structure

The crystal structure of the complex of the rat/human chimeric α1-I domain of the α1β1 integrin and the hAQC2 Fab fragment has an elongated shape (FIG. 20). The dimensions of the complex are 100 Å×50 Å×35 Å.

The Fab fragment exhibits the typical immunoglobulin fold. The light chain and heavy chains of the Fab fragment each form two broad sheets of anti-parallel β-strands which pack tightly together to form a scaffold for the complementarity determining region (CDR) loops which extend from the packed sheets. Both the light chain and the heavy chain contain three CDR loops. The light chain loops are called L1, L2 and L3, while the heavy chain loops are referred to as H1, H2 and H3. The complementarity determining region (CDR) loops correspond to canonical structure 1 for light chain L1, L2 and L3 loops and for heavy chain H1 and H2 loops (Chothia et al., 1989, Nature 342:877-883). The heavy chain H3 loop has a tight β-hairpin-like conformation that is stabilized by internal hydrogen bonds as well as two aromatic residues (Tyr104 and Phe105) that are packed against the light chain. Residue Thr50 of L2 adopts mainchain dihedral angles that fall in the disallowed regions of the Ramachandran diagram. The same observation for the corresponding residue has been made for other antibodies (Muller et al., 1998, Structure 6, pp. 1153-11567) which indicates that this is a natural characteristic of L2 loops.

The α1-I domain in the present invention has a structure very similar to the uncomplexed α1-I domain (PDB accession number 1ck4; Nolte et al., 1999, FEBS Lett. 452:379-385; PDB accession code 1qc5; Rich et al., 1999, J. Biol. Chem. 274:24906-24913). The I domain structure exhibits a "dinucleotide-binding" or "Rossman" fold (Rao & Rossman, 1973, J. Mol. Biol. 76:241-256) in which a central sheet of five parallel β-strands and one small antiparallel-strand is surrounded on both sides by a total of seven α-helices. The six O-strands of the structure in this invention will be referred to as βA, βB, βC, βD, βE, and βF and the seven α-helices are called α1, α2, α3, α4, α5, α6 and α7.

Three characteristic structural features exist for I domains. The first characteristic feature is the presence of an inserted small helix in the βE-α6 loop, termed as the C helix. Most of the C helix loop of molecule A (FIG. 19) in the present invention is associated with weak electron density, which suggests disorder. This appears to be a consequence of absence of crystal contacts or contacts with the Fab that would have stabilized the loop. However, the same loop in molecule B (FIG. 19) in the present invention has well-defined electron density and has been included in the model. The second characteristic feature of α1-I domains is the MIDAS or Metal-Ion-Dependent-Adhesion-Site where metal ions and ligands are implicated to bind to the I domain. Five key residues which form part of the MIDAS are referred to as the "DxSxS-T-D" motif. These residues, which are completely conserved among I domains, coordinate the metal ion (Gotwals et al., 1999, Biochemistry 38:8280-8288). The crystals in the present invention were grown in the presence of manganese and the MIDAS site of the I domain in this structure is observed to contain a $Mn^{+2}$ metal ion. The ion is directly coordinated by the side chains of residues Ser156, Ser158 and Thr224. The 2Fo-Fc electron density map shows no evidence that MIDAS residues Asp 154 and Asp257 make water-mediated indirect coordination of the metal ion (FIG. 20). However, the apparent absence of water molecules could be a consequence of the limited resolution (2.8 Å) of the electron density map. The third feature of I domains is that all determined structures of I domains belong to one of two conformations called "open" and "closed". The differences between the open and closed conformation include a different mode of metal ion coordination and a significant (about 10 Å) positional shift of the C-terminal helix of the I domain. The I domain in the complex in the present invention is in the closed conformation.

In the structure of the complex in the present invention, the Fab fragment binds to its epitope on the front upper surface of the I domain with a footprint 35 Å by 30 Å. The total buried surface area in the antibody-antigen interface is 1534 $\in^2$ which is typical of other antibody-antigen complexes (Davies et al., 1996, Proc. Natl. Acad. Sci. USA 93:7-12; Jones & Thornton, 1996, Proc. Natl. Acad. Sci. USA 93:13-20). The surface is 25% hydrophobic and 75% hydrophilic in character. The heavy chain contributes 65% of the buried surface area for the complex, while the remaining 35% is contributed by the light chain. The antibody epitope consists of residues located in four loops of the I domain (Emsley et al., 2000, Cell 101:47-56). Three of the loops form the MIDAS site: loop 1 (βA-α1) which contains the conserved DXSXS sequence, loop 2 (α3-α4) which contains the MIDAS Thr224 and loop 3 (βD-α5) that contains MIDAS residue Asp257. The fourth loop is the C-helix loop and is involved in only in minor contacts.

The central feature of the antigen-antibody interaction is the coordination of the MIDAS site metal ion by Asp101 from the CDR H3 of the antibody (FIG. 20). The distance between the ion and Oδ1 of Asp101 is 2.4 Å. In addition, the Oδ2 atom of Asp101 is interacting with His261 of the I domain. Interestingly, the CDR H3 contains several glycine residues adjacent to Asp101 (sequence GFGDGGY) (SEQ ID NO:62), presumably to allow enough flexibility to the CDR loop to permit proper coordination of the metal ion. The CDR H3 sequence is essentially invariant in monoclonal antibodies that were raised against the same antigen and found to belong in the same class. Most of the antibody residues that are involved in antibody-antigen contacts are located in L3, H1, H2 and H3CDR loops. A few residues from the L1 (Asn30) and L2 (Tyr48) loops appear to form minor Van Der Waals contacts. L3 primarily contributes to contacts through two large hydrophobic residues, Trp90 and Trp95. In addition, Asn93 from L3 forms hydrogen bonds with Gln223 of the I domain. The side chains of His56 and Tyr58 from the H2 loop form hydrogen bonds with main chain atoms of loop 2 of the I domain. Arg31 of H1 is in contact with Arg291 of loop 4 of the I domain. Arg222 from loop 2 of the I domain is sandwiched between several antibody residues including Tyr58, Trp95 and Asn93. This is the only residue out of the four mutated in the RΔH I domain, that is involved in contacts with the Fab. It is therefore likely to be the only residue responsible for restoring the binding of the antibody after the mutagenesis.

Comparison of the Crystal Structure of the Complex of a Rat/human Chimeric α1-I Domain and the hAQC2 Fab Fragment with Other I Domain Structures The chimeric RΔH α1-I domain has four sequence differences with the rat α1-I domain (rat residues: 217G, 218R, 219Q and 222L), eight sequence differences with the human α1-I domain (human residues: 163D, 166T, 214K, 264H, 268K, 288S, 322I and 380T), and ten sequence differences with the clone used in the crystal structure studies of human α1-I domain (clone residues: 163D, 166T, 174E, 214K, 230I, 264H, 268K, 288S, 322I and 380T). In the unliganded rat α1β1 α1-I domain crystal structure (PDB accession code 1ck4; Nolte et al., 1999, *FEBS Lett.* 452:379-385), the α1-I domain contains no bound metal ions and adopts the "closed" conformation. In the unliganded human α1-I domain crystal structure (accession code 1qc5; Rich et al., 1999, *J. Biol. Chem.* 274:24906-24913), the α1-I domain contains bound $Mg^{+2}$ and similarly adopts the closed conformation. Superimposition of these two structures with the complexed chimeric α1-I domain indicates that there are only minor conformational changes upon hAQC2 antibody binding. The r.m.s. positional deviation between the rat and chimeric α1-I domain is 1.04 Å for all 768 main chain atoms. The r.m.s. positional deviation between the human and chimeric α1-I domain is 0.69 Å for all 764 main chain atoms. The biggest differences (human and chimeric α1-I domain pair) are observed in loop 1 (r.m.s. deviations 1.24 Å for main chain atoms of residues 154-161) and the loop 4 (C helix loop) of the α1-I domain (r.m.s. deviations 1.55 Å for main chain atoms of residues 288-296). However, these differences can be more accurately described as shifts of the whole secondary structure elements rather than complex conformational changes. These are likely to be within the normal range of conformational flexibility of proteins. The r.m.s. positional deviation between the human and chimeric α1-I domain for backbone atoms of amino acid residues Glu192, Gln218, Arg219, Gly220, and Gly221 (crystal numbering) is 0.33 Å. The r.m.s. positional deviation between the rat and chimeric α1-I domain for backbone atoms of amino acid residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering) is 0.97 Å.

The I domain maintains the "closed" I domain conformation that has been observed only for unliganded I domains crystallized in the absence of ligands or pseudo-ligands bound to the MIDAS site. The r.m.s. positional deviation of the C-terminal helices of the human and chimeric I domains (calculated for the main chain atoms of residues 321-335) is 0.64 Å. A simulated annealing omit map calculated for the final refined model unambiguously confirms that the position of the C-terminal helix and adjacent structural elements are consistent with the closed conformation.

In order to investigate the effects of ligand binding to the modes of metal ion coordination, the structure of the present invention was superimposed with the structures of the unliganded α2-I domain (PDB accession code 1aox; Emsley et al., 1997, *J. Biol. Chem.* 272:28512-28517) and the α2-I domain complexed with a collagen peptide (PDB accession code 1dzi; Emsley et al., 2000, *Cell* 101:47-56). The coordination of the metal ion by Asp101 from the antibody is remarkably similar to the coordination of the metal ion of the α2-I domain by a glutamic acid from the collagen peptide. Another feature that is conserved is the simultaneous interaction of the acidic group with His261 (His258 in the α2-I domain). All MIDAS residues of the I domain-Fab complex except Ser156 and Ser158 adopt conformations very similar to those observed in the unliganded I domain. In contrast, the side chains of Ser156 and Ser158, as well as the metal, adopt conformations similar with those of the liganded I domain. It is clear that the coordination of the metal ion by Asp101 does not allow the ion to maintain the position and coordination distances that are observed in the unliganded state. Thus, the metal ion is not directly coordinated by Asp257, a fact that permits the ion to maintain high electrophilicity.

Biological Implications

In the present invention, there is no direct coordination of the metal by Asp257, which may permit high affinity binding by lowering the energy barrier between a closed (no ligand bound) and open (ligand bound) conformation. However, the coordination of the metal by an aspartic acid from the antibody is not sufficient to induce the open conformation to the I domain in the present invention. The I domain-Fab complex structure indicates that it is possible to have strong binding to the I domain that adopts the closed conformation and that coordination of the metal ion by an acidic residue from the ligand may be necessary but not sufficient to induce a conformational change to the open state. Binding of the antibody is expected to stabilize the low affinity state of the integrin and prevent the outside-in signaling that would have accompanied integrin binding to collagen.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention.

What is claimed is:

1. A composition comprising isolated nucleic acid sequences comprising (a) a coding sequence for a light chain of an anti-VLA-1 antibody or antigen binding fragment thereof, and (b) a coding sequence for a heavy chain of an anti-VLA-1 antibody or antigen binding fragment thereof, wherein the light chain and the heavy chain form an antibody or antigen binding fragment thereof that binds VLA-1, and wherein the light chain and heavy chain are selected from one of the light chain and heavy chain pairs of the group consisting of:

(i) a light chain of an anti-VLA-1 antibody, or antigen-binding fragment thereof, which has the sequence of SEQ ID NO:3,
and a heavy chain of an anti-VLA-1 antibody, or antigen-binding fragment thereof, which has the sequence of SEQ ID NO:4;

(ii) a light chain of an anti-VLA-1 antibody, or antigen-binding fragment thereof, whose light chain variable domain has the sequence of SEQ ID NO:49,
and a heavy chain of an anti-VLA-1 antibody, or antigen-binding fragment thereof, whose heavy chain variable domain has the sequence of SEQ ID NO:42;

(iii) a light chain of an anti-VLA-1 antibody, or antigen-binding fragment thereof, whose light chain variable domain has the sequence of SEQ ID NO:51,
and a heavy chain of an anti-VLA-1 antibody, or antigen-binding fragment thereof, whose heavy chain variable domain has the sequence of SEQ ID NO:44;

(iv) a light chain of an anti-VLA-1 antibody, or antigen-binding fragment thereof, whose light chain variable domain has the sequence of SEQ ID NO:54,
and a heavy chain of an anti-VLA-1 antibody, or antigen-binding fragment thereof, whose heavy chain variable domain has the sequence of SEQ ID NO:42;

(v) a light chain of an anti-VLA-1 antibody, or antigen-binding fragment thereof, whose light chain variable domain has the sequence of SEQ ID NO:58,
and a heavy chain of an anti-VLA-1 antibody, or antigen-binding fragment thereof, whose heavy chain variable domain has the sequence of SEQ ID NO:68;

(vi) a light chain of an anti-VLA-1 antibody, or antigen-binding fragment thereof, whose light chain variable domain has the sequence of SEQ ID NO:70,
and a heavy chain of an anti-VLA-1 antibody, or antigen-binding fragment thereof, whose heavy chain variable domain has the sequence of SEQ ID NO:68;

(vii) a light chain of an anti-VLA-1 antibody, or antigen-binding fragment thereof, whose light chain variable domain has the sequence of SEQ ID NO:66,
and a heavy chain of an anti-VLA-1 antibody, or antigen-binding fragment thereof, whose heavy chain variable domain has the sequence of SEQ ID NO:42;

(ix) a light chain of an anti-VLA-1 antibody, or antigen-binding fragment thereof, whose light chain variable domain has the sequence of SEQ ID NO:54,
and a heavy chain of an anti-VLA-1 antibody, or antigen-binding fragment thereof, whose heavy chain variable domain has the sequence of SEQ ID NO:68;

(x) a light chain of an anti-VLA-1 antibody, or antigen-binding fragment thereof, whose light chain variable domain has the sequence of SEQ ID NO:47,
and a heavy chain of an anti-VLA-1 antibody, or antigen-binding fragment thereof, whose heavy chain variable domain has the sequence of SEQ ID NO:68;

(xi) a light chain of an antibody produced by hybridoma mAQC2 (ATCC accession number PTA3273),
and a heavy chain of an antibody produced by hybridoma mAQC2 (ATCC accession number PTA3273);

(xii) a light chain of an antibody produced by cell line hAQC2 (ATCC accession number PTA3275),
and a heavy chain of an antibody produced by cell line hAQC2 (ATCC accession number PTA3275);

(xiii) a light chain of an antibody produced by cell line haAOC2 (ATCC accession number PTA3274),
and a heavy chain of an antibody produced by cell line haAQC2 (ATCC accession number PTA3274); and, (xiv) a light chain of an antibody produced by cell line hsAOC2 (ATCC accession number PTA3356),
and a heavy chain of an antibody produced by cell line hsAQC2 (ATCC accession number PTA3356).

2. A vector comprising the nucleic acid sequences of claim 1.

3. An isolated host cell comprising the vector of claim 2.

4. Isolated nucleic acid sequences comprising (i) a coding sequence for a light chain of an anti-VLA-1 antibody, or antigen-binding fragment thereof, whose light chain complementary determining regions are defined by amino acid residues 24 to 33, 49 to 55, and 88 to 96 of SEQ ID NO:1; and (ii) a coding sequence for a heavy chain of an anti-VLA-1 antibody, or antigen-binding fragment thereof, whose heavy chain complementary determining regions are defined by amino acid residues 31 to 35, 50 to 65, and 98 to 107 of SEQ ID NO:2.

5. The isolated nucleic acid sequences of claim 4, wherein the sequence for the light chain and the sequence for the heavy chain are on two separate vectors.

6. The isolated nucleic acid sequences of claim 4, wherein the anti-VLA-1 antibody comprises a light chain variable domain sequence of SEQ ID NO:1 and a heavy chain variable domain sequence of SEQ ID NO:2.

7. The isolated nucleic acid sequences of claim 4, wherein the anti-VLA-1 antibody, or antigen binding fragment thereof, is a humanized or chimeric antibody or antigen binding fragment thereof.

8. The isolated nucleic acid sequences of claim 4, wherein the anti-VLA-1 antibody or antigen binding fragment thereof comprises at least one of the following residues in its light chain: Q1, L4, P45, W46 and Y70 of SEQ ID NO:1; or at least one of the following residues in its heavy chain: D1, V12, S28, F29, A49, T96, and R97 of SEQ ID NO:2.

9. The isolated nucleic acid sequences of claim 4, wherein the anti-VLA-1 antibody or antigen binding fragment thereof comprises a light chain variable domain sequence defined by amino acid residues 1 to 106 of SEQ ID NO:3, and a heavy chain variable domain sequence defined by amino acid residues 1 to 118 of SEQ ID NO:4.

10. A vector comprising the nucleic acid sequences of claim 4.

11. An isolated host cell comprising the vector of claim 10.

12. A process for preparing an anti-VLA-1 antibody, or alpha1-binding fragment thereof, comprising (i) providing a first nucleic acid comprising a coding sequence for an antibody light chain, or fragment thereof, of claim 1; (ii) providing a second nucleic acid comprising a coding sequence for an antibody heavy chain, or fragment thereof, of claim 1; (iii) transfecting a host cell with the first and second nucleic acids; and (iv) culturing the transfected cell line to produce the anti-VLA-1 antibody or antigen binding fragment thereof.

13. The process of claim 12, wherein the first and second nucleic acids are on two separate vectors.

14. The process of claim 12, wherein the light chain or fragment thereof comprises complementary determining regions defined by amino acid residues 24 to 33, 49 to 55, and 88 to 96 of SEQ ID NO:1, and wherein the heavy chain or fragment thereof comprises complementary determining regions defined by amino acid residues 31 to 35, 50 to 65, and 98 to 107 of SEQ ID NO:2.

15. The process of claim 12, wherein the light or fragment thereof comprises a variable domain sequence defined by amino acid residues 1 to 106 of SEQ ID NO:3, and wherein the heavy chain or fragment thereof comprises a variable domain sequence defined by amino acid residues 1 to 118 of SEQ ID NO:4.

16. The process of claim 12, wherein the host cell is a mammalian cell.

17. The process of claim 12, wherein the antibody or antigen binding fragment thereof is a humanized antibody or a chimeric antibody.

* * * * *

UNITED STATES PATENT AND TRADEMARK OFFICE
CERTIFICATE OF CORRECTION

PATENT NO. : 7,723,073 B2
APPLICATION NO. : 12/015213
DATED : May 25, 2010
INVENTOR(S) : Michael Karpusas et al.

It is certified that error appears in the above-identified patent and that said Letters Patent is hereby corrected as shown below:

At Col. 116, Line 9, replace "haAOC2" with --haAQC2--.

At Col. 116, Line 13, replace "hsAOC2" with --hsAQC2--.

Signed and Sealed this
Fifteenth Day of February, 2011

David J. Kappos
*Director of the United States Patent and Trademark Office*

SEQUENCE LISTING

```
<160> NUMBER OF SEQ ID NOS: 70

<210> SEQ ID NO 1
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 1

Gln Ile Val Leu Thr Gln Phe Pro Ala Leu Met Ser Ala Ser Pro Gly
```

```
                  1               5                  10                 15
Glu Lys Val Thr Met Thr Cys Ser Ala Ser Ser Ser Val Asn His Met
                 20                 25                 30

Phe Trp Tyr Gln Gln Lys Pro Lys Ser Ser Pro Lys Pro Trp Ile Tyr
                 35                 40                 45

Leu Thr Ser Asn Leu Ala Ser Gly Val Pro Ala Arg Phe Ser Gly Ser
             50                 55                 60

Gly Ser Gly Thr Ser Tyr Ser Leu Thr Ile Ser Ser Met Glu Ala Glu
 65                 70                 75                 80

Asp Ala Ala Thr Tyr Tyr Cys Gln Gln Trp Ser Gly Asn Pro Trp Thr
                 85                 90                 95

Phe Gly Gly Gly Thr Lys Leu Glu Ile Lys
                100                105

<210> SEQ ID NO 2
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 2

Asp Val Lys Val Val Glu Ser Gly Gly Gly Leu Val Lys Pro Gly Gly
 1               5                  10                 15

Ser Leu Lys Leu Ala Cys Ala Ala Ser Gly Phe Ser Phe Ser Arg Tyr
                 20                 25                 30

Thr Met Ser Trp Val Arg Gln Ile Pro Glu Lys Arg Leu Glu Trp Val
                 35                 40                 45

Ala Thr Ile Ser Gly Gly Gly His Thr Tyr Tyr Leu Asp Ser Val Lys
             50                 55                 60

Gly Arg Phe Thr Ile Ser Arg Asp Asn Ala Lys Asn Thr Leu Tyr Leu
 65                 70                 75                 80

Gln Met Ser Ser Leu Arg Ser Glu Asp Thr Ala Met Tyr Tyr Cys Thr
                 85                 90                 95

Arg Gly Phe Gly Asp Gly Gly Tyr Phe Asp Val Trp Gly Gln Gly Thr
                100                105                110

Thr Val Thr Val Ser Ser
        115

<210> SEQ ID NO 3
<211> LENGTH: 213
<212> TYPE: PRT
<213> ORGANISM: Artificial Sequence
<220> FEATURE:
<223> OTHER INFORMATION: Synthetically generated peptide

<400> SEQUENCE: 3

Gln Ile Gln Leu Thr Gln Ser Pro Ser Ser Leu Ser Ala Ser Val Gly
 1               5                  10                 15

Asp Arg Val Thr Ile Thr Cys Ser Ala Ser Ser Val Asn His Met
                 20                 25                 30

Phe Trp Tyr Gln Gln Lys Pro Gly Lys Ala Pro Lys Pro Trp Ile Tyr
                 35                 40                 45

Leu Thr Ser Asn Leu Ala Ser Gly Val Pro Ser Arg Phe Ser Gly Ser
             50                 55                 60

Gly Ser Gly Thr Asp Tyr Thr Leu Thr Ile Ser Ser Leu Gln Pro Glu
 65                 70                 75                 80
```

```
Asp Phe Ala Thr Tyr Tyr Cys Gln Gln Trp Ser Gly Asn Pro Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 4
<211> LENGTH: 447
<212> TYPE: PRT
<213> ORGANISM: Artificial Sequence
<220> FEATURE:
<223> OTHER INFORMATION: Synthetically generated peptide

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220
```

```
His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 5
<211> LENGTH: 447
<212> TYPE: PRT
<213> ORGANISM: Artificial Sequence
<220> FEATURE:
<223> OTHER INFORMATION: Synthetically generated peptide

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140
```

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Gln Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 6
<211> LENGTH: 447
<212> TYPE: PRT
<213> ORGANISM: Artificial Sequence
<220> FEATURE:
<223> OTHER INFORMATION: Synthetically generated peptide

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
            35                  40                  45

Ala Thr Ile Ser Gly Gly Gly His Thr Tyr Tyr Leu Asp Ser Val Lys
50                  55                  60
```

```
Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Thr
                 85                  90                  95

Arg Gly Phe Gly Asp Gly Gly Tyr Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 7
<211> LENGTH: 26
<212> TYPE: DNA
<213> ORGANISM: Homo sapiens

<400> SEQUENCE: 7
```

```
caggatccgt cagccccaca tttcaa                                    26

<210> SEQ ID NO 8
<211> LENGTH: 26
<212> TYPE: DNA
<213> ORGANISM: Homo sapiens

<400> SEQUENCE: 8
tcctcgaggg cttgcagggc aaatat                                    26

<210> SEQ ID NO 9
<211> LENGTH: 26
<212> TYPE: DNA
<213> ORGANISM: Rattus sp.

<400> SEQUENCE: 9
caggatccgt cagtcctaca tttcaa                                    26

<210> SEQ ID NO 10
<211> LENGTH: 26
<212> TYPE: DNA
<213> ORGANISM: Rattus sp.

<400> SEQUENCE: 10
tcctcgagcg cttccaaagc gaatat                                    26

<210> SEQ ID NO 11
<211> LENGTH: 31
<212> TYPE: DNA
<213> ORGANISM: Artificial Sequence
<220> FEATURE:
<223> OTHER INFORMATION: Primer

<400> SEQUENCE: 11
tgaggagacg gtgaccgtgg cccttggccc c                              31

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
aggtsmarct gcagsagtcw gg                                        22

<210> SEQ ID NO 13
<211> LENGTH: 40
<212> TYPE: DNA
<213> ORGANISM: Artificial Sequence
<220> FEATURE:
<223> OTHER INFORMATION: Primer

<400> SEQUENCE: 13
actagtcgac atggatttwc aggtgcagat twtcagcttc                     40

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
```

```
actggatggt gggaagatgg a                                          21
```

<210> SEQ ID NO 15
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 15

Asp Val Lys Val Val Glu Ser Gly Gly
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 16

Asp Val Lys Val Val Glu
1               5

<210> SEQ ID NO 17
<211> LENGTH: 54
<212> TYPE: DNA
<213> ORGANISM: Artificial Sequence
<220> FEATURE:
<223> OTHER INFORMATION: Primer

<400> SEQUENCE: 17

```
gcaccaggtg cccactccga cgtcaaggtg gtggagtcag ggggaggctt agtg       54
```

<210> SEQ ID NO 18
<211> LENGTH: 38
<212> TYPE: DNA
<213> ORGANISM: Artificial Sequence
<220> FEATURE:
<223> OTHER INFORMATION: Primer

<400> SEQUENCE: 18

```
ggaggcacca agctggagat ctaacgggct gatgctgc                         38
```

<210> SEQ ID NO 19
<211> LENGTH: 34
<212> TYPE: DNA
<213> ORGANISM: Artificial Sequence
<220> FEATURE:
<223> OTHER INFORMATION: Primer

<400> SEQUENCE: 19

```
cataatgtcc aggggagaaa ttgttctcac ccag                             34
```

<210> SEQ ID NO 20
<211> LENGTH: 93
<212> TYPE: DNA
<213> ORGANISM: Artificial Sequence
<220> FEATURE:
<223> OTHER INFORMATION: Primer

<400> SEQUENCE: 20

```
ggtgcccact ccgacgtcca gctggtcgag tcaggggag gcttagtcca gcctggaggg  60
tccctgagac tctcctgtgc agcctctgga ttc                              93
```

<210> SEQ ID NO 21
<211> LENGTH: 51
<212> TYPE: DNA
<213> ORGANISM: Artificial Sequence
<220> FEATURE:
<223> OTHER INFORMATION: Primer

<400> SEQUENCE: 21
atgtcttggg ttcgccaggc tccggggaag gggctggagt gggtcgcaac c    51

<210> SEQ ID NO 22
<211> LENGTH: 93
<212> TYPE: DNA
<213> ORGANISM: Artificial Sequence
<220> FEATURE:
<223> OTHER INFORMATION: Primer

<400> SEQUENCE: 22
ttcaccatct ccagagacaa ttccaagaac accctgtacc tgcagatgaa cagtctgagg    60
gccgaggaca cagccgtgta ttactgtaca aga    93

<210> SEQ ID NO 23
<211> LENGTH: 39
<212> TYPE: DNA
<213> ORGANISM: Artificial Sequence
<220> FEATURE:
<223> OTHER INFORMATION: Primer

<400> SEQUENCE: 23
tggggccaag gtaccctggt caccgtctcc tcaggtgag    39

<210> SEQ ID NO 24
<211> LENGTH: 51
<212> TYPE: DNA
<213> ORGANISM: Artificial Sequence
<220> FEATURE:
<223> OTHER INFORMATION: Primer

<400> SEQUENCE: 24
tcctgtgcag cctctggatt caccttcagt aggtatacta tgtcttgggt t    51

<210> SEQ ID NO 25
<211> LENGTH: 39
<212> TYPE: DNA
<213> ORGANISM: Artificial Sequence
<220> FEATURE:
<223> OTHER INFORMATION: Primer

<400> SEQUENCE: 25
gcaccaggtg cgcactccga ggtccagctg gtcgagtca    39

<210> SEQ ID NO 26
<211> LENGTH: 39
<212> TYPE: DNA
<213> ORGANISM: Artificial Sequence
<220> FEATURE:
<223> OTHER INFORMATION: Primer

<400> SEQUENCE: 26
gagtcagggg gaggcttaat ccagcctgga gggtccctg    39

<210> SEQ ID NO 27
<211> LENGTH: 81
<212> TYPE: DNA
<213> ORGANISM: Artificial Sequence
<220> FEATURE:

<223> OTHER INFORMATION: Primer

<400> SEQUENCE: 27
caaattgttc tcacccagtc tccatcctcc ctgtctgcgt ctgtagggga cagagtcacc      60
atcacatgca gtgccagctc a      81

<210> SEQ ID NO 28
<211> LENGTH: 45
<212> TYPE: DNA
<213> ORGANISM: Artificial Sequence
<220> FEATURE:
<223> OTHER INFORMATION: Primer

<400> SEQUENCE: 28
ttctggtatc agcagaagcc cgggaaagcc cccaaaccct ggatt      45

<210> SEQ ID NO 29
<211> LENGTH: 105
<212> TYPE: DNA
<213> ORGANISM: Artificial Sequence
<220> FEATURE:
<223> OTHER INFORMATION: Primer

<400> SEQUENCE: 29
gcttctggag tcccttcacg cttcagtggc agtgggtctg ggacagatta cactctcaca      60
atcagcagcc tgcaacctga agattttgcc acttattact gccag      105

<210> SEQ ID NO 30
<211> LENGTH: 33
<212> TYPE: DNA
<213> ORGANISM: Artificial Sequence
<220> FEATURE:
<223> OTHER INFORMATION: Primer

<400> SEQUENCE: 30
ggtggaggca ctaaggtgga gatctaacgg gct      33

<210> SEQ ID NO 31
<211> LENGTH: 39
<212> TYPE: DNA
<213> ORGANISM: Artificial Sequence
<220> FEATURE:
<223> OTHER INFORMATION: Primer

<400> SEQUENCE: 31
cccgggaaag cgcccaaaact cctgatttat ctcacatcc      39

<210> SEQ ID NO 32
<211> LENGTH: 51
<212> TYPE: DNA
<213> ORGANISM: Artificial Sequence
<220> FEATURE:
<223> OTHER INFORMATION: Primer

<400> SEQUENCE: 32
gcctcagtca taatgtcccg gggacaaaatt cagctcaccc agtctccatc c      51

<210> SEQ ID NO 33
<211> LENGTH: 51
<212> TYPE: DNA
<213> ORGANISM: Artificial Sequence
<220> FEATURE:
<223> OTHER INFORMATION: Primer

<400> SEQUENCE: 33
ggtaacccgt ggacgttcgg tcagggcact aaggtggaga tctaacgggc t            51

<210> SEQ ID NO 34
<211> LENGTH: 51
<212> TYPE: DNA
<213> ORGANISM: Artificial Sequence
<220> FEATURE:
<223> OTHER INFORMATION: Primer

<400> SEQUENCE: 34
gcctcagtca taatgtcccg gggacaaatt cagctcaccc agtctccatc c            51

<210> SEQ ID NO 35
<211> LENGTH: 51
<212> TYPE: DNA
<213> ORGANISM: Artificial Sequence
<220> FEATURE:
<223> OTHER INFORMATION: Primer

<400> SEQUENCE: 35
ggtaacccgt ggacgttcgg tcagggcact aaggtggaga tctaacgggc t            51

<210> SEQ ID NO 36
<211> LENGTH: 39
<212> TYPE: DNA
<213> ORGANISM: Artificial Sequence
<220> FEATURE:
<223> OTHER INFORMATION: Primer

<400> SEQUENCE: 36
gggaaagcac ccaaactctg gatctatctc acatccaac                          39

<210> SEQ ID NO 37
<211> LENGTH: 45
<212> TYPE: DNA
<213> ORGANISM: Artificial Sequence
<220> FEATURE:
<223> OTHER INFORMATION: Primer

<400> SEQUENCE: 37
aagcccggga aggcgcccaa acccctgatt tatctcacat ccaac                   45

<210> SEQ ID NO 38
<211> LENGTH: 39
<212> TYPE: DNA
<213> ORGANISM: Artificial Sequence
<220> FEATURE:
<223> OTHER INFORMATION: Primer

<400> SEQUENCE: 38
gtcataatgt cccgggggaga tatccagctc acccagtct                         39

<210> SEQ ID NO 39
<211> LENGTH: 354
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(354)

<400> SEQUENCE: 39 gac gtc aag gtg gtg gag tca ggg gga ggc tta gtg aag cct gga ggg    48
Asp Val Lys Val Val Glu Ser Gly Gly Gly Leu Val Lys Pro Gly Gly
1               5                   10                  15

```
tcc ctg aaa ctc gcc tgt gca gcc tct gga ttc agt ttc agt aga tat        96
Ser Leu Lys Leu Ala Cys Ala Ala Ser Gly Phe Ser Phe Ser Arg Tyr
            20                  25                  30 act atg tct tgg gtt cgc cag att ccg gag aag agg ctg gag tgg gtc       144
Thr Met Ser Trp Val Arg Gln Ile Pro Glu Lys Arg Leu Glu Trp Val
        35                  40                  45 gca acc att agt ggt ggt ggt cac acc tac tat cta gac agt gtg aag       192
Ala Thr Ile Ser Gly Gly Gly His Thr Tyr Tyr Leu Asp Ser Val Lys
    50                  55                  60 ggc cga ttc acc atc tcc aga gac aat gcc aag aac acc ctg tac ctg       240
Gly Arg Phe Thr Ile Ser Arg Asp Asn Ala Lys Asn Thr Leu Tyr Leu
65                  70                  75                  80 caa atg agc agt ctg agg tct gag gac aca gcc atg tat tac tgt aca       288
Gln Met Ser Ser Leu Arg Ser Glu Asp Thr Ala Met Tyr Tyr Cys Thr
                85                  90                  95 aga ggt ttt gga gac ggg ggg tac ttc gat gtc tgg ggc caa ggg acc       336
Arg Gly Phe Gly Asp Gly Gly Tyr Phe Asp Val Trp Gly Gln Gly Thr
            100                 105                 110 acg gtc acc gtc tcc tca                                               354
Thr Val Thr Val Ser Ser
        115

<210> SEQ ID NO 40
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 40

Asp Val Lys Val Val Glu Ser Gly Gly Gly Leu Val Lys Pro Gly Gly
1               5                   10                  15

Ser Leu Lys Leu Ala Cys Ala Ala Ser Gly Phe Ser Phe Ser Arg Tyr
            20                  25                  30

Thr Met Ser Trp Val Arg Gln Ile Pro Glu Lys Arg Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ser Glu Asp Thr Ala Met Tyr Tyr Cys Thr
                85                  90                  95

Arg Gly Phe Gly Asp Gly Gly Tyr Phe Asp Val Trp Gly Gln Gly Thr
            100                 105                 110

Thr Val Thr Val Ser Ser
        115

<210> SEQ ID NO 41
<211> LENGTH: 354
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(354)

<400> SEQUENCE: 41 gac gtc cag ctg gtc gag tca ggg gga ggc tta gtc cag cct gga ggg        48
Asp Val Gln Leu Val Glu Ser Gly Gly Gly Leu Val Gln Pro Gly Gly
1               5                   10                  15
```

```
tcc ctg aga ctc tcc tgt gca gcc tct gga ttc agt ttc agt aga tat    96
Ser Leu Arg Leu Ser Cys Ala Ala Ser Gly Phe Ser Phe Ser Arg Tyr
         20                  25                  30 act atg tct tgg gtt cgc cag gct ccg ggg aag ggg ctg gag tgg gtc   144
Thr Met Ser Trp Val Arg Gln Ala Pro Gly Lys Gly Leu Glu Trp Val
     35                  40                  45 gca acc att agt ggt ggt ggt cac acc tac tat cta gac agt gtg aag   192
Ala Thr Ile Ser Gly Gly Gly His Thr Tyr Tyr Leu Asp Ser Val Lys
 50                  55                  60 ggc cga ttc acc atc tcc aga gac aat tcc aag aac acc ctg tac ctg   240
Gly Arg Phe Thr Ile Ser Arg Asp Asn Ser Lys Asn Thr Leu Tyr Leu
65                  70                  75                  80 cag atg aac agt ctg agg gcc gag gac aca gcc gtg tat tac tgt aca   288
Gln Met Asn Ser Leu Arg Ala Glu Asp Thr Ala Val Tyr Tyr Cys Thr
                 85                  90                  95 aga ggt ttt gga gac ggg ggg tac ttc gat gtc tgg ggc caa ggt acc   336
Arg Gly Phe Gly Asp Gly Gly Tyr Phe Asp Val Trp Gly Gln Gly Thr
             100                 105                 110 ctg gtc acc gtc tcc tca                                           354
Leu Val Thr Val Ser Ser
         115
```

<210> SEQ ID NO 42
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 42

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser
        115

<210> SEQ ID NO 43
<211> LENGTH: 356
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(354)

<400> SEQUENCE: 43

```
gag gtc cag ctg gtc gag tca ggg gga ggc tta atc cag cct gga ggg    48
Glu Val Gln Leu Val Glu Ser Gly Gly Gly Leu Ile Gln Pro Gly Gly
1               5                   10                  15
```

```
tcc ctg aga ctc tcc tgt gca gcc tct gga ttc acc ttc agt agg tat        96
Ser Leu Arg Leu Ser Cys Ala Ala Ser Gly Phe Thr Phe Ser Arg Tyr
        20                  25                  30 act atg tct tgg gtt cgc cag gct ccg ggg aag ggg ctg gag tgg gtc       144
Thr Met Ser Trp Val Arg Gln Ala Pro Gly Lys Gly Leu Glu Trp Val
            35                  40                  45 gca acc att agt ggt ggt ggt cac acc tac tat cta gac agt gtg aag       192
Ala Thr Ile Ser Gly Gly Gly His Thr Tyr Tyr Leu Asp Ser Val Lys
 50                  55                  60 ggc cga ttc acc atc tcc aga gac aat tcc aag aac acc ctg tac ctg       240
Gly Arg Phe Thr Ile Ser Arg Asp Asn Ser Lys Asn Thr Leu Tyr Leu
 65                  70                  75                  80 cag atg aac agt ctg agg gcc gag gac aca gcc gtg tat tac tgt aca       288
Gln Met Asn Ser Leu Arg Ala Glu Asp Thr Ala Val Tyr Tyr Cys Thr
                85                  90                  95 aga ggt ttt gga gac ggg ggg tac ttc gat gtc tgg ggc caa ggt acc       336
Arg Gly Phe Gly Asp Gly Gly Tyr Phe Asp Val Trp Gly Gln Gly Thr
            100                 105                 110 ctg gtc acc gtc tcc tca gg                                            356
Leu Val Thr Val Ser Ser
        115
```

<210> SEQ ID NO 44
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 44

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser
        115
```

<210> SEQ ID NO 45
<211> LENGTH: 356
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(354)

<400> SEQUENCE: 45

```
gag gtc cag ctg gtc gag tca ggg gga ggc tta gtc cag cct gga ggg        48
Glu Val Gln Leu Val Glu Ser Gly Gly Gly Leu Val Gln Pro Gly Gly
1               5                   10                  15
```

```
tcc ctg aga ctc tcc tgt gca gcc tct gga ttc acc ttc agt agg tat      96
Ser Leu Arg Leu Ser Cys Ala Ala Ser Gly Phe Thr Phe Ser Arg Tyr
        20                  25                  30 act atg tct tgg gtt cgc cag gct ccg ggg aag ggg ctg gag tgg gtc     144
Thr Met Ser Trp Val Arg Gln Ala Pro Gly Lys Gly Leu Glu Trp Val
    35                  40                  45 gca acc att agt ggt ggt ggt cac acc tac tat cta gac agt gtg aag     192
Ala Thr Ile Ser Gly Gly Gly His Thr Tyr Tyr Leu Asp Ser Val Lys
50                  55                  60 ggc cga ttc acc atc tcc aga gac aat tcc aag aac acc ctg tac ctg     240
Gly Arg Phe Thr Ile Ser Arg Asp Asn Ser Lys Asn Thr Leu Tyr Leu
65                  70                  75                  80 cag atg aac agt ctg agg gcc gag gac aca gcc gtg tat tac tgt aca     288
Gln Met Asn Ser Leu Arg Ala Glu Asp Thr Ala Val Tyr Tyr Cys Thr
                85                  90                  95 aga ggt ttt gga gac ggg ggg tac ttc gat gtc tgg ggc caa ggt acc     336
Arg Gly Phe Gly Asp Gly Gly Tyr Phe Asp Val Trp Gly Gln Gly Thr
            100                 105                 110 ctg gtc acc gtc tcc tca gg                                          356
Leu Val Thr Val Ser Ser
        115

<210> SEQ ID NO 46
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 46 caa att gtt ctc acc cag ttt cca gca ctc atg tct gcg tct cca ggg      48
Gln Ile Val Leu Thr Gln Phe Pro Ala Leu Met Ser Ala Ser Pro Gly
1               5                   10                  15 gag aag gtc acc atg acc tgc agt gcc agc tca agt gta aat cac atg      96
Glu Lys Val Thr Met Thr Cys Ser Ala Ser Ser Ser Val Asn His Met
            20                  25                  30 ttc tgg tat cag cag aag cca aaa tcc tcc ccc aaa ccc tgg att tat     144
Phe Trp Tyr Gln Gln Lys Pro Lys Ser Ser Pro Lys Pro Trp Ile Tyr
        35                  40                  45 ctc aca tcc aac ctg gct tct gga gtc cct gct cgc ttc agt ggc agt     192
Leu Thr Ser Asn Leu Ala Ser Gly Val Pro Ala Arg Phe Ser Gly Ser
    50                  55                  60 ggg tct ggg acc tct tac tct ctc aca atc agc agc atg gag gct gaa     240
Gly Ser Gly Thr Ser Tyr Ser Leu Thr Ile Ser Ser Met Glu Ala Glu
65                  70                  75                  80 gat gct gcc act tat tac tgc cag cag tgg agt ggt aac ccg tgg acg     288
Asp Ala Ala Thr Tyr Tyr Cys Gln Gln Trp Ser Gly Asn Pro Trp Thr
                85                  90                  95 ttc ggt gga ggc acc aag ctg gag atc aaa                             318
Phe Gly Gly Gly Thr Lys Leu Glu Ile Lys
            100                 105

<210> SEQ ID NO 47
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 47
```

```
Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Asn His Met
            20                  25                  30

Phe Trp Tyr Gln Gln Lys Pro Gly Lys Ala Pro Lys Leu Trp Ile Tyr
            35                  40                  45

Leu Thr Ser Asn Leu Ala Ser Gly Val Pro Ser Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys
            100                 105

<210> SEQ ID NO 48
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 48 caa att gtt ctc acc cag tct cca tcc tcc ctg tct gcg tct gta ggg       48
Gln Ile Val Leu Thr Gln Ser Pro Ser Ser Leu Ser Ala Ser Val Gly
1               5                   10                  15 gac aga gtc acc atc aca tgc agt gcc agc tca agt gta aat cac atg       96
Asp Arg Val Thr Ile Thr Cys Ser Ala Ser Ser Ser Val Asn His Met
            20                  25                  30 ttc tgg tat cag cag aag ccc ggg aaa gcc ccc aaa ccc tgg att tat      144
Phe Trp Tyr Gln Gln Lys Pro Gly Lys Ala Pro Lys Pro Trp Ile Tyr
            35                  40                  45 ctc aca tcc aac ctg gct tct gga gtc cct tca cgc ttc agt ggc agt      192
Leu Thr Ser Asn Leu Ala Ser Gly Val Pro Ser Arg Phe Ser Gly Ser
        50                  55                  60 ggg tct ggg aca gat tac act ctc aca atc agc agc ctg caa cct gaa      240
Gly Ser Gly Thr Asp Tyr Thr Leu Thr Ile Ser Ser Leu Gln Pro Glu
65                  70                  75                  80 gat ttt gcc act tat tac tgc cag cag tgg agt ggt aac ccg tgg acg      288
Asp Phe Ala Thr Tyr Tyr Cys Gln Gln Trp Ser Gly Asn Pro Trp Thr
                85                  90                  95 ttc ggt gga ggc act aag gtg gag atc aaa                              318
Phe Gly Gly Gly Thr Lys Val Glu Ile Lys
            100                 105

<210> SEQ ID NO 49
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 49

Gln Ile Val Leu Thr Gln Ser Pro Ser Ser Leu Ser Ala Ser Val Gly
1               5                   10                  15

Asp Arg Val Thr Ile Thr Cys Ser Ala Ser Ser Ser Val Asn His Met
            20                  25                  30
```

```
Phe Trp Tyr Gln Gln Lys Pro Gly Lys Ala Pro Lys Pro Trp Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gly Gly Thr Lys Val Glu Ile Lys
            100                 105
```

<210> SEQ ID NO 50
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 50

```
caa att gtt ctc acc cag tct cca tcc tcc ctg tct gcg tct gta ggg        48
Gln Ile Val Leu Thr Gln Ser Pro Ser Ser Leu Ser Ala Ser Val Gly
1               5                   10                  15 gac aga gtc acc atc aca tgc agt gcc agc tca agt gta aat cac atg        96
Asp Arg Val Thr Ile Thr Cys Ser Ala Ser Ser Ser Val Asn His Met
                20                  25                  30 ttc tgg tat cag cag aag ccc ggg aaa gcg ccc aaa ctc ctg att tat       144
Phe Trp Tyr Gln Gln Lys Pro Gly Lys Ala Pro Lys Leu Leu Ile Tyr
        35                  40                  45 ctc aca tcc aac ctg gct tct gga gtc cct tca cgc ttc agt ggc agt       192
Leu Thr Ser Asn Leu Ala Ser Gly Val Pro Ser Arg Phe Ser Gly Ser
    50                  55                  60 ggg tct ggg aca gat tac act ctc aca atc agc agc ctg caa cct gaa       240
Gly Ser Gly Thr Asp Tyr Thr Leu Thr Ile Ser Ser Leu Gln Pro Glu
65                  70                  75                  80 gat ttt gcc act tat tac tgc cag cag tgg agt ggt aac ccg tgg acg       288
Asp Phe Ala Thr Tyr Tyr Cys Gln Gln Trp Ser Gly Asn Pro Trp Thr
                85                  90                  95 ttc ggt gga ggc act aag gtg gag atc aaa                               318
Phe Gly Gly Gly Thr Lys Val Glu Ile Lys
            100                 105
```

<210> SEQ ID NO 51
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 51

```
Gln Ile Val Leu Thr Gln Ser Pro Ser Ser Leu Ser Ala Ser Val Gly
1               5                   10                  15

Asp Arg Val Thr Ile Thr Cys Ser Ala Ser Ser Ser Val Asn His Met
                20                  25                  30

Phe Trp Tyr Gln Gln Lys Pro Gly Lys Ala Pro Lys Leu Leu Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
```

```
                65                  70                  75                  80
Asp Phe Ala Thr Tyr Tyr Cys Gln Gln Trp Ser Gly Asn Pro Trp Thr
                    85                  90                  95

Phe Gly Gly Gly Thr Lys Val Glu Ile Lys
            100                 105

<210> SEQ ID NO 52
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 52 caa att cag ctc acc cag tct cca tcc tcc ctg tct gcg tct gta ggg        48
Gln Ile Gln Leu Thr Gln Ser Pro Ser Ser Leu Ser Ala Ser Val Gly
1               5                   10                  15 gac aga gtc acc atc aca tgc agt gcc agc tca agt gta aat cac atg        96
Asp Arg Val Thr Ile Thr Cys Ser Ala Ser Ser Ser Val Asn His Met
                20                  25                  30 ttc tgg tat cag cag aag ccc ggg aaa gcc ccc aaa ccc tgg att tat       144
Phe Trp Tyr Gln Gln Lys Pro Gly Lys Ala Pro Lys Pro Trp Ile Tyr
            35                  40                  45 ctc aca tcc aac ctg gct tct gga gtc cct tca cgc ttc agt ggc agt       192
Leu Thr Ser Asn Leu Ala Ser Gly Val Pro Ser Arg Phe Ser Gly Ser
        50                  55                  60 ggg tct ggg aca gat tac act ctc aca atc agc agc ctg caa cct gaa       240
Gly Ser Gly Thr Asp Tyr Thr Leu Thr Ile Ser Ser Leu Gln Pro Glu
65                  70                  75                  80 gat ttt gcc act tat tac tgc cag cag tgg agt ggt aac ccg tgg acg       288
Asp Phe Ala Thr Tyr Tyr Cys Gln Gln Trp Ser Gly Asn Pro Trp Thr
                    85                  90                  95 ttc ggt cag ggc act aag gtg gag atc aaa                               318
Phe Gly Gln Gly Thr Lys Val Glu Ile Lys
            100                 105

<210> SEQ ID NO 53
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 53 caa att cag ctc acc cag tct cca tcc tcc ctg tct gcg tct gta ggg        48
Gln Ile Gln Leu Thr Gln Ser Pro Ser Ser Leu Ser Ala Ser Val Gly
1               5                   10                  15 gac aga gtc acc atc aca tgc agt gcc agc tca agt gta aat cac atg        96
Asp Arg Val Thr Ile Thr Cys Ser Ala Ser Ser Ser Val Asn His Met
                20                  25                  30 ttc tgg tat cag cag aag ccc ggg aaa gcc ccc aaa ctc ctg att tat       144
Phe Trp Tyr Gln Gln Lys Pro Gly Lys Ala Pro Lys Leu Leu Ile Tyr
            35                  40                  45 ctc aca tcc aac ctg gct tct gga gtc cct tca cgc ttc agt ggc agt       192
Leu Thr Ser Asn Leu Ala Ser Gly Val Pro Ser Arg Phe Ser Gly Ser
        50                  55                  60 ggg tct ggg aca gat tac act ctc aca atc agc agc ctg caa cct gaa       240
```

```
Gly Ser Gly Thr Asp Tyr Thr Leu Thr Ile Ser Ser Leu Gln Pro Glu
 65                  70                  75                  80 gat ttt gcc act tat tac tgc cag cag tgg agt ggt aac ccg tgg acg         288
Asp Phe Ala Thr Tyr Tyr Cys Gln Gln Trp Ser Gly Asn Pro Trp Thr
                 85                  90                  95 ttc ggt cag ggc act aag gtg gag atc aaa                                 318
Phe Gly Gln Gly Thr Lys Val Glu Ile Lys
            100                 105
```

<210> SEQ ID NO 54
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 54

```
Gln Ile Gln Leu Thr Gln Ser Pro Ser Leu Ser Ala Ser Val Gly
 1               5                  10                  15

Asp Arg Val Thr Ile Thr Cys Ser Ala Ser Ser Val Asn His Met
                 20                  25                  30

Phe Trp Tyr Gln Gln Lys Pro Gly Lys Ala Pro Lys Leu Leu Ile Tyr
                 35                  40                  45

Leu Thr Ser Asn Leu Ala Ser Gly Val Pro Ser Arg Phe Ser Gly Ser
     50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Gly Asn Pro Trp Thr
                 85                  90                  95

Phe Gly Gln Gly Thr Lys Val Glu Ile Lys
            100                 105
```

<210> SEQ ID NO 55
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 55

```
gaa att gtt ctc acc cag ttt cca gca ctc atg tct gcg tct cca ggg         48
Glu Ile Val Leu Thr Gln Phe Pro Ala Leu Met Ser Ala Ser Pro Gly
 1               5                  10                  15 gag aag gtc acc atg acc tgc agt gcc agc tca agt gta aat cac atg         96
Glu Lys Val Thr Met Thr Cys Ser Ala Ser Ser Ser Val Asn His Met
                 20                  25                  30 ttc tgg tat cag cag aag cca aaa tcc tcc ccc aaa ccc tgg att tat        144
Phe Trp Tyr Gln Gln Lys Pro Lys Ser Ser Pro Lys Pro Trp Ile Tyr
                 35                  40                  45 ctc aca tcc aac ctg gct tct gga gtc cct gct cgc ttc agt ggc agt        192
Leu Thr Ser Asn Leu Ala Ser Gly Val Pro Ala Arg Phe Ser Gly Ser
     50                  55                  60 ggg tct ggg acc tct tac tct ctc aca atc agc agc atg gag gct gaa        240
Gly Ser Gly Thr Ser Tyr Ser Leu Thr Ile Ser Ser Met Glu Ala Glu
 65                  70                  75                  80 gat gct gcc act tat tac tgc cag cag tgg agt ggt aac ccg tgg acg        288
Asp Ala Ala Thr Tyr Tyr Cys Gln Gln Trp Ser Gly Asn Pro Trp Thr
                 85                  90                  95
```

```
ttc ggt gga ggc acc aag ctg gag atc aaa                          318
Phe Gly Gly Gly Thr Lys Leu Glu Ile Lys
        100                 105

<210> SEQ ID NO 56
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 56

Glu Ile Val Leu Thr Gln Phe Pro Ala Leu Met Ser Ala Ser Pro Gly
1               5                   10                  15

Glu Lys Val Thr Met Thr Cys Ser Ala Ser Ser Ser Val Asn His Met
            20                  25                  30

Phe Trp Tyr Gln Gln Lys Pro Lys Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Gly Asn Pro Trp Thr
                85                  90                  95

Phe Gly Gly Gly Thr Lys Leu Glu Ile Lys
        100                 105

<210> SEQ ID NO 57
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 57 gat atc cag ctc acc cag tct cca tcc tcc ctg tct gcg tct gta ggg    48
Asp Ile Gln Leu Thr Gln Ser Pro Ser Ser Leu Ser Ala Ser Val Gly
1               5                   10                  15 gac aga gtc acc atc aca tgc agt gcc agc tca agt gta aat cac atg    96
Asp Arg Val Thr Ile Thr Cys Ser Ala Ser Ser Ser Val Asn His Met
            20                  25                  30 ttc tgg tat cag cag aag ccc ggg aaa gcc ccc aaa ccc tgg att tat   144
Phe Trp Tyr Gln Gln Lys Pro Gly Lys Ala Pro Lys Pro Trp Ile Tyr
        35                  40                  45 ctc aca tcc aac ctg gct tct gga gtc cct tca cgc ttc agt ggc agt   192
Leu Thr Ser Asn Leu Ala Ser Gly Val Pro Ser Arg Phe Ser Gly Ser
    50                  55                  60 ggg tct ggg aca gat tac act ctc aca atc agc agc ctg caa cct gaa   240
Gly Ser Gly Thr Asp Tyr Thr Leu Thr Ile Ser Ser Leu Gln Pro Glu
65                  70                  75                  80 gat ttt gcc act tat tac tgc cag cag tgg agt ggt aac ccg tgg acg   288
Asp Phe Ala Thr Tyr Tyr Cys Gln Gln Trp Ser Gly Asn Pro Trp Thr
                85                  90                  95 ttc ggt cag ggc act aag gtg gag atc aaa                           318
Phe Gly Gln Gly Thr Lys Val Glu Ile Lys
        100                 105

<210> SEQ ID NO 58
<211> LENGTH: 106
```

```
<212> TYPE: PRT
<213> ORGANISM: Artificial Sequence
<220> FEATURE:
<223> OTHER INFORMATION: Synthetically generated peptide

<400> SEQUENCE: 58

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Asn His Met
            20                  25                  30

Phe Trp Tyr Gln Gln Lys Pro Gly Lys Ala Pro Lys Pro Trp Ile Tyr
                35                  40                  45

Leu Thr Ser Asn Leu Ala Ser Gly Val Pro Ser Arg Phe Ser Gly Ser
            50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys
                100                 105

<210> SEQ ID NO 59
<211> LENGTH: 192
<212> TYPE: PRT
<213> ORGANISM: Artificial Sequence
<220> FEATURE:
<223> OTHER INFORMATION: Rat and human chimeric I domain construct

<400> SEQUENCE: 59

Thr Gln Leu Asp Ile Val Ile Val Leu Asp Gly Ser Asn Ser Ile Tyr
1               5                   10                  15

Pro Trp Glu Ser Val Ile Ala Phe Leu Asn Asp Leu Leu Lys Arg Asn
            20                  25                  30

Asp Ile Gly Pro Lys Gln Thr Gln Val Gly Ile Val Gln Tyr Gly Glu
            35                  40                  45

Asn Val Thr His Glu Phe Asn Leu Asn Lys Tyr Ser Ser Thr Glu Glu
            50                  55                  60

Val Leu Val Ala Ala Asn Lys Ile Val Gln Arg Gly Gly Arg Gln Thr
65                  70                  75                  80

Met Thr Ala Leu Gly Ile Asp Thr Ala Arg Lys Glu Ala Phe Thr Glu
                85                  90                  95

Ala Arg Gly Ala Arg Arg Gly Val Lys Lys Val Met Val Ile Val Thr
            100                 105                 110

Asp Gly Glu Ser His Asp Asn Tyr Arg Leu Lys Gln Val Ile Gln Asp
            115                 120                 125

Cys Glu Asp Glu Asn Ile Gln Arg Phe Ser Ile Ala Ile Leu Gly His
            130                 135                 140

Tyr Asn Arg Gly Asn Leu Ser Thr Glu Lys Phe Val Glu Glu Ile Lys
145                 150                 155                 160

Ser Ile Ala Ser Glu Pro Thr Glu Lys His Phe Phe Asn Val Ser Asp
                165                 170                 175

Glu Leu Ala Leu Val Thr Thr Val Lys Ala Leu Gly Glu Arg Ile Phe
            180                 185                 190

<210> SEQ ID NO 60
<211> LENGTH: 192
<212> TYPE: PRT
<213> ORGANISM: Rattus sp.
```

-continued

<400> SEQUENCE: 60

Thr Gln Leu Asp Ile Val Ile Val Leu Asp Gly Ser Asn Ser Ile Tyr
1               5                   10                  15

Pro Trp Glu Ser Val Ile Ala Phe Leu Asn Asp Leu Leu Lys Arg Met
                20                  25                  30

Asp Ile Gly Pro Lys Gln Thr Gln Val Gly Ile Val Gln Tyr Gly Glu
            35                  40                  45

Asn Val Thr His Glu Phe Asn Leu Asn Lys Tyr Ser Ser Thr Glu Glu
        50                  55                  60

Val Leu Val Ala Ala Asn Lys Ile Gly Arg Gln Gly Gly Leu Gln Thr
65                  70                  75                  80

Met Thr Ala Leu Gly Ile Asp Thr Ala Arg Lys Glu Ala Phe Thr Glu
                85                  90                  95

Ala Arg Gly Ala Arg Arg Gly Val Lys Lys Val Met Val Ile Val Thr
            100                 105                 110

Asp Gly Glu Ser His Asp Asn Tyr Arg Leu Lys Gln Val Ile Gln Asp
        115                 120                 125

Cys Glu Asp Glu Asn Ile Gln Arg Phe Ser Ile Ala Ile Leu Gly His
130                 135                 140

Tyr Asn Arg Gly Asn Leu Ser Thr Glu Lys Phe Val Glu Glu Ile Lys
145                 150                 155                 160

Ser Ile Ala Ser Glu Pro Thr Glu Lys His Phe Phe Asn Val Ser Asp
                165                 170                 175

Glu Leu Ala Leu Val Thr Ile Val Lys Ala Leu Gly Glu Arg Ile Phe
            180                 185                 190

<210> SEQ ID NO 61
<211> LENGTH: 192
<212> TYPE: PRT
<213> ORGANISM: Homo sapiens

<400> SEQUENCE: 61

Thr Gln Leu Asp Ile Val Ile Val Leu Asp Gly Ser Asn Ser Ile Tyr
1               5                   10                  15

Pro Trp Asp Ser Val Thr Ala Phe Leu Asn Asp Leu Leu Lys Arg Met
                20                  25                  30

Asp Ile Gly Pro Lys Gln Thr Gln Val Gly Ile Val Gln Tyr Gly Glu
            35                  40                  45

Asn Val Thr His Glu Phe Asn Leu Asn Lys Tyr Ser Ser Thr Glu Glu
        50                  55                  60

Val Leu Val Ala Ala Lys Lys Ile Val Gln Arg Gly Gly Arg Gln Thr
65                  70                  75                  80

Met Thr Ala Leu Gly Ile Asp Thr Ala Arg Lys Glu Ala Phe Thr Glu
                85                  90                  95

Ala Arg Gly Ala Arg Arg Gly Val Lys Lys Val Met Val Ile Val Thr
            100                 105                 110

Asp Gly Glu Ser His Asp Asn His Arg Leu Lys Lys Val Ile Gln Asp
        115                 120                 125

Cys Glu Asp Glu Asn Ile Gln Arg Phe Ser Ile Ala Ile Leu Gly Ser
130                 135                 140

Tyr Asn Arg Gly Asn Leu Ser Thr Glu Lys Phe Val Glu Glu Ile Lys
145                 150                 155                 160

Ser Ile Ala Ser Glu Pro Thr Glu Lys His Phe Phe Asn Val Ser Asp
                165                 170                 175

```
Glu Ile Ala Leu Val Thr Ile Val Lys Thr Leu Gly Glu Arg Ile Phe
            180                 185                 190

<210> SEQ ID NO 62
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 62

Gly Phe Gly Asp Gly Gly Tyr
1               5

<210> SEQ ID NO 63
<211> LENGTH: 214
<212> TYPE: PRT
<213> ORGANISM: Rattus sp.

<400> SEQUENCE: 63

Val Ser Pro Thr Phe Gln Val Val Asn Ser Phe Ala Pro Val Gln Glu
1               5                   10                  15

Cys Ser Thr Gln Leu Asp Ile Val Ile Val Leu Asp Gly Ser Asn Ser
            20                  25                  30

Ile Tyr Pro Trp Glu Ser Val Ile Ala Phe Leu Asn Asp Leu Leu Lys
        35                  40                  45

Arg Met Asp Ile Gly Pro Lys Gln Thr Gln Val Gly Ile Val Gln Tyr
50                  55                  60

Gly Glu Asn Val Thr His Glu Phe Asn Leu Asn Lys Tyr Ser Ser Thr
65                  70                  75                  80

Glu Glu Val Leu Val Ala Ala Lys Lys Ile Gly Arg Gln Gly Gly Leu
                85                  90                  95

Gln Thr Met Thr Ala Leu Gly Ile Asp Thr Ala Arg Lys Glu Ala Phe
            100                 105                 110

Thr Glu Ala Arg Gly Ala Arg Arg Gly Val Lys Lys Val Met Val Ile
        115                 120                 125

Val Thr Asp Gly Glu Ser His Asp Asn Tyr Arg Leu Lys Gln Val Ile
130                 135                 140

Gln Asp Cys Glu Asp Glu Asn Ile Gln Arg Phe Ser Ile Ala Ile Leu
145                 150                 155                 160

Gly His Tyr Asn Arg Gly Asn Leu Ser Thr Glu Lys Phe Val Glu Glu
                165                 170                 175

Ile Lys Ser Ile Ala Ser Glu Pro Thr Glu Lys His Phe Phe Asn Val
            180                 185                 190

Ser Asp Glu Leu Ala Leu Val Thr Ile Val Lys Ala Leu Gly Glu Arg
        195                 200                 205

Ile Phe Ala Leu Glu Ala
    210

<210> SEQ ID NO 64
<211> LENGTH: 214
<212> TYPE: PRT
<213> ORGANISM: Homo sapiens

<400> SEQUENCE: 64

Val Ser Pro Thr Phe Gln Val Val Asn Ser Ile Ala Pro Val Gln Glu
1               5                   10                  15

Cys Ser Thr Gln Leu Asp Ile Val Ile Val Leu Asp Gly Ser Asn Ser
            20                  25                  30
```

```
                20                  25                  30
Ile Tyr Pro Trp Asp Ser Val Thr Ala Phe Leu Asn Asp Leu Leu Lys
            35                  40                  45

Arg Met Asp Ile Gly Pro Lys Gln Thr Gln Val Gly Ile Val Gln Tyr
 50                  55                  60

Gly Glu Asn Val Thr His Glu Phe Asn Leu Asn Lys Tyr Ser Ser Thr
 65                  70                  75                  80

Glu Glu Val Leu Val Ala Ala Lys Lys Ile Val Gln Arg Gly Gly Arg
                85                  90                  95

Gln Thr Met Thr Ala Leu Gly Thr Asp Thr Ala Arg Lys Glu Ala Phe
            100                 105                 110

Thr Glu Ala Arg Gly Ala Arg Arg Gly Val Lys Lys Val Met Val Ile
            115                 120                 125

Val Thr Asp Gly Glu Ser His Asp Asn His Arg Leu Lys Lys Val Ile
            130                 135                 140

Gln Asp Cys Glu Asp Glu Asn Ile Gln Arg Phe Ser Ile Ala Ile Leu
145                 150                 155                 160

Gly Ser Tyr Asn Arg Gly Asn Leu Ser Thr Glu Lys Phe Val Glu Glu
                165                 170                 175

Ile Lys Ser Ile Ala Ser Glu Pro Thr Glu Lys His Phe Phe Asn Val
            180                 185                 190

Ser Asp Glu Leu Ala Leu Val Thr Ile Val Lys Thr Leu Gly Glu Arg
            195                 200                 205

Ile Phe Ala Leu Glu Ala
            210

<210> SEQ ID NO 65
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 65

Asp Ile Val Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Tyr Leu
            20                  25                  30

Asn Trp Tyr Gln Gln Lys Pro Gly Lys Ala Pro Lys Leu Leu Ile Tyr
            35                  40                  45

Ala Ala Ser Ser Leu Gln Ser Gly Val Pro Ser Arg Phe Ser Gly Ser
 50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Ser Tyr Ser Thr Pro Leu Thr
                85                  90                  95

Phe Gly Gly Gly Thr Lys Val Glu Ile Lys
            100                 105

<210> SEQ ID NO 66
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 66
```

Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Asn His Met
            20                  25                  30

Phe Trp Tyr Gln Gln Lys Pro Gly Lys Ala Pro Lys Pro Trp Ile Tyr
            35                  40                  45

Leu Thr Ser Asn Leu Ala Ser Gly Val Pro Ser Arg Phe Ser Gly Ser
50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys
            100                 105

<210> SEQ ID NO 67
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 67

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ser Ile Arg Phe Leu Glu Trp Ser Phe Asp Tyr Trp Gly Gln Gly Thr
            100                 105                 110

Leu Val Thr Val Ser Ser
        115

<210> SEQ ID NO 68
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
            35                  40                  45

Ala Thr Ile Ser Gly Gly Gly His Thr Tyr Tyr Leu Asp Ser Val Lys
50                  55                  60

Gly Arg Phe Thr Ile Ser Arg Asp Asn Ser Lys Asn Thr Leu Tyr Leu
65                  70                  75                  80

```
Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser
        115

<210> SEQ ID NO 69
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser
        115

<210> SEQ ID NO 70
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 70

Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Asn His Met
            20                  25                  30

Phe Trp Tyr Gln Gln Lys Pro Gly Lys Ala Pro Lys Pro Leu Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys
        100                 105
```